United States Patent
Venkatraman et al.

(10) Patent No.: US 7,592,419 B2
(45) Date of Patent: Sep. 22, 2009

(54) MACROCYCLIC INHIBITORS OF HEPATITIS C VIRUS NS3-SERINE PROTEASE

(75) Inventors: Srikanth Venkatraman, Woodbridge, NJ (US); F. George Njoroge, Warren, NJ (US); Wanli Wu, Edison, NJ (US); Viyyoor M. Girijavallabhan, Parsippany, NJ (US); Brian McKittrick, New Vernon, NJ (US); Jing Su, Scotch Plains, NJ (US); Francisco Velazquez, Clinton, NJ (US); Patrick A. Pinto, Morris Plains, NJ (US)

(73) Assignee: Schering Corporation, Kenilworth, NJ (US)

( * ) Notice: Subject to any disclaimer, the term of this patent is extended or adjusted under 35 U.S.C. 154(b) by 477 days.

(21) Appl. No.: 10/948,367

(22) Filed: Sep. 23, 2004

(65) Prior Publication Data

US 2005/0119168 A1    Jun. 2, 2005

Related U.S. Application Data

(60) Provisional application No. 60/506,637, filed on Sep. 26, 2003.

(51) Int. Cl.
*A61K 38/12* (2006.01)
*A61K 38/00* (2006.01)
(52) U.S. Cl. .................................. 530/317; 530/323
(58) Field of Classification Search ................... None
See application file for complete search history.

(56) References Cited

U.S. PATENT DOCUMENTS

| | | | |
|---|---|---|---|
| 5,712,145 | A | 1/1998 | Houghton et al. |
| 2003/0162167 | A1 | 8/2003 | Houghton et al. |

FOREIGN PATENT DOCUMENTS

| | | |
|---|---|---|
| WO | WO 89/04669 | 6/1989 |
| WO | WO 98/14181 | 4/1998 |
| WO | WO 98/17679 | 4/1998 |
| WO | WO 98/22496 | 5/1998 |
| WO | WO 99/07734 | 2/1999 |
| WO | WO 00/09543 | 2/2000 |
| WO | WO 00/09558 | 2/2000 |
| WO | WO 00/59929 | 10/2000 |
| WO | WO 01/74768 | 10/2001 |
| WO | WO 01/77113 | 10/2001 |
| WO | WO 01/81325 | 11/2001 |
| WO | WO 01/81325 A2 | 11/2001 |
| WO | WO 02/08198 | 1/2002 |
| WO | WO 02/08244 | 1/2002 |
| WO | WO 02/08251 | 1/2002 |
| WO | WO 02/08256 | 1/2002 |
| WO | WO 02/48172 | 6/2002 |
| WO | WO 03/062228 * | 7/2003 |
| WO | WO 03/062228 A1 | 7/2003 |
| WO | WO 2004/072243 A2 | 8/2004 |
| WO | WO 2004/093798 A2 | 11/2004 |

OTHER PUBLICATIONS

Goudreau, Nathalie, et al., "Potent Inhibitors of the Hepatitis . . . ," J. Org. Chem. 69:6185-6201 (2004).
Tsantrizos, Youl S., et al., "Macrocyclic Inhibitors of . . . ," Angew. Chem. Int. Ed. 42(12):1356-1360 (2003).
PCT International Search Report dated Feb. 2, 2005 for corresponding PCT Application No. PCT/US2004/031136.
Berenguer, Marina, et al., "Hepatitis B and C Viruses: Molecular Identification and Targeted Antiviral Therapies," *Proceedings of the Association of American Physicians* 110(2):98-112 (1998).
Dimasi, Nazzareno, et al., "Characterization of Engineered Hepatitis C Virus NS3 Protease Inhibitors Affinity Selected from Human Pancreatic Secretory Trypsin Inhibitor and Minibody Repertoires," *Journal of Virology* (Oct. 1997) 71(10):7461-7469.
Elzouki, Abdul-Nasser, et al., "Serine protease inhibitors in patients with chronic viral hepatitis," *Journal of Hepatology* (1997) 27:42-48.
Failla, Cristina Maria, et al., "Redesigning the substrate specificity of the hepatitis C virus NS3 protease," *Folding & Design* 1(1):35-42 (1996).
Han, Wei, et al., "α-Ketoamides, α-Ketoesters and α-Diketones as HCV NS3 Protease Inhibitors," *Bioorganic & Medicinal Chemistry Letters* (2000) 10:711-713.
Hoofnagle, Jay H., et al., "The Treatment of Chronic Viral Hepatitis," *The New England Journal of Medicine* 336(5):347-356.
Ingallinella, Paolo, et al., "Potent Peptide Inhibitors of Human Hepatitis C Virus NS3 Protease Are Obtained by Optimizing the Cleavage Products," *Biochemistry* (1998) 37:8906-8914.
Kolykhalov, A.A., et al., "Specificity of the hepatitis C virus NS3 serine protease: effects of substitutions at the 3/4A, 4A/4B, 4B/5A, and 5A/5B cleavage sites on polyprotein processing," *Journal of Virology* (Nov. 1994) 68(11):7525-7533.
Komoda, Y., et al., "Substrate requirements of hepatitis C virus serine proteinase for intermolecular polypeptide cleavage in *Escherichia coli*," *Journal of Virology* (Nov. 1994) 68(11):7351-7357.

(Continued)

*Primary Examiner*—Andrew D Kosar
*Assistant Examiner*—Thomas S Heard
(74) *Attorney, Agent, or Firm*—Palaiyur S. Kalyanaraman; Serena Farquharson-Torres

(57) ABSTRACT

The present invention discloses novel compounds which have HCV protease inhibitory activity as well as pharmaceutical compositions comprising such compounds and methods of using them to treat disorders associated with the HCV protease. The novel compounds typically include a 15-20 member macrocycle and have the general structure of structural Formula 1:

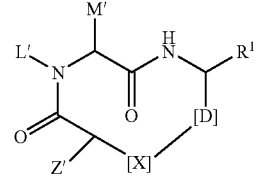

Formula 1 wherein Z', L', M', $R_1$, X and D are defined herein.

36 Claims, No Drawings

OTHER PUBLICATIONS

Landro, James A., et al., "Mechanistic Role of an NS4A Peptide Cofactor with the Truncated NS3 Protease of Hepatitis C Virus: Elucidation of the NS4A Stimulatory Effect via Kinetic Analysis and Inhibitor Mapping," *Biochemistry* (1997) 36:9340-9348.

Llinás-Brunet, Montse, et al., "Peptide-Based Inhibitors of the Hepatitis C Virus Serine Protease," *Bioorganic & Medicinal Chemistry Letters* (1998) 8:1713-1718.

Marchetti, Antonella, et al., "Synthesis of Two Novel Cyclic Biphenyl Ether Analogs of an Inhibitor of HCV NS3 Protease," *Synlett* S1:1000-1002 (1999).

Martin, F., et al., "Affinity selection of a camelized $V_H$ domain antibody inhibitor of hepatitis C virus NS3 protease," *Protein Engineering* 10(5):607-614 (1997).

Martin, Franck, et al., "Design of Selective Eglin Inhibitors of HCV NS3 Proteinase," *Biochemistry* 37:11459-11468 (1998).

Pizzi, Elisabetta, et al., "Molecular model of the specificity pocket of the hepatitis C virus protease: Implications for substrate recognition," *Proc. Natl. Acad. Sci.* USA 91:888-892 (Feb. 1994).

BioWorld Today 9(217):4 (Nov. 10, 1998).

U.S. Appl. No. 10/052,386 filed Jan. 18, 2002.

\* cited by examiner

MACROCYCLIC INHIBITORS OF HEPATITIS C VIRUS NS3-SERINE PROTEASE

This application claims priority from U.S. provisional patent application Ser. No. 60/506,637 filed Sep. 26, 2003.

FIELD OF INVENTION

The present invention relates to novel hepatitis C virus ("HCV") protease inhibitors, pharmaceutical compositions containing one or more such inhibitors, methods of preparing such inhibitors and methods of using such inhibitors to treat hepatitis C and related disorders. This invention additionally discloses novel macrocyclic compounds as inhibitors of the HCV NS3/NS4a serine protease.

BACKGROUND OF THE INVENTION

Hepatitis C virus (HCV) is a (+)-sense single-stranded RNA virus that has been implicated as the major causative agent in non-A, non-B hepatitis (NANBH), particularly in blood-associated NANBH (BB-NANBH) (see, International Patent Application Publication No. WO 89/04669, equal to US 2003162167). NANBH is to be distinguished from other types of viral-induced liver disease, such as hepatitis A virus (HAV), hepatitis B virus (HBV), delta hepatitis virus (HDV), cytomegalovirus (CMV) and Epstein-Barr virus (EBV), as well as from other forms of liver disease such as alcoholism and primary biliar cirrhosis.

Recently, an HCV protease necessary for polypeptide processing and viral replication has been identified, cloned and expressed; (see, e.g., U.S. Pat. No. 5,712,145). This approximately 3000 amino acid polyprotein contains, from the amino terminus to the carboxy terminus, a nucleocapsid protein (C), envelope proteins (E1 and E2) and several non-structural proteins (NS1, 2, 3, 4a, 5a and 5b). NS3 is an approximately 68 kda protein, encoded by approximately 1893 nucleotides of the HCV genome, and has two distinct domains: (a) a serine protease domain consisting of approximately 200 of the N-terminal amino acids; and (b) an RNA-dependent ATPase domain at the C-terminus of the protein. The NS3 protease is considered a member of the chymotrypsin family because of similarities in protein sequence, overall three-dimensional structure and mechanism of catalysis. Other chymotrypsin-like enzymes are elastase, factor Xa, thrombin, trypsin, plasmin, urokinase, tPA and PSA. The HCV NS3 serine protease is responsible for proteolysis of the polypeptide (polyprotein) at the NS3/NS4a, NS4a/NS4b, NS4b/NS5a and NS5a/NS5b junctions and is thus responsible for generating four viral proteins during viral replication. This has made the HCV NS3 serine protease an attractive target for antiviral chemotherapy. The inventive compounds can inhibit such protease. They also can modulate the processing of hepatitis C virus (HCV) polypeptide.

It has been determined that the NS4a protein, an approximately 6 kda polypeptide, is a co-factor for the serine protease activity of NS3. Autocleavage of the NS3/NS4a junction by the NS3/NS4a serine protease occurs intramolecularly (i.e., cis) while the other cleavage sites are processed intermolecularly (i.e., trans).

Analysis of the natural cleavage sites for HCV protease revealed the presence of cysteine at P1 and serine at P1' and that these residues are strictly conserved in the NS4a/NS4b, NS4b/NS5a and NS5a/NS5b junctions. The NS3/NS4a junction contains a threonine at P1 and a serine at P1'. The Cys→Thr substitution at NS3/NS4a is postulated to account for the requirement of cis rather than trans processing at this junction. See, e.q., Pizzi et al. (1994) *Proc. Natl. Acad. Sci (USA)* 91:888-892, Failla et al. (1996) *Folding & Design* 1:35-42. The NS3/NS4a cleavage site is also more tolerant of mutagenesis than the other sites. See, e.g., Kollykhalov et al. (1994) *J. Virol.* 68:7525-7533. It has also been found that acidic residues in the region upstream of the cleavage site are required for efficient cleavage. See, e.g., Komoda et al. (1994) *J. Virol.* 68:7351-7357.

Inhibitors of HCV protease that have been reported include antioxidants (see, International Patent Application Publication No. WO 98/14181), certain peptides and peptide analogs (see, International Patent Application Publication No. WO 98/17679 (equal to US2002032175), Landro et al. (1997) *Biochem.* 36:9340-9348, Ingallinella et al. (1998) *Biochem.* 37:8906-8914, Llinàs-Brunet et al. (1998) *Bioorg. Med. Chem. Lett.* 8:1713-1718), inhibitors based on the 70-amino acid polypeptide eglin c (Martin et al. (1998) *Biochem.* 37:11459-11468, inhibitors affinity selected from human pancreatic secretory trypsin inhibitor (hPSTI-C3) and minibody repertoires (MBip) (Dimasi et al. (1997) *J. Virol.* 71:7461-7469), $cV_HE2$ (a "camelized" variable domain antibody fragment) (Martin et al. (1997) *Protein Eng.* 10:607-614), and α1-antichymotrypsin (ACT) (Elzouki et al.) (1997) *J. Hepat.* 27:42-28). A ribozyme designed to selectively destroy hepatitis C virus RNA has recently been disclosed (see, *BioWorld Today* 9(217): 4 (Nov. 10, 1998)).

Reference is also made to the PCT Publications, No. WO 98/17679, published Apr. 30, 1998 (Vertex Pharmaceuticals Incorporated); WO 98/22496, published May 28, 1998 (equal to U.S. Pat. No. 6,018,020 and U.S. Pat. No. 5,866,684; F. Hoffmann-La Roche AG); and WO 99/07734, published Feb. 18, 1999 (equal to U.S. Pat. No. 6,143,715; Boehringer Ingelheim Canada Ltd.).

HCV has been implicated in cirrhosis of the liver and in induction of hepatocellular carcinoma. The prognosis for patients suffering from HCV infection is currently poor. HCV infection is more difficult to treat than other forms of hepatitis due to the lack of immunity or remission associated with HCV infection. Current data indicates a less than 50% survival rate at four years post cirrhosis diagnosis. Patients diagnosed with localized resectable hepatocellular carcinoma have a five-year survival rate of 10-30%, whereas those with localized unresectable hepatocellular carcinoma have a five-year survival rate of less than 1%.

Reference is made to WO 00/59929 (equal to US2004002448 and U.S. Pat. No. 6,608,027; Assignee: Boehringer Ingelheim (Canada) Ltd.; Published Oct. 12, 2000) which discloses peptide derivatives of the formula:

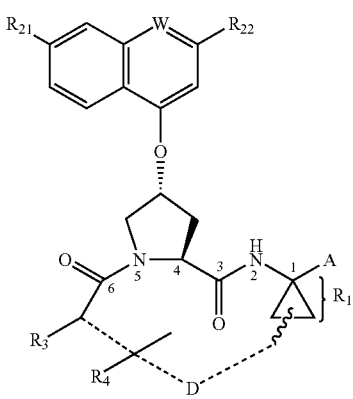

Reference is made to A. Marchetti et al, *Synlett*, S1, 1000-1002 (1999) describing the synthesis of bicylic analogs of an inhibitor of HCV NS3 protease. A compound disclosed therein has the formula:

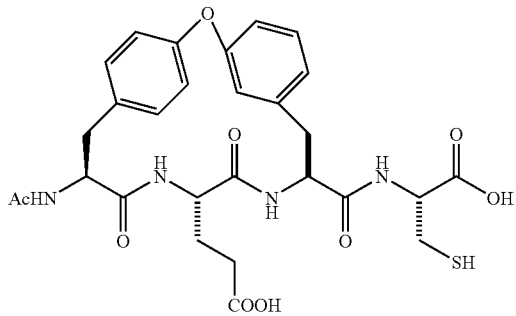

Reference is also made to W. Han et al, *Bioorganic & Medicinal Chem. Lett*, (2000) 10, 711-713, which describes the preparation of certain α-ketoamides, α-ketoesters and α-diketones containing allyl and ethyl functionalities.

Reference is also made to WO 00/09558 (Assignee: Boehringer Ingelheim Limited; Published Feb. 24, 2000) which discloses peptide derivatives of the formula:

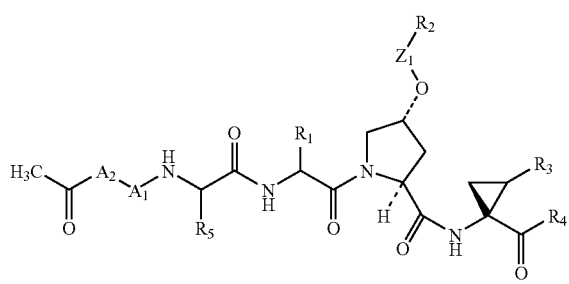

where the various elements are defined therein. An illustrative compound of that series is:

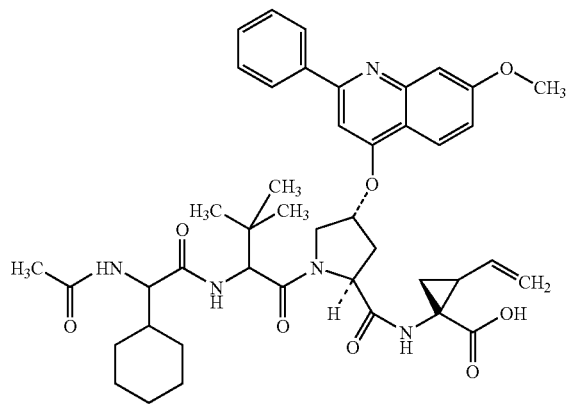

Reference is also made to WO 00/09543 (equal to US2002016442 and US 2002037998; Assignee: Boehringer Ingelheim Limited; Published Feb. 24, 2000) which discloses peptide derivatives of the formula:

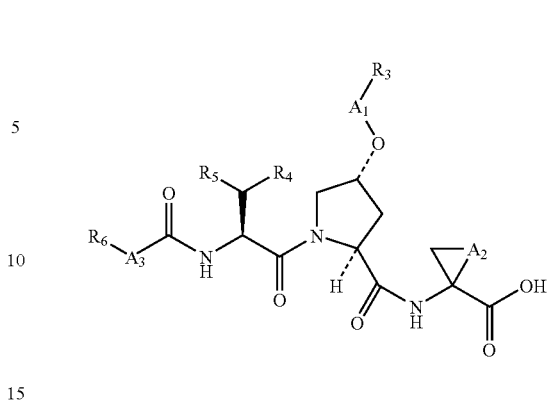

where the various elements are defined therein. An illustrative compound of that series is:

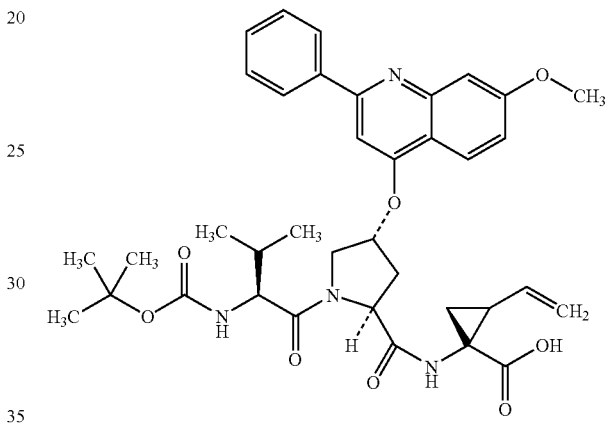

Current therapies for hepatitis C include interferon-α ($INF_\alpha$) and combination therapy with ribavirin and interferon. See, e.g., Beremguer et al. (1998) *Proc. Assoc. Am. Physicians* 110(2):98-112. These therapies suffer from a low sustained response rate and frequent side effects. See, e.g., Hoofnagle et al. (1997) *N. Engl. J. Med.* 336:347. Currently, no vaccine is available for HCV infection.

Reference is further made to WO 01/74768 (equal to US 2003236242; Assignee: Vertex Pharmaceuticals Inc) published Oct. 11, 2001, which discloses certain compounds of the following general formula (R is defined therein) as NS3-serine protease inhibitors of Hepatitis C virus:

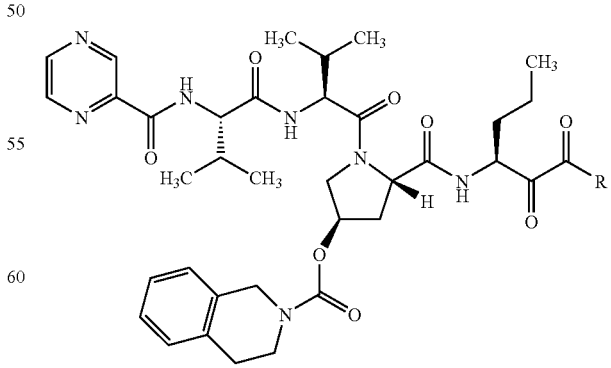

A specific compound disclosed in the afore-mentioned WO 01/74768 has the following formula:

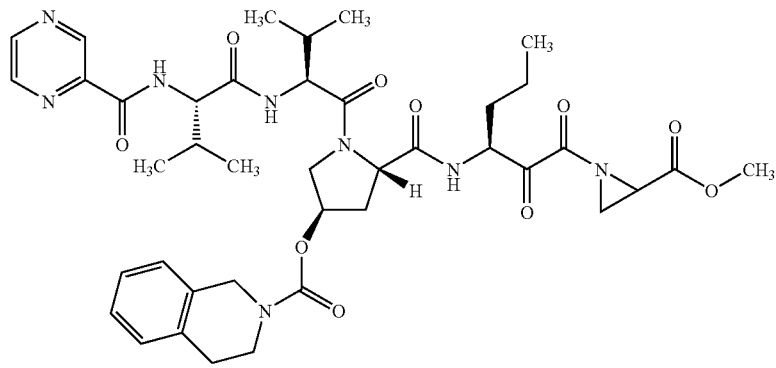

PCT Publications WO 01/77113; WO 01/081325; WO 02/08198; WO 02/08256; WO 02/08187; WO 02/08244; WO 02/48172; WO 02/08251; and pending U.S. patent application Ser. No. 10/052,386, filed Jan. 18, 2002, disclose various types of peptides and/or other compounds as NS-3 serine protease inhibitors of hepatitis C virus. The disclosures of those applications are incorporated herein by reference thereto.

There is a need for new treatments and therapies for HCV infection. There is a need for compounds useful in the treatment or prevention or amelioration of one or more symptoms of hepatitis C.

There is a need for methods of treatment or prevention or amelioration of one or more symptoms of hepatitis C.

There is a need for methods for modulating the activity of serine proteases, particularly the HCV NS3/NS4a serine protease, using the compounds provided herein.

There is a need for methods of modulating the processing of the HCV polypeptide using the compounds provided herein.

SUMMARY OF THE INVENTION

In its many embodiments, the present invention provides a novel class of inhibitors of the HCV protease, pharmaceutical compositons containing one or more of the compounds, methods of preparing pharmaceutical formulations comprising one or more such compounds, and methods of treatment or prevention of HCV or amelioration of one or more of the symptoms of hepatitis C using one or more such compounds or one or more such formulations. Also provided are methods of modulating the interaction of an HCV polypeptide with HCV protease. Among the compounds provided herein, compounds that inhibit HCV NS3/NS4a serine protease activity are preferred. The present invention discloses compounds having the general structure shown in structural Formula 1:

Formula 1

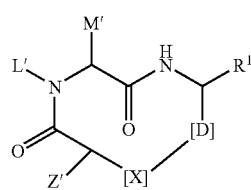

or pharmaceutically acceptable salts or solvates of said compound wherein:

(1) $R^1$ is $-C(O)R^5$ or $-B(OR)_2$;

(2) $R^5$ is H, $-OH$, $-OR^8$, $-NR^9R^{10}$, $-C(O)OR^8$, $-C(O)NR^9R^{10}$, $-CF_3$, $-C_2F_5$, $-C_3F_7$, $-CF_2R^6$, $-R^6$, $-C(O)R^7$ or $NR^7SO_2R^8$;

(3) $R^7$ is H, $-OH$, $-OR^8$, or $-CHR^9R^{10}$;

(4) $R^6$, $R^8$, $R^9$ and $R^{10}$ can be the same or different, each being independently selected from the group consisting of H: alkyl, alkenyl, aryl, heteroalkyl, heteroaryl, cycloalkyl, arylalkyl, heteroarylalkyl, $R^{14}$, $-CH(R^{1'})CH(R^{1'})C(O)OR^{11}$, $-[CH(R^{1'})]_pC(O)OR^{11}$, $-[CH(R^{1'})]_pC(O)NR^{12}R^{13}$, $-[CH(R^{1'})]_pS(O_2)R^{11}$, $-[CH(R^{1'})]_pC(O)R^{11}$, $-[CH(R^{1'})]_pS(O_2)NR^{12}R^{13}$, $-CH(R^{1'})C(O)N(H)CH(R^{2'})(R')$, $-CH(R^{1'})CH(R^{1'})C(O)NR^{12}R^{13}$, $-CH(R^{1'})CH(R^{1'})S(O_2)R^{11}$, $-CH(R^{1'})CH(R^{1'})S(O_2)NR^{12}R^{13}$, $-CH(R^{1'})CH(R^{1'})C(O)R^{11}$, $-[CH(R^{1'})]_pCH(OH)R^{11}$, $-CH(R^{1'})C(O)N(H)CH(R^{2'})C(O)OR^{11}$, $-C(O)N(H)CH(R^{2'})C(O)OR^{11}$, $-C(O)N(H)CH(R^{2'})C(O)R^{11}$, $-CH(R^{1'})C(O)N(H)CH(R^{2'})C(O)NR^{12}R^{13}$, $-CH(R^{1'})C(O)N(H)CH(R^{2'})R'$, $-CH(R^{1'})C(O)N(H)CH(R^{2'})C(O)N(H)CH(R^{3'})C(O)OR^{11}$, $-CH(R^{1'})C(O)N(H)CH(R^{2'})C(O)CH(R^{3'})NR^{12}R^{13}$, $-CH(R^{1'})C(O)N(H)CH(R^{2'})C(O)N(H)CH(R^{3'})C(O)NR^{12}R^{13}$, $-CH(R^{1'})C(O)N(H)CH(R^{2'})C(O)N(H)CH(R^{3'})C(O)N(H)CH(R^{4'})C(O)OR^{11}$, $-CH(R^{1'})C(O)N(H)CH(R^{2'})C(O)N(H)CH(R^{3'})C(O)N(H)CH(R^{4'})C(O)NR^{12}R^{13}$, $-CH(R^{1'})C(O)N(H)CH(R^{2'})C(O)N(H)CH(R^{3'})C(O)N(H)CH(R^{4'})C(O)N(H)CH(R^{5'})C(O)OR^{11}$, and $-CH(R^{1'})C(O)N(H)CH(R^{2'})C(O)N(H)CH(R^{3'})C(O)N(H)CH(R^{4'})C(O)N(H)CH(R^{5'})C(O)NR^{12}R^{13}$;

wherein $R^{1'}$, $R^{2'}$, $R^{3'}$, $R^{4'}$, $R^{5'}$, $R^{11}$, $R^{12}$ and $R^{13}$ can be the same or different, each being independently selected from the group consisting of: H, halogen, alkyl, aryl, heteroalkyl, heteroaryl, cycloalkyl, alkoxy, aryloxy, alkenyl, alkynyl, alkylaryl, alkyl-heteroaryl, heterocycloalkyl, aryl-alkyl and heteroaralkyl;

or $R^{12}$ and $R^{13}$ are linked together such that the combination is cycloalkyl, heterocycloalkyl, aryl or heteroaryl;

$R^{14}$ is present or not and if present is selected from the group consisting of: H, alkyl, aryl, heteroalkyl, heteroaryl, cycloalkyl, alkyl-aryl, allyl, alkyl-heteroaryl, alkoxy, arylalkyl, alkenyl, alkynyl and heteroaralkyl;

(5) R and R' are present or not and if present can be the same or different, each being independently selected from the group consisting of: H, OH, $C_1$-$C_{10}$ alkyl, $C_2$-$C_{10}$ alkenyl, $C_3$-$C_8$ cycloalkyl, $C_3$-$C_8$ heterocycloalkyl, alkoxy, aryloxy, alkylthio, arylthio, alkylamino, arylamino, amino, amido, arylthioamino, arylcarbonylamino, arylaminocarboxy, alkylaminocarboxy, heteroalkyl, alkenyl, alkynyl, (aryl)alkyl, heteroarylalkyl, ester, carboxylic acid, carbamate, urea, ketone, aldehyde, cyano, nitro, halogen, (cycloalkyl)alkyl, aryl, heteroaryl, (alkyl)aryl, alkylheteroaryl, alkyl-heterocyclyl and (heterocycloalkyl)alkyl, wherein said cycloalkyl is made of three to eight carbon atoms, and zero to six oxygen, nitrogen, sulfur, or phosphorus atoms, and said alkyl is of one to six carbon atoms;

(6) L' is H, OH, alkyl, heteroalkyl, aryl, heteroaryl, cycloalkyl, or heterocyclyl;

(7) M' is H, alkyl, heteroalkyl, aryl, heteroaryl, cycloalkyl, arylalkyl, heterocyclyl or an amino acid side chain;

or L' and M' are linked together to form a ring structure such that the portion of structural Formula 1 represented by

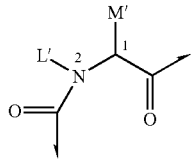

(the numbers 1 and 2 having been added to show the location of a certain carbon atom and a certain nitrogen atom respectively)

is represented by structural Formula 2:

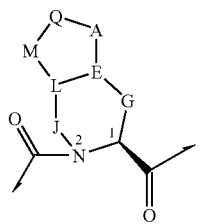

Formula 2 wherein in Formula 2:

E is present or absent and if present is C, CH, N or C(R);

J is present or absent, and when J is present, J is $(CH_2)_p$, $(CHR—CHR')_p$, $(CHR)_p$, $(CRR')_p$, $S(O_2)$, $N(H)$, $N(R)$ or $O$; when J is absent and G is present, L is directly linked to the nitrogen atom marked position 2;

p is a number from 0 to 6;

L is present or absent, and when L is present, L is C(H) or C(R); when L is absent, M is present or absent; if M is present with L being absent, then M is directly and independently linked to E, and J is directly and independently linked to E;

G is present or absent, and when G is present, G is $(CH_2)_p$, $(CHR)_p$, $(CHR—CHR')_p$ or $(CRR')_p$; when G is absent, J is present and E is directly connected to the carbon atom marked position 1;

Q is present or absent, and when Q is present, Q is NR, PR, (CR=CR), $(CH_2)_p$, $(CHR)_p$, $(CRR')_p$, $(CHR—CHR')_p$, O, NR, S, SO, or $SO_2$; when Q is absent, M is (i) either directly linked to A or (ii) an independent substituent on L, said independent substituent being selected from —OR, —CH(R)(R'), $S(O)_{0-2}R$ or —NRR' or (iii) absent; when both Q and M are absent, A is either directly linked to L, or A is an independent substituent on E, said independent substituent being selected from —OR, —CH(R)(R'), $S(O)_{0-2}R$ or —NRR' or A is absent;

A is present or absent and if present A is O, O(R), $(CH_2)_p$, $(CHR)_p$, $(CHR—CHR')_p$, $(CRR')_p$, $N(R)$, NRR', S, $S(O_2)$, —OR, CH(R)(R') or NRR'; or A is linked to M to form an cycloalkyl, aliphatic or heterocyclic bridge;

M is present or absent, and when M is present, M is halogen, O, OR, N(R), S, $S(O_2)$, $(CH_2)_p$, $(CHR)_p$ $(CHR—CHR')_p$, or $(CRR')_p$; or M is linked to A to form a cycloalkyl, aliphatic or heterocycloalkyl bridge;

(8) Z' is represented by either (i), (ii), (iii), (iv) or (v) shown below:

(i)

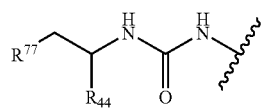

Formula A wherein:

$R^{44}$ is selected from the group consisting of:

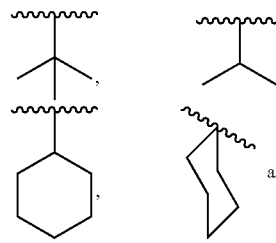 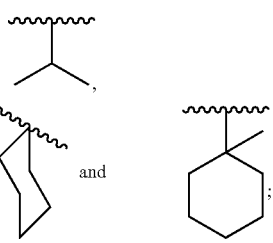

and $R^{77}$ is selected from the group consisting of:

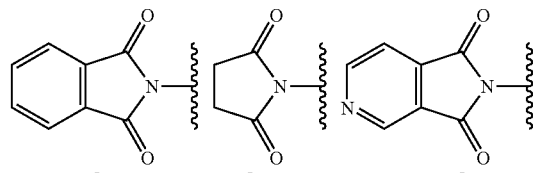

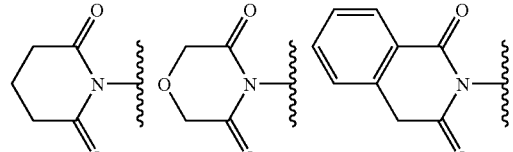

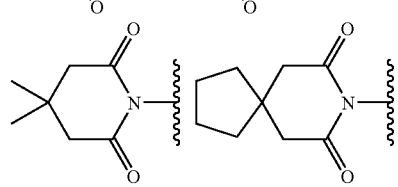

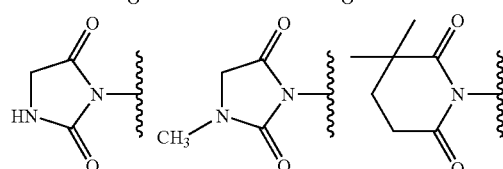

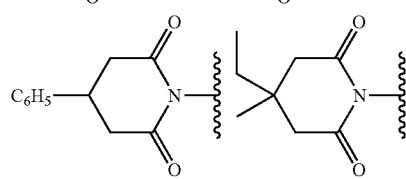

-continued
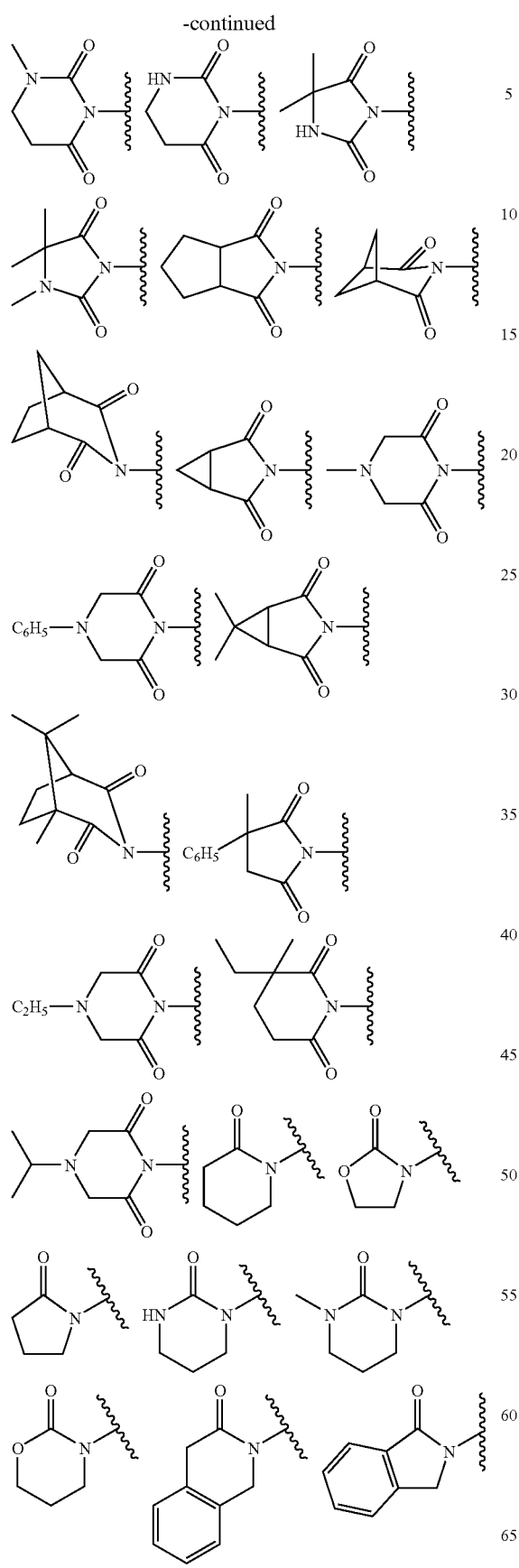
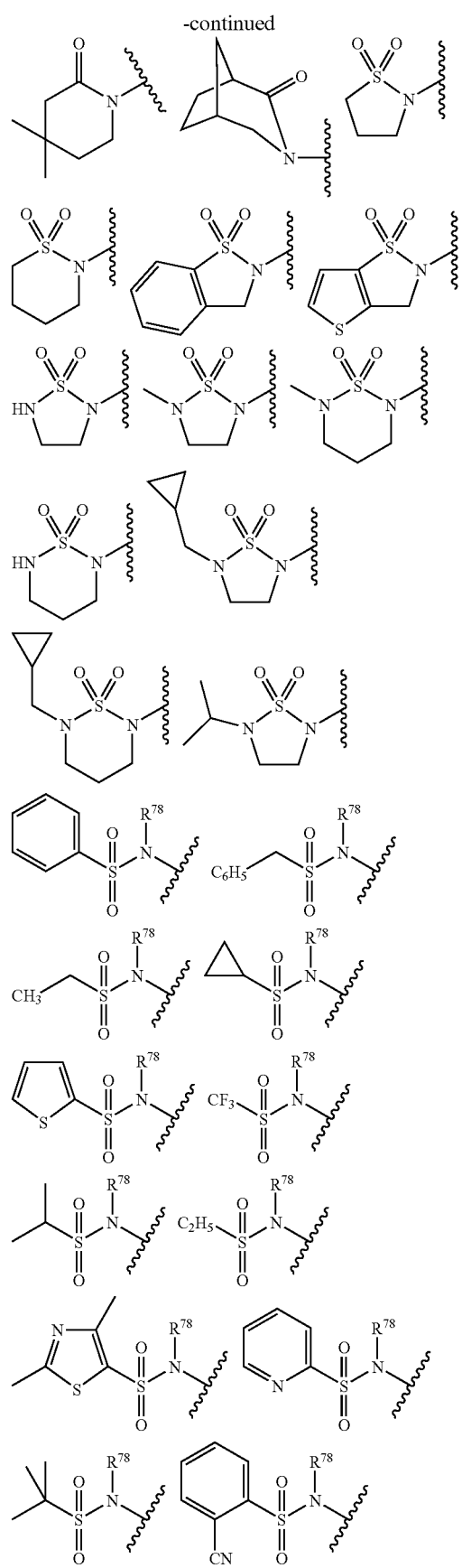

-continued
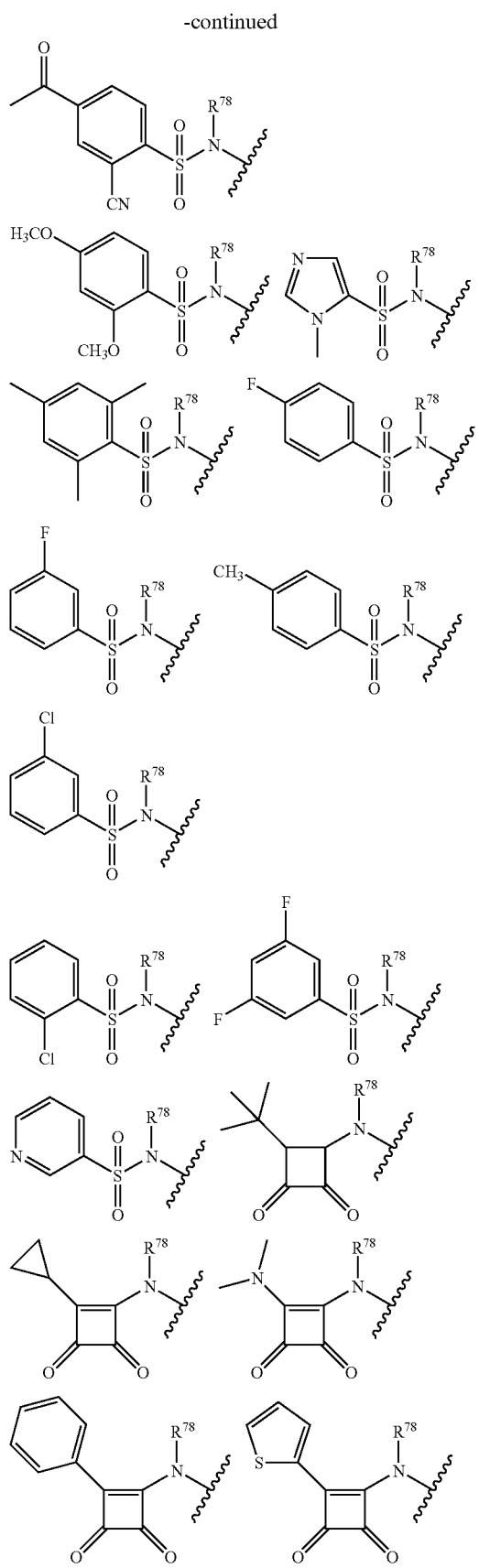
-continued
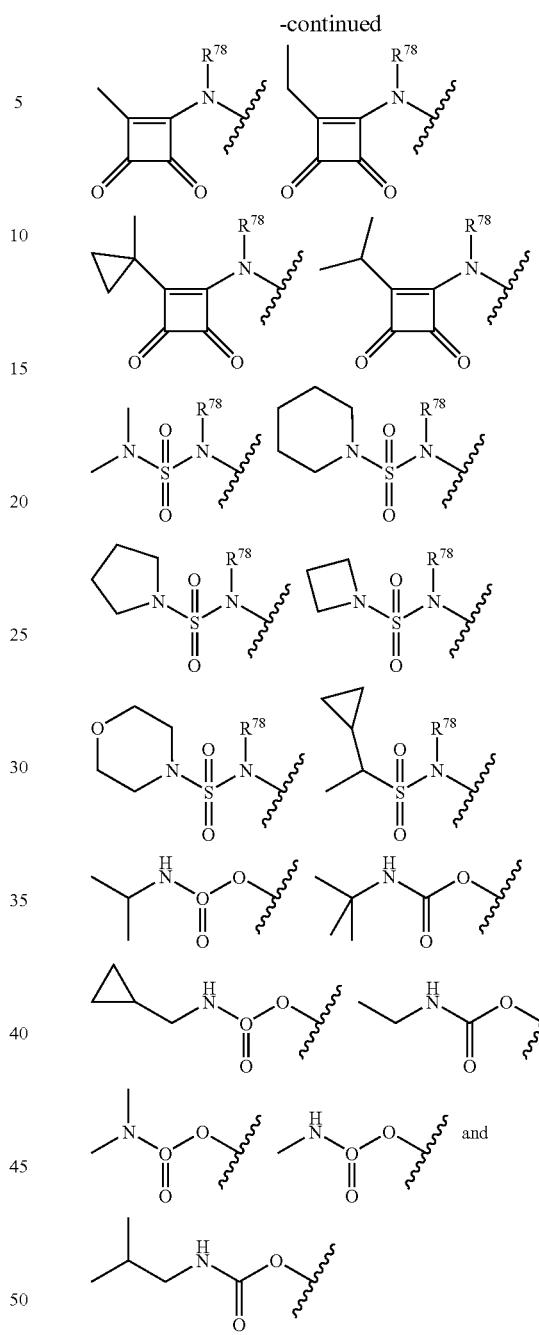
where $R^{78}$ is selected from methyl, ethyl, isopropyl, tert-butyl and phenyl;
(ii)
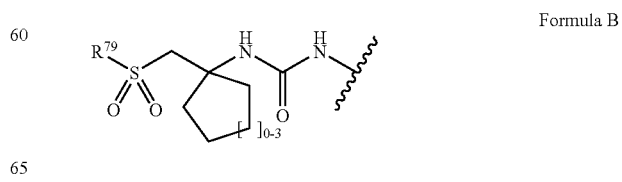
Formula B
where $R^{79}$ is selected from the group consisting of:

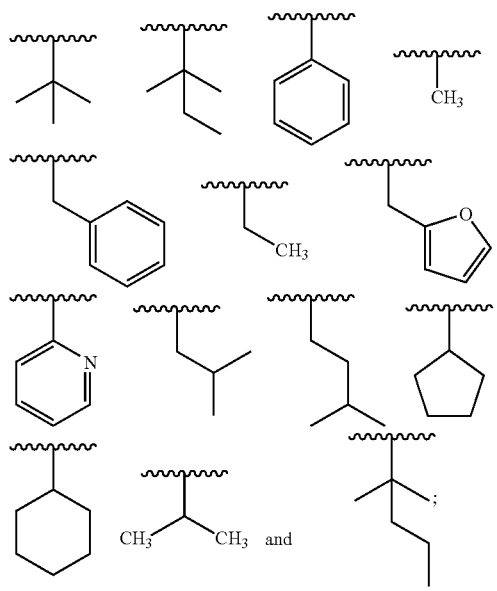
wherein the sulfone ring is optionally substituted with alkyl and cycloalkyl;
(iv) the moiety:
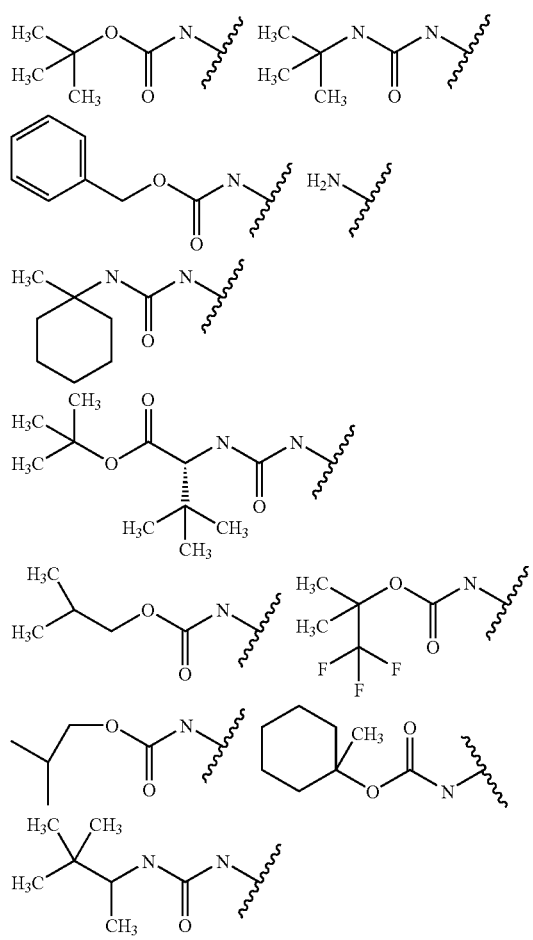
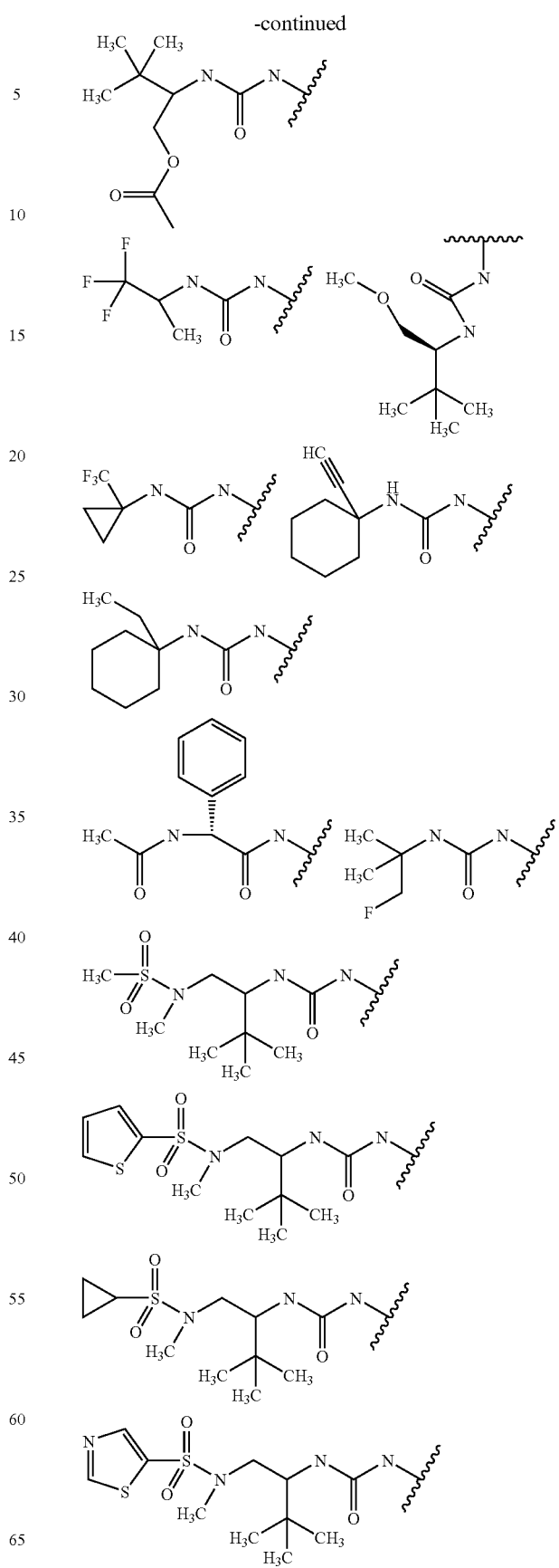

-continued
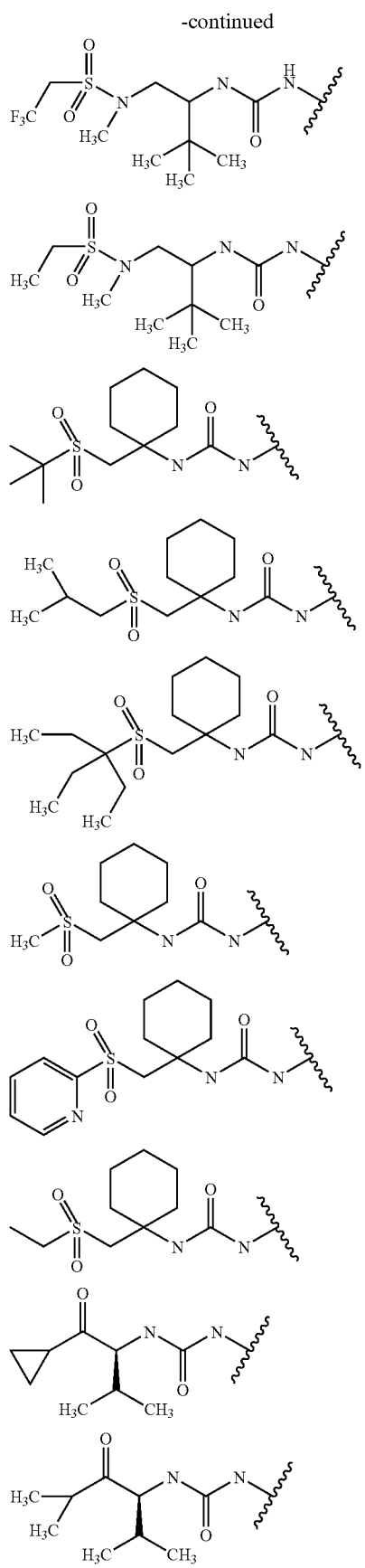
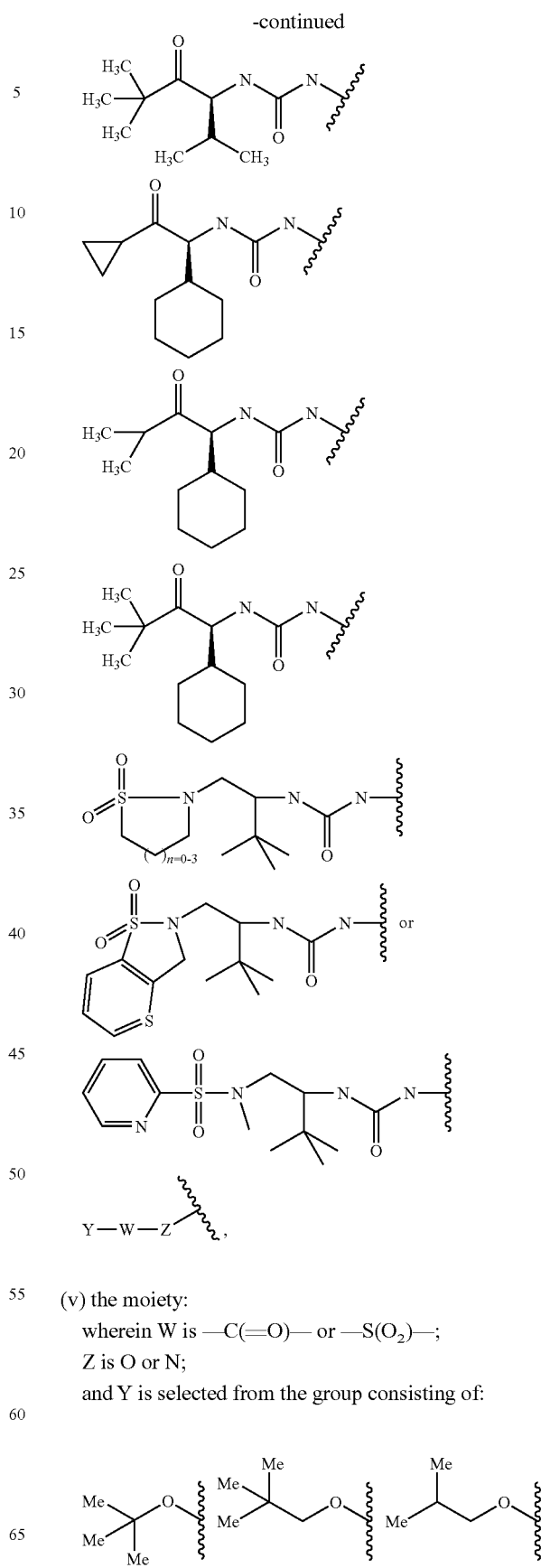
(v) the moiety:
wherein W is —C(=O)— or —S(O₂)—;
Z is O or N;
and Y is selected from the group consisting of:

-continued
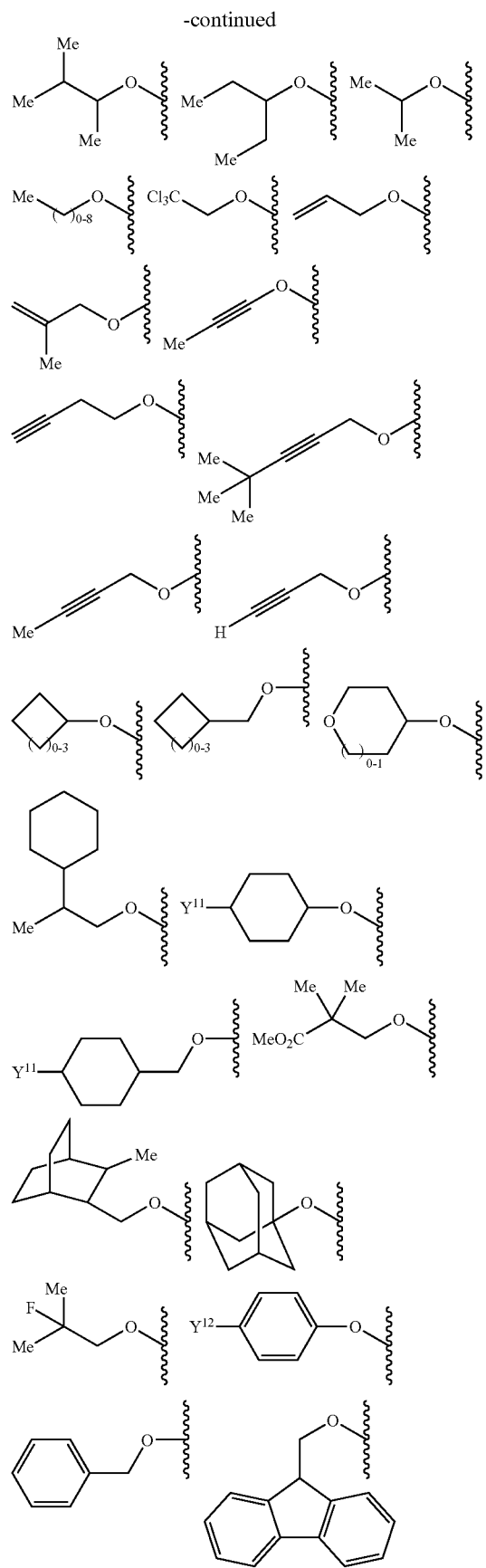
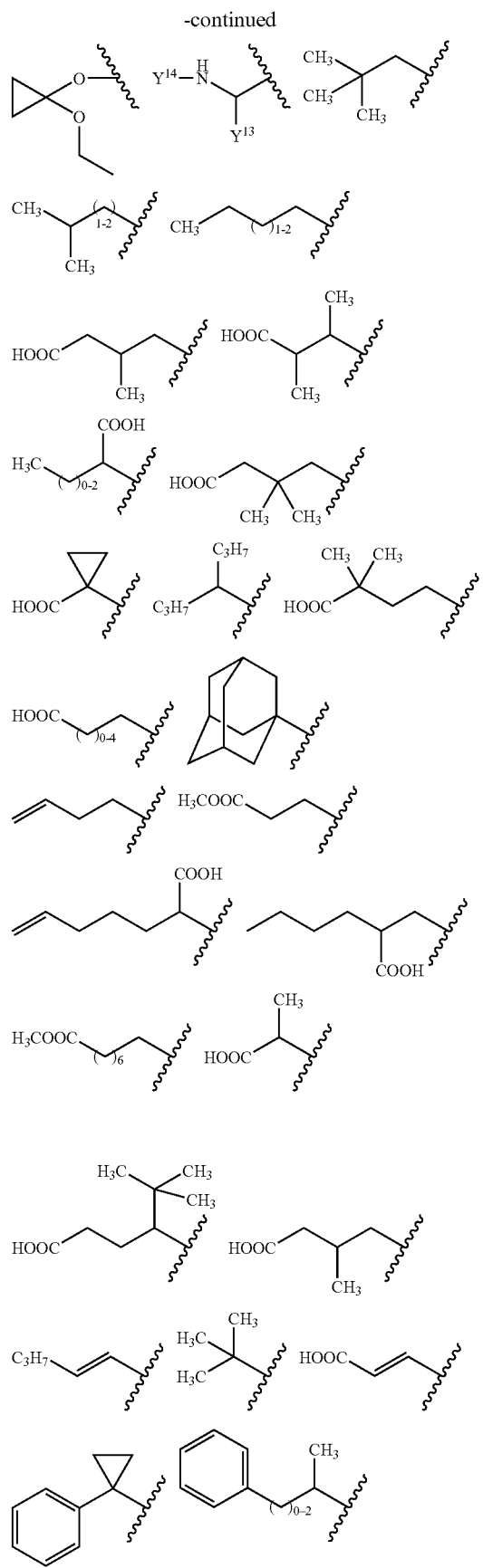

-continued
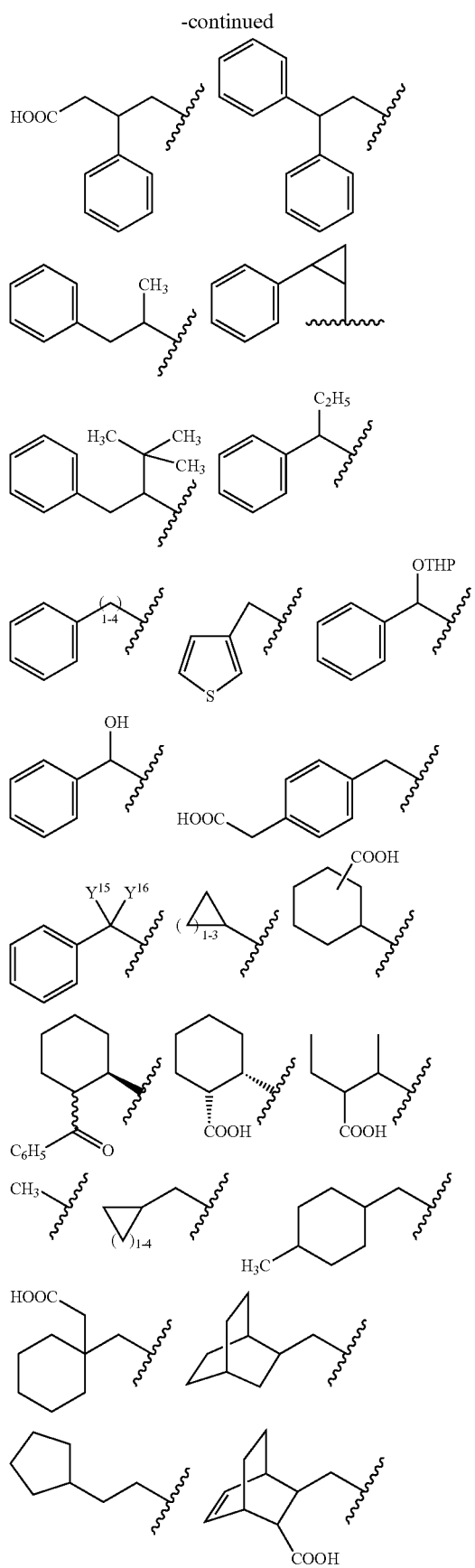
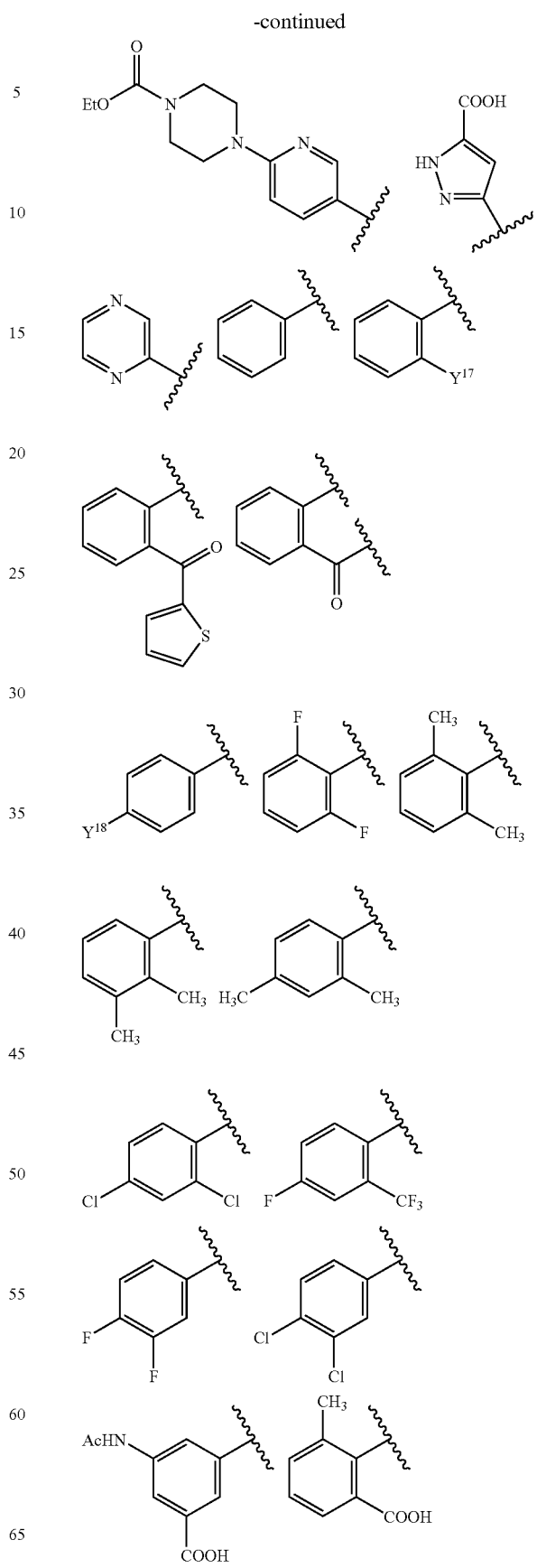

-continued
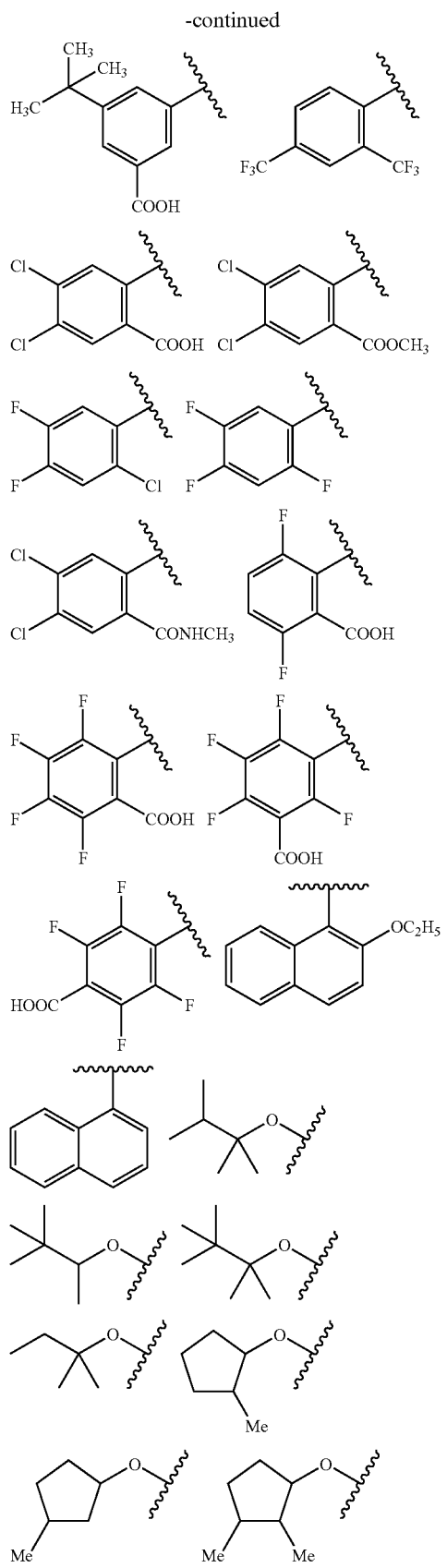
-continued
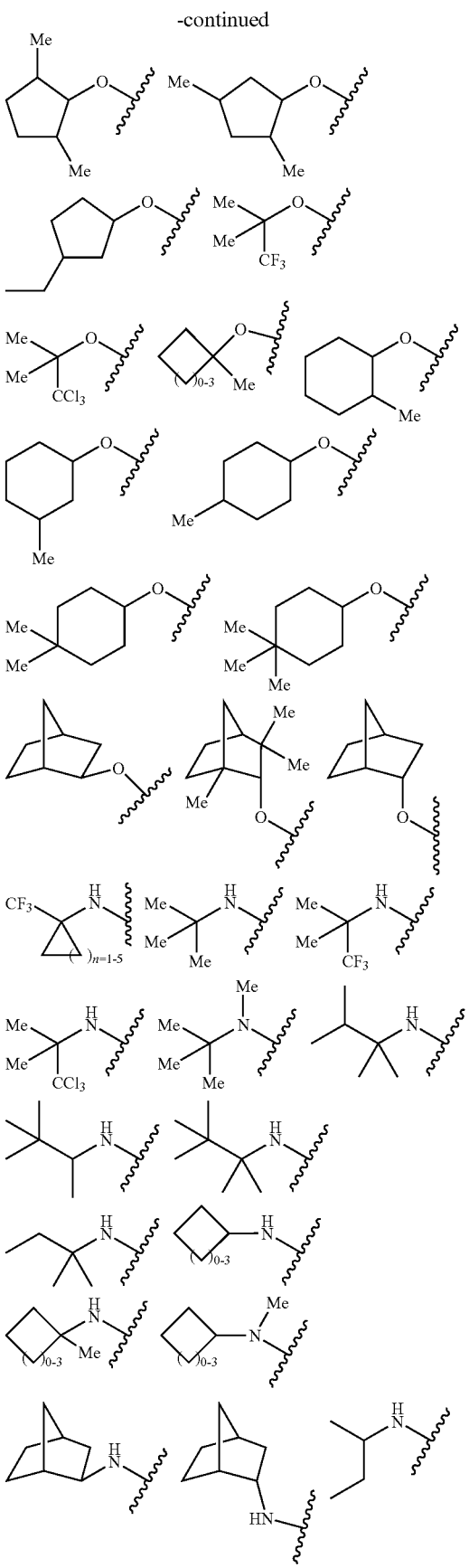

-continued

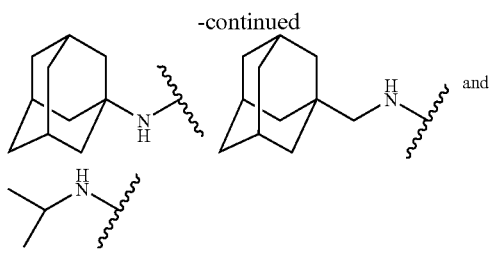

and wherein:

Y$^{11}$ is selected from the group consisting of: H, —C(O)OH, —C(O)OEt, —OMe, —Ph, —OPh, —NHMe, —NHAc, —NHPh, —CH(Me)$_2$, 1-triazolyl, 1-imidazolyl and —NHCH$_2$COOH;

Y$^{12}$ is selected from the group consisting of: H, —C(O)OH, —C(O)OMe, —OMe, F, Cl and Br;

Y$^{13}$ is selected from the group consisting of the following moieties:

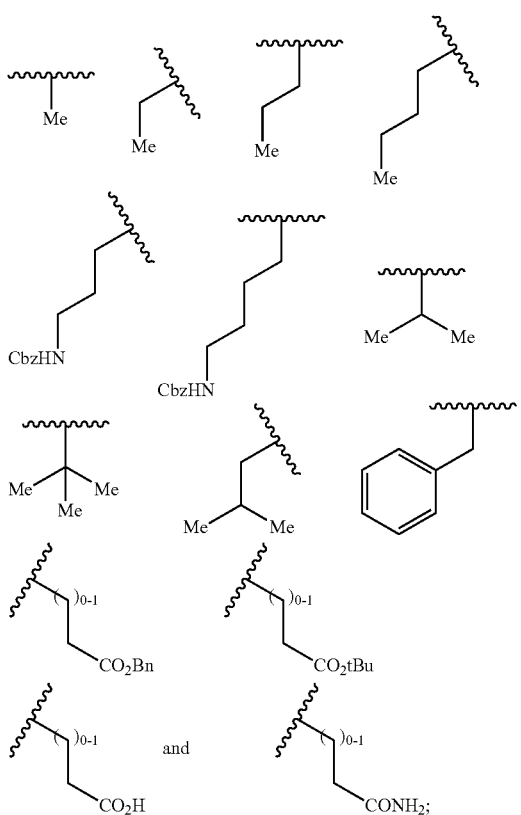

Y$^{14}$ is MeS(O$_2$)—, -Ac, -Boc, -iBoc, -Cbz, or -Alloc;

Y$^{15}$ and Y$^{16}$ can be the same or different and are independently selected from the group consisting of: alkyl, aryl, heteroalkyl, and heteroaryl;

Y$^{17}$ is —CF$_3$, —NO$_2$, —C(O)NH$_2$, —OH, —C(O)OCH$_3$, —OCH$_3$, —OC$_6$H$_5$, —C$_6$H$_5$, —C(O)C$_6$H$_5$, —NH$_2$, or —C(O)OH; and Y$^{18}$ is —C(O)OCH$_3$, —NO$_2$, —N(CH$_3$)$_2$, F, —OCH$_3$, —C(H$_2$)C(O)OH, —C(O)OH, —S(O$_2$)NH$_2$, or —N(H)C(O)CH$_3$;

(9) X is represented by structural Formula 4:

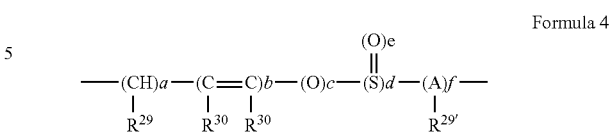

Formula 4 wherein in Formula 4, a is 2, 3, 4, 5, 6, 7, 8 or 9;

b, c, d, e and f can be the same or different, each being independently 0, 1, 2, 3, 4 or 5;

A is C, N, S or O;

R$^{29}$ and R$^{29'}$ are independently present or absent and if present can be the same or different, each being independently one or two substituents independently selected from the group consisting of: H, halo, alkyl, aryl, cycloalkyl, cycloalkylamino, cycloalkylaminocarbonyl, cyano, hydroxy, alkoxy, alkylthio, amino, —NH(alkyl), —NH(cycloalkyl), —N(alkyl)$_2$, carboxyl, —C(O)O-alkyl, heteroaryl, aralkyl, alkylaryl, aralkenyl, heteroaralkyl, alkylheteroaryl, heteroaralkenyl, hydroxyalkyl, aryloxy, aralkoxy, acyl, aroyl, nitro, aryloxycarbonyl, aralkoxycarbonyl, alkylsulfonyl, arylsulfonyl, heteroarylsulfonyl, alkylsulfinyl, arylsulfinyl, heteroarylsulfinyl, arylthio, heteroarylthio, aralkylthio, heteroaralkylthio, cycloalkenyl, heterocyclyl, heterocyclenyl, Y$_1$Y$_2$N-alkyl-, Y$_1$Y$_2$NC(O)— and Y$_1$Y$_2$NSO$_2$—, wherein Y$_1$ and Y$_2$ can be the same or different and are independently selected from the group consisting of hydrogen, alkyl, aryl, and aralkyl; or R$^{29}$ and R$^{29'}$ are linked together such that the combination is an aliphatic or heteroaliphatic chain of 0 to 6 carbons;

R$^{30}$ is present or absent and if present is one or two substituents independently selected from the group consisting of: H, alkyl, aryl, heteroaryl and cycloalkyl;

(10) D in Formula 1 is represented by structural Formula 5:

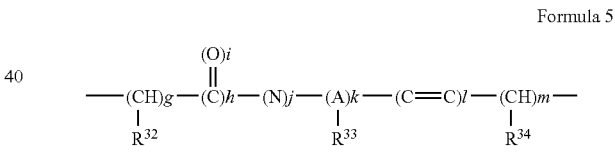

Formula 5 wherein in Formula 5, R$^{32}$, R$^{33}$ and R$^{34}$ are present or absent and if present are independently one or two substituents independently selected from the group consisting of: H, halo, alkyl, aryl, cycloalkyl, cycloalkylamino, spiroalkyl, cycloalkylaminocarbonyl, cyano, hydroxy, alkoxy, alkylthio, amino, —NH(alkyl), —NH(cycloalkyl), —N(alkyl)$_2$, carboxyl, —C(O)O-alkyl, heteroaryl, aralkyl, alkylaryl, aralkenyl, heteroaralkyl, alkylheteroaryl, heteroaralkenyl, hydroxyalkyl, aryloxy, aralkoxy, acyl, aroyl, nitro, aryloxycarbonyl, aralkoxycarbonyl, alkylsulfonyl, arylsulfonyl, heteroarylsulfonyl, alkylsulfinyl, arylsulfinyl, heteroarylsulfinyl, arylthio, heteroarylthio, aralkylthio, heteroaralkylthio, cycloalkenyl, heterocyclyl, heterocyclenyl, Y$_1$Y$_2$N-alkyl-, Y$_1$Y$_2$NC(O)— and Y$_1$Y$_2$NSO$_2$—, wherein Y$_1$ and Y$_2$ can be the same or different and are independently selected from the group consisting of hydrogen, alkyl, aryl, and aralkyl;

or

R$^{32}$ and R$^{34}$ are linked together such that the combination forms a portion of a cycloalkyl group;

g is 1, 2, 3, 4, 5, 6, 7, 8 or 9;

h, i, j, k, l and m can be the same or different, each being independently 0, 1, 2, 3, 4 or 5; and A is C, N, S or O,

(11) provided that in Formula 1 when structural Formula 2:

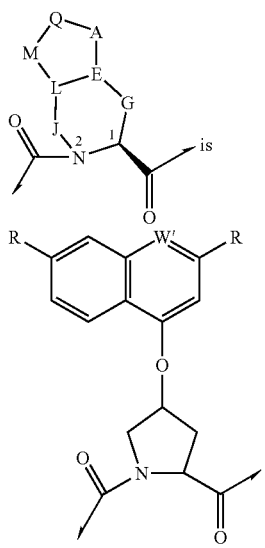

Formula 2 and

W' is CH or N, both the following conditional exclusions (i) and (ii) apply:

conditional exclusion (i): Z' is not —NH—$R^{36}$, wherein $R^{36}$ is H, $C_6$ aryl, $C_{10}$ aryl, heteroaryl, —C(O)—$R^{37}$, —C(O)—$OR^{37}$ or —C(O)—$NHR^{37}$, wherein $R^{37}$ is $C_{1-6}$ alkyl or $C_{3-6}$ cycloalkyl;

and conditional exclusion (ii): $R^1$ is not —C(O)OH, a pharmaceutically acceptable salt of —C(O)OH, an ester of —C(O)OH or —C(O)$NHR^{38}$ wherein $R^{38}$ is selected from the group consisting of $C_{1-8}$ alkyl, $C_{3-6}$ cycloalkyl, $C_6$ aryl, $C_{10}$ aryl, or $C_{7-16}$ aralkyl.

A further feature of the invention is pharmaceutical compositions containing as active ingredient at least one compound of Formula 1 (or its salts, esters, solvate or isomers) together with a pharmaceutically acceptable carrier or excipient.

The invention also provides methods for preparing compounds of Formula 1 as well as methods for treating diseases such as, for example, HCV, AIDS (Acquired Immune Deficiency Syndrome), and related disorders. The methods for such treatment comprise administering to a patient suffering from one or more of the above diseases or one or more related diseases a therapeutically effective amount of at least one compound of Formula 1 or a pharmaceutical composition comprising at least one compound of Formula 1.

Also disclosed is the use of at least one compound of Formula 1 for the manufacture of a medicament for treating HCV, AIDS, and related disorders.

Further disclosed is a method of treatment of a hepatitis C virus associated disorder, comprising administering an effective amount of one or more of the inventive compounds.

In still yet further embodiments there is provided methods of modulating the activity of hepatitis C virus (HCV) protease, comprising contacting HCV protease with one or more inventive compounds as well as methods of treating or preventing HCV, or ameliorating one or more symptoms of hepatitis C, comprising administering an effective amount of one or more of the inventive compounds. Such modulation, treatment, prevention or amelioration can also be done with the inventive pharmaceutical compositions or formulations. Without being limited to theory, it is believed that the HCV protease may be the NS3 or NS4a protease. The inventive compounds can inhibit such protease. They can also modulate the processing of hepatitis C virus (HCV) polypeptide.

DESCRIPTION OF THE INVENTION

As used above, and throughout this disclosure, the following terms, unless otherwise indicated, shall be understood to have the following meanings:

"Patient" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. The alkyl group may be optionally substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, carboxy and —C(O)O-alkyl. Non-limiting examples of suitable alkyl groups include methyl, ethyl, n-propyl, isopropyl and t-butyl.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. The term "substituted alkynyl" means that the alkynyl group may be substituted by one or more substituents which may be the same or different, each substituent being independently selected from the group consisting of alkyl, aryl and cycloalkyl.

"Aliphatic" means and includes straight or branched chains of paraffinic, olefinic or acetylenic carbon atoms. The aliphatic group can be optionally substituted by one or more substituents which may be the same or different, each substituent being independently selected from the group consisting of H, halo, halogen, alkyl, aryl, cycloalkyl, cycloalkylamino, alkenyl, heterocyclic, alkynyl, cycloalkylaminocarbonyl, hydroxyl, thio, cyano, hydroxy, alkoxy, alkylthio, amino, —NH(alkyl), —NH(cycloalkyl), —N(alkyl)$_2$, carboxyl, —C(O)O-alkyl, heteroaryl, aralkyl, alkylaryl, aralkenyl, heteroaralkyl, alkylheteroaryl, heteroaralkenyl, heteroalkyl, carbonyl, hydroxyalkyl, aryloxy, aralkoxy, acyl, aroyl, nitro, amino, amido, ester, carboxylic acid aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkenyl, heterocyclyl, heterocyclenyl, carbamate, urea, ketone, aldehyde, cyano, sulfonamide, sulfoxide, sulfone, sulfonyl urea, sulfonyl, hydrazide, hydroxamate, S(alkyl)$Y_1Y_2$N-alkyl-, $Y_1Y_2$N-alkyl-, $Y_1Y_2$NC(O)— and $Y_1Y_2$NSO$_2$—, wherein $Y_1$ and $Y_2$ can be the same or different and are independently selected from the group consisting of hydrogen, alkyl, aryl, and aralkyl.

"Heteroaliphatic" means an otherwise aliphatic group that contains at least one heteroatom (such as oxygen, nitrogen or sulfur). The term heteroaliphatic includes substituted heteroaliphatic.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroalkyl" means an alkyl as defined above, wherein one or more hydrogen atoms are substituted by a heteroatom selected from N, S, or O.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl- group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl- group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like, as well as partially saturated species such as, for example, indanyl, tetrahydronaphthyl and the like.

"Halogen" means fluorine, chlorine, bromine, or iodine. Preferred are fluorine, chlorine and bromine.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —C(=N—CN)—NH$_2$, —C(=NH)—NH$_2$, —C(=NH)—NH(alkyl), Y$_1$Y$_2$N—, Y$_1$Y$_2$N-alkyl-, Y$_1$Y$_2$NC(O)—, Y$_1$Y$_2$NSO$_2$— and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, —C(CH$_3$)$_2$— and the like which form moieties such as, for example:

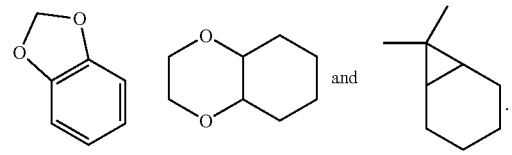

"Heterocyclyl" or "heterocycloalkyl" or "heterocyclic" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

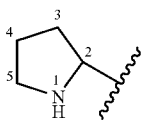

there is no —OH attached directly to carbons marked 2 and 5.

It should also be noted that tautomeric forms such as, for example, the moieties:

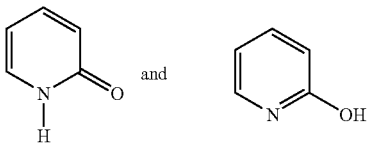

are considered equivalent in certain embodiments of this invention.

"Alkynylalkyl" means an alkynyl-alkyl- group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl- group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl- group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S($O_2$)— group. Preferred groups are those in which the alkyl group is lower alkyl. The bond to the parent moiety is through the sulfonyl.

"Arylsulfonyl" means an aryl-S($O_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "isolated" or "in isolated form" for a compound refers to the physical state of said compound after being isolated from a synthetic process or natural source or combination thereof. The term "purified" or "in purified form" for a compound refers to the physical state of said compound after being obtained from a purification process or processes described herein or well known to the skilled artisan, in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent or in Formula I, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of Formula I or a salt and/or solvate thereof. A discussion of prodrugs is provided in T. Higuchi and V. Stella, *Pro-drugs as Novel Delivery Systems* (1987) 14 of the *A.C.S. Symposium Series*, and in *Bioreversible Carriers in Drug Design*, (1987) Edward B. Roche, ed., American Pharmaceutical Association and Pergamon Press, both of which are incorporated herein by reference thereto.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

"Effective amount" or "therapeutically effective amount" is meant to describe an amount of compound or a composition of the present invention effective in inhibiting the desired diseases and thus producing the desired therapeutic, ameliorative, inhibitory or preventative effect.

The compounds of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

One or more compounds of the invention may also exist as, or optionally converted to, a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I.R. spectroscopy, show the presence of the solvent (or water) in the crystals as a solvate (or hydrate).

Compounds of Formula I, and salts, solvates, esters and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" "prodrug" and the like, is intended to equally apply to the salt, solvate and prodrug of enantiomers, stereoisomers, rotamers, tautomers, positional isomers, racemates or prodrugs of the inventive compounds.

Polymorphic forms of the compounds of Formula I and of the salts, solvates and prodrugs of the compounds of Formula I, are intended to be included in the present invention.

In general, the arrows →and ←on structural Formulas in this application refer to the respective points of connection of the concerned Formula to the points shown in the structure of its parent Formula.

In one embodiment, the present invention discloses compounds of Formula 1 as inhibitors of HCV protease, especially the HCV NS3/NS4a serine protease, or a pharmaceutically acceptable derivative thereof, where the various definitions are given above.

In another embodiment, R¹ is ketoamide, acid, ketoacid, ketoester, ketoaldehyde, diketone, boronic acid or trifluoroketone.

In another embodiment, the present invention discloses compounds of Formula 1 wherein the portion of structural Formula 1 represented by structural Formula 2:

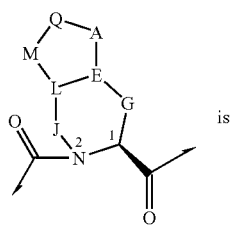

Formula 2 is

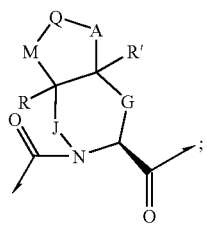

where the arrows →and ←refer to points of connection of Formula 2 to the points shown in Formula 1, and G and J immediately may or may not be present and if present can be the same or different and are independently selected from the group consisting of $(CH_2)_p$, $(CHR)_p$, $(CHR—CHR')_p$, and $(CRR')_p$;

A and M immediately may or may not be present and if present can be the same or different and are independently selected from the group consisting of O, S, $S(O_2)$, N(R), $(CH_2)_p$, $(CHR)_p$, $(CHR—CHR')_p$, and $(CRR')_p$; or A and M are linked together to form an cycloalkyl or heterocyclic bridge; and Q may or may not be present and if present is $(CH_2)_p$, N(R), O, S, $S(O_2)$, $(CHR)_p$, or $(CRR')_p$.

When Q is absent, and either M or A is absent, the remaining (present) A or M can optionally form a cycloalkyl or heterocyclyl structure with the carbon C(R) or C(R') in Formula 1. Some representative examples are shown in some of the structures that follow below.

In an embodiment of the present invention, the portion represented by structural Formula 2 is selected from the following structures:

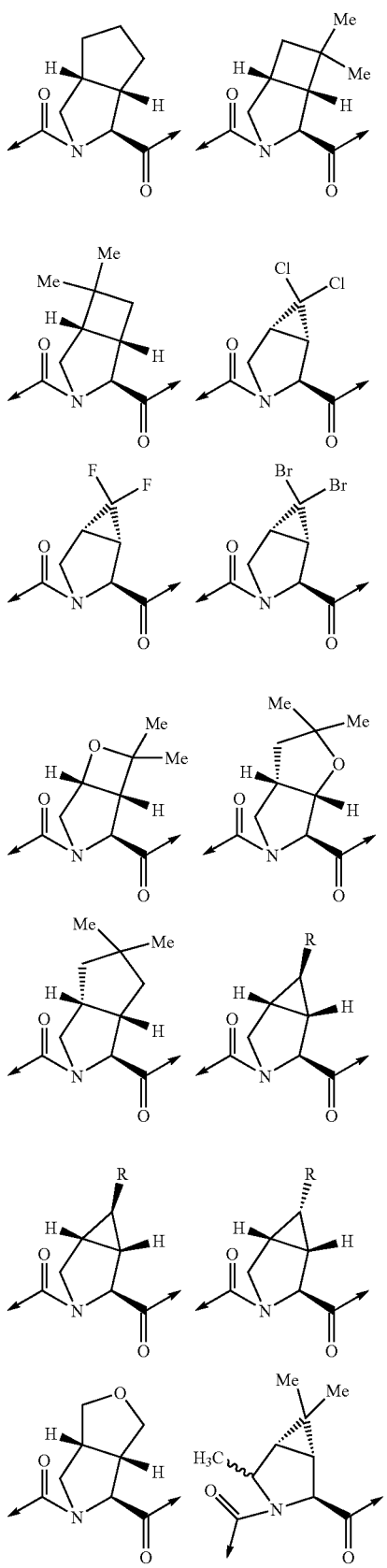

-continued
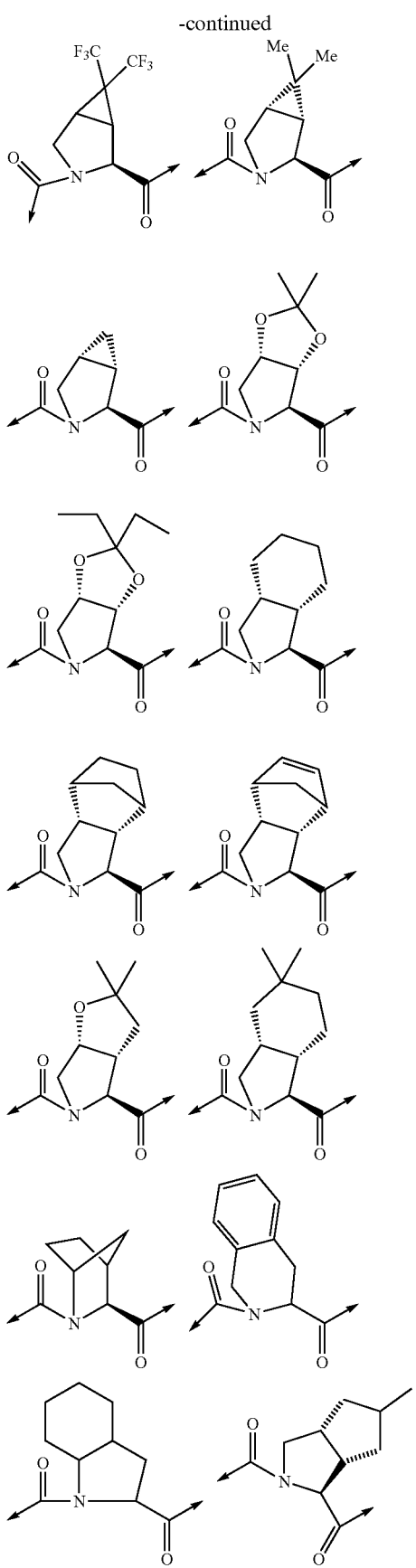
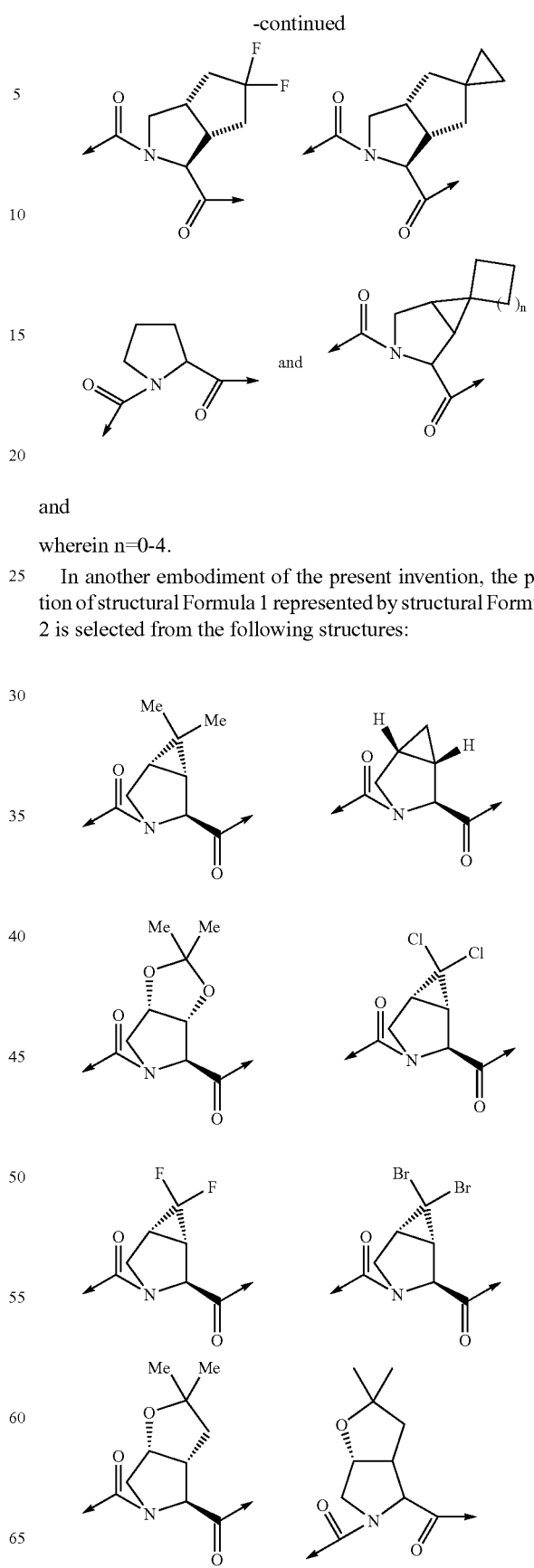
and
wherein n=0-4.
In another embodiment of the present invention, the portion of structural Formula 1 represented by structural Formula 2 is selected from the following structures:

-continued

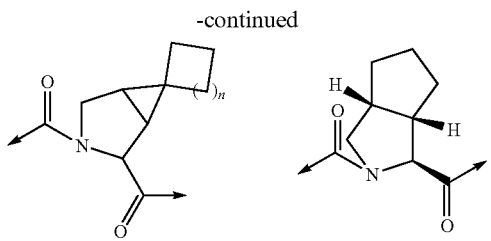

In another embodiment of the present invention, the portion of structural Formula 1 represented by structural Formula 2 is selected from the following structures:

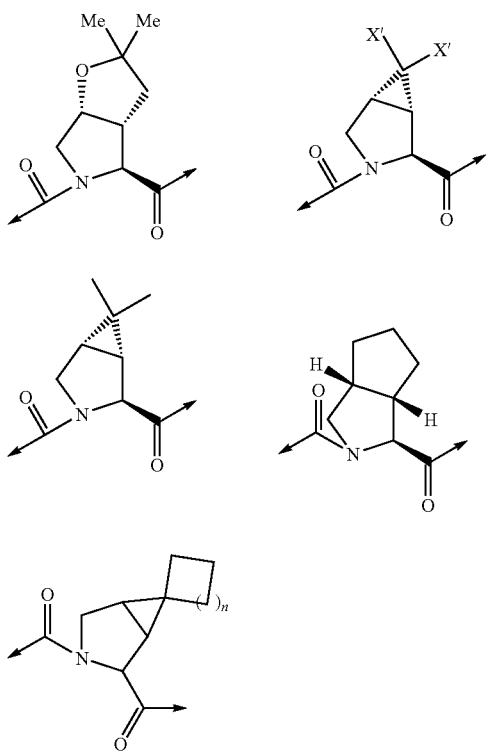

wherein X' is H, F, Cl or Br.

In still another embodiment of the present invention, the portion of structural Formula 1 represented by structural Formula 2:

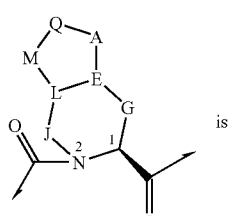

Formula 2

-continued

Q may be present or absent, and if Q is absent, M is directly linked to A.

In still yet another embodiment of the present invention, the portion of structural Formula 1 represented by structural Formula 2 is selected from the following structures:

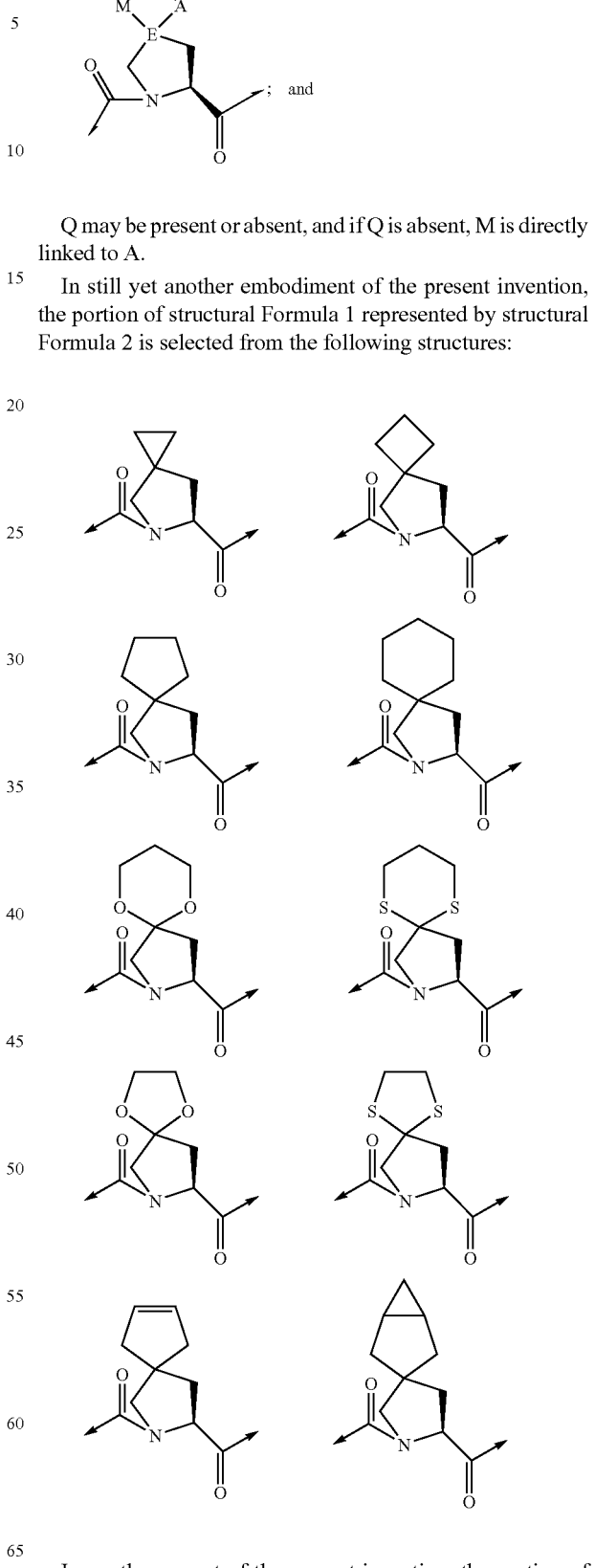

In another aspect of the present invention, the portion of structural Formula 1 represented by structural Formula 2:

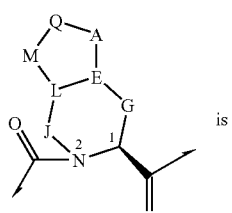
Formula 2
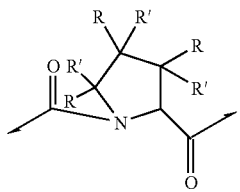
In still another aspect of the present invention, the portion of structural Formula 1 represented by structural Formula 2 is selected from the following structures:
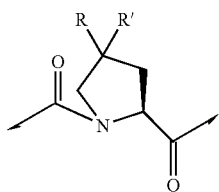 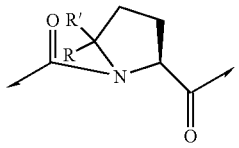
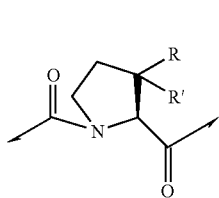 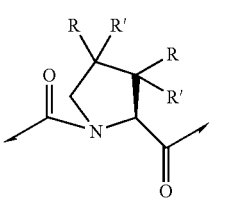
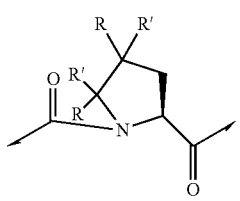 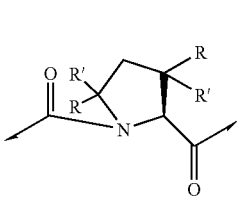
In yet another aspect of the present invention, the portion of structural Formula 1 represented by structural Formula 2 is selected from the following structures:
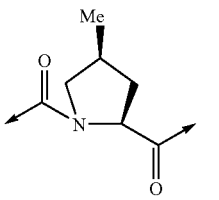 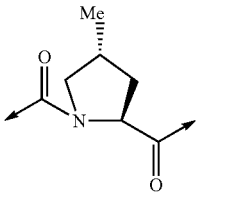
-continued
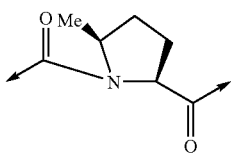 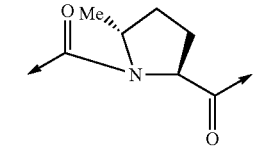
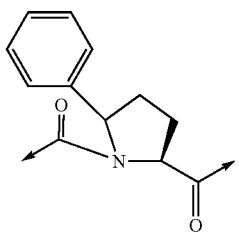 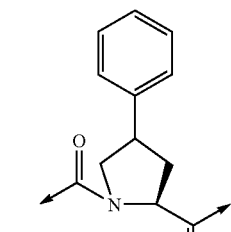
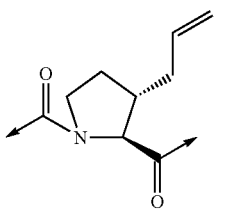 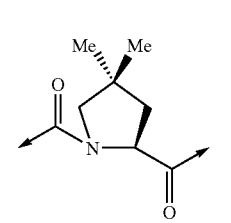
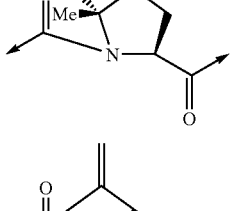 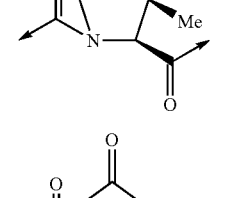
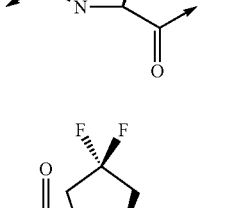 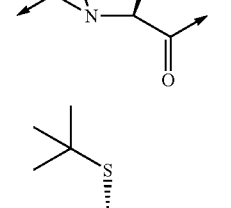
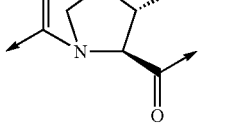 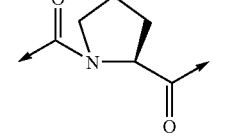
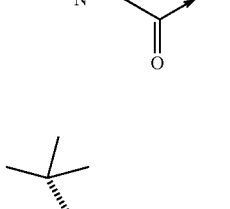 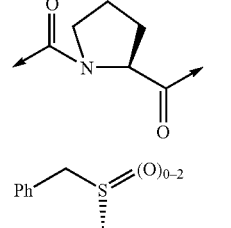
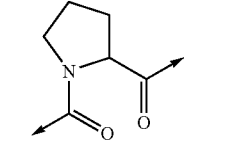 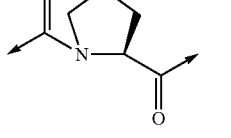

-continued

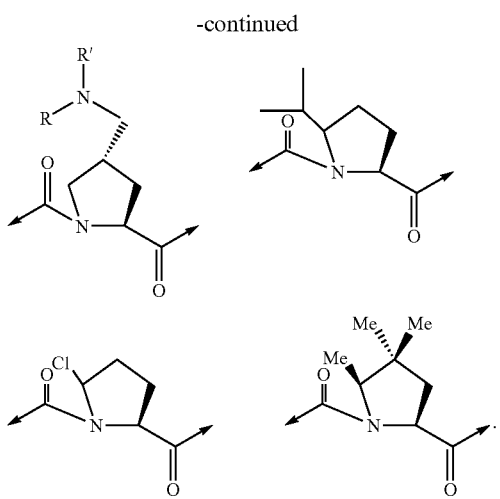

In still yet another aspect of the present invention, the portion of structural Formula 1 represented by structural Formula 2:

Formula 2

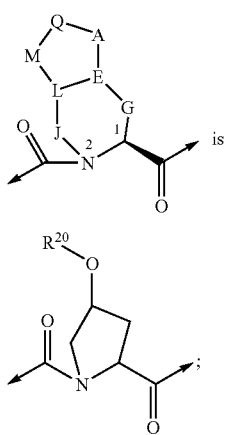

is and

R²⁰ is selected from the following structures:

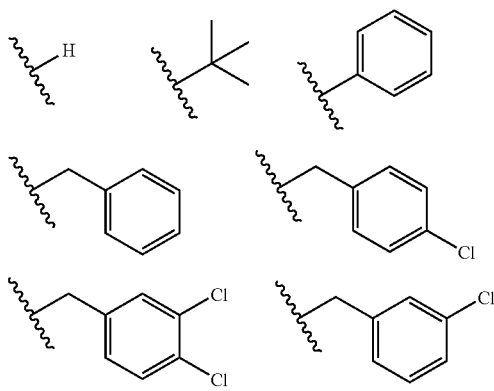

-continued

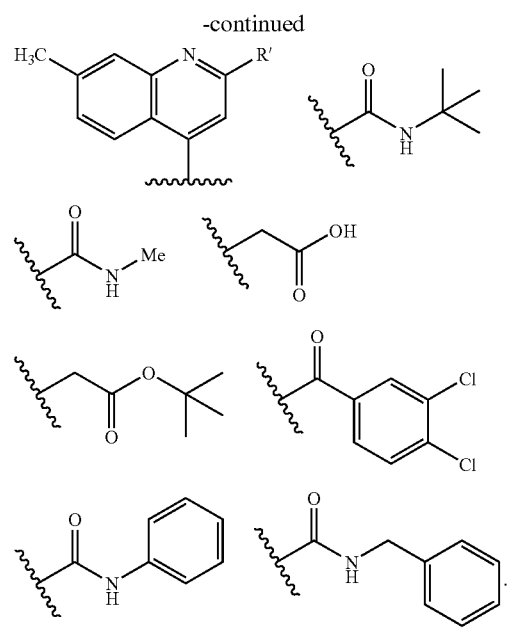

In another aspect of the present invention, the portion of structural Formula 1 represented by structural Formula 2:

Formula 2

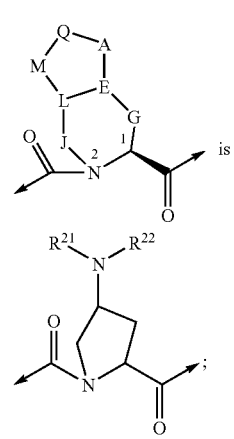

and $R^{21}$ and $R^{22}$ may be the same or different and are independently selected from the group consisting of the following structures:

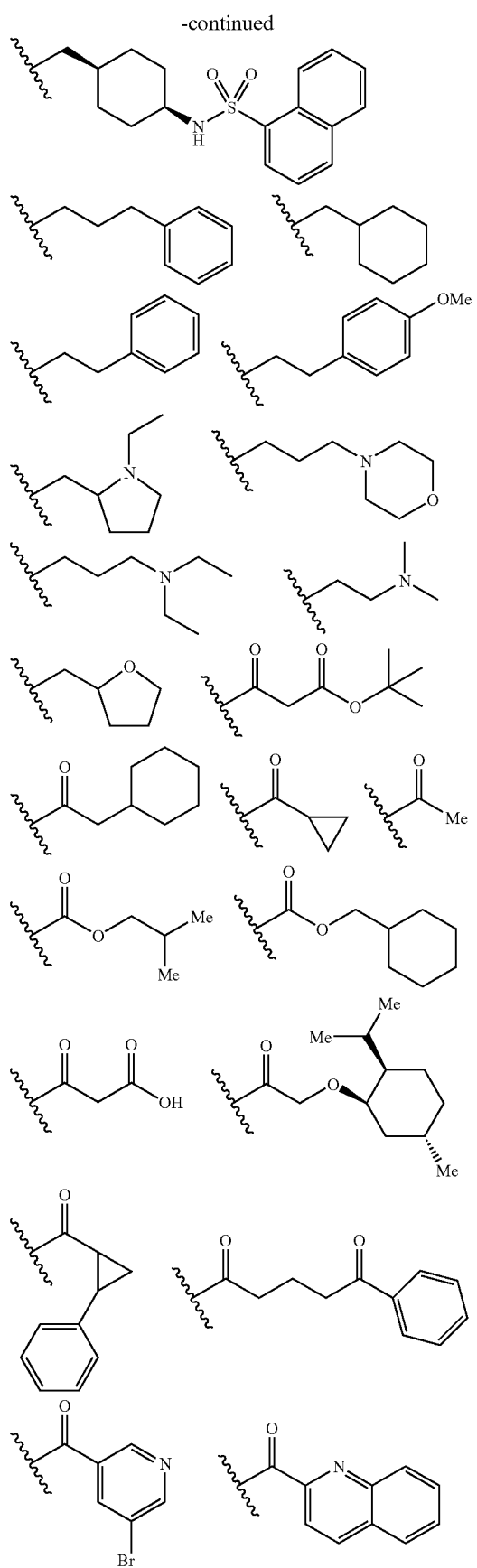

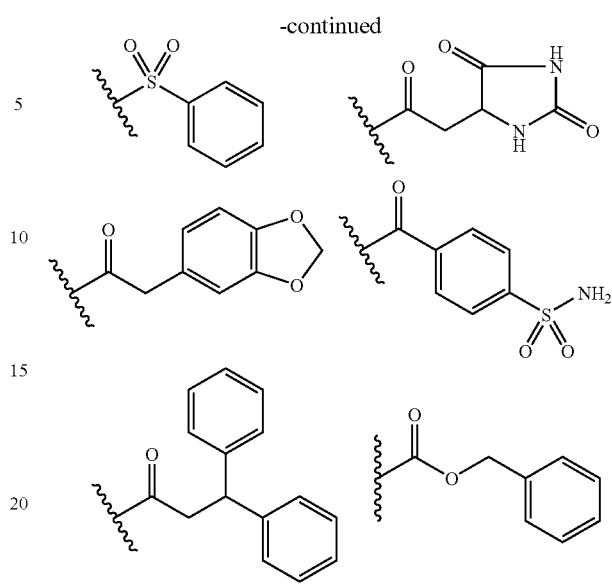

In another aspect of the present invention, L and M are absent, and J is directly linked to E.

In another aspect of the present invention, L, J and M are absent and E is directly linked to N.

In another aspect of the present invention, G and M are absent.

In still another aspect of the present invention, M' is

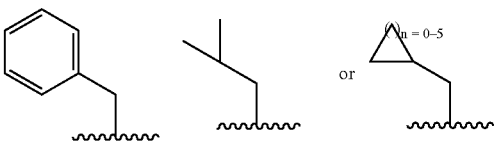

In yet another aspect of the present invention, X is selected from the group consisting of the following structures:

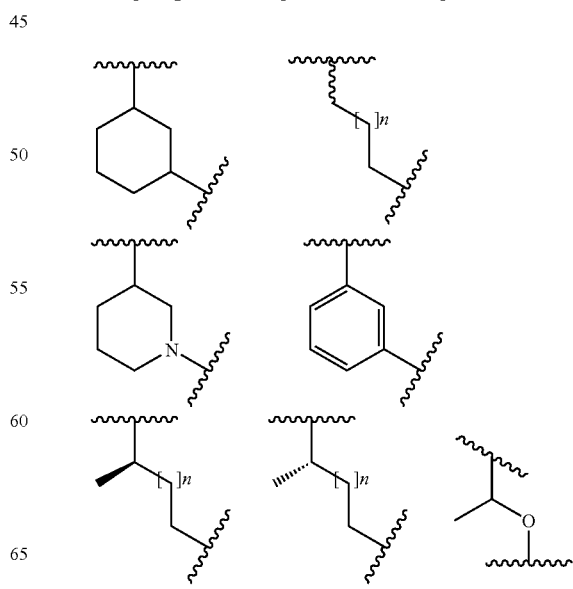

-continued

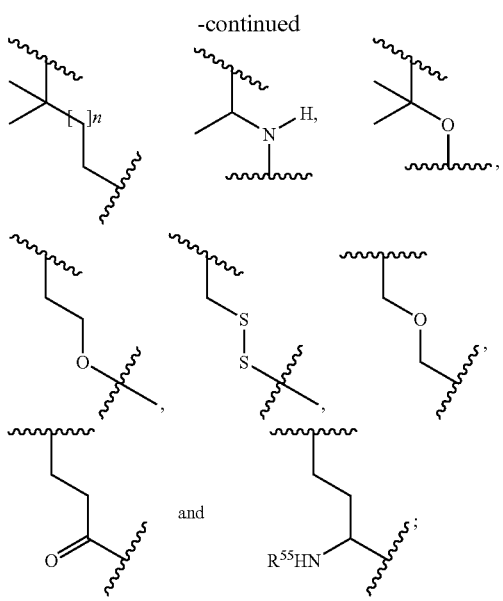

and $R^{55}$ is alkyl, cycloalkyl, carbamate or urea; and n=0-5.

In still yet another aspect of the present invention, X is selected from the group consisting of the following structures:

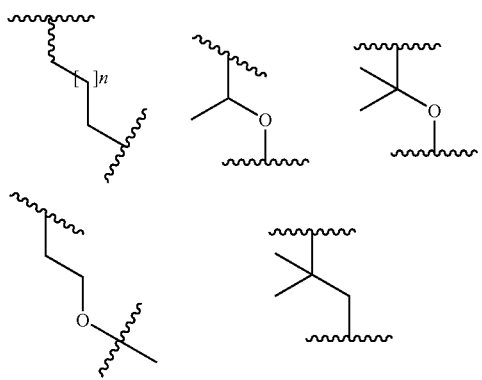

In still yet another aspect of the present invention, $R^1$ is a ketoamide, ketoaldehyde, diketone, ketoacid or ketoester.

In another embodiment of the present invention, $R^1$ is $-C(O)C(O)NR^9R^{10}$;

$R^9$ is H; and $R^{10}$ is H, $-R^{14}$,
—$[CH(R^{1'})]_pC(O)OR^{11}$,
—$[CH(R^{1'})]_pC(O)NR^{12}R^{13}$,
—$[CH(R^{1'})]_pS(O_2)R^{11}$,
—$[CH(R^{1'})]_pS(O_2)NR^{12}R^{13}$,
—$[CH(R^{1'})]_pC(O)R^{11}$,
—$CH(R^{1'})C(O)N(H)C(H)(R^{2'})C(O)OR^{11}$,
—$CH(R^{1'})C(O)N(H)CH(R^{2'})C(O)NR^{12}R^{13}$, or
—$CH(R^{1'})C(O)N(H)CH(R^{2'})(R')$.

In another embodiment of the present invention, $R^{10}$ is H, —$R^{14}$,
—$CH(R^{1'})C(O)OR^{11}$,
—$CH(R^{1'})CH(R^{1'})C(O)OR^{11}$,
—$CH(R^{1'})C(O)NR^{12}R^{13}$,
—$CH(R^{1'})CH(R^{1'})C(O)NR^{12}R^{13}$,
—$CH(R^{1'})CH(R^{1'})S(O_2)R^{11}$,
—$CH(R^{1'})CH(R^{1'})S(O_2)NR^{12}R^{13}$,
—$CH(R^{1'})CH(R^{1'})C(O)R^{11}$,
—$CH(R^{1'})C(O)N(H)CH(R^{2'})C(O)OR^{11}$,
—$CH(R^{1'})C(O)N(H)CH(R^{2'})C(O)NR^{12}R^{13}$, or
—$CH(R^{1'})C(O)N(H)CH(R^{2'})(R')$;

$R^{1'}$ is H or alkyl; and $R^{2'}$ is phenyl, substituted phenyl, hetero atom-substituted phenyl, cycloalkyl, heterocycloalkyl, piperidyl or pyridyl.

In another embodiment of the present invention, $R^{1'}$ is H.

In still another embodiment of the present invention, $R^{11}$ is H, methyl, ethyl, allyl, tert-butyl, benzyl, α-methylbenzyl, α,α-dimethylbenzyl, 1-methylcyclopropyl or 1-methylcyclopentyl;

$R'$ is hydroxymethyl or —$CH_2C(O)NR^{12}R^{13}$;

$R^{2'}$ is independently selected from the group consisting of the following structures:

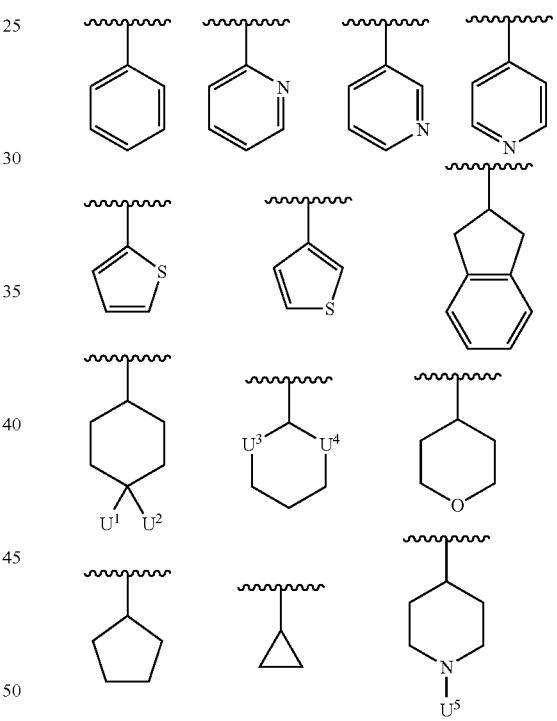

wherein $U^1$ and $U^2$ may be same or different and are independently selected from the group consisting of: H, F, —$CH_2C(O)OH$, —$CH_2C(O)OMe$, —$CH_2C(O)NH_2$, —$CH_2C(O)NHMe$, —$CH_2C(O)NMe_2$, azido, amino, hydroxyl, substituted amino and substituted hydroxyl;

$U^3$ and $U^4$ are the same or different and are independently O or S;

$U^5$ is alkyl sulfonyl, aryl sulfonyl, heteroalkyl sulfonyl, heteroaryl sulfonyl, alkyl carbonyl, aryl carbonyl, heteroalkyl carbonyl, heteroaryl carbonyl, alkoxycarbonyl, aryloxycarbonyl, heteroaryloxycarbonyl, alkylaminocarbonyl, arylaminocarbonyl, or heteroarylaminocarbonyl or a combination thereof;

$NR^{12}R^{13}$ is selected from the group consisting of:
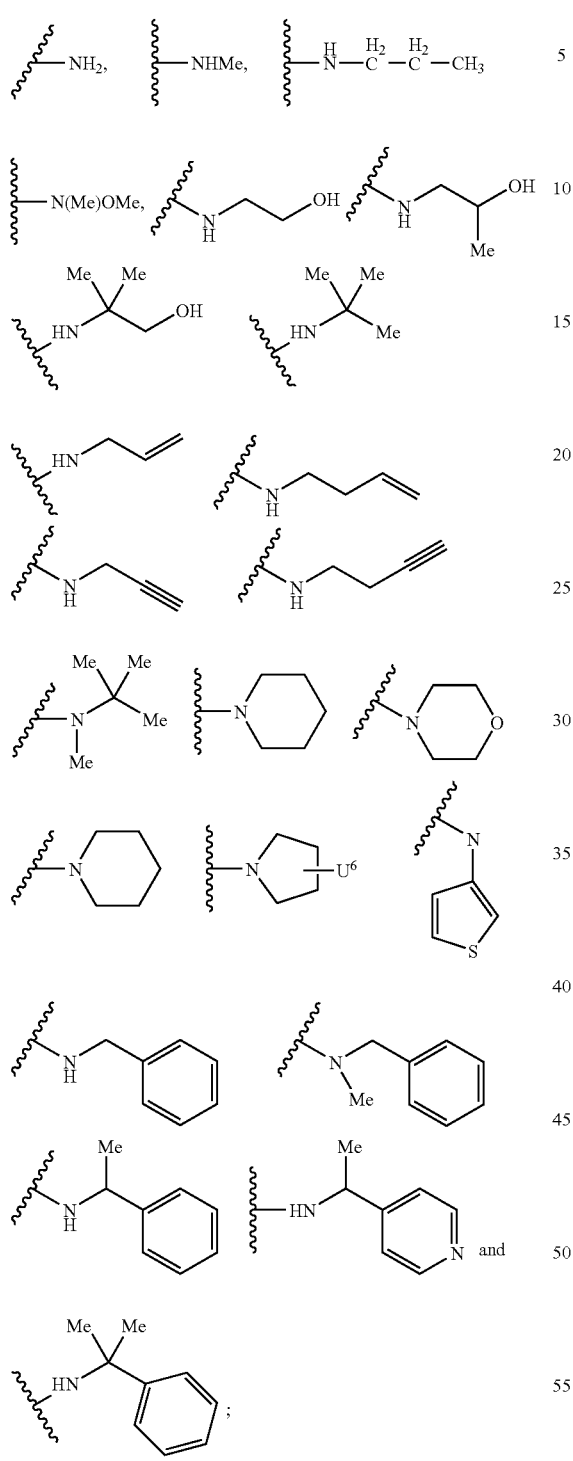
$U^6$ is H, OH, or $CH_2OH$, and
$R^{14}$ is selected from the group consisting of: H, —$CH_3$, Et, n-propyl, methoxy, cyclopropyl, n-butyl, 1-but-3-enyl, benzyl, α-methylbenzyl, phenethyl, allyl, 1-but-3-enyl, —$OCH_3$ and cyclopropylmethyl. In still another embodiment of the present invention, $R^1$ is selected from the following structures:
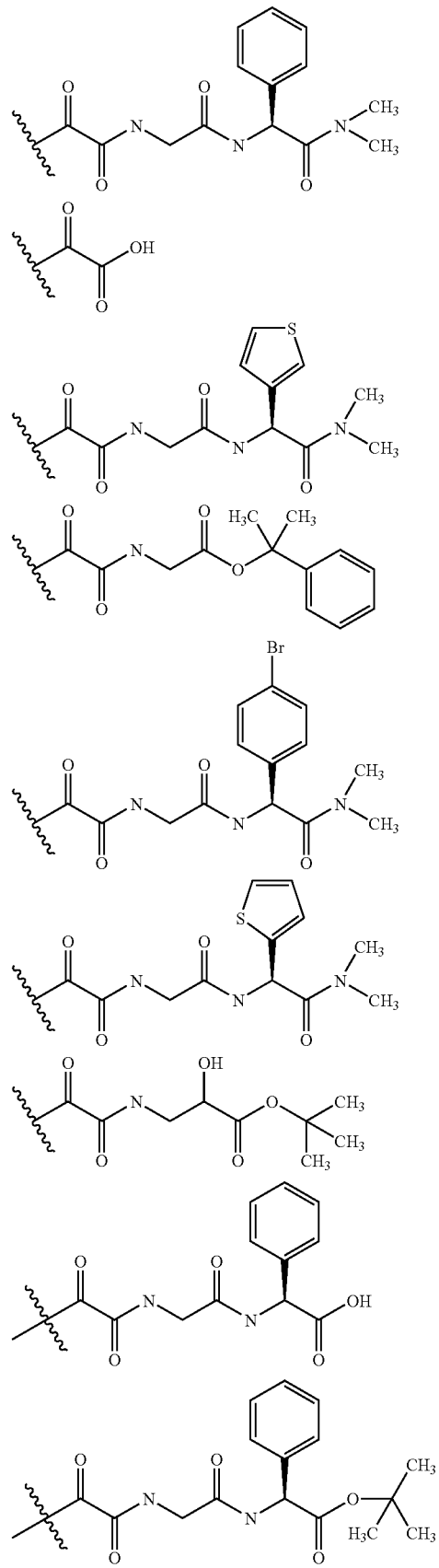

-continued

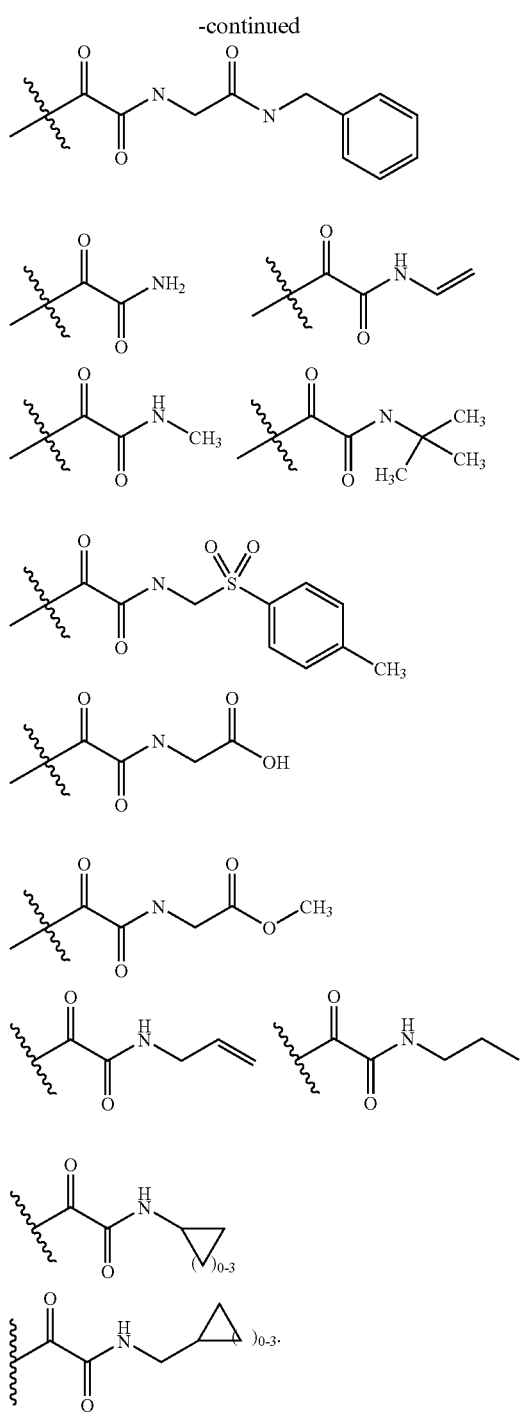

In another aspect of the present invention, D and X taken together form a divalent $C_7$-$C_{12}$ unbranched paraffinic linking chain forming a portion of a 14-19 member macrocycle.

In another aspect of the present invention, D and X taken together form a C8 or C9 unbranched paraffinic linking chain forming a portion of a 15 or 16 membered heterocycle.

In another aspect of the present invention, D and X taken together form a divalent C7-C12 unbranched olefinic linking chain forming a portion of a 14-19 member macrocycle having a single degree of unsaturation.

In another aspect of the present invention, D and X taken together form a C8 or C9 unbranched olefinic linking claim forming a portion of a 15 or 16 member heterocycle having a single degree of unsaturation.

In another aspect of the present invention, D and X taken together form a divalent C2-C12 unbranched aliphatic chain forming a portion of a 9-19 membered heterocycle.

In another aspect of the present invention, D is selected from the following structures:

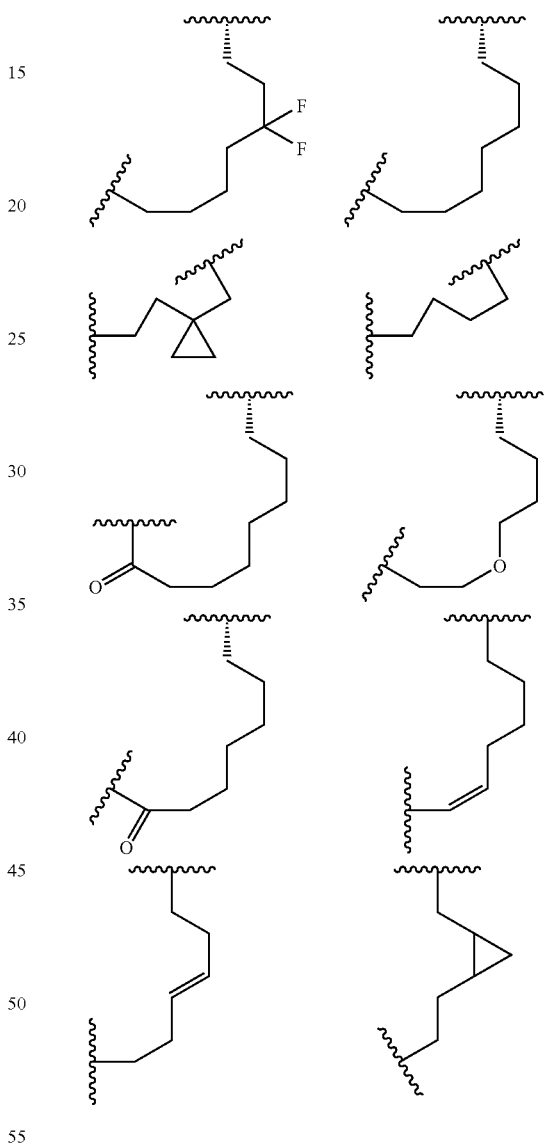

In still yet another aspect of the present invention, the portion of Formula 1 represented by

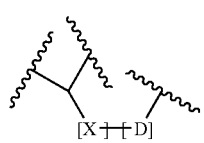

is selected from the following structures:

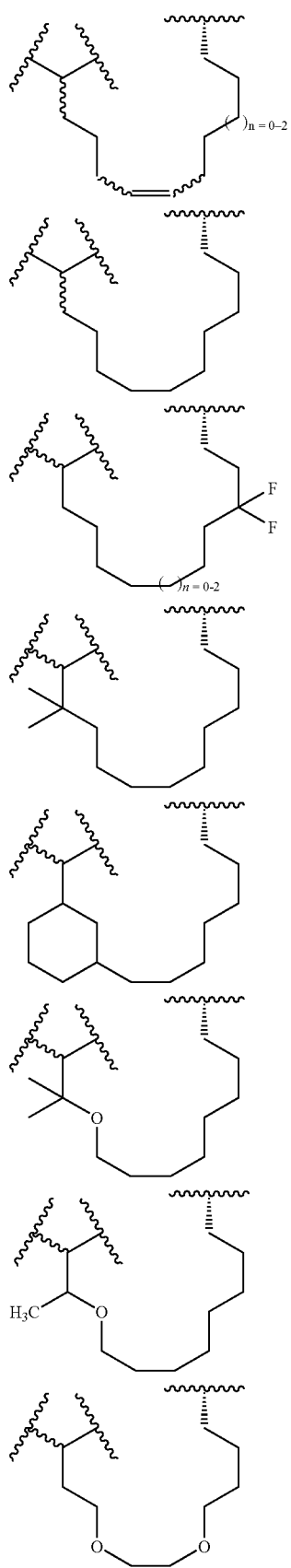
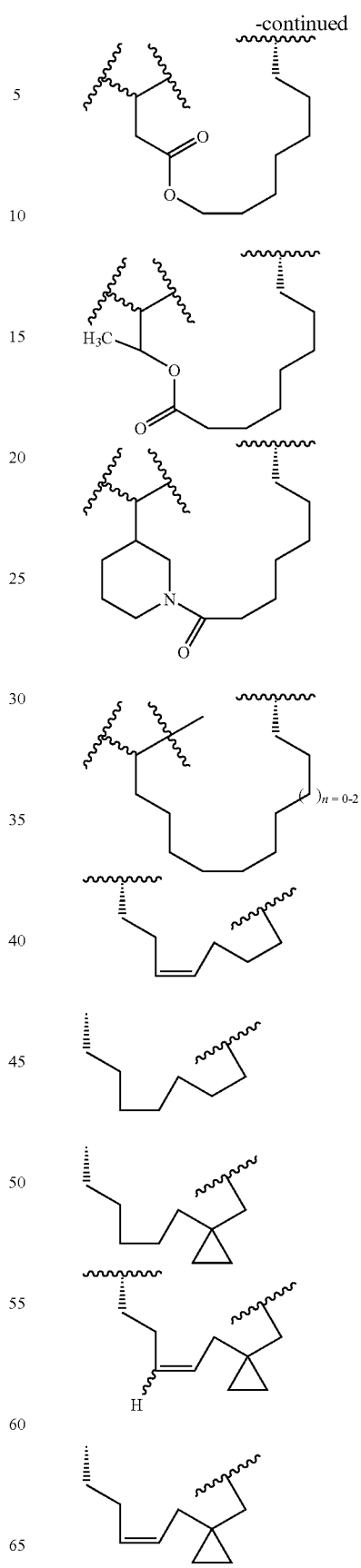

In another embodiment of the present invention, Z' is selected from the group consisting of:
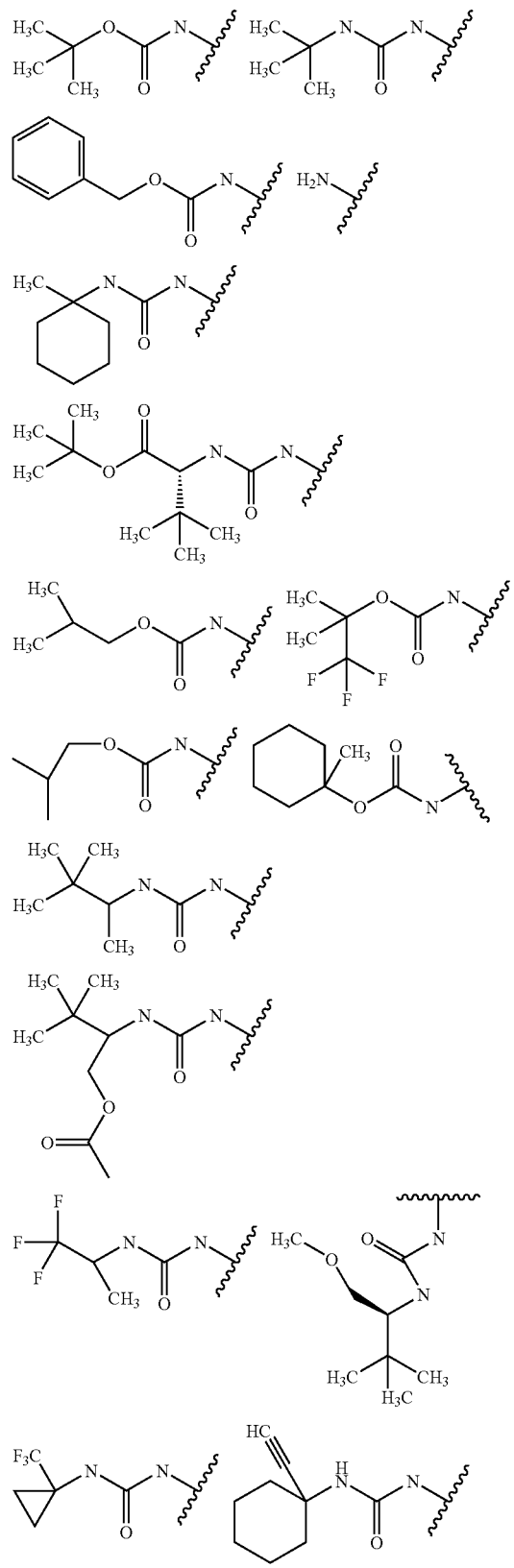
-continued
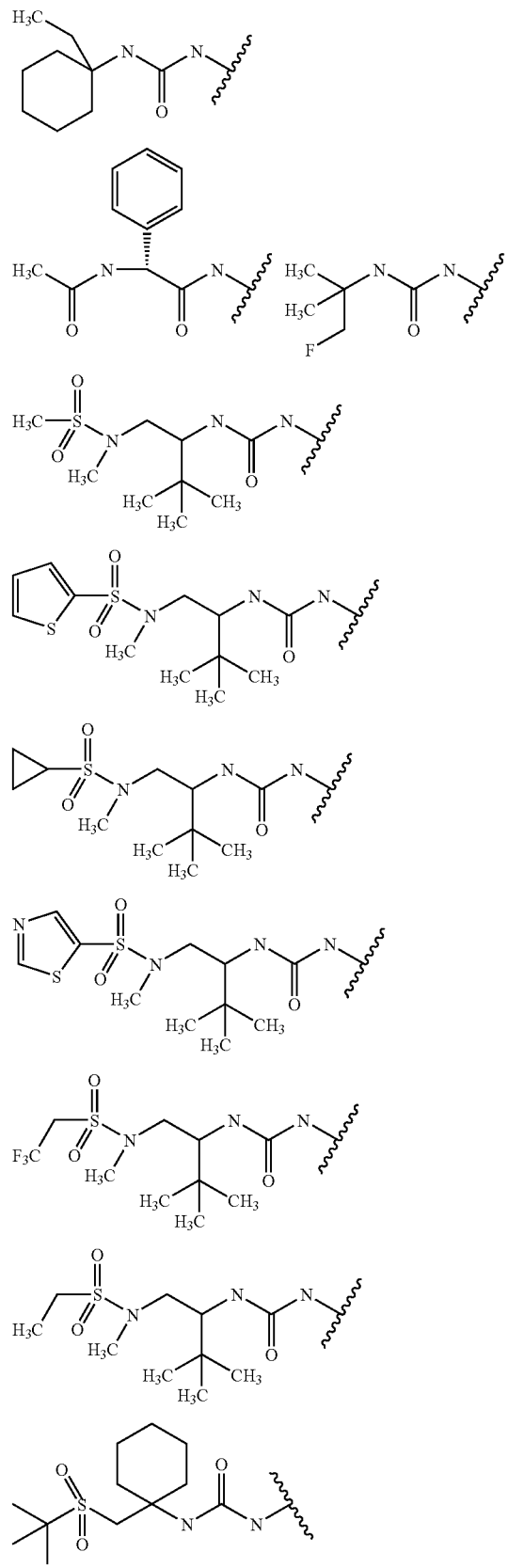

-continued
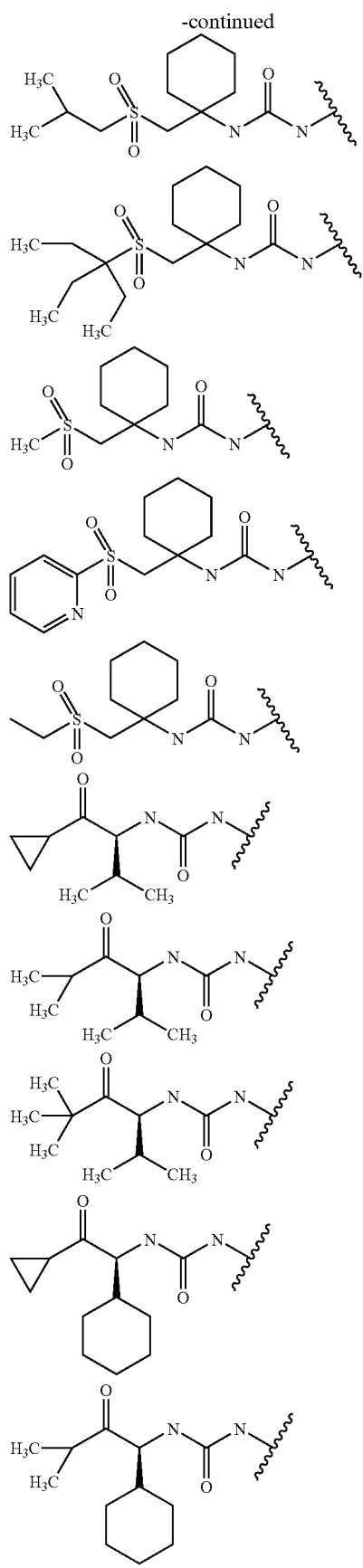
-continued
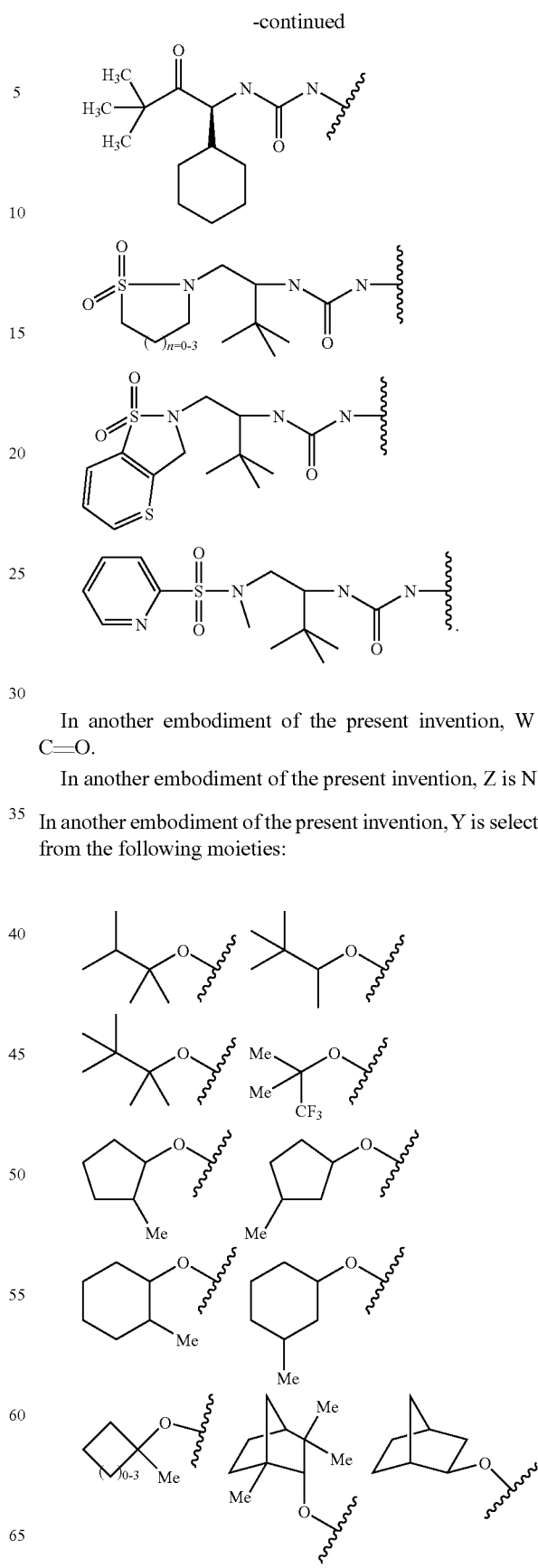
In another embodiment of the present invention, W is C=O.
In another embodiment of the present invention, Z is N.
In another embodiment of the present invention, Y is selected from the following moieties:

-continued
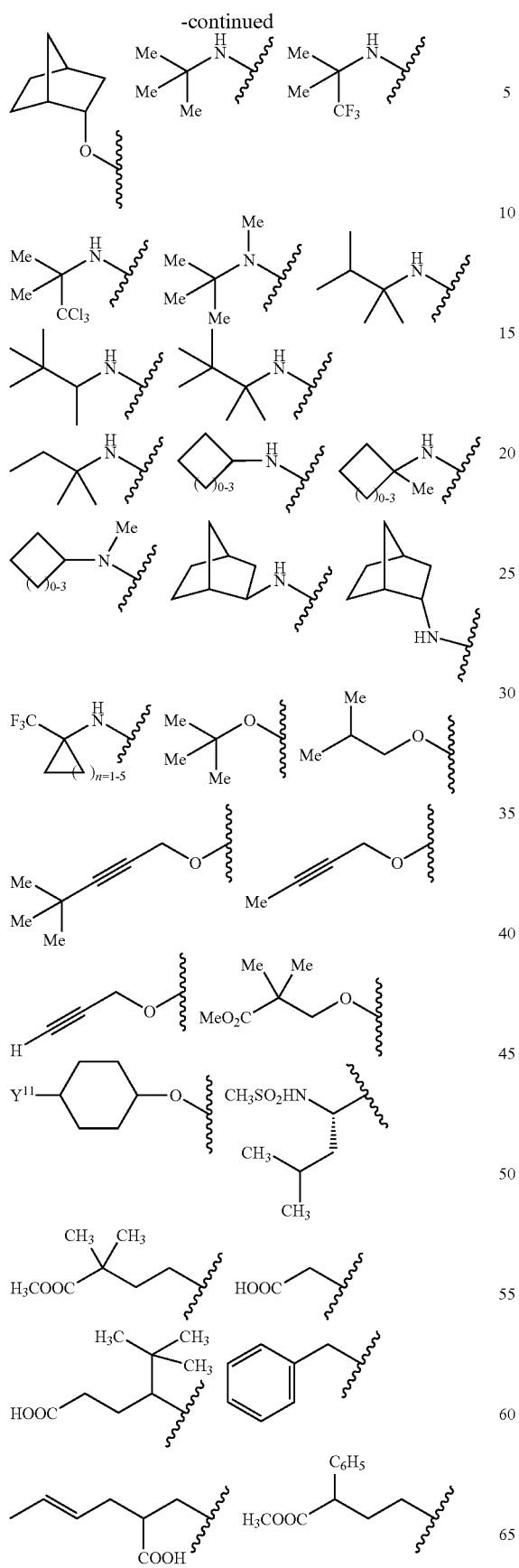
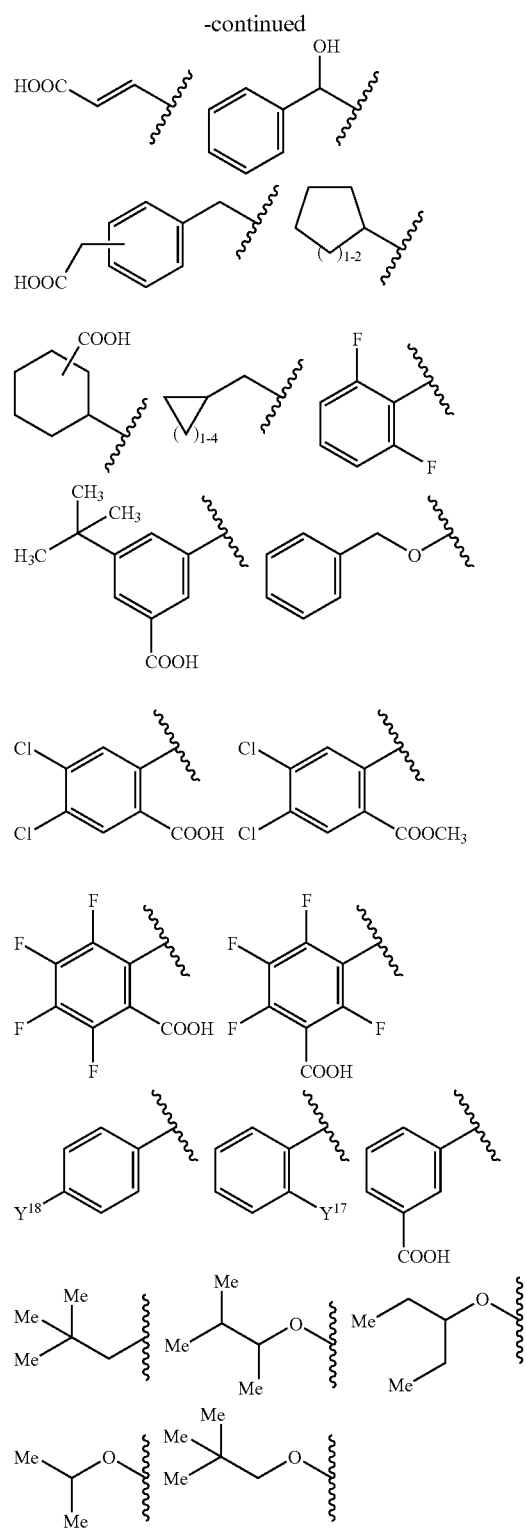
wherein $Y^{17}$ is $CF_3$, $NO_2$, $C(O)NH_2$, OH, $NH_2$ or $C(O)OH$; and
$Y^{18}$ is F or $C(O)OH$.
In still another embodiment of the present invention, Y is selected from the group consisting of the following structures:

-continued
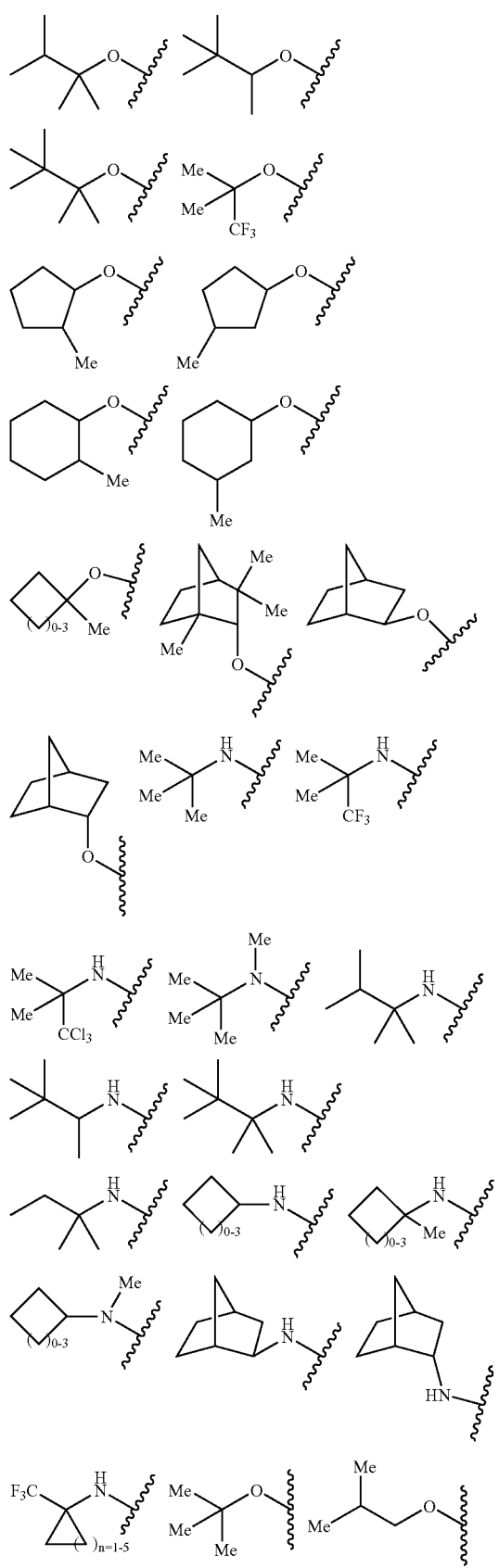
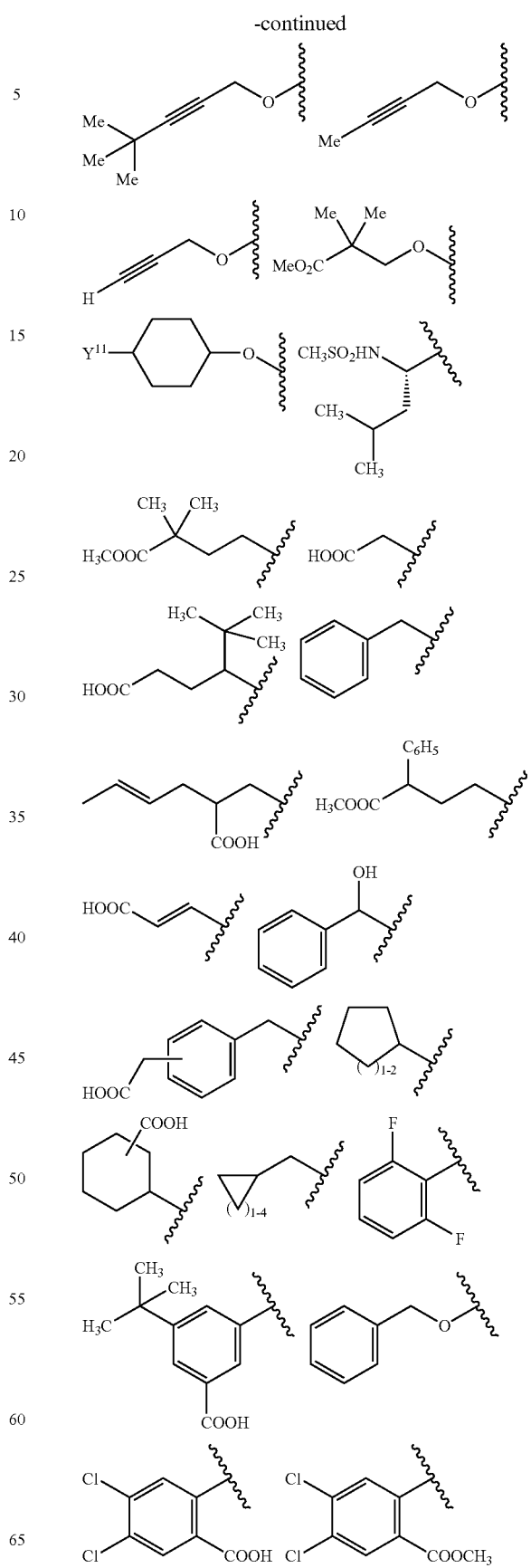

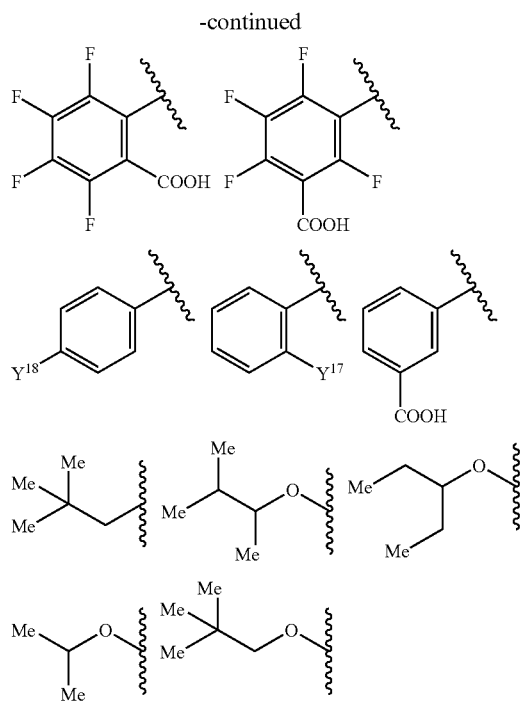
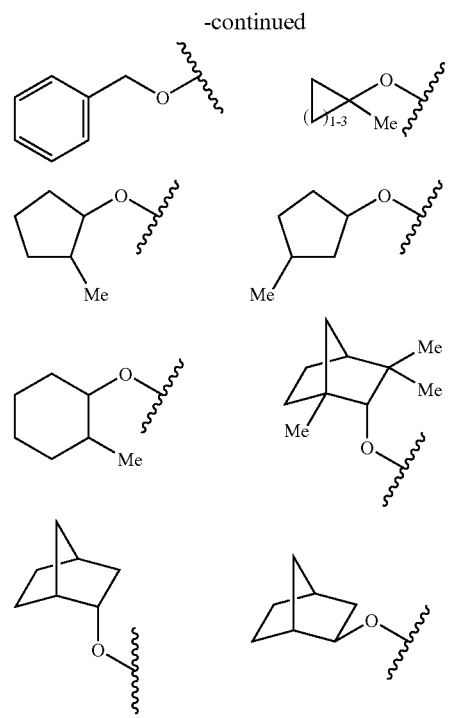
wherein $Y^{17}$ is $CF_3$, $NO_2$, $C(O)NH_2$, OH, $NH_2$ or $C(O)OH$; and
$Y^{18}$ is F or $C(O)OH$.
In still another embodiment of the present invention, Y is selected from the group consisting of the following structures:
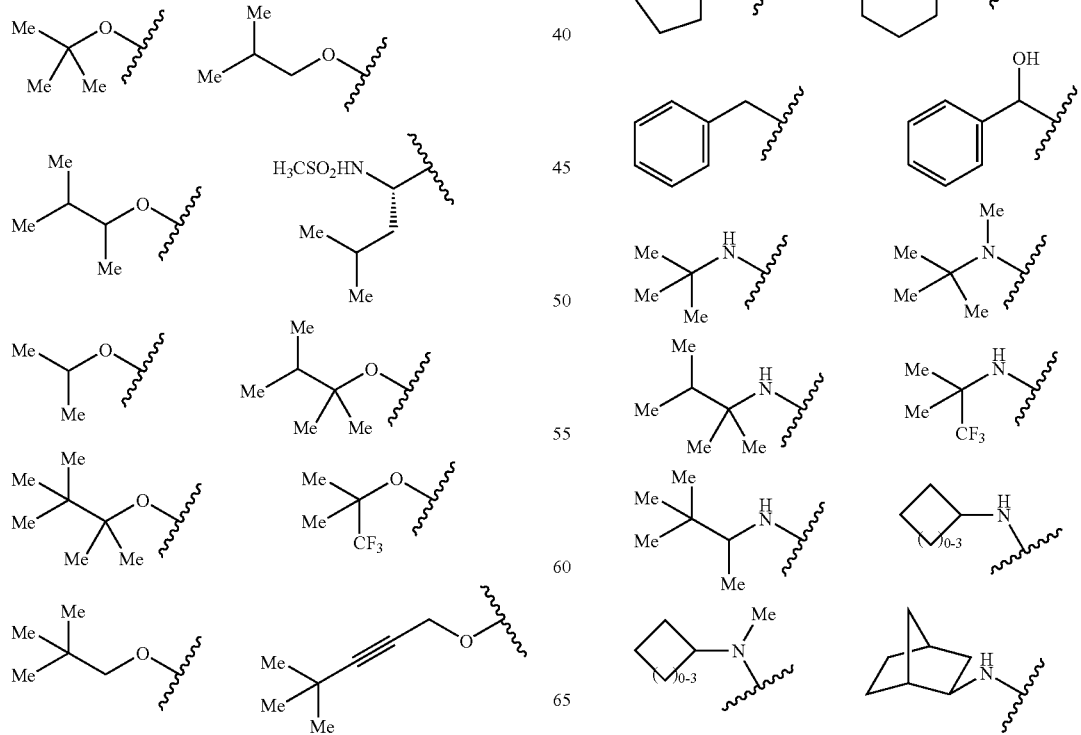

-continued

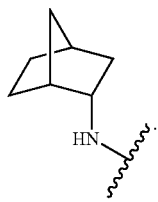

In still yet another embodiment of the present invention, Y is selected from the group consisting of the following structures:

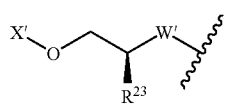

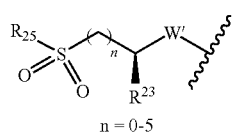

n = 0-5

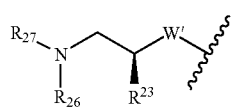

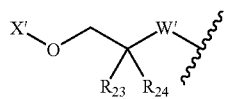

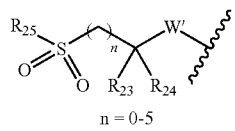

n = 0-5

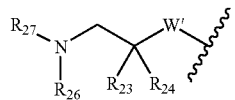

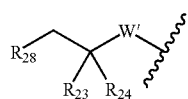

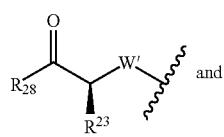 and

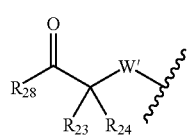

W' is N or O;

$R^{23}$ is H, alkyl, aryl, heteroaryl, cycloalkyl or heterocycloalkyl wherein each of said aryl, heteroaryl, cycloalkyl, heterocycloalkyl may be substituted with an alkyl moiety;

$R^{24}$ is H, alkyl, aryl, heteroaryl, cycloalkyl or heterocycloalkyl wherein each of said aryl, heteroaryl, cycloalkyl, heterocycloalkyl may be substituted with an alkyl moiety;

or $R^{23}$ and $R^{24}$ taken together form a cyclic ring containing a carbocycle or heterocycle;

$R^{25}$ is H, alkyl, heteroalkyl, aryl, heteroaryl, alkylamino, arylamino, heteroalkylamino or cycloalkyl, $R^{26}$ is selected from the group consisting of: H, carbamate, sulfonamides, alkylcarbonyl, alkylsulfonyl, arylsulfonyl, heteroaryl, sulfonyl, heteroalkylsulfonyl, aryloxycarbonyl, heteroalkoxycarbonyl, heteroaryloxycarbonyl, alkylaminocarbonyl, arylaminocarbonyl and urea;

$R^{27}$ is H, alkyl, cycloalkyl, aryl or heteroaryl;

$R^{28}$ is H, alkyl, heteroalkyl, aryl or heteroaryl; and

X'—O— is an ether, ester or carbamate.

In still yet another embodiment of the present invention:

(a) the portion of Formula 1 represented by structural Formula 2:

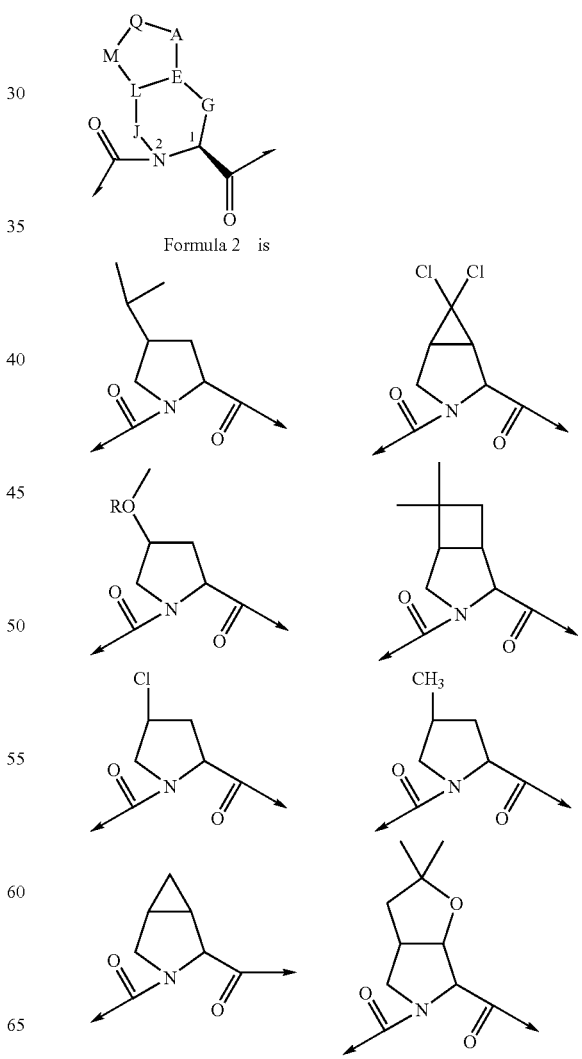

Formula 2 is

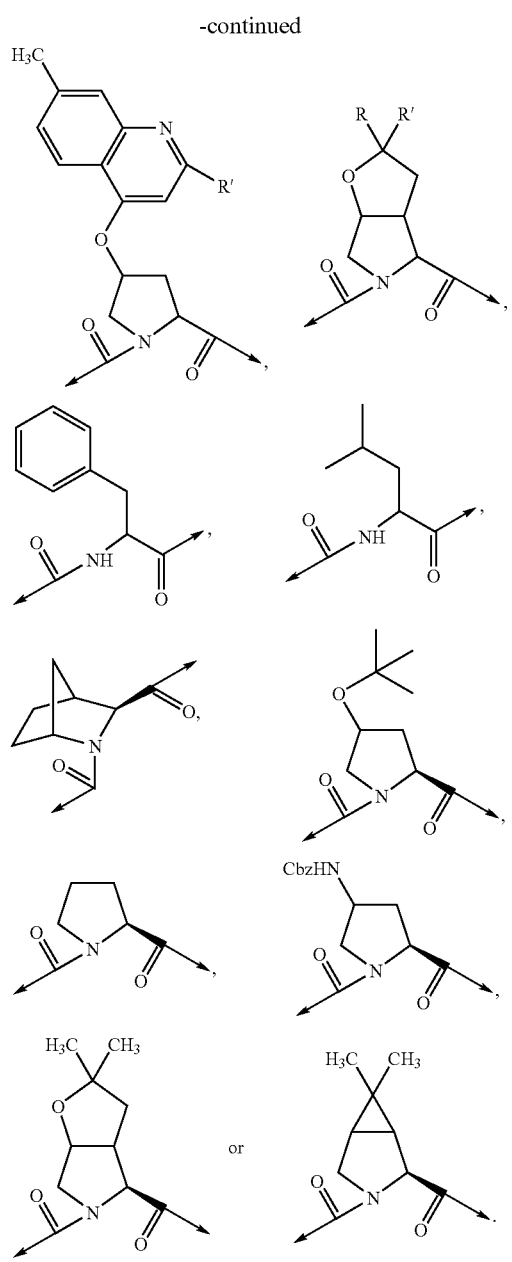
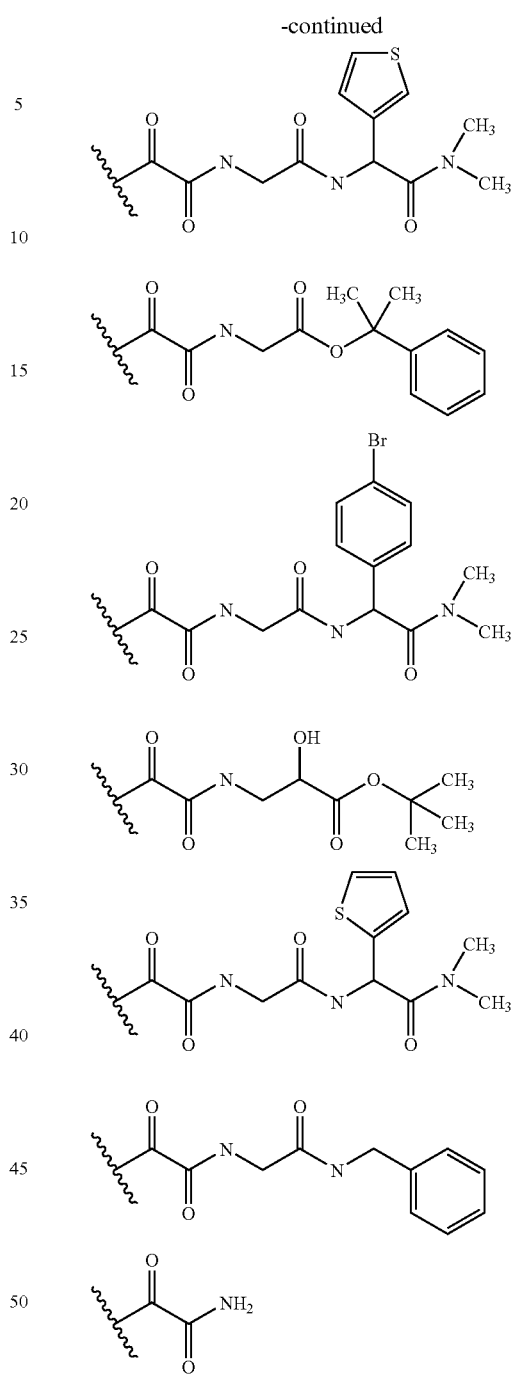
(b) $R^1$ is selected from the following structures:
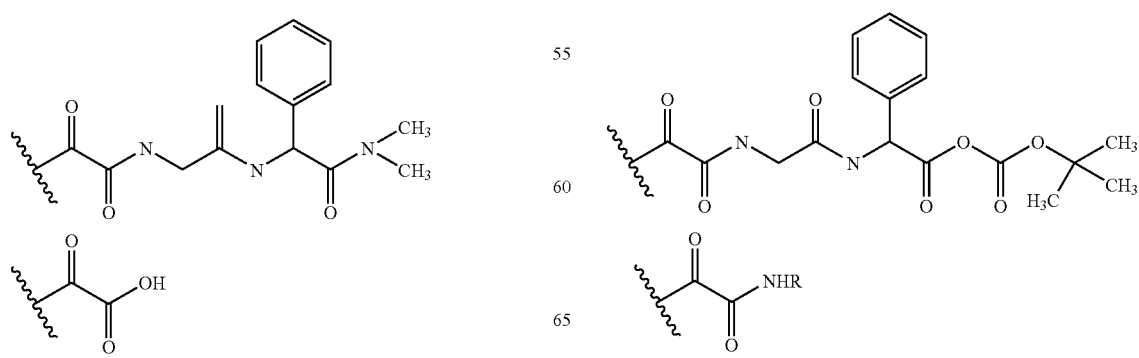

-continued
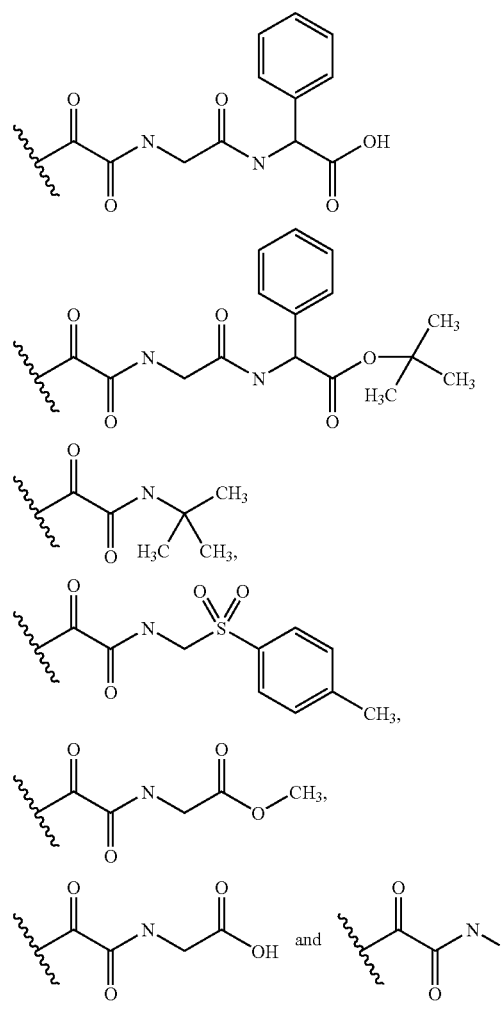
(c) Z' is represented by either (i), (ii), or (iii) shown below:
(i)
Formula A
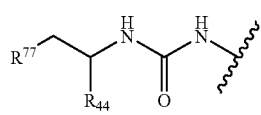
wherein:
R$^{44}$ is selected from the group consisting of:
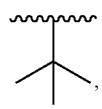 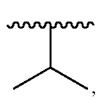
-continued
and R$^{77}$ is selected from the group consisting of:
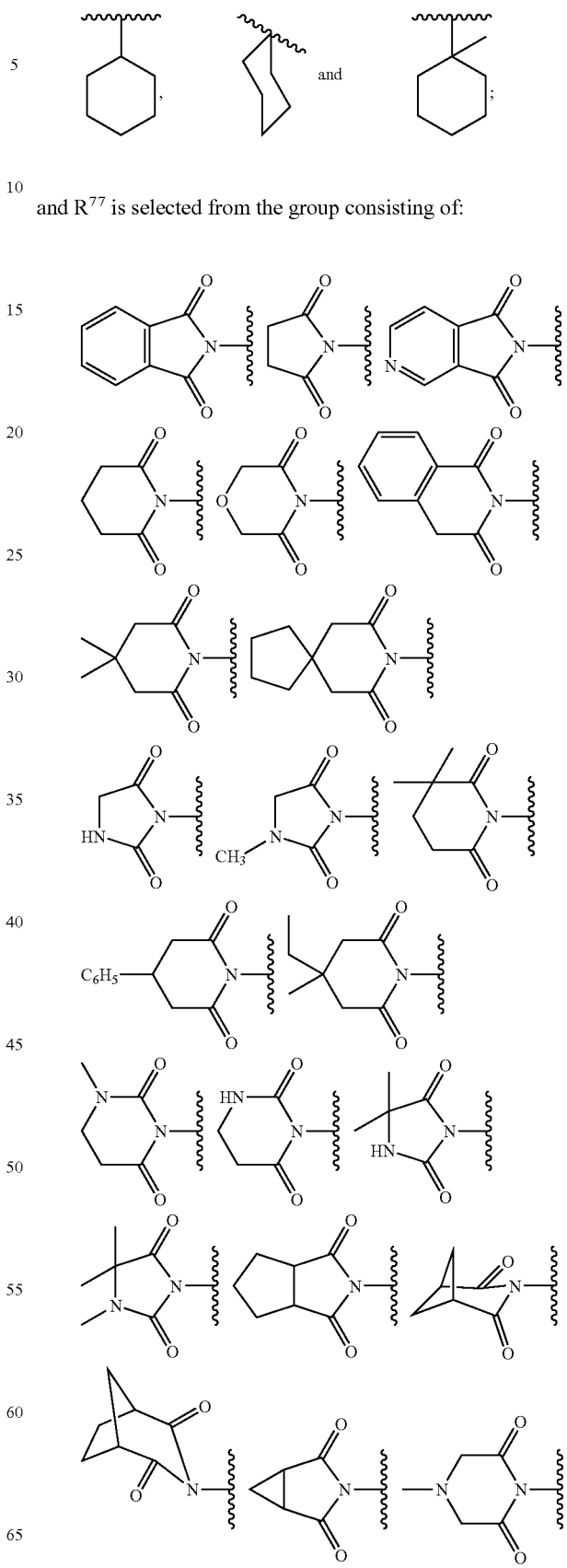

-continued
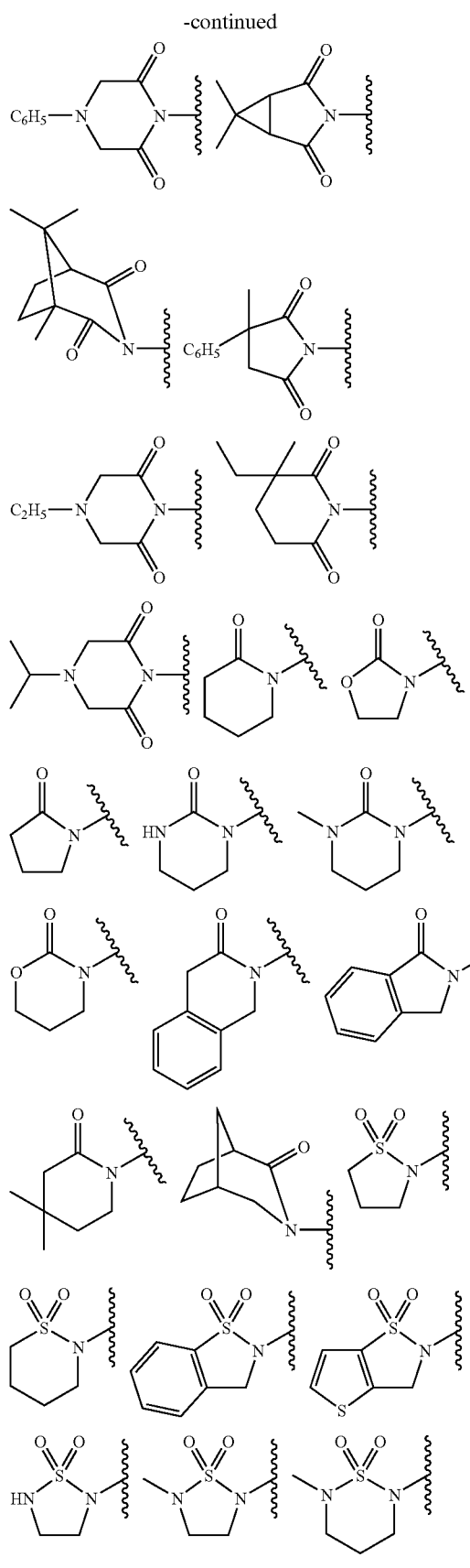
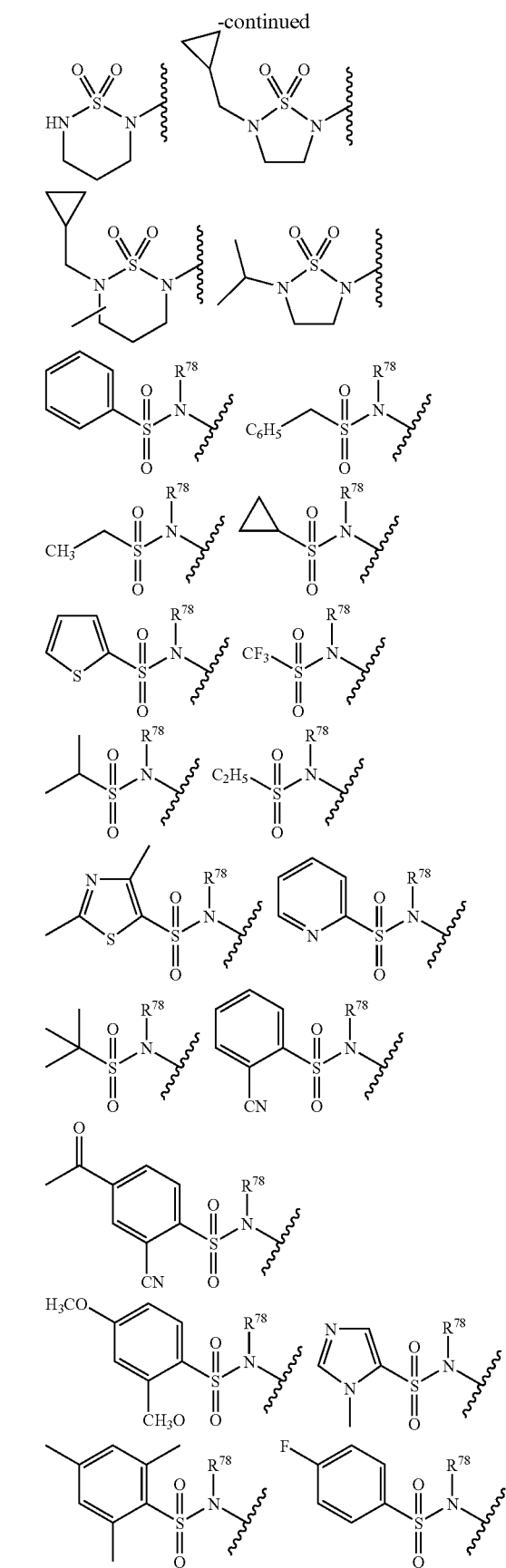

-continued
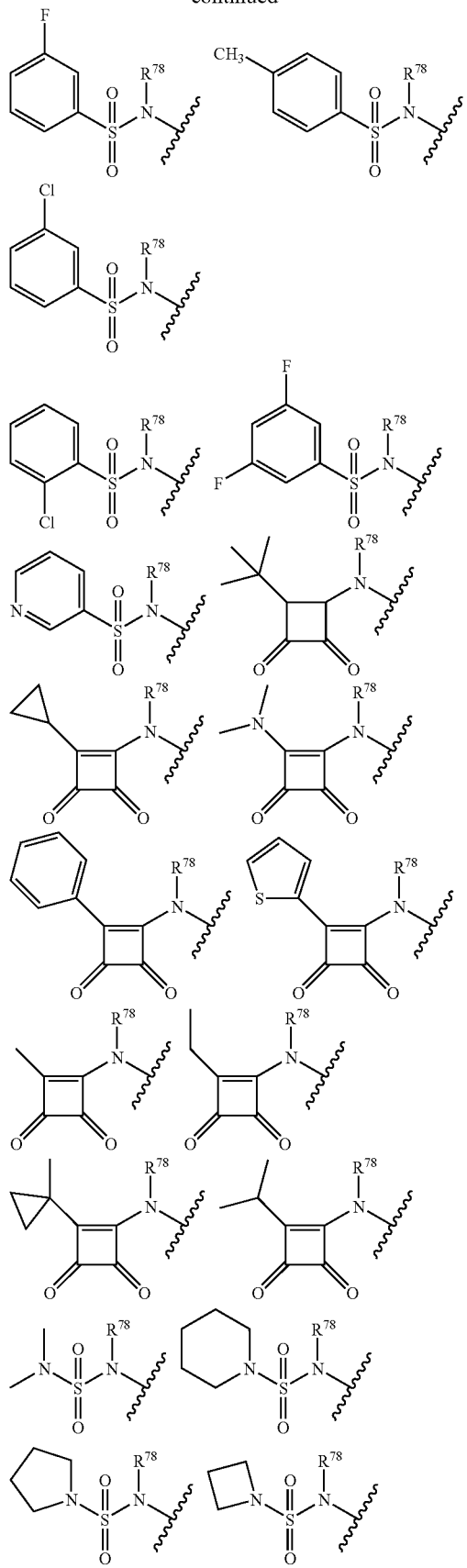
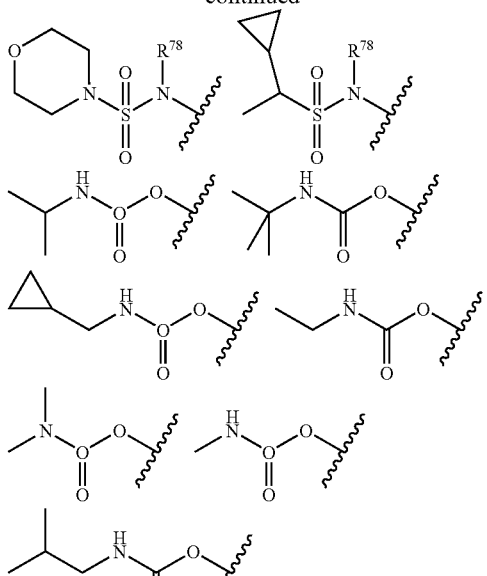
where $R^{78}$ is selected from methyl, ethyl, isopropyl, tert-butyl and phenyl;
(ii)
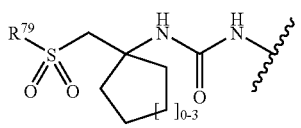
Formula B
where $R^{79}$ is selected from the group consisting of:
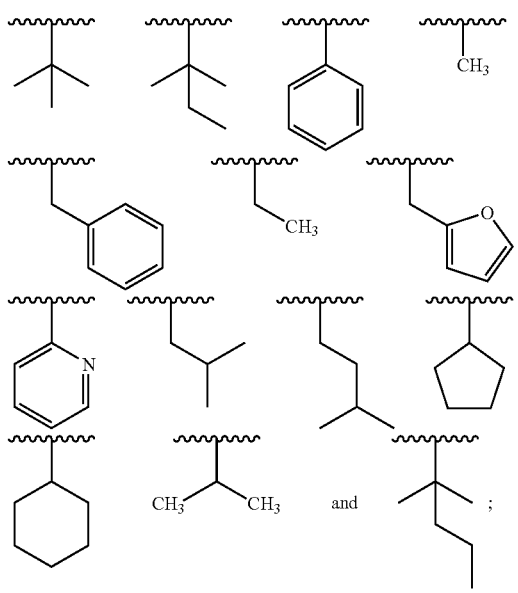
wherein the sulfone ring is optionally substituted with alkyl and cycloalkyl; and (d) the portion of Formula 1 represented by
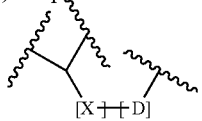
is selected from the following structures:
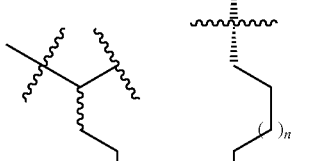
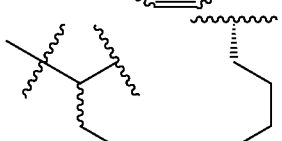
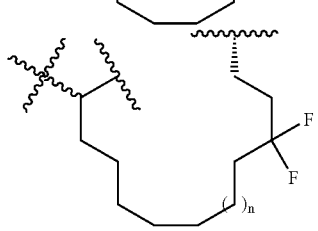
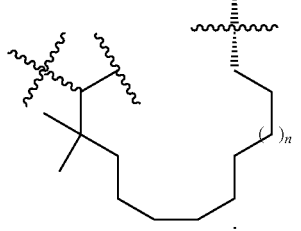
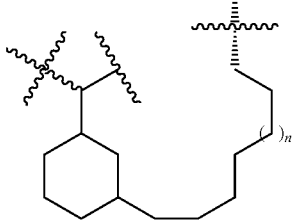
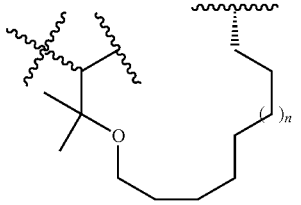
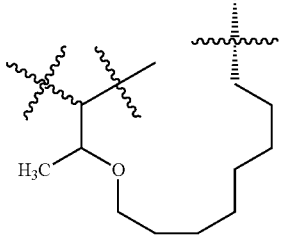
-continued
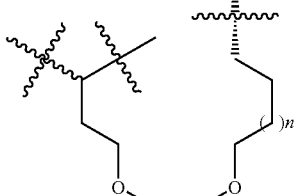
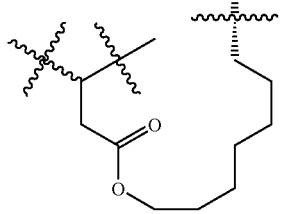
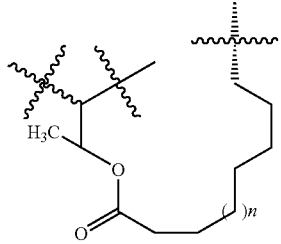
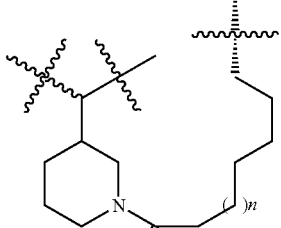
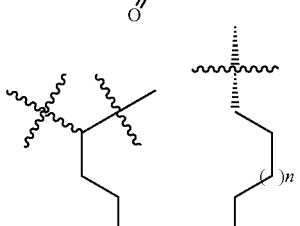
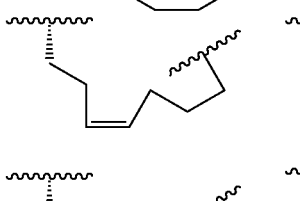
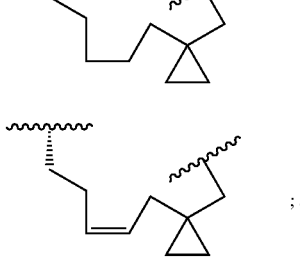
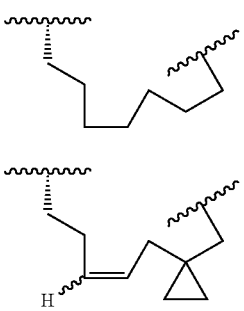
; and n=0 to 3.
Further the following compounds are non-limiting representatives of embodiments of the present invention:
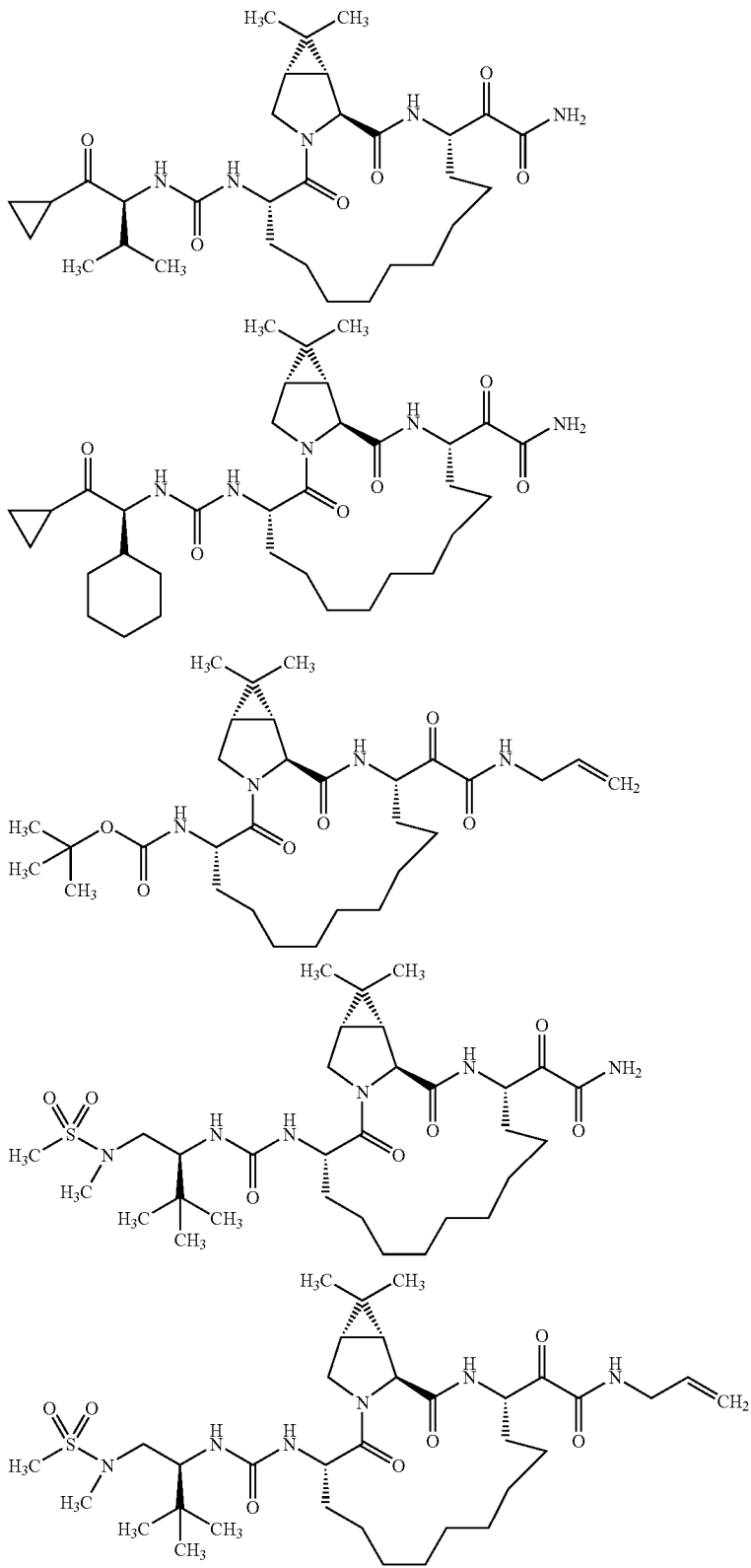

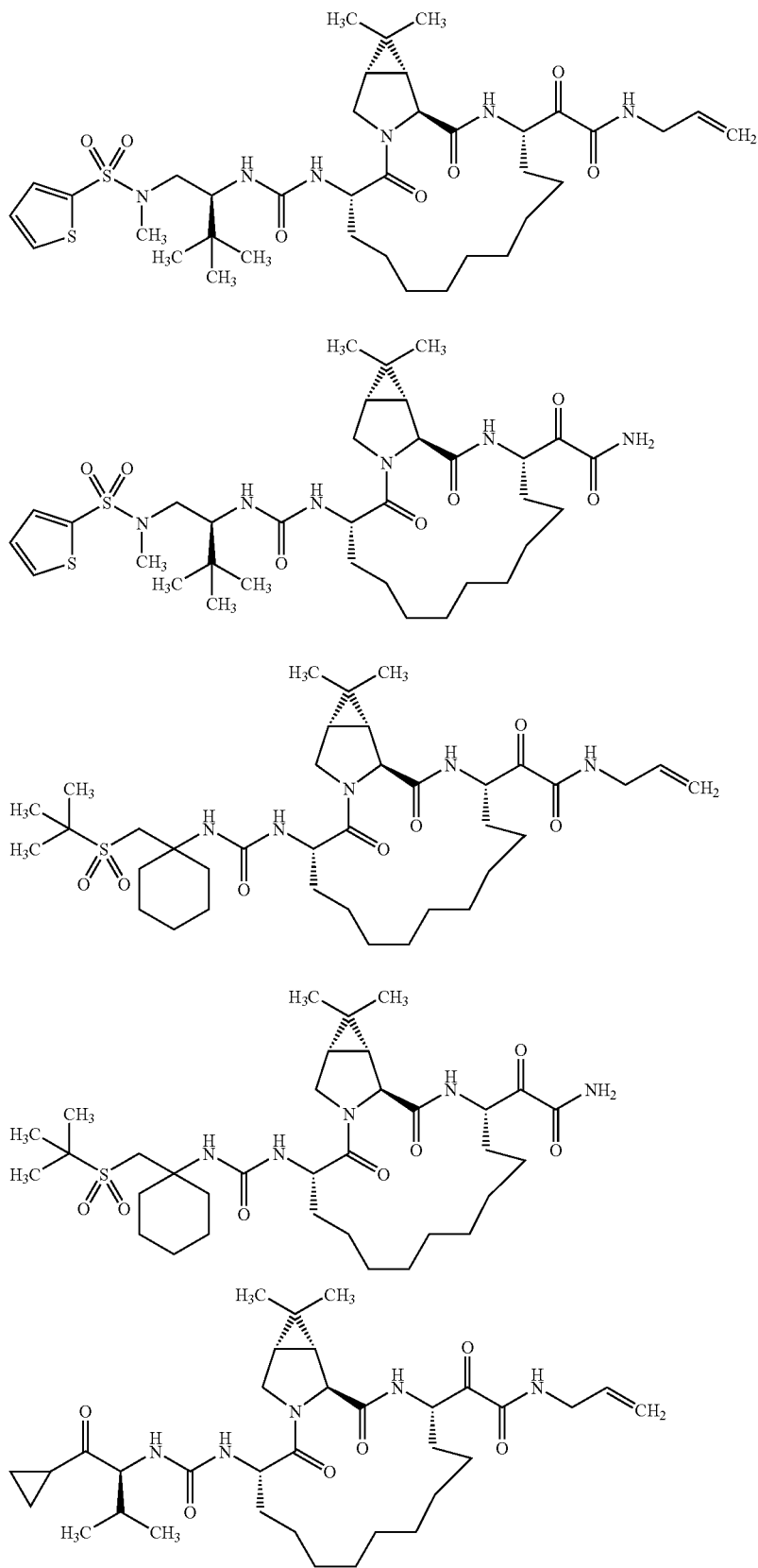

-continued
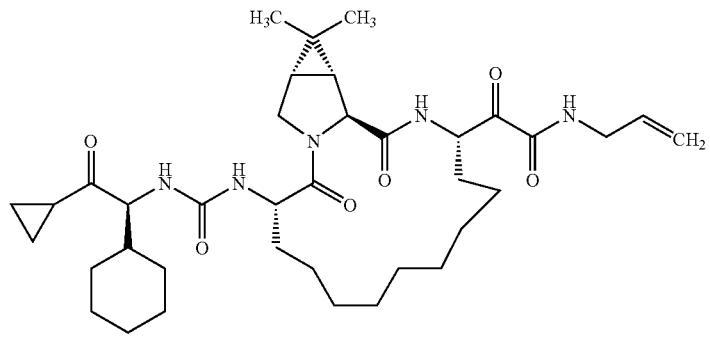
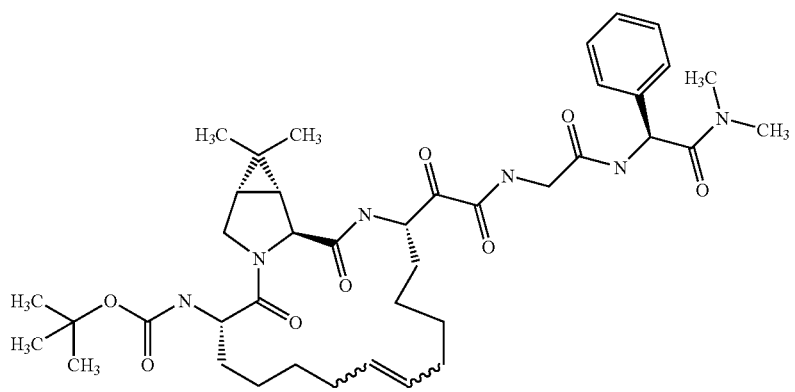
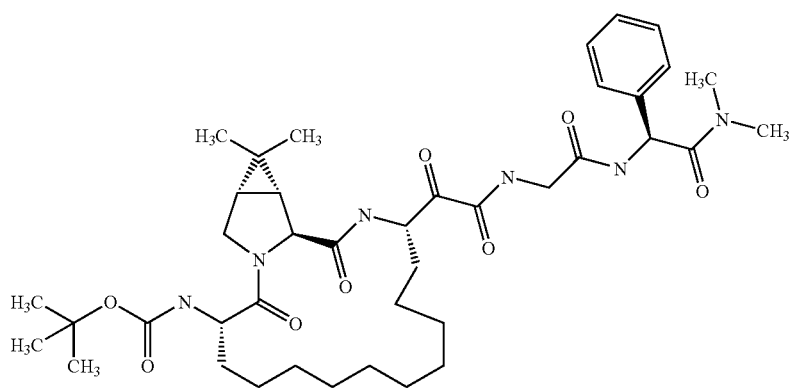
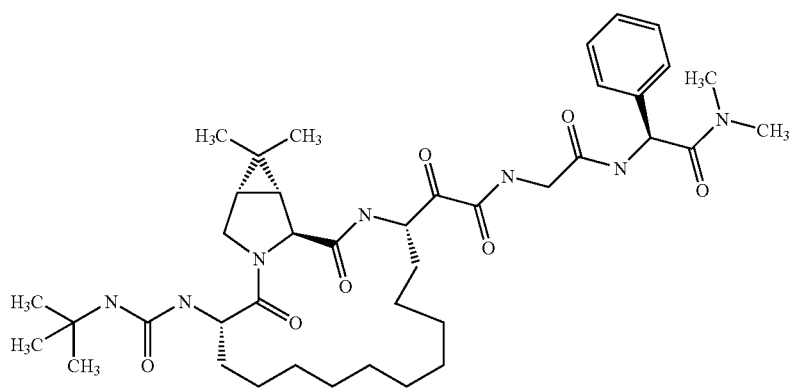

81 82
-continued
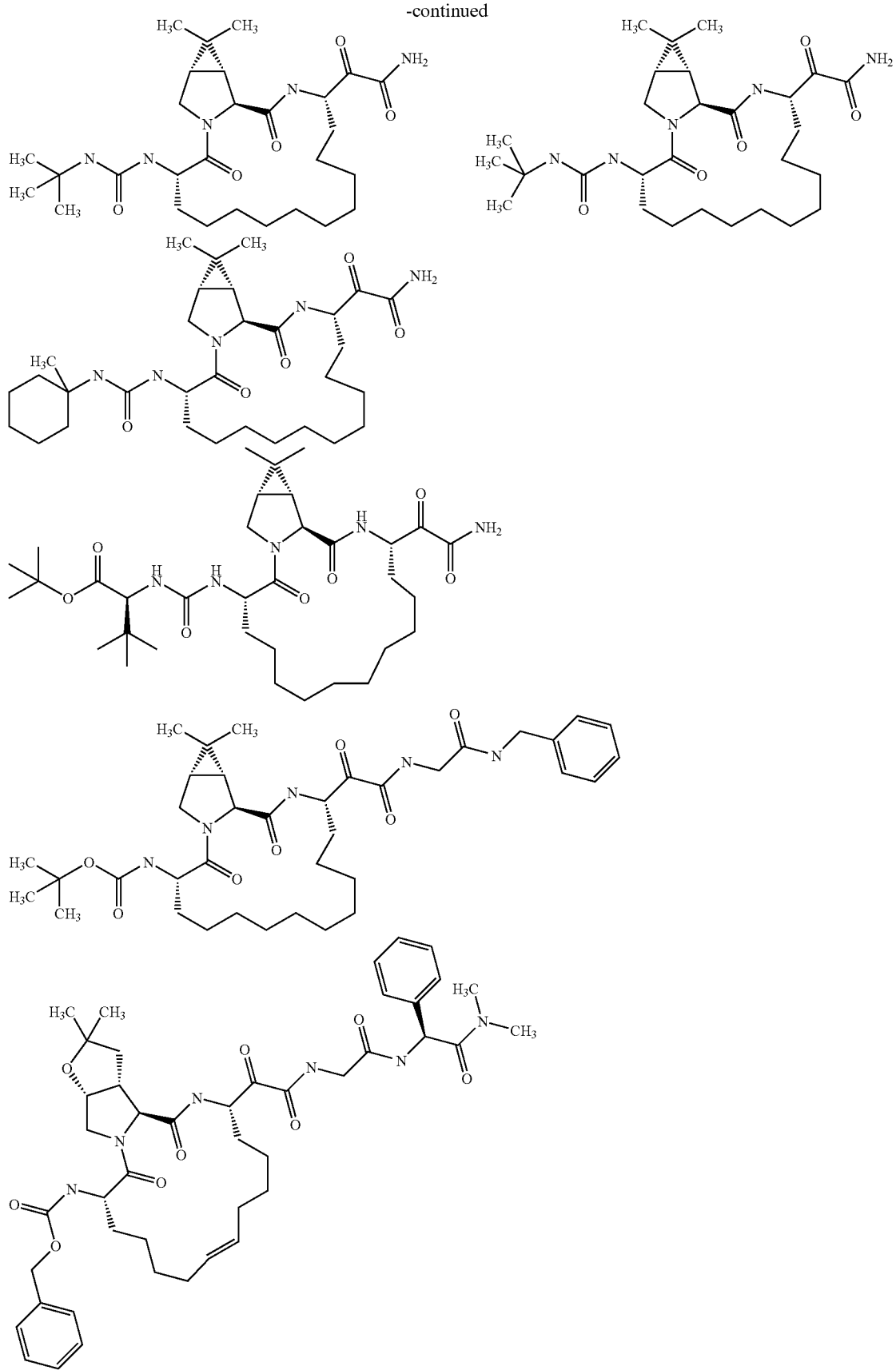

-continued
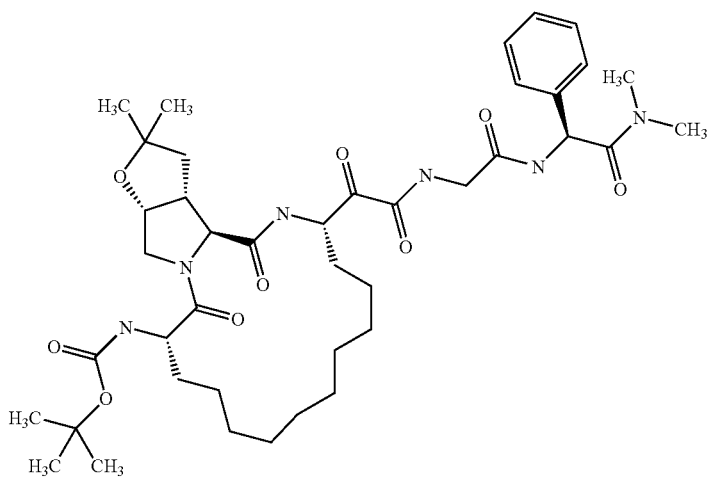
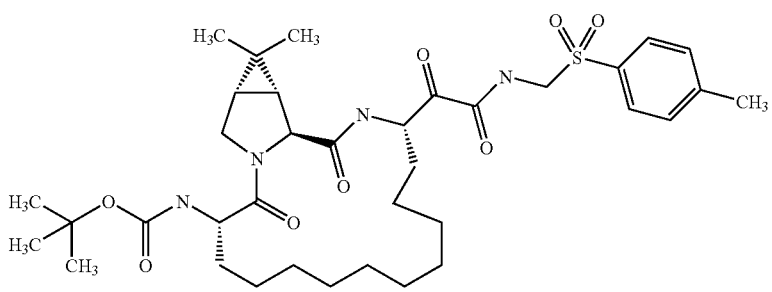
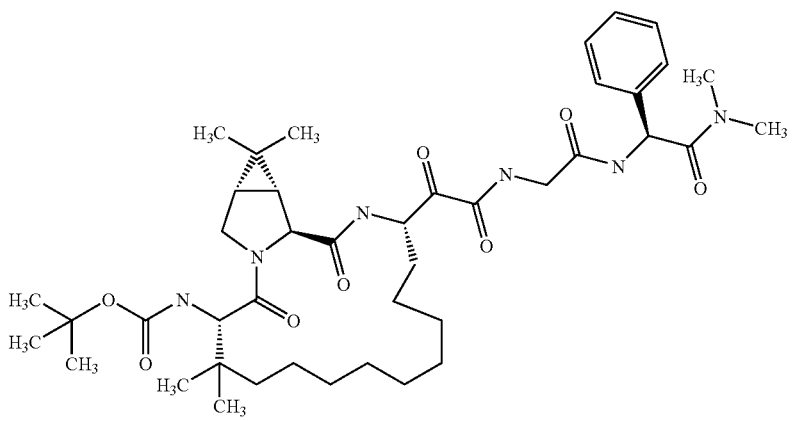
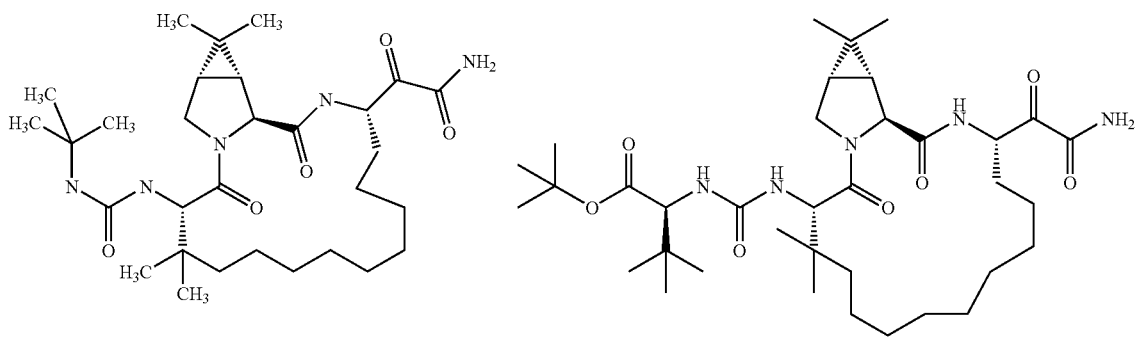

-continued
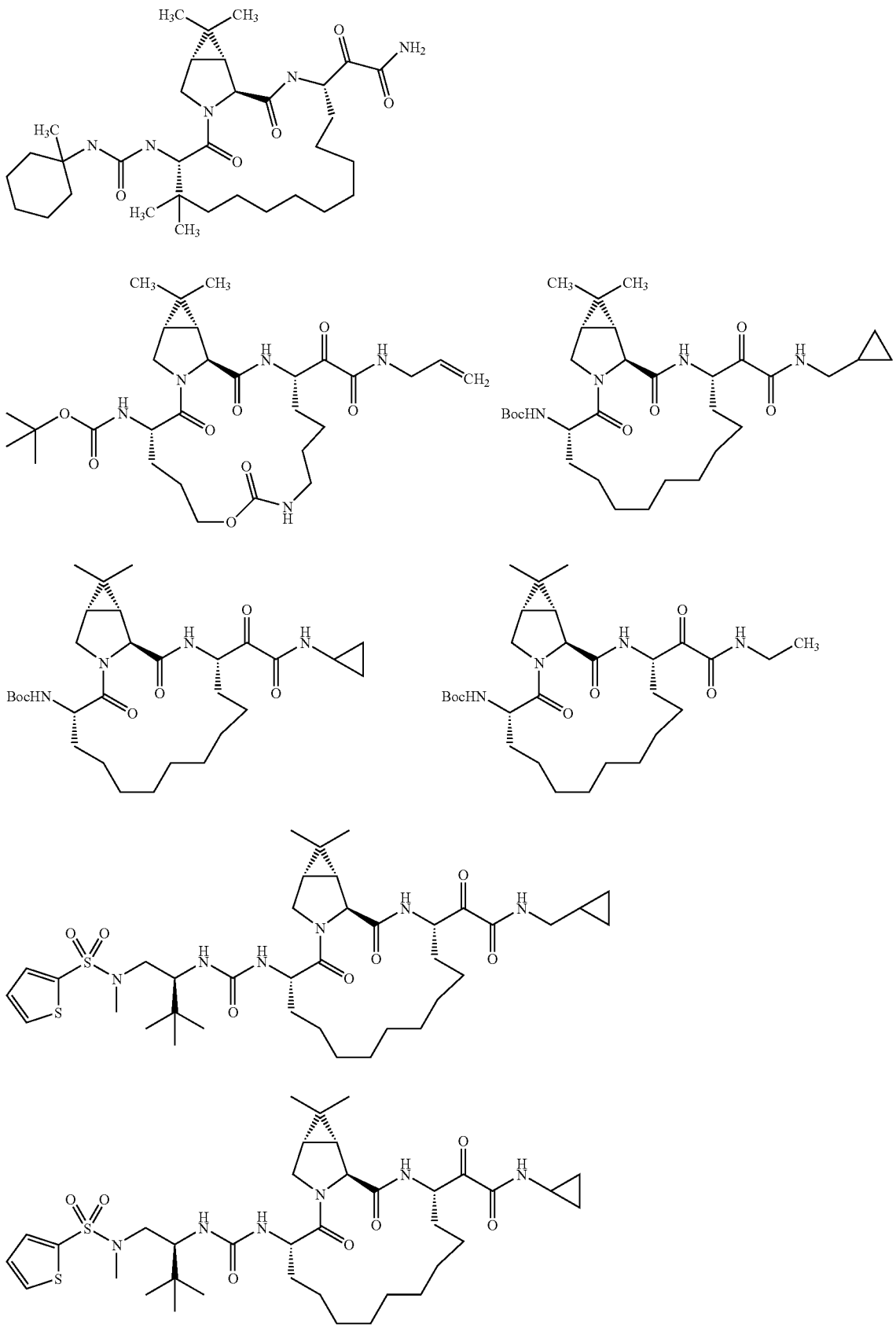

-continued
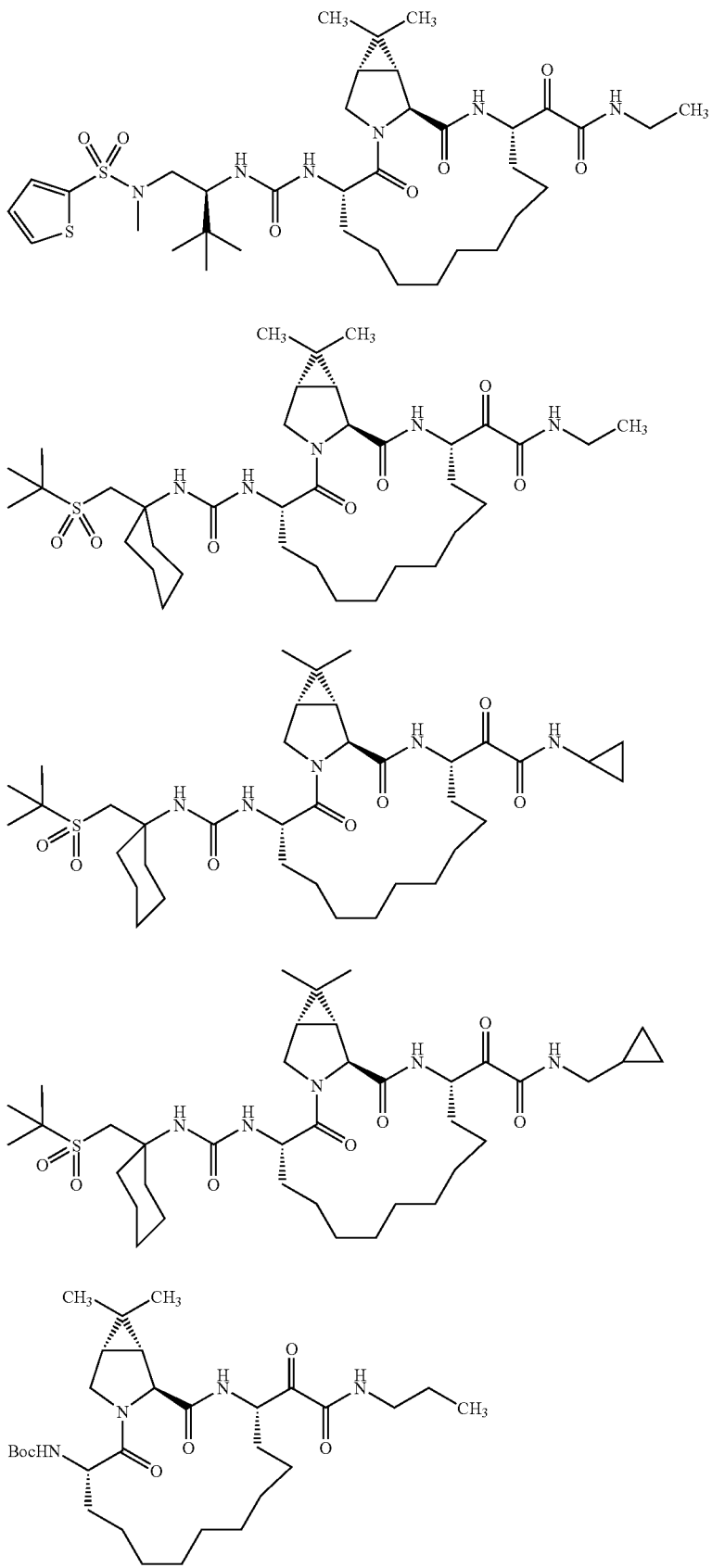

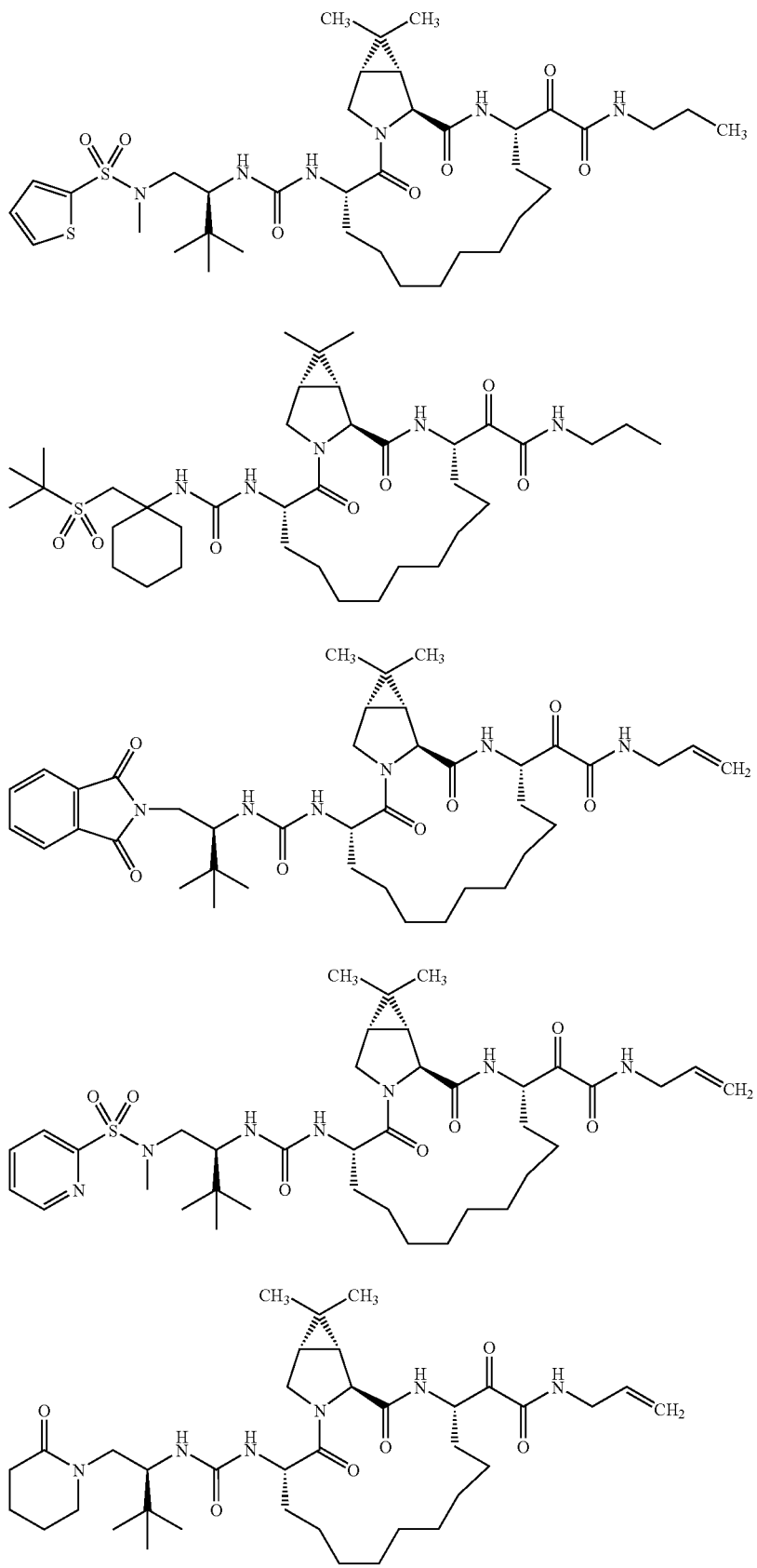

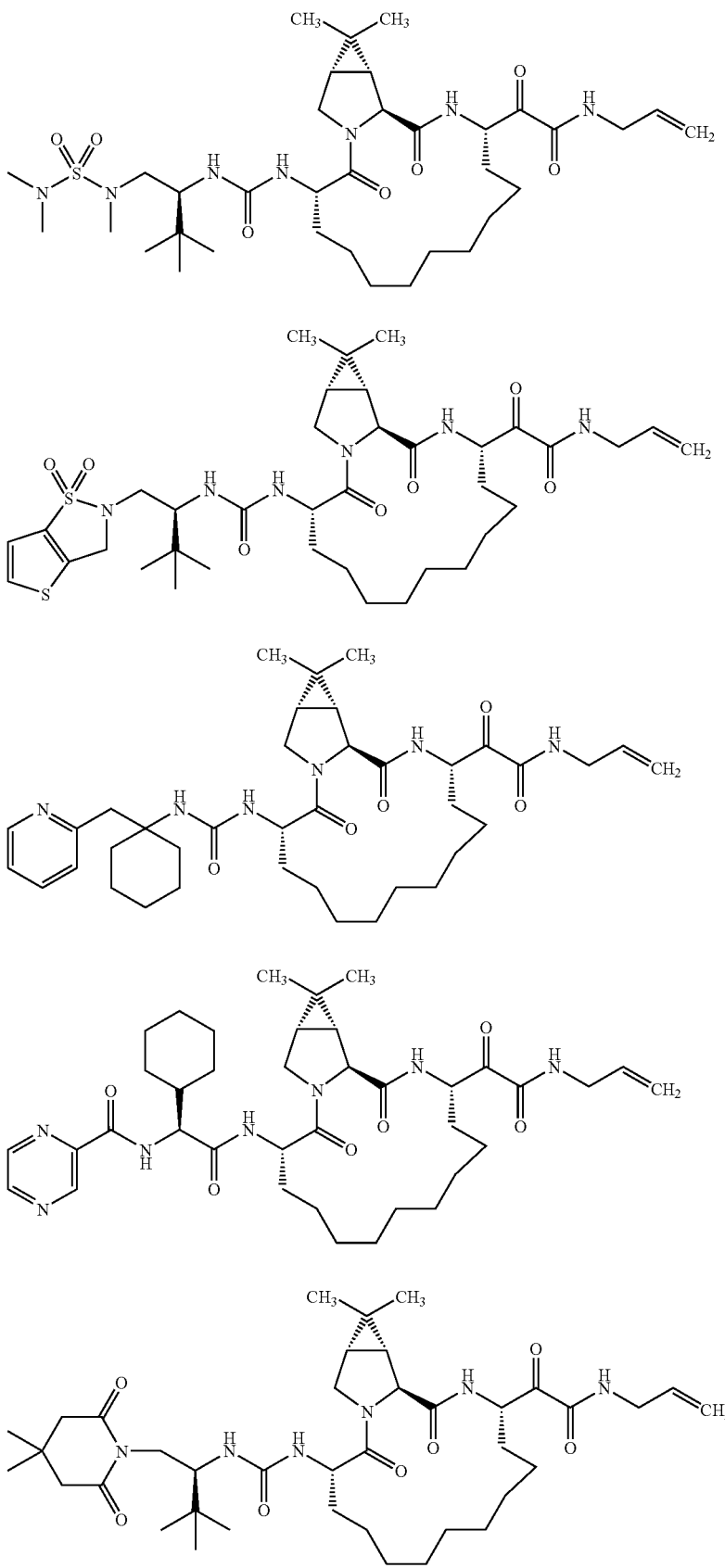

-continued
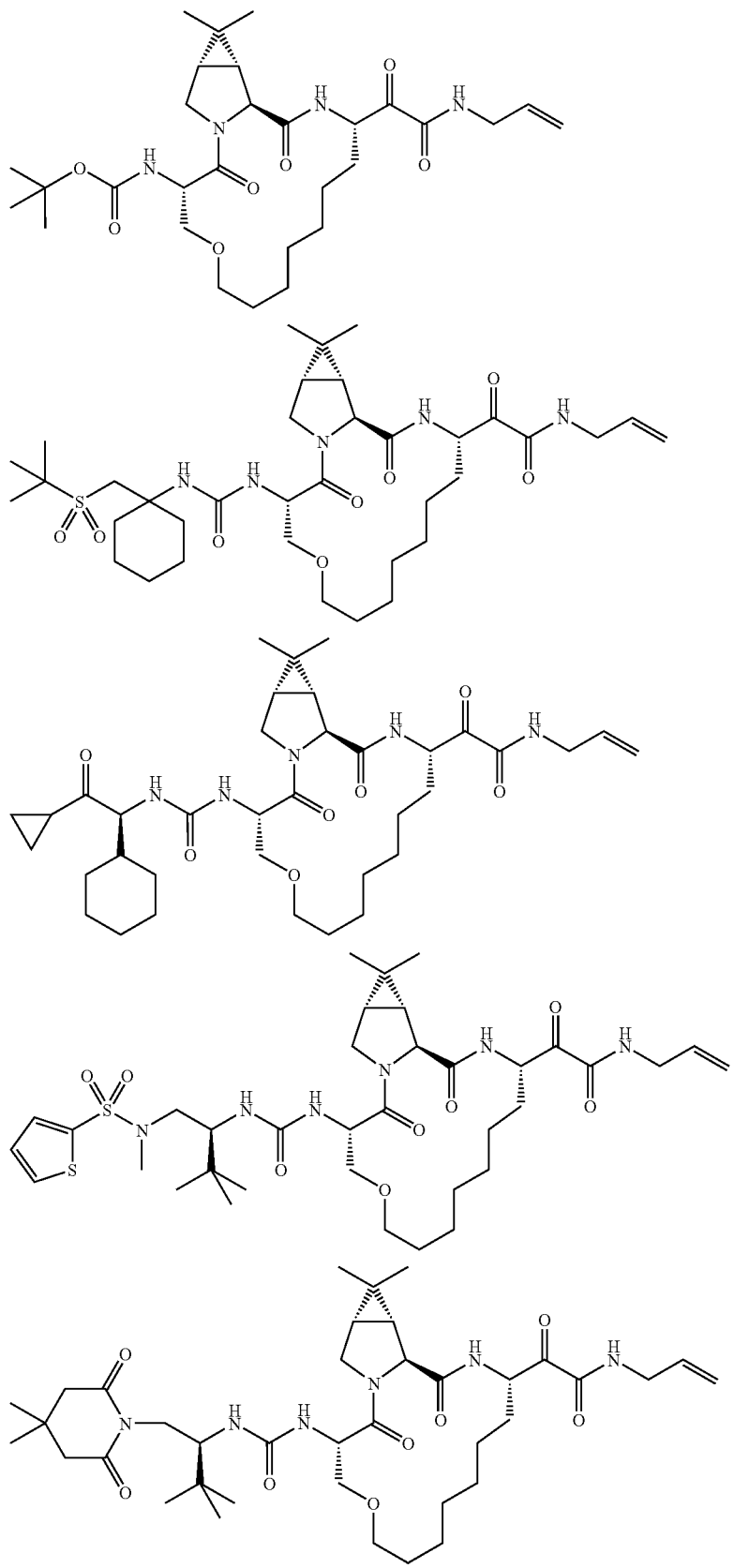

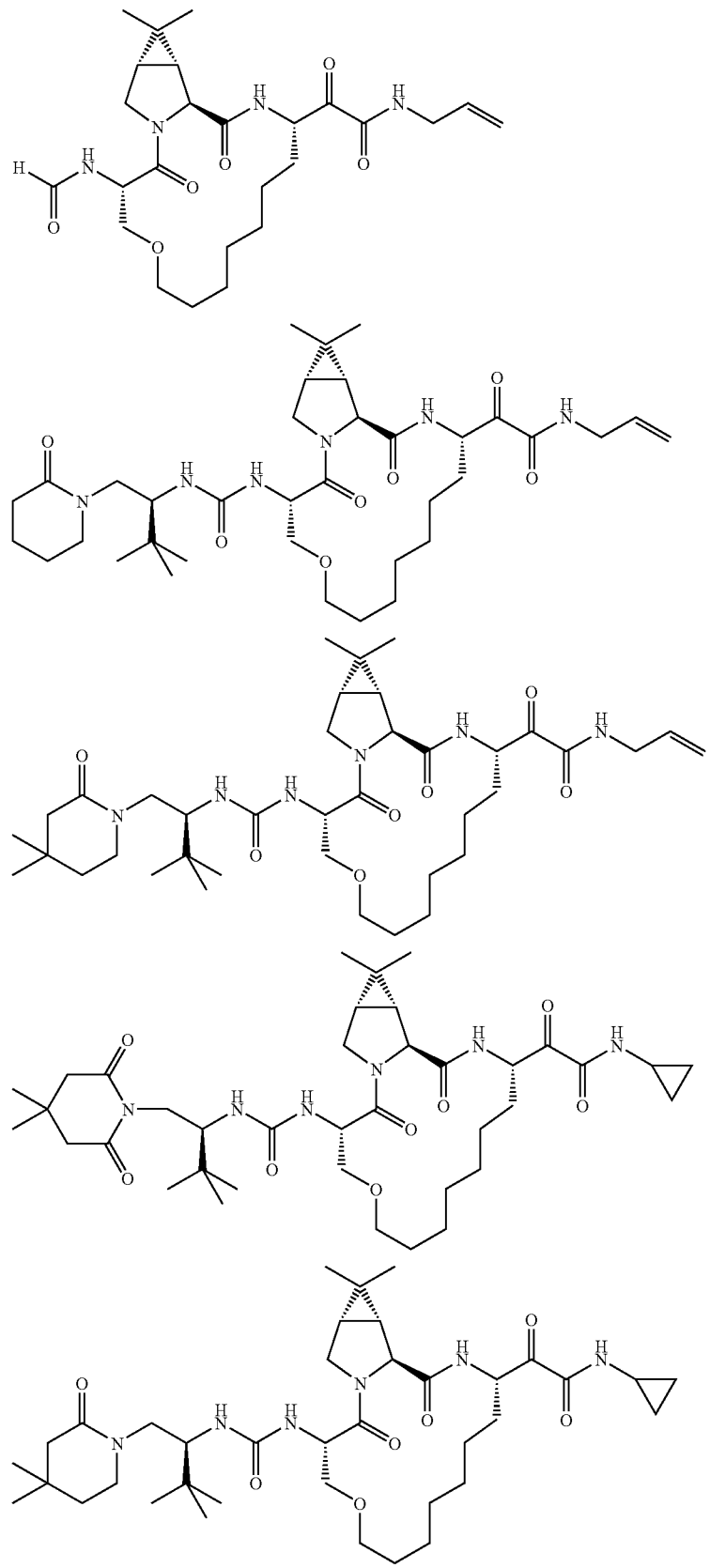

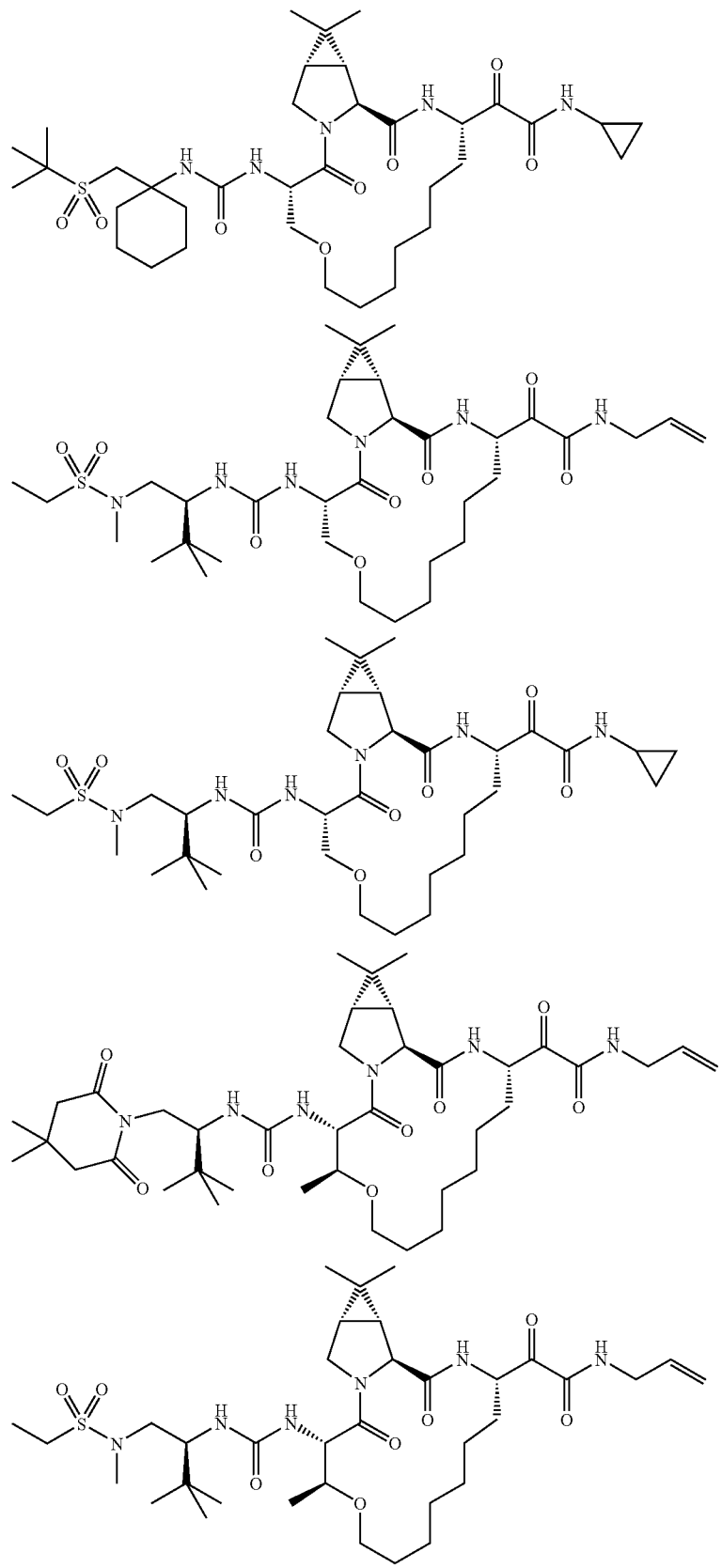

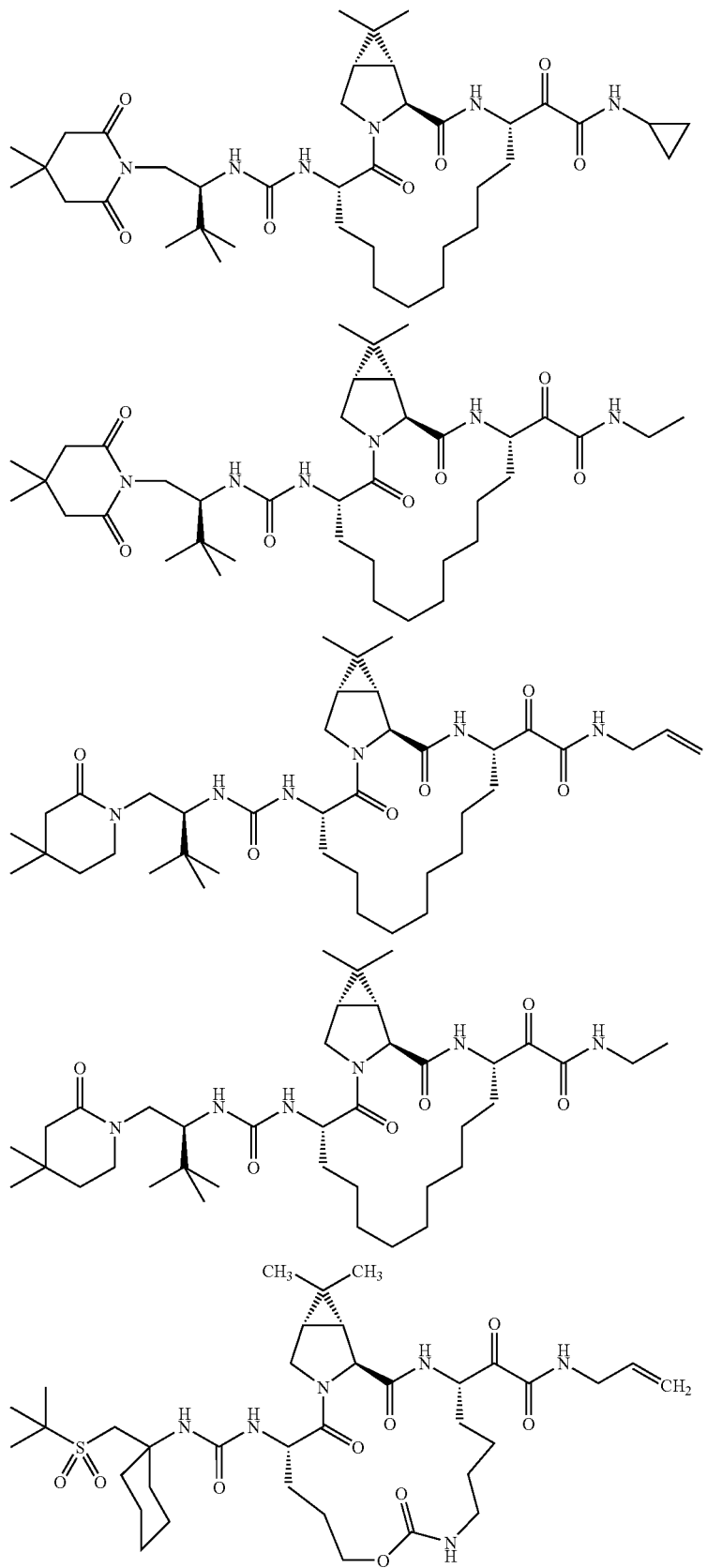

-continued
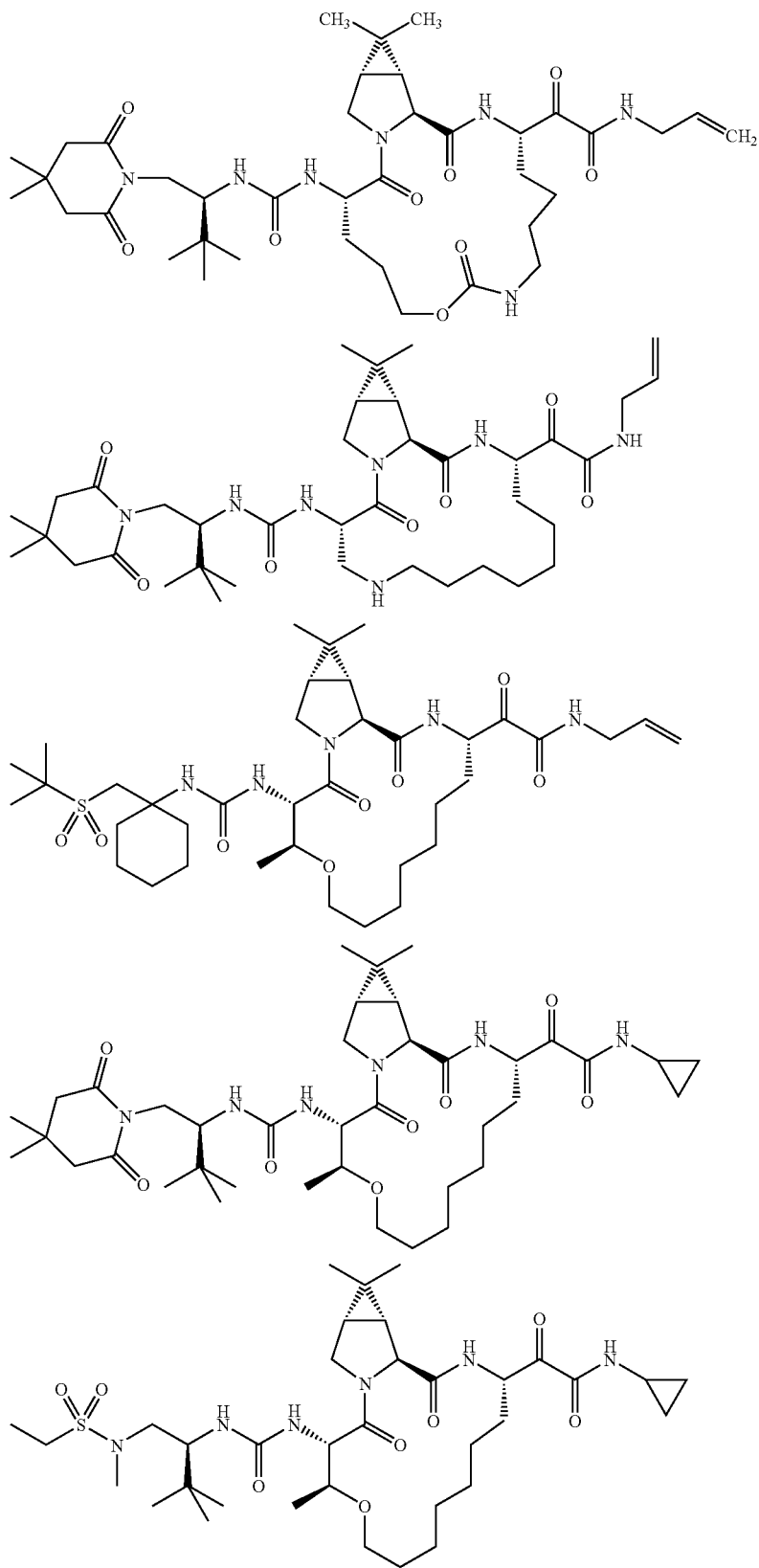

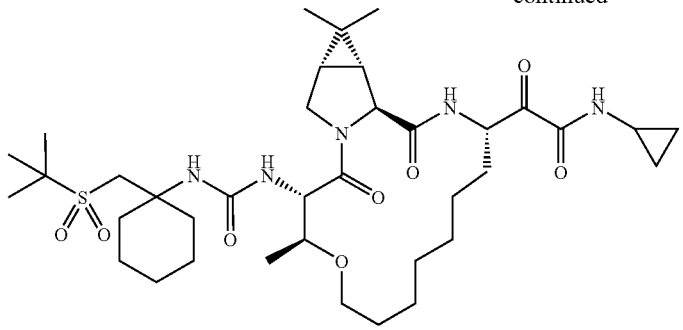

In still yet another aspect of the invention there is provided a pharmaceutical composition comprising as an active ingredient a compound of Formula 1 which is for use in treating disorders associated with HCV. The composition would generally include a pharmaceutically acceptable carrier. The composition may contain one or more additional agents such as, for example, an antiviral agent, an interferon or pegylated interferon and the like. A preferred antiviral agent is ribavirin and a preferred interferon is α-interferon.

A method of treating disorders associated with the HCV protease comprises administering to a patient in need of such treatment therapeutically effective amounts of a compound of Formula 1, or a pharmaceutical composition which comprises therapeutically effective amounts of a compound of Formula 1. The administration may be oral or subcutaneous.

The compounds of Formula 1 may be used for the manufacture of a medicament to treat disorders associated with the HCV protease, for example, the method comprising bringing into intimate contact a compound of Formula 1 a pharmaceutically acceptable carrier. These and other aspects of the invention are described in further detail below.

In embodiments described above, the present invention discloses compounds of Formula 1 as inhibitors of HCV protease, especially the HCV NS3/NS4a serine protease, or a pharmaceutically acceptable derivative thereof, where the various definitions are given above.

In another embodiment, this invention provides pharmaceutical compositions comprising the inventive peptides as an active ingredient. The pharmaceutical compositions generally additionally comprise a pharmaceutically acceptable carrier diluent, excipient or carrier (collectively referred to herein as carrier materials). Because of their HCV inhibitory activity, such pharmaceutical compositions possess utility in treating hepatitis C and related disorders. The HCV inhibitory activity can also lead to use of the inventive compounds and/or compositions for treating diseases (e.g., AIDS, etc) that are associated or connected with HCV.

In yet another embodiment, the present invention discloses methods for preparing pharmaceutical compositions comprising the inventive compounds as an active ingredient. In the pharmaceutical compositions and methods of the present invention, the active ingredients will typically be administered in admixture with suitable carrier materials suitably selected with respect to the intended form of administration, i.e. oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Moreover, when desired or needed, suitable binders, lubricants, disintegrating agents and coloring agents may also be incorporated in the mixture. Powders and tablets may be comprised of from about 5 to about 95 percent inventive composition.

Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum and the like.

Sweetening and flavoring agents and preservatives may also be included where appropriate. Some of the terms noted above, namely disintegrants, diluents, lubricants, binders and the like, are discussed in more detail below.

Additionally, the compositions of the present invention may be formulated in sustained release form to provide the rate controlled release of any one or more of the components or active ingredients to optimize the therapeutic effects, i.e. HCV inhibitory activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

Liquid form preparations include solutions, suspensions and emulsions. As an example may be mentioned water or water-propylene glycol solutions for parenteral injections or addition of sweeteners and pacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier such as inert compressed gas, e.g. nitrogen.

For preparing suppositories, a low melting wax such as a mixture of fatty acid glycerides such as cocoa butter is first melted, and the active ingredient is dispersed homogeneously therein by stirring or similar mixing. The molten homogeneous mixture is then poured into convenient sized molds, allowed to cool and thereby solidify.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions may take the form of creams, lotions, aerosols and/or emulsions and can be included in a transdermal patch of the matrix or reservoir type as are conventional in the art for this purpose.

The compounds of the invention may also be administered orally, intravenously, intranasally or subcutaneously.

The compounds of the invention may also comprise preparations which are in a unit dosage form. In such form, the preparation is subdivided into suitably sized unit doses containing appropriate quantities of the active components, e.g., an effective amount to achieve the desired purpose.

The quantity of the inventive active composition in a unit dose of preparation may be generally varied or adjusted from about 1.0 milligram to about 1,000 milligrams, preferably from about 1.0 to about 950 milligrams, more preferably from about 1.0 to about 500 milligrams, and typically from about 1 to about 250 milligrams, according to the particular application. The actual dosage employed may be varied depending upon the patient's age, sex, weight and severity of the condition being treated. Such techniques are well known to those skilled in the art.

Generally, the human oral dosage form containing the active ingredients can be administered 1 or 2 times per day. The amount and frequency of the administration will be regulated according to the judgment of the attending clinician. A generally recommended daily dosage regimen for oral administration may range from about 1.0 milligram to about 1,000 milligrams per day, in single or divided doses.

Some useful terms are described below:

Capsule—refers to a special container or enclosure made of methyl cellulose, polyvinyl alcohols, or denatured gelatins or starch for holding or containing compositions comprising the active ingredients. Hard shell capsules are typically made of blends of relatively high gel strength bone and pork skin gelatins. The capsule itself may contain small amounts of dyes, opaquing agents, plasticizers and preservatives.

Tablet—refers to a compressed or molded solid dosage form containing the active ingredients with suitable diluents. The tablet can be prepared by compression of mixtures or granulations obtained by wet granulation, dry granulation or by compaction.

Oral gel—refers to the active ingredients dispersed or solubilized in a hydrophillic semi-solid matrix.

Powder for constitution refers to powder blends containing the active ingredients and suitable diluents which can be suspended in water or juices.

Diluent—refers to substances that usually make up the major portion of the composition or dosage form. Suitable diluents include sugars such as lactose, sucrose, mannitol and sorbitol; starches derived from wheat, corn, rice and potato; and celluloses such as microcrystalline cellulose. The amount of diluent in the composition can range from about 10 to about 90% by weight of the total composition, preferably from about 25 to about 75%, more preferably from about 30 to about 60% by weight, even more preferably from about 12 to about 60%.

Disintegrant—refers to materials added to the composition to help it break apart (disintegrate) and release the medicaments. Suitable disintegrants include starches; "cold water soluble" modified starches such as sodium carboxymethyl starch; natural and synthetic gums such as locust bean, karaya, guar, tragacanth and agar; cellulose derivatives such as methylcellulose and sodium carboxymethylcellulose; microcrystalline celluloses and cross-linked microcrystalline celluloses such as sodium croscarmellose; alginates such as alginic acid and sodium alginate; clays such as bentonites; and effervescent mixtures. The amount of disintegrant in the composition can range from about 2 to about 15% by weight of the composition, more preferably from about 4 to about 10% by weight.

Binder—refers to substances that bind or "glue" powders together and make them cohesive by forming granules, thus serving as the "adhesive" in the formulation. Binders add cohesive strength already available in the diluent or bulking agent. Suitable binders include sugars such as sucrose; starches derived from wheat, corn rice and potato; natural gums such as acacia, gelatin and tragacanth; derivatives of seaweed such as alginic acid, sodium alginate and ammonium calcium alginate; cellulosic materials such as methylcellulose and sodium carboxymethylcellulose and hydroxypropylmethylcellulose; polyvinylpyrrolidone; and inorganics such as magnesium aluminum silicate. The amount of binder in the composition can range from about 2 to about 20% by weight of the composition, more preferably from about 3 to about 10% by weight, even more preferably from about 3 to about 6% by weight.

Lubricant—refers to a substance added to the dosage form to enable the tablet, granules, etc. after it has been compressed, to release from the mold or die by reducing friction or wear. Suitable lubricants include metallic stearates such as magnesium stearate, calcium stearate or potassium stearate; stearic acid; high melting point waxes; and water soluble lubricants such as sodium chloride, sodium benzoate, sodium acetate, sodium oleate, polyethylene glycols and d'l-leucine. Lubricants are usually added at the very last step before compression, since they must be present on the surfaces of the granules and in between them and the parts of the tablet press. The amount of lubricant in the composition can range from about 0.2 to about 5% by weight of the composition, preferably from about 0.5 to about 2%, more preferably from about 0.3 to about 1.5% by weight.

Glident—material that prevents caking and improve the flow characteristics of granulations, so that flow is smooth and uniform. Suitable glidents include silicon dioxide and talc. The amount of glident in the composition can range from about 0.1% to about 5% by weight of the total composition, preferably from about 0.5 to about 2% by weight.

Coloring agents—excipients that provide coloration to the composition or the dosage form. Such excipients can include food grade dyes and food grade dyes adsorbed onto a suitable adsorbent such as clay or aluminum oxide. The amount of the coloring agent can vary from about 0.1 to about 5% by weight of the composition, preferably from about 0.1 to about 1%.

Bioavailability—refers to the rate and extent to which the active drug ingredient or therapeutic moiety is absorbed into the systemic circulation from an administered dosage form as compared to a standard or control.

Conventional methods for preparing tablets are known. Such methods include dry methods such as direct compression and compression of granulation produced by compaction, or wet methods or other special procedures. Conventional methods for making other forms for administration such as, for example, capsules, suppositories and the like are also well known.

Another embodiment of the invention discloses the use of the pharmaceutical compositions disclosed above for treatment of diseases such as, for example, hepatitis C and the like. The method comprises administering a therapeutically effective amount of the inventive pharmaceutical composition to a patient having such a disease or diseases and in need of such a treatment.

In yet another embodiment, the compounds of the invention may be used for the treatment of HCV in humans in monotherapy mode or in a combination therapy (e.g., dual combination, triple combination etc.) mode such as, for example, in combination with antiviral and/or immunomodulatory agents. Examples of such antiviral and/or immunomodulatory agents include Ribavirin (from Schering-Plough Corporation, Madison, N.J.) and Levovirin™ (from ICN Pharmaceuticals, Costa Mesa, Calif.), VP 50406™ (from Viropharma, Incorporated, Exton, Pa.), ISIS 14803™ (from ISIS Pharmaceuticals, Carlsbad, Calif.), Heptazyme™ (from Ribozyme Pharmaceuticals, Boulder, Colo.), VX 497™ (from Vertex Pharmaceuticals, Cambridge, Mass.), Thymosin™ (from SciClone Pharmaceuticals, San Mateo, Calif.), Maxamine™ (Maxim Pharmaceuticals, San Diego, Calif.), mycophenolate mofetil (from Hoffman-LaRoche, Nutley, N.J.), interferon (such as, for example, interferon-alpha, PEG-interferon alpha conjugates) and the like. "PEG-interferon alpha conjugates" are interferon alpha molecules covalently attached to a PEG molecule. Illustrative PEG-interferon alpha conjugates include interferon alpha-2a (Roferon™, from Hoffman La-Roche, Nutley, N.J.) in the form of pegylated interferon alpha-2a (e.g., as sold under the trade name PegaSys™), interferon alpha-2b (Intron™, from Schering-Plough Corporation) in the form of pegylated interferon alpha-2b (e.g., as sold under the trade name PEG-Intron™), interferon alpha-2c (Berofor Alpha™, from Boehringer Ingelheim, Ingelheim, Germany) or consensus interferon as defined by determination of a consensus sequence of naturally occurring interferon alphas (Infergen™, from Amgen, Thousand Oaks, Calif.).

As stated earlier, the invention includes tautomers, rotamers, enantiomers and other stereoisomers of the inventive compounds also. Thus, as one skilled in the art appreciates, some of the inventive compounds may exist in suitable isomeric forms. Such variations are contemplated to be within the scope of the invention.

Another embodiment of the invention discloses a method of making the compounds disclosed herein. The compounds may be prepared by several techniques known in the art. Representative illustrative procedures are outlined in the following reaction schemes. The invention disclosed herein is then further exemplified by preparative examples and example compounds which should not be construed to limit the scope of the invention which is defined in the appended claims. Alternative mechanistic pathways and analogous structures will be apparent to those skilled in the art.

It is to be understood that while the following illustrative schemes describe the preparation of a few representative inventive compounds, suitable substitution of any of both the natural and unnatural amino acids will result in the formation of the desired compounds based on such substitution. Such variations are contemplated to be within the scope of the invention.

For the procedures described below, the following abbreviations are used:
AcOH: Acetic acid
ADDP: 1,1'-(Azodicarbobyl)dipiperidine
Boc means t-butyloxy or tert-Butyloxycarbonyl
$^t$Bu, TBu or Bu$^t$: tert-Butyl
Cbz: Benzyloxycarbonyl
Bop: Benzotriazol-1-yl-oxy-tris(dimethylamino) hexafluorophosphate
Bn or Bzl: Benzyl
Bz: Benzoyl
Chg: Cyclohexylglycine
Cp: Cylcopentyldienyl
DCM means diclhloromethane;
DCC: 1,3-Dicyclohexylcarbodiimide
DEAD: Diethylazodicarboxylate
DMAP: 4-N,N-Dimethylaminopyridine
DMF means N,N-dimethylformamide;
DMSO means dimethyl sulfoxide;
EDCl: 1-(3-dimethylaminopropyl)-3-ethylcarbodiimide hydrochloride;
Et: Ethyl;
EtOAc means ethyl acetate;
Et$_2$O: Diethyl ether;
HATU means O-(7-azabenzotriazol-1-yl)-1,1,3,3-tetramethyluronium;
HOOBt: 3-Hydroxy-1,2,3-benzotriazin-4(3H)-one;
HOBt: N-Hydroxybenzotriazole;
iBoc: isobutoxycarbonyl;
iPr: isopropyl;
KHMDS means Potassium hexamethyl disilylamide;
LiHMDS means hexamethyldisilazide;
Me: Methyl;
MS means mass spectrum;
nBuLi means n-butyl lithium;
NMM means N-methyl morpholine;
NMR means nuclear magnetic resonance;
Phg: Phenylglycine;
Ph: Phenyl;
Pd/C means palladium on charcoal catalyst;
PyBrOP: Bromo-tris-pyrrolidinophosphonium hexafluorophosphate;
TBuNCO means t-butyl isocyanate;
TEMPO: 2,2,6,6-Tetramethyl-1-piperidinyloxy;
THF means tetrahydrofuran;
THP means tetrahydrofuran;
TMSI means trimethyl silyl iodide;
T$_3$N means triethylamine;
Ts: p-toluenesulfonyl.

Several of the intermediates and/or preparative examples used in the following synthetic procedures have been disclosed in WO 01/77113; WO 01/081325; WO 02/08198; WO 02/08256; WO 02/08187; WO 02/08244; WO 02/48172; WO 02/08251; and pending U.S. patent application Ser. No. 10/052,386, filed Jan. 18, 2002. The disclosures of those applications are incorporated herein by reference thereto.

GENERAL PREPARATIVE SCHEMES AND PROCEDURES FOR PREPARATIVE EXAMPLES

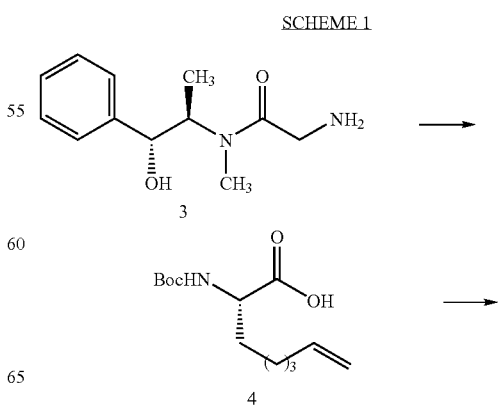

SCHEME 1

109
-continued
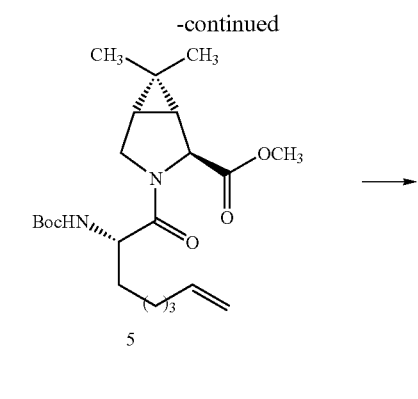
5
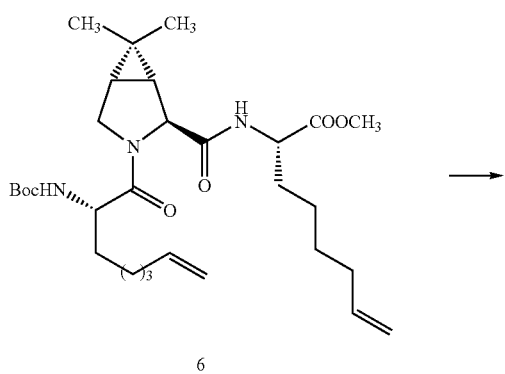
6
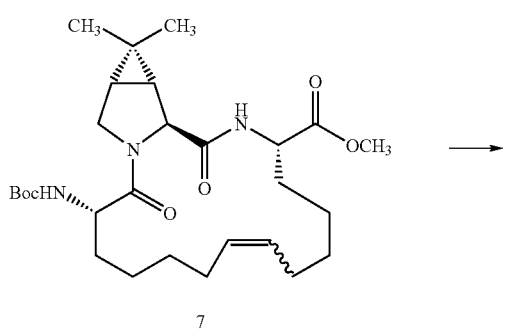
7
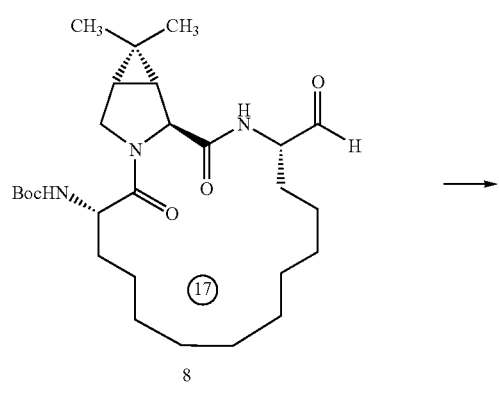
8
110
-continued
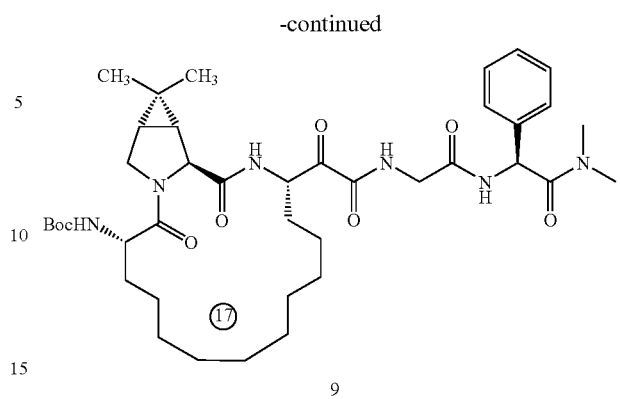
9
SCHEME 2
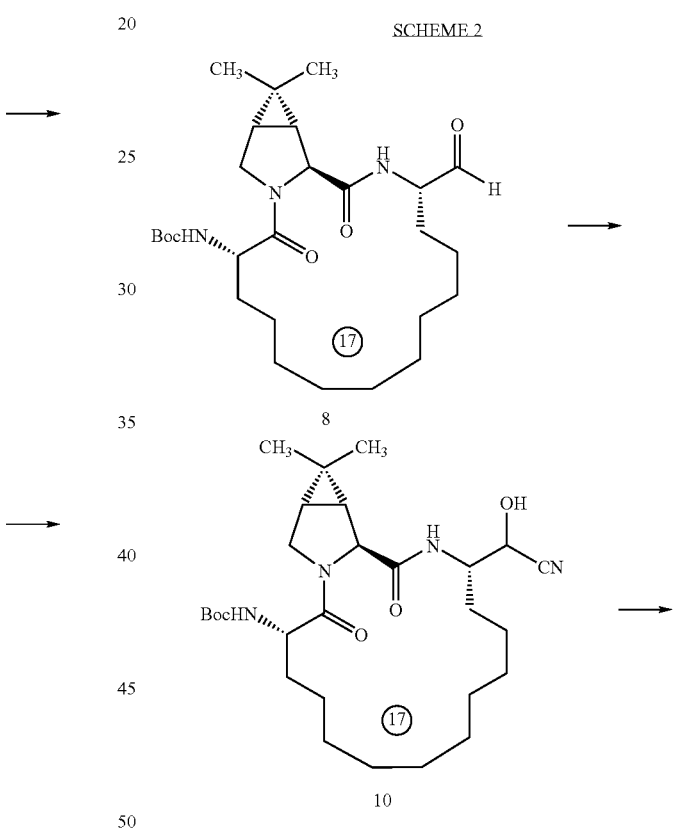
8
10
11

-continued

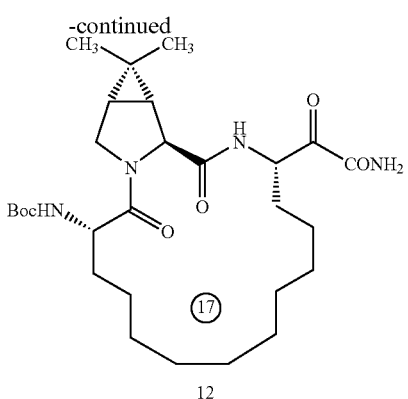

12

SCHEME 3

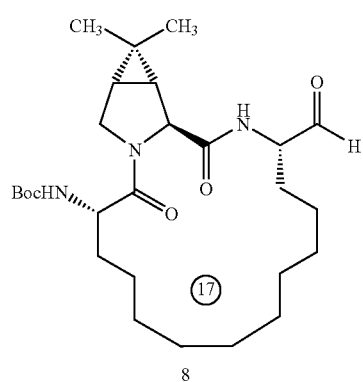

8

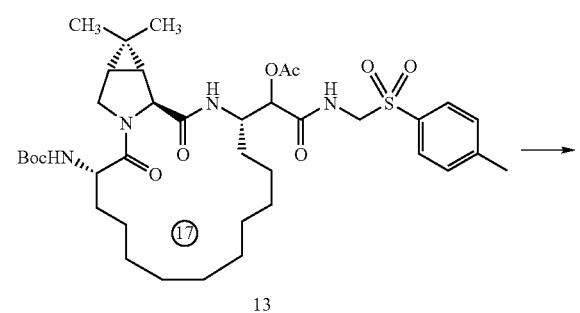

13

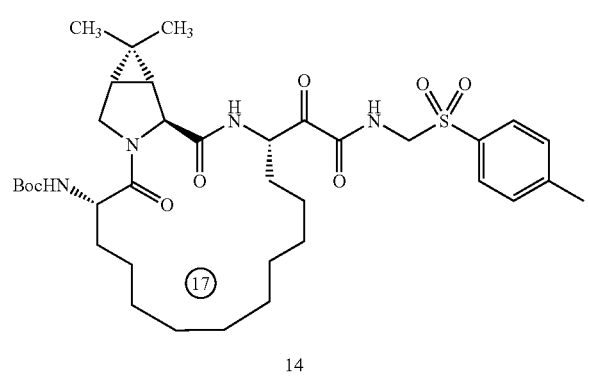

14

PROCEDURES FOR PREPARATIVE EXAMPLES

Preparative Example 1

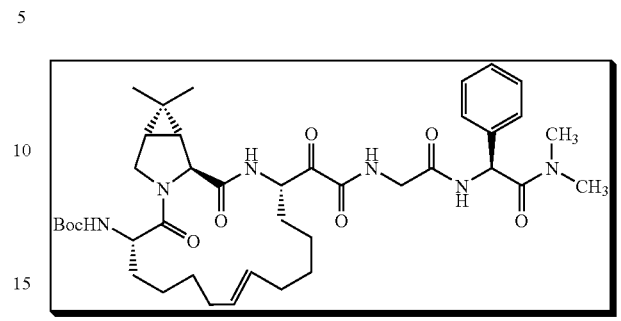

1

Step A

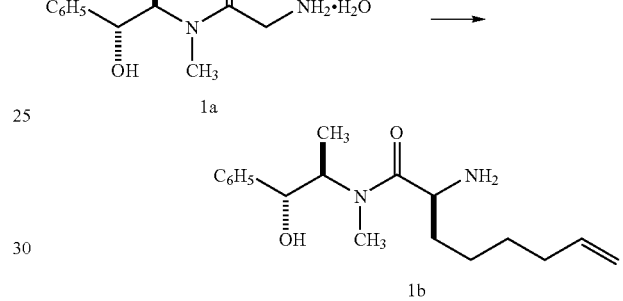

1a

1b

The synthesis of 1b can be accomplished using the procedure of (1) Myers, A. G.; Gleason, J. L.; Yoon, T.; Kung, D. W.; *J. Am. Chem. Soc* 1997, 119, 656; (2) Myers, A. G.; Schnider, P.; Kwon, S.; Kung, D. W.; *J. Org. Chem.*, 1999, 64, 3322.; or (3) Myers, A. G.; Gleason, J. L.; *Org. Synth.* 1998, 76, 57.

A solution of amine 1a (24 g, 120 mmol) in THF (300 mL) was treated with anhydrous LiCl (16.80 g, 400 mmol) over 0.5 h and stirred till the reaction mixture turns homogeneous. The reaction mixture was cooled to 0° C. and treated with a THF solution of LiHMDS (66.80 g, 400 mmol in 300 ml of THF) over 20 min. The reaction mixture was stirred at 0° C. for 0.5 h and treated with 6-bromohexene (19.44 g, 120 mmol) and stirred at rt. for 24 h. The reaction mixture was dissolved in aq. 1 M HCl and concentrated in vacuo to remove THF. The mostly aq. layer was further diluted with 3M aq HCl (300 mL) and extracted with ether (2×200 mL). The aqueous layer was basified to pH 14 using aq. NaOH (50%) and extracted with $CH_2Cl_2$ (3×300 mL). The combined organic layers were dried with $MgSO_4$ filtered concentrated in vacuo to yield crude 1b (15.1 g) that was used in next step without further purification.

Step B

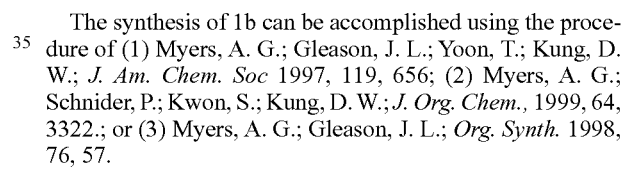

1b

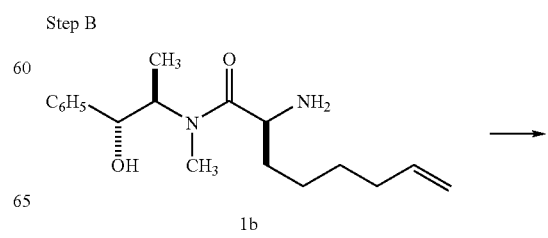

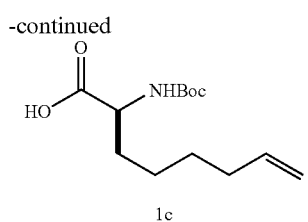

1c

A solution of 1b (12.5 g, 41.2 mmol) was dissolved in aq. NaOH (1 M, 88.0 mL, 88 mmol) and heated at reflux for 3 h. The reaction mixture was cooled to rt. and extracted with CH$_2$Cl$_2$ (3×100 mL). The aq. layer was treated with 100 mL of dioxane followed by NaHCO$_3$ (8.00 g, 95.2 mmol) and di-tertbutyl dicarbonate (8.95 g, 41 mmol) and stirred at rt. for 5 h. The reaction mixture was extracted with ether (2×250 mL) and the aqueous layer was acidified to pH~2 with aq. HCl and extracted with CH$_2$Cl$_2$ (2×200 mL). The combined organic layers were dried with MgSO$_4$, filtered concentrated in vacuo to yield acid 1c (10.8 g) as a colorless oil.

Step C

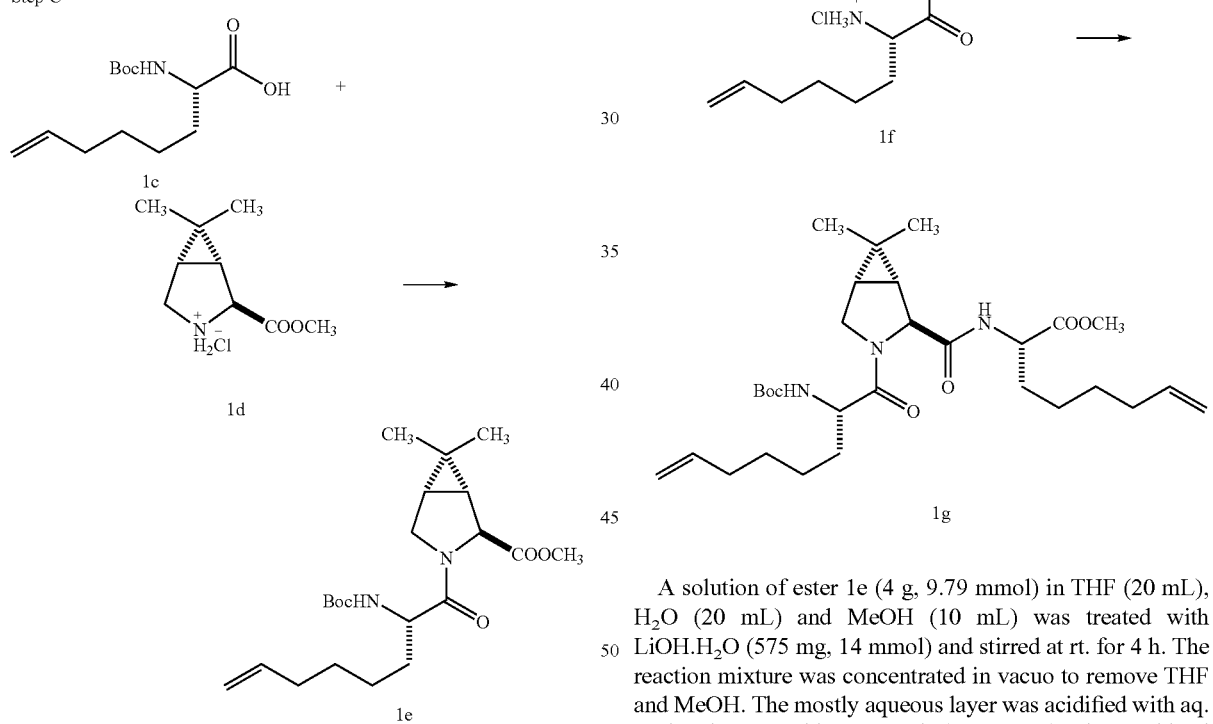

A solution of acid 1c (5 g, 19.44 mmol) and amine 1d (3.98 g, 19.44 mmol) in CH$_2$Cl$_2$ (30 mL), DMF (30 mL) at 0° C. was treated with HATU (8.87 g, 23.31 mmol) and NMM (4.91 g, 5.33 mL) and stirred overnight at 0° C. The reaction mixture was concentrated in vacuo and diluted with 650 mL of CH$_2$Cl$_2$. The aqueous layer was washed with aq. HCl (1M, 2×300 mL), aq. NaHCO$_3$ (1M, 2×300 mL). The organic layers were dried with MgSO$_4$, filtered concentrated in vacuo and purified by chromatography (SiO$_2$, Acetone/Hexanes 5:1) to yield 1e as a colorless oil (5.5 g).

$^1$H NMR: (CD$_3$OD, 300 MHz) δ5.87-5.76 (m, 1H), 4.97-4.92 (dd, 2H), 4.26 (bt, 1H, J=7.8 Hz), 3.98 (d, 1H, J=10.2 Hz), 3.61 (dd, 2H, J=5.1, 5.1 Hz), 3.73 (s, 3H), 2.14-2.07 (m, 2H), 1.74-1.42 (m, 9H), 1.41 (s, 9H), 1.12 (s, 3 H), 0.92 (s, 3H).

$^{13}$C NMR: (CD$_3$OD, 75 MHz), d 173.8, 173.2, 158.0, 139.8, 115.0, 80.4, 60.91, 53.42, 52.80, 34.7, 33.5, 32.3, 31.4, 29.8, 28.7, 26.4, 26.1, 20.6, 12.9.

Step D

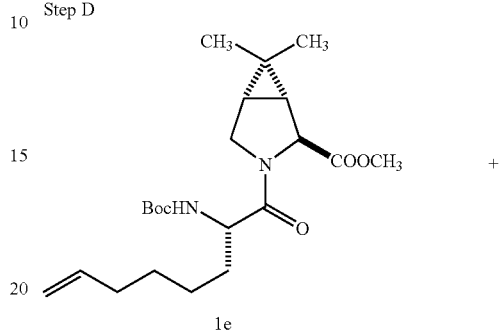

A solution of ester 1e (4 g, 9.79 mmol) in THF (20 mL), H$_2$O (20 mL) and MeOH (10 mL) was treated with LiOH.H$_2$O (575 mg, 14 mmol) and stirred at rt. for 4 h. The reaction mixture was concentrated in vacuo to remove THF and MeOH. The mostly aqueous layer was acidified with aq. HCl and extracted into CH$_2$Cl$_2$ (3×100 mL). The combined organic layers were dried with MgSO$_4$, filtered, concentrated in vacuo and used as it is.

A solution of acid obtained from hydrolysis of 1e, amine segment 1f (2.02 g, 9.79 mmol) in DMF (40 mL), CH$_2$Cl$_2$ (40 mL) at 0° C. was treated with HATU (4.46 g, 11.84 mmol) and NMM (3.5 g, 35 mmol) and stirred at 0° C. for 24 h. The reaction mixture was concentrated in vacuo and diluted with aq. HCl (100 mL). The aqueous layer was extracted with CH$_2$Cl$_2$ (3×75 mL). The combined organic layers were washed with aq saturated NaHCO$_3$ (3×100 mL), brine dried with MgSO$_4$, filtered concentrated in vacuo and purified by silica gel chromatography (EtOAc/Hex 1:3) to yield 1 g (4.5 g) as a colorless foam.

Step E

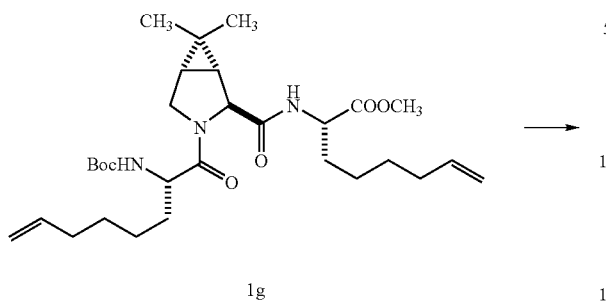

1g

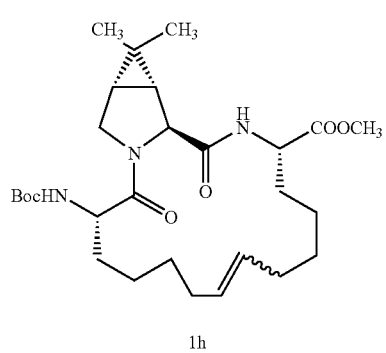

1h

A solution of diene 1 g (1.1 g, 2.0 mmol) in dry CH$_2$Cl$_2$ (20 mL) was treated with Grubbs catalyst [(Cy)$_3$RuCl$_2$=CHC$_6$H$_5$, 83.8 mg, 0.1 mmol) and stirred at rt. for 24 h. The reaction mixture was concentrated in vacuo and purified by chromatography (SiO$_2$, EtOAc/Hex 1:3) to yield 1 h (501 mg) as a colorless solid and mixture of E/Z isomers.

$^1$H NMR (CDCl$_3$, 300 MHz) δ, 7.38 (d, 1H, J=8.1 Hz), 5.30-5.18 (m, 2H), 4.55 (dt, 1H, J=2.4, 9.6 Hz), 3.92 (bs, 1H), 3.77 (s, 3H), 3.79-3.77 (bm, 1H), 2.06-2.1 (bm, 3H). 1.95-1.81 (m, 2H), 1.79-1.77 (m, 13H), 1.31 (s, 9H), 1.05 (s, 3H), 0.85 (s, 3H).

MS (ESI), m/z, relative intensity 542 [(M+Na)$^+$ 45], 464 (20), 448 (25) 420 (100).

Step F

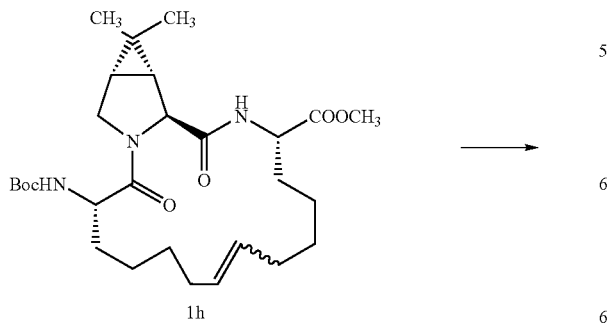

1h

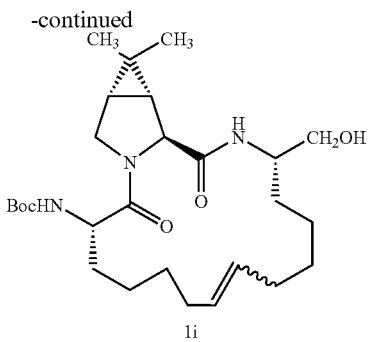

1i

A solution of ester 1h (100 mg, 0.19 mmol) in dry THF (1 mL) was treated with LiBH$_4$ (2M soln. in THF, 0.2 mL) and stirred at rt. for 16 h. The reaction mixture was quenched with aqueous HCl (1M, 30 mL) and extracted with CH$_2$Cl$_2$ (3×30 mL). The combined organic layers were washed with aq. NaHCO$_3$ (100 ml) brine, dried with MgSO$_4$ filtered concentrated in vacuo and purified by chromatography (SiO$_2$, acetone/hexanes 1:3) to yield 1i (70 mg) as an amorphous solid.

$^1$H NMR (CDCl$_3$, 300 MHz) δ 6.96 (d, 1H, J=8.1 Hz), 5.32-5.21 (m, 2H), 4.43-4.37 (m, 2H) 4.01-3.93 (m, 1H), 3.77 (dd, 1H, J=5.7, 4.8 Hz), 3.65 (dd, 1H, J=3.9, 6.6 Hz), 3.53 (dd, 1H, J=6.0, 10.8 Hz), 2.11-1.77 (m, 6H), 1.55-1.31 (m, 12H), 1.45 (s, 9H), 1.05 (s, 3H), 0.87 (s, 3H).

MS (ESI), m/z, relative intensity 530 [(M+K)$^+$, 10], 514 [(M+Na)$^+$, 70], 492 [(M+1)$^+$, 20], 392 (100).

Step H

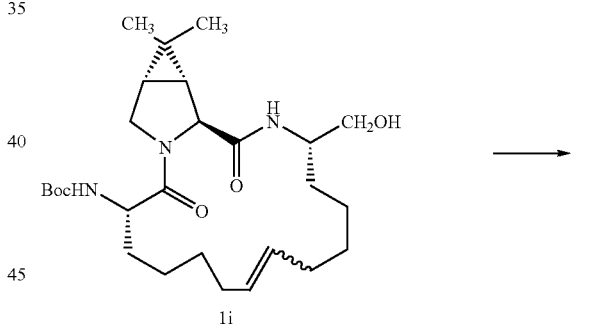

1i

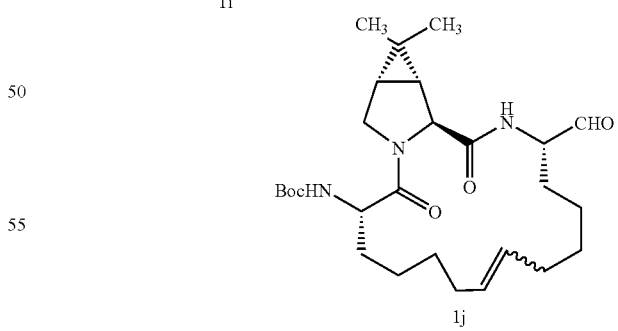

1j

A solution of alcohol 1i (70 mg, 0.15 mmol), in CH$_2$Cl$_2$ (3 mL) was treated with Dess Martin reagent (85 mg, 0.2 mmol) and stirred at rt. for 2 h. The reaction mixture was quenched with Na$_2$S$_2$O$_3$ solution (10%, 10 mL) and saturated NaHCO$_3$ solution (10 mL) and stirred at rt. for 0.5 h. The reaction mixture was extracted with CH$_2$Cl$_2$ (50 mL). The organic layer was dried with MgSO$_4$, filtered concentrated in vacuo and purified by chromatography (SiO$_2$, acetone/hexanes 4:1) to yield lj (50 mg) as a colorless fluffy solid.

$^1$H NMR (CDCl$_3$, 300 MHz) δ9.54 (s, 1H), 7.43 (d, 1H, J=7.8 Hz), 5.30-5.19 (m, 2H), 4.55-4.40 (m, 2H), 3.93 (d, 1H, J=10.2 Hz), 3.77 (dd, 1H, J=5.4, 5.1 Hz), 2.04-1.78 (m, 4H), 1.55-1.27 (m, 14), 1.31 (s, 9H), 1.02 (s, 3H), 0.95 (s, 3H).

MS (ESI), m/z, relative intensity 512 [(M+Na)$^+$, 80], 490 [(M+1)$^+$, 10], 434 (20), 390 (100).

Step I

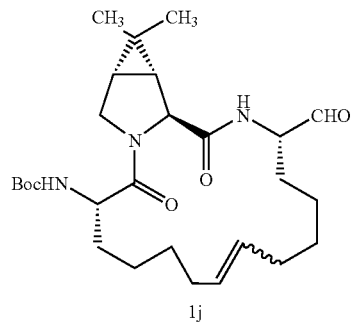

1j

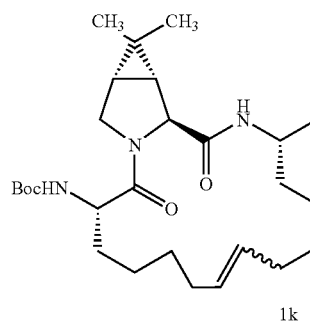

1k

A solution of aldehyde 1j (50 mg, 0.11 mmol) in dry CH$_2$Cl$_2$ (2 mL) was treated with CH$_3$COOH (19 mg, 0.31 mmol) and methylisocyanoacetate (31 mg, 0.31 mmol). The reaction mixture was stirred at rt. for 48 h and concentrated in vacuo. The residue was purified by chromatography (SiO$_2$, acetone/hexanes 1:2) to yield 1k (50 mg) as a mixture of diastereomers. MS (ESI), m/z, relative intensity 671 [(M+Na)$^+$, 45], 649 [(M+1)$^+$, 30], 549 (100).

Step J

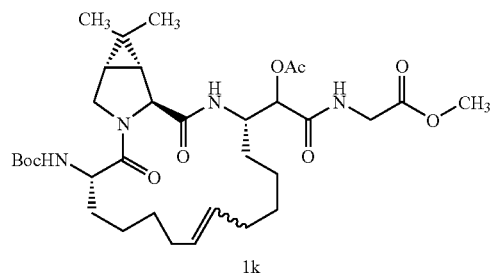

1k

-continued

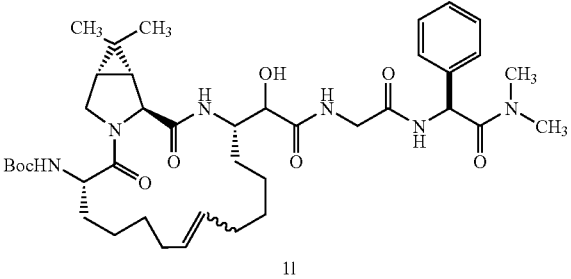

11

A solution of methyl ester 1k (50 mg, 0.078 mmol) in THF (2 mL), H$_2$O (2 mL) and CH$_3$OH (2 mL) was treated with LiOH.H$_2$O (20 mg, 0.5 mmol) and stirred at rt. for 2 h. After the completion of the reaction it was acidified with aq. HCl (2 mL) and concentrated in vacuo. The residue was dried in vacuo and used as it with out further purification.

The acid was dissolved in CH$_2$Cl$_2$ (2 mL), DMF (2 mL) and treated with H-Phg-N(CH)$_2$.HCl (26 mg, 0.12 mmol), NMM (32 mg, 0.32 mmol) HATU (45 mg, 0.12 mmol) and stirred at 0° C. for 24 h. The yellow colored solution was concentrated in vacuo and diluted with CH$_2$Cl$_2$ (70 mL). The organic layers were washed with saturated aq. NaHCO$_3$, aq. HCl and brine. The reaction mixture was dried (MgSO$_4$) filtered concentrated in vacuo and used as it is in next step (47 mg).

Step K

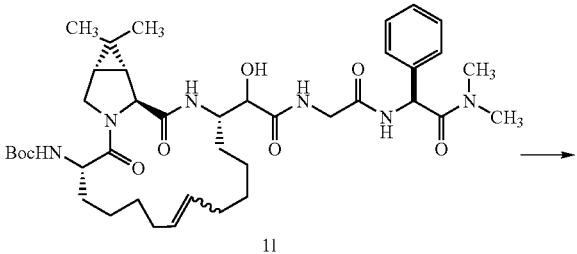

11

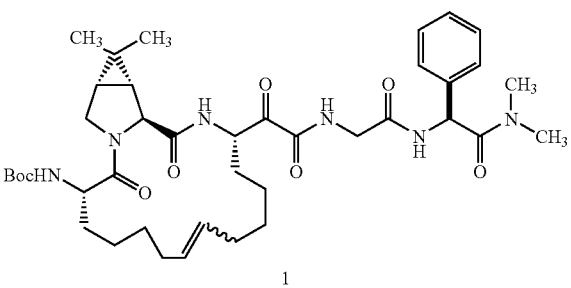

1

A solution of alcohol 11 (50 mg, 0.066 mmol) in CH$_2$Cl$_2$ (2 mL) was treated with Dess-Martin reagent (60 mg, 0.14 mmol) and stirred at rt. for 2 h. The reaction was diluted with aq Na$_2$S$_2$O$_3$ solution and aq. NaHCO$_3$ solution (20 mL each) and extracted with CH$_2$Cl$_2$ (50 mL). The organic layer was washed with satd. NaHCO$_3$, brine, dried with MgSO$_4$ filtered concentrated in vacuo and purified by chromatography (acetone/hexanes 2:3) to yield 1 (22 mg) as a colorless solid.

MS (ESI), m/z, relative intensity 773 [(M+Na)$^+$, 80], 751 [(M+1)$^+$, 60], 651 (100).

Preparative Example 2

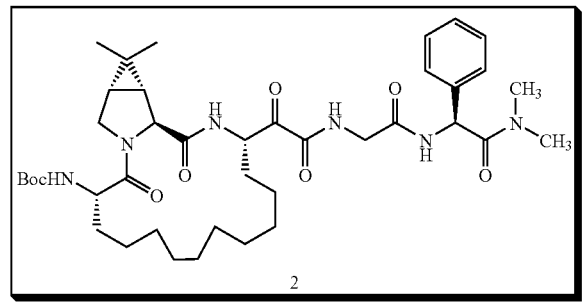

Step A

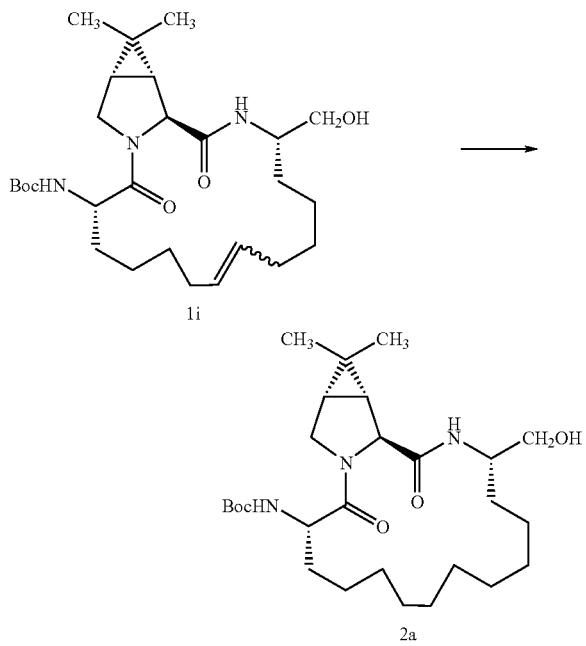

A solution of alcohol 1i (1.1 g, 2.25 mmol) in methanol (30 mL) was treated with Pd/C (10% w/w, 100 mg) and hydrogenated at 60 psi for 3 h. The reaction mixture was filtered through a plug of celite, concentrated in vacuo to yield 2a which was used in the next step without further purification.

Step B

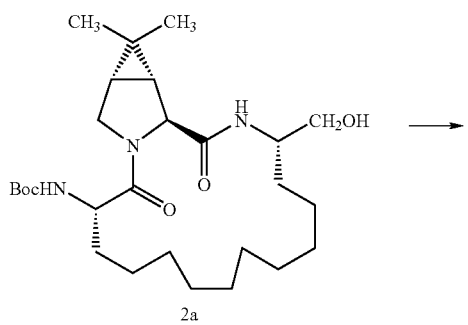

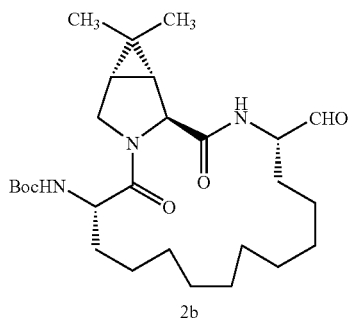

Crude 2a from step A was oxidized using Dess-Martin reagent (1.14 g, 2.68 mmol) following the procedure similar to step H (preparative example 1) to yield 2b (760 mg) as a colorless foam.

MS (ESI), m/z, relative intensity 1005 [(2M+Na)$^+$, 10], 530 [(M+K)$^+$, 20], 514 [(M+Na)$^+$, 90], 492 [(M+1)$^+$, 30], 436 (40), 392 (100).

Step C

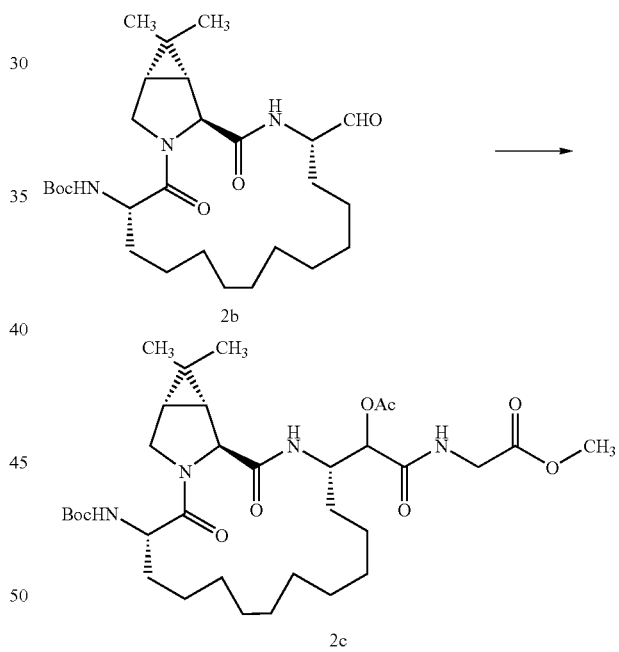

Compound 2b (200 mg, 0.41 mmol) from step B was converted to 2c (250 mg) using CH$_3$COOH (60 mg) and methylisocyanoacetate (99 mg, 1 mmol) following the procedure similar to step I (preparative example 1) as a mixture of diastereomers.

$^1$H NMR (CDCl$_3$, 300 MHz, mixture of diastereomers) 8.05, 7.93 (d, 1H), 6.60 (d, 1H, J=7.8 Hz), 5.20, 5.09 (d, 1H), 4.58-4.49 (bt, 1H), 4.34 (s, 1H), 4.34-4.31 (bt, 1H), 4.11-4.06 (m, 1H), 3.95-3.86 (m, 3H), 3.73, 3.71 (s, 3H), 2.21, 2.19 (s, 3H), 1.99-1.06 (m, 31H), 0.99-0.94 (6H).

MS (ESI), m/z, relative intensity 689 [(M+K)$^+$, 5], 673 [(M+Na)$^+$, 30], 651 [(M+1)$^+$, 35], 551 (100).

Step D

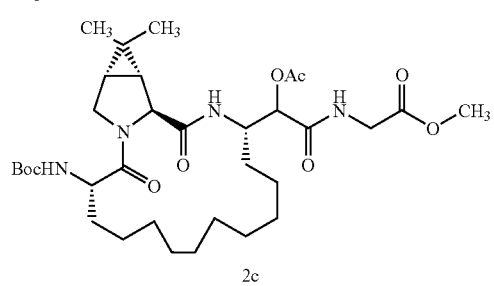

2c

Step E

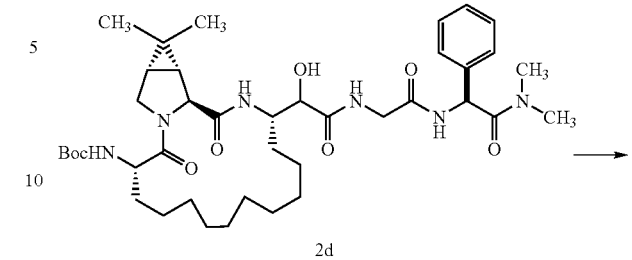

2d

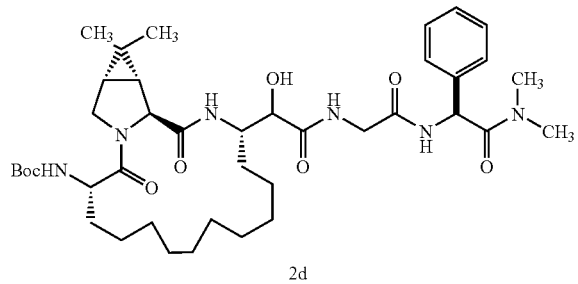

2d

2

Methyl ester 2c (250 mg, 0.39 mmol) was hydrolyzed to acid using LiOH.H$_2$O (42 mg, 1 mmol) and coupled to H-Phg-N(CH)$_2$.HCl (90 mg, 0.42 mmol) using NMM (126 mg, 1.26 mmol) and HATU (160 mg, 0.42 mmol) as outlined in preparative example 1, step J to yield crude 2d directly used for oxidation.

Hydroxy amide 2d was oxidized using Dess-Martin reagent (200 mg, 0.48 mmol) which was purified by chromatography (SiO$_2$, acetone/CH$_2$Cl$_2$ 1:4) to yield 2 (110 mg) as colorless solid.

MS (ESI), m/z, relative intensity 775 [(M+Na)$^+$, 60], 753 [(M+1)$^+$, 50], 653 (100), 277 (80), 232 (60), 162 (30), 162 (40), 148 (80), 217 (95).

Preparative Example 3

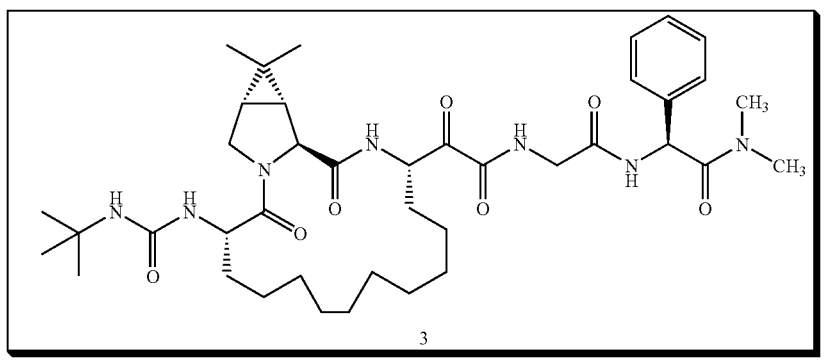

3

Step A

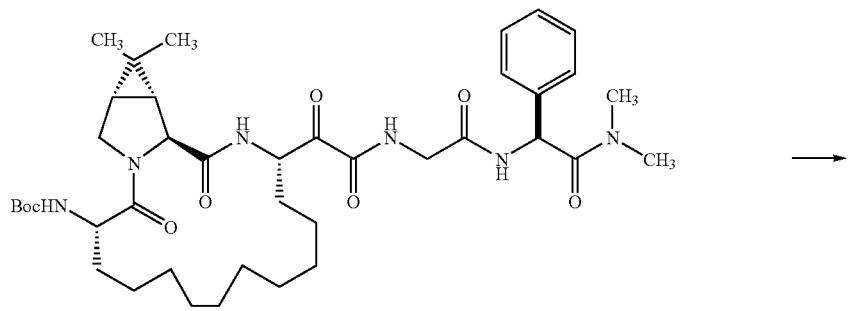

2

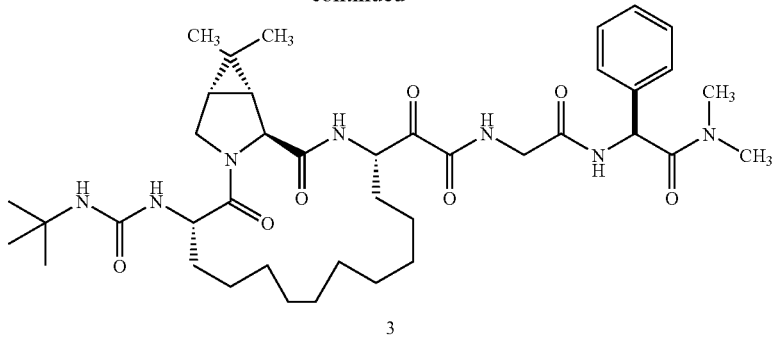

A solution of 2 (40 mg, 0.0053 mmol) in HCOOH (2 mL) was stirred at rt. for 2 h and concentrated in vacuo. The residue was repeatedly dissolved in toluene and dried in vacuo to remove residual formic acid. The residue was dissolved in CH$_2$Cl$_2$/DMF (1 mL each) and treated with $^t$BuNCO (10 μL) and NMM (15 μL) at 0° C. and left in the refrigerator for 12 h. The reaction mixture was concentrated in vacuo and purified by chromatography (SiO$_2$, acetone/hexanes 1:2) to yield 3 (21 mg) as a colorless solid.

MS (ESI), m/z, relative intensity 774 [(M+Na)$^+$, 50], 752 [(M+1)$^+$, 70], 653 (90), 420 (30), 297 (30), 148 (100), 134 (40).

Preparative Example 4

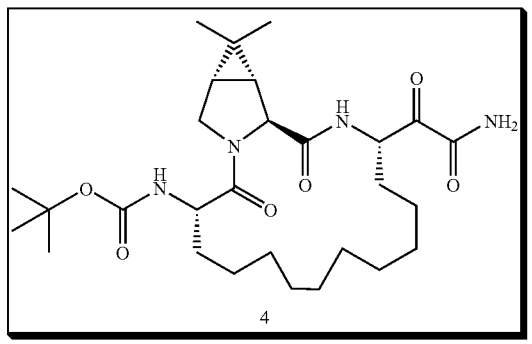

Step A

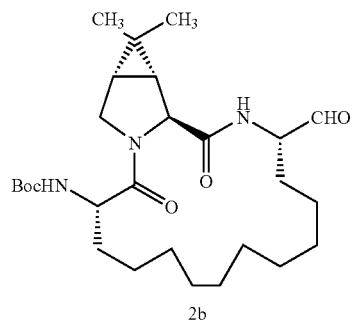

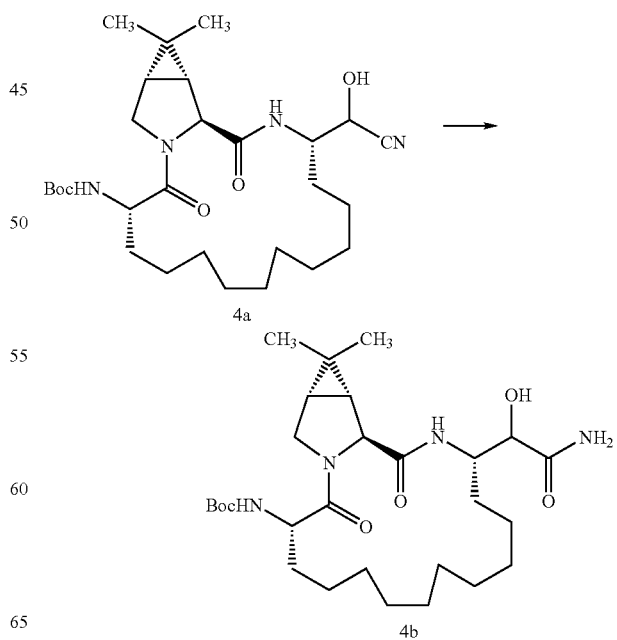

A solution of aldehyde 2b (100 mg, 0.2 mmol) in CH$_2$Cl$_2$ (2 mL) was treated with Et$_3$N (50 mg, 0.5 mmol) and acetone cyanohydrin (43 mg, 0.5 mmol). The reaction mixture was stirred at rt. for 2 h and concentrated in vacuo. The residue was purified by chromatography (SiO$_2$, acetone/hexanes 1:4) to yield 4a (100 mg) as a colorless solid.

MS (ESI), m/z, relative intensity 541 [(M+Na)$^+$, 60], 519 [(M+1)$^+$, 10], 463 (30), 419 (100).

Step B

A solution of cyanohydrin 4a (100 mg, 0.2 mmol) in DMSO (3 mL) was treated with H₂O₂ (35%, 0.3 mL) and K₂CO₃ (43 mg, 0.3 mL) and stirred at rt. for 4 h. The reaction mixture was diluted with CH₂Cl₂ (150 mL) and washed with aq. Na₂S₂O₃ solution (10%, 30 mL) and brine (30 mL). The reaction mixture was dried (MgSO₄) filtered concentrated in vacuo and directly used in step C without further purification.

Step C

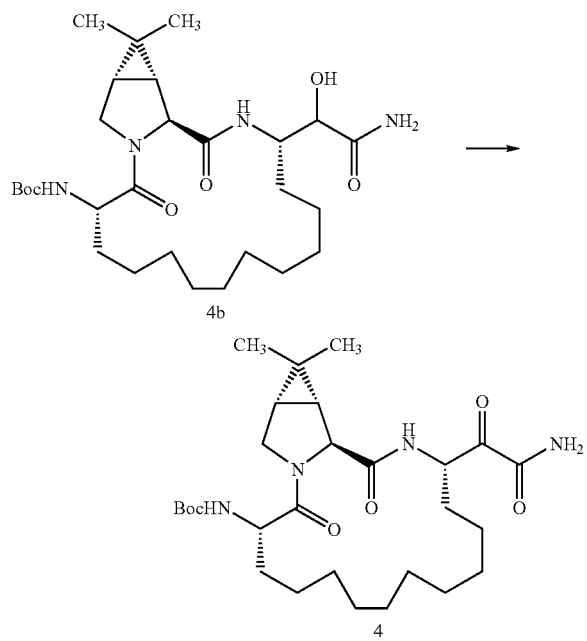

A solution of hydroxy amide 4b (100 mg, 0.18 mmol) in toluene/DMSO (1:1, 5 mL) at 0° C. was treated with EDCl (356 mg, 1.86 mmol) and Cl₂CHCOOH (120 mg, 0.93 mmol) and stirred at 0° C. for 3 h. The reaction mixture was diluted with EtOAc (150 mL) and washed with satd. aq. NaHCO₃ (100 mL) and brine (100 mL). The ethyl acetate layer was dried (MgSO₄), concentrated and purified by chromatography (SiO₂, acetone/hexanes 2:3) to yield 4 (20 mg) as colorless solid MS (ESI), m/z, relative intensity 435 [(M+1)⁺, 85], 390 (100).

Preparative Example 5

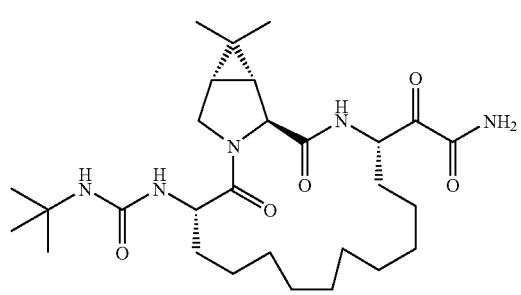

-continued

Step A

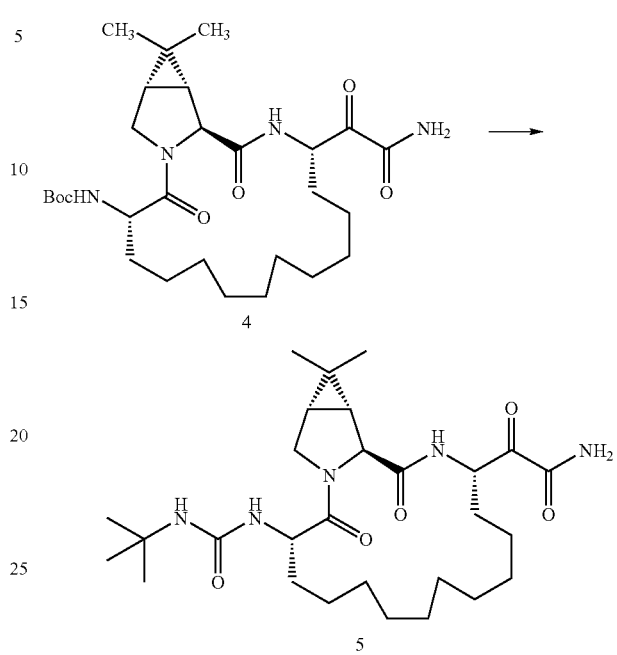

Carbamate 4 (40 mg, 0.1 mmol) was converted to urea 5 (7.5 mg) following the procedure similar to preparative example 3, Step A.

Preparative Example 6

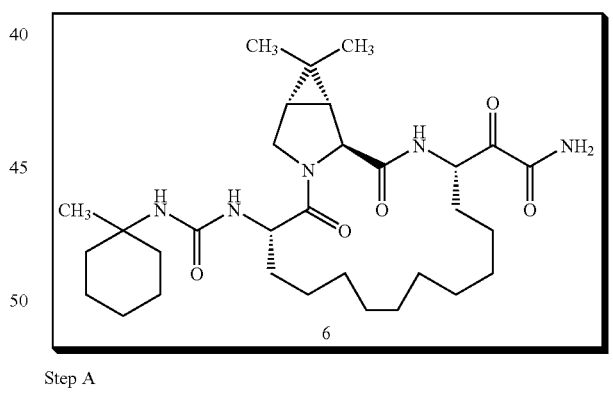

Step A

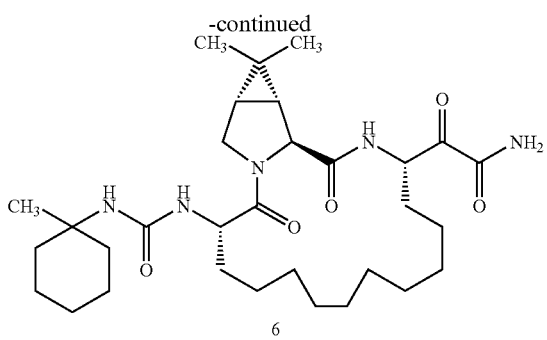

6

The synthesis of 6 was achieved using the similar procedure so synthesis of 5. A solution of 4 (180 mg 0.34 mmol) in HCOOH (3.0 mL) was stirred at rt. for 3 h an concentrated in vacuo. The residue was dried in vacuo and taken in CH$_2$Cl$_2$ (4 mL) and treated with methyl cyclohexylisocyanate (72 mg, 0.52 mmol) and Et$_3$N (52 mg, 0.52 mmol). The reaction mixture was stirred at 0° C. for 16 h and concentrated in vacuo. The residue was purified by chromatography (SiO$_2$, acetone/hexanes 1:3) to yield 6 (10 mg) as colorless solid.

MS (ESI), m/z, relative intensity 574 [(M+1)$^+$, 20], 435 (100), 390 (50).

Preparative Example 7

7

Step A

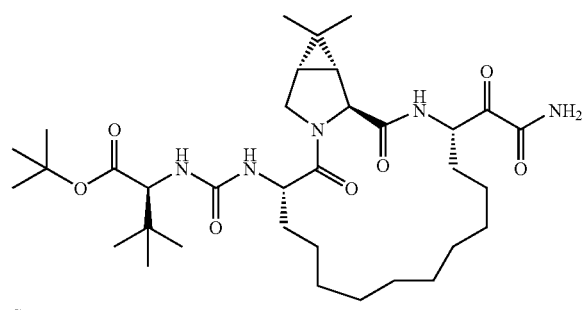

4

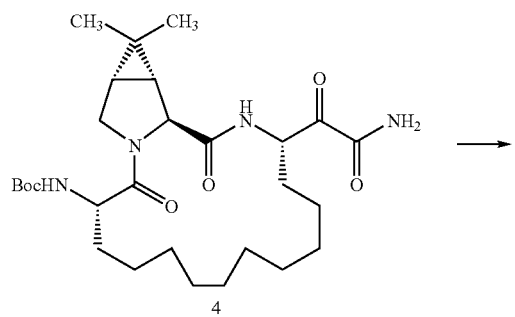

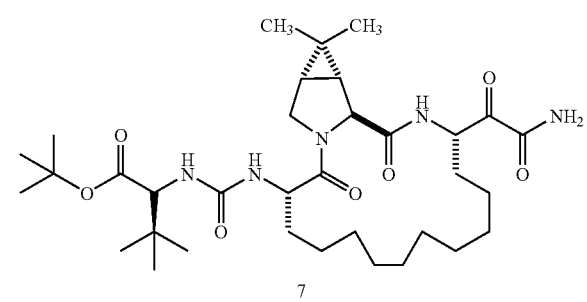

7

The synthesis of 7 was achieved using the similar procedure so synthesis of 5. A solution of 4 (180 mg 0.34 mmol) in HCOOH (3.0 mL) was stirred at rt. for 3 h and concentrated in vacuo. 50 mg (0.12 mmol) of this residue was dried in vacuo and taken in CH$_2$Cl$_2$ (4 mL) and treated with isocyanate of tert-butyl glycine tertbutyl ester (74 mg, 0.0.35 mmol) and Et$_3$N (35 mg, 0.0.35 mmol). The reaction mixture was stirred at 0° C. for 16 h and concentrated in vacuo. The residue was diluted with CH$_2$Cl$_2$ and washed with aq HCl, aq satd. NaHCO$_3$ and brine. The organic layers were dried (MgSO$_4$) and purified by chromatography (SiO$_2$, acetone/hexanes 1:3) to yield 7 (15 mg) as colorless solid.

MS (ESI), m/z, relative intensity 648 [(M+1)$^+$, 45], 592 (25), 435 (100).

Preparative Example 8

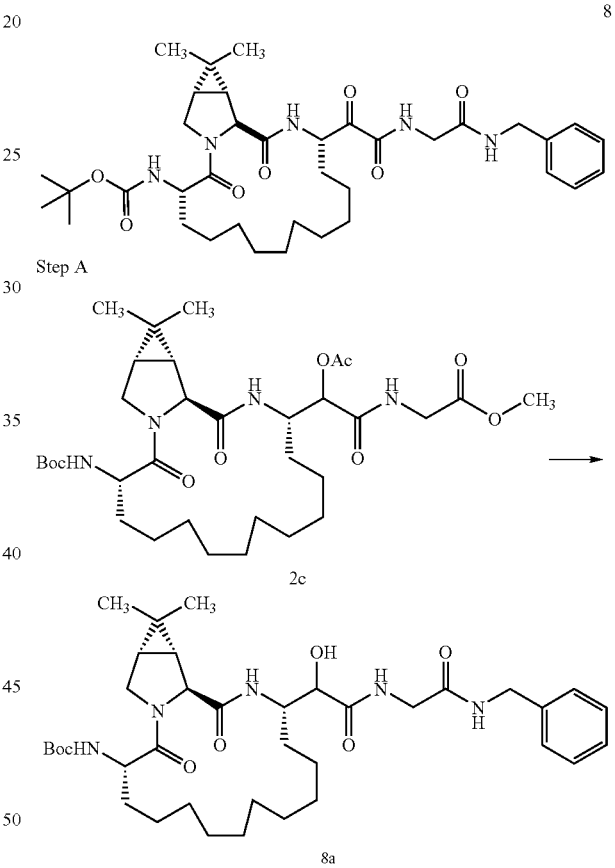

A solution of methyl ester 2c (100 mg, 0.15 mmol) in THF (2 mL), H$_2$O (2 mL) and CH$_3$OH (2 mL) was treated with LiOH.H$_2$O (41 mg, 1.0 mmol) and stirred at rt. for 2 h. After the completion of the reaction it was acidified with aq. HCl (2 mL) and concentrated in vacuo. The residue was dried in vacuo and used as it with out further purification.

The acid was dissolved in CH$_2$Cl$_2$ (2 mL), DMF (2 mL) and treated with benzyl amine (107 mg, 0.22 mmol), NMM (42 mg, 0.42 mmol) HATU (53 mg, 0.14 mmol) and stirred at 0° C. for 24 h. The yellow colored solution was concentrated in vacuo and diluted with CH$_2$Cl$_2$ (100 mL). The organic layers were washed with saturated aq. NaHCO$_3$, aq. HCl and brine. The reaction mixture was dried (MgSO$_4$) filtered concentrated in vacuo and used as it is in next step (63 mg).

Step B

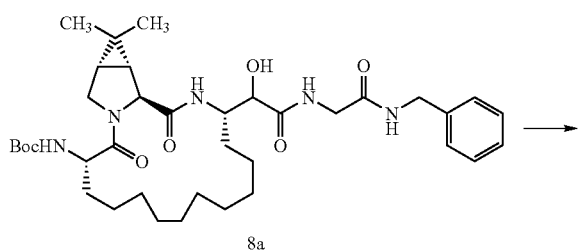

8a

Hydroxyamide 8a (62 mg) in CH$_2$Cl$_2$ (3 mL) was treated with Dess-Martin reagent (62 mg, 0.15 mmol) and stirred at rt. for 1.5 h. The reaction mixture was diluted with CH$_2$Cl$_2$ (20 mL) and treated with aq. soln of Na$_2$S$_2$O$_3$ (10%, 25 mL) and satd. NaHCO$_3$ (25 mL) and stirred for 20 min. The aqueous layer was separated and extracted once again with CH$_2$Cl$_2$. The combined organic layers were dried (MgSO$_4$), filtered, concentrated in vacuo and purified by chromatography (SiO$_2$, acetone/hexanes 1:2) to yield 8 as a colorless solid (21 mg).

MS (ESI), m/z, relative intensity 704 [(M+Na)$^+$, 40], 682 [(M+1)$^+$, 20], 582 (100), 150 (70), 117 (30).

Preparative Example 9

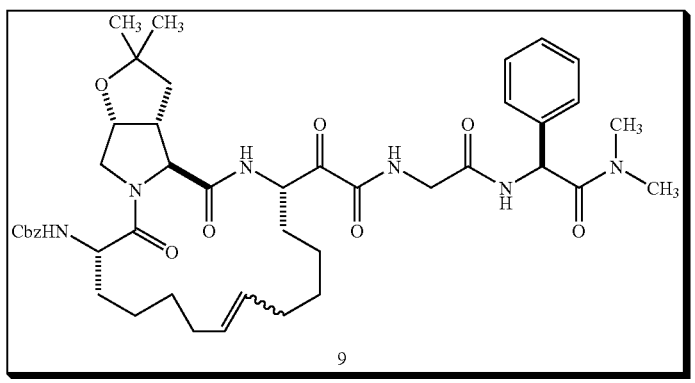

9

Step A

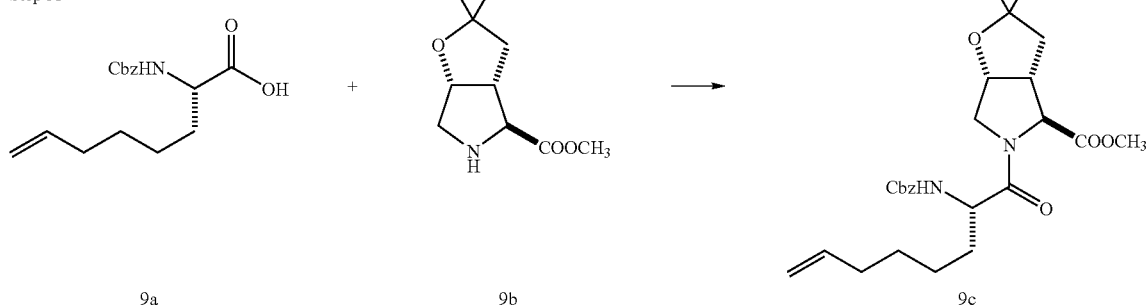

9a            9b            9c

A solution of acid 9a (3.6 g, 18.1 mmol), amine 9b (5.53 g, 18.1 mmol) HATU (8.59 mmol, 22.62 mmol) and NMM in CH$_2$Cl$_2$ (50 mL), DMF (50 mL) was stirred at 0° C. overnight. The reaction mixture was concentrated in vacuo and diluted with aq. HCl (1M, 500 mL) and extracted with CH$_2$Cl$_2$ (3×250 mL). The combined organic layers were washed with aq. HCl 500 ml), aqueous saturated NaHCO$_3$ (500 mL) brine (300 mL) and purified by chromatography (SiO$_2$, acetone/hexanes 1:4) to yield 9c (6.7 g) as colorless solid.

-continued

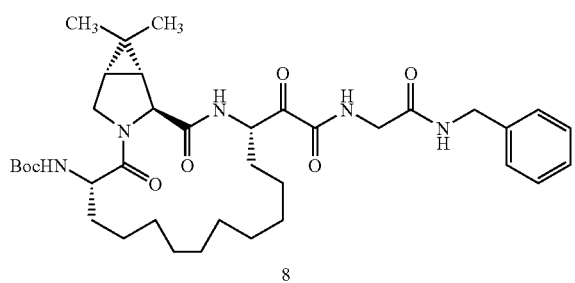

8

MS (ESI), m/z, relative intensity 495 (M+Na)$^+$, 90], 473 [(M+1)$^+$, 60], 429 (70), 391 (40), 200 (100), 140 (30).

Step B

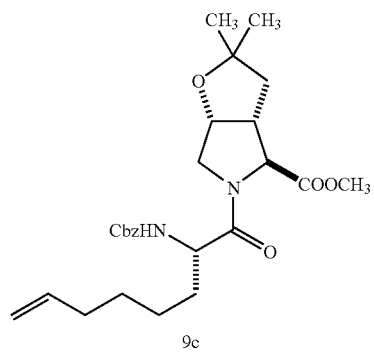

9c

+

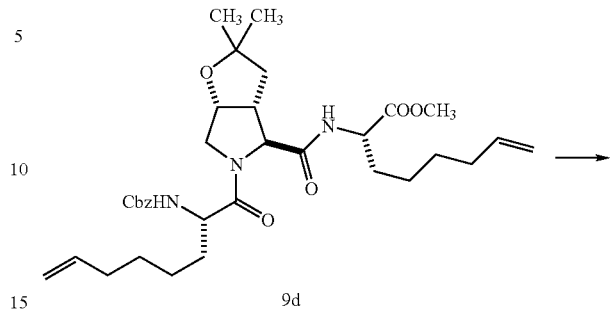

9d

1f

9d

A solution of methyl ester 9c (5.5 g, 11.59 mmol) in CH₃OH/THF/H₂O (300 mL) was treated with LiOH.H₂O (700 mg, 16.7 mmol) and stirred at rt. for 1.5 h. The reaction mixture was diluted with aq. HCl and extracted into CH₂Cl₂ (700 mL). The organic layer was dried with MgSO₄ filtered concentrated in vacuo and used as it is in subsequent steps.

A solution of crude acid in CH₂Cl₂ (50 mL), DMF (50 mL) was treated with HATU (5.5 g, 17.35 mmol), NMM (4.07 g, 40.32 mmol) and stirred at 0° C. for 24 h. The reaction mixture was concentrated in vacuo and taken in aq. HCl (300 mL). The acidic layers was extracted into CH₂Cl₂ (2×200 mL) and the combined organic layers were washed with saturated NaHCO₃, brine and purified by chromatography (SiO₂, acetone/hexanes 4:1) to yield 9d (7.1 g) as a colorless solid.

Step c

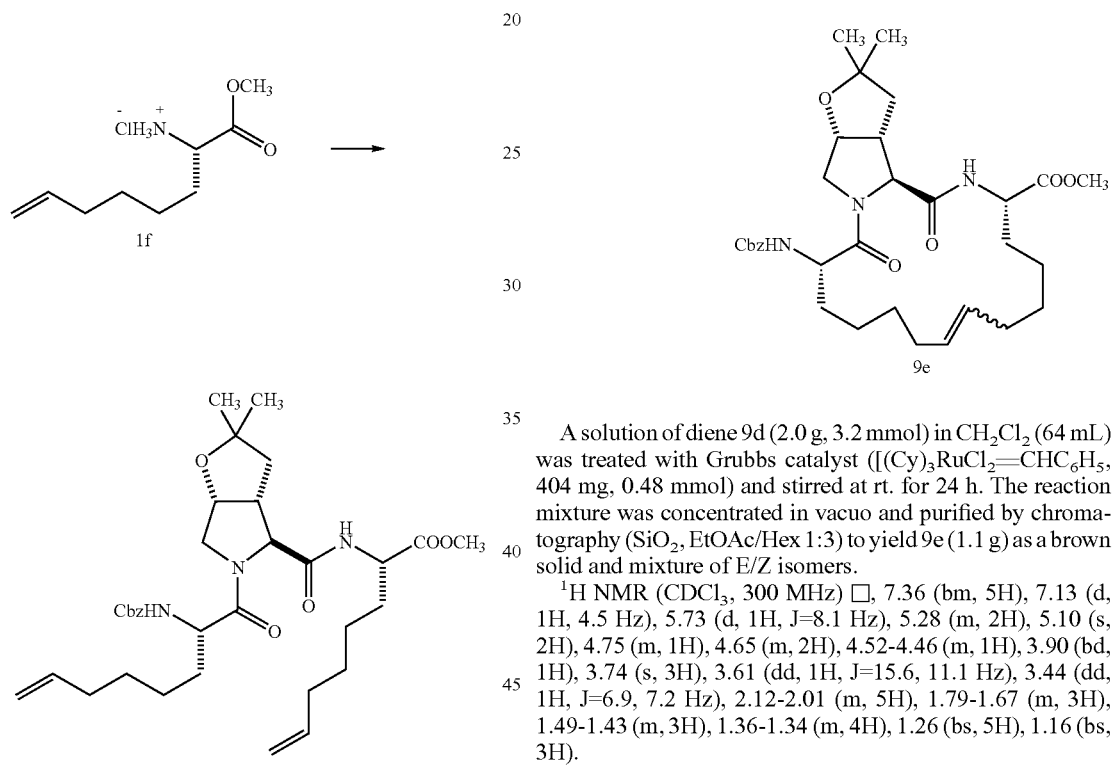

9e

A solution of diene 9d (2.0 g, 3.2 mmol) in CH₂Cl₂ (64 mL) was treated with Grubbs catalyst ([(Cy)₃RuCl₂=CHC₆H₅, 404 mg, 0.48 mmol) and stirred at rt. for 24 h. The reaction mixture was concentrated in vacuo and purified by chromatography (SiO₂, EtOAc/Hex 1:3) to yield 9e (1.1 g) as a brown solid and mixture of E/Z isomers.

¹H NMR (CDCl₃, 300 MHz) □, 7.36 (bm, 5H), 7.13 (d, 1H, 4.5 Hz), 5.73 (d, 1H, J=8.1 Hz), 5.28 (m, 2H), 5.10 (s, 2H), 4.75 (m, 1H), 4.65 (m, 2H), 4.52-4.46 (m, 1H), 3.90 (bd, 1H), 3.74 (s, 3H), 3.61 (dd, 1H, J=15.6, 11.1 Hz), 3.44 (dd, 1H, J=6.9, 7.2 Hz), 2.12-2.01 (m, 5H), 1.79-1.67 (m, 3H), 1.49-1.43 (m, 3H), 1.36-1.34 (m, 4H), 1.26 (bs, 5H), 1.16 (bs, 3H).

MS (ESI), m/z, relative intensity 606 [(M+Na)+70], 584 (100), 540 (30).

Step D

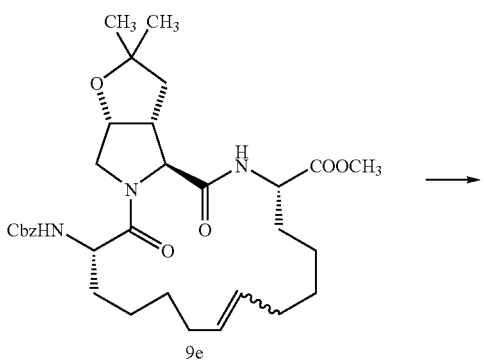

9e

-continued

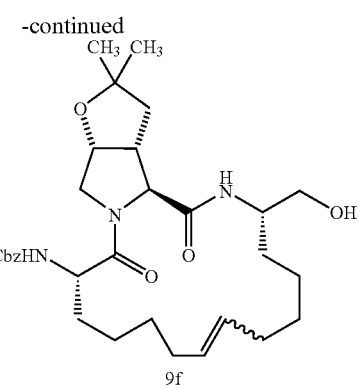

9f

A solution of ester 9e (200 mg, 0.32 mmol) in dry THF (5 mL) was treated with LiBH$_4$ (2M soln. in THF, 0.32 mL) and stirred at rt. for 3 h. The reaction mixture was quenched with aqueous HCl (1M, 100 mL) and extracted with CH$_2$Cl$_2$ (3×50 mL). The combined organic layers were washed with aq. NaHCO$_3$ (100 ml) brine, dried with MgSO$_4$ filtered concentrated in vacuo and purified by chromatography (SiO$_2$, acetone/hexanes 1:3) to yield 9f (2.1 g).

$^1$H NMR (CDCl$_3$, 300 MHz) δ.

MS (ESI), m/z, relative intensity 578 [(M+Na)$^+$, 40], 556 [(M+1)$^+$, 80], 512, (30), 295 (100).

Step E

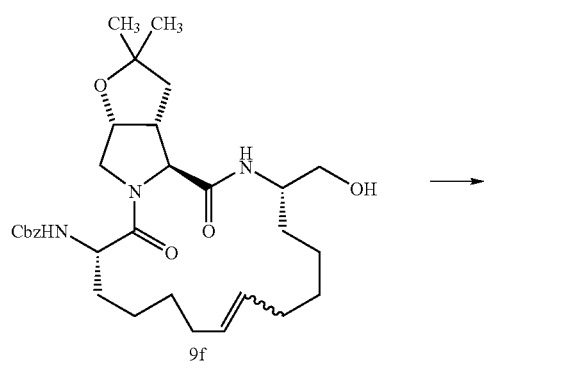

9f

9g

A solution of alcohol 9f (100 mg, 0.19 mmol), in CH$_2$Cl$_2$ (3 mL) was treated with Dess Martin reagent (106 mg, 0.25 mmol) and stirred at rt. for 2 h. The reaction mixture was quenched with Na$_2$S$_2$O$_3$ solution (10%, 10 mL) and saturated NaHCO$_3$ solution (10 mL) and stirred at rt. for 0.2 h. The reaction mixture was extracted with CH$_2$Cl$_2$. The organic layer was dried with MgSO$_4$, filtered concentrated in vacuo and purified by chromatography (SiO$_2$, acetone/hexanes 3:1) to yield 9g (80 mg).

$^1$H NMR (CDCl$_3$, 300 MHz) δ 9.52 (s, 1H), 7.36 (bs, 5H), 7.11 (d, 1H, J=7.2 Hz), 5.67 (d, 1H, J=7.8 Hz), 5.24-5.11 (m, 2H), 5.11 (s, 2H), 4.77-4.45 (m, 5H), 3.92 (d, 1H, J=12 Hz), 3.58 (dd, 1H, J=6.6, 5.5 Hz), 3.51-3.46 (m, 1H), 2.17-1.00 (m, 25H).

MS (ESI), m/z, relative intensity 576 [(M+Na)$^+$, 15], 554 [(M+1)$^+$, 100], 510 (40).

Step F

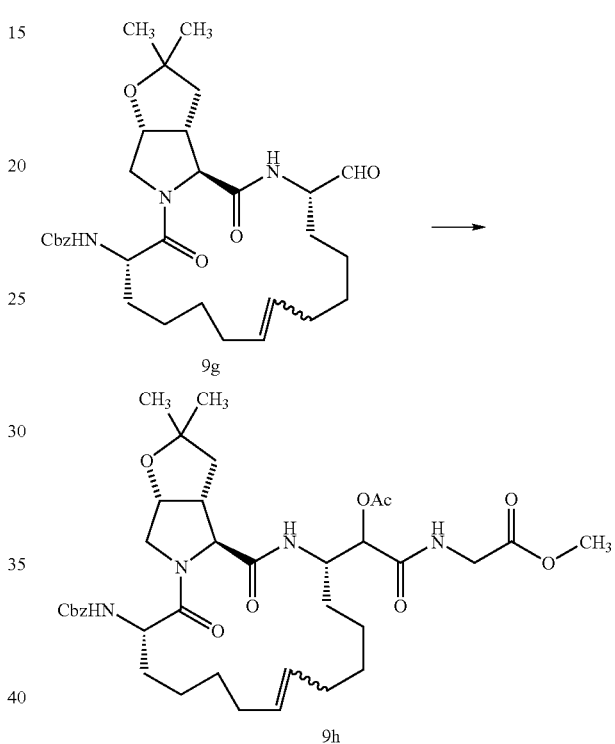

9g

9h

A solution of aldehyde 9g (80 mg, 0.15 mmol) in dry CH$_2$Cl$_2$ (2 mL) was treated with CH$_3$COOH (30 mg, 0.50 mmol) and methylisocyanoacetate (50 mg, 0.50 mmol). The reaction mixture was stirred at rt. for 24 h and concentrated in vacuo. The residue was purified by chromatography (SiO$_2$, acetone/hexanes 1:3) to yield 9h as a mixture of diastereomers.

MS (ESI), m/z, relative intensity 735 [(M+Na)$^+$, 70], 713 [(M+1)$^+$, 100].

Step F

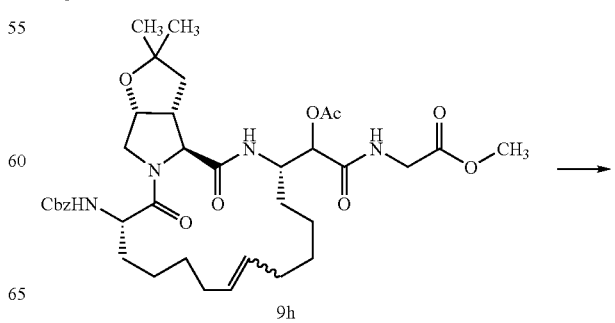

9h

-continued

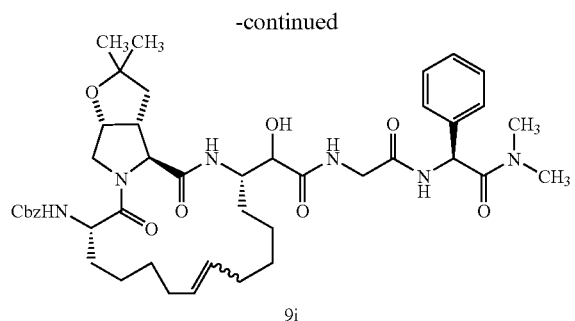

9i

Methyl ester 9h (600 mg, 0.92 mmol) was hydrolyzed to acid using LiOH.H₂O and coupled to H-Phg-N(CH)₂ HCl (235 mg, 1.09 mmol) using NMM (303 mg, 3.0 mmol) and HATU (437 mg, 1.15 mmol) as outlined in preparative example 1, step J to yield 9i that was directly used for oxidation.

Step G

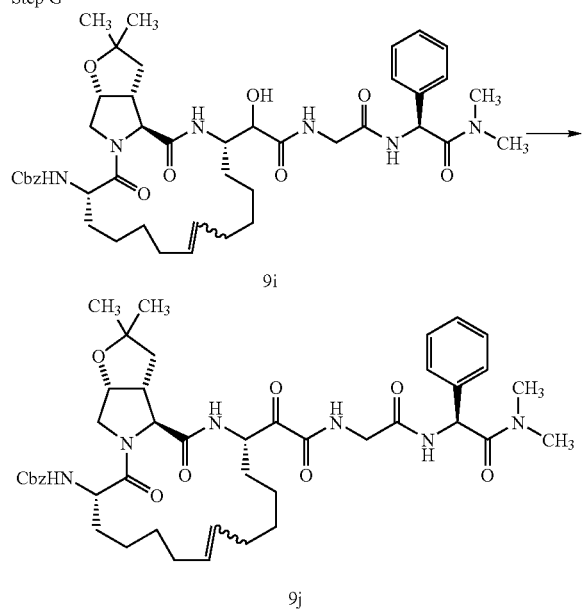

9i

9j

Crude 9j (470 mg, 0.58 mmol) from step F was oxidized using Dess-Martin reagent (424 mg, 1.00 mmol) following the procedure similar to step H (preparative example 1) to yield 9j (310 mg) as a colorless solid.

MS (ESI), m/z, relative intensity 869 [(M+CH₃OH+Na)⁺, 100], 815 [(M+1)⁺, 40], 770 (30).

Preparative Example 10

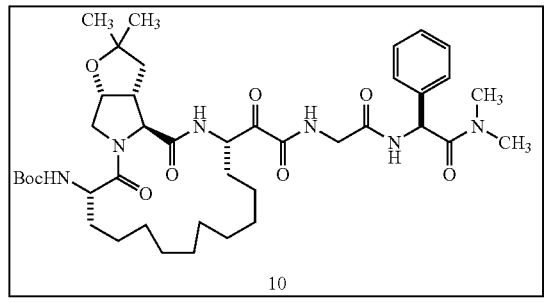

10

-continued

Step A

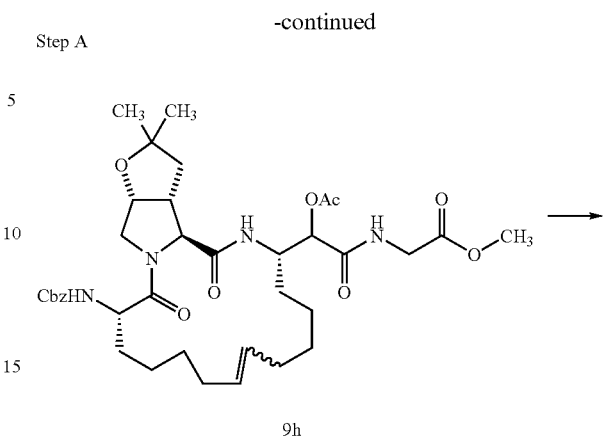

9h

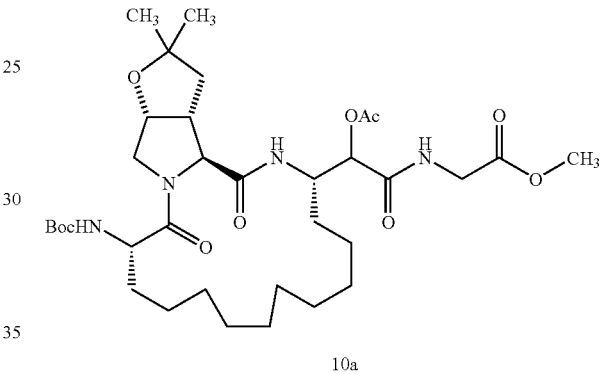

10a

A solution of 9h (200 mg, 0.3 mmol) in methanol (5 ml) was treated with Pd(OH)₂/C (wet, 10%) and hydrogenated for 3 h. The reaction mixture was filtered through a plug of celite and the filtrate was concentrated in vacuo. The residue was dissolved in methylene chloride and treated with ditertbutyidicarbonate (200 mg, 0.92 mmol). The reaction mixture was stirred at rt. for 24 h and purified by chromatography (SiO₂, acetone/Hexanes 1:2) to yield 10a (85 mg) as a colorless solid.

Step B

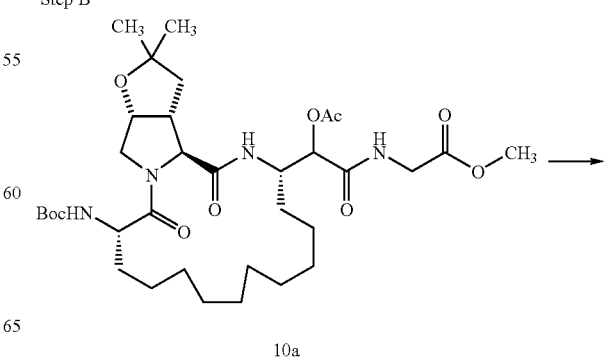

10a

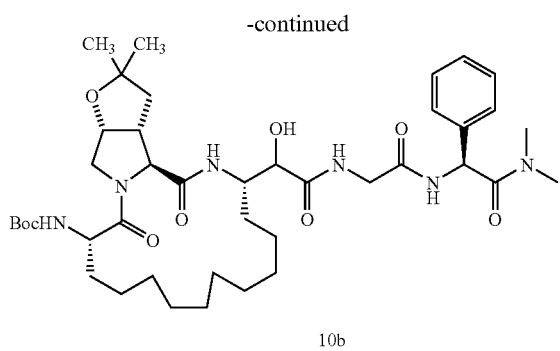

10b

Methyl ester 10a (80 mg, 0.15 mmol) was hydrolyzed to acid using LiOH.H₂O (41 mg, 1 mmol) and coupled to H-Phg-N(CH)₂.HCl (32 mg, 0.15 mmol) using NMM (40 mg, 0.40 mmol) and HATU (64.6 mg, 0.17 mmol) as outlined in preparative example 1, step J to yield 10b directly used for oxidation.

Step C

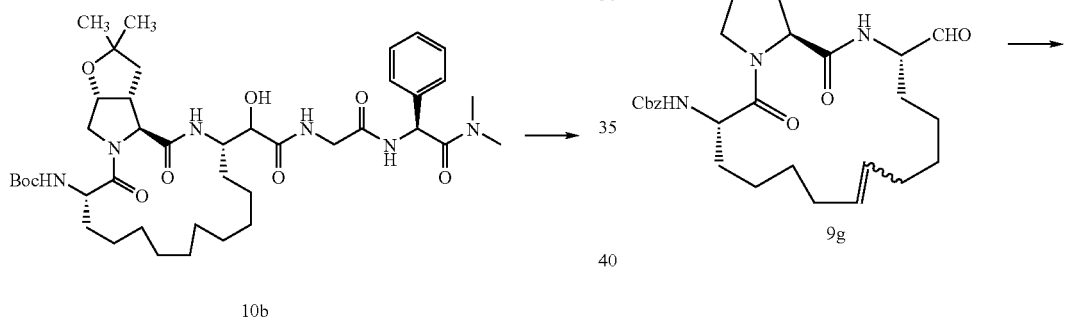

10b

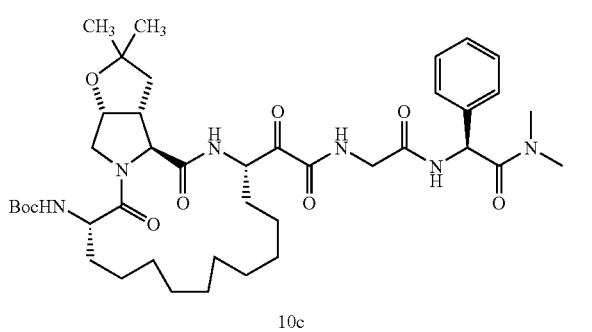

10c

Hydroxy amide 10b (60 mg, 0.08 mmol) was oxidized using Dess-Martin reagent (60 mg, 0.14 mmol) which was purified by chromatography (SiO₂, acetone/CH₂Cl₂ 1:2) to yield 10c (21 mg) as colorless solid.

MS (ESI), m/z, relative intensity 805 [(M+Na)⁺, 20], 783 [(M+1)⁺, 20], 683 (30), 369 (40), 210 (70), 116 (100).

Preparative Example 11

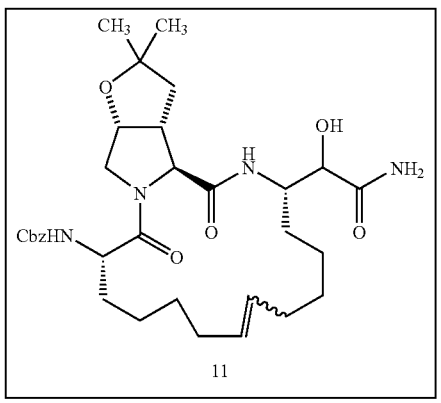

11

Step A

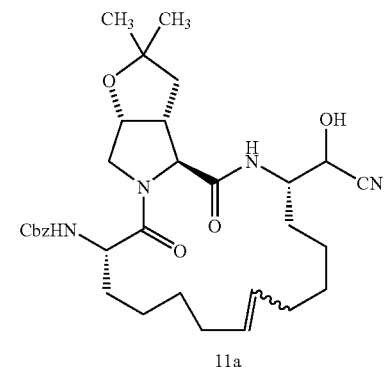

11a

A solution of aldehyde 9g (400 mg, 0.73 mmol) in CH₂Cl₂ was treated with Et₃N (150 mg, 1.5 mmol) and acetone cyanohydrin (170 mg, 1.5 mmol). The reaction mixture was stirred at rt. for 3 h and concentrated in vacuo. The residue was purified by chromatography (SiO₂, acetone/hexanes 1:4) to yield 4a (286 mg) as a colorless solid.

MS (ESI), m/z, relative intensity 603 [(M+Na)⁺, 60], 581 [(M+1)⁺, 70], 464 (50), 420 (100).

Step B

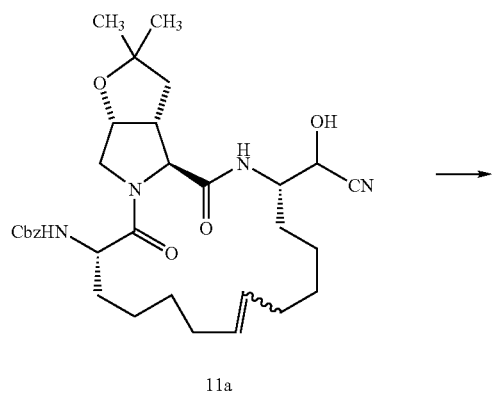
11a

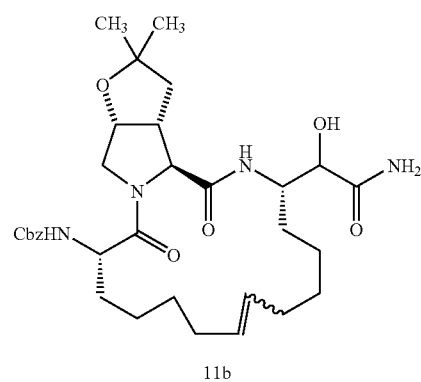
11b

A solution of cyanohydrin 11a (600 mg, 1.1 mmol) in DMSO (12 mL) was treated with $H_2O_2$ (35%, 1.0 mL) and $K_2CO_3$ (43 mg, 0.3 mL) and stirred at rt. for 8 h. The reaction mixture was diluted with $CH_2Cl_2$ (150 mL) and washed with aq. $Na_2S_2O_3$ solution (10%) and brine (30 mL). The reaction mixture was dried ($MgSO_4$) filtered concentrated in vacuo and directly used in step C without further purification.

MS (ESI), m/z, relative intensity 621 [(M+Na)$^+$, 70], 599 [(M+1)$^+$, 100], 554 (40).

Step C

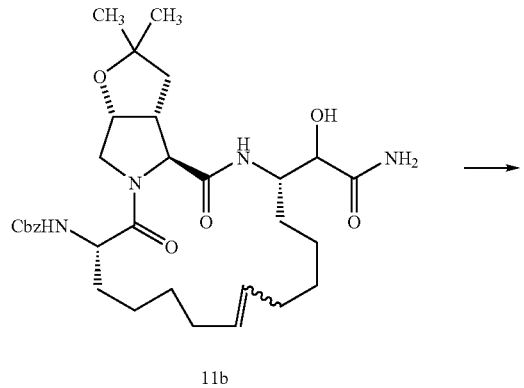
11b

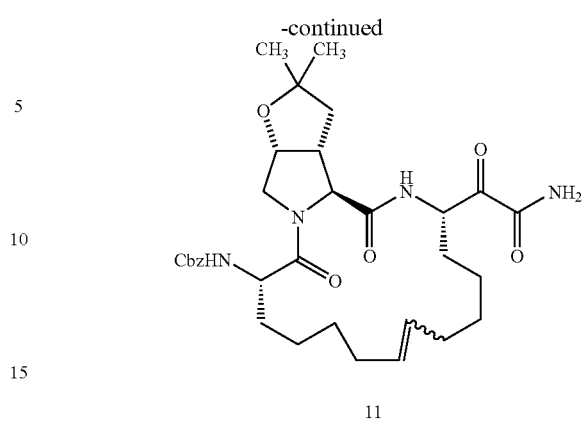
11

A solution of hydroxy amide 11b (320 mg, 0.54 mmol) in toluene/DMSO (1:1, 10 mL) at 0° C. was treated with EDCl (1.1 g, 5.40 mmol) and $Cl_2CHCOOH$ (350 mg, 2.7 mmol) and stirred at rt. for 4 h. The reaction mixture was diluted with $CH_2Cl_2$ (150 mL) and washed with satd. aq. $NaHCO_3$ and brine. The organic layer was dried ($MgSO_4$), concentrated and purified by chromatography ($SiO_2$, acetone/hexanes 1:2) to yield 11 (173 mg) as colorless solid.

MS (ESI), m/z, relative intensity 619 [(M+1)$^+$, 20], 597 (100).

Preparative Example 12

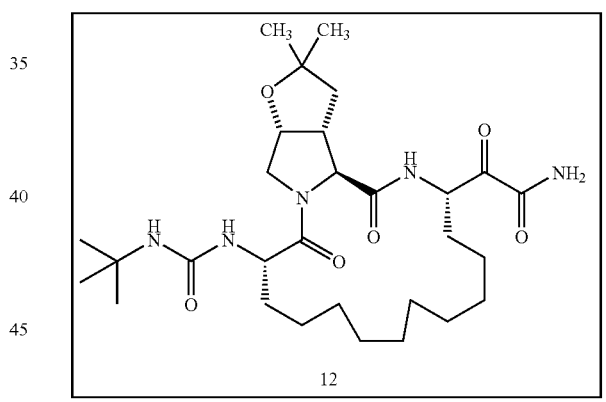
12

Step A

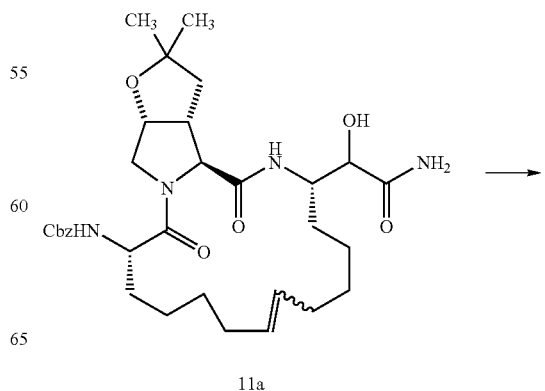
11a

-continued

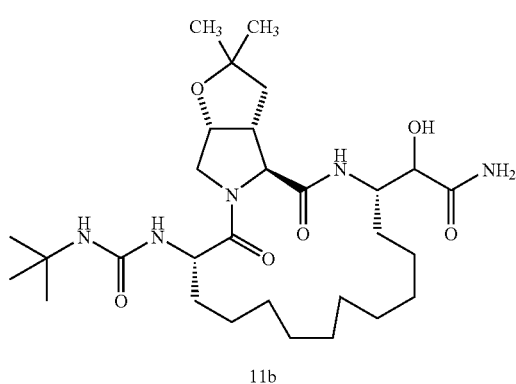

11b

A solution of 11a was hydrogenated using Pd/C and the amine obtained was dissolved in $CH_2Cl_2$ and treated with tert-butylisocyanide at 0° C. The reaction mixture was stirred at rt. for 12 h and diluted with water. The reaction mixture was extracted with $CH_2Cl_2$ (30 mL) and combined organic layers were dried ($MgSO_4$) filtered concentrated in vacuo to obtain 11 b that was used in oxidation without further purification.

Step B

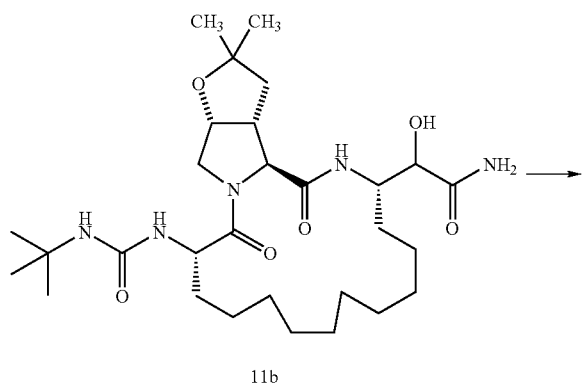

11b

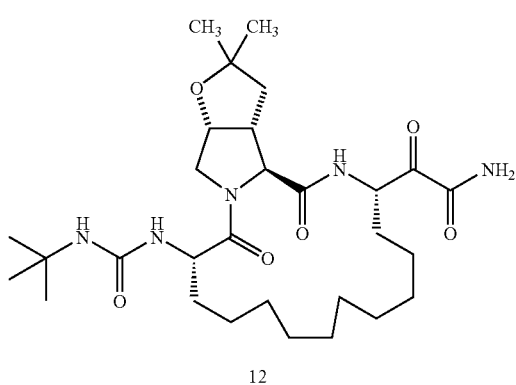

12

A solution of hydroxy amide 11 b (320 mg, 0.54 mmol) in toluene/DMSO (1:1, 10 mL) at 0° C. was treated with EDCl (1.1 g, 5.40 mmol) and $Cl_2CHCOOH$ (350 mg, 2.7 mmol) and stirred at rt. for 4 h. The reaction mixture was diluted with $CH_2Cl_2$ (150 mL) and washed with satd. aq. $NaHCO_3$ and brine. The organic layer was dried ($MgSO_4$), concentrated and purified by chromatography ($SiO_2$, acetone/hexanes 1:2) to yield 11 (173 mg) as colorless solid.

MS (ESI), m/z, relative intensity 619 [(M+1)$^+$, 20], 597 (100).

Preparative Example 13

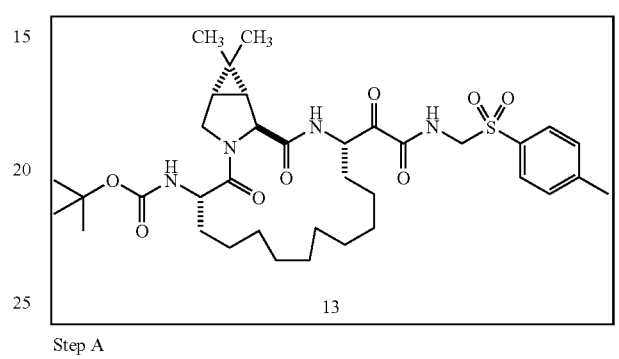

13

Step A

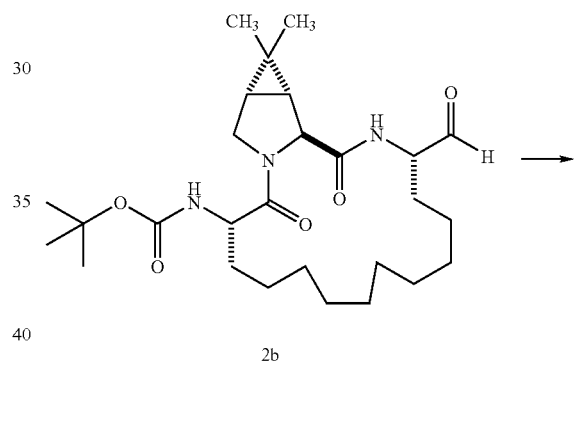

2b

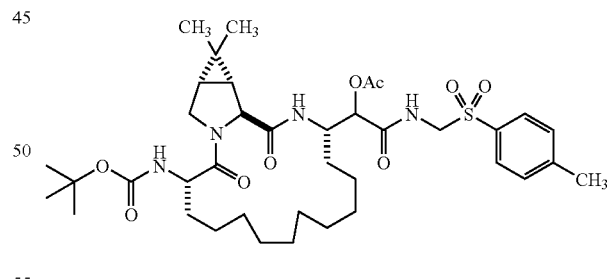

13a

A solution of aldehyde 2b (50 mg, 0.1 mmol) in dry $CH_2Cl_2$ (5 mL) was treated with $CH_3COOH$ (21 mg, 0.3 mmol) and TOSMIC (59 mg, 0.3 mmol, 3.0 eq.). The reaction mixture was stirred at rt. for 40 h and concentrated in vacuo. The residue was purified by chromatography ($SiO_2$, EtOAc/hexanes 2:3) to yield 1k (60 mg) as a mixture of diastereomers.

MS (ESI), m/z, relative intensity 769 [(M+Na)$^+$, 30], 747 [(M+1)$^+$, 20], 647 (100).

Step B

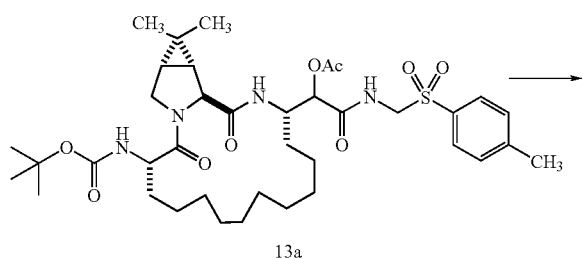
13a

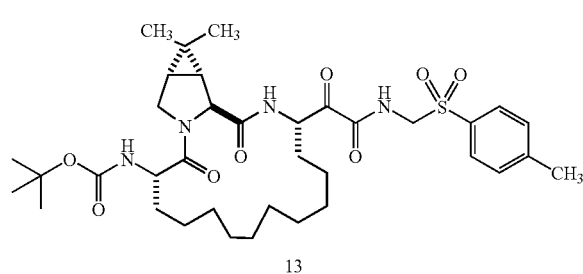
13

A solution of 13a (60 mg, 0.08 mmol) in methanol was treated with a 8 drops of concentrated HCl and stirred at rt for 12 h. The acetate ester was hydrolyzed with partially deprotection of Boc group which was reprotected with ditertbutyidicarbonate (16 mg, 0.073 mmol).

The hydroxyamide (46 mg, 0.07 mmol) in CH$_2$Cl$_2$ was treated with Dess-Martin reagent (55 mg, 0.13 mmol) and stirred at rt for 10 min. Satd aq. Na$_2$S$_2$O$_3$ was added and reaction mixture was extracted into CH$_2$Cl$_2$. The reaction mixture was dried (MgSO$_4$) filtered concentrated in vacuo and purified by chromatography to yield 13 (61 mg).

MS (ESI), m/z, relative intensity 703 [(M+1)$^+$, 11], 603 (100).

Preparative Example 14

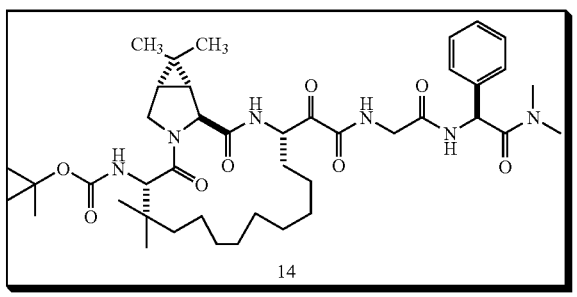
14

Step A

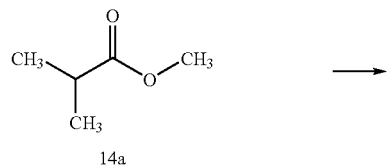
14a

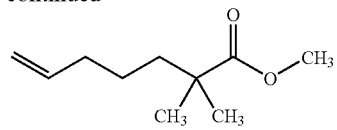

A solution of methylisobutyrate (2.0 g, 19.5 mmol) in THF was added dropwise to a solution of KHMDS in THF (4.65 g, 23.5 mmol) at −78° C. and stirred for 0.5 h. The reaction mixture was treated with 5-bromo-1-pentene (3.5 g, 23.5 mmol) and shirred at rt. for 1 h. The reaction mixture was quenched with aq. HCl and extracted into ether (150 mL). The organic layer was dried (MgSO$_4$) filtered concentrated in vacuo and purified by chromatography (EtOAc/Hexane 1:19) to yield 2.1 g of 14b as colorless liquid.

$^1$H NMR: (CDCl$_3$, 300 MHz) δ, 5.83-5.70 (m, 1H), 5.00-4.91 (dd, 2H), 3.65 (s, 3H), 2.01 (dt, 2H), 1.53-1.48 (m, 2H), 1.35-1.30 (m, 2H), 1.1 (s, 9H).

Step B

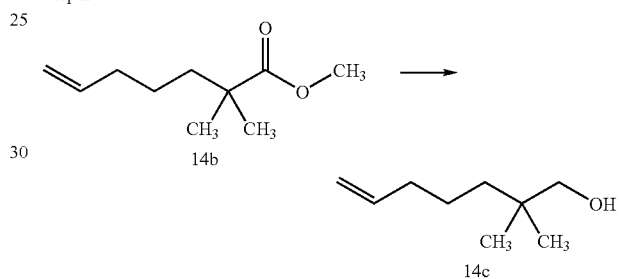

A solution of ester (2.6 g, 16 mmol) in ether (30 mL) was treated with LiAlH$_4$ (1M soln in THF, 20 mL) at −78° C. and warmed to rt. The reaction mixture was quenched with a solution of KHSO$_4$ and filtered through a plug of celite and MgSO$_4$. The filtrate was concentrated in vacuo and used as it is in the next step.

Step C

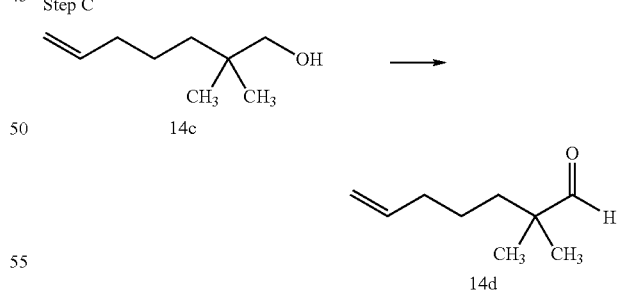

A solution of oxalyl chloride (1.48 g, 11.7 mmol) in dry CH$_2$Cl$_2$ was treated with DMSO (1.53 g, 19.5 mmol) at −78° C. and stirred for 15 min. To this mixture was added alcohol 14c (1.1 g, 7.8 mmol) and stirred at −78° C. for 15 min. Triethyl amine (5.0 mL, 35.5 mmol) was added and the reaction mixture was warmed to rt. The reaction mixture was acidified and extracted with EtOAc (200 mL). The combined organic layers were washed with aq. HCl, dried (MgSO$_4$) filtered, concentrated in vacuo and used in next reaction.

¹H NMR (CDCl₃, 300 MHz) δ 9.42 (s, 1H), 5.82-5.68 (m, 1H), 5.00-4.91 (m, 2H), 2.03 (dt, 2H), 1.48-1.23 (m, 4H), 1.03 (s, 3H).

Step D

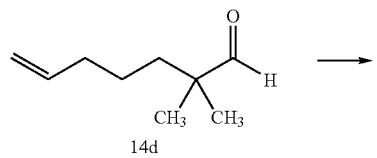

A solution of aldehyde 14d (18 g, 129 mmol) in CH₂Cl₂ (150 mL) was treated with (R)-phenyglycinol (20.33 g, 148.3 mmol) and stirred at 0° C. for 1 h. The reaction mixture was treated with TMS-CN (25.6 g, 258 mmol) and stirred at rt. for 12 h. The reaction mixture was quenched with saturated aqueous NaHCO₃ and extracted with EtOAc (3×150 mL). The combined organic layers were dried (MgSO₄) filtered concentrated in vacuo and the residue was dissolved in THF (100 mL) and treated with aq HCl (100 mL). The aqueous layer was basified with aq. NaOH (1 M) and extracted with (EtOAc, 450 mL). The combined organic layers were dried, filtered concentrated in vacuo and purified with chromatography (SiO₂, EtOAc/Hexanes 6:1) to yield 14e 21 g as a colorless oil.

Step E

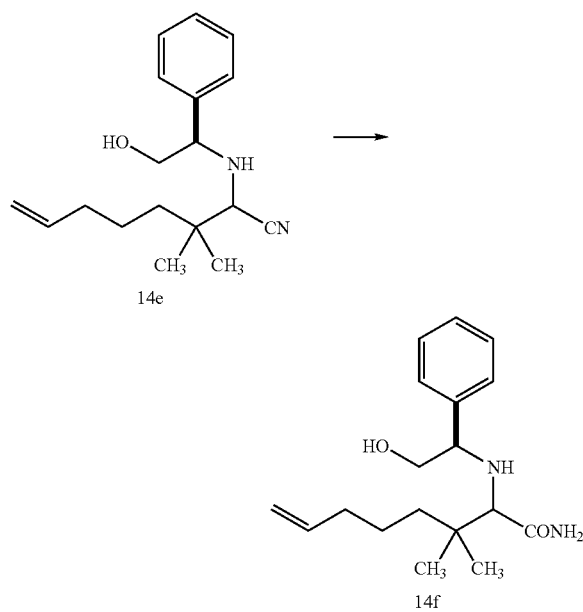

A solution of 14e (20 g) in CH₃OH (200 mL) was treated with H₂O₂ (60 mL) and LiOH.H₂O (5.88 g, 209.6 mmol) at 0° C. The reaction mixture was stirred at rt. for 12 h and cooled to 0° C. and carefully quenched with aq. Na₂S₂O₃ solution (10%). The reaction mixture was concentrated in vacuo and the aq. layer was extracted with EtOAc (600 mL). The combined organic layers were washed extensively with aq. Na₂S₂O₃, dried (MgSO₄) concentrated in vacuo and purified by crystallization (EtOAc/Hexanes) to yield pure diastereomer directly used in the next reaction.

¹H NMR (CDCl₃, 300 MHz) δ 7.30 (bs, 5H), 6.25 (s, 1H), 6.17 (s, 1H), 5.79-5.66 (m, 2H), 4.98-4.89 (m, 2H), 3.71-3.60 (m, 3H), 2.68 (bs, 1H), 1.98-1.90 (3H), 1.03 (s, 3H), 0.99 (s, 3H), 1.03-0.99 (m, 1H).

Step F

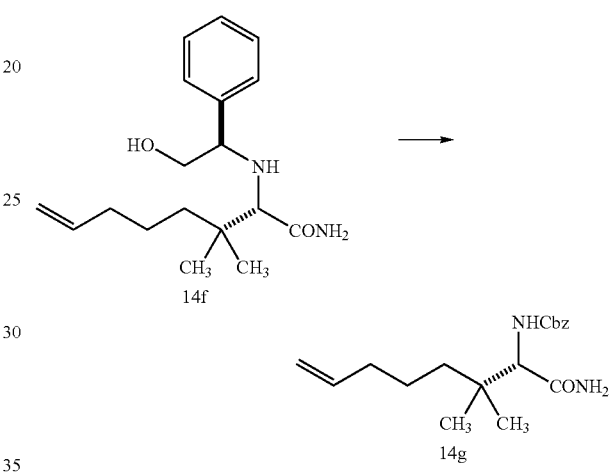

A solution of amide 14f (8.00 g, 26.3 mmol) in CH₂Cl₂ (160 mL), CH₃OH (80 mL) at 0° C. was treated with Pb(OAc)₄ (13.45 mmol, 30.3 mmol), at 0° C. for 1 h. the yellow solution was treated with aq. NaHCO₃ (250 mL, and stirred for 15 min. The reaction mixture was filtered and concentrated in vacuo. The mostly aqueous layer was extracted in CH₂Cl₂ (3×300 mL) concentrated in vacuo and directly used in further reaction.

A solution of the crude imine was taken in THF (200 mL) and treated with aq HCL (1 M, 200 mL) and stirred at rt. for 1 h. The reaction mixture was concentrated in vacuo and extracted with Ether (2×250 mL). The aqueous layer was basified with aq. NaOH (50%) at 0° C. and extracted with CH₂Cl₂ (600 mL). The combined organic layers were extracted with brine, dried (MgSO₄) filtered concentrated in vacuo and directly used in the next reaction.

The residue was dissolved in CH₂Cl₂ (200 mL) and cooled to −78° C. and treated with NMM (4.2 g, 40 mmol) and Cbz-Cl (5.4 g, 31.58 mmol). The reaction mixture was stirred at rt. for 12 h and washed with aq. HCl. The organic layer was separated and the aq. layer was extracted with CH₂Cl₂ (200 mL) The combined organic layers were extracted with brine, dried and purified by chromatography (SiO₂, EtOAc/Hexanes 2:3) to yield 14g (6.8 g) as a colorless solid.

¹H NMR (CDCl₃, 300 MHz) δ 7.37-7.30 (m, 5H), 6.23 (bs, 1H), 5.86 (bs, 1H), 5.82-5.64 (m, 1H), 5.63 (d, 1H, J=9.3 Hz), 5.12-4.93 (m, 4H), 4.07 (d, 1H, J=9 Hz), 2.0-1.9 (m, 2H), 1.42-1.30 (m, 4H), 0.96 (s, 6H).

MS (ESI), m/z, relative intensity 341[M+Na]⁺, 100], 319 [(M+1)⁺, 30], 274 (50), 230 (70), 213 (30), 140 (30).

Step G

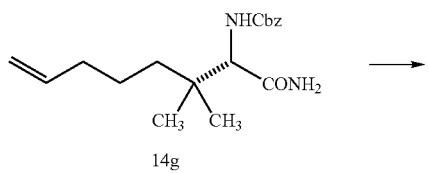

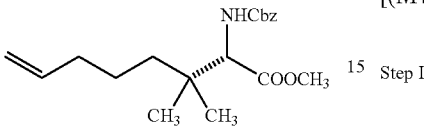

A solution of amide 14g (6.8 g, 21.4 mmol) in CH$_2$Cl$_2$ (200 mL) was treated with Me$_3$OBF$_4$ (10.36 g, 69.9 mmol) and K$_3$PO$_4$ (12.11 g, 69.52 mmol) and stirred at rt. for 12 h. The reaction mixture was concentrated in vacuo and dissolved in CH$_3$OH (280 mL) and aq. HCl (140 mL, 1 M) and heated at reflux for 1 h. The reaction mixture was concentrated and the aqueous layer was further extracted with CH$_2$Cl$_2$ (3×150 mL). The combined organic layers were dried (MgSO$_4$), filtered concentrated in vacuo and purified by chromatography (SiO$_2$, EtOAc/hexanes 1:19) to yield 14h (5.6 g) as colorless oil.

$^1$H NMR (CDCl$_3$, 300 MHz) δ 7.36 (bs, 5H), 5.85-5.71 (m, 1H), 5.32 (d, 1H, J=9.9 Hz), 5.10 (dd, 2H, J=12, 3.9 Hz), 5.03-4.93 (m, 2H), 4.27 (d, 1H, J=9.9 Hz), 3.72 (s, 3H), 2.05-1.98 (m, 2H), 1.47-1.24 (m, 4H), 0.93 (s, 9H).

MS (ESI), m/z, relative intensity 356 [M+Na)$^+$, 95], 334 [(M+1)$^+$, 10], 290 (100), 230 (60), 213 (20).

Step H

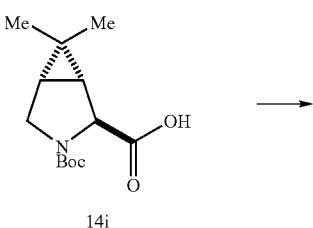

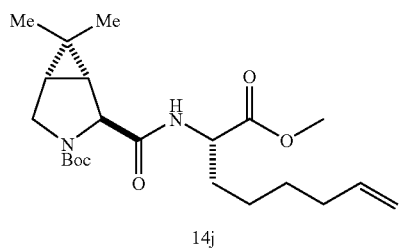

A solution of acid 14i (4.5 g, 17.64 mmol) and amine 1f (3.66 g, 17.64 mmol) in CH$_2$Cl$_2$ (50 mL), DMF (50 mL) at 0° C. was treated with HATU (8.39 g, 22.05 mmol) and NMM (5.35 g, 52.92 mmol) and stirred overnight at 0° C. The reaction mixture was concentrated in vacuo and diluted with 450 mL of CH$_2$Cl$_2$. The aqueous layer was washed with aq. HCl (1M, 2×300 mL), aq. NaHCO$_3$ (1M, 2×300 mL). The organic layers were dried with MgSO$_4$, filtered concentrated in vacuo and purified by chromatography (SiO$_2$, Acetone/Hexanes 5:1) to yield 14j as a colorless oil (5.8 g).

$^1$H NMR (CDCl$_3$, 300 MHz) δ 7.03, 6.39 (d, 1H, J=7.5 Hz), 5.8-5.7 (m, 1H), 4.99-4.90 (m, 2H), 4.66-4.54 (m, 1H). 3.72 (s, 3H), 3.62-3.42 (m, 2H), 2.01 (bs, 2H), 1.88-1.63 (m, 4H), 1.61, 1.43 (s, 9H), 1.6-1.3 (m, 4H), 1.02 (s, 3H), 0.90 (s, 3H).

MS (ESI), m/z, relative intensity 431 [(M+Na)$^+$, 60], 409 [(M+1)$^+$, 40], 353 (40), 309 (100), 110 (80).

Step I

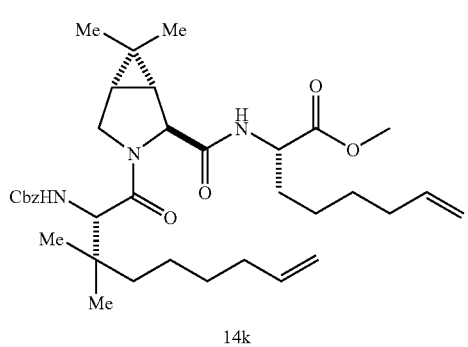

A solution of ester 14h (5.4 g, 16.2 mmol) in H$_2$O (30 mL), THF (30 mL) and CH$_3$OH (30 mL) was stirred with LiOH.H$_2$O (1.36 g, 32.42 mmol) for 24 h and concentrated in vacuo. The aqueous layer was acidified with aq. HCl (1M) and extracted into CH$_2$Cl$_2$ (400 mL). The combined organic layers were dried (MgSO$_4$), filtered concentrated in vacuo and used as it is in further reactions.

A solution of acid (4.0 g, 12.5 mmol) and deprotected amine* in CH$_2$Cl$_2$ (30 mL), DMF (30 mL) at 0° C. was treated with HATU (7.15 g, 18.79 mmol) and NMM (4.5 g, 45.0 mmol) and stirred at 0° C. for 48 h, and 25° C. for 24 h. The reaction mixture was concentrated in vacuo and diluted with 300 mL of CH$_2$Cl$_2$. The aqueous layer was washed with aq. HCl (1M, 3×100 mL), aq. NaHCO$_3$ (satd, 3×100 mL). The organic layers were dried with MgSO$_4$, filtered concentrated in vacuo and purified by chromatography (SiO$_2$, EtOAc/Hexanes 3:1) to yield 14k as a colorless oil (4 g of pure 14k and 2 g of partially impure 14k).

* Amine was obtained by the deportation of 14j with 4 M HCl in dioxane.

$^1$H NMR (CDCl$_3$, 300 MHz) δ 7.34-7.32 (bs, 5H), 6.92 (d, 1H, J=7.5 Hz), 5.48-5.69 (m, 2H), 5.37 (d, 1H, J=9.9 Hz), 5.08-4.92 (m, 6H), 4.56-4.33 (M, 1 h), 3.97-3.93 (m, 2H), 3.84-3.80 (m, 2H), 3.74 (s, 3H), 2.03-1.97 (m, 4H), 1.86-1.87-1.39 (m, 12H), 1.12 (s, 3H), 0.98 (s, 6H), 084 (s, 3H).

MS (ESI), m/z, relative intensity 632 [(M+Na)$^+$, 20], 610 [(M+1)$^+$, 100], 309 (60).

Step J

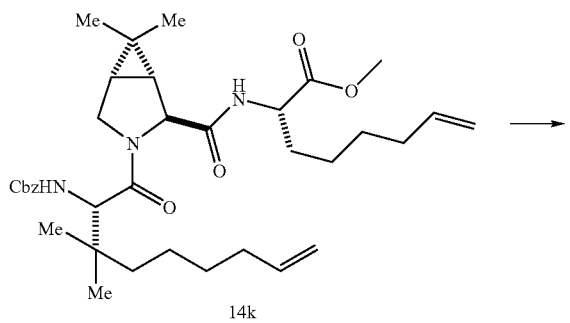

14k

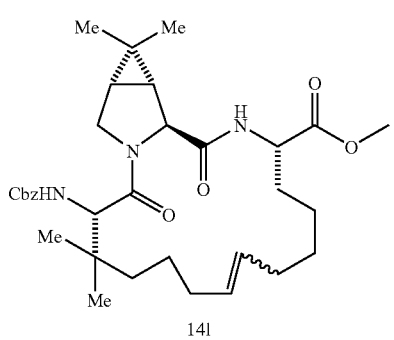

14l

A solution of diene 14k (4.00 g, 6.57 mmol) in CH$_2$Cl$_2$ (65.0 mL) at rt. was saturated with N$_2$ and treated with Grubbs catalyst (551 mg, 0.657 mmol) and stirred for 24 h. The reaction mixture was concentrated in vacuo and purified by chromatography (SiO$_2$, EtOAc/hexanes 1:3) to yield 14l (1.7 g) as a tan colored solid.

$^1$H NMR (CDCl$_3$, 300 MHz) δ 7.34-7.31 (bs, 5H), 7.08 (d, 1H, J=7.8 Hz), 5.43 (d, 1H, J=10.2 Hz), 5.28 (m, 2H), 5.13-5.02 (m, 2H), 4.56-4.32 (m, 1H), 4.49-4.28 (m, 2H), 3.96-3.79 (m, 2H), 3.74 (s, 9H), 2.05-1.29 (m, 16H), 1.0 (s, 3H), 0.96 (s, 3H), 0.94 (s, 3H), 0.86 (s, 3H).

MS (ESI), m/z, relative intensity 550 [(M+1)$^+$, 50], 450 (100).

Step K

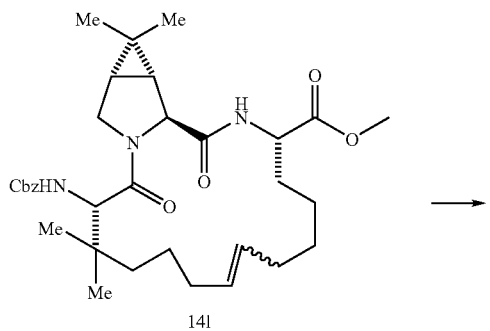

14l

-continued

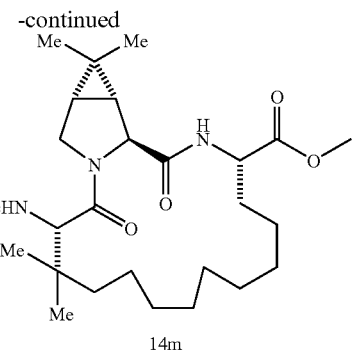

14m

A solution of alkene 14l (200 mg, 0.35 mmol) in CH$_3$OH (20 mL) was treated with Pd/C (5%, 200 mg), ditertbutyldicarbonate (200 mg, 0.92 mmol) and hydrogenated at rt. for 12 h. The reaction mixture was filtered through a plug of celite and concentrated in vacuo. The reaction mixture was purified by chromatography (SiO$_2$, acetone/hexanes 1:5) to yield 14m (81 mg).

$^1$H NMR (CDCl$_3$, 300 MHz) δ 6.84 (d, 1H, J=7.8 Hz), 5.14 (d, 1H), 4.61-4.55 (m, 1H), 4.31 (s, 1H), 4.22 (d, 1H, J=10 Hz), 4.03 (d, 1H, J=10.5 Hz), 3.88-3.85 (m, 1H), 3.75 (s, 3H), 1.89-1.76 (m, 1H), 1.59-1.76 (m, 28H), 1.02 (s, 3H), 0.97 (s, 3H), 0.94 (s, 3H), 0.86 (s, 3H).

MS (ESI), m/z, relative intensity 610 [(M+AcOH+1)$^+$, 40], 550 [(M+1)$^+$, 50], 450 (100), 309 (20).

Step L

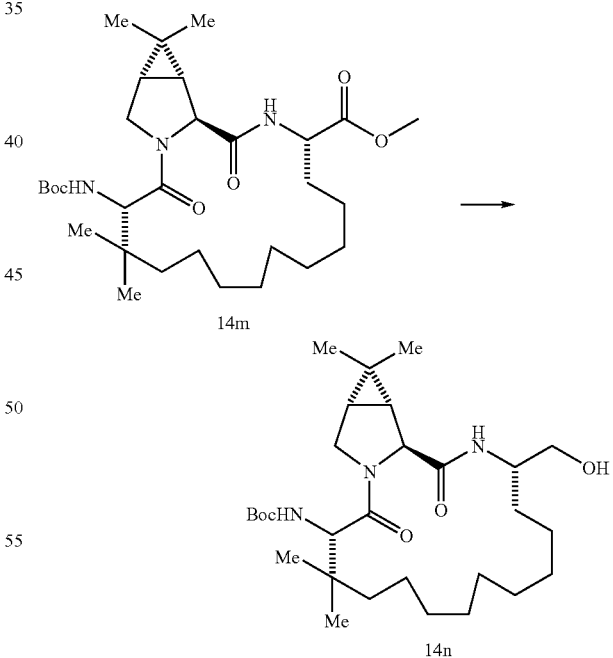

14m

14n

A solution of ester 14m (80 mg, 0.15 mmol) in dry THF (2 mL) was treated with LiBH$_4$ (2M soln. in THF, 0.1 mL) and stirred at rt. for 4 h. The reaction mixture was quenched with aqueous HCl (1M, drops) and extracted with CH$_2$Cl$_2$ (3×30 mL). The combined organic layers were washed with aq. NaHCO$_3$ (100 ml) brine, dried with MgSO$_4$ filtered concentrated in vacuo and purified by chromatography (SiO$_2$, acetone/hexanes 1:3) to yield 14n (70 mg) as an amorphous solid.

MS (ESI), m/z, relative intensity 544 [(M+Na)$^+$, 30], 522 [(M+1)$^+$, 40], 422 (100).

Step M

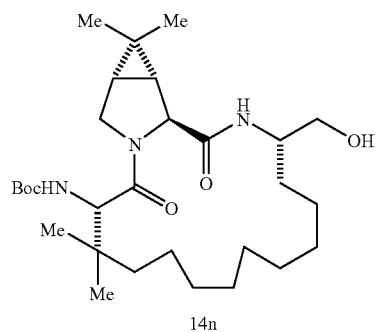

14n

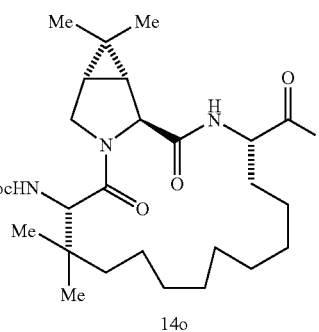

14o

A solution of alcohol 14n (30 mg, 0.05 mmol), in CH$_2$Cl$_2$ (2 mL) was treated with Dess Martin reagent (30 mg, 0.07 mmol) and stirred at rt. for 2 h. The reaction mixture was quenched with Na$_2$S$_2$O$_3$ solution (10%, 10 mL) and saturated NaHCO$_3$ solution (10 mL) and stirred at rt. for 0.5 h. The reaction mixture was extracted with CH$_2$Cl$_2$ (3×10 mL). The organic layer was dried with MgSO$_4$, filtered concentrated in vacuo and used as it is in further reaction.

MS (ESI), m/z, relative intensity 552 [(M+1)$^+$, 100], 248 (40).

Step N

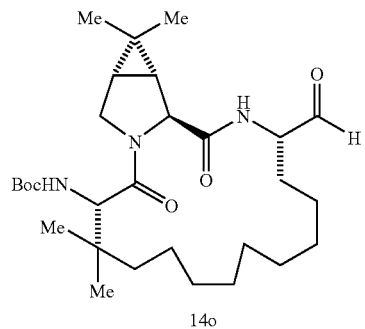

14o

-continued

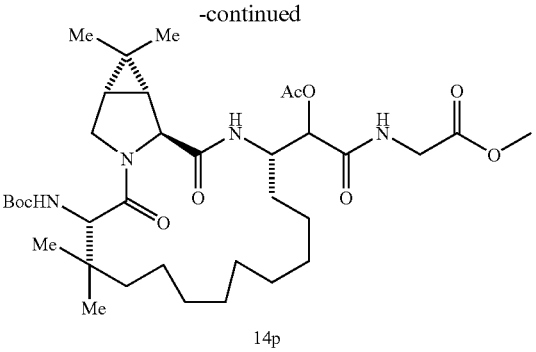

14p

Compound 14o from step M was converted to 14p (40 mg) using CH$_3$COOH (20 □L) and methylisocyanoacetate (20 □L) following the procedure similar to step I (preparative example 1) as a mixture of diastereomers.

MS (ESI), m/z, relative intensity 711 [(M+1)$^+$, 100], 240 (20).

Step O

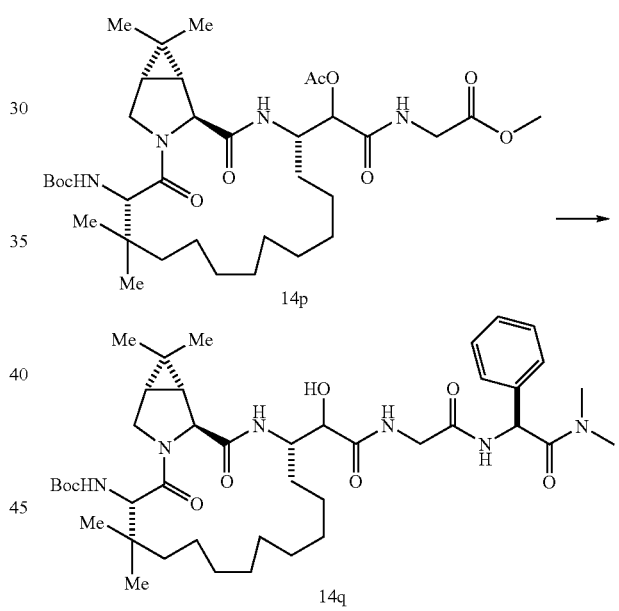

A solution of methyl ester 14p (80 mg, 0.12 mmol) in THF (3 mL), H$_2$O (3 mL) and CH$_3$OH (3 mL) was treated with LiOH.H$_2$O (41 mg, 1 mmol) and stirred at rt. for 2 h. After the completion of the reaction it was acidified with aq. HCl (15 mL) and extracted with CH$_2$Cl$_2$ (3×30 mL). The combined organic layers were dried (MgSO$_4$), filtered and concentrated in vacuo. The residue was dried in vacuo and used as it with out further purification.

The acid was dissolved in CH$_2$Cl$_2$ (2 mL), DMF (2 mL) and treated with H-Phg-N(CH)$_2$.HCl (40 mg, 0.2 mmol), NMM (40 mg, 0.4 mmol) HATU (68 mg, 0.16 mmol) and stirred at 0° C. for 24 h. The yellow colored solution was concentrated in vacuo and diluted with CH$_2$Cl$_2$ (75 mL). The organic layers were washed with saturated aq. NaHCO$_3$, aq. HCl and brine. The reaction mixture was dried (MgSO$_4$) filtered concentrated in vacuo and used as it is in next step (90 mg).

Step P

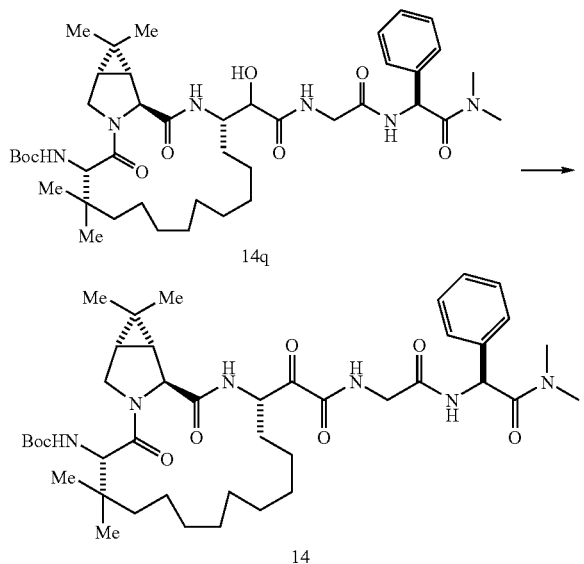

A solution of alcohol 14q (90 mg, 0.11 mmol) in CH$_2$Cl$_2$ (2 mL) was treated with Dess-Martin reagent (100 mg, 0.24 mmol) and stirred at rt. for 2 h. The reaction was diluted with aq Na$_2$S$_2$O$_3$ solution (30 mL) and aq. NaHCO$_3$ solution (30 mL each) and extracted with CH$_2$Cl$_2$ (50 mL). The organic layer was washed with satd. NaHCO$_3$, brine, dried with MgSO$_4$ filtered concentrated in vacuo and purified by chromatography (acetone/hexanes 2:3) to yield 14 (22 mg) as a colorless solid.

MS (ESI), m/z, relative intensity 813 [(M+1)$^+$, 100], 768 (20).

Preparative Example 15

To 45 mL THF, diisopropylamine (4.70 mL, 33.51 mmol, 2 eq.) and LiCl (4.26 g, 6 eq) at −78° C. was added nBuLi (20.4 mL, 1.95 eq) under nitrogen atmosphere. 10 min later, the solution of 1a/30 mL THF was transferred to the above solution over 10 min. After 20 min, the brownish yellow mixture was warmed up to 0° C. Another 20 min later, the solution became opaque bright yellow and 4-iodo-1-butene (3.35 g, 1.1 eq) was added in dropwise. The solution became even brighter and 60 min later 115 mL 1 M HCl was added to quench the reaction. The THF was removed and 150 mL EtOAc was added in for extraction. The organic layer was further washed with 115 mL 1M HCl. The aqueous layers were combined and adjusted to pH 14 by 6M NaOH at 0° C. Extraction was done with dichloromethane 110 mL×4. The organic layer was dried over sodium carbonate. Filtration through celite and removal of the solvent afforded 4 g of the oil which upon standing, became solid. Flash chromatography with 5:5:90 Et$_3$N/MeOH/DCM provided 2.63 g pure 15a in 57% yield. (R$_f$=0.64, 5:5:90 Et$_3$N/MeOH/DCM).

$^1$H NMR (4:1 rotamer ratio. * denotes minor rotamer peaks. CDCl$_3$): δ 0.96* (d, 3H, J=6.7 Hz) 1.15 (d, 3H, J=6.9 Hz) 1.45-1.55 (m, 2H) 2.05-2.20 (m, 2H) 2.80 (s, 3H) 2.92* (s, 3H) 3.55-3.60 (m, 2H) 4.00* (m, 1H) 4.35-4.45* (m, 1H) 4.60-4.65 (m, 2H) 4.92-5.02 (m, 2H) 5.68-5.80 (m, 1H) 7.20-7.40 (m, 5H).

$^{13}$C NMR(CDCl$_3$): δ 11.26 15.68 31.11 35.67 47.17 52.22 76.92 116.46 127.50 128.67 129.34 138.60 143.19 178.08.

MS: C$_{16}$H$_{24}$N$_2$O$_2$: 277 (M+H)$^+$;

HRMS: calcd: 277.1916; found: 277.1917.

Step B

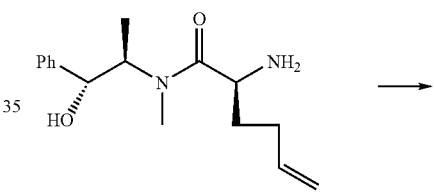

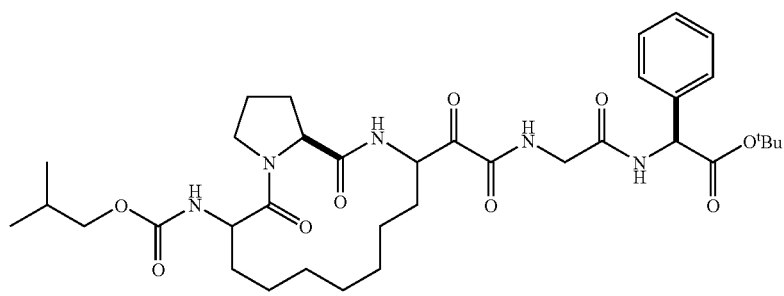

Step A

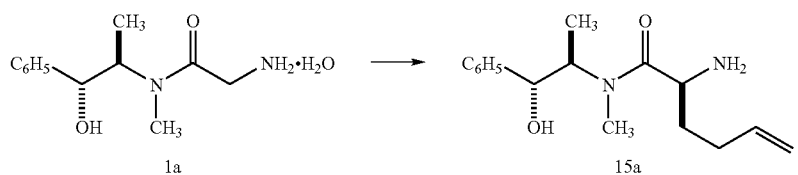

-continued

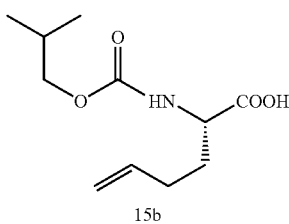

15b 1.9 g of 15a (6.88 mmol, 1 eq) was treated with 2N NaOH (7.0 mL, 2 eq), 7 mL of water and refluxed at 100° C. for 3 h. The mixture was cooled to room temperature. 20 mL of DCM, 10 mL of water was added and the organic layer was separated. The aqueous layer was washed with 20 mL of DCM. The combined organic layers were further washed with 10 mL of water. The combined aqueous layer was treated with 1.3 mL 12 N HCl. 20 mL of dioxane was added and the solution was adjusted to pH 8-9 by adding saturated $NaHCO_3$. 1.48 g of iBOC-OSU (1 eq) was added and the mixture was stirred for overnight. After decreasing the solvent volume to one half, 10 mL of water and 10 mL DCM was added for extraction. The aqueous layer was then treated with 12 N HCl dropwise until it precipitated (pH 2). Extraction with EtOAc 40 mL×2 followed by $MgSO_4$ drying and celite filtration afforded 1.52 g colorless oil 15b in 90% yield.

$^1$H NMR($CDCl_3$): δ 0.88 (d, 6H, J=6.6 Hz) 1.78-2.00 (m, 3H) 2.10-2.20 (m, 2H) 3.80-3.82 (m, 2H) 4.40 (m, 1H) 5.00-5.06 (m, 2H) 5.10 (m, 1H) 5.80 (m, 1H).

$^{13}$C NMR($CDCl_3$): δ 20.0 26.2 29.0 32.8 54.2 72.8 117.0 138.0 157.8 177.6.

MS for $C_{11}H_{19}NO_4$: 230 (M+H)$^+$.

Step C

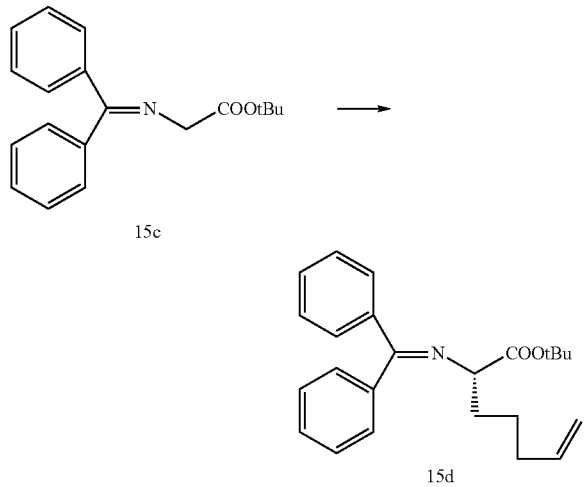

Imine 15c (9.42 g, 31.88 mmol, 1 eq) was mixed with the Corey's catalyst (*J. Am. Chem. Soc.*, 1997, 119, 12414) (1.93 g, 0.1 eq), cesium hydroxide monohydrate (53.55 g, 10 eq) in 150 mL DCM. The solution was cooled down to −60° C. followed by addition of 5-iodo-1-pentene (25 g, 4 eq) under nitrogen. The crude was stirred for 60 h when 100 mL ethyl ether was added in. After washing with water 100 mL×2 and brine 70 mL×1, the organic layer was dried over $MgSO_4$.

Celite filtration and removal of the solvent afforded the crude 28.56 g. 5.1 g of the crude was chromatographed with pure hexane first and then 1:40 to 1:20 EtOAc/hexane. A 2.56 g of a mixture of 15d, 5-iodo-1-pentene and benzophenone (1:2.5: 0.8) was obtained. (15d: $R_f$=0.39, 1:20 EtOAc/hexane).

Step D

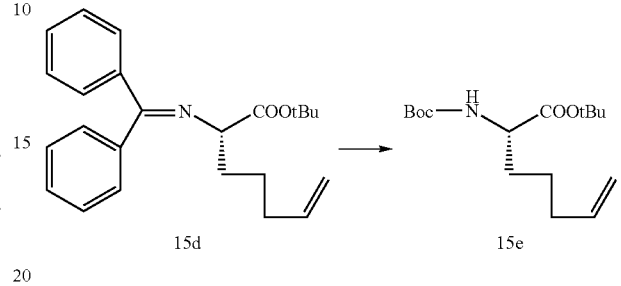

0.5 g of the above crude 15 d (2.56 g) was treated with 4 mL HOAc/THF/water 1:1:1 for 90 min when TLC shows disappearance of the starting material. Two pipetful of saturated $NaHCO_3$ was added. 10 mL water and 20 mL hexane was added for extraction. The aqueous layer was then further basified to pH 9-10. $(Boc)_2O$ (0.15 g) and dioxane 4 mL were added and after 2.5 h, the solvent was removed and the pH of the solution was adjusted to 3-4. Extraction with ether followed by chromatography with 1:10 EtOAc/hexane afforded 0.16 g of 15e in 48% overall yield from 15c. ($R_f$=0.44, 1:10 EtOAc/hexane).

Step E

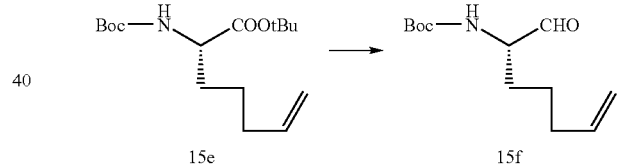

4.88 g of 15e (13.87 mmol) was dissolved in 20 mL of toluene at −78° C. and was treated with 21 mL $LiAlH_4$ (1 M in $Et_2O$, 1.6 eq) for 40 min. The mixture was warmed up to 0° C. and was quenched by EtOAc and 20 mL 5% $NaHSO_4$. Extraction with ether, filtration through celite and removal of solvent afforded the residue which was chromatographed with 1/5 EtOAc/hexane. 2.8 g of the desired aldehyde 15f ($R_f$=0.4) along with the alcohol (1.43 g, $R_f$=0.04) were obtained. The latter could be converted to the aldehyde by Dess-Martin reaction.

Step F

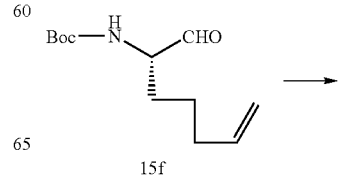

-continued

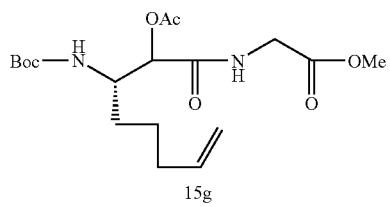
15g 1.26 g of 15f (5.55 mmol, 1 eq), methyl isocyanoacetate (0.50 mL, 1 eq), acetic acid (0.32 mL, 1 eq) were mixed in 20 mL DCM and stirred for 80 h. Removal of the solvent and flash chromatography provided 1.10 g of 15g in 51% yield. ($R_f$=0.29, 1:1 EtOAc/hexane).

$^1$H NMR(CDCl$_3$): δ 1.42 (s, 9H) 1.50-1.60 (m, 2H) 1.99-2.20 (m, 4H) 2.18 (s, 3H) 3.76 and 3.78 (two singlets, 3H, 1:1 diastereomers) 3.90-4.20 (m, 4H) 4.90-5.00 (m, 2H) 5.20 (br s, 1H) 5.70 (m, 1H) 6.62 (br s, 1H).

$^{13}$C NMR(CDCl$_3$): δ 21.93 26.26 29.46 31.25 34.41 41.99 52.53 53.50 75.57 80.41 115.74 139.14 156.28 168.91 169.38 170.79.

HRMS for C$_{18}$H$_{30}$N$_2$O$_7$: calcd: 387.2131 (M+H)$^+$; found 387.2133.

Step G

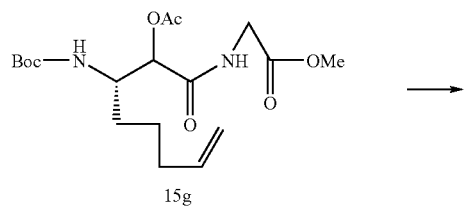

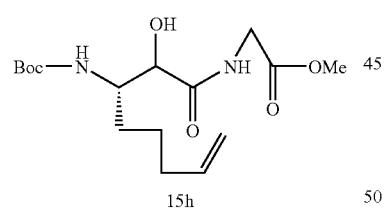
15h

Compound 15g (1.08 g, 2.8 mmol, 1 eq), 60 mg K$_2$CO$_3$ (0.15 eq) in 6 mL MeOH were stirred at room temperature for 1 h and then another 2 h at 40° C. Removal of solid followed by flash chromatography afforded the desired product 15h as white solid (0.65 g, 68% yield).

$^1$H NMR(CDCl$_3$): δ 1.40 (s, 9H) 1.40-1.70 (m, 4H) 1.99-2.10 (m, 2H) 3.70 (s, 3H) 3.80 (br, 1H) 4.00-4.25 (m, 4H) 4.90-5.00 (m, 2H) 5.10 (br s, 1H) 5.30 (m, 1H) 5.78 (m, 1H) 7.40 (br s, 1H).

$^{13}$C NMR(CDCl$_3$): δ 26.83 29.48 30.76 34.53 42.03 53.51 54.95 75.05 81.07 115.76 139.30 157.92 170.84 174.16.

C$_{16}$H$_{28}$N$_2$O$_6$: 345 (M+H)$^+$.

HRMS: calcd: 345.2026; found: 345.2033.

Step H

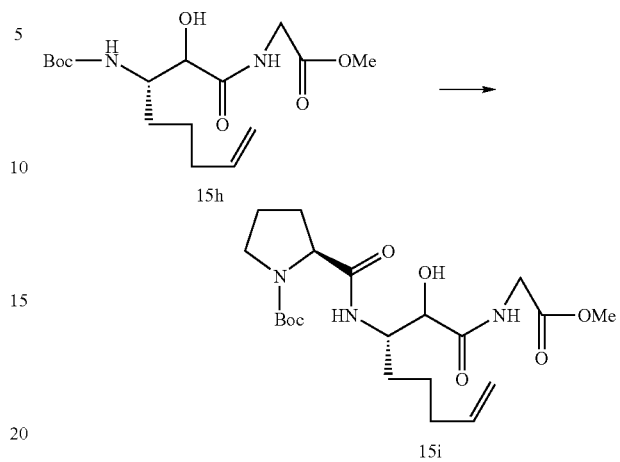

Compound 15h (0.39 g, 1.13 mmol) was stirred with 4 M HCl in dioxane (4 mL) at room temperature for 2 h when solid precipitates formed. The solvent was removed and 20 mL DCM was added. The pH was adjusted to 7 by using Hunig's base. The solvent was then removed and the residue was treated with 10 mL THF, Boc-Pro-OH (0.73 g, 3 eq), HATU (1.29 g, 3 eq), Hunig's base (1.18 mL, 6 eq) and 1 mL DMF. After stirring at room temperature for 7 h, the solvent was removed in vacuo. The residue was dissolved in 20 mL EtOAc and washed with 10 mL saturated NaHCO$_3$, 10 mL 0.5 M HCl twice, water 20 mL and brine 5 mL. Chromatography provided 0.68 g 15i ($R_f$=0.31, 5% MeOH in DCM).

Step I

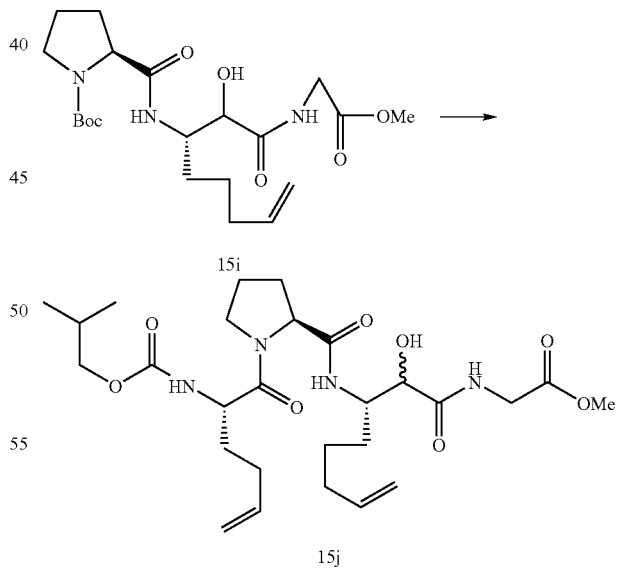

15i was treated with 2 mL DCM, 3 mL 4 M HCl in dioxane for 1 h. 30 mL DCM was added followed by neutralization with Hunig's base at 0° C. The solvent was removed and the crude was dissolved in 5 mL DCM, 10 mL THF. After addition of 15b (0.26 g, 1 eq), HATU (0.43 g, 1 eq) and Hunig's base (0.41 mL, 2.1 eq) and stirred for 4 h, the solvent was removed and 30 mL EtOAc was added. The solution was then washed with 10 mL saturated NaHCO$_3$, 10 mL 1 M HCl, 10 mL 0.5 M HCl, water 20 mL, brine 5 mL. Chromatography gave the desired product 15j (0.3 g, 48% from 15h).

$^{13}$C NMR(CDCl$_3$): δ 20.20 26.26 26.72 29.18 29.55 30.58 33.25 34.60 41.95 48.57 52.90 53.00 53.40 54.68 61.56 72.34 75.68 115.64 116.73 138.07 139.33 157.47 171.04 171.15 173.06 174.23.

C$_{27}$H$_{44}$N$_4$O$_8$: 553 (M+H)$^+$.

HRMS: calcd: 553.3237; found: 553.3259.

Step J

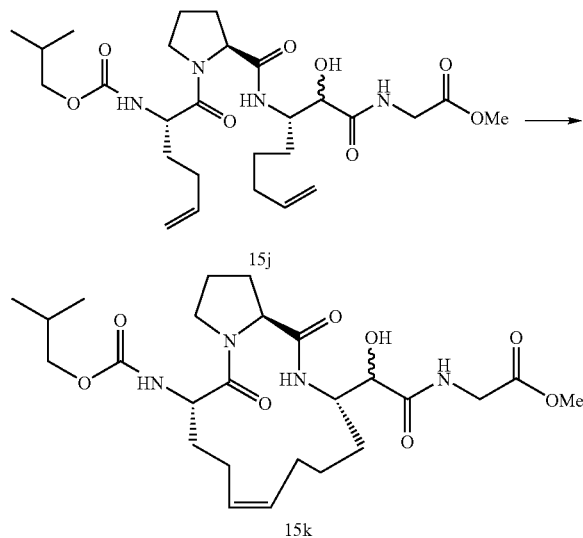

Compound 15j (0.37 g, 0.67 mmol) was treated with 0.138 g Grubbs' catalyst (0.25 eq) in 223 mL DCM under argon. After stirring at room temperature for 65 h, NMR shows the mixture contained the S.M. 15j, the desired product 15k (about 20% yield) and PO(C$_6$H$_{11}$)$_3$. The R$_f$ for these three are 0.34, 0.24, 0.74, respectively in 5% HOAc/EtOAc. Repeated flash chromatography could provide the pure sample of 15k.

$^1$H NMR(CDCl$_3$): δ 0.90 (d, 6H, J=6.6 Hz) 1.40-2.00 (m, 14H) 2.05-2.50 (m, 3H) 3.60 (m, 1H) 3.70 (s, 3H) 3.75-4.00 (m, 3H) 4.00-4.20 (m, 2H) 4.50 (m, 1H) 4.70 (d, 1H, J=7.5 Hz, diastereomer) 4.81 (d, 1H, J=7.9 Hz, another diastereomer) 5.38 (m, 1H) 5.58 (m, 1H) 5.65 (br s, 1H) 7.20 (d, 1H J=7.0 Hz) 7.38 (d, 1H, J=7.1 Hz).

$^{13}$C NMR(CDCl$_3$): δ 20.26 23.05 26.54 27.02 27.67 27.73 29.21 31.06 34.03 41.97 48.71 52.40 52.80 53.53 60.54 72.43 75.08 130.44 130.56 157.02 171.13 172.01 173.13 173.38.

LC/MS: Tr=5.11 min (gradient A (acetonitrile)/B (water with 0.1% TFA): from 5% A/B to 95% A/B in 10 min.) C$_{25}$H$_{40}$N$_4$O$_8$: 525 (M+1)$^+$.

HRMS: calcd: 525.2924; found: 525.2908.

Step K

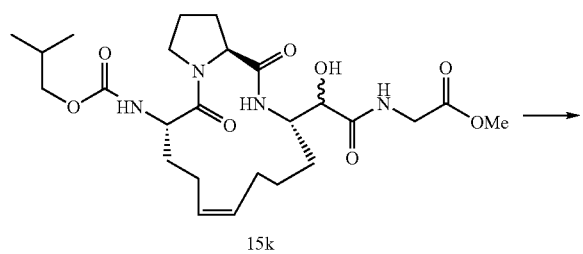

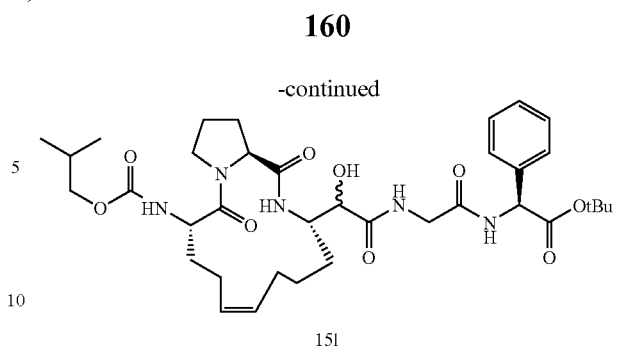

Compound 15k (92 mg, 0.18 mmol, 1 eq), 60 mg K$_2$CO$_3$ (2.5 eq) in 5 mL MeOH were stirred at 40° C. for 2 h when TLC shows complete disappearance of S.M. After removal of the solvent, 44 mL 0.01 M HCl in DCM (2.5 eq) was added to neutralize the solution. The solvent was removed followed by addition of 10 mL THF, 1 mL DMF, PhG-O-tBu (HCl salt, 51 mg, 1.2 eq), 80 mg of HATU (1.2 eq), 0.11 mL of Hunig's base (3.5 eq). The mixture was stirred for 12 h. After removal of solvent, direct chromatography provided the product 15l (97 mg, 79% yield from 15j). R$_f$=0.32, 5% MeOH/DCM).

$^1$H NMR(CDCl$_3$): δ 0.90 (d, 6H, J=6.6 Hz) 1.30 (s, 9H) 1.40-2.00 (m, 14H) 2.15-2.20 (m, 1H) 3.60 (m, 1H) 3.75-3.90 (m, 3H) 4.00-4.09 (m, 1H) 4.10-4.35 (m, 2H) 4.50 (m, 1H) 4.62 (d, 1H, J=7.5 Hz, diastereomer) 4.72 (d, 1H, J=7.9 Hz, another diastereomer) 5.20-5.38 (m, 1H) 5.44 (d, 1H, J=6.6 Hz) 5.50 (m, 1H) 5.98 (m, 1H) 7.30 (m, 5H) 7.45 (d, 1H, J=7.0 Hz) 7.55 (d, 1H, J=7.1 Hz) 7.70 (br s, 1H).

$^{13}$C NMR(CDCl$_3$): δ 20.30 23.35 26.38 26.78 27.29 28.02 29.18 31.42 34.89 43.97 48.70 51.90 52.93 58.22 60.40 72.44 74.96 75.93 83.80 120.88 128.10 128.12 129.63 129.70 130.33 137.74 157.20 169.32 170.69 173.70 174.47.

LC/MS: Tr=6.61 min (gradient A (acetonitrile)/B (water with 0.1% TFA): from 5% A/B to 95% A/B in 10 min.) MS: C$_{36}$H$_{53}$N$_5$O$_9$: 700 (M+H)$^+$.

Step L

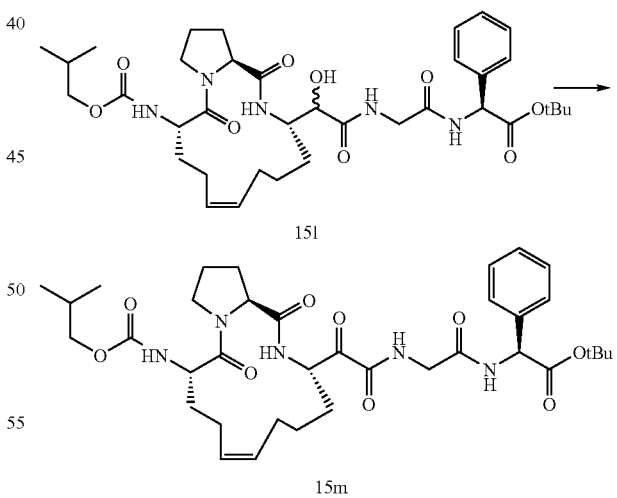

Compound 15l (90 mg, 0.13 mmol) was treated with 109 mg of Dess-Martin reagent (2 eq) in 10 mL DCM at room temperature for 12 h. After removal of the solvent, direct chromatography with 7:3 EtOAc/hexane provided 15m (40%) as white solid.

$^1$H NMR(CDCl$_3$): δ0.95 (d, 6H, J=6.6 Hz) 1.40 (s, 9H) 1.50-2.10 (m, 14H) 2.20-2.30 (m, 1H) 3.60 (m, 1H) 3.75-3.90 (m, 3H) 3.93 (dd, 1H, J=5.9, 16.8 Hz) 4.10 (m, 1H) 4.50 (dd, 1H, J=8.0, 13.9 Hz) 4.80 (d, 1H, J=6.6 Hz) 5.20-5.40 (m, 3H)

5.41 (d, 1H, J=6.6 Hz) 5.60 (dd, 1H, J=7.3, 10 Hz) 6.82 (d, 1H, J=7.3 Hz) 7.30 (m, 5H) 7.50 (m, 1H) 7.80 (d, 1H, J=6.7 Hz).

$^{13}$C NMR(CDCl$_3$): δ 20.29 23.65 26.34 26.75 29.02 29.20 30.37 30.95 31.56 35.07 43.71 48.83 52.95 54.20 58.14 60.23 72.54 84.15 128.03 129.41 129.68 129.87 130.62 137.60 156.99 160.33 167.41 171.37 173.84 187.26 196.36.

LC/MS: Tr=6.81 min (gradient A (acetonitrile)/B (water with 0.1% TFA): from 5% A/B to 95% A/B in 10 min.) MS: C$_{36}$H$_{51}$N$_5$O$_9$: 698 (M+H)$^+$.

HRMS: calcd 698.3765 found 698.3762.

Step M

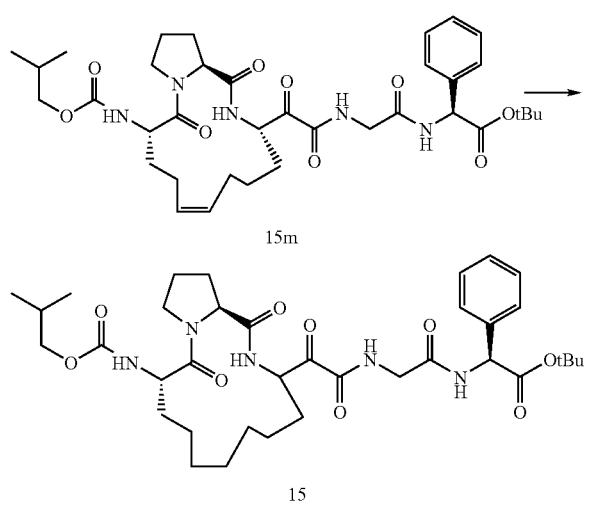

Compound 15m (4 mg) was treated with 5 mL MeOH, 2 mg of Pd—C under hydrogen balloon for 1.5 h. The solution was filtered through celite. The filtrate was dried in vacuo and the NMR shows exclusive formation of 15.

$^1$H NMR(CDCl$_3$): δ 0.95 (d, 6H, J=6.6 Hz) 1.40 (s, 9H) 1.50-2.10 (m, 16H) 2.20-2.30 (m, 1H) 3.60 (m, 1H) 3.75-3.90 (m, 3H) 3.93 (dd, 1H, J=5.9, 16.8 Hz) 4.10 (m, 1H) 4.50 (dd, 1H, J=8.0, 13.9 Hz) 4.80 (d, 1H, J=6.6 Hz) 5.30 (m, 1H) 5.41 (d, 1H, J=6.6 Hz) 5.55 (d, 1H, J=7.0 Hz) 6.82 (d, 1H. J=7.3 Hz) 7.30 (m, 5H) 7.50 (m, 1H) 7.80 (d, 1H, J=6.7 Hz).

LC/MS: Tr=5.26 min (gradient A (acetonitrile)/B (water with 0.1% TFA): from 5% A/B to 95% A/B in 10 min.) MS: C$_{36}$H$_{53}$N$_5$O$_9$: 700 (M+H)$^+$.

HRMS: calcd: 700.3922; found: 700.3925.

Preparative Example 16

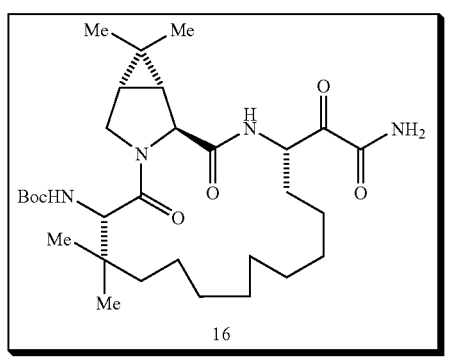

Step A

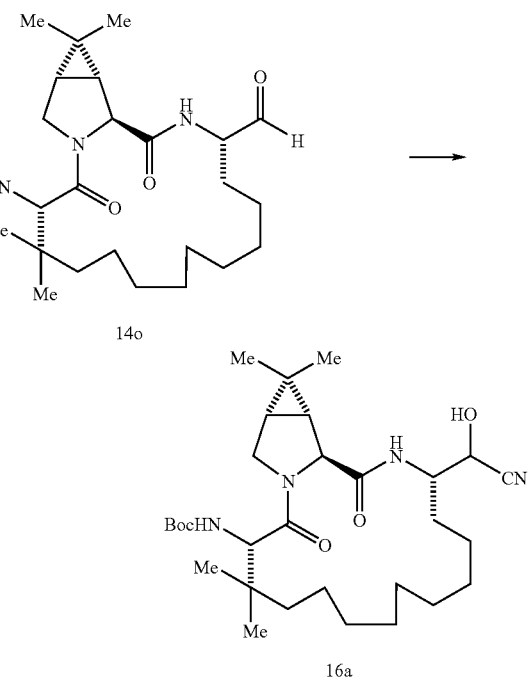

A solution of aldehyde 14o (590 mg, 1.15 mmol) in CH$_2$Cl$_2$ (10 mL) was treated with Et$_3$N (240 mg, 2.4 mmol) and acetone cyanohydrin (240 mg, 2.82 mmol). The reaction mixture was stirred at rt for 2 h and concentrated in vacuo. The residue was purified by chromatography (SiO$_2$, acetone/hexanes 1:4) to yield 16a (600 mg) as a colorless solid.

MS (ESI), m/z, relative intensity 569 [(M+Na)$^+$, 20], 547 [(M+1)$^+$, 40], 447 (100).

Step B

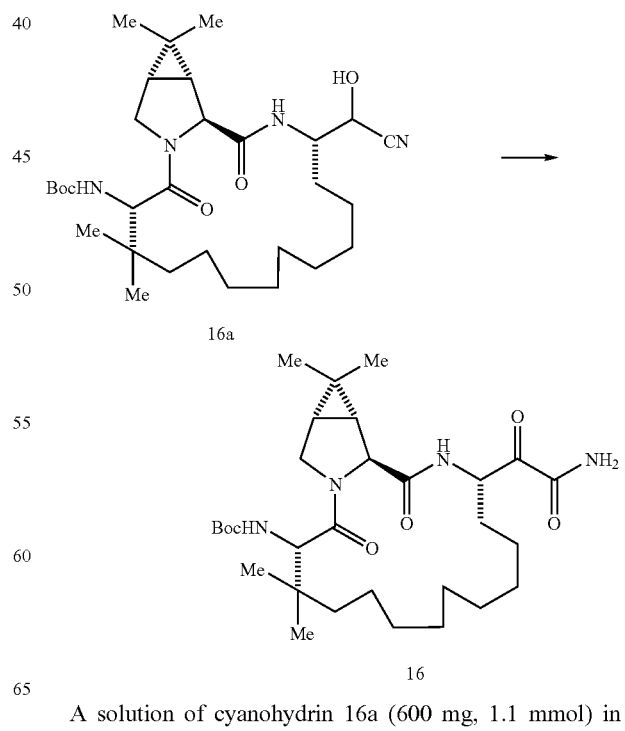

A solution of cyanohydrin 16a (600 mg, 1.1 mmol) in DMSO (10 mL) was treated with H$_2$O$_2$ (35%, 1.5 mL) and K₂CO₃ (252 mg, 1.83 mmol) and stirred at rt. for 15 h. The reaction mixture was diluted with CH₂Cl₂ (200 mL) and washed with aq. Na₂S₂O₃ solution (10%, 50 mL) and brine (30 mL). The reaction mixture was dried (MgSO₄) filtered concentrated in vacuo and directly used in oxidation without further purification.

A solution of hydroxy amide in toluene/DMSO (2:1, 15 mL) was treated with EDCl (1.9 g, 10.00 mmol) and Cl₂CHCOOH (317 mg, 2.49 mmol) and stirred at 0° C. for 3 h. The reaction mixture was diluted with CH₂Cl₂ (300 mL) and washed with satd. aq. NaHCO₃ (2×100 mL) and brine (100 mL). The organic layer was dried (MgSO₄), concentrated and purified by chromatography (SiO₂, acetone/hexanes 1:5) to yield 16 as colorless solid. MS (ESI), m/z, relative intensity 617 [(M+CH₃OH+Na)⁺, 20], 595 [(M+CH₃OH+1)⁺, 40], 507 [(M+1)⁺, 20], 463 (100).

Preparative Example 17

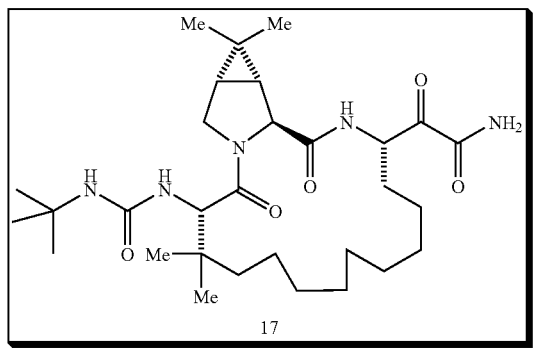

Step A

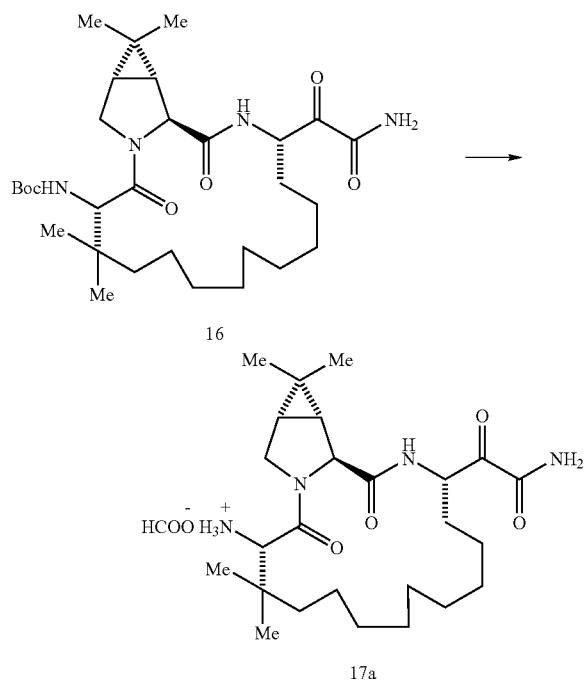

A solution of 16 (300 mg 0.54 mmol) in HCOOH (10.0 mL) was stirred at rt for 2 h and concentrated in vacuo. The residue was dried in vacuo and used in further reactions without further purification.

Step B

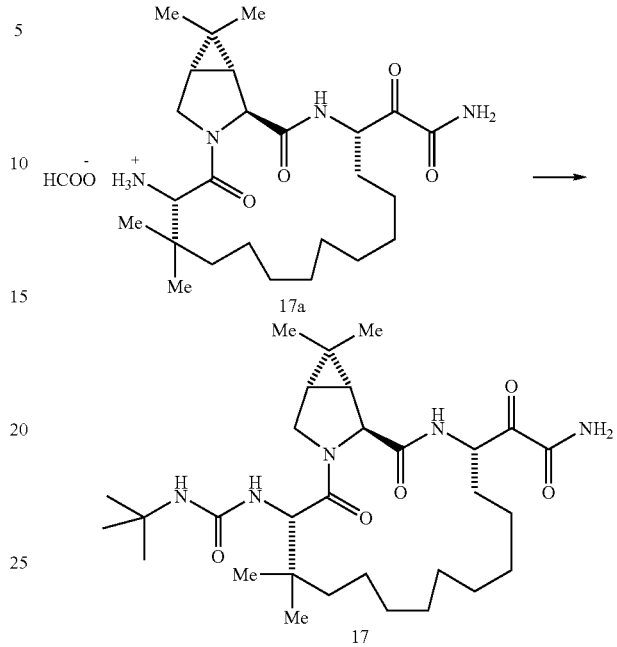

A solution of 17a (100 mg) in DMF/CH₂Cl₂ (1:1, 3 mL) was treated with t-BuNCO (50 □L and NMM (52 mg, 0.52 mmol). The reaction mixture was stirred at rt for 16 h and concentrated in vacuo. and diluted with CH₂Cl₂ (60 mL) and washed with aq. HCl (1M, 2×30 mL), dried, concentrated in vacuo. The residue was purified by chromatography (SiO₂, acetone/hexanes 1:2) to yield 17 (34 mg) as colorless solid.

MS (ESI), m/z, relative intensity 584 [(M+1)⁺, 30], 463 (100).

Preparative Example 18

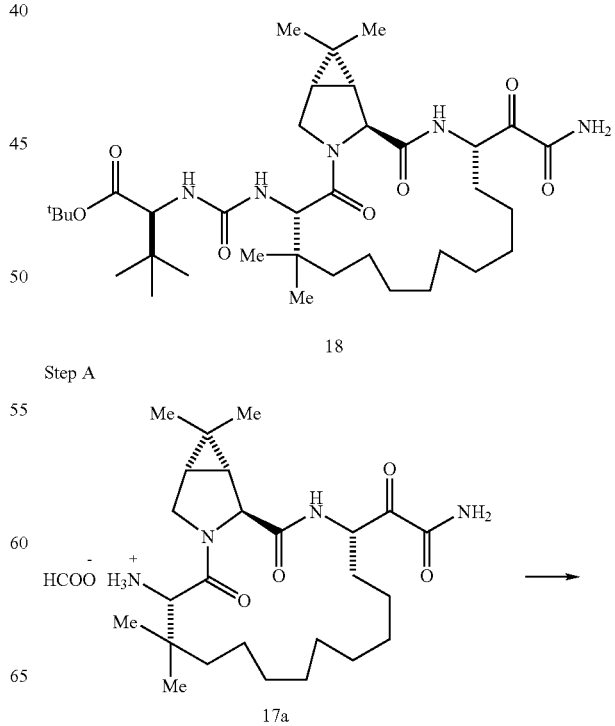

Step A

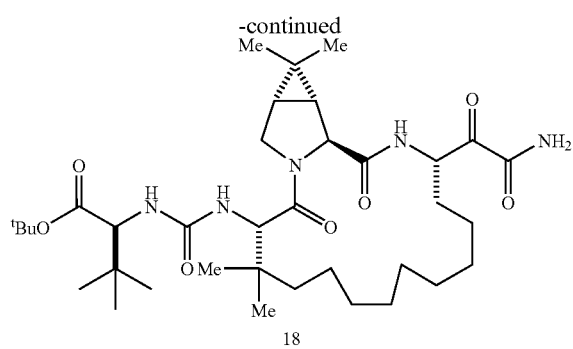

18

A solution of 17a (100 mg) in DMF/CH$_2$Cl$_2$ (1:1, 3 mL) was treated with isocyanate of tertbutylester of tert-butylglycine (100 mg, 0.46 mmol) and 15 NMM (52 mg, 0.52 mmol). The reaction mixture was stirred at rt for 16 h and concentrated in vacuo. and diluted with CH$_2$Cl$_2$ (60 mL) and washed with aq. HCl (1M, 2×30 mL), dried, concentrated in vacuo. The residue was purified by chromatography (SiO$_2$, acetone/hexanes 1:2) to yield 18 (42 mg) as colorless solid.

MS (ESI), m/z, relative intensity 698 [(M+Na)$^+$, 40], 676 [(M+1)$^+$, 100], 463 (20).

Preparative Example 19

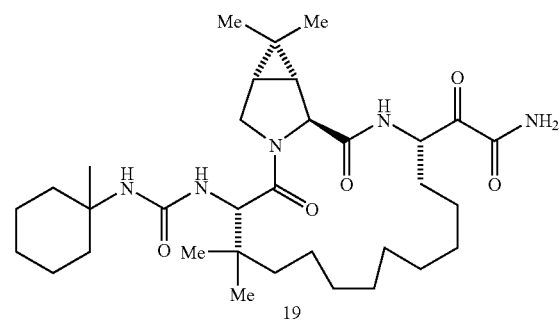

19

Step A

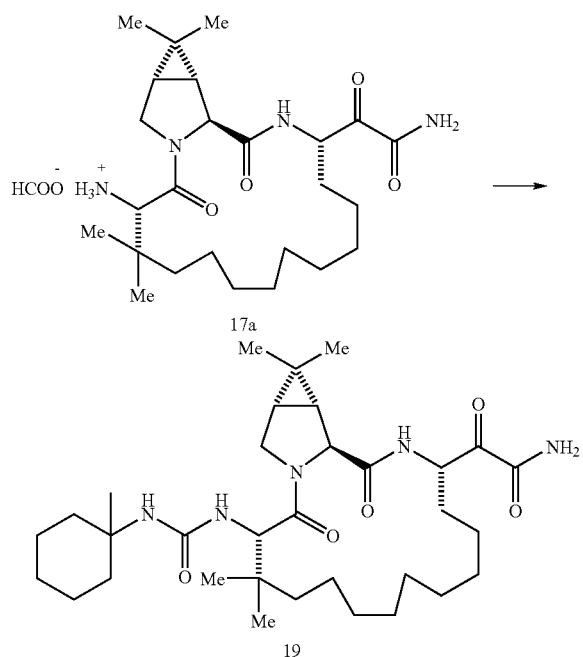

A solution of 17a (100 mg) in DMF/CH$_2$Cl$_2$ (1:1, 3 mL) was treated with isocyanate of α-methyl-cyclohexylamine (100 μL) and NMM (52 mg, 0.52 mmol). The reaction mixture was stirred at rt for 16 h and concentrated in vacuo. and diluted with CH$_2$Cl$_2$ (60 mL) and washed with aq. HCl (1M, 2×30 mL), dried, concentrated in vacuo. The residue was purified by chromatography (SiO$_2$, acetone/hexanes 1:2) to yield 20 (21 mg) as colorless solid.

MS (ESI), m/z, relative intensity 624 [(M+Na)$^+$, 30], 602 [(M+1)$^+$, 15], 463 (100), 449 (20), 129 (30).

Preparative Example 20

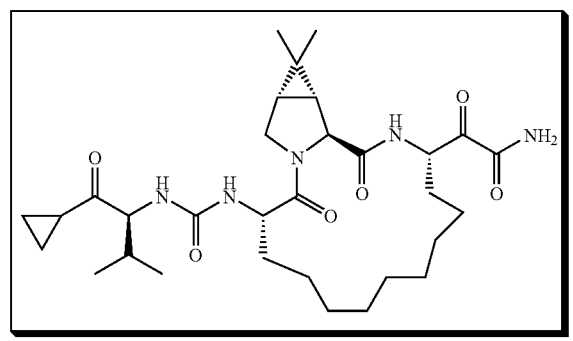

20

Step A

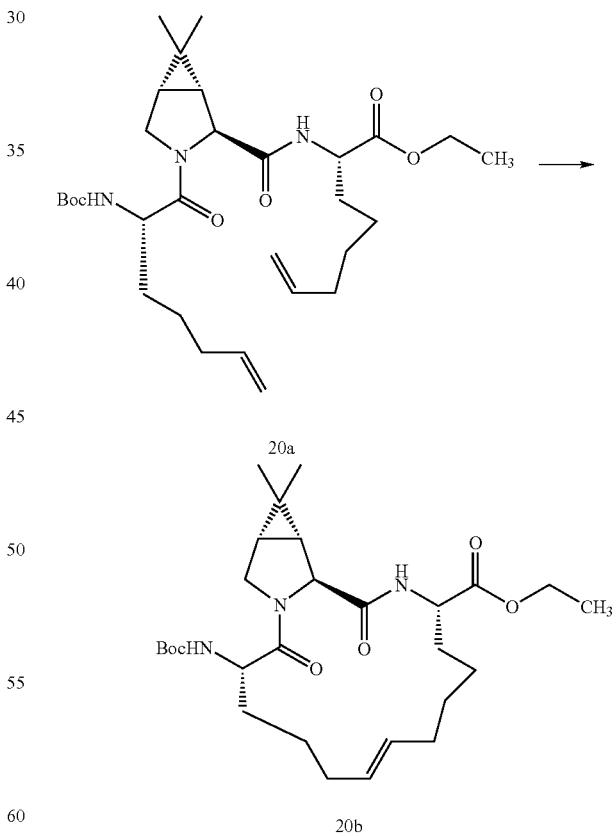

A solution of acyclic diene 20a (6.00 g, 10.954 mmol) in dry toluene (500 mL), degassed with Argon for 0.5 h, was treated with Grubbs catalyst (1.35 g, 1.643 mmol) and heated at 60° C. for 12 h. The reaction mixture was concentrated in vacuo and purified by chromatography (SiO$_2$, EtOAc/hexanes 1:3) to yield 20b as a brown foam.

Step B

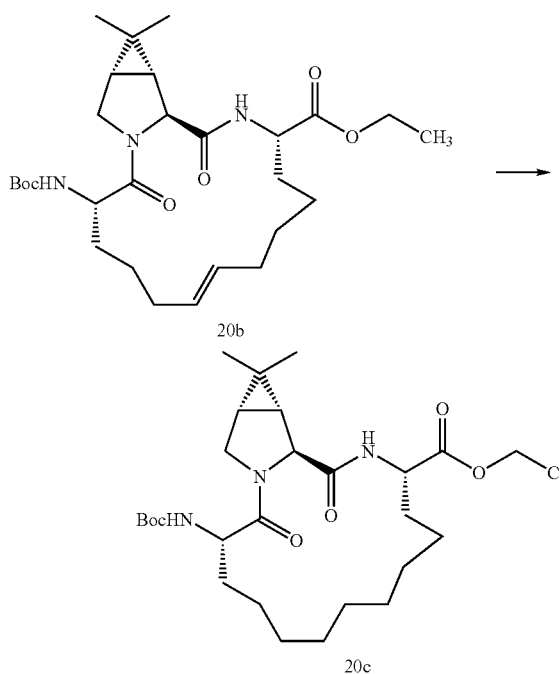

A solution of alkene 20b (5.00 g mg, 0.865 mmol) in methanol (100 mL) was treated with Pd/C (1.2 g, 5% w/w) and hydrogenated at 50 psi for 3 h. The reaction was filtered through a plug of celite and concentrated in vacuo. The residue was purified by chromatography using THF/hexanes gradient from 10-40% to isolated 20c (3.00 g) as a colorless solid.

Step C

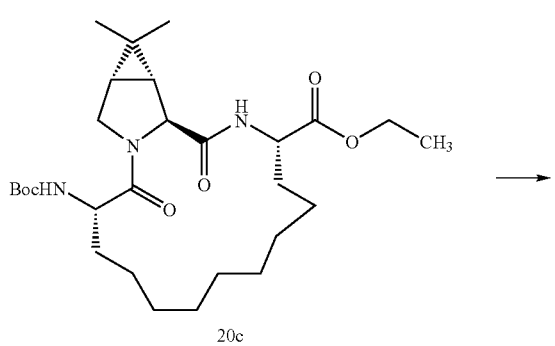

A solution of ester 20c (3.00 g, 5.75 mmol) in dry THF (50 mL) was treated with $LiBH_4$ (2M soln in THF, 3.5 mL, 6.90 mmol) and stirred at rt for 3 h. The reaction was followed by TLC (EtOAc/Hexanes 1:2). The reaction was quenched with methanol (2 mL) and diluted with aq. HCl (1 M, 30 mL) and extracted into $CH_2Cl_2$ (3×100 mL). The combined organic layers were washed with aq. saturated $NaHCO_3$ (30 mL), brine, dried ($MgSO_4$), filtered concentrated in vacuo and purified by chromatography ($SiO_2$, Acetone/Hexanes 1:2) to yield 20d (2.21 g) as colorless solid. MS (m/z, relative intensity) 518 [(M+K)$^+$, 15], 480 [(M+H)$^+$, 75], 380(100).

Step D

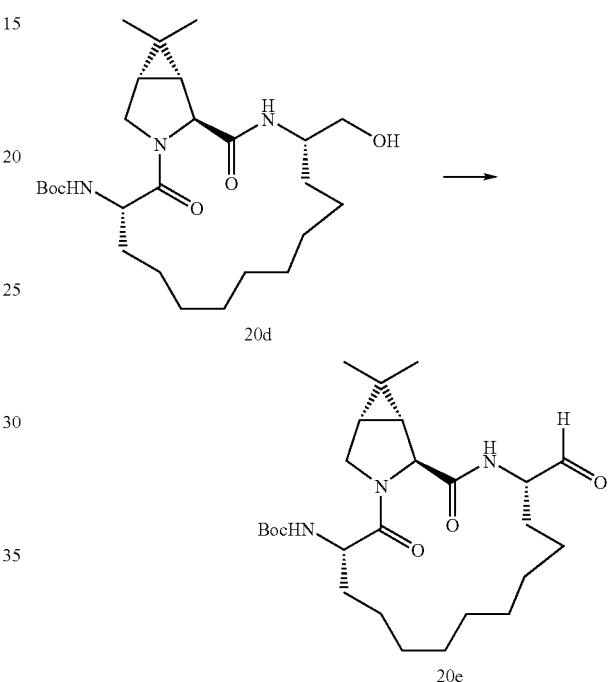

A solution of alcohol 20d (2.2 g, 4.58 mmol) in dry $CH_2Cl_2$ (50 mL) was treated with Dess-Martin reagent (2.91 g, 6.880 mmol) and stirred at rt for 2 h. The reaction mixture was diluted with aq. $Na_2S_2O_3$ (5%, 50 mL) and aq. saturated $NaHCO_3$ (50 mL) and stirred at rt. for 15 min. The reaction mixture was extracted with $CH_2Cl_2$ (500 mL) and the combined organic layers were dried ($MgSO_4$), filtered, concentrated in vacuo to yield crude 20e (1.9 g) that was used in the next reaction without further purification.

Step E

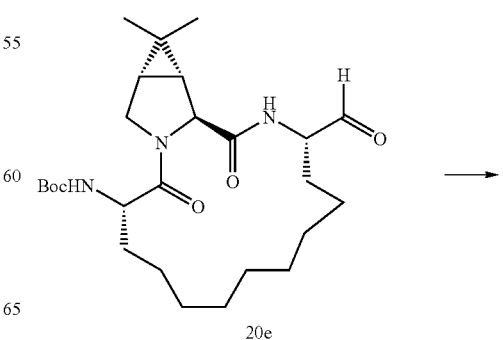

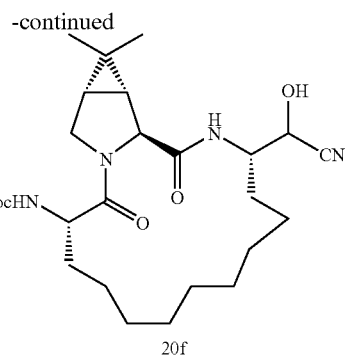

20f

A solution of crude 20e_(1.00 g, 2.094 mmol) in CH$_2$Cl$_2$ (15 ml) was cooled to 0° C. and treated with acetone cyanohydrin (356 mg, 4.187 mmol) and triethylamine (424 mg, 4.187 mmol). The reaction mixture was stirred at 0° C. for 12 h and concentrated in vacuo. The residue was purified by chromatography (SiO$_2$, EtOAc/Hexanes 1:5-->1:1) to yield 20f (500 mg) as a colorless oil.

Step F

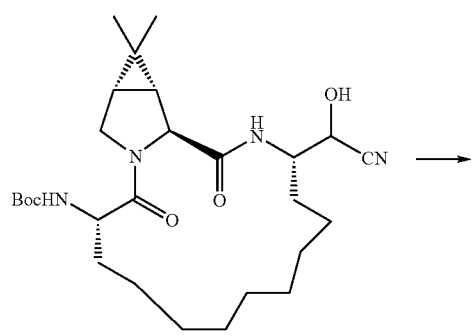

20f

→

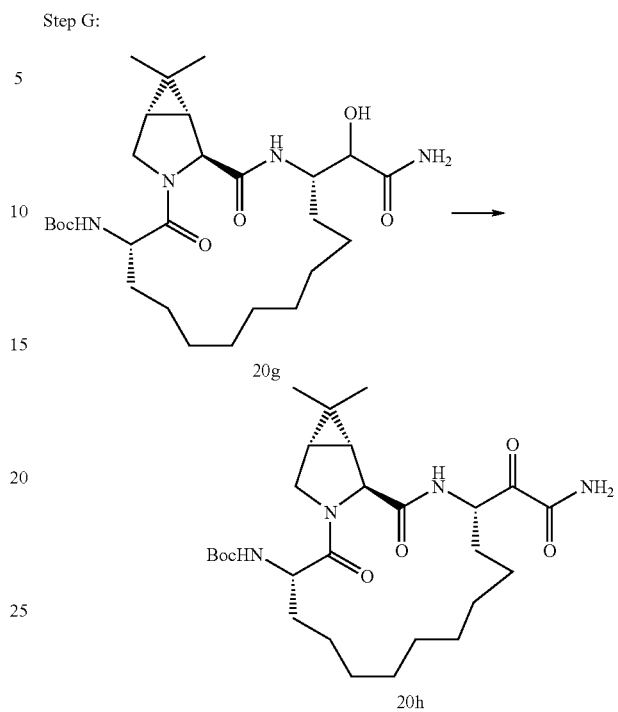

A solution of cyanohydrin 20f_(500 mg, ~1.00 mmol) in DMSO (5 mL) was treated with H$_2$O$_2$ (5 mL), K$_2$CO$_3$ (276 mg, 2.00 mmol) and stirred at rt. for 12 h. The reaction mixture was diluted with aq. Na$_2$S$_2$O$_3$ (5%, 100 mL) and extracted with CH$_2$Cl$_2$ (2×100 mL). The combined organic layers were dried (MgSO$_4$), filtered, concentrated in vacuo to yield 20g that was used as it is for further oxidation without purification.

Step G:

A solution of hydroxylamine 20g_(850 mg, 1.626 mmol) in toluene (5 mL) and DMSO (5 mL) was treated with EDCI (3.117 g, 16.26 mmol), and dichloroacetic acid (1.048 g, 8.13 mmol, 698 μL) and stirred at rt. for 3 h. The reaction mixture was diluted with CH$_2$Cl$_2$ (200 mL) and washed with aq. saturated NaHCO$_3$ (200 mL), aq. HCl (1 M, 200 mL), brine (30 mL), dried (MgSO$_4$) filtered, concentrated in vacuo and purified by chromatography (SiO$_2$, acetone/Hexanes 1:2) to yield 20h (300 mg) as a colorless solid.

Step H:

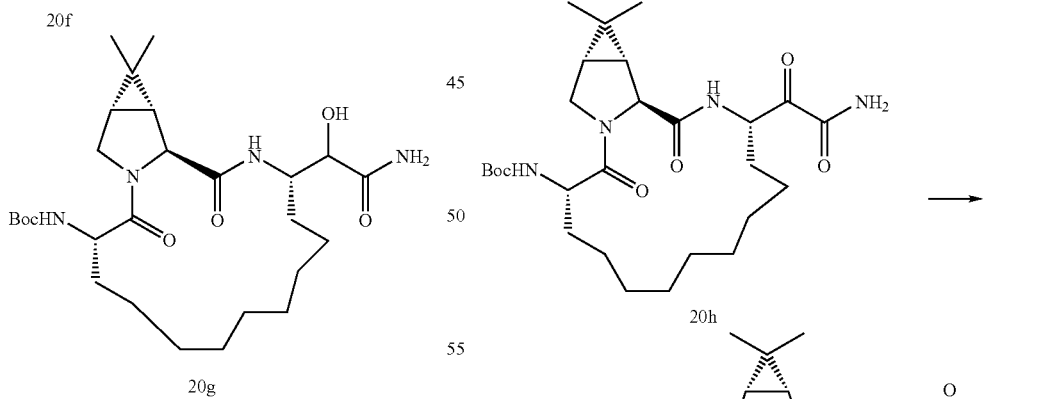

A solution of Boc protected ketoamide 20h in formic acid (5 mL) was stirred at rt for 3 h and concentrated in vacuo and used as it is in the next step without further purification.

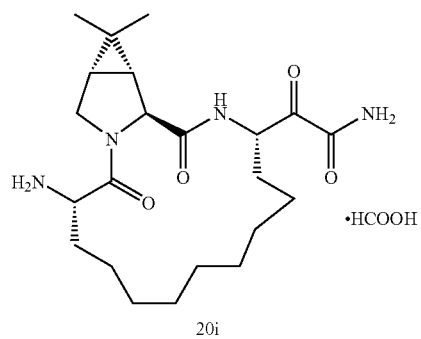

20i

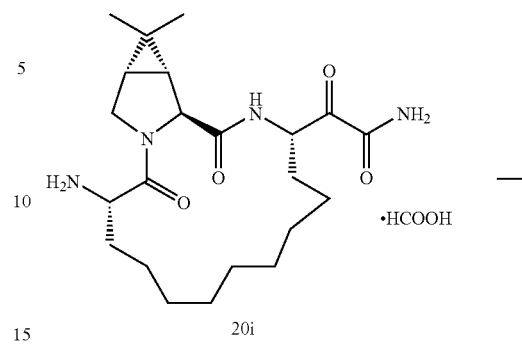

20i

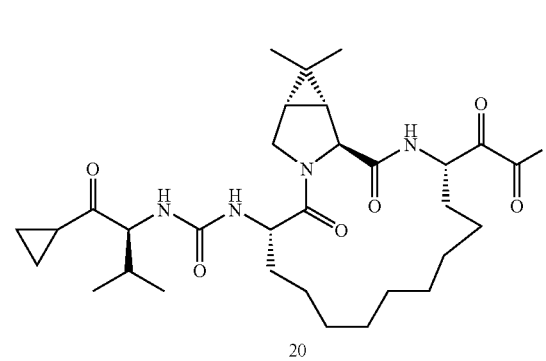

20

A solution of amine 20i (40 mg, 0.1 mmol) in methylene chloride (3.0 mL) was treated with NMM (30 mg, 0.3 mmol) and cooled to 0° C. A solution of isocyanate in CH$_2$Cl$_2$ was added and the reaction mixture was stirred at rt. for 1.5 h. The reaction mixture was diluted with methylene chloride (60 mL) and washed with aq. HCl (1 M, 30 mL). The organic layers were dried with (MgSO$_4$) filtered concentrated in vacuo and purified by chromatography (SiO$_2$, acetone/hexanes 20→50%) to yield 20 as a colorless solid. MS (m/z, relative intensity) 588 [(M+H)$^+$, 100], 421 (40). HRMS (ESI) Calcd. for C$_{31}$H$_{50}$N$_5$O$_6$: 588.3761 (M+H)$^+$; Found: 588.3751.

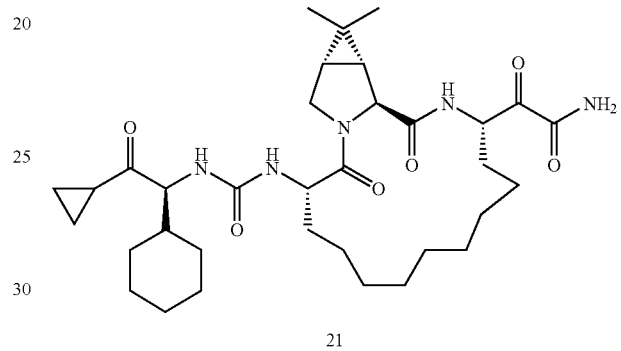

21

A solution of amine 20i (40 mg, 0.1 mmol) in methylene chloride (3.0 mL) was treated with NMM (30 mg, 0.3 mmol) and cooled to 0° C. A solution of 2-cyclohexyl-1-cyclopropyl-2-isocyanato ethanone (0.15 mmol) in CH$_2$Cl$_2$ was added and the reaction mixture was stirred at rt. for 1.5 h. The reaction mixture was diluted with methylene chloride (60 mL) and washed with aq. HCl (1 M, 30 mL). The organic layers were dried with (MgSO$_4$) filtered concentrated in vacuo and purified by chromatography (SiO$_2$, acetone/hexanes 20→50%) to yield 21 as colorless solid.

Preparative Example 21

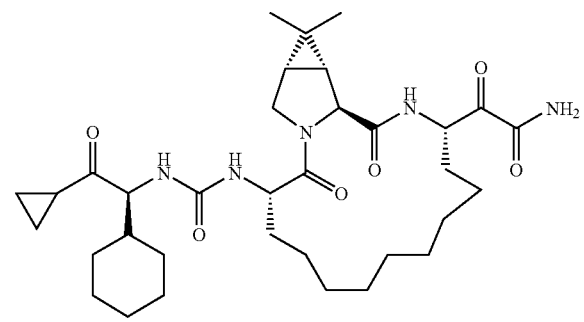

21

Preparative Example 22

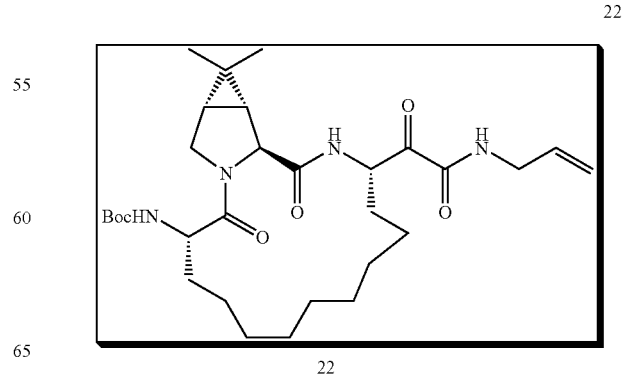

22

Step A:

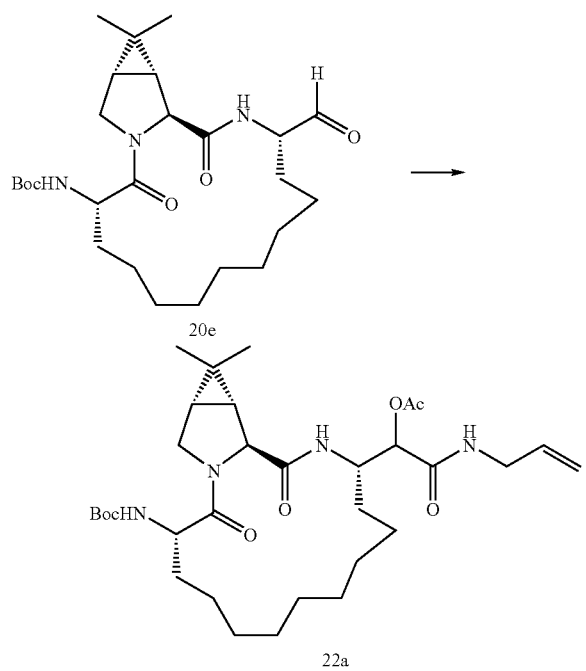

A solution of aldehyde 20e (100 mg, 0.210 mmol) in methylene chloride (4 mL) was treated with allyl isocyanide (28.01 mg, 0.411 mmol) and acetic acid and stirred at rt. for 12 h. The reaction was concentrated in vacuo and purified by chromatography (SiO$_2$, acetone/hexanes 1:4→1:1) to obtain 22a (75 mg) as colorless solid. MS (m/z, relative intensity) 605 [(M+H)$^+$, 100], 505 (98).

Step B:

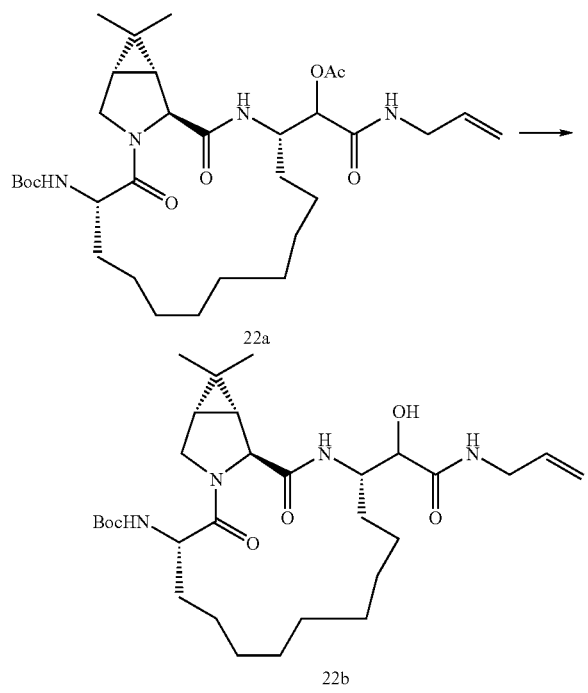

A solution of 22b (275 mg, 0.454 mmol) in methanol (4 mL), THF (4.0 mL) and water (4.0 mL) was treated with LiOH.H$_2$O (22 mg, 0.55 mmol) and stirred at rt. for 2 h. The reaction mixture was diluted with aq. HCl (1 M, 30 mL) and extracted in CH$_2$Cl$_2$ (2×40 mL). The combined organic layer were dried (MgSO$_4$), filtered, concentrated in vacuo, and used as it is in next step without further purification.

Step C:

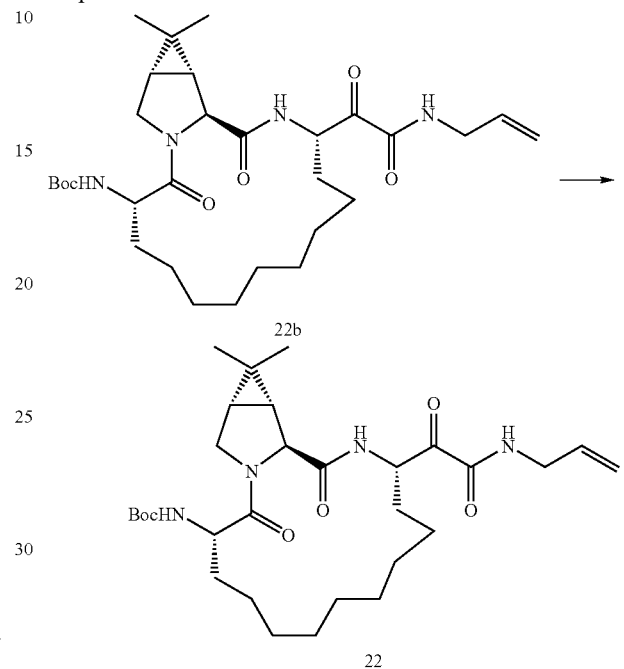

A solution of alcohol 22b (300 mg, 0.534 mmol) in dry CH$_2$Cl$_2$ (15 mL) was treated with Dess-Martin reagent (453 mg, 1.06 mmol) and stirred at rt. for 2 h. The reaction mixture was diluted with aq. Na$_2$S$_2$O$_3$ (5%, 30 mL) and aq. saturated NaHCO$_3$ (30 mL) and stirred at rt. for 15 min. The reaction mixture was extracted with CH$_2$Cl$_2$ (3×50 mL) and the combined organic layers were dried (MgSO$_4$), filtered, concentrated in vacuo and purified by chromatography (SiO$_2$, acetone/hexanes 0:1→1:1) to yield 22 as a colorless solid. MS (m/z, relative intensity) 561 [(M+H)$^+$, 100], 461 (99). HRMS (ESI) Calcd. for C$_{31}$H$_{50}$N$_5$O$_6$: 588.3761 (M+H)$^+$; Found: 588.3751.

Preparative Example 23

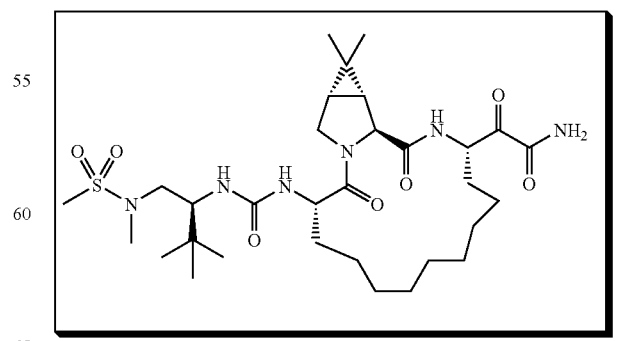

Step A:

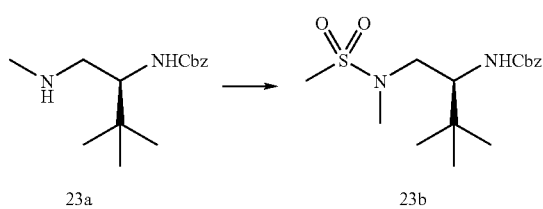

A solution of amine 23a (900 mg, 3.40 mmol) in CH$_2$Cl$_2$ at 0° C. was treated with NMM (511 mg, 5.10 mmol) and methanesulfonyl chloride (585 mg, 5.10 mmol) and stirred at 0° C. for 12 h. The reaction mixture was diluted with CH$_2$Cl$_2$ (300 mL) and washed with excess aq. HCl (1M, 500 mL). The organic layer was dried (MgSO$_4$) filtered concentrated in vacuo and purified by chromatography (SiO$_2$, Hex/EtOAc 1:9→1:1) to yield methylsulfonamide 23b (1.00 g).

Step B:

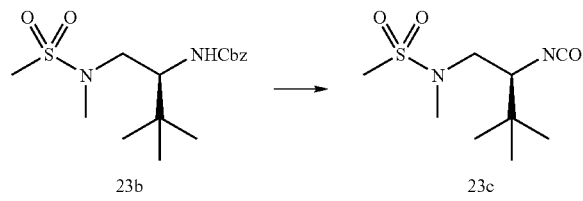

A solution methanesulfonamide 23b (1.0 g, 2.9 mmol) in methanol (30 mL) was treated with palladium (200 mg, 10% wt/C) and hydrogenated at 60 psi for 3 h. The reaction mixture was filtered through a plug of celite and the filtrate was concentrated in vacuo. The residue was directly used in further reaction without further purification.

A solution of deprotected amine in CH$_2$Cl$_2$ (10 mL) aq. saturated NaHCO$_3$ (10 mL) at 0° C. was treated with phosgene (5 mL, 15% soln. in toluene) and stirred at 0° C. for 2 h. The reaction mixture was diluted with CH$_2$Cl$_2$ (50 mL) and the organic layer was washed with cold aq NaHCO$_3$. The organic layer was dried (MgSO$_4$) filtered and further diluted with 10 mL toluene, concentrated the methylene chloride layer and used as a solution of 23c.

Step C:

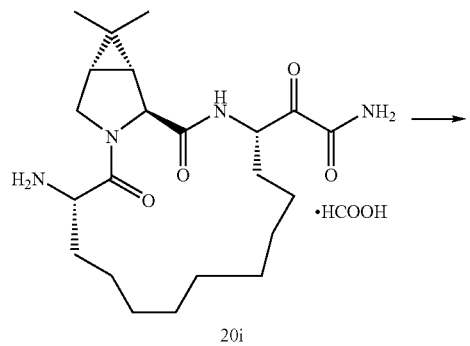

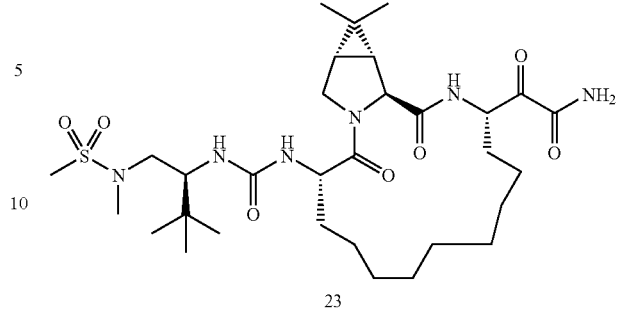

A solution of amine 20i (40 mg, 0.1 mmol) in methylene chloride (3.0 mL) was treated with NMM (30 mg, 0.3 mmol) and cooled to 0° C. A solution of isocyanate 23 in CH$_2$Cl$_2$ was added and the reaction mixture was stirred at rt. for 1.5 h. The reaction mixture was diluted with methylene chloride (60 mL) and washed with aq. HCl (1 M, 30 mL). The organic layers were dried with (MgSO$_4$) filtered concentrated in vacuo and purified by chromatography (SiO$_2$, acetone/hexanes 20→50%) to yield 23. MS (m/z, relative intensity) 693 [(M+K)$^+$, 10], 677 [(M+Na)$^+$, 20], 655 [(M+H)$^+$, 100], 449 (30), 421 (30); HRMS (ESI) Calcd. for C$_{31}$H$_{54}$N$_6$O$_7$SNa 677.3672 (M+Na)$^+$; Found: 677.3685.

Preparative Example 24

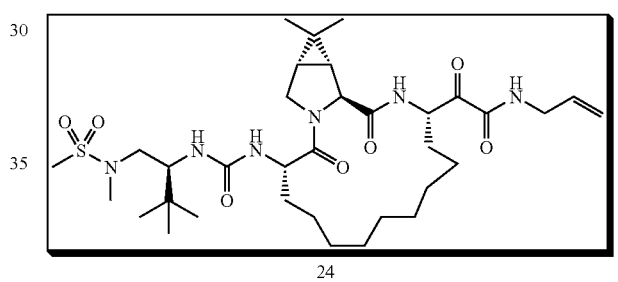

Step A:

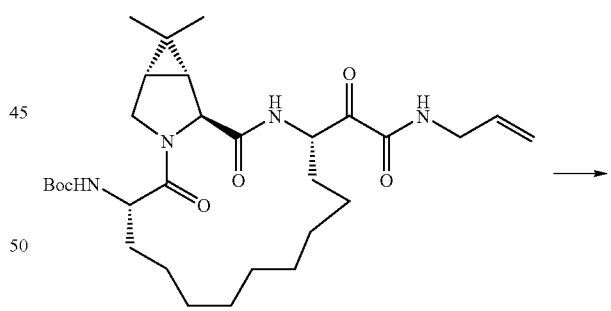

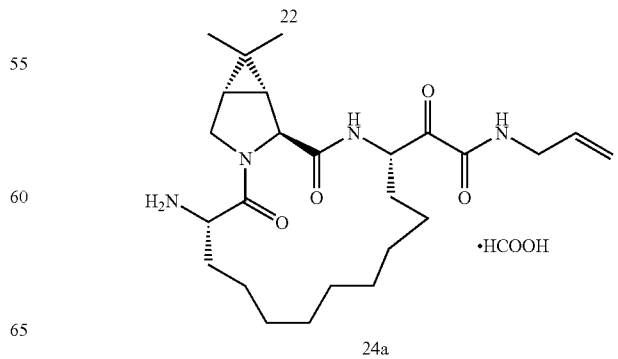

A solution of Boc protected ketoamide 22 (220 mg, 0.39 mmol) in formic acid (5 mL) was stirred at rt. for 3 h and concentrated in vacuo and used as it is in the next step without further purification.

Step B:

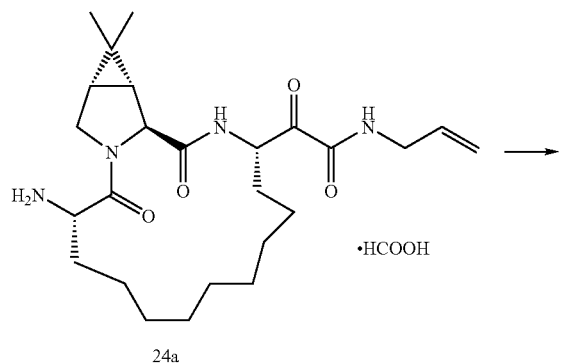

24a

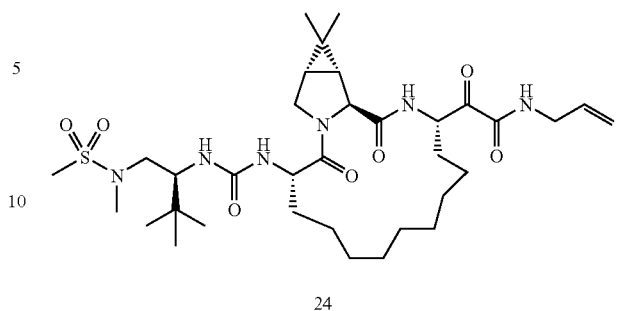

24

A solution of amine 24a (40 mg, 0.1 mmol) in methylene chloride (3.0 mL) was treated with NMM (30 mg, 0.3 mmol) and cooled to 0° C. A solution of isocyanate in CH$_2$Cl$_2$ was added and the reaction mixture was stirred at rt. for 1.5 h. The reaction mixture was diluted with methylene chloride (60 mL) and washed with aq. HCl (1 M, 30 mL). The organic layers were dried with (MgSO$_4$) filtered concentrated in vacuo and purified by chromatography (SiO$_2$, acetone/hexanes 20→50%) to yield 24 (27_mg) MS (m/z, relative intensity) 734 [(M+K)$^+$, 10], 695 [(M+H)$^+$, 100], 461 (20), 443 (20); HRMS (FAB) Calcd. for C$_{34}$H$_{59}$N$_6$O$_7$S 695.4166 (M+H)$^+$; Found: 695.4161.

Preparative Example 25

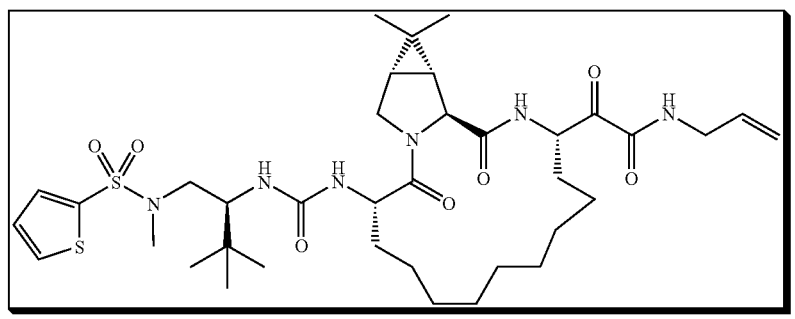

25

Step A:

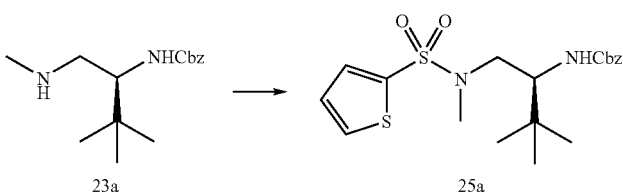

A solution of amine 23a (900 mg, 3.40 mmol) in CH$_2$Cl$_2$ at 0° C. was treated with NMM (511 mg, 5.10 mmol) and thiophene sulfonyl chloride (928 mg, 5.10 mmol) and stirred at 0° C. for 12 h. The reaction mixture was diluted with CH$_2$Cl$_2$ (300 mL) and washed with excess aq. HCl (1M, 500 mL). The organic layer was dried (MgSO$_4$) filtered concentrated in vacuo and purified by chromatography (SiO$_2$, Hex/EtOAc 1:9→1:1) to yield sulfonamide 25a (1.00 g) of colorless solid.

Step B:

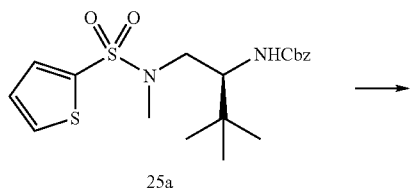

25a

Step C:

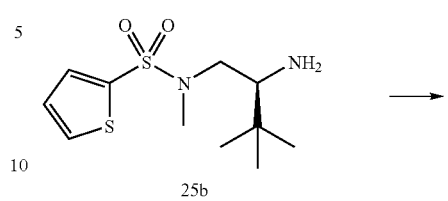

25b

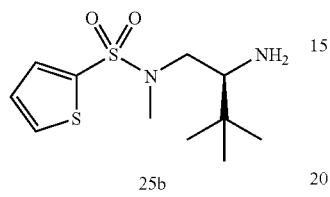

25b

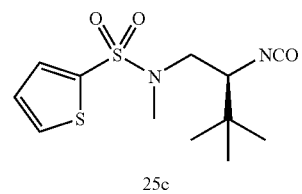

25c

A solution of Cbz-protected compound 25a (1.00 g, 2.118 mmol) was treated with TFA (30 mL) and dimethylsulfide (7.78 mL) at 0° C. and stirred at rt. for 3 h. The reaction mixture was concentrated in vacuo and diluted with aq. NaOH (100 mL). The amine was extracted with methylene chloride (2×100 mL) and the combined organic layers were dried with (MgSO$_4$) filtered concentrated in vacuo and to yield 25b (800 mg) that was used in further reaction without purification. MS (m/z, relative intensity) 277 [(M+H)$^+$, 100], 190 (50).

A solution of deprotected amine 25b (800 mg, 2.9 mmol) in CH$_2$Cl$_2$ (10 mL) aq. saturated NaHCO$_3$ (10 mL) at 0° C. was treated with phosgene (5 mL, 15% soln. in toluene) and stirred at 0° C. for 2 h. The reaction mixture was diluted with CH$_2$Cl$_2$ (50 mL) and the organic layer was washed with cold aq NaHCO$_3$. The organic layer was dried (MgSO$_4$) filtered and further diluted with 10 mL toluene, concentrated the methylene chloride layer and used as a solution of 25c.

Step D:

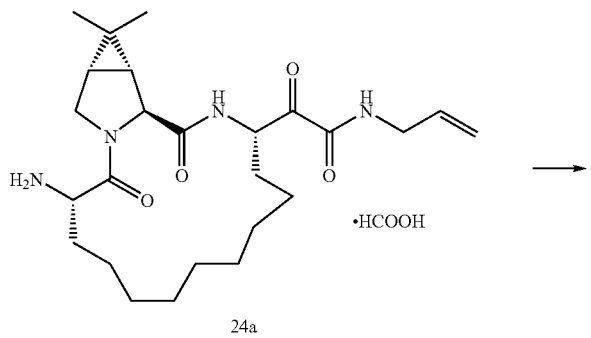

24a

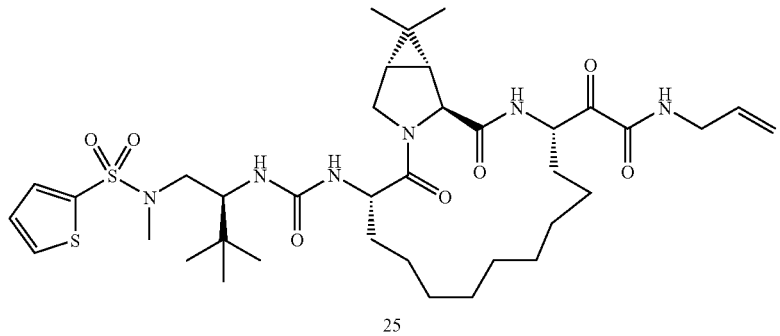

25

A solution of amine 24a (40 mg, 0.1 mmol) in methylene chloride (3.0 mL) was treated with NMM (30 mg, 0.3 mmol) and cooled to 0° C. A solution of isocyanate in CH$_2$Cl$_2$ was added and the reaction mixture was stirred at rt. for 1.5 h. The reaction mixture was diluted with methylene chloride (60 mL) and washed with aq. HCl (1 M, 30 mL). The organic layers were dried with (MgSO$_4$) filtered concentrated in vacuo and purified by chromatography (SiO$_2$, acetone/hexanes 20→50%) to yield 25 (39 mg) as a colorless solid. MS (m/z, relative intensity) 801 [(M+K)$^+$, 10], 763 [(M+H)$^+$, 100], 461 (15), 277 (20); HRMS (ESI) Calcd. for C$_{37}$H$_{58}$N$_6$O$_7$S$_2$Na 785.3706 (M+Na)$^+$; Found: 785.3706.

Preparative Example 26

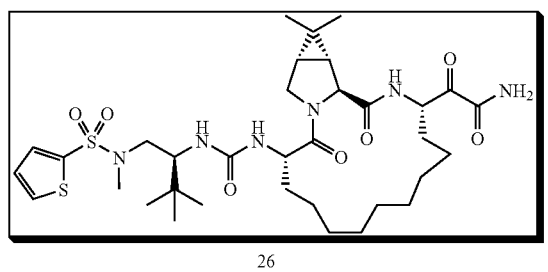

26

Step A:

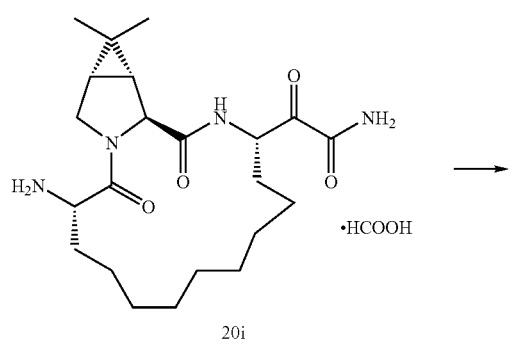

20i

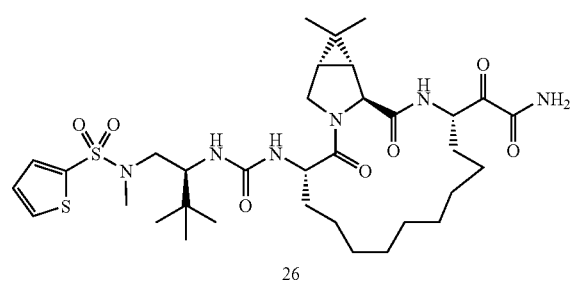

26

A solution of amine 20i (40 mg, 0.1 mmol) in methylene chloride (3.0 mL) was treated with NMM (30 mg, 0.3 mmol) and cooled to 0° C. A solution of isocyanate in CH$_2$Cl$_2$ was added and the reaction mixture was stirred at rt. for 1.5 h. The reaction mixture was diluted with methylene chloride (60 mL) and washed with aq. HCl (1 M, 30 mL). The organic layers were dried with (MgSO$_4$) filtered concentrated in vacuo and purified by chromatography (SiO$_2$, acetone/hexanes 20→50%) to yield 26 as colorless solid (31 mg). MS (m/z, relative intensity) 761 [(M+K)$^+$, 10], 720 [(M+H)$^+$, 100], 421 (20); HRMS (ESI) Calcd. for C$_{34}$H$_{54}$N$_6$O$_7$S$_2$Na 745.3393 (M+Na)$^+$; Found: 745.3396.

Preparative Example 27

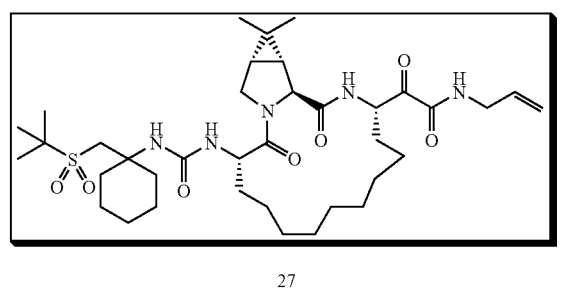

27

Step A:

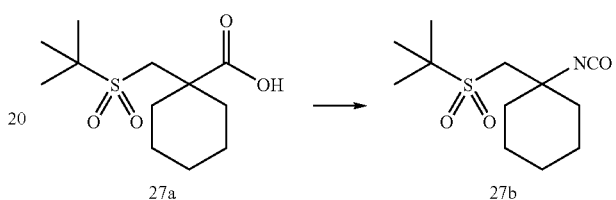

27a → 27b

A solution of acid 27a (100 mg, 0.385 mmol) in toluene (5 mL) was treated with DPPA (116.5 mg, 0.425 mmol) and Et$_3$N (42.5 mg, 0.425 mmol) and stirred at reflux for 1.5 h. The reaction mixture was diluted with saturated NaHCO$_3$ (30 mL) and extracted into CH$_2$Cl$_2$ (2×20 mL). The combined organic layers were washed with aq. NaHCO$_3$ (30 mL), brine (30 mL), dried (MgSO$_4$), filtered, concentrated in vacuo, and used as a solution of isocyanate in toluene.

Step B:

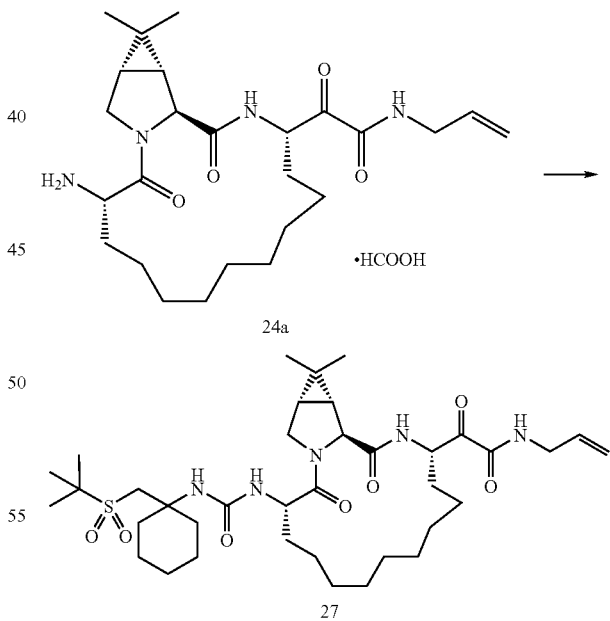

24a

27

A solution of amine 24a (40 mg, 0.1 mmol) in methylene chloride (3.0 mL) was treated with NMM (30 mg, 0.3 mmol) and cooled to 0° C. A solution of isocyanate 27b (3 equiv) in CH$_2$Cl$_2$ was added and the reaction mixture was stirred at rt. for 1.5 h. The reaction mixture was diluted with methylene chloride (60 mL) and washed with aq. HCl (1 M, 30 mL). The organic layers were dried with (MgSO$_4$) filtered concentrated in vacuo and purified by chromatography (SiO$_2$, acetone/hexanes 20→50%) to yield 27 as a colorless solid. MS (m/z, relative intensity) 720 [(M+H)$^+$, 85], 461(100); HRMS (ESI) Calcd. for C$_{37}$H$_{61}$N$_5$O$_7$SNa 742.4189 (M+Na)$^+$; Found: 742.4200.

Preparative Example 28

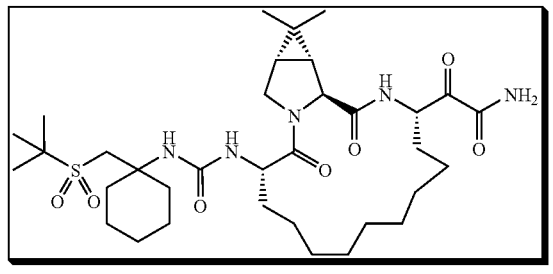

28

Step A:

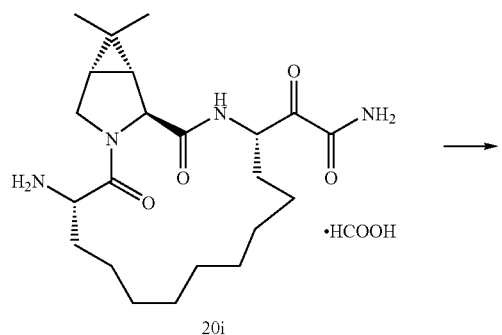

20i

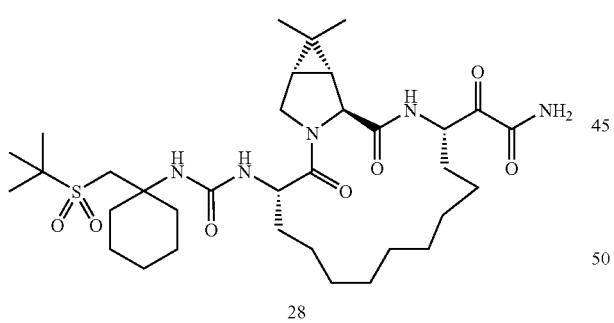

28

A solution of amine 20i (40 mg, 0.1 mmol) in methylene chloride (3.0 mL) was treated with NMM (30 mg, 0.3 mmol) and cooled to 0° C. A solution of isocyanate 27b (3.00 equiv) in CH$_2$Cl$_2$ was added and the reaction mixture was stirred at rt. for 1.5 h. The reaction mixture was diluted with methylene chloride (60 mL) and washed with aq. HCl (1 M, 30 mL). The organic layers were dried with (MgSO$_4$) filtered concentrated in vacuo and purified by chromatography (SiO$_2$, acetone/hexanes 20→60%) to yield 28 (29 mg) as a colorless solid. MS (m/z, relative intensity) 718 [(M+K)$^+$, 10], 702 [(M+Na)$^+$, 20], 680 [(M+H)$^+$, 80], 421 (100); HRMS (ESI) Calcd. for C$_{34}$H$_{57}$N$_5$O$_7$SNa 702.3876 (M+Na)$^+$; Found: 702.3889.

Preparative Example 29

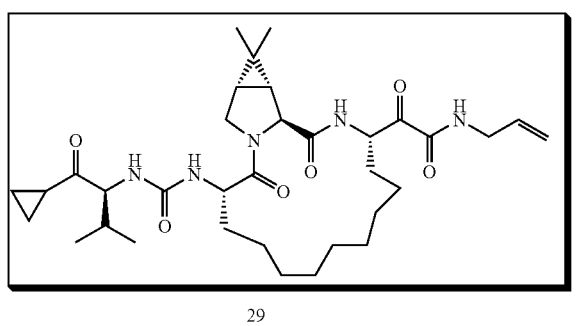

29

Step A:

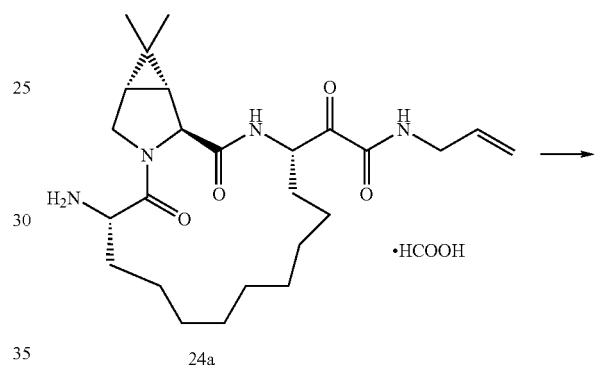

24a

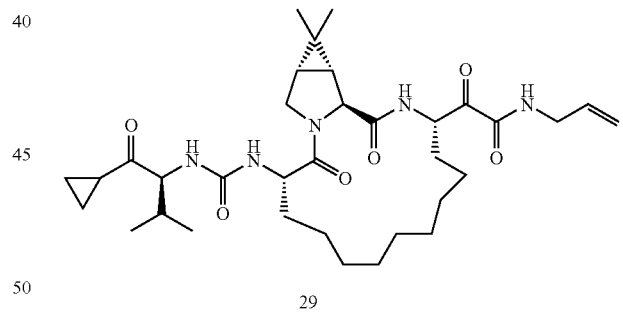

29

A solution of amine 24a (50 mg, 0.1 mmol) in methylene chloride (3.0 mL) was treated with NMM (30 mg, 0.3 mmol) and cooled to 0° C. A solution of isocyanate in CH$_2$Cl$_2$ was added and the reaction mixture was stirred at rt. for 1.5 h. The reaction mixture was diluted with methylene chloride (60 mL) and washed with aq. HCl (1 M, 30 mL). The organic layers were dried with (MgSO$_4$) filtered concentrated in vacuo and purified by chromatography (SiO$_2$, acetone/hexanes 20→50%) to yield 29 as a colorless solid (41 mg). MS (m/z, relative intensity) 628 [(M+H)$^+$, 100], 129 (35).

Preparative Example 30

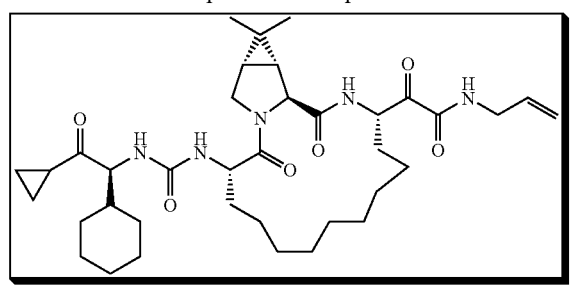

Step A:

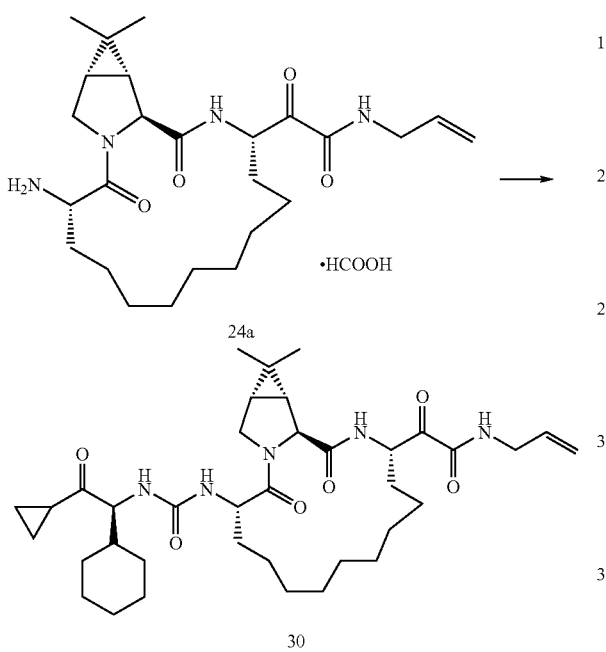

A solution of amine 24a (50 mg, 0.1 mmol) in methylene chloride (3.0 mL) was treated with NMM (30 mg, 0.3 mmol) and cooled to 0° C. A solution of isocyanate (3.0 equiv.) in CH$_2$Cl$_2$ was added and the reaction mixture was stirred at rt. for 1.5 h. The reaction mixture was diluted with methylene chloride (60 mL) and washed with aq. HCl (1 M, 30 mL). The organic layers were dried with (MgSO$_4$) filtered concentrated in vacuo and purified by chromatography (SiO$_2$, acetone/hexanes 20→50%) to yield 30 as a colorless solid. MS (m/z, relative intensity) 668 [(M+H)$^+$, 100], 169 (50), 128 (80).

Preparative Example 31
Preparation of 31

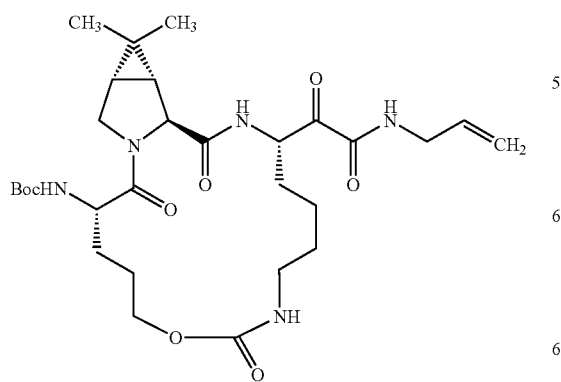

Step A:

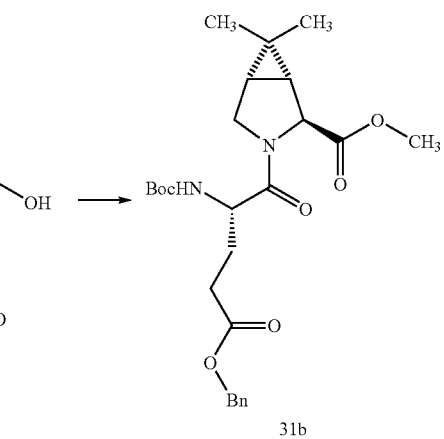

A solution of Boc-Glu-OBn 31a (1.8 g, 5.36 mmol) and amine 1d (1 g, 4.87 mmol) was reacted as in preparative example 1, step C and purified by silica gel chromatography (10% to 25% EtOAc/hexanes) to give 31 b (1.28 g).

Step B:

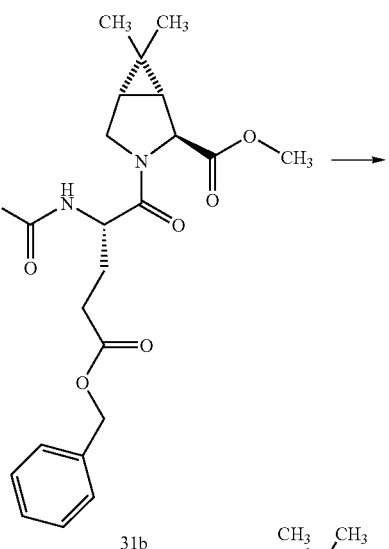

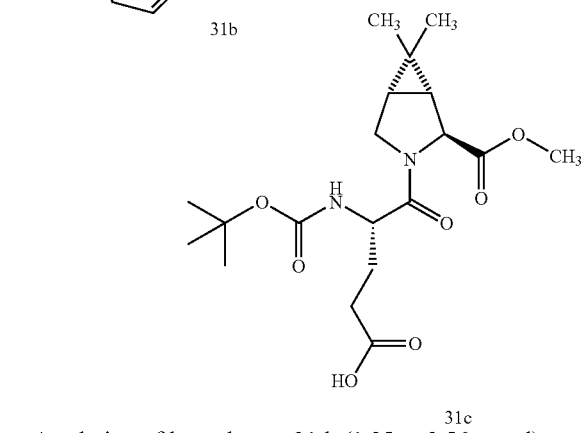

A solution of benzyl ester 31 b (1.25 g, 2.56 mmol) was treated with 10% Pd/C in EtOH and hydrogenated (1 atm., rt.) for 12 hours. The reaction mixture was filtered through a plug of celite and concentrated under vacuum to give 31c (997 mg) which was used in the next reaction without further purification.

Step C

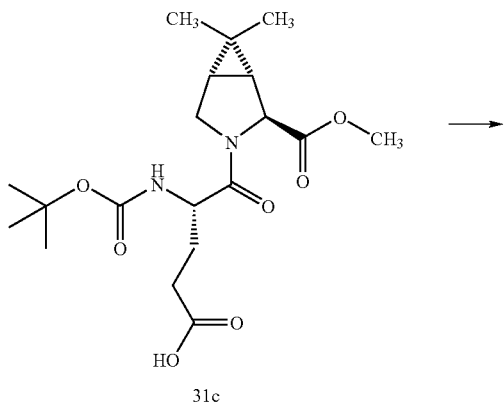

31c

A solution of acid 31c (20.4 g, 48.7 mmol) in THF (300 ml) was cooled to 0° C. and treated with Et₃N (7.47 ml, 53.6 mmol) and ethyl chloroformate (4.89 ml, 51.2 mmol) and stirred for 2 hours. The white precipitate formed was filtered and washed with cold THF. The filtrate was cooled to 0° C. and NaBH₄ (2.39 g, 63.4 mmol) was added. MeOH (20 ml) was added dropwise over 1 hour and stirred for an additional 2.5 hours. Solvent was removed under vacuum, CH₂Cl₂ added and washed with water, brine and dried over Na₂SO₄. Na₂SO₄ was filtered and solvent removed to dryness. The residue was purified by silica gel chromatography (50% to 90% EtOAc/hexanes) to give 31d (8.15 g).

Step D:

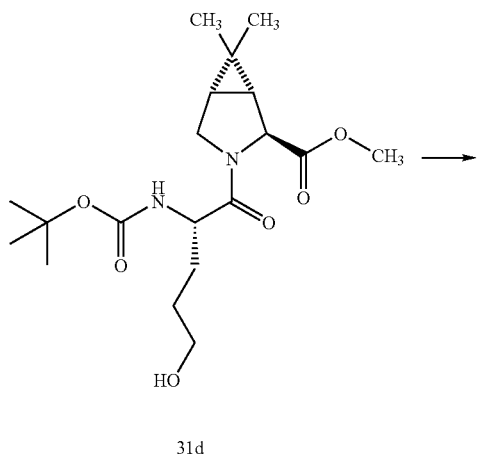

31d

-continued

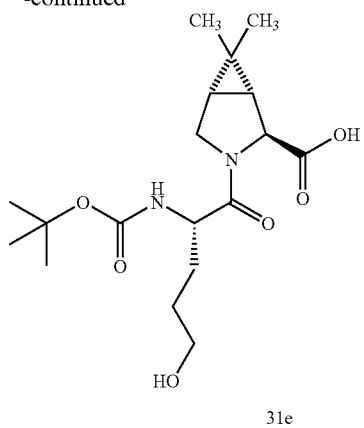

31e

A solution of ester 31d (8 g, 20.8 mmol) in MeOH (120 ml) and H₂O (24 ml) was treated with LiOH.H₂O (2.62 g, 62.5 mmol) at room temperature for 12 hours. Solvent was removed under vacuum to dryness. CH₂Cl₂ was added and stirred for 5 minutes with 1N. HCl (72.9 mmol). CH₂Cl₂ layer was separated, washed with brine and dried over Na₂SO₄. Na₂SO₄ was filtered and solvent was removed to dryness to give white solid 31e (7.65 g).

Step E:

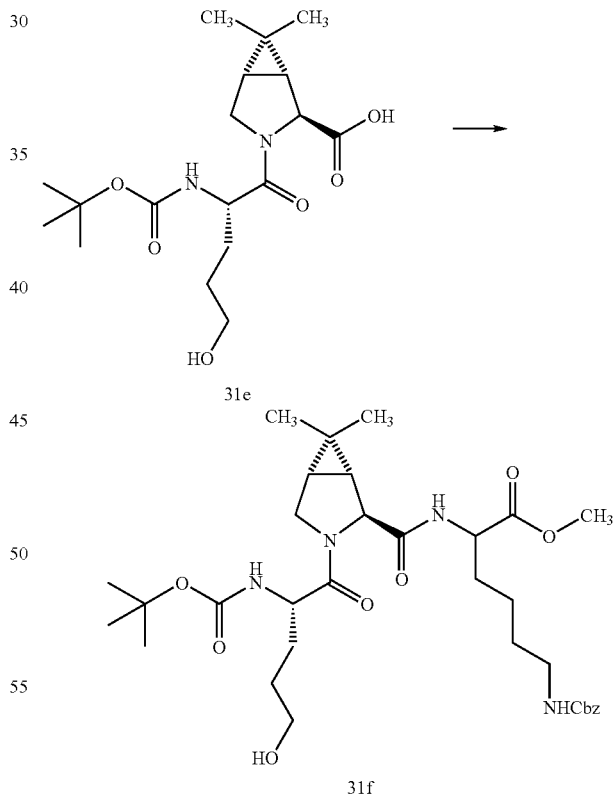

31e

31f

A solution of acid 31e in anhydrous DMF (75 ml) and anhydrous CH₂Cl₂ (75 ml) was cooled to 0° C. and stirred with HOOBt (3.68 g, 22.5 mmol), NMM (6.77 ml, 61.6 mmol) and EDCl (5.11 g, 26.7 mmol) for 5 minutes. H-Lys (Z)-OMe.HCl (7.13 g, 21.5 mmol) was added and stirred for 3.5 hours at 0° C. Reaction was held 12 hours at 5° C. after which CH₂Cl₂ was removed, EtOAc added and washed with sat. NaHCO$_3$, 5% H$_3$PO$_4$, Brine and filtered through Na$_2$SO$_4$. Solvent was removed under vacuum to dryness to give 31f (12.7 g).

Step F

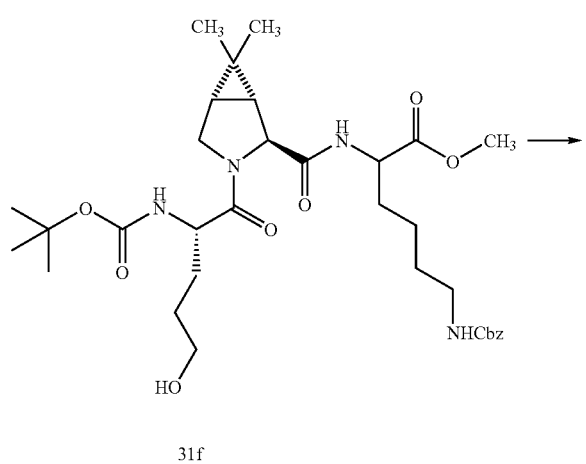

31f

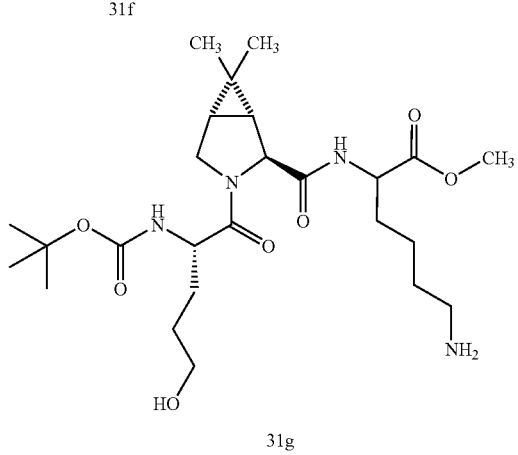

31g

A solution of 31f (5.5 g, 8.51 mmol) was treated with 10% Pd/C in EtOH (100 ml) and hydrogenated (1 atm., rt.) for 12 hours. The reaction mixture was filtered through a plug of celite and concentrated under vacuum to give 31g (4.25 g).

Step G:

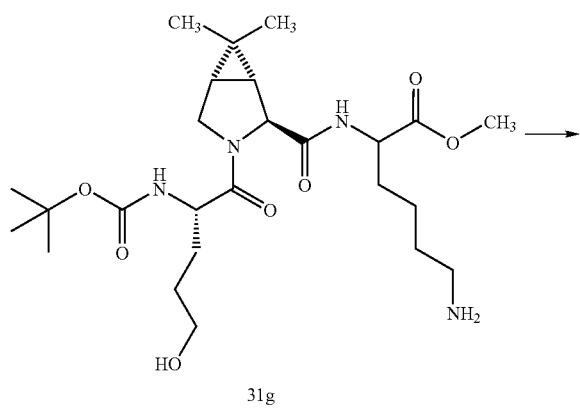

31g

-continued

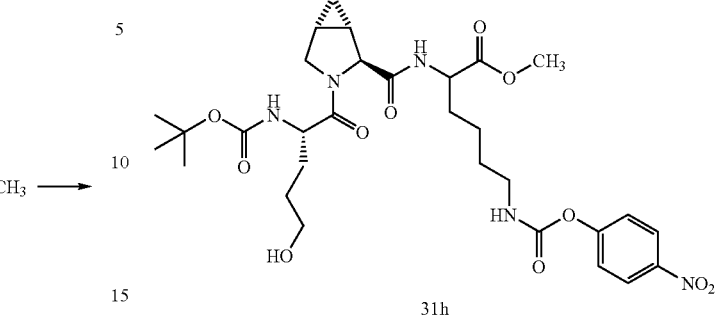

31h

A solution of amine 31g (4.25 g, 8.3 mmol) in anhydrous CH$_2$Cl$_2$ (750 ml) was stirred with triethylamine (1.5 ml, 10.7 mmol) and 4-nitrophenyl chloroformate (2.0 g, 9.96 mmol) at room temperature for 5 hours. Solvent was removed under vacuum to ~200 ml, then washed with sat. NaHCO$_3$, water, 5% H$_3$PO$_4$, brine and filtered through Na$_2$SO$_4$. Na$_2$SO$_4$ was filtered and solvent was removed to give 31 h (5.82 g).

Step H:

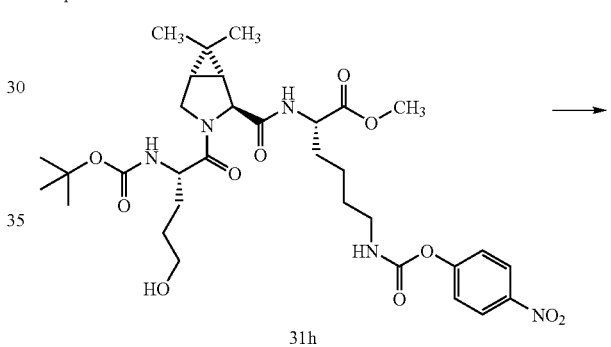

31h

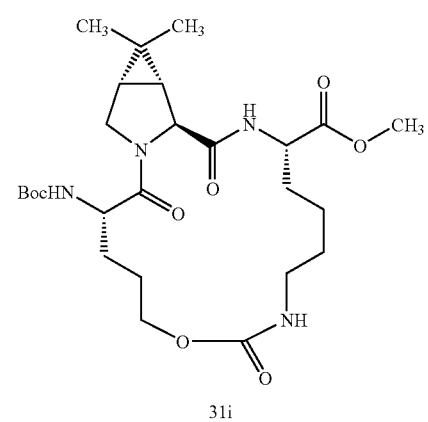

31i

A solution of 31h (5.8 g, 8.3 mmol) in anhydrous THF (600 ml) was treated with 60% NaH (996 mg, 24.9 mmol) at room temperature for 22 hours. Reaction was quenched by adding H$_2$O (5 ml) then 1N. HCl (50 ml) over 3 minutes. Solvent was removed under vacuum, CH$_2$Cl$_2$ was added and washed with 5% H$_3$PO$_4$, Brine and filtered through Na$_2$SO$_4$. Na$_2$SO$_4$ was filtered, solvent was removed and the residue was chromatographed on silica gel column with 0.25% to 3% MeOH/ CH$_2$Cl$_2$ to give 31i (2.86 g, 64% yield).

Step I:

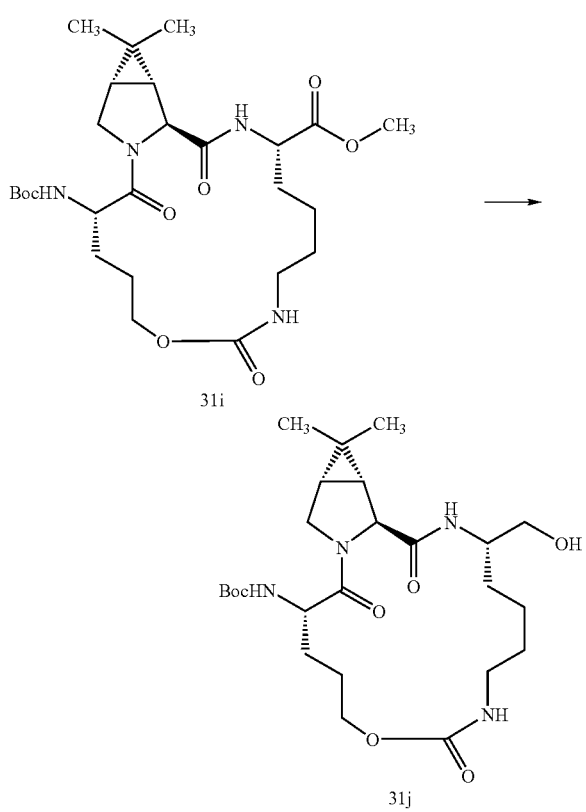

A solution of 31i (613 mg, 1.13 mmol) was reacted as in preparative example 1, step F and purified by silica gel chromatography (3% to 6% MeOH/CH$_2$Cl$_2$) to give alcohol 31j (500 mg).

Step J:

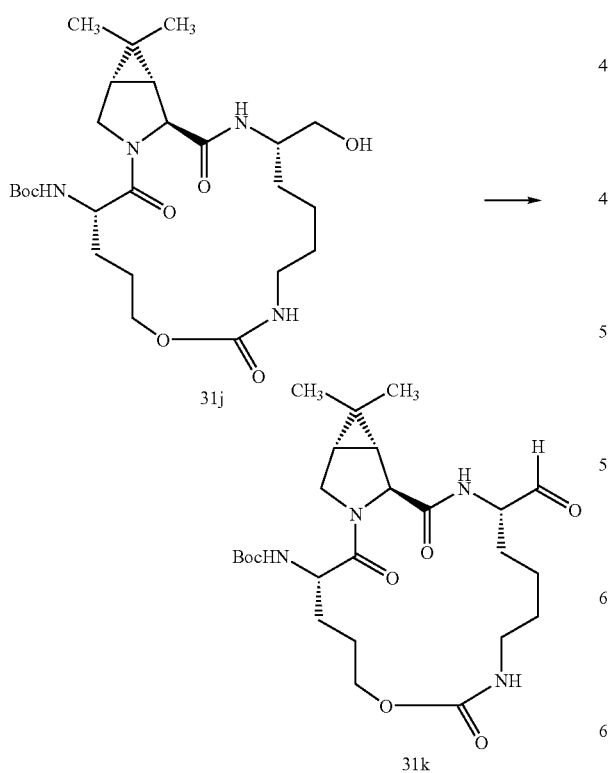

A solution of alcohol 31j (480 mg, 0.94 mmol) was reacted as in preparative example 1, step H and purified by silica gel chromatography (30% to 60% acetone/hexanes) to give aldehyde 31k (383 mg).

Step K:

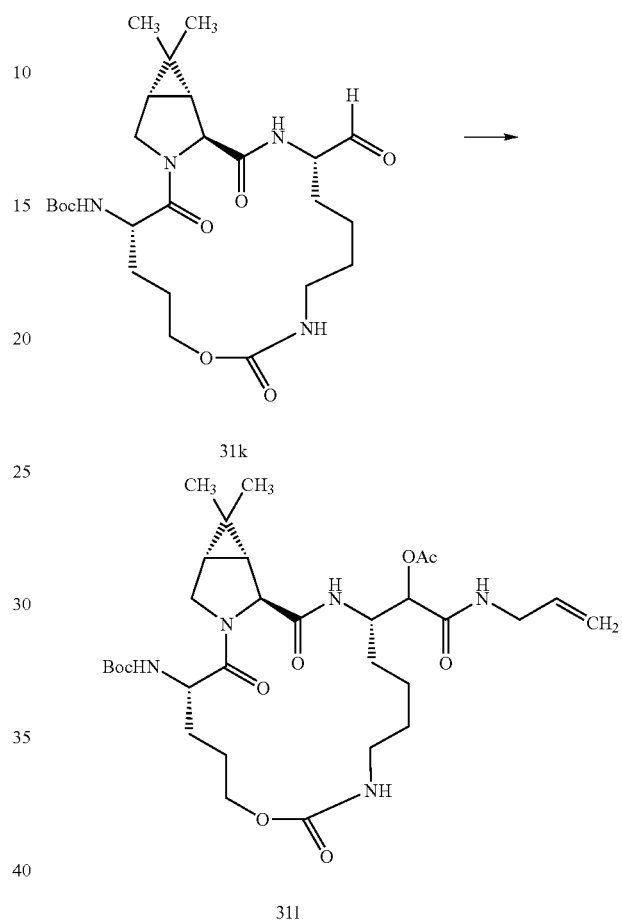

A solution of aldehyde 31j (365 mg, 0.71 mmol) was reacted as in preparative example 22, step A and purified by silica gel chromatography (30% to 50% acetone/hexanes) to give 31k (426 mg).

Step L:

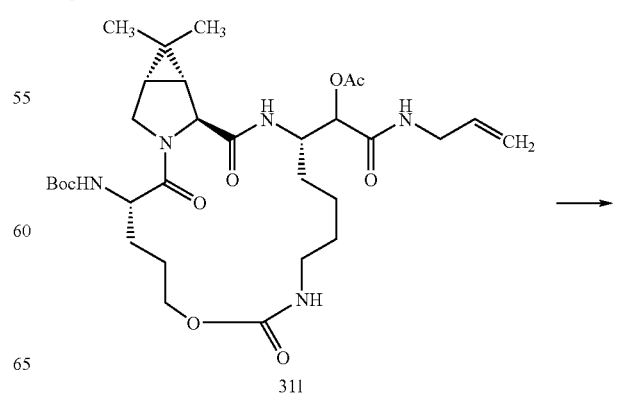

193

-continued

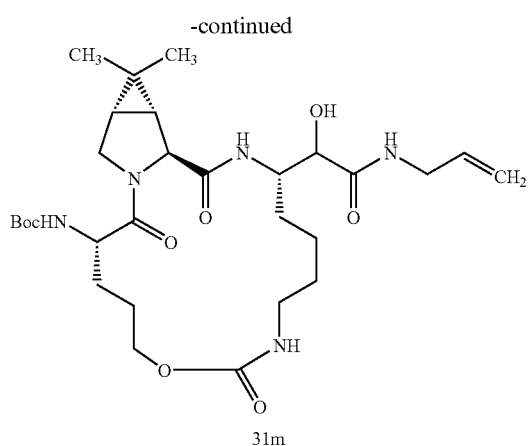

31m

A solution of 31l (357 mg, 0.56 mmol) was reacted as in preparative example 22, step B to give 31m (426 mg).

Step M:

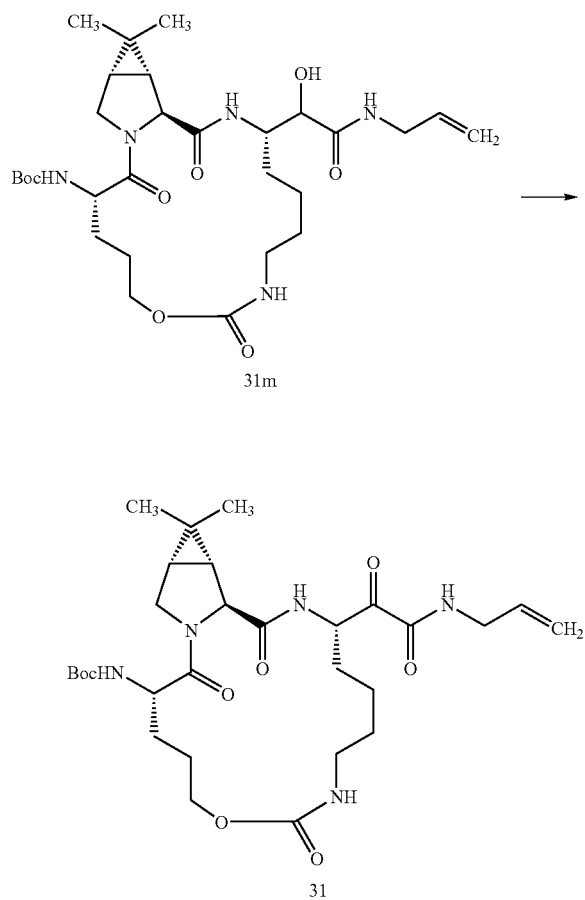

31m

31

A solution of 31 m (350 mg, 0.59 mmol) was reacted as in preparative example 22, step C and purified by silica gel chromatography (30% to 50% acetone/hexanes) to give 31 (335 mg). MS (ES) m/z relative intensity 492 [(M-BOC+1)+, 80]; 592 [(M+1)+, 100]. Calcd. for $C_{29}H_{46}N_5O_8$ [M+1]+: 592.3346; Found 592.3359.

194

Preparative Example 32

Preparation of

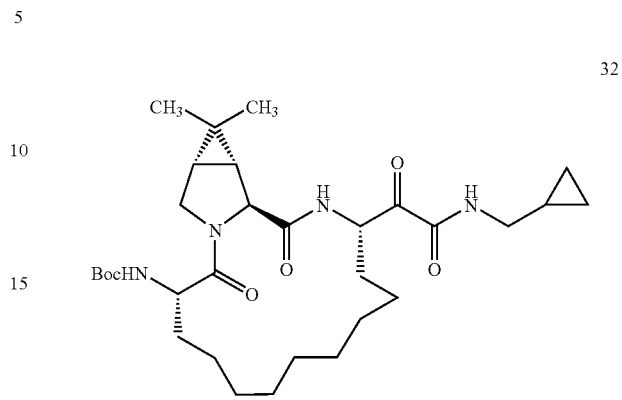

32

Step A:

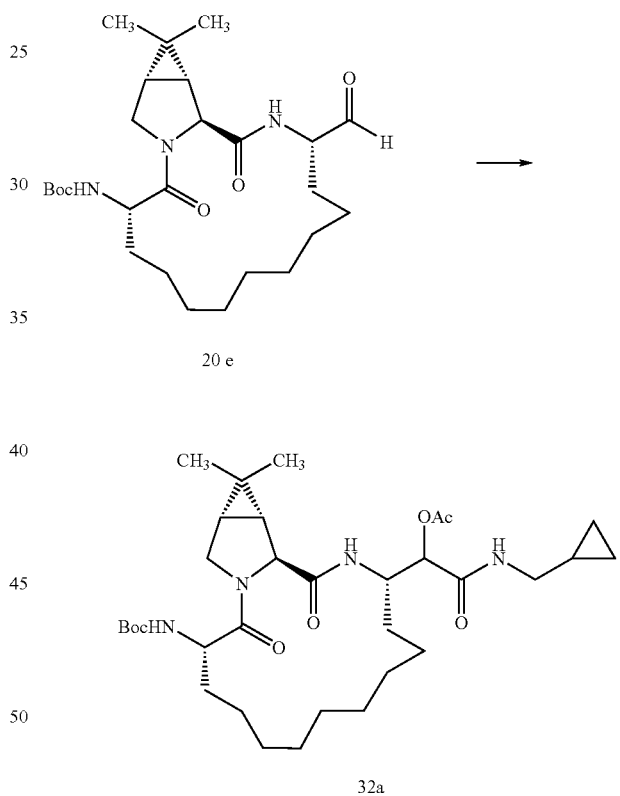

20 e

32a

A solution of aldehyde 20e (200 mg, 0.42 mmol) in methylene chloride (10 mL) was treated with cyclopropylmethyl-isocyanide (66.5 mg, 4.11 mmol) and acetic acid (50 mg, 0.82 mmol) and stirred at rt. for 12 h. The reaction was concentrated in vacuo and residue was purified by chromatography ($SiO_2$, acetone/hexanes 1:90 1:1) to obtain 32a (230 mg).

MS (ES) m/z relative intensity 641 [(M+Na)+, 70]; 619 [(M+1)+, 100], 519 (50).

Step B:

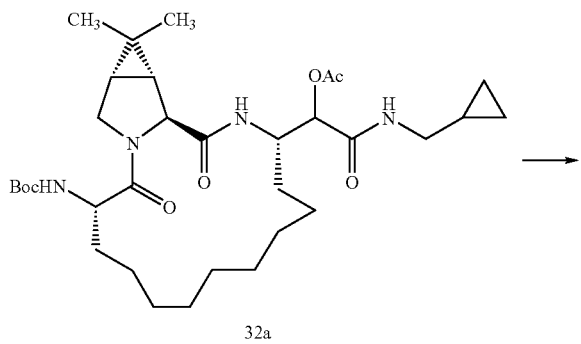

32a

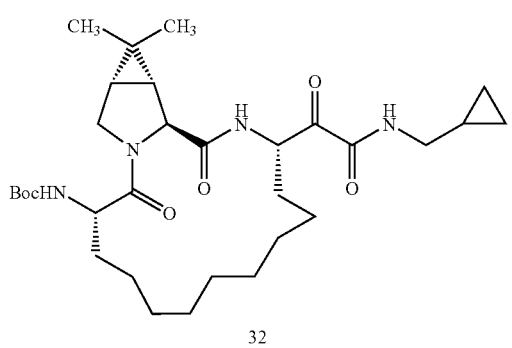

32

A solution of acetate 32a (230 mg, 0.371 mmol) in methanol (5.0 mL), THF (5.0 mL) and water (5.0 mL) was treated with LiOH.H$_2$O (25 mg, 0.55 mmol) and stirred at rt. for 1 h. The reaction mixture was diluted with aq. HCl (1 M, 30 mL) and extracted in CH$_2$Cl$_2$ (2×50 mL). The combined organic layer were dried (MgSO$_4$), filtered, concentrated in vacuo, and used as it is in next step without further purification.

A solution of alcohol in dry CH$_2$Cl$_2$ (15 mL) was treated with Dess-Martin reagent (237 mg, 0.558 mmol) and stirred at rt. for 2-h. The reaction mixture was diluted with aq. Na$_2$S$_2$O$_3$ (5%, 30 mL) and aq. saturated NaHCO$_3$ (30 mL) and stirred at rt. for 15 min. The reaction mixture was extracted with CH$_2$Cl$_2$ (3×50 mL) and the combined organic layers were dried (MgSO$_4$), filtered, concentrated in vacuo and purified by chromatography (SiO$_2$, acetone/hexanes 0:1→1:1) to yield 32 as a colorless solid (275 mg) MS (ES) m/z relative intensity 629 [(M+isobutene)$^+$, 40], 575 [(M+1)$^+$, 100], 475 (90).

Similar procedures were used to synthesize compounds: 33 and 34 using cyclopropyl and ethyl isocyanide for Step A: preparative example 32:

Preparative Example 35

Preparation of

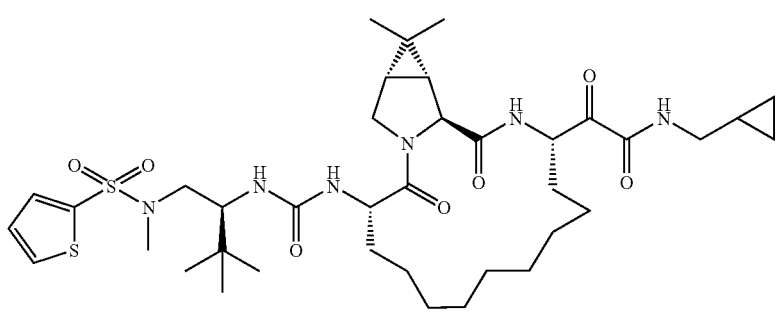

35

Step A:

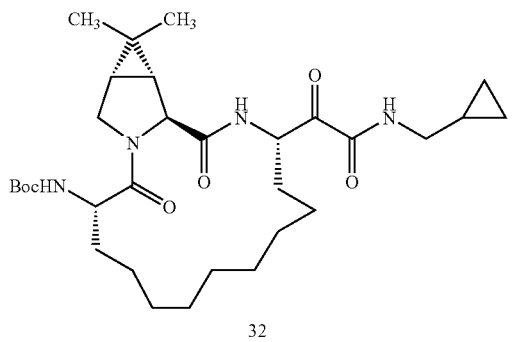

32

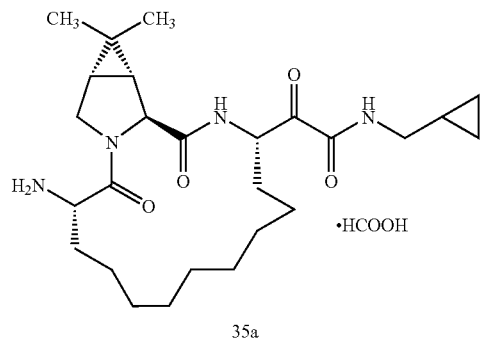

35a 32 (200 mg, 0.39 mmol) was deprotected by dissolving in formic acid 20 mL and standing for 2 h. The reaction mixture was concentrated in vacuo to yield 35a and used in further reactions without purification.

Step B:

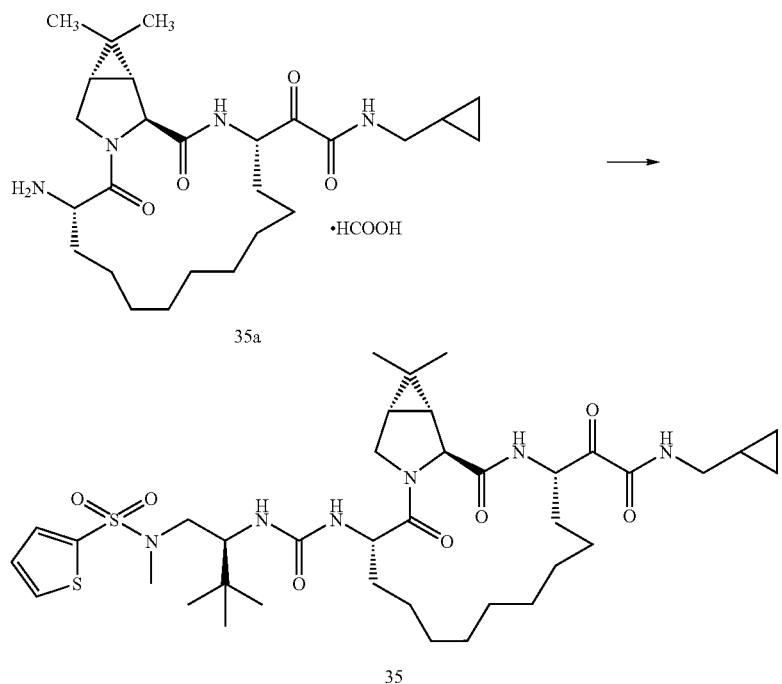

A solution of amine 35a (70 mg, 0.13 mmol) in methylene chloride (3.0 mL) was treated with NMM (50 mg, 0.5 mmol) and cooled to 0° C. A solution of isocyanate 25c (1 ml, 0.25 mmol) in $CH_2Cl_2$ was added and the reaction mixture was stirred at rt. for 1.5 h. The reaction mixture was diluted with methylene chloride (150 mL) and washed with aq. HCl (1 M, 30 mL). The organic layers were dried with ($MgSO_4$) filtered concentrated in vacuo and purified by chromatography ($SiO_2$, EtOAc/$CH_2Cl_2$ 50☐ 100%) to yield 35 as a colorless solid.

MS (ES) m/z relative intensity 799 [(M+Na)$^+$, 60]; 777 [(M+1)$^+$, 100].

Preparative Example 36

Preparation of

Step A:

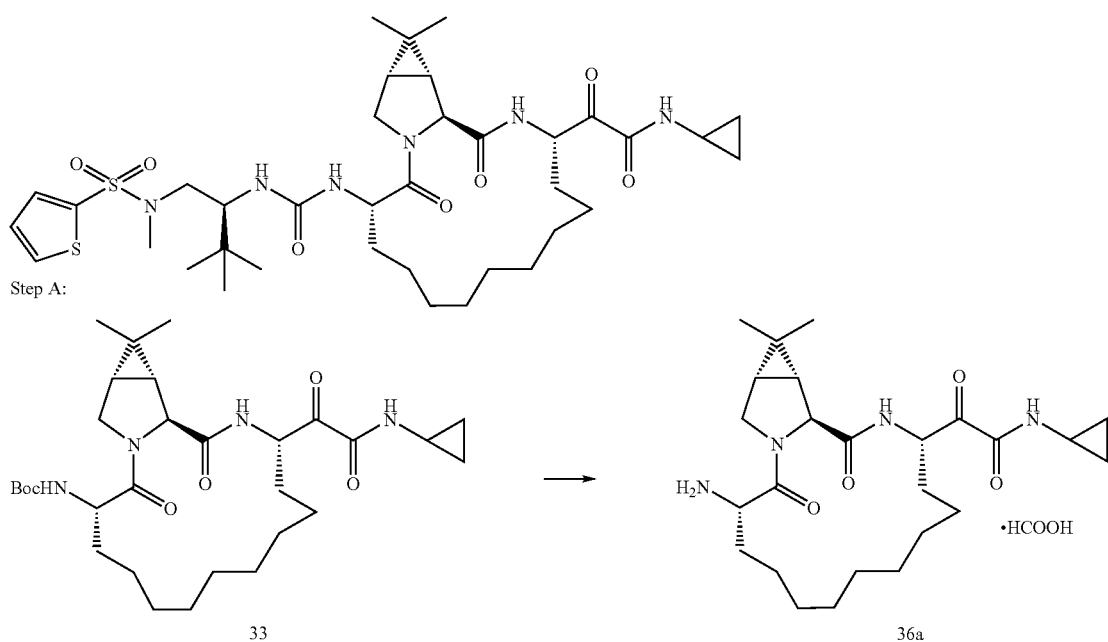

33 (200 mg, 0.39 mmol) was deprotected by dissolving in formic acid 20 mL and standing for 2 h. The reaction mixture was concentrated in vacuo to yield 36a and used in further reactions without purification.

Step B:

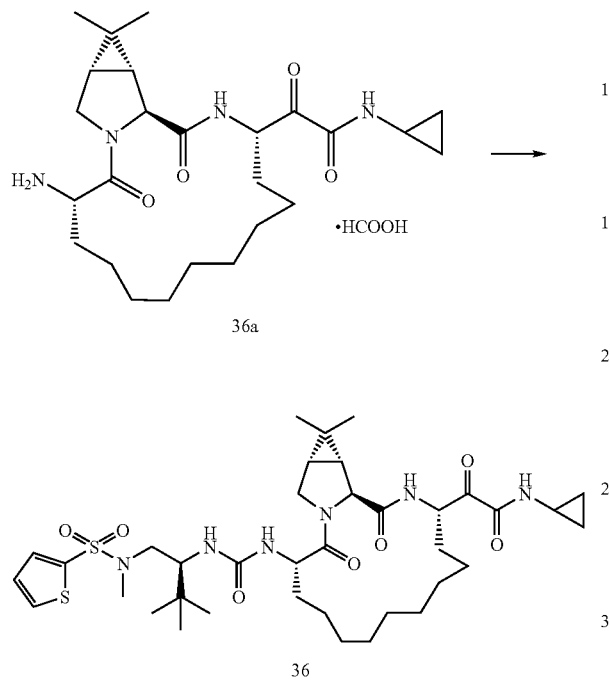

36a

36

A solution of amine 36a (70 mg, 0.13 mmol) in methylene chloride (3.0 mL) was treated with NMM (50 mg, 0.5 mmol) and cooled to 0° C. A solution of isocyanate 25c (1 ml, 0.25 mmol) in $CH_2Cl_2$ was added and the reaction mixture was stirred at rt. for 1.5 h. The reaction mixture was diluted with methylene chloride (150 mL) and washed with aq. HCl (1 M, 30 mL). The organic layers were dried with ($MgSO_4$) filtered concentrated in vacuo and purified by chromatography ($SiO_2$, EtOAc/$CH_2Cl_2$ 0100%) to yield 36 as a colorless solid. MS (ES) m/z relative intensity 785 [(M+Na)$^+$, 50]; 763 [(M+1)$^+$, 100]; 593 (60).

Preparative Example 37

Preparation of

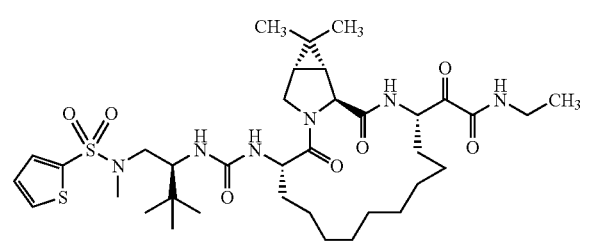

37

-continued

Step A:

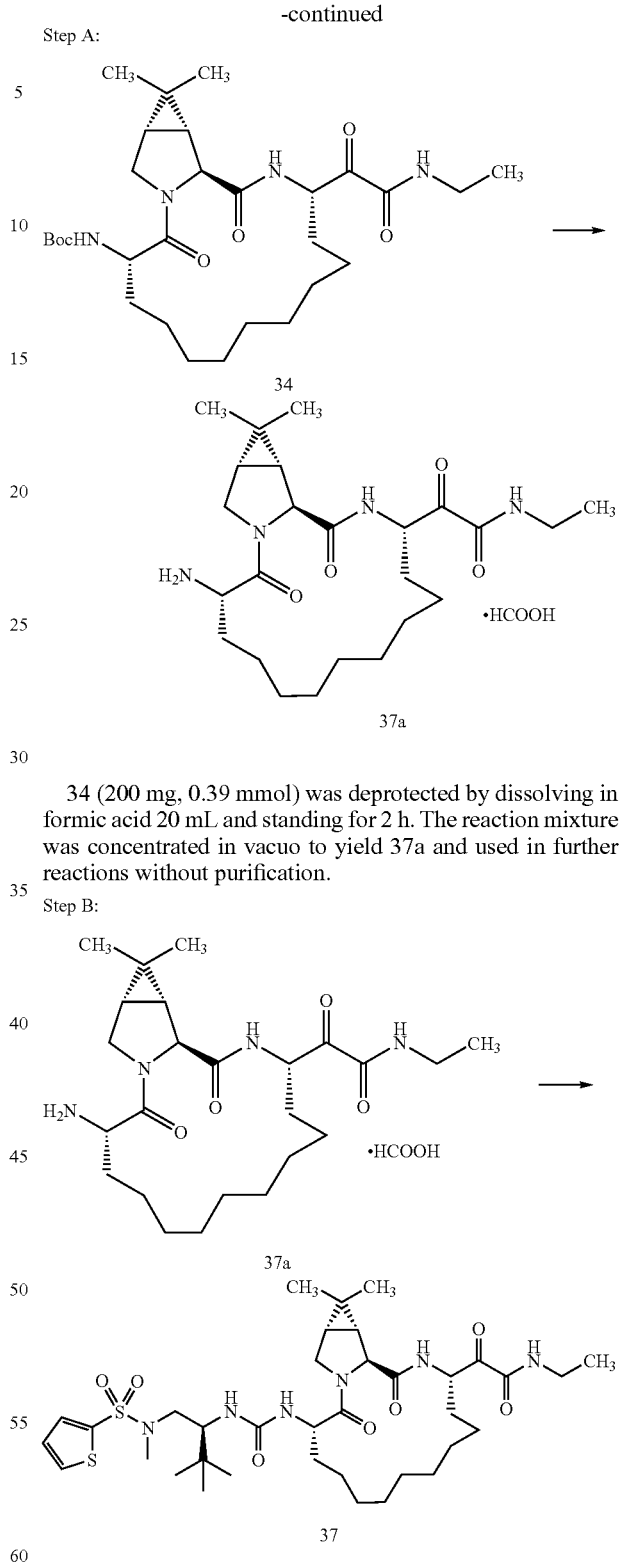

34

37a 34 (200 mg, 0.39 mmol) was deprotected by dissolving in formic acid 20 mL and standing for 2 h. The reaction mixture was concentrated in vacuo to yield 37a and used in further reactions without purification.

Step B:

37a

37

A solution of deprotected amine 37a (70 mg, 0.13 mmol) in methylene chloride (3.0 mL) was treated with NMM (50 mg, 0.5 mmol) and cooled to 0° C. A solution of isocyanate 25c (1 ml, 0.25 mmol) in $CH_2Cl_2$ was added and the reaction mixture was stirred at rt. for 1.5 h. The reaction mixture was diluted with methylene chloride (150 mL) and washed with aq. HCl (1 M, 30 mL). The organic layers were dried with (MgSO$_4$) filtered concentrated in vacuo and purified by chromatography (SiO$_2$, EtOAc/CH$_2$Cl$_2$ 50☐ 100%) to yield 37.

MS (ES) m/z relative intensity 773 [(M+Na)$^+$, 100]; 751 [(M+1)$^+$, 70].

Preparative Example 38

Preparation of

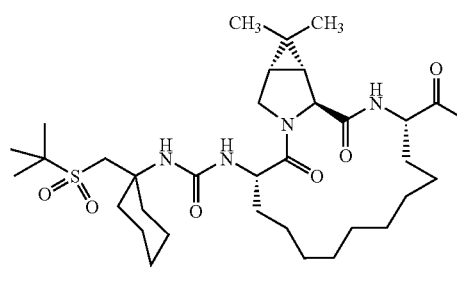

38

Step A:

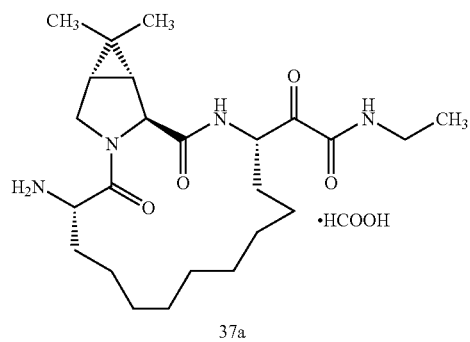

37a

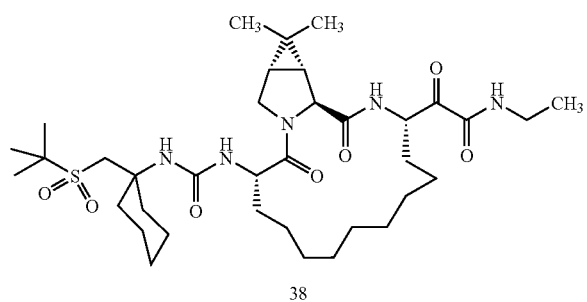

38

A solution of deprotected amine 37a (70 mg, 0.13 mmol) in methylene chloride (3.0 mL) was treated with NMM (50 mg, 0.5 mmol) and cooled to 0° C. A solution of isocyanate 27b (1.5 ml, 0.25 mmol) in CH$_2$Cl$_2$ was added and the reaction mixture was stirred at rt. for 1.5 h. The reaction mixture was diluted with methylene chloride (150 mL) and washed with aq. HCl (1 M, 30 mL). The organic layers were dried with (MgSO$_4$) filtered concentrated in vacuo and purified by chromatography (SiO$_2$, EtOAc/CH$_2$Cl$_2$ 50☐ 100%) to yield 38 as colorless solid. MS (ES) m/z relative intensity 730 [(M+Na)$^+$, 30]; 708 [(M+1)$^+$, 100]; 409 (30).

Preparative Example 39

Preparation of

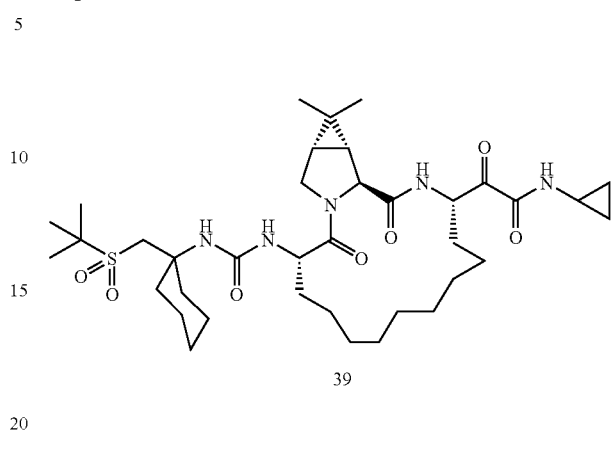

39

Step A:

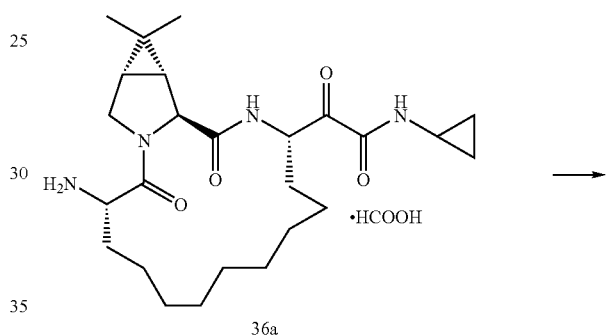

36a

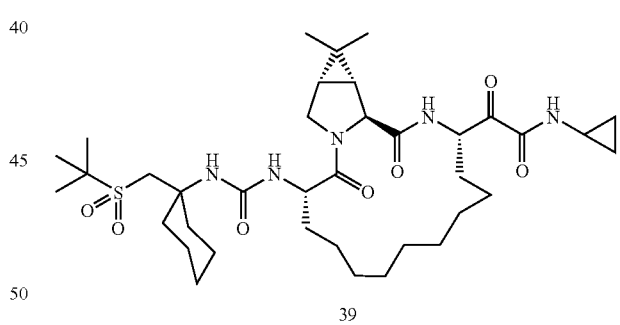

39

A solution of amine 36a (70 mg, 0.13 mmol) in methylene chloride (3.0 mL) was treated with NMM (50 mg, 0.5 mmol) and cooled to 0° C. A solution of isocyanate 27b_(1 mL, 0.25 mmol) in CH$_2$Cl$_2$ was added and the reaction mixture was stirred at rt. for 1.5 h. The reaction mixture was diluted with methylene chloride (150 mL) and washed with aq. HCl (1 M, 30 mL). The organic layers were dried with (MgSO$_4$) filtered concentrated in vacuo and purified by chromatography (SiO$_2$, EtOAc/CH$_2$Cl$_2$ 50☐ 100%) to yield 39. MS (ES) m/z relative intensity 742 [(M+Na)$^+$, 70]; 720 [(M+1)$^+$, 100]; 461 (40). HRMS Calcd. for C$_{37}$H$_{62}$N$_5$O$_7$S [M+1]$^+$: 720.4370; Found 720.4350.

Preparative Example 40

Preparation of

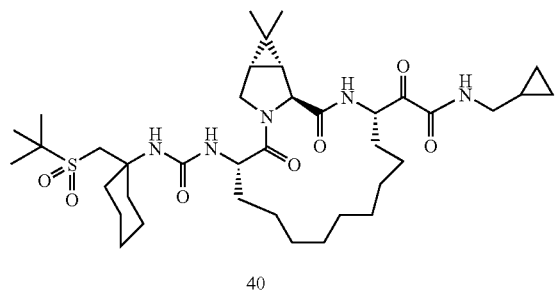

Step A:

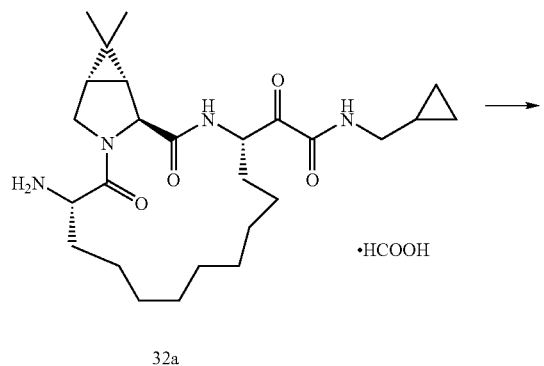

A solution of amine 32a (70 mg, 0.13 mmol) in methylene chloride (3.0 mL) was treated with NMM (50 mg, 0.5 mmol) and cooled to 0° C. A solution of isocyanate 27b_(1 mL, 0.25 mmol) in $CH_2Cl_2$ was added and the reaction mixture was stirred at rt. for 1.5 h. The reaction mixture was diluted with methylene chloride (150 mL) and washed with aq. HCl (1 M, 30 mL). The organic layers were dried with ($MgSO_4$) filtered concentrated in vacuo and purified by chromatography ($SiO_2$, EtOAc/$CH_2Cl_2$ 50□ 100%) to yield 40.

$^1$H NMR (dmso, 500 MHz), 6, 8.80 (t, 1H, J=6.0 Hz), 8.37 (d, 1H, J=9.5 Hz), 6.22 (d, 1H, J=8.8 Hz), 5.88 (s, 1H), 5.31 (dt, 1H, J=2.8 & 9.5 Hz), 4.35 (s, 1H), 4.28-4.22 (m, 1H), 3.85 (d, 1H, J=10 Hz), 3.76 (q, 1H, J=5.4 Hz), 3.59 (t, 1H, J=13.5 Hz), 3.41 (d, 1H, J=13.9 Hz), 3.07-2.95 (m, 2H), 2.22-2.15 (m, 2H), 1.69-1.00 (b, 23H), 1.25 (s, 9H), 0.99 (s, 3H), 0.99-0.70 (m, 1H), 0.88 (s, 3H), 0.42-0.38 (m, 2H), 0.21-0.18 (m, 2H).

$^{13}$C NMR (dmso, 125 MHz) δ, 198.5, 172.1, 171.3, 162.0, 157.3, 60.5, 60.1, 54.4, 52.8, 51.5, 47.6, 43.8, 35.4, 35.1, 34.8, 32.3, 31.6, 31.4, 28.3, 28.0, 27.9, 27.3, 26.9, 26.6, 25.8, 25.6, 24.6, 23.4, 22.4, 21.5, 19.5, 13.7, 11.5. MS (ES) m/z relative intensity 756 [(M+Na)$^+$, 45]; 734 [(M+1)$^+$, 100]; 475 (20). HRMS cacld. for $C_{38}H_{64}N_5O_7S$ [M+1]$^+$: 734.4526; Found 734.4535.

Preparative Example 41

Preparation of

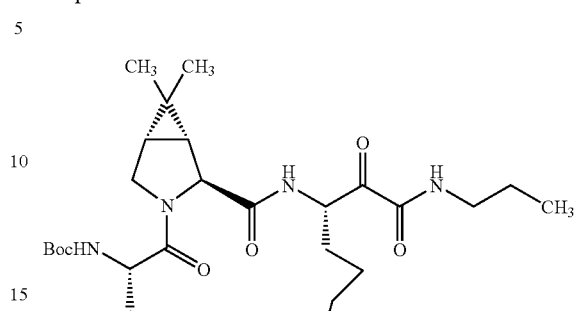

Step A:

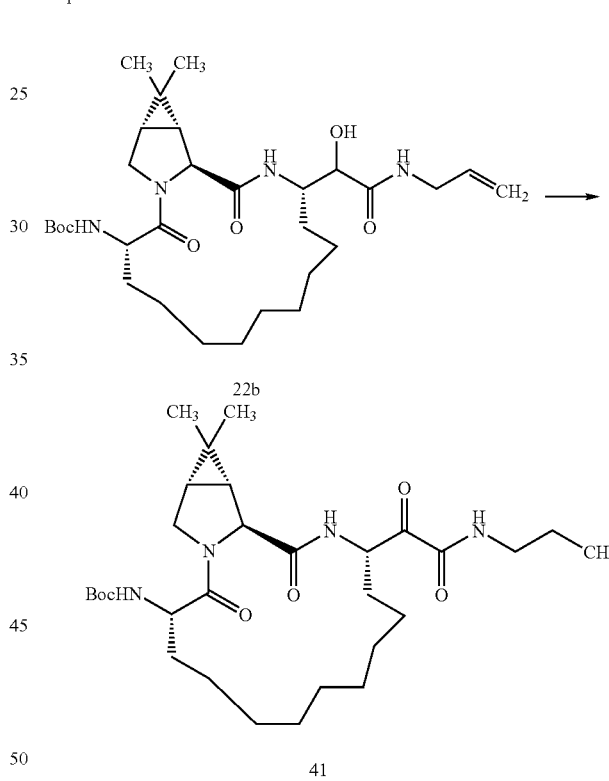

A solution of intermediate 22b (300 mg, 0.54 mmol) was taken in methanol (25 mL) and treated with 10% Pearlman's catalyst and hydrogenated at 50 psi for 4 h. The reaction mixture was filtered through a plug of celite® and concentrated in vacuo to yield reduced product that was used in further reaction without purification.

A solution of reduced alcohol in dry $CH_2Cl_2$ (5 mL) was treated with Dess-Martin reagent (350 mg, 0.82 mmol) and stirred at rt. for 2 h. The reaction mixture was diluted with aq. $Na_2S_2O_3$ (5%, 30 mL) and aq. saturated $NaHCO_3$ (30 mL) and stirred at rt. for 15 min. The reaction mixture was extracted with $CH_2Cl_2$ (3×75 mL) and the combined organic layers were dried ($MgSO_4$), filtered, concentrated in vacuo and purified by chromatography ($SiO_2$, acetone/hexanes 0:1→1:1) to yield 41 (270 mg) as a colorless solid.

Preparative Example 42
Preparation of
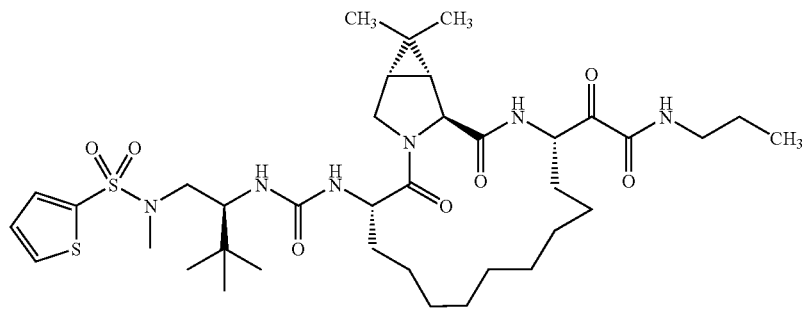
42
Step A:
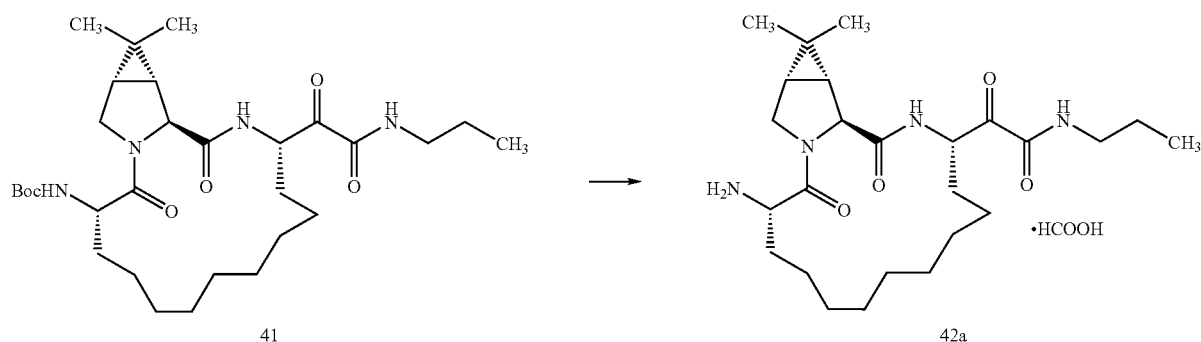
41 was deprotected by dissolving in formic acid 20 mL and standing for 2 h. The reaction mixture was concentrated in vacuo to yield 42a and used in further reactions without purification.
Step B:
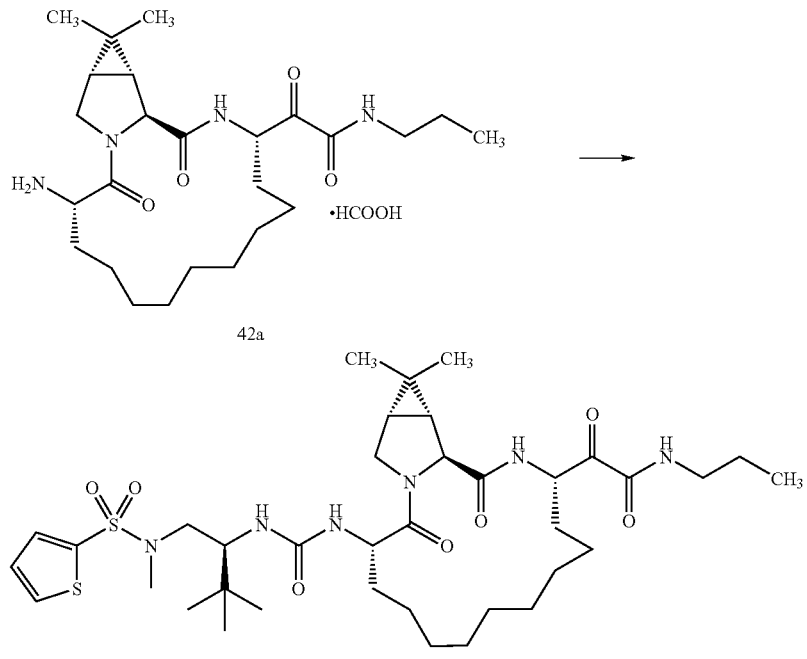

A solution of amine 42a (100 mg, 0.196 mmol) in methylene chloride (3.0 mL) was treated with NMM (60 mg, 0.6 mmol) and cooled to 0° C. A solution of isocyanate 25c (1.5 mL, 0.25 mmol, 0.38 mmol) in toluene was added and the reaction mixture was stirred at rt. for 2 h. The reaction mixture was diluted with methylene chloride (100 mL) and washed with aq. HCl (1 M, 50 mL). The organic layers were dried with (MgSO$_4$) filtered, concentrated in vacuo and purified by chromatography (SiO$_2$, Ethyl acetate/hexanes 1:1□ 1:0) yield 42 (65 mg) as a colorless solid. $^1$H NMR (dmso, 500 MHz), 6, 8.71 (t, 1H, J=6.3 Hz), 8.36 (d, 1H, J=9 Hz), 8.00 (dd, 1H, J=1.3 & 5.0 Hz), 7.65 (dd, 1H, J=1.3 & 2.5 Hz), 7.25 (dd, 1H, J=3.8 &1.3 Hz), 6.15 (d, 1H, J=9.0 Hz), 5.88 (d, 1H, J=10 Hz), 5.31 (m, 1H), 4.34 (s, 1H), 4.30 (m, 1H), 3.93 (d, 1H, J=10.5 Hz), 3.79-3.75 (q, 1H, J=5.0 Hz), 3.67-3.62 (dt, 1H, J=4.1 & 5.6 Hz), 3.12-3.05 (m, 2H), 2.95-2.91 (m, 2H), 2.67 (s, 3H), 1.70-1.61 (m, 2H) 1.40-1.00 (b, 20H), 0.99 (s, 3H), 0.85 (s, 3H), 0.83 (s, 9H), 0.83 (t, 3H). $^{13}$C NMR (dmso, 125 MHz) □, 198.5, 172.0, 171.7, 162.2, 158.3, 137.7, 133.9, 133.1, 129.0, 60.5, 55.8, 55.7, 52.7, 51.6, 51.5, 47.6, 36.0, 35.0, 32.2, 31.6, 31.3, 28.5, 27.9, 27.4, 27.1, 26.9, 26.7, 26.3, 24.4, 22.8, 22.3, 19.5, 13.7, 12.1. MS (ES) m/z relative intensity 788 [(M+Na)$^+$, 50]; 765 [(M+1)$^+$, 100].

Preparative Example 43

Preparation of

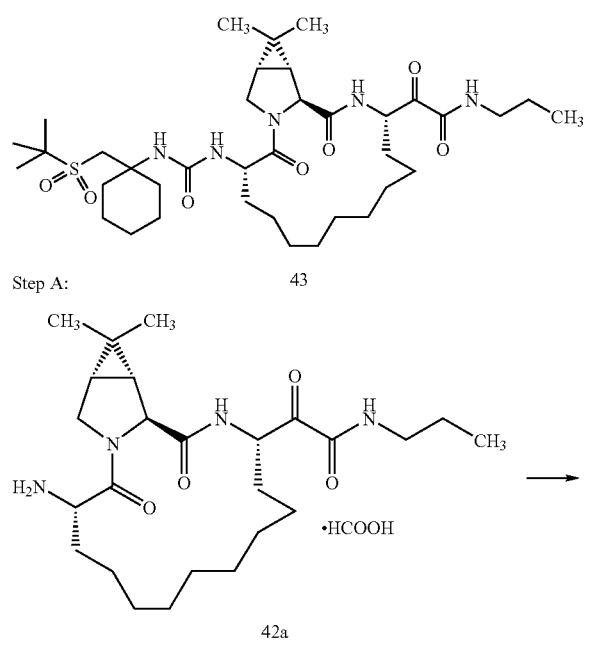

Step A:

42a

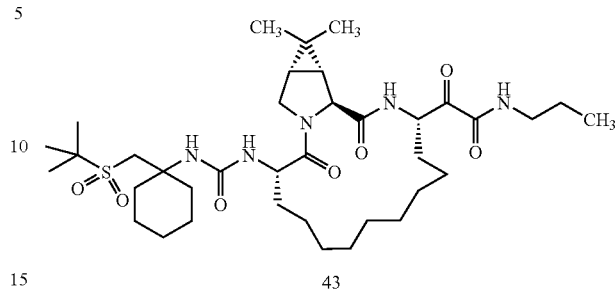

43

A solution of amine 42a (100 mg, 0.196 mmol) in methylene chloride (3.0 mL) was treated with NMM (60 mg, 0.6 mmol) and cooled to 0° C. A solution of isocyanate 27b (3 mL, 0.1 M soln., 0.3 mmol) in toluene was added and the reaction mixture was stirred at rt. for 2 h. The reaction mixture was diluted with methylene chloride (100 mL) and washed with aq. HCl (1 M, 50 mL). The organic layers were dried with (MgSO$_4$) filtered concentrated in vacuo and purified by chromatography (SiO$_2$, EtOAc/Hexanes 1:1→1:0) yield 43 (42 mg) as a colorless solid. $^1$H NMR (dmso, 500 MHz) δ, 8.71 (t, 1H, J=6.0 Hz), 8.36 (d, 1H, J=9.0 Hz), 6.22 (d, 1H, J=8.5 Hz), 5.88 (s, 1H), 5.29 (dt, 1H, J=9.5 & 2.5 Hz), 4.34 (s, 1H), 4.23 (t, 1H, J=9.0 Hz), 3.86 (d, 1H, J=10.5 Hz), 3.76 (dd, 1H, J=5.0 & 5.5 Hz), 3.60 (d, 1H, J=13.5 Hz), 3.41 (d, 1H, J=13.5 Hz), 3.13-3.04 (m, 2H), 2.23-2.15 (m, 2H), 1.67-0.9 (bm, 30H), 1.25 (s, 9H), 0.99 (s, 3H), 0.88 (s, 3H), 0.83 (t, 3H, J=7.0 Hz). $^{13}$C NMR (dmso, 125 MHz) δ, 198.5, 172.1, 171.3, 162.1, 157.3, 60.5, 60.1, 55.8, 54.3, 52.8, 51.0, 47.6, 35.4, 35.1, 32.3, 31.7, 31.3, 28.3, 28.0, 27.9, 27.3, 26.9, 26.6, 26.2, 25.8, 24.6, 23.3, 22.8, 21.5, 19.5, 13.7, 12.2. MS (ES) m/z relative intensity 744 [(M+Na)$^+$, 40]; 722 [(M+1)$^+$, 100].

Preparative Example 44

Preparation of

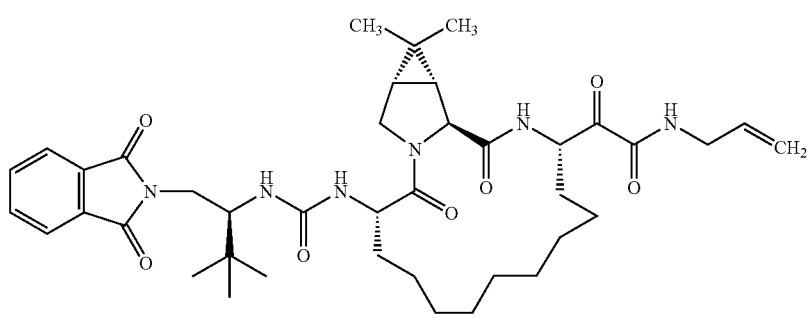

44

Step A:

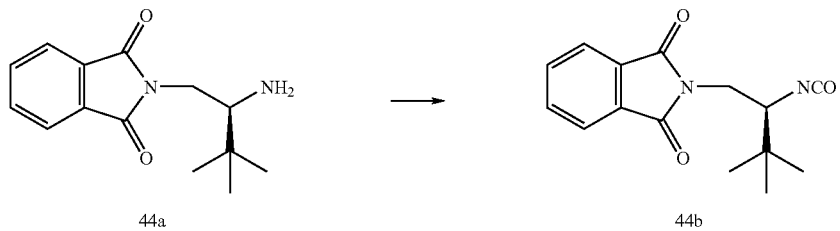

A solution of deprotected amine 44a (Busacca, C. A.; Grossbach, D.; Spinelli, E. *Tetrahedron: Asymmetry;* 2000, 9, 1907) in CH$_2$Cl$_2$ (10 mL) aq. saturated NaHCO$_3$ (10 mL) at 0° C. was treated with phosgene (5 mL, 15% soln. in toluene) and stirred at 0° C. for 2 h. The reaction mixture was diluted with CH$_2$Cl$_2$ (50 mL) and the organic layer was washed with cold aq NaHCO$_3$. The organic layer was dried (MgSO$_4$) filtered and further diluted with 10 mL toluene, concentrated the methylene chloride layer and used as a solution Step B:

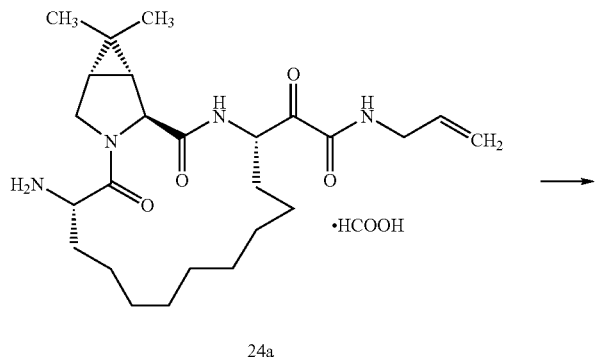

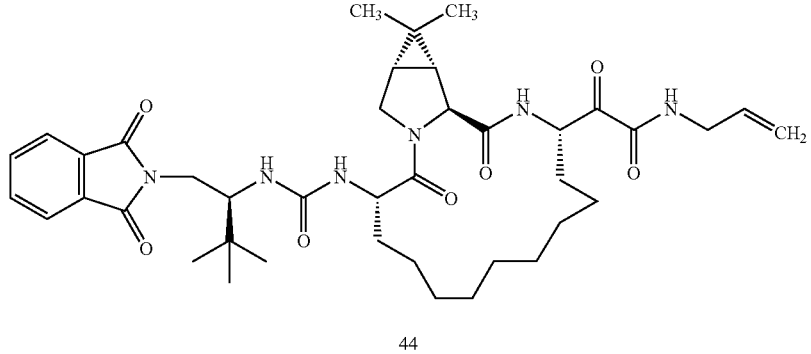

A solution of amine 24a (100 mg, 0.196 mmol) in methylene chloride (3.0 mL) was treated with NMM (60 mg, 0.6 mmol) and cooled to 0° C. A solution of isocyanate 44b (2.5 mL, 0.25 mmol) in toluene was added and the reaction mixture was stirred at rt. for 2 h. The reaction mixture was diluted with methylene chloride (100 mL) and washed with aq. HCl (1 M, 50 mL). The organic layers were dried with (MgSO$_4$) filtered concentrated in vacuo and purified by chromatography (SiO$_2$, ethyl acetate/hexanes 1:1☐ 1:0) yield 44 (31 mg) as a colorless solid. MS (ES) m/z relative intensity 755 [(M+Na)$^+$, 40]; 733 [(M+1)$^+$, 100].

Preparative Example 45

Preparation of

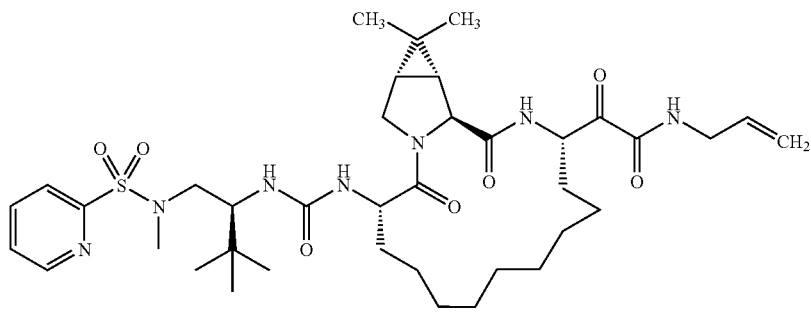

45

Step A:

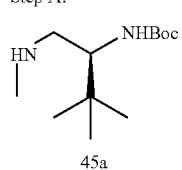

45a

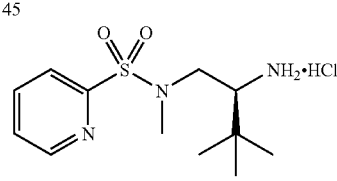

45b

A solution of amine 45a* (2.00 g, 9.20 mmol) in $CH_2Cl_2$ at 0° C. was treated with $(C_2H_5)_3N$ (3.7 g, 37 mmol) and 2-pyridinesulfonyl chloride (2.4 g, 11.2 and stirred at rt. for 12 h. The reaction mixture was diluted with $CH_2Cl_2$ (300 mL) and washed with excess aq. $NaHCO_3$ (1M, 500 mL). The organic layer was dried ($MgSO_4$) filtered concentrated in vacuo and purified by chromatography ($SiO_2$, Acetone/Hexanes 0:1→1:1) to yield sulfonamide (2.3 g). A solution of Boc-protected amine was deprotected by dissolving (2.1 g, 5.7 mmol) in 4M soln. of HCl in dioxane and stirred at rt. for 2 h. The reaction mixture was concentrated in vacuo and used as it is in next step without further purification.

* obtained by the protection of tert-leucine-N-methylamide (TCl-Jpn) with ditertbutyidicarbonate and subsequent reduction with $BH_3 \cdot DMS$ in THF (reflux, 2 h).

Step B:

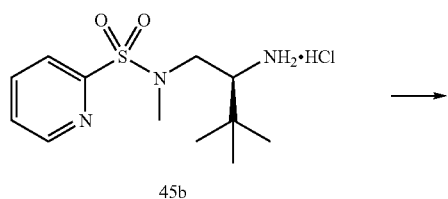

45b

-continued

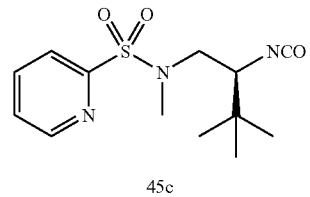

45c

A solution of amine 45b (300 mg, 1 mmol) in $CH_2Cl_2$ (3 mL) aq. saturated $NaHCO_3$ (3 mL) at 0° C. was treated with phosgene (2.5 mL, 15% soln. in toluene) and stirred at 0° C. for 2 h. The reaction mixture was diluted with $CH_2Cl_2$ (30 mL) and the organic layer was washed with cold aq $NaHCO_3$. The organic layer was dried ($MgSO_4$) filtered and further diluted with 3 mL toluene, concentrated the methylene chloride layer and used as a solution.

Step C:

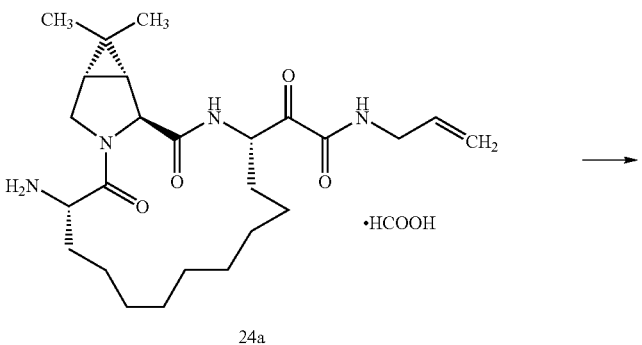

24a

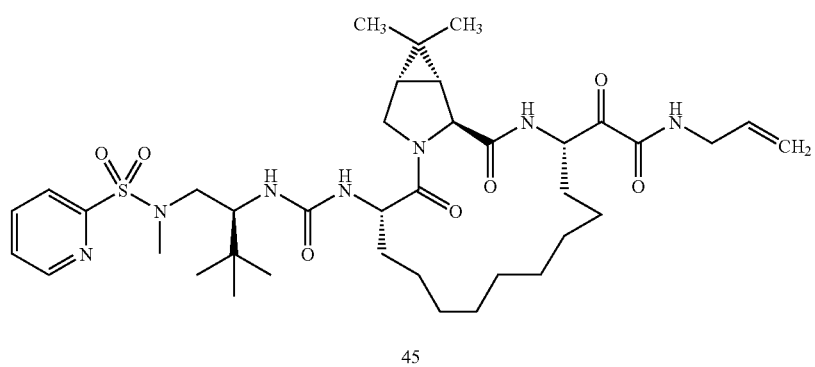

45

A solution of amine 24a (100 mg, 0.197 mmol) in methylene chloride (3.0 mL) was treated with NMM (60 mg, 0.6 mmol) and cooled to 0° C. A solution of isocyanate 45c (2.5 mL, 0.25 mmol) in toluene was added and the reaction mixture was stirred at rt. for 2 h. The reaction mixture was diluted with methylene chloride (100 mL) and washed with aq. HCl (1 M, 50 mL). The organic layers were dried with (MgSO$_4$) filtered concentrated in vacuo and purified by chromatography (SiO$_2$, ethyl acetate/hexanes 1:1→1:0) yield product 45 as a colorless solid. The crude mixture was further purified using HPLC to yield pure product 45 (27 mg). $^1$H NMR (dmso, 500 MHz) δ 8.89 (t, 1H, J=7.0 Hz), 8.72 (d, 1H, J=6.0 Hz), 8.37 (d, 1H, J=10.5 Hz), 8.07 (t, 1H, J=9.0 Hz), 7.88 (d, 1H, J=9.0 Hz), 7.66 (dd, 1H, J=6.5 &3.5 Hz), 6.12 (d, 1H, J=11 Hz), 5.84-5.75 (m, 2H), 4.27 (s, 1H), 4.22 (bt, 1H, J=11.5 Hz), 3.92 (d, 1H, J=13 Hz), 3.77-3.60 (m, 4H), 3.33 (bd, 1H), 3.06 (bt, 1H, J=12.5 Hz), 2.75 (s, 3H), 1.68-1.59 (m, 2H), 1.44-1.12 (m, 18H), 0.98 (s, 3H), 0.83 (s, 3H), 0.78 (s, 9H). $^{13}$C NMR (dmso, 125 MHz) δ, 198.3, 172.1, 171.7, 162.1, 158.3, 157.1, 151.0, 139.6, 135.0, 127.9, 123.3, 116.4, 60.5, 55.8, 52.8, 52.2, 51.5, 36.4, 35.0, 28.0, 27.1, 26.9, 26.3, 19.5, 13.7. MS (ES) m/z relative intensity 780 [(M+Na)$^+$, 50]; 758 [(M+1)$^+$, 100].

Preparative Example 46

Preparation of

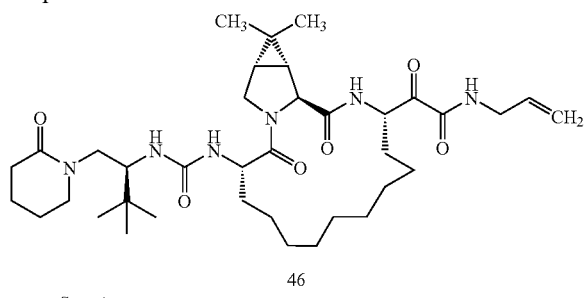

Step A:

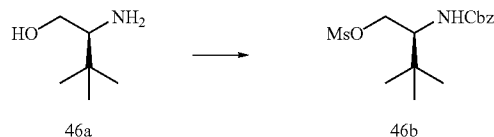

A solution of (S)-tert-leucinol (5.0 g, 42.7 mmol, Aldrich) 46a at 0° C. in CH$_2$Cl$_2$ (100.0 mL) was treated with benzyl chloroformate (6.7 mL, 47.0 mmol), followed by Hunig's base (9.3 mL, 53.3 mmol). The reaction mixture was allowed to warm to room temperature and stirred overnight. The reaction mixture was diluted with ethyl acetate (500 mL), washed with 10% KH$_2$PO$_4$, followed by saturated NaHCO$_3$ and brine. The organic layer was dried over MgSO$_4$ and concentrated to yield protected leucinol (10.7 g, 100%) that was used in further reaction without any purification.

To a solution of protected leucinol (crude) (10.7 g, 42.7 mmol) in CH$_2$Cl$_2$ (100.0 mL) at 0° C. was added pyridine (20.0 mL) and methanesulfonyl chloride (3.63 mL, 47.0 mmol). The reaction mixture was allowed to warm to room temperature and stirred overnight, concentrated, redissolved in ethyl acetate (500 mL), washed with saturated NaHCO$_3$ and brine. The organic layer was dried (MgSO$_4$), concentrated and purified by flash chromatography over SiO$_2$ using ethyl acetate/hexane (1:4) to yield 46b (14.0 g, 100%).

Step B:

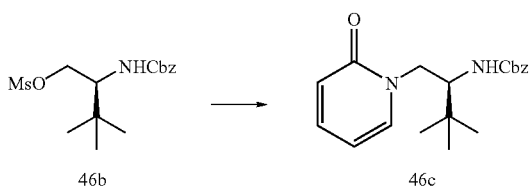

A solution of 46b (3.1 g, 9.9 mmol) in toluene (72 mL) containing water (400 μL) was treated with (C$_4$H$_9$)$_4$NBr (582 mg, 1.8 mmol), K$_2$CO$_3$ (2.72 g, 1.97 mmol) and 2-hydroxypyridine (937 mg, 9.85 mmol). The reaction mixture was refluxed overnight with stirring, filtered and the filtrate was concentrated in vacuo. The residue was purified by flash chromatography over SiO$_2$ using ethyl acetate/CH$_2$Cl$_2$ (1:9 to 1:1) to yield 46c (1.15 g, 35%) as a colorless oil.

Step C:

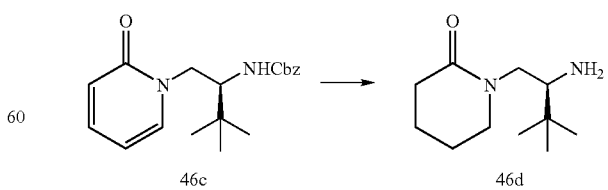

A solution of pyridone 46c (1.15 g) in MeOH (50 mL) was treated with Pd/C (10% w/w, 450 mg) and placed in a Parr® shaker and hydrogenated at 40 psi for 4 h. The reaction Step D:

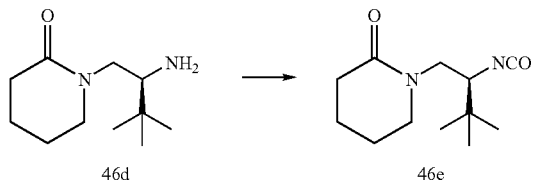

A solution of amine 46d (600 mg, 3.03 mmol) in CH₂Cl₂ (10 mL) aq. saturated NaHCO₃ (10 mL) at 0° C. was treated with phosgene (5 mL, 15% soln. in toluene) and stirred at 0° C. for 2 h. The reaction mixture was diluted with CH₂Cl₂ (50 mL) and the organic layer was washed with cold aq NaHCO₃. The organic layer was dried (MgSO₄) filtered and further diluted with 3 mL toluene, concentrated the methylene chloride layer and used as a solution in toluene.

Step E:

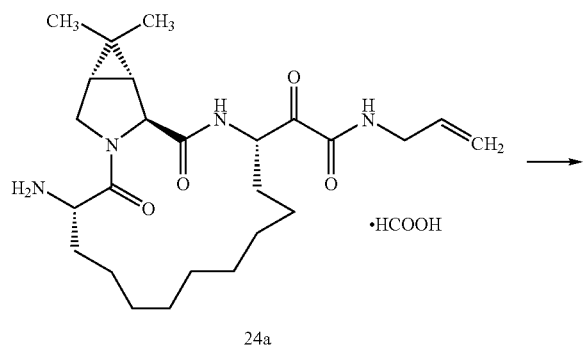

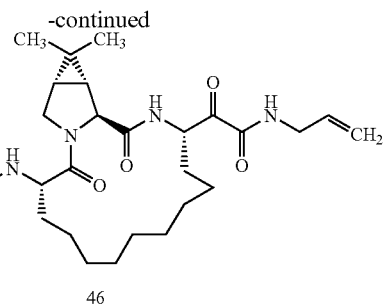

A solution of amine 24a (100 mg, 0.197 mmol) in methylene chloride (3.0 mL) was treated with NMM (60 mg, 0.6 mmol) and cooled to 0° C. A solution of isocyanate 46e (1.5 mL, 0.25 mmol) in toluene was added and the reaction mixture was stirred at rt. for 2 h. The reaction mixture was diluted with methylene chloride (100 mL) and washed with aq. HCl (1 M, 50 mL). The organic layers were dried with (MgSO₄) filtered concentrated in vacuo and purified by chromatography (SiO₂, ethyl acetate/hexanes 1:1 ◊ 1:0) and 100% ethyl acetate to yield 46 (30 mg) as a colorless solid. ¹H NMR (dmso, 500 MHz) δ, 8.92 (t, 1H, J=6.5 Hz), 8.39 (d, 1H, J=9.0 Hz), 6.17 (d, 1H, J=9.0 Hz), 5.81 (m, 1H), 5.69 (d, 1H, J=10.5 Hz), 5.29 (bt, 1H, J=10.0 Hz), 5.13-5.10 (m, 2H), 4.33 (s, 1H), 4.30-4.26 (m, 1H), 3.86-3.65 (m, 6H), 3.50 (bt, 1H, J=12 Hz), 3.15-3.08 (m, 2H), 2.21-2.05 (m, 2H), 1.74-1.54 (bm, 6H), 1.46-1.11 (bm, 18H), 0.99 (s, 3H), 0.84 (s, 3H), 0.82 (s, 9H). ¹³C NMR (dmso, 125 MHz) δ, 198.2, 172.1, 171.3, 169.3, 162.1, 158.2, 135.0, 116.4, 60.5, 55.8, 55.1, 52.8, 51.5, 48.3, 47.6, 47.0, 41.7, 34.6, 33.0, 32.4, 31.5, 28.3, 28.0, 27.8, 27.2, 26.9, 26.2, 24.5, 23.7, 22.4, 21.9, 19.5, 13.7.

Preparative Example 47

Preparation of

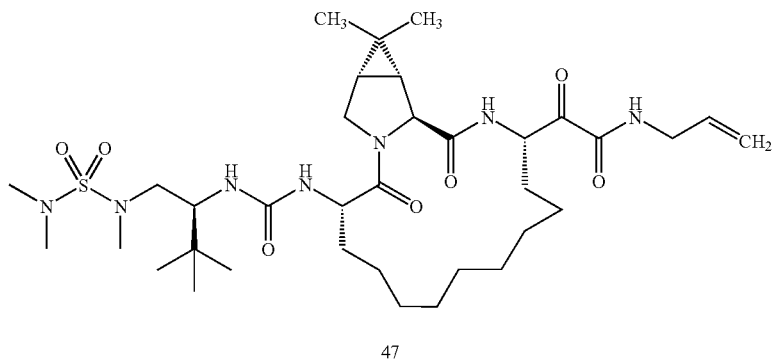

Step A:

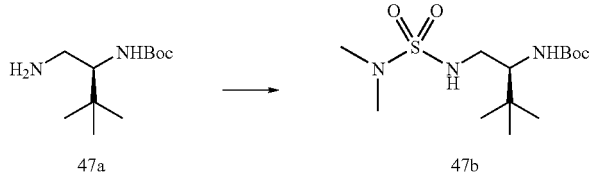

The amine, 47a, (C. A. Busacca et al, *Tetrahedron: Asymmetry;* (2000) 9 1907) (1.5 g, 6.9 mmol, 1 equiv.) was dissolved in dry dichloromethane (20 ml) and cooled to −78° C. Added 3 ml (3 equiv.) of Et₃N followed by the slow addition of dimethylsulfamyl chloride (1.5 eq., Sigma-Aldrich) dissolved in DCM. The temperature was kept at −78° C. until the addition is complete and then stirred overnight allowing it to rise to room temperature. Diluted with methylene chloride and washed with water, aq. 1N HCl and finally brine. The organic layers were dried over anhydrous sodium sulfate, filtered, and concentrated in vacuo. Crude product isolated was purified via flash column (10→30% EtOAc-Hexane) to afford 1.27 g (58%) of 47b. ¹H NMR (CDCl₃, 300 MHz) δ, 4.6 (d, 1H), 3.45 (m, 1H), 3.25 (d, 1H), 2.89 (s, 6H), 1.89 (bs, NH), 1.22 (s, 9H), 0.98 (s, 9H).

MS (ESI), m/z, relative intensity 324 [(M+1) 85], 268 (100), 224 (50).

Step B:

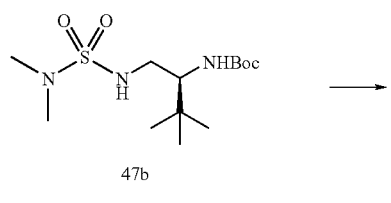

47b

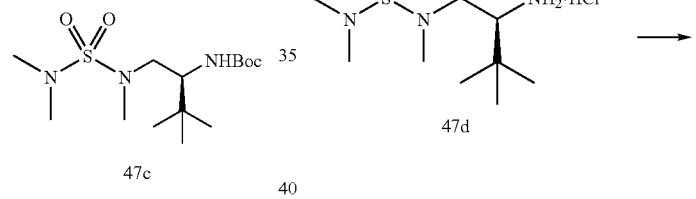

47c

To the Boc protected sulfonyl urea 47b (440 mg, 1.25 mmol, 1 equiv.) in DMF (10 mL) at 0° C. was added Cs₂CO₃ (613 mg, 1.5 equiv, 1.88 mmol) and MeI (6.36 mmol, 5 equiv., 0.601 mL) under inert atmosphere. The reaction mixture was stirred at room temperature for 90 min and quenched with water. The aqueous layers were extracted with EtOAc, washed 4 times with water and brine. The organic layers were dried over anhydrous sodium sulfate, filtered and evaporated off the solvent to afford 420 mg (91%) of 47c that was used in the next reaction without further purification. ¹H NMR (CDCl₃, 300 MHz) δ 4.59 (d, 1H), 3.62-3.58 (m, 1H), 3.29-3.22 (m, 1H), 2.80 (s, 3H), 2.79 (s, 6H), 1.89 (bs, NH), 1.22 (s, 9H), 0.98 (s, 9H). MS (ESI), m/z, relative intensity 338 [(M+1) 60], 282 (100), 238 (90).

Step C:

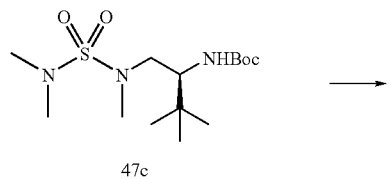

47c

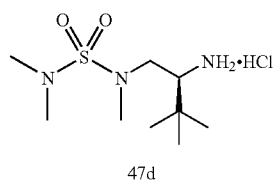

47d

To the Boc-protected sulfonyl urea 47c (890 mg, 1 equiv.) was added 4 M solution of HCl in dioxane (25 mL) at room temperature and stirred for 1 hr. After the disappearance of starting material (TLC), the reaction mixture was concentrated and azeotroped with hexanes and ether. The residue was triturated with ether and the solid separating out was filtered and dried in vacuum to afford a pale yellow solid (720 mg, ~100%). It was used in further reaction without purification.

Step D:

47d

47e

To the amine hydrochloride salt 47d (720 mg, 2.63 mmol) in dichloromethane (15 ml) was added 15 ml of aq. saturated NaHCO₃ and stirred vigorously at 0° C. for 5 min. A solution of phosgene (2 equiv. 20% in toluene) was syringed out to the lower layer and restored the vigorous stirring immediately. Checked the TLC at times and after 2 hrs, it showed complete consumption of starting material. The methylene chloride layer was separated and the aqueous layer was extracted with dichloromethane (30 ml). The combined organic layers were dried over anhydrous sodium sulfate, filtered and concentrated using rotary evaporator under reduced pressure at rt. to half the volume and then flushed N₂ for 15 minutes. Diluted the solution to 130 mL with dichloromethane and used as 0.02 M solution in further reactions.

Step E:

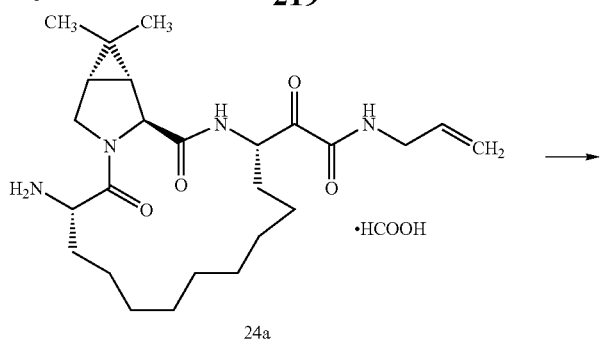

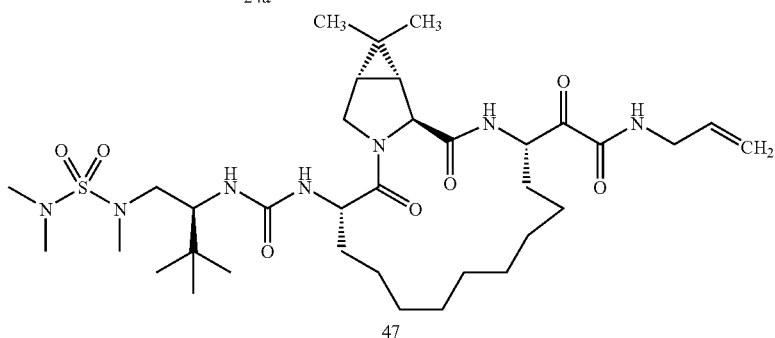

A solution of amine 24a (100 mg, 0.197 mmol) in methylene chloride (3.0 mL) was treated with NMM (60 mg, 0.6 mmol) and cooled to 0° C. A solution of isocyanate 47e (1.5 mL, 0.25 mmol) in toluene was added and the reaction mixture was stirred at rt. for 2 h. The reaction mixture was diluted with methylene chloride (100 mL) and washed with aq. HCl (1 M, 50 mL). The organic layers were dried with (MgSO$_4$) filtered concentrated in vacuo and purified by chromatography (SiO$_2$, ethyl acetate/hexanes 1:1 ◊ 1:0) and 100% ethyl acetate to yield 47 (49 mg) as a colorless solid.

$^1$H NMR (dmso, 500 MHz) δ, 8.89 (t, 1H, J=6 Hz), 8.37 (d, 1H, J=9.0 Hz), 6.15 (d, 1H, J=9.0 Hz) 5.83-5.76 (m, 2H), 5.31-5.27 (m, 2H), 4.33 (s, 1H), 4.30-4.28 (m, 1H), 3.91 (d, 1H, J=10.5 Hz), 3.80-3.70 (m, 4H), 3.63-3.59 (m, 1H), 2.93 (dd, 1H), 2.7 (s, 3H), 2.69 (s, 6H), 1.73-1.65 (m, 2H), 1.51-1.02 (m, 18H), 0.99 (s, 3H), 0.84 (s, 3H), 0.81 (m, 9H) $^{13}$C NMR (dmso, 125 MHz) δ, 198.3, 172.1, 171.7, 162.1, 158.2, 135.0, 116.5, 60.5, 55.8, 52.8, 51.7, 1.3, 47.6, 41.1, 38.5, 36.0, 34.9, 32.3, 31.6, 31.3, 28.5, 28.4, 27.9, 27.4, 27.4, 27.1. MS (ES) m/z relative intensity 746 [(M+Na)$^+$, 40]; 724 [(M+1)$^+$, 100].

Preparative Example 48

Preparation of

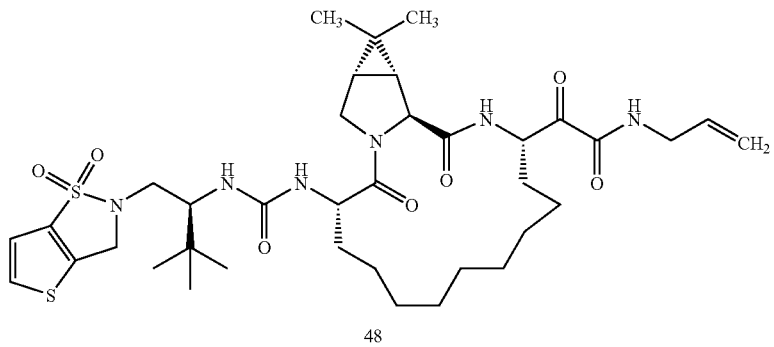

Step A:

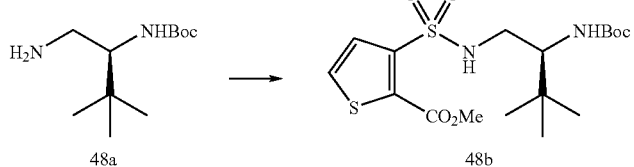

Compound 48b was prepared from 48a and 2-carbomethoxy-3-thiophenesulfonyl chloride according to the procedures described for the preparation of compound 45b.

Step B:

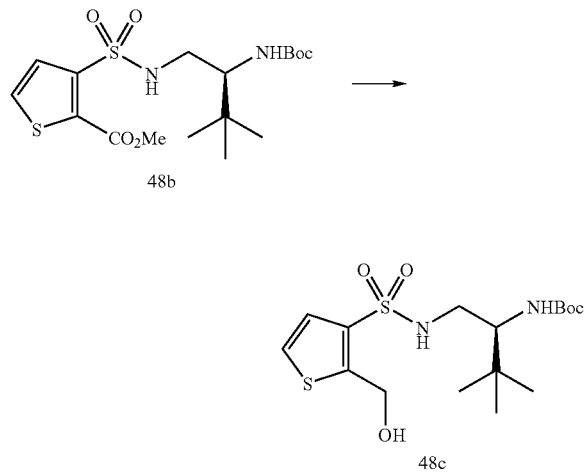

To the solution of ester 48b (4.65 g, 11.1 mmol) in anhydrous toluene (40 mL) at −78° C. was added a solution of DIBAL-H in toluene (23.0 mL, 34.5 mmol). The mixture was stirred at −78° C. for 20 min and at rt. for 2 h. Methanol (20 mL) was added followed by 10% aqueous citric acid solution (100 mL). After stirred for 5 min, EtOAc (200 mL) was added and layers were separated. The aqueous solution was extracted with EtOAc (2×100 mL). The organic solutions were combined, dried (MgSO$_4$), filtered and concentrated. The residue was purified by flash column chromatography using 10-50% acetone/hexanes to give 4.6 g (quant.) of 48c.

Step C:

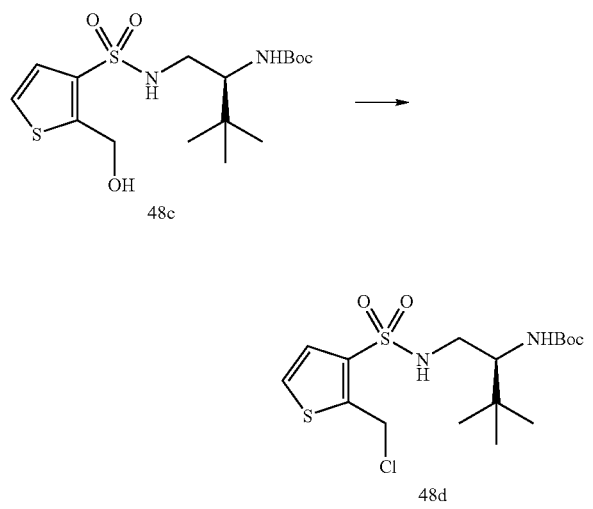

To a solution of 48c (1.04 g, 2.65 mmol) in CH$_2$Cl$_2$ I (50 mL) at 0° C. was added methanesulfonyl chloride (0.23 mL, 2.97 mmol) and triethylamine (0.80 mL, 5.74 mmol). The mixture was warmed to rt along with ice bath and stirred for 18 h. EtOAc (200 mL) and 5% H$_3$PO$_4$ solution (100 mL) was added and the layers were separated. The organic solutions were washed with 1 N sodium carbonate solution (100 mL) before it was dried (MgSO$_4$), filtered and concentrated. The residue was purified by flash column chromatography using 10-50% acetone/hexanes to give 0.80 g (73%) of 48d.

Step D:

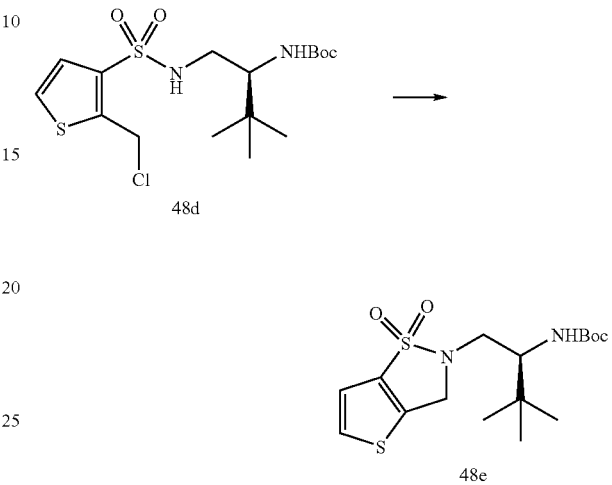

A suspension of 48d (1.17 g, 2.85 mmol) and cesium carbonate (1.40 g, 4.30 mmol) in anhydrous DMF (100 mL) was stirred at rt. for 18 h. Water (50 mL), brine (50 mL) and EtOAc (300 mL) were added and the layers were separated. The organic solution was washed water (3×150 mL) before it was dried, filtered and concentrated to give 0.99 g of the desired product 48e (93%).

Step E:

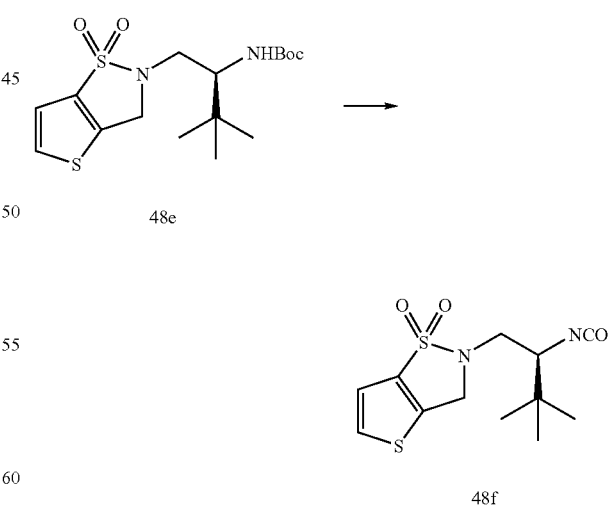

Compound 48f was prepared from 48e according to the procedures described for the preparation of compounds 45b and 45c.

Step F:

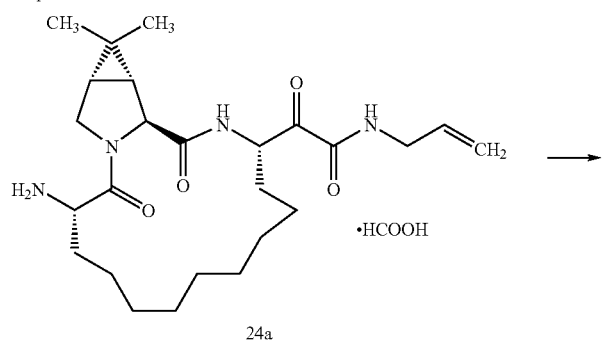

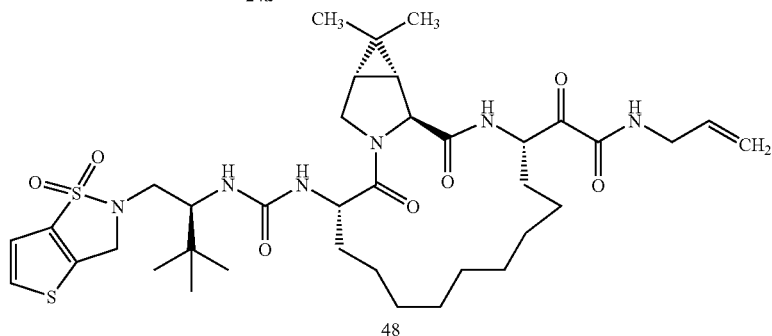

A solution of amine 24a (100 mg, 0.197 mmol) in methylene chloride (3.0 mL) was treated with NMM (60 mg, 0.6 mmol) and cooled to 0° C. A solution of isocyanate 48f (2 mL, 0.25 mmol) in toluene was added and the reaction mixture was stirred at rt. for 2 h. The reaction mixture was diluted with methylene chloride (100 mL) and washed with aq. HCl (1 M, 50 mL). The organic layers were dried with (MgSO$_4$) filtered concentrated in vacuo and purified by chromatography (SiO$_2$, ethyl acetate/hexanes 1:1→1:0) and 100% ethyl acetate to yield 48 as a colorless solid.

Preparative Example 49

Preparation of

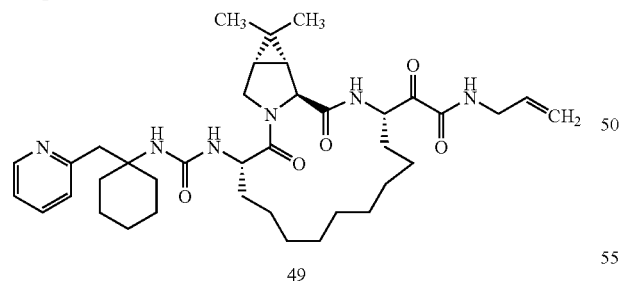

Step A:

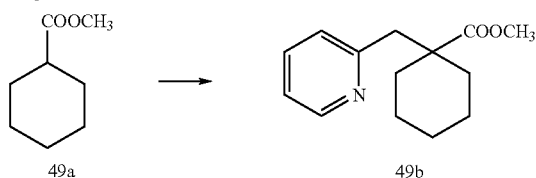

A solution of 2 M LDA/THF-heptane (Acros Chemical Co.) in 50 mL of THF was cooled to −70° C., methyl cyclohexanecarboxylate 49a was added drop wise at <−60° C. After an additional 0.5 hr stirring at −70° C., 2-picolyl chloride in 40 mL ether was added drop wise at <−60° C. The temperature was then allowed to rise slowly to room temperature over 2 hr, and stirred an additional 2 hr. The reaction was quenched in a cold mixture of 200 mL 20% aqueous KH$_2$PO$_4$ and 5 mL of 12 N HCl, the mixture was extracted with EtOAc, the extract was washed with brine, and then dried with MgSO$_4$. The mixture was filtered, the filtrate was evaporated, the residue was evaporated twice from xylene, and the final residue was chromatographed on silica gel (1:3 Et$_2$O—CH$_2$Cl$_2$ to 1:1 acetone-CH$_2$Cl$_2$) to obtain 49b.

Step B:

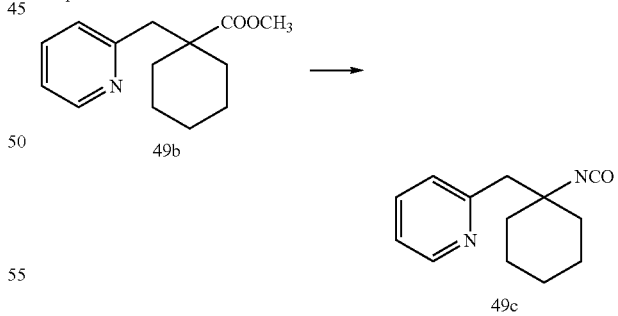

A solution of ester 49b in 20 mL of dioxane was treated with 30 mL of 1 N aqueous LiOH, and the mixture was stirred at 100° C. for 6 hr. The mixture was quenched in ice-water, extracted with ether, and the cold aqueous was slowly acidified to pH ~4 with 3 N HCl. The precipitate was filtered, washed with water, and dried to leave product acid that was used in the following step without further purification. The conversion of the acid to the isocyanate 49c was identical to the synthesis of 27b in preparative example 27.

Step C:

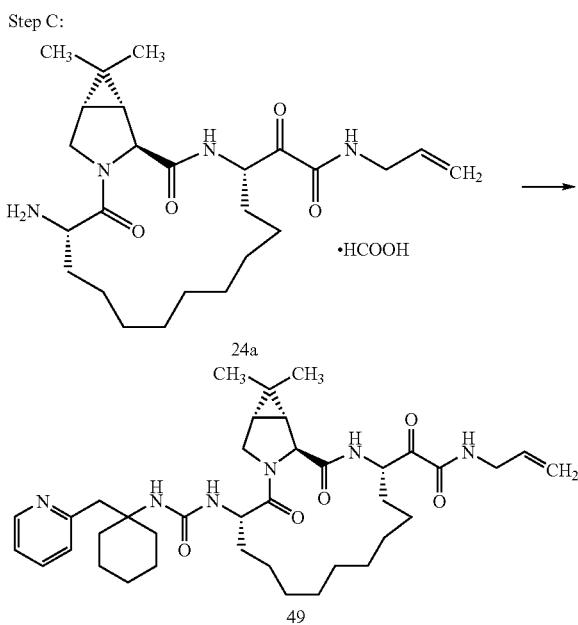

A solution of amine 24a (100 mg, 0.197 mmol) in methylene chloride (3.0 mL) was treated with NMM (60 mg, 0.6 mmol) and cooled to 0° C. A solution of isocyanate 49c (2.9 mL, 0.25 mmol) in toluene was added and the reaction mixture was stirred at rt. for 2 h. The reaction mixture was diluted with methylene chloride (100 mL) and washed with aq. HCl (1 M, 50 mL). The organic layers were dried with (MgSO₄) filtered concentrated in vacuo and purified by chromatography (SiO₂, ethyl acetate/hexanes 1:1 ◊ 1:0) and 100% ethyl acetate to yield 49 as a colorless solid.

Preparative Example 50

Preparation of

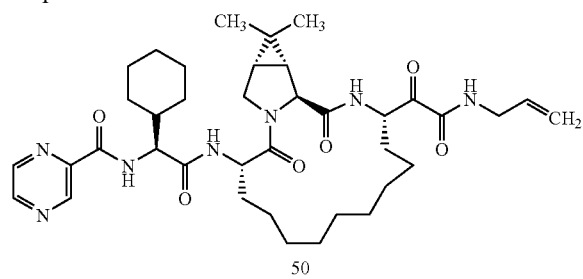

Step A:

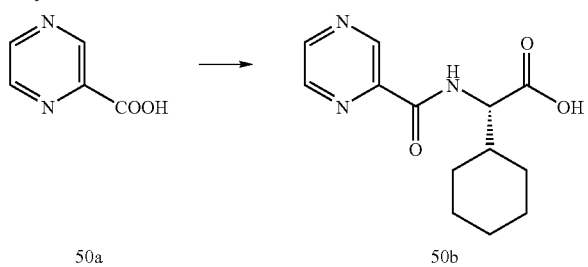

A solution of pyrazinecarboxylic acid 50a (Aldrich, 3 g) in 150 mL of dry dichloromethane and 150 mL of dry DMF was stirred at 0° C. and treated with HATU (1.4 eq, 6.03 g).

L-cyclohexylglycine-methyl ester hydrochloride (1.2 eq, 6.03 g) was added in small portions. Then, N-methylmorpholine (4 eq, 10 mL, d 0.920) was added dropwise. The reaction mixture was gradually warmed to room temperature and stirred for 20 h. All the volatiles were removed under vacuum and the residue was dissolved in 500 mL of ethyl acetate. The organic layer was washed with water (100 mL), aq. 1N HCl (100 mL), aq. saturated sodium bicarbonate solution (100 mL), and brine (100 mL). The organic layer was dried over magnesium sulfate, filtered and concentrated under reduced pressure. The residue was chromatographed on silica gel (gradient: acetone/hexanes; 5:95 to 3:7) to afford the product 50b (6.5 g, 95%) as a white solid.

Step B:

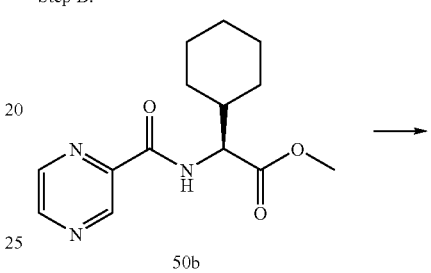

A solution of methyl ester 50b (6.5 g) in 270 mL of a 1:1:1 mixture of THF/MeOH/H₂O was cooled to 0° C. and treated with lithium hydroxide monohydrate (2.5 eq, 2.45 g). The mixture was stirred and monitored by TLC (acetone/hexanes; 2:8). When all the starting material had been consumed, the reaction mixture was treated with 100 mL of aq 1N HCl and the mixture was concentrated in vacuo. Dichloromethane (250 mL) was added and layers separated. The aqueous layer was extracted with dichloromethane (3×80 mL). The combined organic layers were dried over magnesium sulfate, filtered, and concentrated to afford acid 50c.

Step C:

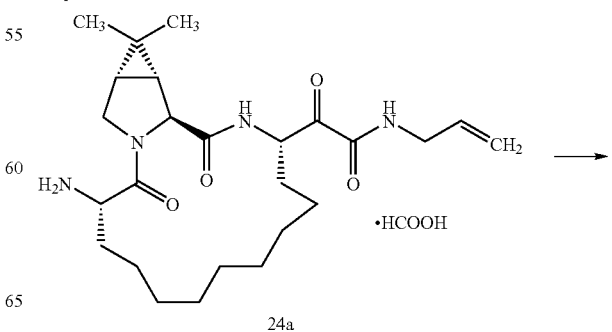

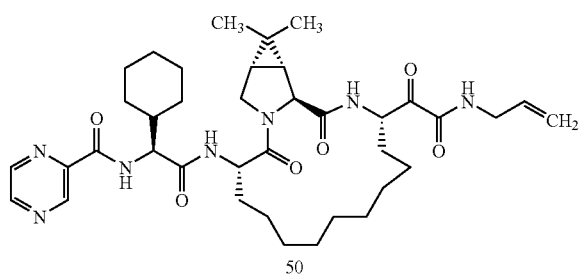
50

A solution of acid 24a (100 mg, 0.197 mmol) in dry CH₂Cl₂ (2 mL) and DMF (2 mL) was cooled to 0° C. and treated with acid 50c (51.8 mg, 0.197 mmol), HATU (94 mg, 0.25 mmol) and NMM (45 mg, 0.45 mmol). The reaction was stirred at 0° C. for 12 h and concentrated in vacuo. The residue was dissolved in CH₂Cl₂ (100 mL) and washed with aq. HCl (1 M, 2×30 mL), aq. saturated NaHCO₃ (2×30 mL), brine (30 mL), dried (MgSO₄), filtered, concentrated in vacuo. The crude dipeptide was purified by chromatography (SiO₂, acetone/Hexanes 0:1→1:1) to yield 50. ¹H NMR (dmso, 400 MHz) δ, 9.16 (δ, 1H, J=12 Hz), 8.89 (d, 1H, J=2.4 Hz), 8.74 (s, 1H), 8.59 (d, 1H, J=7.4 Hz), 8.43-8.38 (m, 2H), 5.81-5.75 (m, 1H), 5.28 (t, 1H, J=10.8 Hz), 5.11-5.03 (m, 2H), 4.45-4.31 (m, 3H), 3.88-3.70 (m, 5H), 1.65-1.22 (m, 31H), 0.97 (s, 3H), 0.83 (s, 3H). MS (ES) m/z relative intensity 728 [(M+Na)⁺, 4]; 706 [(M+1)⁺, 80].

A solution of the alcohol 51a (1.00 g, 4.6 mmol) in anhydrous CH₂Cl₂ (30 mL) in an inert atmosphere was treated with triphenylphosphine (1.52 g, 5.75 mmol) and dimethylglutarimide (780 mg, 5.52 mmol). The reaction mixture was cooled to 0° C. and treated with DIAD (930 mg, 4.60 mmol, in 4 mL CH₂Cl₂) dropwise and warmed to rt. It was stirred at rt. for 5 h and concentrated in vacuo. The residue was purified by chromatography (SiO₂, Hexanes/acetone 1:0→1:1) to obtained 51b (600 mg) as a colorless solid.

Step B:

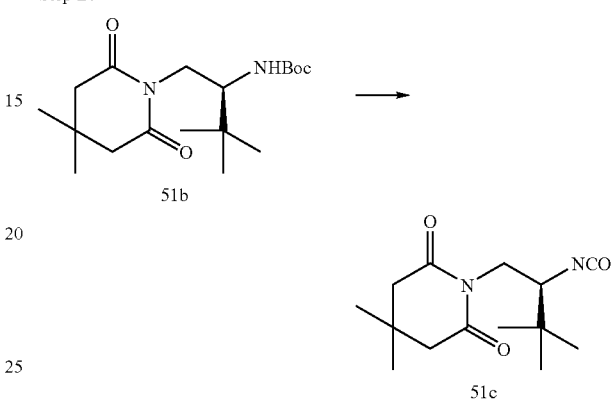

A solution of 51b (500 mg, 1.5 mmol) in HCl (15 mL, 4M soln. in dioxane) was stirred at rt. for 1 h and concentrated in vacuo. The residue was used in further reaction without purification. A solution of the deprotected amine in CH₂Cl₂ (10 mL) aq. saturated NaHCO₃ (10 mL) at 0° C. was treated with phosgene (5 mL, 15% soln. in toluene) and stirred at 0° C. for 2 h. The reaction mixture was diluted with CH₂Cl₂ (50 mL) and the organic layer was washed with cold aq. NaHCO₃. The organic layer was dried (MgSO₄) filtered and further diluted with 3 mL toluene, concentrated the methylene chloride layer and used as a solution.

Preparative Example 51

Preparation of

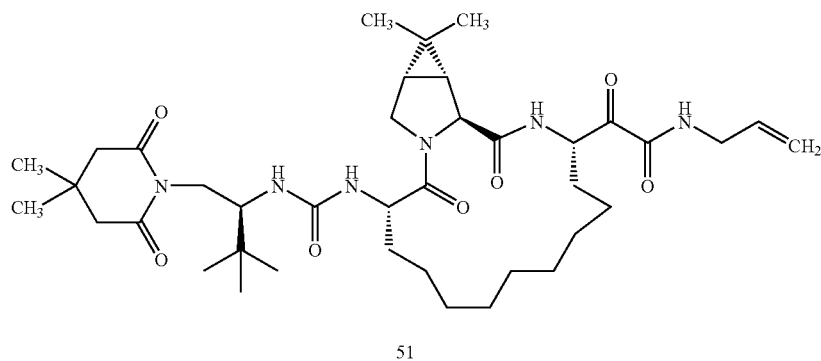
51

Step A:

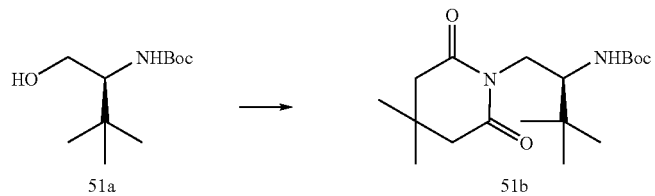

Step C:

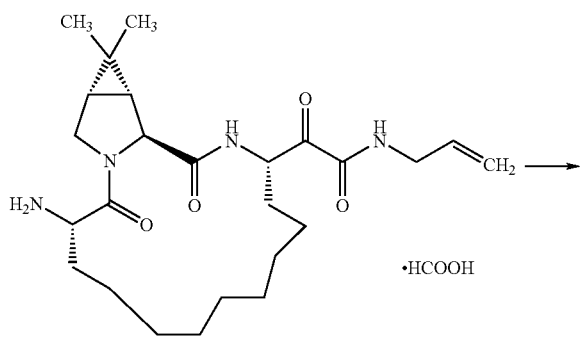

24a

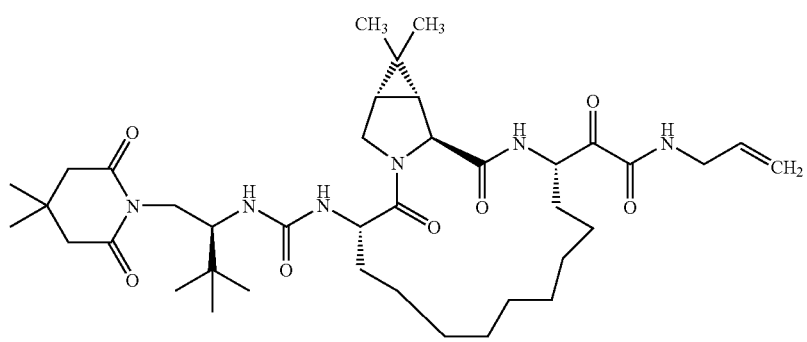

51

A solution of amine 24a (100 mg, 0.196 mmol) in methylene chloride (3.0 mL) was treated with NMM (60 mg, 0.6 mmol) and cooled to 0° C. A solution of isocyanate 51c (2 mL, 0.5 mmol) in toluene was added and the reaction mixture was stirred at rt. for 2 h. The reaction mixture was diluted with methylene chloride (100 mL) and washed with aq. HCl (1 M, 50 mL). The organic layers were dried with (MgSO$_4$) filtered concentrated in vacuo and purified by chromatography (SiO$_2$ Acetone/hexanes 0:1→1:1) yield 51 as a colorless solid. $^1$H NMR (dmso, 500 MHz) δ, 8.91 (d, 1H), 6.19 (d, 1H, J=8.5 Hz), 5.84-5.57 (m, 1H), 5.58 (d, 1H, J=10.5 Hz), 5.28 (t, 1H, J=7.0 Hz), 5.10-5.05 (m, 2H), 4.31 (s, 1H), 4.18 (t, 1H, J=8.5 Hz), 3.83-3.57 (m, 7H), 2.44-2.38 (AB, 4H), 1.66-1.62 (m, 2H), 1.44-1.03 (m, 18H), 0.98 & 0.96 (2s, 9H), 0.84 & 0.81 (2s, 12H). $^{13}$C NMR (dmso, 125 MHz) δ, 198.2, 172.7, 172.1, 171.3, 162.1, 158.1, 135.0, 116.4, 60.5, 55.5, 52.9, 51.3, 47.5, 46.4, 41.7, 39.6, 35.0, 32.4, 31.5, 31.3, 29.3, 28.3, 27.9, 27.0, 26.9, 26.6, 26.1, 24.5, 22.4, 19.5, 13.7. MS (ES) m/z relative intensity 749 [(M+Na)$^+$, 20]; 727 [(M+1)$^+$, 100].

Preparative Example 52

Preparation of

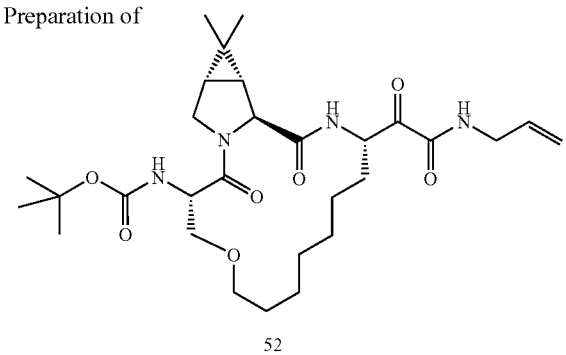

52

-continued

Step A:

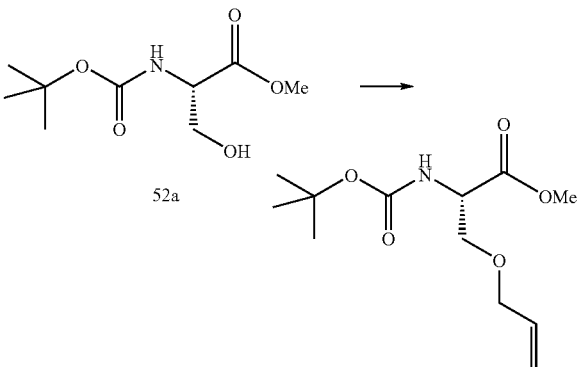

52a

52b

A solution of N-Boc-L-Ser-OMe (3.6 g, Aldrich) in 150 mL of dry THF was degassed (vacuum/N$_2$-flush) and treated with allylmethyl carbonate (1.4 eq, 2.6 mL, d 1.022). A catalytic amount of tetrakis(triphenylphosphine)palladium (0.02 mol %, 379 mg) was added. The slightly yellow mixture was degassed again and heated at 60° C. for about 3 h until TLC analysis (acetone/hexanes; 2:8) showed no more starting material left (reaction mixture became brown). The THF was removed under reduced pressure and the residue was diluted with 300 mL of ethyl acetate and washed with 80 mL of aqueous saturated sodium bicarbonate solution and 80 mL of brine. The organic layer was dried over magnesium sulfate, filtered and concentrated under reduced pressure. The residue was chromatographed on silica gel (gradient: acetone/hexanes; 5:95 to 2:8) to afford the product 52b as a clear oil (2.7 g, 64%).

Step B

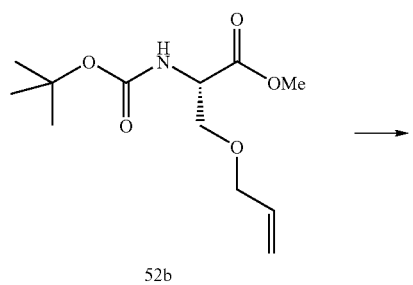

52b

A solution of methyl ester 52b (1.5 g) in 90 mL of a mixture of THF/MeOH/H$_2$O (1:1:1) was treated with lithium hydroxide monohydrate (2.5 eq, 630 mg). Reaction was stirred at room temperature and monitored by TLC (acetone/hexanes; 1:9). After 45 min, all the volatiles were removed under reduced pressure. The residue was partitioned between 80 mL of aqueous 1N HCl and 200 mL of dichloromethane. The aqueous layer was back extracted with dichloromethane (2×80 mL). The combined organic layers were dried over magnesium sulfate, filtered, and concentrated under reduced pressure to afford the product 52c as a clear oil (1.4 g, 95%).

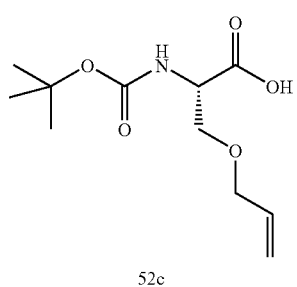

52c

Step C

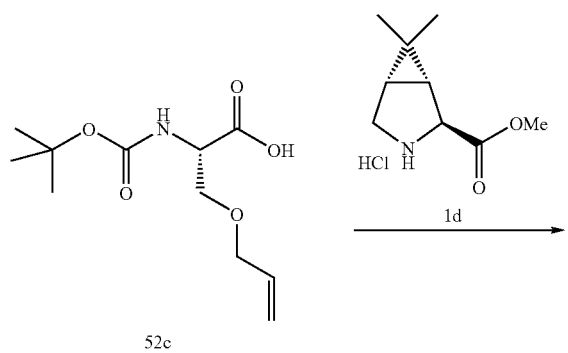

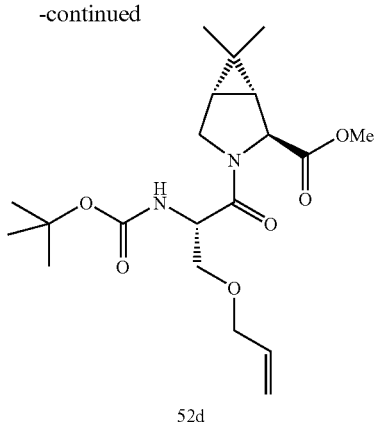

52d

A solution of acid 52c (6 mmol) in 40 mL of dry dichloromethane and 40 mL of dry DMF was stirred at 0° C. and treated with HATU (1.4 eq, 3.2 g). The amine hydrochloride 1d (1.3 eq, 1.6 g) and N-methylmorpholine (4 eq, 2.6 mL, d 0.920) were successively added. The reaction mixture was gradually warmed to room temperature and stirred overnight. All the volatiles were removed under vacuum and the residue was taken into 300 mL of ethyl acetate. The organic layer was washed with aqueous 1N HCl (50 mL), aqueous saturated sodium bicarbonate (50 mL), and brine (50 mL). The organic layer was dried over magnesium sulfate, filtered, and concentrated under reduced pressure. The residue was chromatographed on silica gel (gradient: acetone/hexanes; 5:95 to 2:8) to afford the desired product 52d (2.23 g, 93%) as a clear oil.

Step D

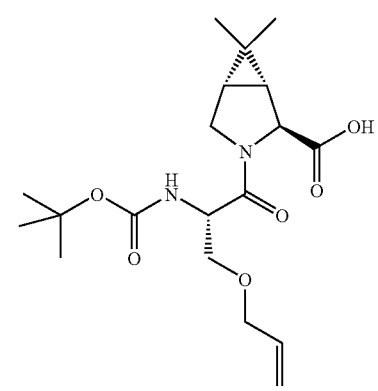

52e

A solution of methyl ester 52d (2.23 g) in 45 mL of a mixture of THF/MeOH/H₂O (1:1:1) was treated with lithium hydroxide monohydrate (2.5 eq, 300 mg) at 0° C. The cooling bath was removed and the reaction mixture was stirred at room temperature and monitored by TLC (acetone/hexanes; 2:8). After 1 h, 10 mL of aq 1N HCl were added and all the volatiles were removed under reduced pressure. The residue was partitioned between 30 mL of aqueous 1N HCl and 100 mL of dichloromethane. The aqueous layer was back extracted with dichloromethane (2×50 mL). The combined organic layers were dried over magnesium sulfate, filtered, and concentrated under reduced pressure to afford the product 52e (1.88 g, 88%) as a clear oil.

Step E

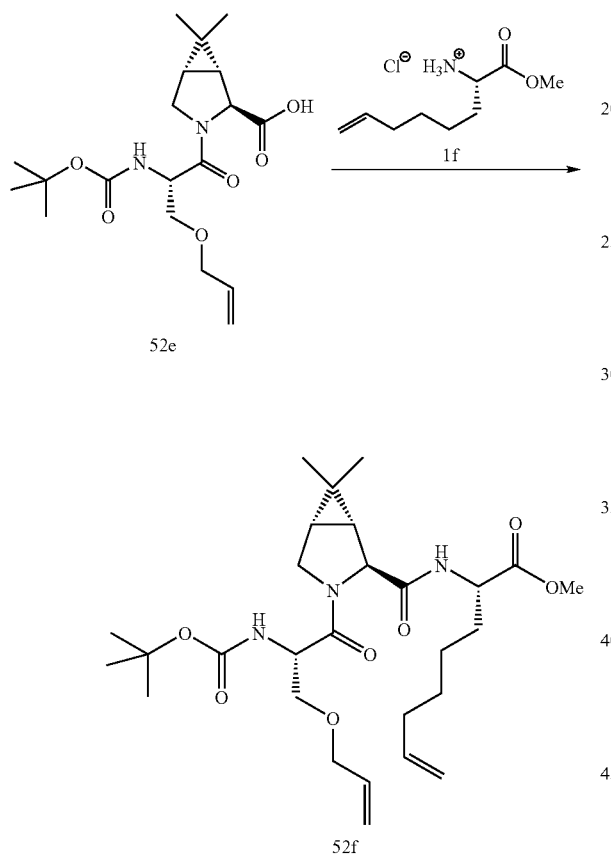

A solution of acid 52e (830 mg) in 20 mL of dry dichloromethane and 20 mL of dry DMF was stirred at 0° C. and treated with HATU (1.4 eq, 1.15 g). The amine hydrochloride 1f (1.1 eq, 227 mg) was added in 10 mL of dichloromethane followed by N-methylmorpholine (4 eq, 0.95 mL, d 0.920). The reaction mixture was kept in the freezer (−20° C.) for 48 h. All the volatiles were removed under vacuum and the residue was dissolved in 200 mL of ethyl acetate. The organic layer was washed with water (50 mL), aqueous 1N HCl (50 mL), aqueous saturated sodium bicarbonate solution (50 mL), and brine (50 mL). The organic layer was dried over magnesium sulfate, filtered and concentrated under reduced pressure. The residue was chromatographed on silica gel (gradient: acetone/hexanes; 5:95 to 3:7) to afford the product 52f (680 mg) as a white solid along with a minor diastereomeric product (130 mg) for a combined yield of 70%.

Step F

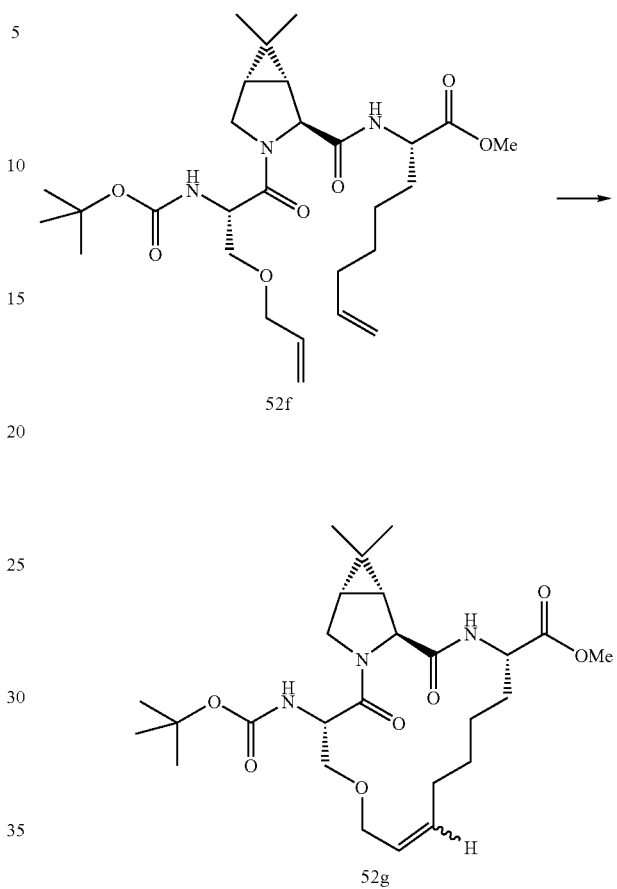

A 0.01M solution of diene 52f (670 mg) in toluene was degassed for 30 min (argon bubbling) and treated with Grubb's catalyst (0.2 eq, 205 mg). The pink solution was heated to 60° C. for 16 h (the solution became dark after heating 10 min). The solvent was removed under reduced pressure and the residue was chromatographed on silica gel (gradient: ethyl acetate/hexanes; 2:8 to 1:1) to afford the alkene product 52g (570 mg, 90%) as a mixture of E- and Z-isomers (approx 4:1).

Step G

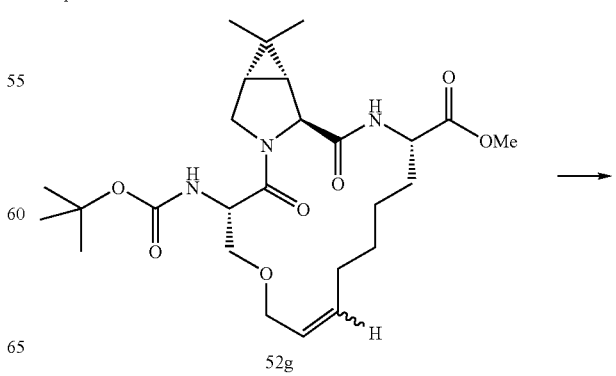

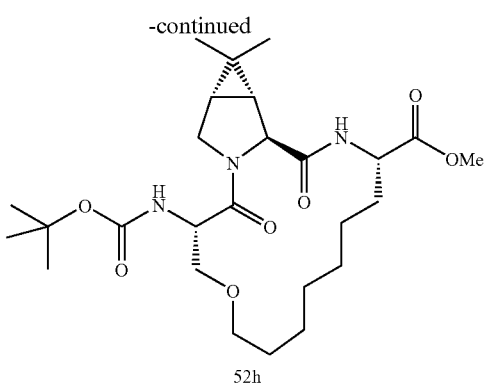

52h

A solution of alkene 52g (570 mg) in 20 mL of methanol was treated with palladium dihydroxide on carbon (0.1 mol %, 78 mg of 20% Pd(OH)$_2$/C). The mixture was hydrogenated at 50 psi until all the starting material had been consumed. The reaction mixture was diluted with 100 mL of dichloromethane and filtered thru a short path of celite. The filtrate was concentrated and the residue was chromatographed on silica gel to afford the product 52h (590 mg, 70%) as a clear oil.

Step H

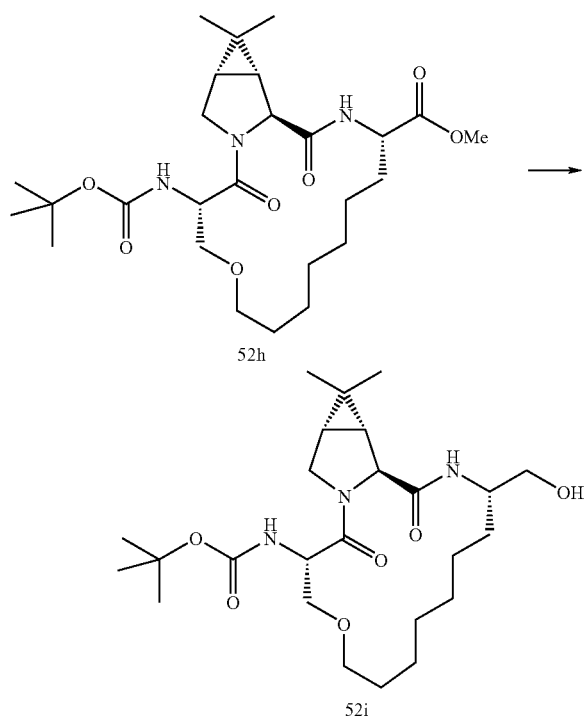

A solution of methyl ester 52h (580 mg) in 20 mL of dry THF was treated with lithium borohydride (2.1 eq, 1.2 mL of a 2M soln in THF). The reaction mixture was stirred at room temperature and monitored by TLC (acetone/hexanes; 3:7) for disappearance of the starting material. After 5 h, the excess lithium borohydride was quenched by addition of aqueous saturated ammonium chloride solution (3 mL). The mixture was partitioned between ethyl acetate (100 mL) and aqueous saturated sodium bicarbonate solution (50 mL). The aqueous layer was back extracted with ethyl acetate (2×30 mL) and dichloromethane (2×30 mL). The combined organic layers were dried over magnesium sulfate, filtered and concentrated under reduced pressure. The residue was chromatographed on silica gel (gradient: acetone/hexanes; 1:9 to 5:5) to afford the product 52i (360 mg, 68%) as a white solid.

Step I

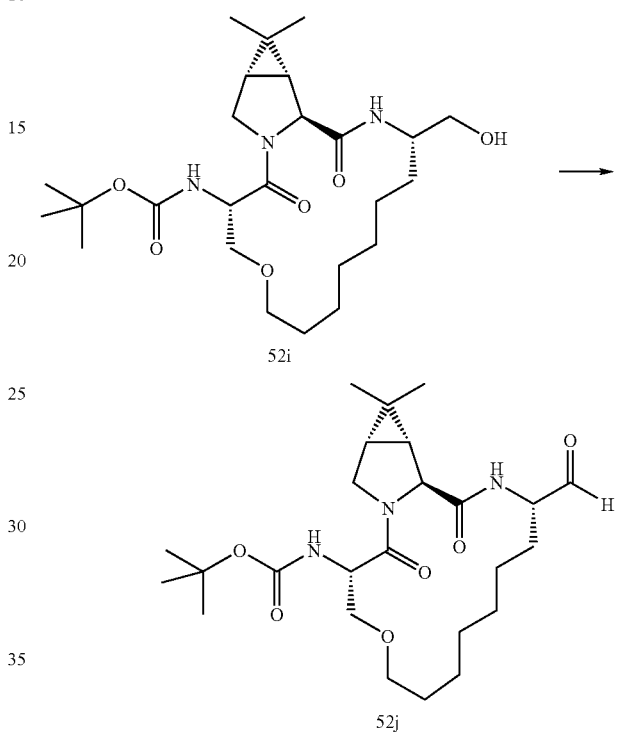

A solution of alcohol 52i (350 mg) in 20 mL of dry dichloromethane was treated with Dess-Martin periodinane (3 eq, 925 mg). The reaction mixture was stirred at room temperature for 45 min. The mixture was treated with aqueous 1M sodium thiosulfate solution (15 mL) and aqueous saturated sodium bicarbonate solution (15 mL) and stirred for 15 min. The mixture was extracted with dichloromethane (3×50 mL). The combined organic layers were dried over magnesium sulfate, filtered, and concentrated. The residue was chromatographed on silica gel (gradient: acetone/hexanes; 1:9 to 4:6) to afford the product 52j (285 mg, 83%) as a colorless solid.

Step J

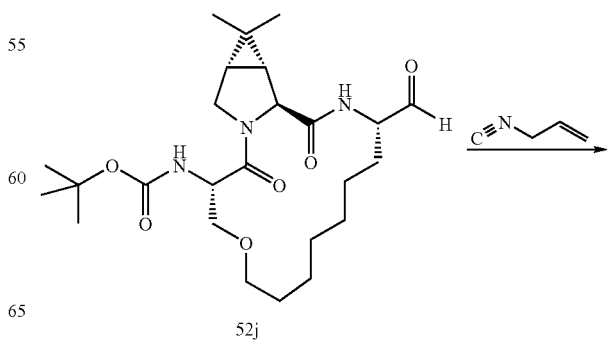

-continued

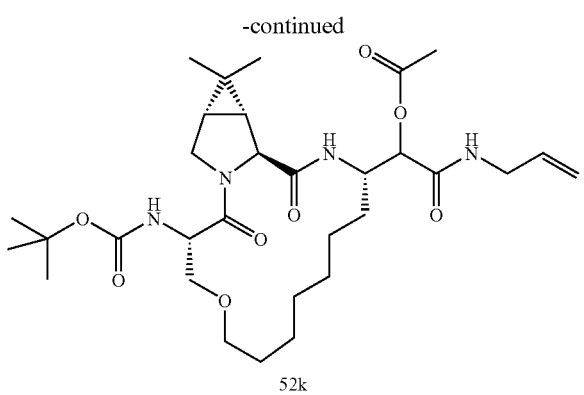

52k

A solution of aldehyde 52j (270 mg) in 10 mL of dry dichloromethane was treated with allylisocyanide (2 eq, 77 mg) and acetic acid (2 eq, 0.064 mL, d 1.049). The mixture was stirred for about 5 h. All the volatiles were removed under vacuum and the residue was chromatographed on silica gel (gradient: acetone/hexanes; 1:9 to 1:1) to afford the product 52k (303 mg, 90%) as a white solid.

Step K

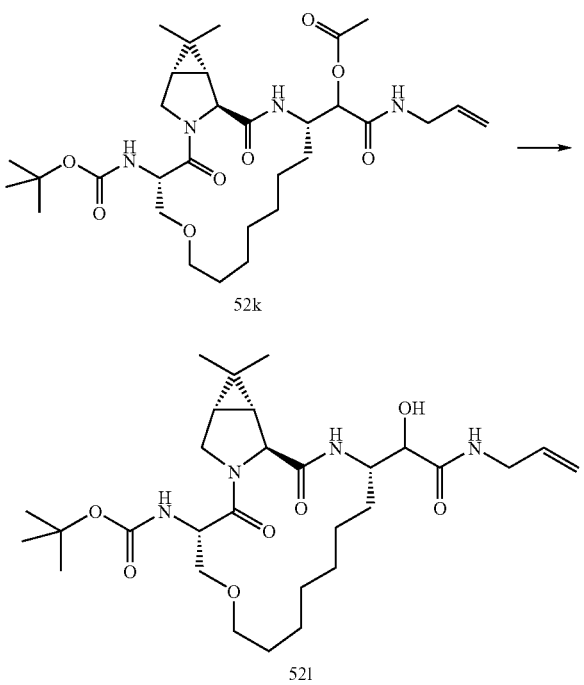

The acetate 52k (300 mg) was dissolved in 15 mL of a 1:1:1 mixture of THF/MeOH/H$_2$O and treated with lithium hydroxide monohydrate (2.5 eq, 51 mg). The flow of the reaction was followed by TLC (acetone/hexanes; 4:6). After 15 min the reaction mixture was concentrated in the rotavap and the residue was partitioned between dichloromethane (80 mL) and aqueous saturated sodium bicarbonate solution (20 mL). The aqueous layer was back extracted with dichloromethane (3×50 mL). The combined organic layers were dried over magnesium sulfate, filtered, and concentrated. The crude product 52l (276 mg, 98%) was used without further purification.

Step L

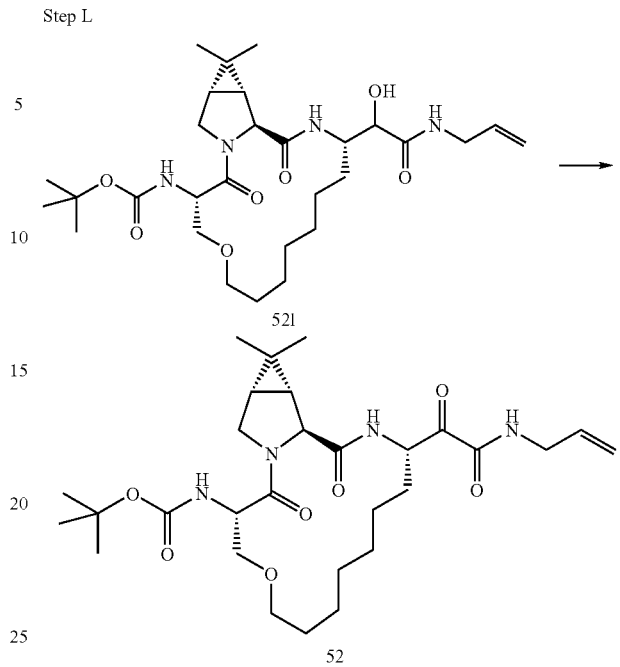

A solution of hydroxyamide 52l (276 mg) in 20 mL of dry dichloromethane was treated with Dess-Martin periodinane (3 eq, 424 mg). The reaction mixture was stirred at room temperature for 30 min. The mixture was treated with aqueous 1M sodium thiosulfate solution (20 mL) and aqueous saturated sodium bicarbonate solution (10 mL) and stirred for 10 min. The mixture was extracted with dichloromethane (3×20 mL). The combined organic layers were dried over magnesium sulfate, filtered, and concentrated. The residue was chromatographed on silica gel (gradient: acetone/hexanes; 1:9 to 4:6) to afford the product 52 (236 mg, 86%) as a white solid. $^1$H NMR (500 MHz, CDCl$_3$): δ, 7.47 (d, 1H, J=7.56 Hz), 7.03 (dd, 1H, J=5.68, 5.99 Hz), 5.88 (ddt, 1H, J=5.6, 10.0, 17.0 Hz), 5.50 (d, 1H, J=8.83 Hz), 5.46 (m, 1H), 5.28 (dd, 1H, J=0.9, 17.0 Hz), 5.25 (dd, 1H, J=0.9, 10.0 Hz), 4.61 (m, 1H), 4.51 (s, 1H), 3.99 (dt, 2H, J=1.2, 5.6 Hz), 3.88 (dd, 1H, J=5.0, 10.8 Hz), 3.83 (d, 1H, J=11.0 Hz), 3.66 (m, 2H), 3.48 (dd, 2H, J=4.7, 5.6 Hz), 1.95 (m, 1H), 1.81 (d, 1H, J=7.56 Hz), 1.47 (s, 9H), 1.27-1.63 (m, 12H), 1.09 (s, 3H), 0.93 (s, 3H); $^{13}$C NMR (CDCl$_3$, 125 MHz): δ 196.7, 170.9, 170.7, 159.3, 155.6, 133.2, 117.9, 80.4, 71.0, 70.8, 61.2, 54.5, 52.9, 48.2, 42.1, 31.4, 29.3, 28.7, 27.8, 26.8, 26.6, 26.4, 23.6, 23.4, 19.2, 13.2 ppm; HRMS calcd for C$_{29}$H$_{47}$N$_4$O$_7$ [M+H]$^+$: 563.3445, found 563.3457.

Preparative Example 53

Preparation of

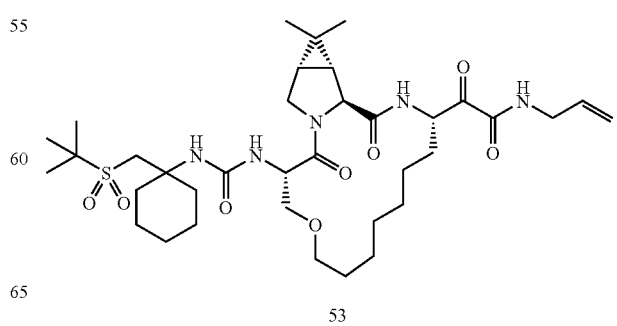

53

Step A

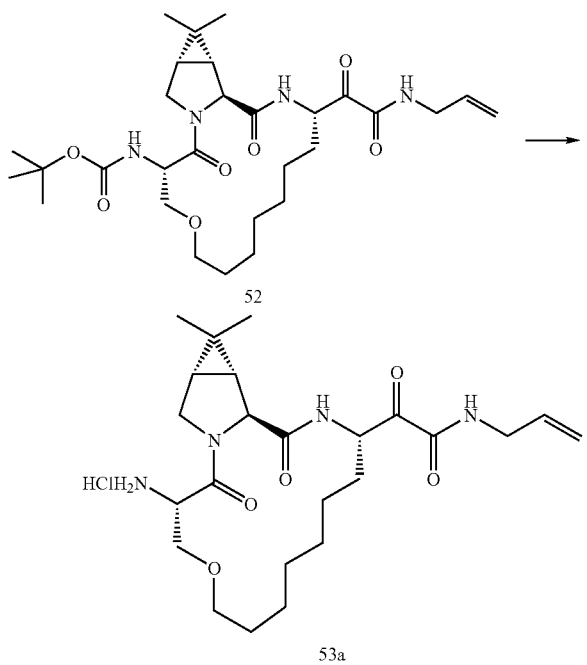

The N-Boc protected amine 52 (60 mg) was dissolved in 10 mL of 4M HCl solution in dioxanes and stirred at room temperature for 1 h. All the volatiles were removed under reduced pressure and the product was placed under high vacuum for 3 h. No further purification was done for the product 53a (99%). The amine salt 53a (31 mg) was dissolved in 5 mL of dry dichloromethane and cooled to 0° C. Then, 10 drops of aqueous saturated sodium bicarbonate solution were added. After 10 min, a solution of the isocyanate 27b (2.5 eq, 0.8 mL of a 0.2M solution in toluene) was added and stirring was continued for 10 min. The cooling bath was removed and the mixture was stirred at room temp for 3 h. The residue was chromatographed on silica gel (gradient: acetone/hexanes; 1:9 to 4:6) to yield the product 53 (25 mg, 58%) as a white solid. $^1$H NMR (500 MHz, CDCl$_3$): δ, 7.90 (d, 1H, J=8.5 Hz), 7.38 (br s, 1H), 5.9 (ddt, 1H, J=5.6, 10.4, 17.0 Hz), 5.61 (ddd, 1H, J=1.6, 8.8, 10.4 Hz), 5.27 (dd, 1H, J=1.26, 17.3 Hz), 5.24 (dd, 1H, J=1.26, 10.0 Hz), 4.9 (dd, 1H, J=3.4, 8.8 Hz), 4.53 (s, 1H), 3.94-4.08 (m, 4H), 3.62 (dd, 1H, J=8.5, 8.8 Hz), 3.56 (m, 1H), 3.47 (dd, 1H, J=4.0, 7.9 Hz), 3.37 (ddd, 1H, J=2.2, 7.2, 9.4), 3.15 (d, 1H, J=13.5 Hz), 2.4 (m, 1H), 2.24 (m, 1H), 1.95 (m, 1H), 1.85 (m, 1H), 1.27-1.70 (m, 20H), 1.4 (s, 9H), 1.2 (m, 1H), 1.07 (s, 3H), 0.94 (s, 3H), 0.92 (m, 1H); $^{13}$C NMR (CDCl$_3$, 125 MHz): δ 198.0, 172.1, 171.0, 159.5, 157.0, 133.3, 117.7, 70.8, 70.5, 61.0, 60.8, 54.9, 53.8, 51.0, 48.4, 42.2, 36.2, 32.0, 30.5, 28.7, 27.9, 27.2, 27.0, 26.8, 25.9, 24.1, 23.9, 23.5, 21.9, 21.8, 19.3, 13.4 ppm; HRMS calcd for C$_{36}$H$_{60}$N$_5$O$_8$S [M+H]$^+$: 722.4163, found 722.4193.

Preparative Example 54

Preparation of

Step B

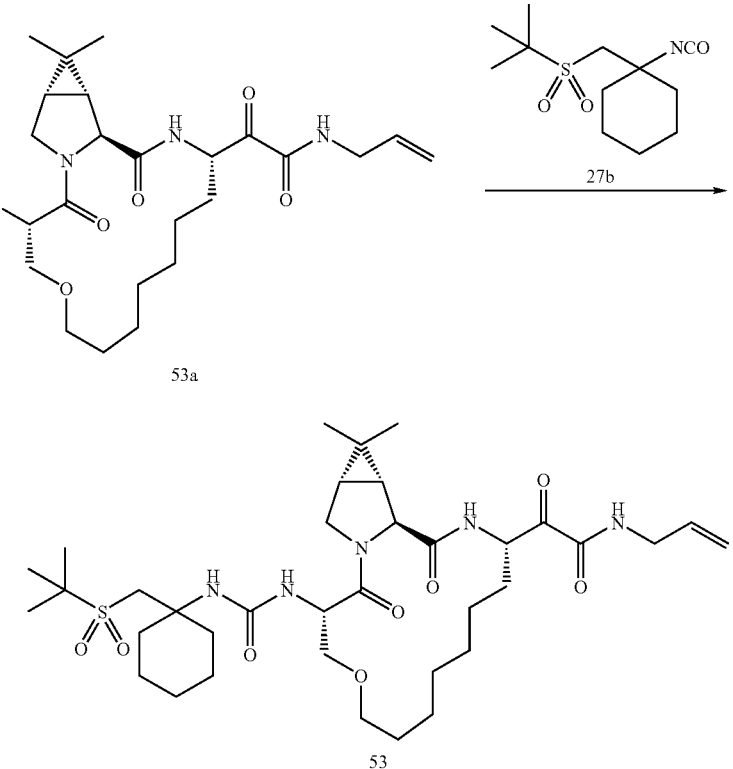

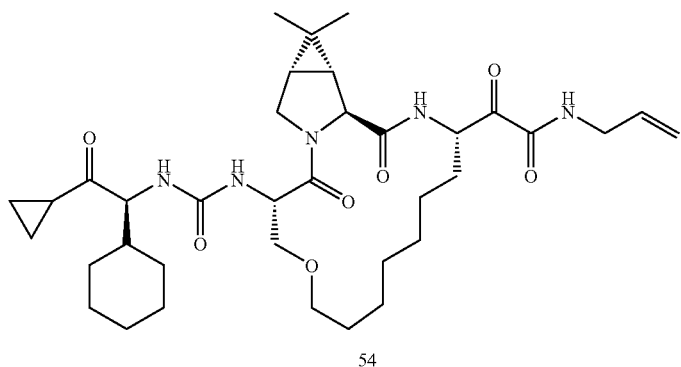

54

Step A

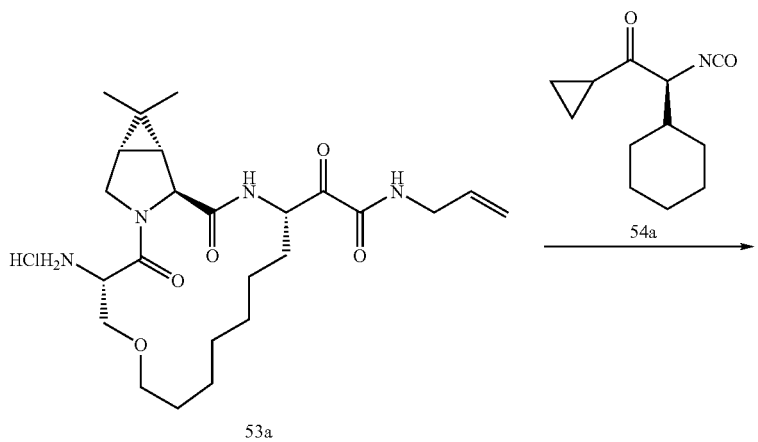

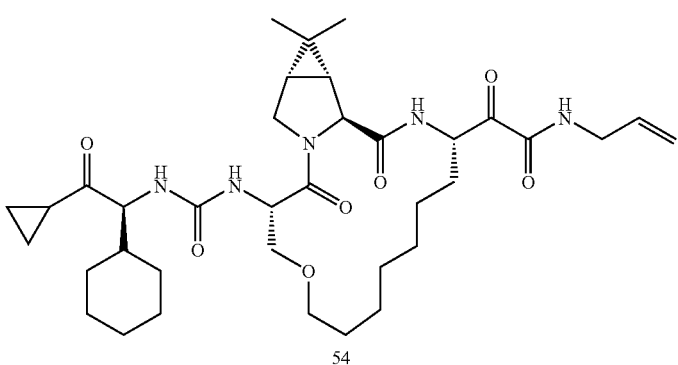

54

A solution of amine salt 53a (17 mg) in 2 mL of dry dichloromethane was treated with solid sodium bicarbonate (3 eq, 8 mg) followed by the addition of isocyanate 54a (2.5 eq, 0.26 mL of a 0.307M solution in toluene). The resulting heterogeneous mixture was stirred at room temperature for approximately 3 h. The mixture was diluted with 50 mL of ethyl acetate and washed with aqueous 1M HCl (10 mL), and brine (10 mL). The organic layer was dried over magnesium sulfate, filtered and concentrated under reduced pressure. The residue was chromatographed on silica gel (gradient: acetone/hexanes; 2:8 to 1:1) to yield the product 54 (8 mg, 34%) as a white solid. $^1$H NMR (500 MHz, CDCl$_3$): δ, 7.91 (br s, 1H), 7.40 (m, 1H), 6.37 (br s, 1H), 5.91 (ddt, 1H, J=5.6, 10.4, 17.3 Hz), 5.88 (br s, 1H), 5.62 (dt, 1H, J=1.26, 9.45 Hz), 5.28 (dd, 1H, J=1.26, 17.3 Hz), 5.23 (dd, 1H, J=1.26, 10.4 Hz), 4.92 (ddd, 1H, J=3.46, 8.5, 8.5 Hz), 4.77 (dd, 1H, J=4.7, 8.8 Hz), 4.55 (s, 1H), 3.94-4.06 (m, 4H), 3.63 (t, 1H, J=8.2 Hz), 3.54 (ddd, 1H, J=3.4, 6.6, 9.7 Hz), 3.47 (m, 1H), 3.38 (m, 1H), 2.09 (ddd, 1H, J=4.4, 7.8, 12.3 Hz), 1.91 (m, 2H), 0.91-1.83 (m, 27H), 1.07 (s, 3H), 0.94 (s, 3H); HRMS calcd for C$_{36}$H$_{56}$N$_5$O$_7$ [M+H]$^+$: 670.4180, found 670.4177.

Preparative Example 55

Preparation of

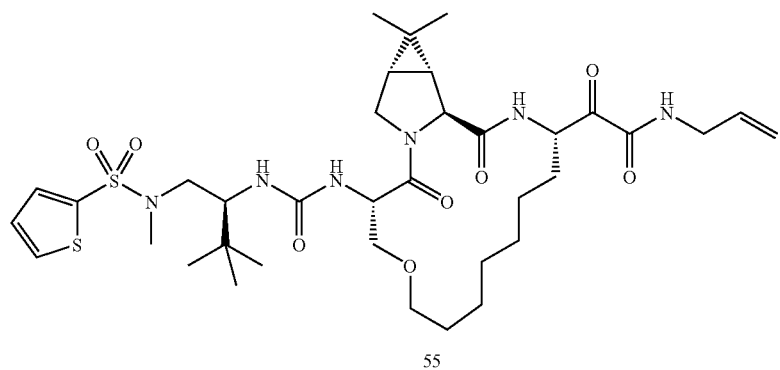

Step A

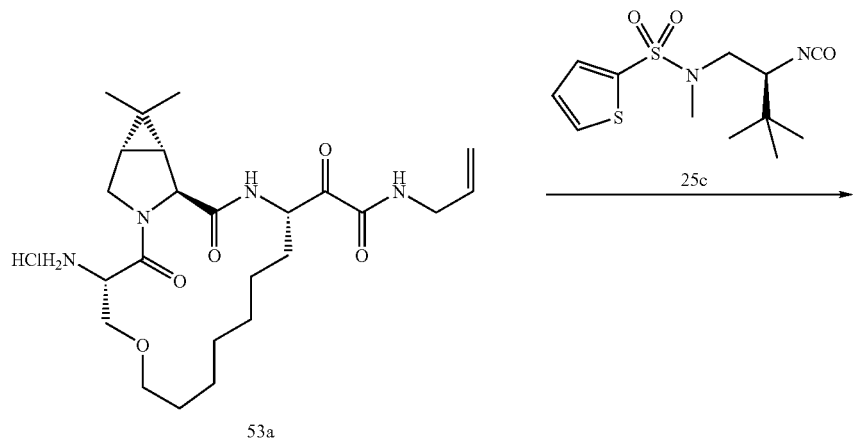

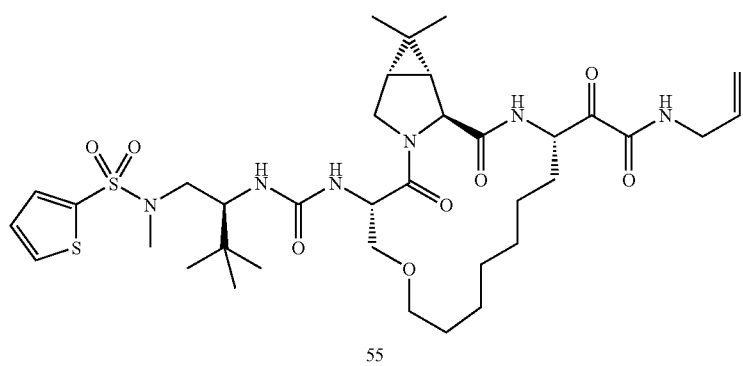

A solution of amine salt 53a (17 mg) in 2 mL of dry dichloromethane was treated with solid sodium bicarbonate (3 eq, 8 mg) followed by the addition of isocyanate 25c (2.5 eq, 0.45 mL of a 0.18M solution in toluene). The resulting heterogeneous mixture was stirred at room temperature for approximately 3 h. The mixture was diluted with 50 mL of ethyl acetate and washed with aq 1M HCl (10 mL), and brine (10 mL). The organic layer was dried over magnesium sulfate, filtered and concentrated under reduced pressure. The residue was chromatographed on silica gel (gradient: acetone/hexanes; 2:8 to 1:1) to yield the product 55 (8 mg, 30%) as a white solid. HRMS calcd for $C_{36}H_{57}N_6O_8S_2$ [M+H]$^+$: 765.3679, found 765.3687.

Preparative Example 56

Preparation of

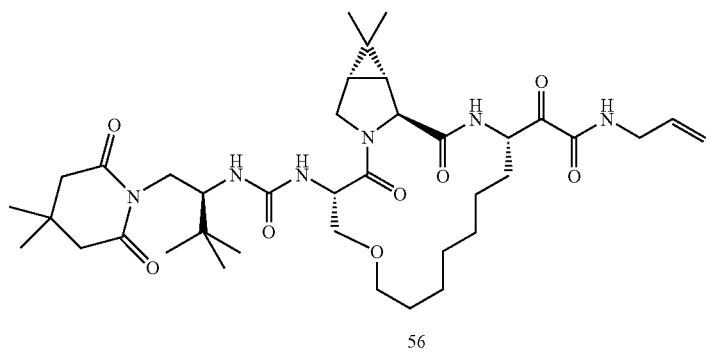
56

Step A

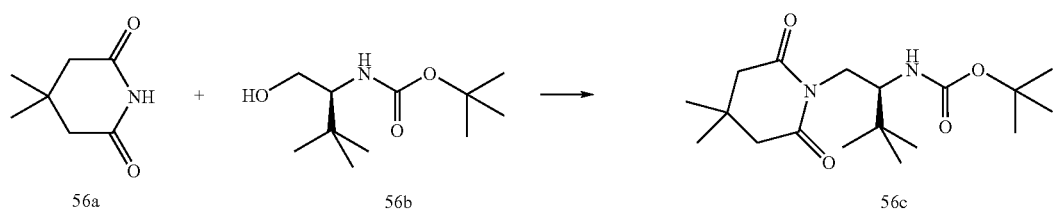

56a    56b    56c

A solution of 4,4-dimethylglutarimide 56a (Aldrich, 1.5 eq, 4.86 g) in 200 mL of dry THF was cooled to 0° C. and treated with triphenylphosphine (3 eq, 18.07 g) and S-Boc-tert-butylglycinol 56b (Aldrich, 5 g).

Diisopropylazodicarboxylate (2.5 eq, 11.3 mL, d 1.027) was added dropwise and the resulting solution was stirred at 0° C. After 10 min, the mixture became a slurry and stirring was continued overnight (0 to 25° C.). The mixture was concentrated under reduced pressure and the residue was dissolved in 80 mL of ether. Hexanes (100 mL) was added and the precipitated solids were filtered off. The filtrate was concentrated to half its volume and hexanes (100 mL) was added again. The solids were filtered off. The filtrate was concentrated under reduced pressure. The residue was chromatographed on silica gel (ethyl acetate/hexanes; 2:8) to afford the product 56c (4.0 g, 51%) as a white solid.

-continued

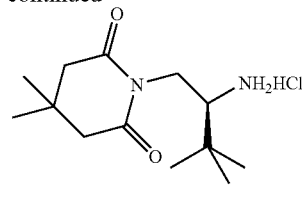

56d

The N-Boc protected amine 56c (4.0 g) was dissolved in 200 mL of 4M HCl solution in dioxanes. The mixture was stirred at room temperature and a white solid precipitated after 10 min. The mixture was further stirred for 2 h. All the volatiles were removed under reduced pressure to afford the product 56d (3.24 g, 98%) as a white solid.

Step C

Step B

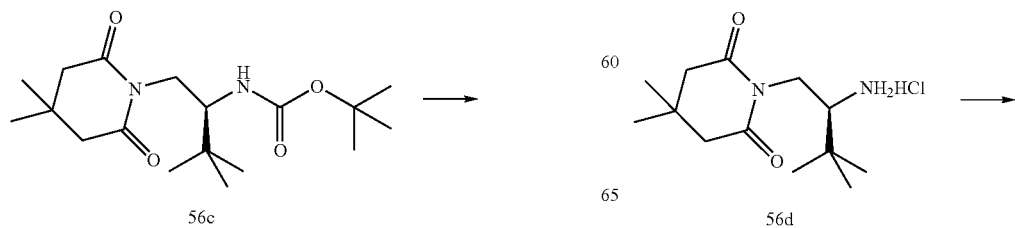

56c    56d

-continued

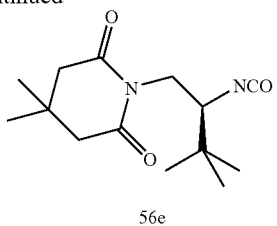

56e

A solution of amine hydrochloride 56d (1.5 g) in 60 mL of dichloromethane was treated with 50 mL of aqueous saturated sodium bicarbonate solution and stirred vigorously for 10 min at 0° C. Stirring was stopped and layers were allowed to separate. Phosgene (15 mL of 20% soln in toluene) was added through a needle to the organic layer (lower layer) in one portion. The mixture was vigorously stirred immediately after addition for 10 min at 0° C. and further stirred at room temp for 2.5 h. The mixture was diluted with 100 mL of dichloromethane and layers were separated. The organic layer was washed with 40 mL of cold aqueous saturated sodium bicarbonate solution and dried over magnesium sulfate. The organic layer was filtered and diluted with 50 mL of toluene. The product 56e (1.44 g, 98%) was kept as a 0.216M solution in toluene.

stirred at room temperature for 30 min. All the volatiles were removed under reduced pressure and the residue was placed under high vacuum for 3 h. The resulting amine salt was dissolved in 5 mL of dry dichloromethane and cooled to 0° C. Then, 10 drops of aqueous saturated sodium bicarbonate solution were added. After 10 min, a solution of the isocyanate 56e was added dropwise (1.2 eq, 1.97 mL of a 0.216M solution in toluene) and stirring was continued for 10 min. The cooling bath was removed and the mixture was stirred at room temp for 2 h. The reaction mixture was diluted with dichloromethane (70 mL) and washed with aqueous saturated sodium bicarbonate solution (20 mL). The organic layer was dried over magnesium sulfate, filtered and concentrated under reduced pressure. The residue was chromatographed on silica gel (gradient: acetone/hexanes; 15:85 to 55:45) to afford the product 56 (172 mg, 66%) as a white solid. $^1$H NMR (400 MHz, CDCl$_3$): δ, 7.95 (d, 1H, J=8.8 Hz), 7.59 (br s, 1H), 5.91 (br s, 1H), 5.84 (ddt, 1H, J=5.8, 10.2, 16.8 Hz), 5.61 (ddd, 1H, J=1.5, 8.7, 10.2 Hz), 5.21 (dd, 1H, J=1.4, 17.5 Hz), 5.17 (dd, 1H, J=1.4, 10.2 Hz), 5.13 (br s, 1H), 4.86 (br s, 1H), 4.52 (s, 1H), 4.05 (d, 1H, J=10.2 Hz), 3.80-3.99 (m, 6H), 3.50 (m, 2H), 3.27 (m, 2H), 2.51 (d, 2H, J=16.8 Hz), 2.43 (d, 2H, J=16.8 Hz), 1.88 (m, 1H), 1.77 (m, 1H), 0.84-1.58 (m, 12H), 1.05 (s, 6H), 0.97 (s, 3H), 0.92 (s, 9H), 0.81 (s, 3H); $^{13}$C NMR (CDCl$_3$, 125 MHz): δ 198.6, 172.8, 172.0, 171.2, Step C

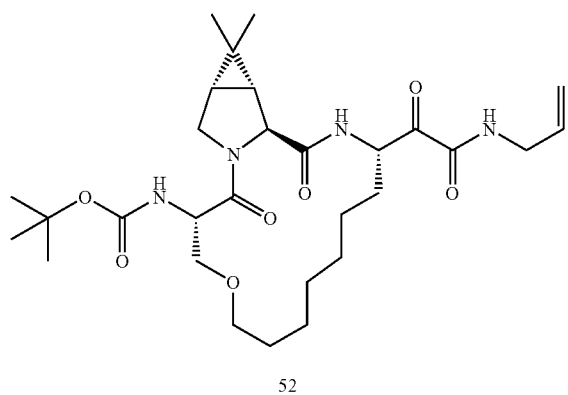

52

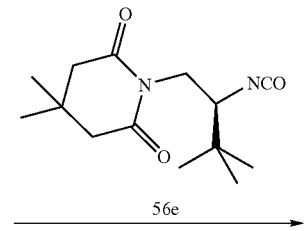

56e

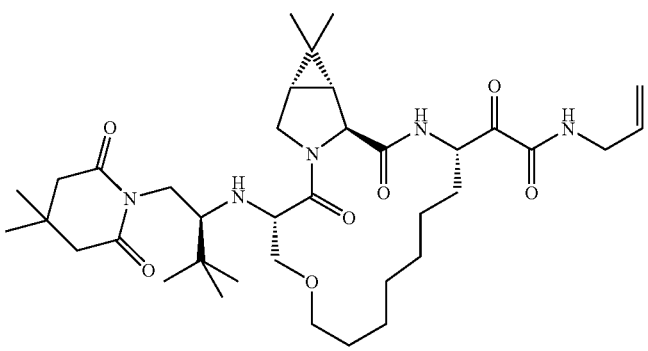

56

The N-Boc amine 52 (200 mg) was dissolved in 20 mL of 4M HCl solution in dioxanes. The resulting solution was 159.3, 157.8, 133.4, 117.7, 71.4, 70.8, 60.7, 57.0, 53.5, 48.5, 46.8, 42.2, 40.0, 34.9, 32.1, 30.9, 29.4, 28.7, 28.1, 27.7, 27.4, 26.9, 24.3, 19.3, 13.5 ppm; HRMS calcd for $C_{38}H_{61}N_6O_8$ [M+H]$^+$: 729.4551, found 729.4529.

Preparative Example 57

Preparation of

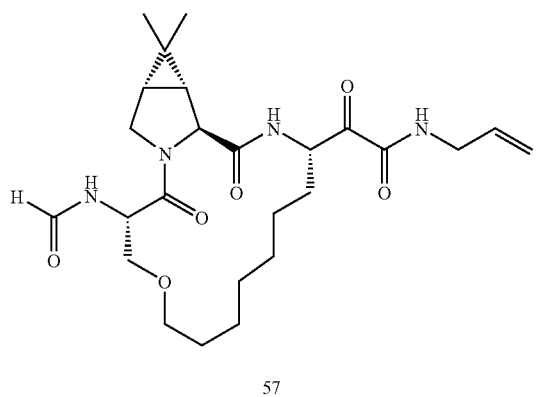

57

Step A

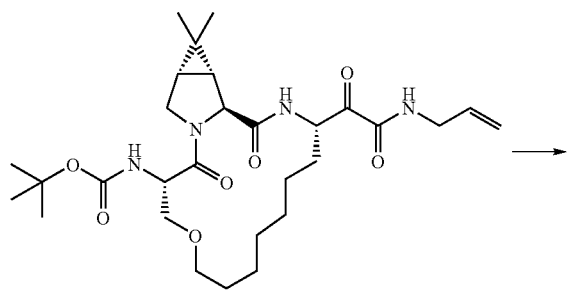

52

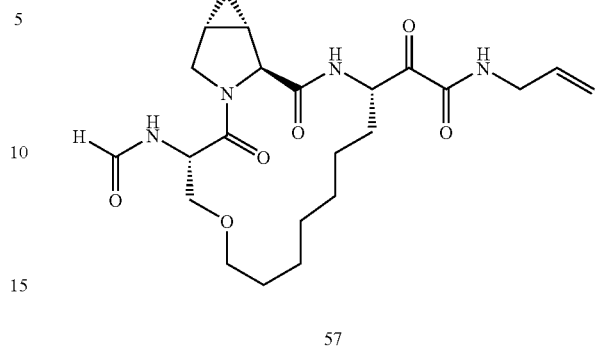

57

The N-Boc protected amine 52 (101 mg) was dissolved in 10 mL of formic acid and stirred at room temperature for 1 h. All the volatiles were removed in rotovap and the residue was chromatographed on silica gel (gradient: acetone/hexanes; 2:8 to 6:4) to give the formylated product 57 (35 mg, 40%) as a white solid. $^1$H NMR (500 MHz, CDCl$_3$) δ, 8.24 (s, 1H), 7.35 (d, 1H, J=7.8 Hz), 7.07 (br s, 1H), 6.83 (d, 1H, J=6.9 Hz), 5.89 (ddt, 1H, J=5.6, 10.0, 17.0 Hz), 5.47 (m, 1H), 5.28 (dd, 1H, J=1.2, 17.3 Hz), 5.25 (dd, 1H, J=1.2, 10.4 Hz), 4.95 (ddd, 1H, J=3.1, 5.9, 8.5 Hz), 4.51 (s, 1H), 3.99 (m, 2H), 3.92 (dd, 1H, J=5.3, 11.0 Hz), 3.75 (d, 1H, J=11.0 Hz), 3.74 (m, 1H), 3.70 (dd, 0.1H, J=5.6, 9.1 Hz), 3.48 (m, 2H), 1.96 (m, 1H), 1.77 (d, 1H, J=7.8 Hz), 1.76 (m, 1H), 1.27-1.63 (m, 11H), 1.10 (s, 3H), 0.92 (s, 3H); $^{13}$C NMR (CDCl$_3$, 125 MHz) δ 196.8, 170.5, 169.4, 160.8, 159.3, 133.1, 117.9, 71.3, 70.0, 61.5, 54.4, 50.8, 48.2, 42.1, 32.0, 31.5, 29.4, 28.6, 27.8, 26.7, 26.6, 23.6, 23.5, 19.3, 14.5, 13.2 ppm; HRMS calcd for $C_{25}H_{39}N_4O_6$ [M+H]$^+$: 491.2870, found 491.2882.

Preparative Example 58

Preparation of

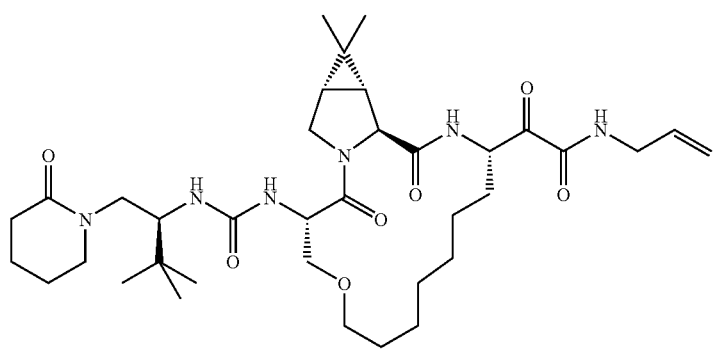

58

Step A

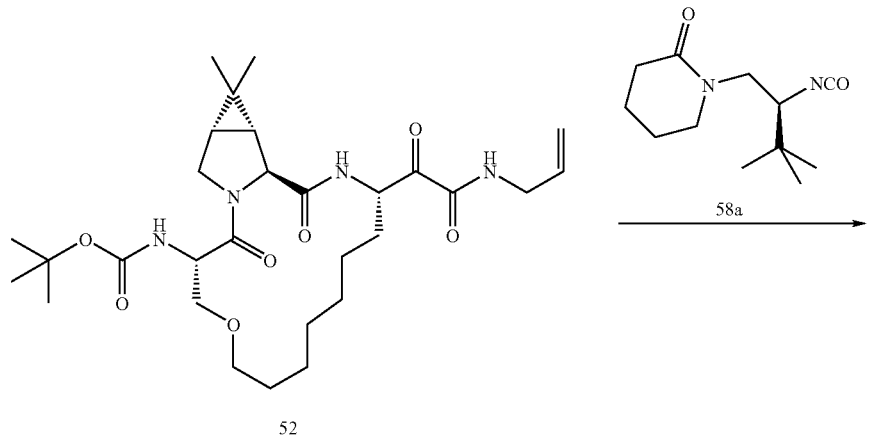

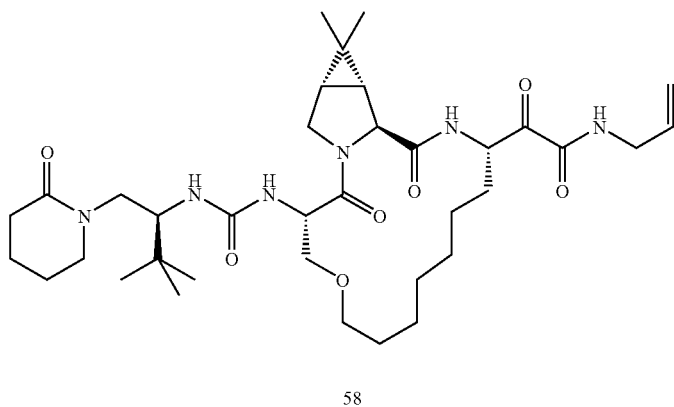

The N-Boc protected amine 52 (80 mg) was dissolved in 5 mL of 4M HCl soln in dioxanes and stirred at room temperature for 45 min. All the volatiles were removed under reduced pressure and the residue was placed under high vacuum for 3 h. The resulting amine salt was dissolved in 3 mL of dry dichloromethane and treated with N-methylmorpholine (3 eq, 0.05 mL, d 0.920). The isocyanate 58a was added in solution (2 eq, 3.8 mL of a 0.075M solution in toluene). The reaction mixture was stirred at room temperature for about 3 h. The mixture was diluted with ethyl acetate (50 mL) and washed with aqueous 1M HCl (10 mL), aqueous saturated sodium bicarbonate (10 mL) and brine (10 mL). The organic layer was dried over magnesium sulfate, filtered and concentrated under reduced pressure. The residue was chromatographed on silica gel (gradient: acetone/hexanes; 3:7 to 7:3) to afford the product 58 (16 mg, 16%) as a white solid. $^1$H NMR (500 MHz, CDCl$_3$) δ, 8.19-8.39 (br s, 1H), 8.05 (d, 1H, J=8.5 Hz), 6.22 (br s, 1H), 5.91 (ddt, 1H, J=5.6, 10.0, 17.0 Hz), 5.71 (dd, 1H, J=9.4, 10.0 Hz), 5.33 (d, 1H, J=9.4 Hz), 5.28 (m, 1H), 5.26 (dd, 1H, J=1.2, 17.0 Hz), 5.20 (dd, 1H, J=1.2, 10.4 Hz), 4.96 (ddd, 1H, J=4.0, 9.4, 9.4 Hz), 4.60 (s, 1H), 4.32 (t, 1H, J=12.6 Hz), 4.12 (d, 1H, J=10.7 Hz), 3.86-4.07 (m, 4H), 3.49-3.63 (m, 3H), 3.38 (dd, 1H, J=4.1, 7.9 Hz), 3.31 (m, 1H), 3.16 (m, 1H), 2.66 (dd, 1H, J=2.8, 13.8 Hz), 2.39 (dt, 1H, J=5.6, 17.3 Hz), 2.27 (dt, 1H, J=6.6, 17.3 Hz), 1.89-2.04 (m, 2H), 1.71-1.87 (m, 4H), 0.88-1.64 (m, 11H), 1.03 (s, 3H), 0.93 (s, 9H), 0.90 (s, 3H); $^{13}$C NMR (CDCl$_3$, 125 MHz) δ 196.2, 171.8, 171.3, 159.5, 158.2, 133.7, 117.3, 71.4, 70.8, 60.6, 55.7, 53.5, 51.0, 48.3, 48.1, 46.5, 42.2, 34.3, 32.7, 31.8, 31.0, 28.7, 27.8, 27.6, 27.0, 26.9, 24.6, 24.4, 23.5, 21.7, 19.2, 13.5 ppm; HRMS calcd for $C_{36}H_{59}N_6O_7$ [M+H]$^+$: 687.4445, found 687.4434.

Preparative Example 59

Preparation of

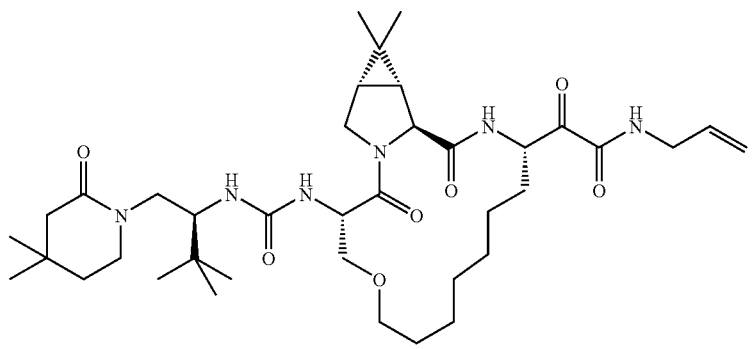

Step A

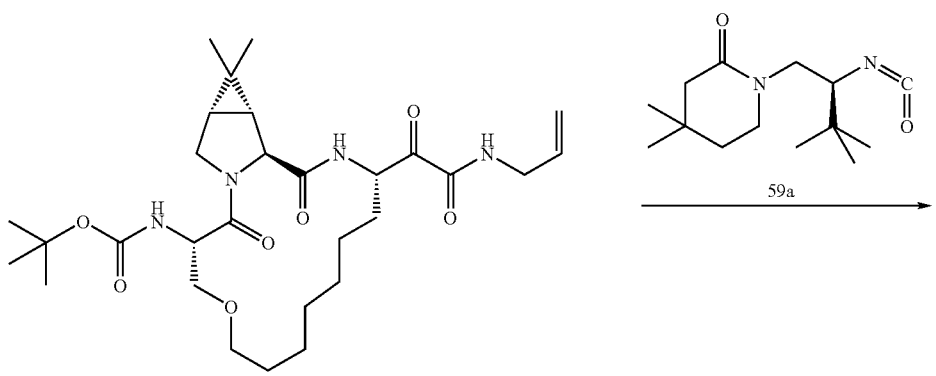

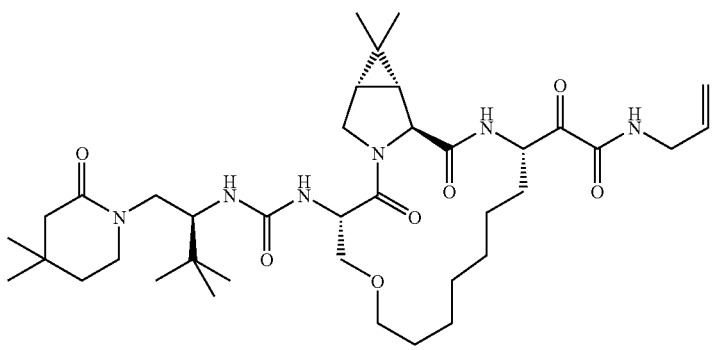

The N-Boc amine 52 (56 mg) was dissolved in 10 mL of 4M HCl solution in dioxanes. The resulting solution was stirred at room temperature for 30 min. All the volatiles were removed under reduced pressure and the residue was placed under high vacuum for 3 h. The resulting amine salt was dissolved in 5 mL of dry dichloromethane and cooled to 0° C. Then, 15 drops of aqueous saturated sodium bicarbonate solution were added. After 10 min, a soln of the isocyanate 59a was added dropwise (1.0 eq) and stirring was continued for 10 min. The cooling bath was removed and the mixture was stirred at room temp for 2 h. The reaction mixture was diluted with ethyl acetate (50 mL) and washed with aqueous 1M HCl (10 mL) and brine (10 mL). The organic layer was dried over magnesium sulfate, filtered and concentrated under reduced pressure. The residue was chromatographed on silica gel (gradient: acetone/hexanes; 2:8 to 6:4) to afford the product 59 (35 mg, 50%) as a white solid. HRMS calcd for $C_{38}H_{63}N_6O_7$ $[M+H]^+$: 715.4758, found 715.4739.

Preparative Example 60

Preparation of

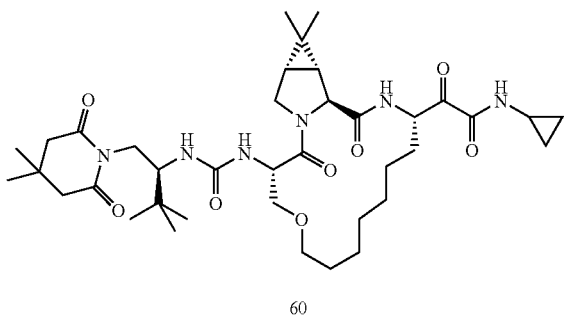

60

Step A

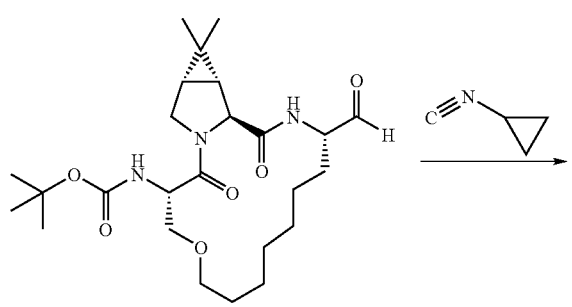

A solution of aldehyde 52j (405 mg) in 15 mL of dry dichloromethane was treated with cyclopropylisocyanide (Oakwood Prod., 2 eq, 117 mg) and acetic acid (2 eq, 0.1 mL, d 1.049). The mixture was stirred at room temperature overnight. All the volatiles were removed under reduced pressure and the residue was chromatographed on silica gel (gradient: acetone/hexanes; 1:9 to 1:1) to afford the product 60a (500 mg, 98%) as a white solid.

Step B

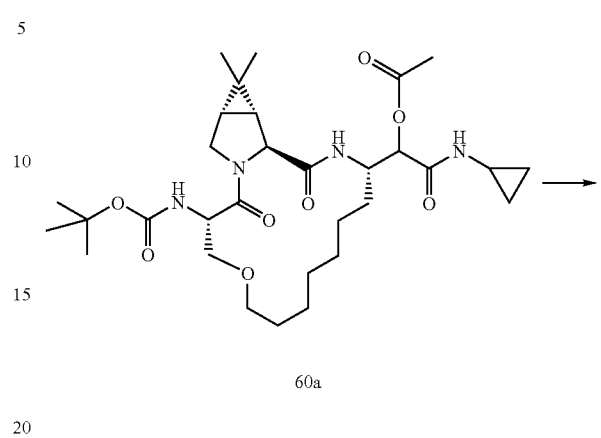

A solution of acetate 60a (500 mg) in 15 mL of a 1:1:1 mixture of THF/MeOH/water was treated with lithium hydroxide monohydrate (2.5 eq, 86 mg) and stirred for approx. 30 min until all the starting material had been consumed as determined by TLC analysis (ethyl acetate/hexanes; 6:4). The reaction mixture was diluted with 30 mL of aqueous saturated sodium bicarbonate solution and extracted with dichloromethane (3×50 mL). The combined organic layers were dried over magnesium sulfate, filtered and concentrated to afford the crude product 60b (464 mg, 98%) as a colorless semi-solid which was used without further purification.

Step C

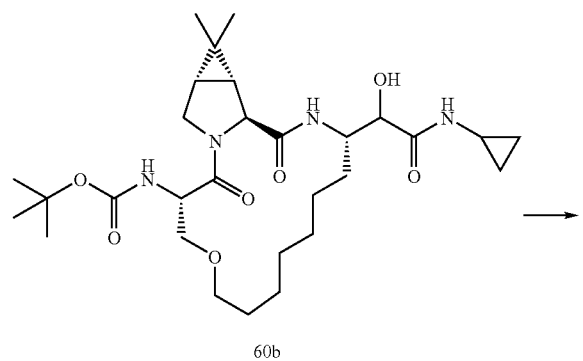

-continued

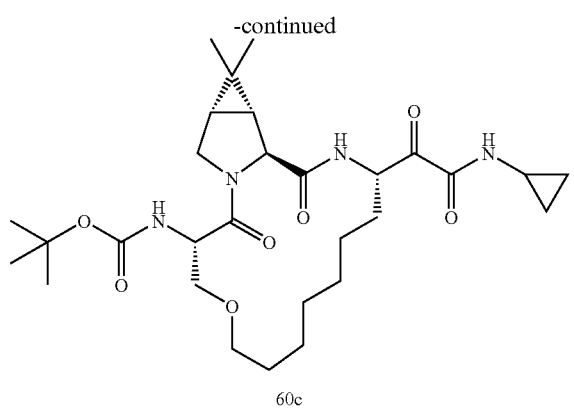
60c

A solution of hydroxyamide 60b (0.824 mmol) in 20 mL of dry dichloromethane was treated with Dess-Martin periodinane (2.0 eq, 698 mg). The reaction mixture was stirred at room temperature for 30 min. The mixture was treated with aqueous 1M sodium thiosulfate solution (15 mL) and stirred for 5 min. Aqueous saturated sodium bicarbonate solution (20 mL) was also added and stirring was continued for further 10 min. The mixture was extracted with dichloromethane (3×50 mL). The combined organic layers were dried over magnesium sulfate, filtered, and concentrated. The residue was chromatographed on silica gel (gradient: acetone/hexanes; 5:95 to 35:65) to afford the product 60c (333 mg, 72%) as white solid.

Step D

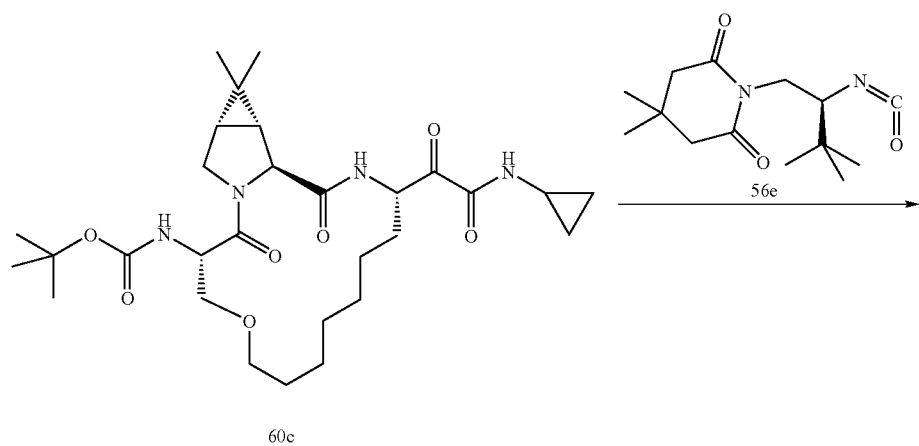
60c            56e

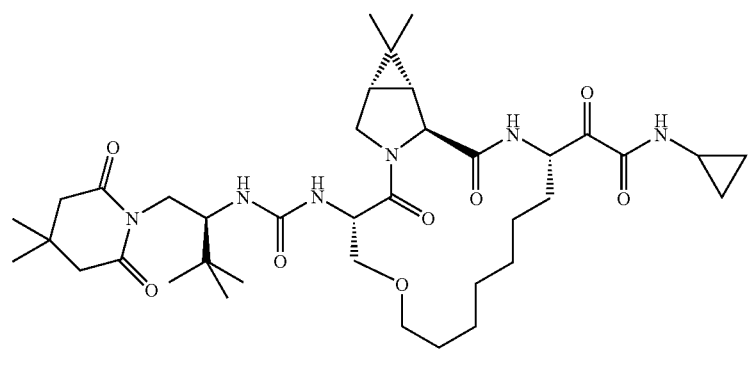
60

The N-Boc amine 60c (70 mg) was dissolved in 10 mL of 4M HCl solution in dioxanes. The resulting solution was stirred at room temperature for 30 min. All the volatiles were removed under reduced pressure and the residue was placed under high vacuum overnight. The resulting amine salt was dissolved in 5 mL of dry dichloromethane and cooled to 0° C. Then, 20 drops of aqueous saturated sodium bicarbonate solution were added followed by a solution of the isocyanate 56e (1.3 eq, 0.7 mL of a 0.241M solution in toluene) and stirring was continued for 10 min. The cooling bath was removed and the mixture was stirred at room temp for 2 h. The reaction mixture was diluted with dichloromethane (50 mL) and washed with aqueous saturated sodium bicarbonate solution (10 mL). The organic layer was dried over magnesium sulfate, filtered and concentrated under reduced pressure. The residue was chromatographed on silica gel (gradient: acetone/hexanes; 2:8 to 55:45) to afford the product 60 (70 mg, 77%) as a white solid. $^1$H NMR (500 MHz, CDCl$_3$): δ 7.95 (br s, 1H), 7.56 (br s, 1H), 5.86 (br s, 1H), 5.65 (t, 1H, J=8.8 Hz), 5.09 (br s, 1H), 4.91 (br s, 1H), 4.56 (s, 1H), 4.07 (d, 1H, J=10.4 Hz), 3.98 (dd, 1H, J=5.0, 10.7 Hz), 3.91 (m, 3H), 3.54 (m, 2H), 3.34 (m, 2H), 2.88 (ddd, 1H, J=3.7, 7.5, 15.1 Hz), 2.56 (d, 2H, J=16.7 Hz), 2.50 (d, 2H, J=16.7 Hz), 1.94 (m, 1H), 0.87-1.76 (m, 15H), 1.11 (s, 6H), 1.03 (s, 3H), 0.97 (s, 9H), 0.86 (s, 3H), 0.70 (m, 2H); $^{13}$C NMR (CDCl$_3$, 125 MHz) δ 198.0, 172.9, 172.0, 171.2, 160.8, 157.7, 71.5, 70.8, 60.7, 56.9, 53.4, 51.1, 48.4, 46.8, 39.9, 34.9, 32.1, 30.8, 29.4, 28.7, 28.1, 27.7, 27.5, 26.9, 26.8, 24.4, 23.0, 19.2, 13.5, 6.8, 6.7 ppm. HRMS calcd for C$_{38}$H$_{61}$N$_6$O$_8$ [M+H]$^+$: 729.4551, found 729.4558.

Preparative Example 61

Preparation of

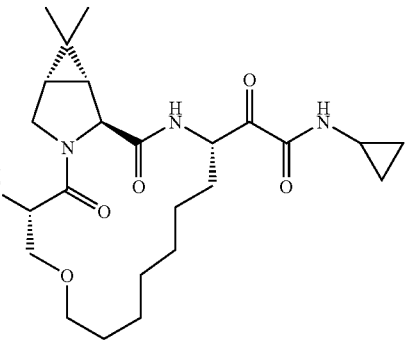

61

Step A

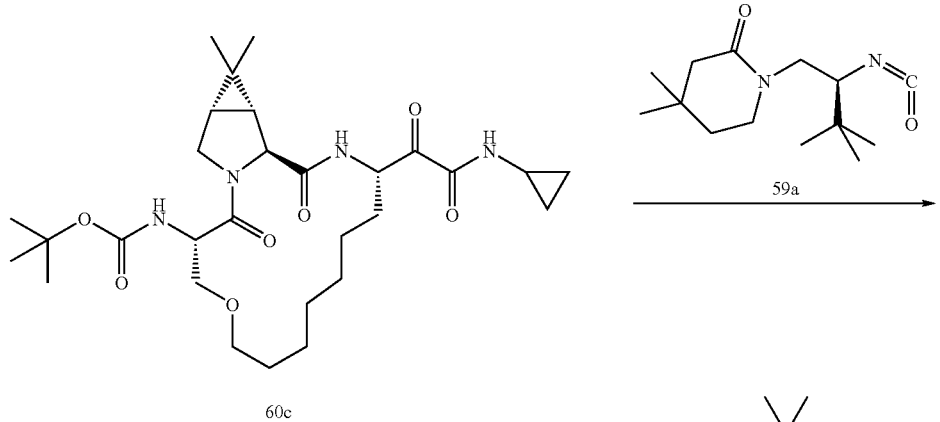

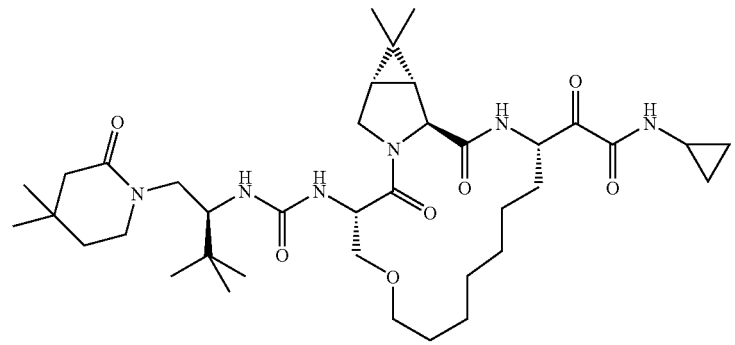

61

The N-Boc amine 60c (56 mg) was dissolved in 10 mL of 4M HCl solution in dioxanes. The resulting solution was stirred at room temperature for 30 min. All the volatiles were removed under reduced pressure and the residue was placed under high vacuum for 3 h. The resulting amine salt was dissolved in 5 mL of dry dichloromethane and cooled to 0° C. Then, 20 drops of aqueous saturated sodium bicarbonate solution were added followed by a soln of the isocyanate 59a in toluene (1.3 eq) and stirring was continued for 10 min. The cooling bath was removed and the mixture was stirred at room temp for 2 h. The reaction mixture was diluted with dichloromethane (60 mL) and washed with aqueous saturated sodium bicarbonate solution (20 mL). The organic layer was dried over magnesium sulfate, filtered and concentrated under reduced pressure. The residue was chromatographed on silica gel (gradient: acetone/hexanes; 2:8 to 6:4) to afford the product 61 (52 mg, 73%) as a white solid. $^1$H NMR (500 MHz, CDCl$_3$): δ 8.30-8.53 (br s, 1H), 8.15 (d, 1H, J=8.8 Hz), 6.13 (br s, 1H), 5.74 (dd, 1H, J=8.8, 9.7 Hz), 5.38 (d, 1H, J=9.1 Hz), 4.96 (br s, 1H), 4.59 (s, 1H), 4.35 (dd, 1H, J=12.9, 12.9 Hz), 4.10 (d, 1H, J=10.4 Hz), 4.01 (dd, 1H, J=5.0, 10.4 Hz), 3.94 (m, 1H), 3.56 (m, 2H), 3.50 (dd, 1H, J=8.5, 8.8 Hz), 3.31 (m, 2H), 3.17 (ddd, 1H, J=5.6, 6.0, 12.3 Hz), 2.91 (ddd, 1H, J=4.0, 7.8, 15.4 Hz), 2.67 (dd, 1H, J=3.4, 13.5 Hz), 2.17 (d, 1H, J=17.0 Hz), 2.10 (d, 1H, J=17.0 Hz), 1.94 (m, 3H), 1.24-1.70 (m, 12H), 1.14 (m, 1H), 1.04 (s, 3H), 1.02 (s, 3H), 1.00 (s, 3H), 0.91 (s, 9H), 0.89 (s, 3H), 0.84 (m, 2H), 0.73 (m, 2H); $^{13}$C NMR (CDCl$_3$, 125 MHz) δ 199.9, 171.9, 171.3, 171.0, 160.9, 158.0, 71.4, 70.9, 60.4, 55.4, 53.2, 48.2, 46.3, 45.0, 35.8, 34.6, 31.7, 30.3, 28.8, 28.7, 27.8, 27.7, 27.6, 27.1, 26.9, 26.8, 24.8, 24.7, 23.2, 19.1, 13.4, 6.4 ppm. HRMS calcd for C$_{38}$H$_{63}$N$_6$O$_7$ [M+H]$^+$: 715.4758, found 715.4768.

Preparative Example 62

Preparation of

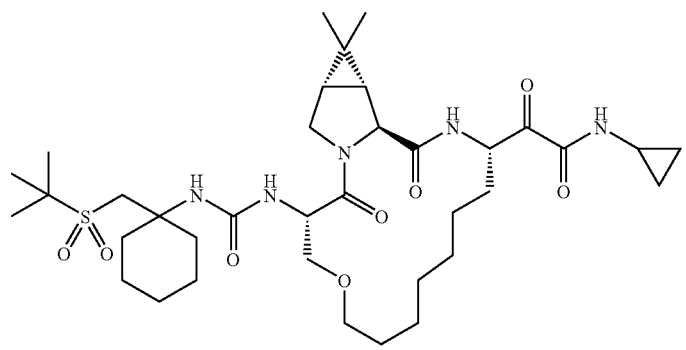

62

Step A

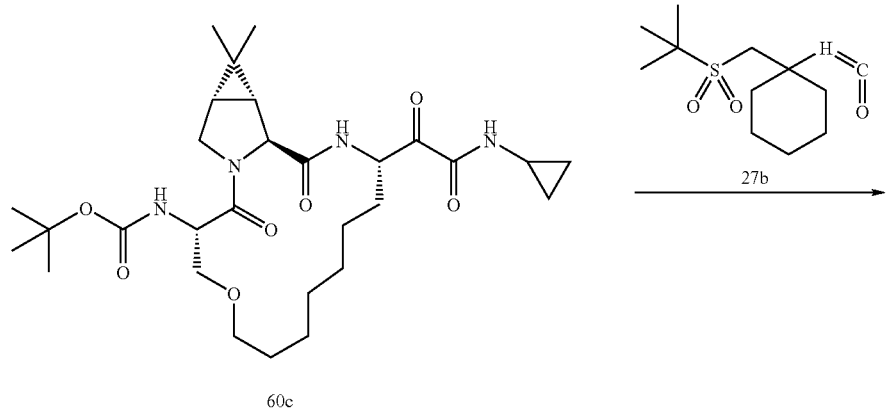

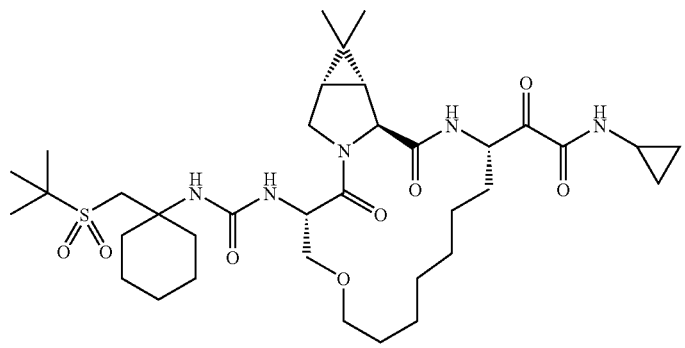

62

The N-Boc amine 60c (60 mg) was dissolved in 10 mL of 4M HCl solution in dioxanes. The resulting solution was stirred at room temperature for 30 min. All the volatiles were removed under reduced pressure and the residue was placed under high vacuum for 3 h. The resulting amine salt was dissolved in 5 mL of dry dichloromethane and cooled to 0° C. Then, 20 drops of aqueous saturated sodium bicarbonate solution were added followed by a soln of the isocyanate 27b in toluene (1.2 eq) and stirring was continued for 10 min. The cooling bath was removed and the mixture was stirred at room temp for 2 h. The reaction mixture was diluted with dichloromethane (60 mL) and washed with aqueous saturated sodium bicarbonate solution (20 mL). The organic layer was dried over magnesium sulfate, filtered and concentrated under reduced pressure. The residue was chromatographed on silica gel (gradient: acetone/hexanes; 2:8 to 6:4) to afford the product 62 (65 mg, 85%) as a white solid. $^1$H NMR (500 MHz, CDCl$_3$): δ7.84 (d, 1H, J=8.2 Hz), 7.28 (br s, 1H), 5.73-6.02 (br s, 1H), 5.57 (ddd, 1H, J=1.9, 8.2, 8.5 Hz), 5.22 (br s, 1H), 4.88 (dd, 1H, J=3.4, 8.5 Hz), 4.51 (s, 1H), 4.01 (m, 3H), 3.62 (dd, 1H, J=8.5, 8.5 Hz), 3.55 (ddd, 1H, J=3.7, 6.3, 9.7 Hz), 3.48 (dd, 1H, J=4.0, 8.1 Hz), 3.38 (m, 1H), 3.18 (d, 1H, J=13.5 Hz), 2.86 (ddd, 1H, J=3.8, 7.2, 14.8 Hz), 2.41 (d, 1H, J=11.6 Hz), 2.24 (d, 1H, J=11.6 Hz), 1.93 (m, 1H), 1.72-1.89 (m, 4H), 1.40 (s, 9H), 1.28-1.70 (m, 16H), 1.21 (m, 1H), 1.06 (s, 3H), 0.93 (s, 3H), 0.91 (m, 2H), 0.70 (m, 2H); $^{13}$C NMR (CDCl$_3$, 125 MHz) δ 197.9, 172.0, 171.0, 160.9, 157.0, 70.8, 70.6, 61.0, 60.8, 54.9, 53.7, 51.1, 48.4, 36.2, 32.0, 30.5, 28.7, 27.9, 27.2, 26.9, 26.8, 25.9, 24.1, 23.8, 23.5, 23.0, 21.9, 21.8, 19.3, 13.4, 6.9, 6.8 ppm.

Preparative Example 63

Preparation of

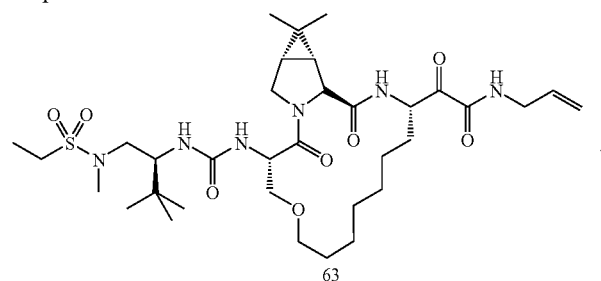

Step A

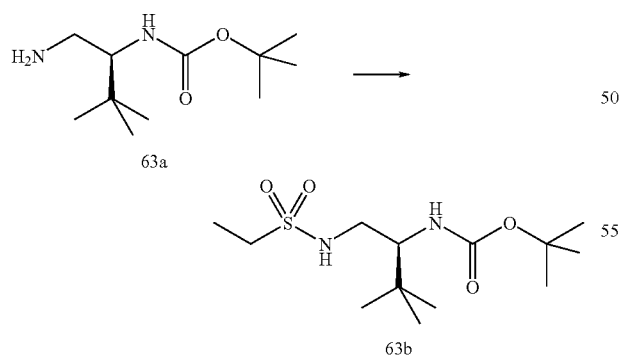

A solution of amine 63a (2.0 g) in 100 mL of dry dichloromethane was cooled to 0° C. and treated with pyridine (3.0 eq, 2.24 mL, d 0.978) and ethanesulfonyl chloride (1.2 eq, 1.05 mL, d 1.357). The resulting yellow homogeneous solution was stirred overnight (temp 0 to 25° C.). The mixture was diluted with 200 mL of ether and washed with aqueous 1M HCl (100 mL) and brine (100 mL). The organic layer was dried over magnesium sulfate, filtered and concentrated. The residue was chromatographed on silica gel (gradient: dichloromethane to ethyl acetate/dichloromethane 3:7) to afford the product 63b (850 mg, 30%) as a white solid.

Step B

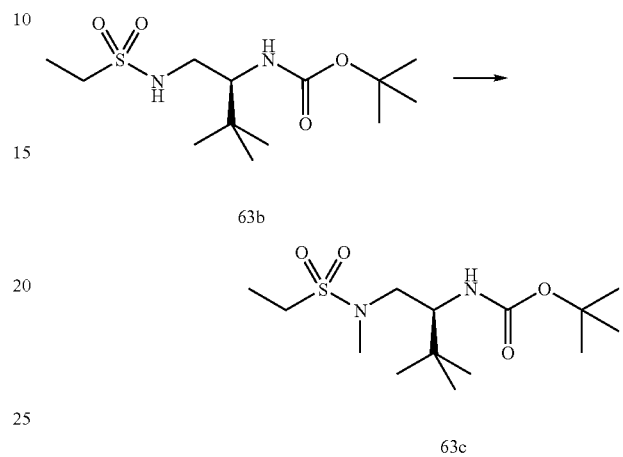

A solution of ethylsulfonamide 63b (850 mg) in dry DMF (30 mL) was treated with cesium carbonate (3.0 eq, 2.74 g) and iodomethane (3.0 eq, 0.51 mL, d 2.280). The reaction mixture was stirred for approximately 4 h. TLC analysis (acetone/hexanes; 2:8) showed that all the starting material had been consumed. The mixture was diluted with ethyl acetate (300 mL) and washed with water (3×50 mL) and brine (1×50 mL). The organic layer was dried over magnesium sulfate, filtered, and concentrated under reduced pressure to afford the product 63c (860 mg, 97%) as a white solid. No further purification was carried out for the product.

Step C

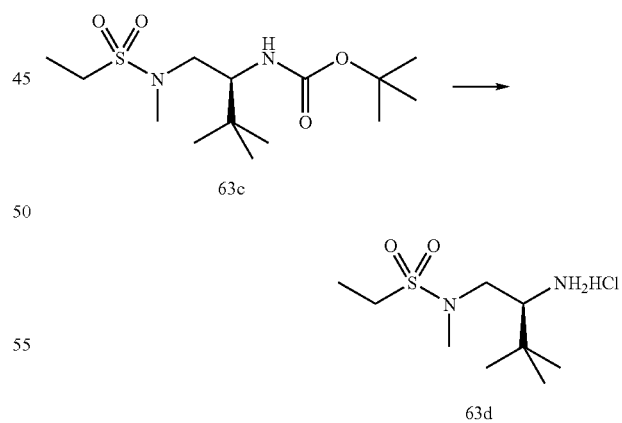

The N-Boc protected amine 63c (850 mg) was dissolved in 100 mL of 4M HCl solution in dioxanes. The resulting solution was stirred at room temperature until all the starting material had been consumed as determined by TLC (acetone/hexanes; 2:8). All the volatiles were removed under reduced pressure and the residue was placed under high vacuum to afford the product 63d (680 mg, 98%).

Step D

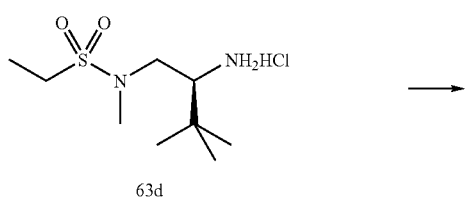

in one portion. The mixture was vigorously stirred immediately after addition for 10 min at 0° C. and further stirred at room temp for 2.5 h. The mixture was diluted with 100 mL of dichloromethane and layers were separated. The organic layer was washed with 30 mL of cold aqueous saturated sodium bicarbonate solution and dried over magnesium sulfate. The organic layer was filtered and the filtrate was diluted with 50 mL of toluene. The product 63e (654 mg, 98%) was concentrated and kept as a 0.131M solution in toluene (the solution contains about 2 mL of dichloromethane).

Step E

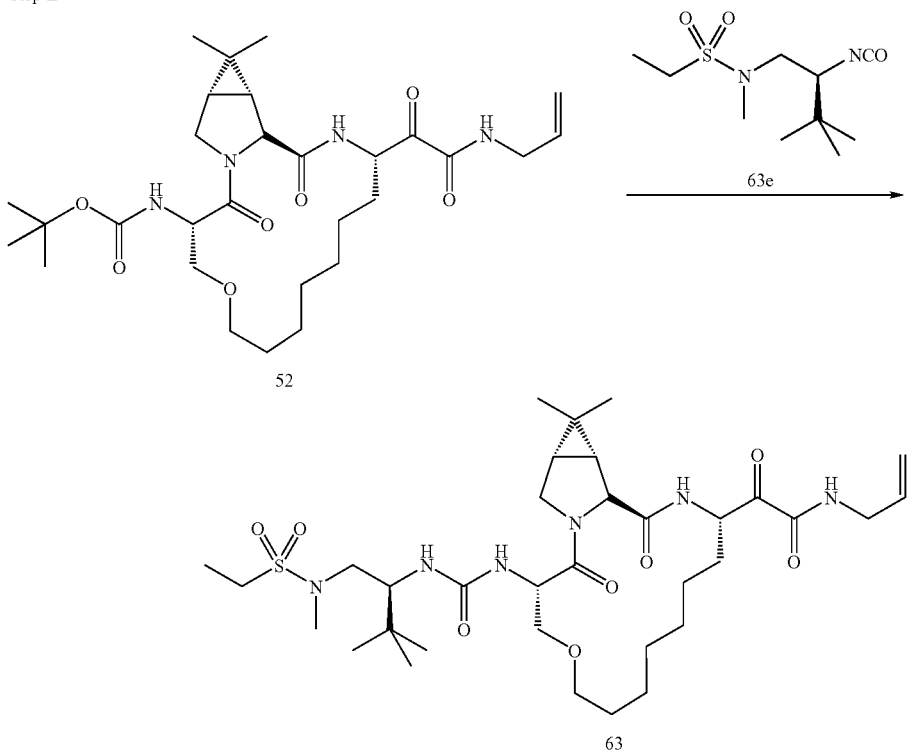

-continued

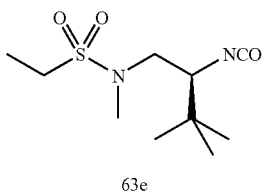

63e

A solution of amine hydrochloride 63d (2.636 mmol) in 40 mL of dichloromethane was treated with 40 mL of aqueous saturated sodium bicarbonate solution and stirred vigorously for 10 min at 0° C. Stirring was stopped and layers were allowed to separate. Phosgene (10 mL of 20% soln in toluene) was added through a needle to the organic layer (lower layer)

The N-Boc amine 52 (60 mg) was dissolved in 10 mL of 4M HCl solution in dioxanes. The resulting solution was stirred at room temperature for 30 ml. All the volatiles were removed under reduced pressure and the residue was placed under high vacuum for 3 h. The resulting amine salt was dissolved in 5 mL of dry dichloromethane and cooled to 0° C. Then, 10 drops of aqueous saturated sodium bicarbonate solution were added. After 10 min. a soln of the isocyanate 63e was added dropwise (1.2 eq, 0.97 mL of a 0.131M solution in toluene) and stirring was continued for 10 ml. The cooling bath was removed and the mixture was stirred at room temp for 2 h. The reaction mixture was diluted with dichloromethane (70 mL) and washed with aqueous saturated sodium bicarbonate solution (20 mL). The organic layer was dried over magnesium sulfate, filtered and concentrated under reduced pressure. The residue was chromatographed on silica gel (gradient: acetone/hexanes; 2:8 to 6:4) to afford the product 63 (49 mg, 65%) as a white solid. $^1$H NMR (500 MHz, CDCl$_3$): δ 8.04 (d, 1H, J=8.5 Hz), 7.52 (br s, 1H), 6.04

(br s, 1H), 5.89 (ddt, 1H, J=5.6, 10.4, 17.0 Hz), 5.65 (dd, 1H, J=8.8, 10.4 Hz), 5.26 (dd, 1H, J=1.2, 17.0 Hz), 5.22 (dd, 1H, J=1.2, 10.0 Hz), 5.17 (d, 1H, J=10.0 Hz), 4.99 (br s, 1H), 4.61 (s, 1H), 4.19 (d, 1H, J=10.7 Hz), 4.02 (m, 2H), 3.95 (m, 2H), 3.60 (dd, 1H, J=8.1, 9.1 Hz), 3.54 (m, 1H), 3.49 (d, 1H, 1.9 Hz), 3.44 (m, 1H), 3.32 (m, 1H), 3.07 (m, 3H), 2.94 (s, 3H), 1.93 (m, 1H), 1.35 (t, 3H, J=7.5 Hz), 1.27-1.62 (m, 15H), 1.16 (m, 1H), 1.03 (s, 3H), 0.92 (s, 9H), 0.91 (s, 3H); $^{13}$C NMR (CDCl$_3$, 125 MHz) δ, 198.6, 172.3, 171.3, 159.4, 158.0, 133.4, 117.6, 71.1, 70.6, 60.7, 54.7, 53.5, 51.0, 50.6, 48.4, 45.8, 42.2, 34.8, 34.5, 32.0, 30.9, 28.7, 27.8, 27.3, 27.0, 26.9, 24.3, 24.2, 19.2, 13.5, 8.6 ppm; HRMS calcd for C$_{34}$H$_{59}$N$_6$O$_8$S [M+H]$^+$: 711.4115, found 711.4133.

Preparative Example 64

Preparation of

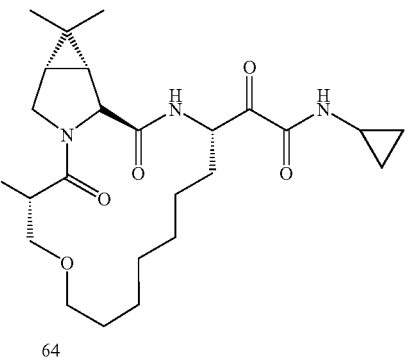

Step A

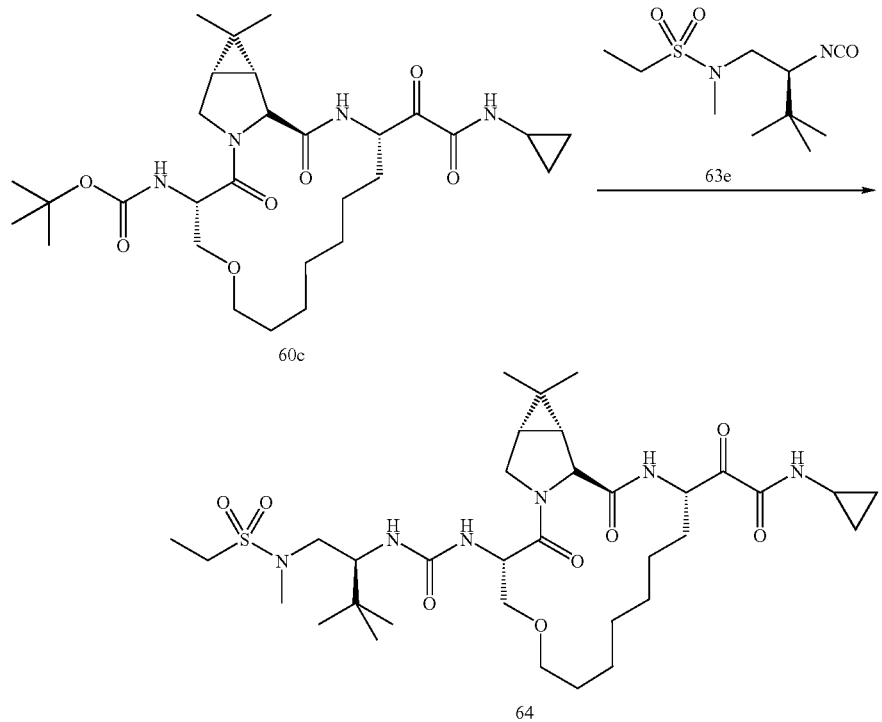

The N-Boc amine 60c (60 mg) was dissolved in 10 mL of 4M HCl solution in dioxanes. The resulting solution was stirred at room temperature for 30 min. All the volatiles were removed under reduced pressure and the residue was placed under high vacuum for 3 h. The resulting amine salt was dissolved in 5 mL of dry dichloromethane and cooled to 0° C. Then, 10 drops of aqueous saturated sodium bicarbonate solution were added. After 10 min, a soln of the isocyanate 63e was added dropwise (1.2 eq, 0.97 mL of a 0.131M solution in toluene) and stirring was continued for 10 min. The cooling bath was removed and the mixture was stirred at room temp for 2 h. The reaction mixture was diluted with dichloromethane (70 mL) and washed with aqueous saturated sodium bicarbonate solution (20 mL). The organic layer was dried over magnesium sulfate, filtered and concentrated under reduced pressure. The residue was chromatographed on silica gel (gradient: acetone/hexanes; 2:8 to 6:4) to afford the product 64 (62 mg, 82%) as a white solid. $^1$H NMR (500 MHz, CDCl$_3$): δ 8.10 (br s, 1H), 7.47 (br s, 1H), 5.94-6.19 (br s, 1H), 5.65 (dd, 1H, J=8.8, 10.7 Hz), 5.21 (d, 1H, J=7.8 Hz), 5.00 (dd, 1H, J=3.7, 9.4 Hz), 4.59 (s, 1H), 4.21 (d, 1H, J=10.7

Hz), 4.02 (dd, 1H, J=5.0, 10.7 Hz), 3.93 (dd, 1H, J=9.1, 9.7 Hz), 3.55 (m, 2H), 3.48 (d, 1H, J=12.6 Hz), 3.40 (m, 1H), 3.29 (m, 1H), 3.07 (q, 2H, J=7.2 Hz), 3.06 (m, 1H), 2.93 (s, 3H), 2.85 (dddd, 1H, J=1.8, 4.0, 7.5, 15.1 Hz), 1.91 (m, 1H), 1.34 (t, 3H, J=7.2 Hz), 1.25-1.61 (m, 12H), 1.13 (m, 1H), 1.01 (s, 3H), 0.90 (s, 9H), 0.89 (s, 3H), 0.87 (m, 2H), 0.69 (m, 2H); $^{13}$C NMR (CDCl$_3$, 125 MHz) δ 198.9, 172.3, 171.4, 160.9, 158.0, 71.0, 70.6, 60.6, 53.2, 50.9, 50.6, 48.4, 45.9, 34.8, 34.5, 32.1, 31.1, 28.7, 27.8, 27.5, 27.0, 26.9, 24.4, 23.0, 19.2, 13.6, 8.6, 6.7 ppm; HRMS calcd for $C_{34}H_{59}N_6O_8S$ [M+1]$^+$: 711.4115, found 711.4133.

Preparative Example 65

Preparation of

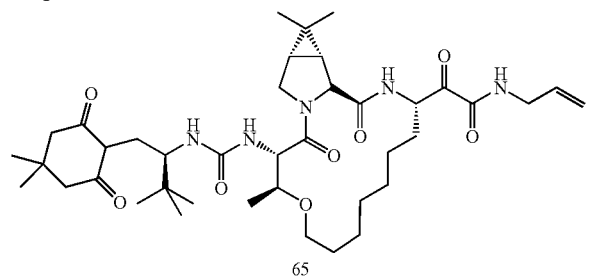

Step A

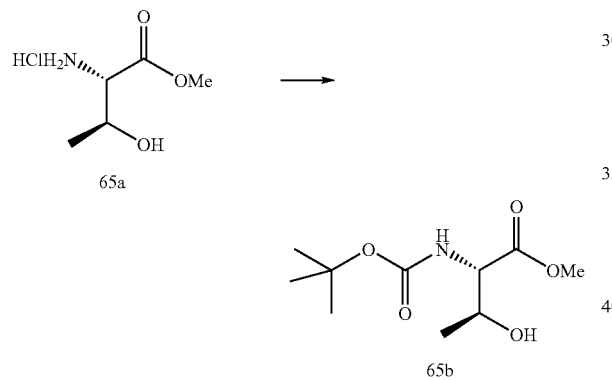

A solution of (S)-allo-threonine-OMe hydrochloride 65a (Chem-Impex, 5 g) in dry dichloromethane (150 mL) was cooled to 0° C. and treated with di-tert-butyldicarbonate (1.1 eq, 7.0 g) in 50 mL of dry dichloromethane. N-methylmorpholine (2.5 eq, 8.1 mL, d 0.920) was added dropwise and the mixture was stirred for 30 min. The cooling bath was removed and the mixture was stirred for further 3 h. The mixture was concentrated to one third of its volume and then diluted with ethyl acetate (300 mL) and washed with aqueous 1M HCl (100 mL), aqueous saturated sodium bicarbonate (80 mL) and brine (80 mL). The organic layer was dried over magnesium sulfate, filtered and concentrated under reduced pressure to afford the product 65b (6.78 g, 98%) as a colorless oil.

Step B

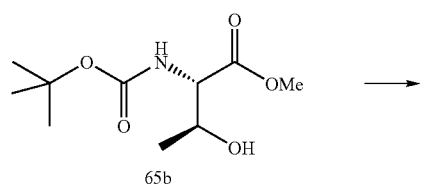

-continued

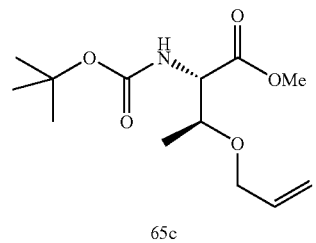

A solution of Boc-L-allo-Thr-OMe 65b (6.8 g) in 250 mL of dry THF was degassed (vacuum/N2-flush) and treated with allylmethyl carbonate (1.3 eq, 4.3 mL, d 1.022). A catalytic amount of tetrakis(triphenylphosphine)palladium (0.02 mol %, 673 mg) was added. The slightly yellow mixture was degassed again and heated at 60° C. for about 3 h until TLC analysis (acetone/hexanes; 2:8) showed no more starting material left (reaction mixture became brown). The mixture was concentrated under reduced pressure and the residue was chromatographed on silica gel (ethyl acetate/hexanes; 1:9) to afford the product 65c (5.72 g, 72%) as a colorless oil.

Step C

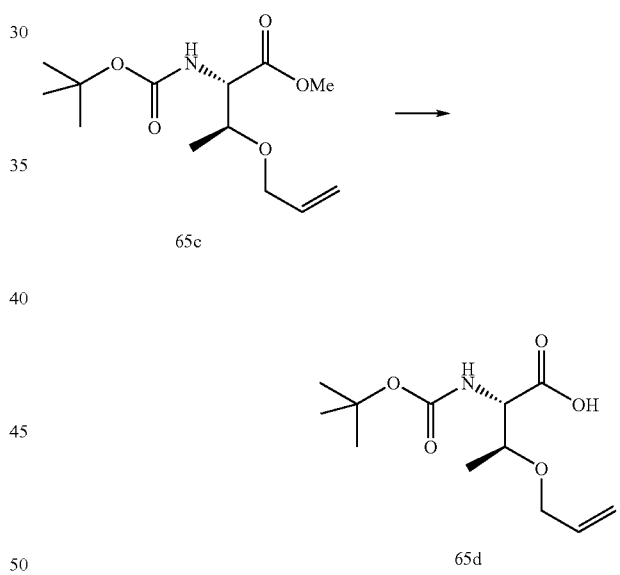

A solution of methyl ester 65c (1.45 g) in 250 mL of a 4:2:1 mixture of THF/water/MeOH was cooled to 0° C. and treated with lithium hydroxide monohydrate (2.5 eq, 2.19 mg). The cooling bath was removed after 30 min and the mixture was stirred at room temp for further 4 h until all the starting material had been consumed as determined by TLC analysis (acetone/hexanes; 15:85). The reaction mixture was treated with 200 mL of aqueous 1M HCl (pH of mixture=1) and the product was taken into dichloromethane (4×100 mL). The combined organic extracts were dried over magnesium sulfate, filtered and concentrated under reduced pressure to afford the product. No further purification was carried out for the product 65d (5.42 g, 98%).

Step D

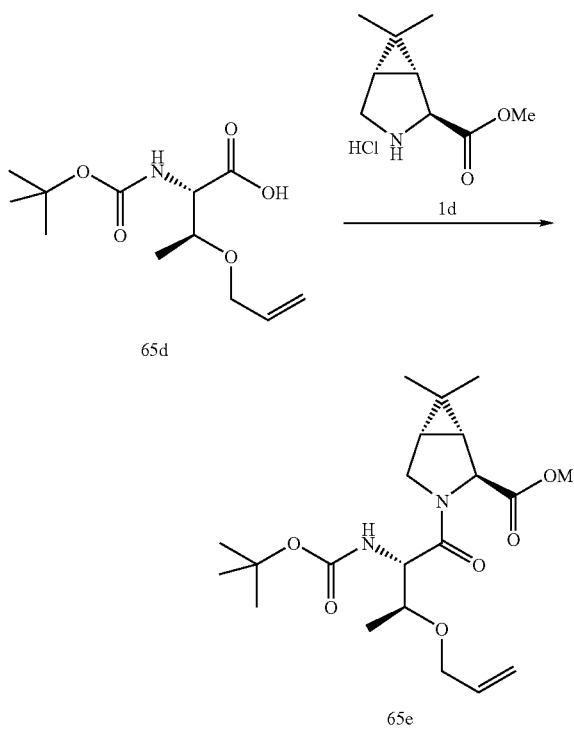

A solution of acid 65d (20.92 mmol) in 200 mL of dry dichloromethane and 100 mL of dry DMF was stirred at 0° C. and treated with HATU (1.4 eq, 11.16 g). The amine salt 1d (1.2 eq, 5.16 g) was added followed by N-methylmorpholine (4 eq, 9.19 mL, d 0.920). The reaction mixture was stirred overnight. All the volatiles were removed under vacuum and the residue was dissolved in 500 mL of ethyl acetate. The organic layer was washed with water (200 mL), aqueous 1M HCl (100 mL), aqueous saturated sodium bicarbonate solution (100 mL), and brine (100 mL). The organic layer was dried over magnesium sulfate, filtered and concentrated under reduced pressure. The residue was chromatographed on silica gel (ethyl acetate/hexanes; 2:8) to give the product 65e (7.6 g, 88%) as a colorless oil along with a small amount of its corresponding diastereomeric product.

Step E

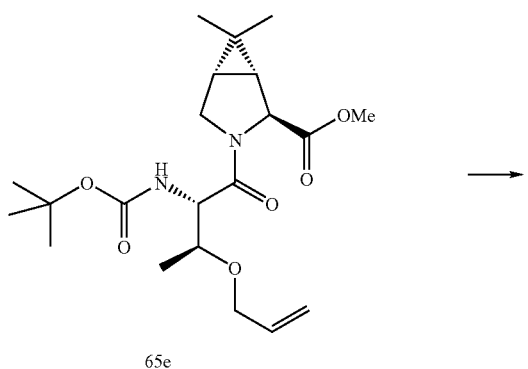

-continued

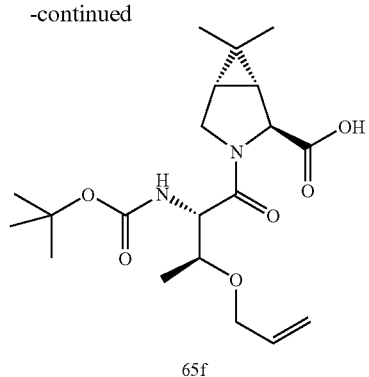

A solution of methylester 65e (7.6 g) in 300 mL of a 2:1 mixture of THF/water was cooled to 0° C. and treated with lithium hydroxide monohydrate (2.5 eq, 1.93 mg). The cooling bath was removed after 30 min and the mixture was stirred at room temp for further 4 h until all the starting material had been consumed as determined by TLC analysis (ethyl acetate/hexanes; 25:75). The reaction mixture was treated with 200 mL of aqueous 1M HCl (pH of mixture=1) and the product was taken into dichloromethane (4×100 mL). The combined organic extracts were dried over magnesium sulfate, filtered and concentrated under reduced pressure to afford the product 65f (6.86 g, 93%) as a colorless solid.

Step F

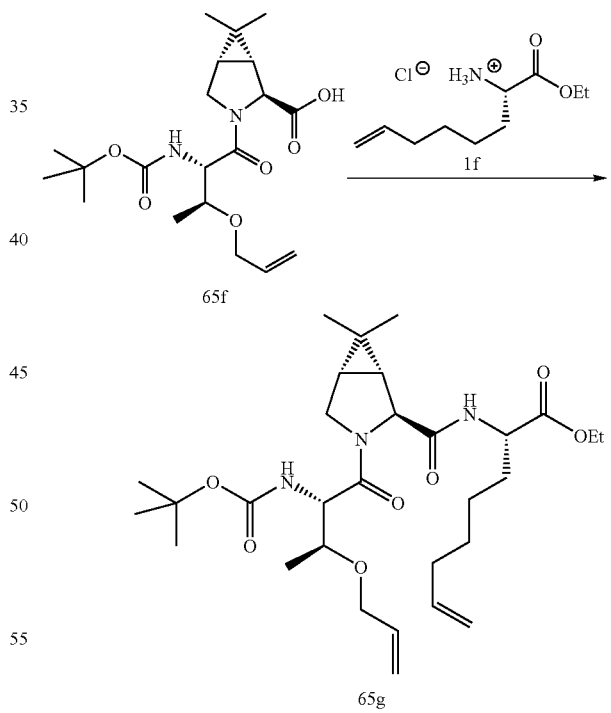

A solution of acid 65f (6.86 g) in 100 mL of dry dichloromethane and 100 mL of dry DMF was stirred at 0° C. and treated with HATU (1.4 eq, 9.23 g). The amine salt 1f (1.1 eq, 4.21 g) was added in 100 mL of dichloromethane followed by addition of N-methylmorpholine (4 eq, 7.6 mL, d 0.920). The reaction mixture was stirred at 0° C. overnight. All the volatiles were removed under vacuum and the residue was dissolved in 500 mL of ethyl acetate. The organic layer was washed with water (2×100 mL), aqueous 1M HCl (100 mL), aqueous saturated sodium bicarbonate solution (100 mL), and brine (100 mL). The organic layer was dried over magnesium sulfate, filtered and concentrated under reduced pressure. The residue was chromatographed on silica gel (ethyl acetate/hexanes; 3:7) to afford the product 65g (8.17 g, 84%) as a colorless oil.

Step G

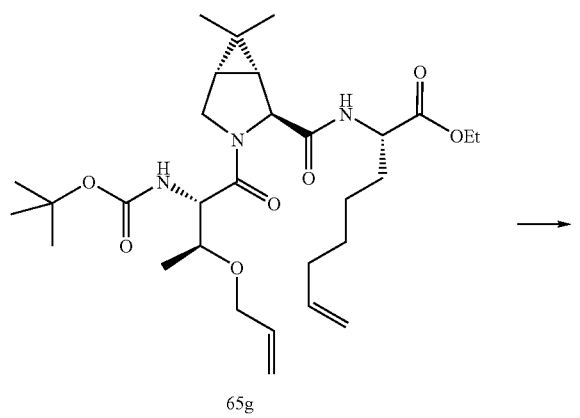

65g

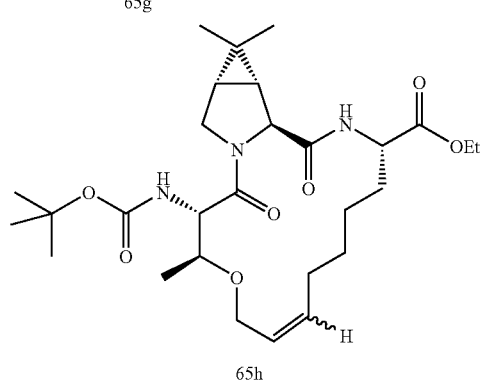

65h

A solution of diene 65g (8.17 g) in 1.5 L of toluene was degassed for 30 min (argon bubbling) and treated with Grubb's catalyst (0.2 eq, 2.38 g). The pink solution was heated to 60° C. for 18 h (the solution became dark after 10 min of heating). The solvent was removed under reduced pressure and the residue was chromatographed on silica gel (ethyl acetate/hexanes; 3:7) to give the alkene product 65h (7.0 g, 90%) as a mixture of E- and Z-isomers (approx 4:1).

Step H

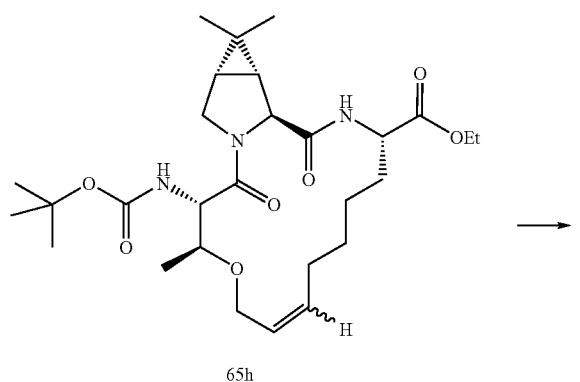

65h

-continued

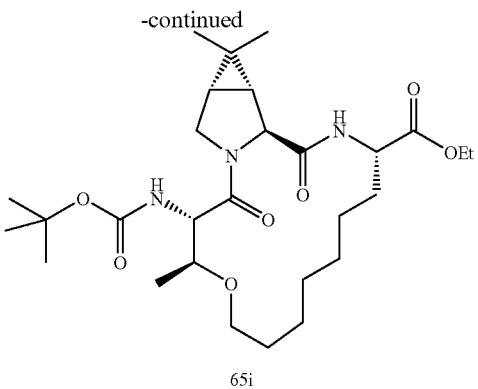

65i

A solution of alkene 65h (7.0 g) in 300 mL of methanol was treated with palladium on carbon (0.1 mol %, 1.37 g of 10% Pd/C). The mixture was hydrogenated at 35 psi until all the starting material had been consumed (approx 3 h). The reaction mixture was diluted with 300 mL of dichloromethane and filtered thru a short path of celite. The filtrate was concentrated and the residue was chromatographed on silica gel (ethyl acetate/hexanes; 3:7) to afford the product 65i (5.33 g, 76%) as a white solid.

Step I

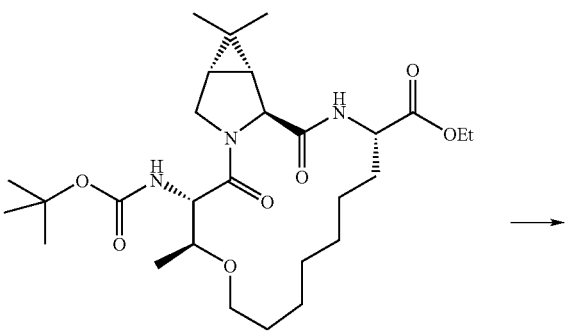

65i

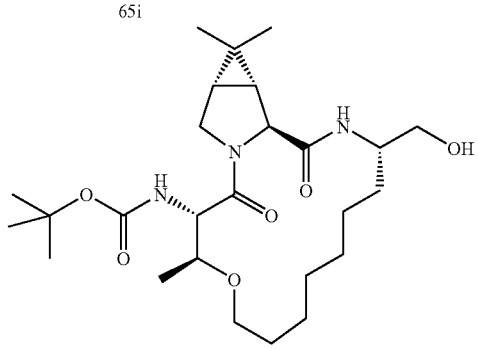

65j

A solution of ethyl ester 65i (5.33 g) in 100 mL of dry THF was treated with lithium borohydride (2.1 eq, 10.4 mL of a 2M soln in THF). The reaction mixture was stirred at room temperature and monitored by TLC (acetone/hexanes; 3:7) for disappearance of the starting material. After 2 h, more lithium borohydride solution was added (1 eq) and stirring was continued for 1 h. The excess lithium borohydride was quenched by addition of aqueous saturated ammonium chloride solution. The mixture was partitioned between ethyl acetate (300 mL) and aqueous saturated sodium bicarbonate solution (100 mL). The aqueous layer was back extracted with ethyl acetate (2×100 mL). The combined organic layers were dried over magnesium sulfate, filtered and concentrated under reduced pressure. The residue was chromatographed on silica gel (acetone/hexanes; 3:7) to afford the product 65j (3.93 g, 80%) as a white solid.

Step J

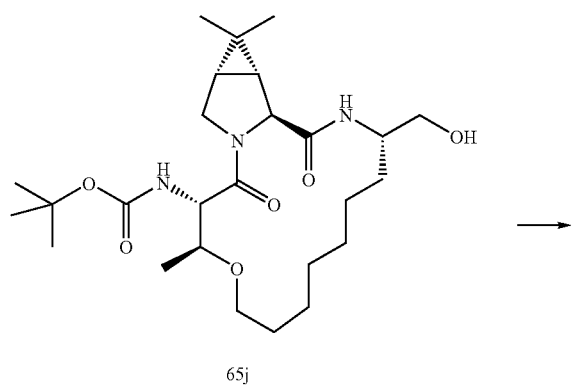

65j

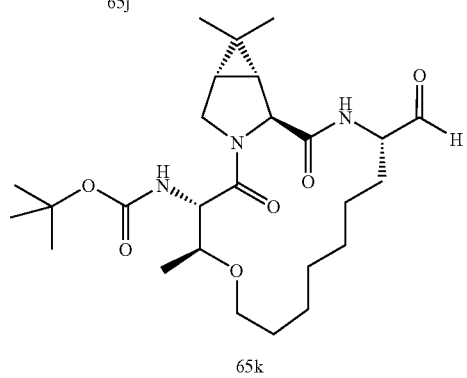

65k

A solution of alcohol 65j (1.0 g) in 40 mL of dry dichloromethane was treated with Dess-Martin periodinane (1.5 eq, 1.28 g). The reaction mixture was stirred at room temperature for 3 h. The mixture was treated with aqueous 1M sodium thiosulfate solution (10 mL) and stirred for 5 min. Aqueous saturated sodium bicarbonate solution (30 mL) was also added and stirring was continued for further 10 min. The mixture was extracted with dichloromethane (3×80 mL). The combined organic layers were dried over magnesium sulfate, filtered, and concentrated. The residue was chromatographed on silica gel (gradient: ethyl acetate/hexanes; 4:6 to 8:2) to afford the product 65k (750 mg, 75%) as a colorless solid.

Step K

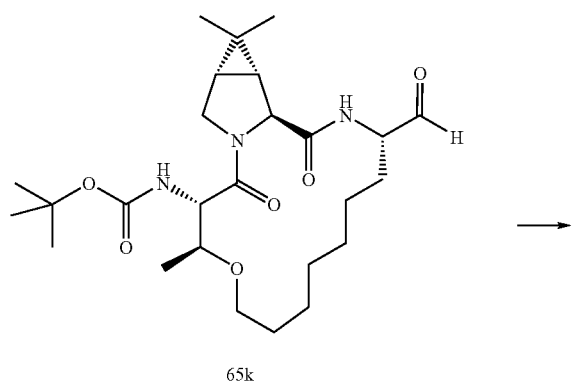

65k

-continued

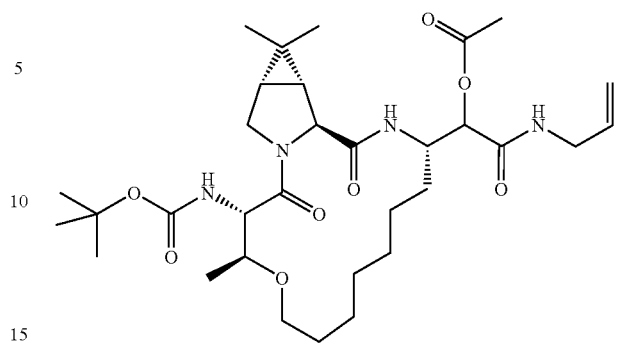

65l

A solution of aldehyde 65k (750 mg) in 20 mL of dry dichloromethane was treated with allylisocyanide (2 eq, 0.26 mL, d 0.8) and acetic acid (2 eq, 0.17 mL, d 1.049). The mixture was stirred at room temperature for about 5 h. All the volatiles were removed under vacuum and the residue was chromatographed on silica gel (gradient: acetone/hexanes; 1:9 to 45:55) to afford the product 65l (700 mg, 74%) as a white solid.

Step L

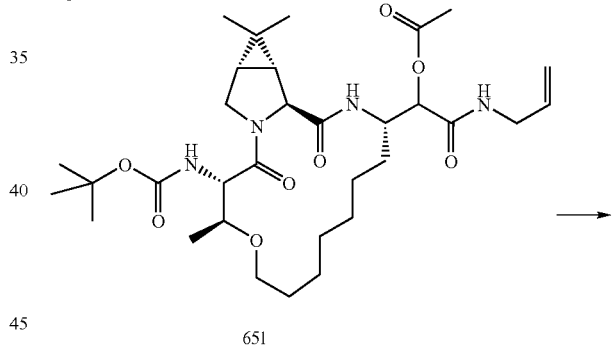

65l

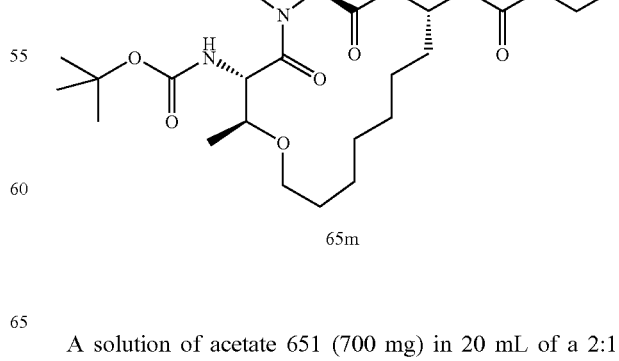

65m

A solution of acetate 65l (700 mg) in 20 mL of a 2:1 mixture of THF/water was treated with lithium hydroxide monohydrate (2.5 eq, 118 mg) and stirred for approx 30 min until all the starting material had been consumed as determined by TLC analysis (ethyl acetate/hexanes; 8:2). The reaction mixture was diluted with 50 mL of aqueous saturated sodium bicarbonate solution and extracted with dichloromethane (3×80 mL). The combined organic layers were dried over magnesium sulfate, filtered and concentrated to afford the product 65m (651 mg, 98%) as a colorless semi-solid which was used without further purification.

-continued

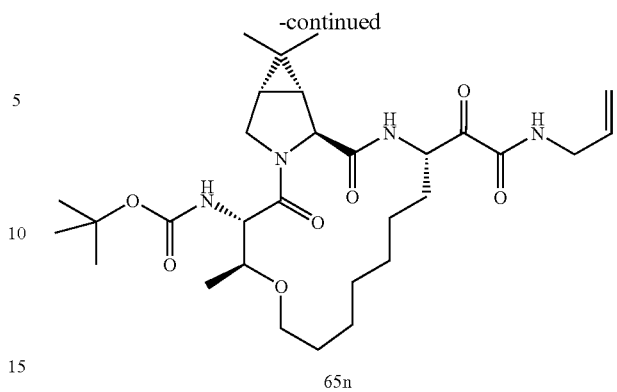

65n

Step M

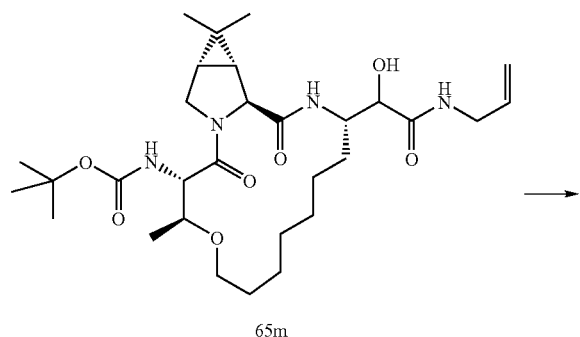

65m

A solution of hydroxyamide 65m (1.127 mmol) in 25 mL of dry dichloromethane was treated with Dess-Martin periodinane (2.0 eq, 956 mg). The reaction mixture was stirred at room temperature for 30 min. The mixture was treated with aqueous 1M sodium thiosulfate solution (20 mL) and stirred for 5 min. Aqueous saturated sodium bicarbonate solution (30 mL) was also added and stirring was continued for further 10 min. The mixture was extracted with dichloromethane (3×80 mL). The combined organic layers were dried over magnesium sulfate, filtered, and concentrated. The residue was chromatographed on silica gel (gradient: acetone/hexanes; 1:9 to 45:55) to afford the product 65n (585 mg, 90%) as white solid.

Step N

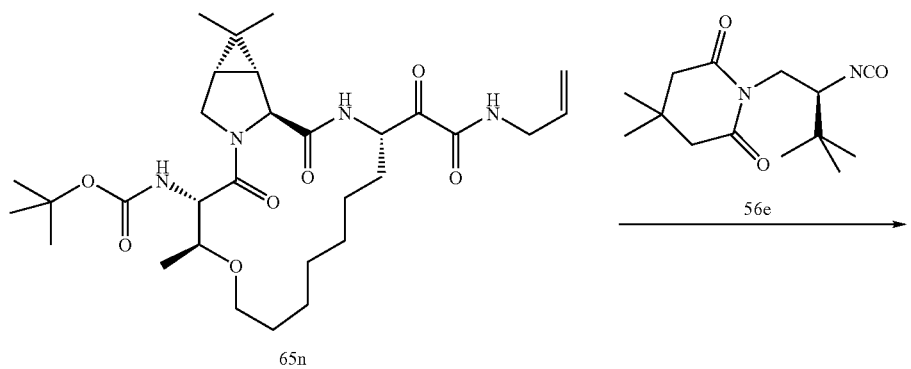

65n

56e

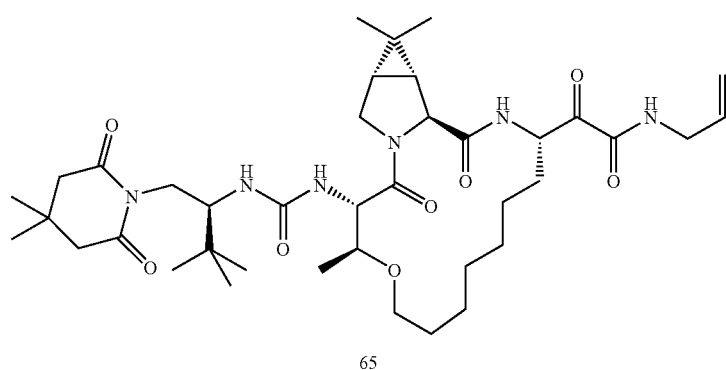

65

The N-Boc amine 65n (60 mg) was dissolved in 10 mL of 4M HCl solution in dioxanes. The resulting solution was stirred at room temperature for 30 min. All the volatiles were removed under reduced pressure and the residue was placed under high vacuum for 3 h. The resulting amine salt was dissolved in 5 mL of dry dichloromethane and cooled to 0° C. Then, 10 drops of aqueous saturated sodium bicarbonate solution were added. After 10 min, a soln of the isocyanate 56e was added dropwise (1.2 eq, 0.57 mL of a 0.216M solution in toluene) and stirring was continued for 10 min. The cooling bath was removed and the mixture was stirred at room temp for 2 h. The reaction mixture was diluted with dichloromethane (70 mL) and dried over magnesium sulfate, filtered and concentrated under reduced pressure. The residue was chromatographed on silica gel (gradient: acetone/hexanes; 15:85 to 5:5) to afford the product 65 (50 mg, 65%) as a white solid. $^1$H NMR (500 MHz, CDCl$_3$): δ8.13 (br s, 1H), 7.42-7.82 (br s, 1H), 6.30 (br s, 1H), 5.90 (ddt, 1H, J=5.6, 10.4, 17.0 Hz), 5.71 (br s, 1H), 5.38 (br s, 1H), 5.27 (dd, 1H, J=1.2, 17.0 Hz), 5.23 (dd, 1H, J=1.2, 10.4 Hz), 4.63 (dd, 1H, J=7.8, 8.1 Hz), 4.50 (br s, 1H), 4.23 (d, 1H, J=10.4 Hz), 4.05 (m, 2H), 3.98 (dd, 1H, J=5.6, 5.9 Hz), 3.95 (d, 1H, J=11.0 Hz), 3.88 (dd, 1H, J=10.7, 10.8 Hz), 3.82 (q, 1H, J=11.6 Hz), 3.71 (m, 1H), 3.62 (ddd, 1H, J=5.0, 5.3, 9.4 Hz), 3.20 (m, 1H), 2.55 (d, 2H, J=16.7 Hz), 2.47 (d, 2H, J=16.7 Hz), 1.73-1.97 (m, 4H), 1.14 (d, 3H, J=6.0 Hz), 1.10 (s, 6H), 1.00 (s, 3H), 0.99 (s, 9H), 0.83 (s, 3H); $^{13}$C NMR (CDCl$_3$, 125 MHz) δ 198.0, 172.8, 171.5, 159.4, 157.8, 117.7, 75.5, 68.1, 60.8, 57.2, 55.9, 48.7, 46.8, 42.3, 35.2, 29.3, 28.7, 28.3, 27.8, 27.6, 26.9, 26.8, 24.7, 24.4, 19.4, 16.3, 13.6 ppm; HRMS calcd for C$_{39}$H$_{63}$N$_6$O$_8$ [M+H]$^+$: 743.4707, found 743.4717.

Preparative Example 66

Preparation of

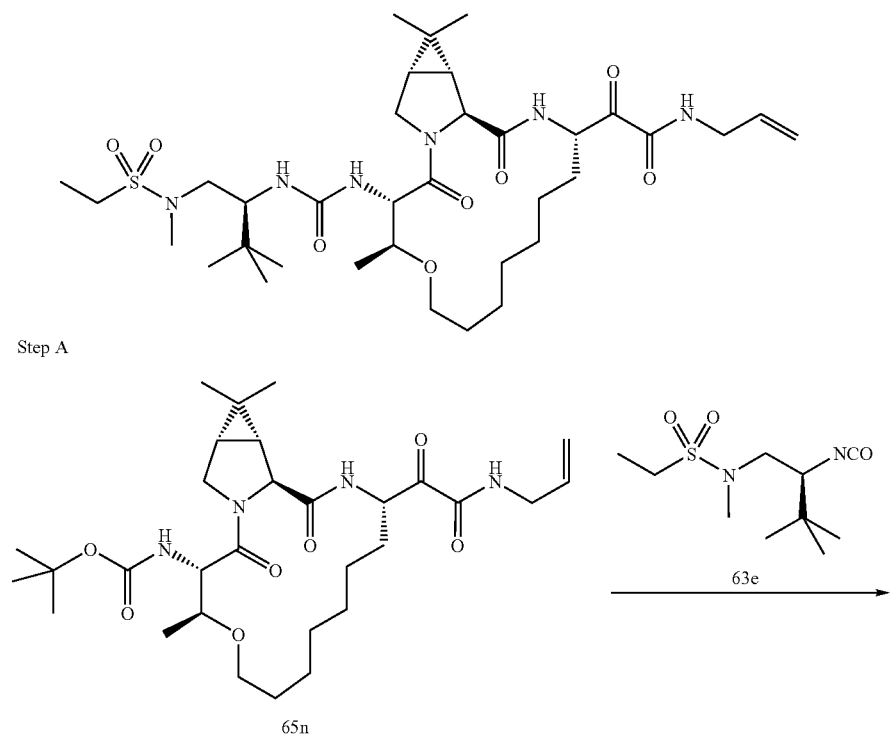

Step A

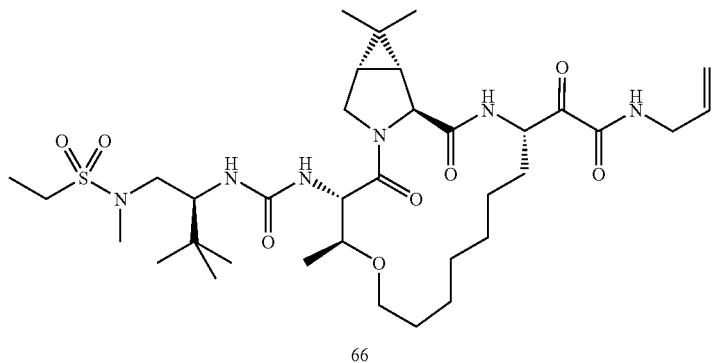

The N-Boc amine 65n (60 mg) was dissolved in 10 mL of 4M HCl solution in dioxanes. The resulting solution was stirred at room temperature for 30 min. All the volatiles were removed under reduced pressure and the residue was placed under high vacuum overnight. The resulting amine salt was dissolved in 5 mL of dichloromethane and cooled to 0° C. Then, 10 drops of aqueous saturated sodium bicarbonate solution were added. After 10 min, a soln of the isocyanate 63e was added dropwise (1.2 eq, 0.95 mL of a 0.131M solution in toluene) and stirring was continued for 10 min. The cooling bath was removed and the mixture was stirred at room temp for 3 h. The reaction mixture was diluted with dichloromethane (70 mL) and dried over magnesium sulfate, filtered and concentrated under reduced pressure. The residue was chromatographed on silica gel (gradient: acetone/hexanes; 2:8 to 6:4) to afford the product 66 (55 mg, 73%) as a white solid. $^1$H NMR (500 MHz, CDCl$_3$): δ 8.20 (d, 1H, J=6.6 Hz), 7.58-7.77 (br s, 1H), 6.13 (br s, 1H), 5.90 (ddt, 1H, J=5.6, 10.0, 17.0 Hz), 5.76 (br s, 1H), 5.27 (dd, 1H, J=1.2, 17.0 Hz), 5.22 (dd, 1H, J=1.2, 10.0 Hz), 5.15 (d, 1H, J=9.1 Hz), 4.69 (dd, 1H, J=8.8, 8.8 Hz), 4.57 (s, 1H), 4.29 (d, 1H, J=10.7 Hz), 3.91-4.09 (m, 4H), 3.61 (m, 2H), 3.47 (dd, 1H, J=11.9, 13.5 Hz), 3.19 (m, 1H), 3.07 (m, 3H), 2.94 (s, 3H), 1.95 (m, 1H), 1.35 (t, 3H, J=7.5 Hz), 1.27-1.69 (m, 12H), 1.22 (d, 3H, J=6.3 Hz), 1.14 (m, 1H), 1.02 (s, 3H), 0.93 (s, 9H), 0.89 (s, 3H); $^{13}$C NMR (CDCl$_3$, 125 MHz) δ 199.0, 172.8, 171.5, 159.3, 158.1, 133.5, 117.5, 75.8, 68.4, 60.7, 56.2, 50.4, 48.6, 45.6, 42.2, 34.7, 34.5, 32.0, 31.6, 28.6, 27.7, 27.0, 26.9, 26.7, 24.8, 24.6, 19.3, 16.2, 14.5, 13.5, 8.5 ppm; HRMS calcd for C$_{35}$H$_{61}$N$_6$O$_8$S [M+H]$^+$: 725.4272, found 725.4285.

Preparative Example 67

Preparation of

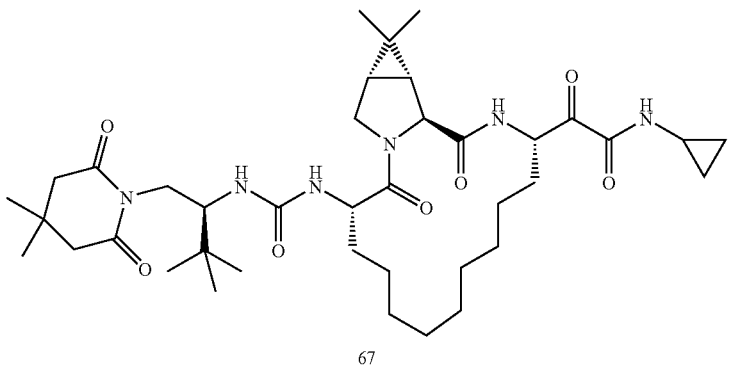

67

Step A

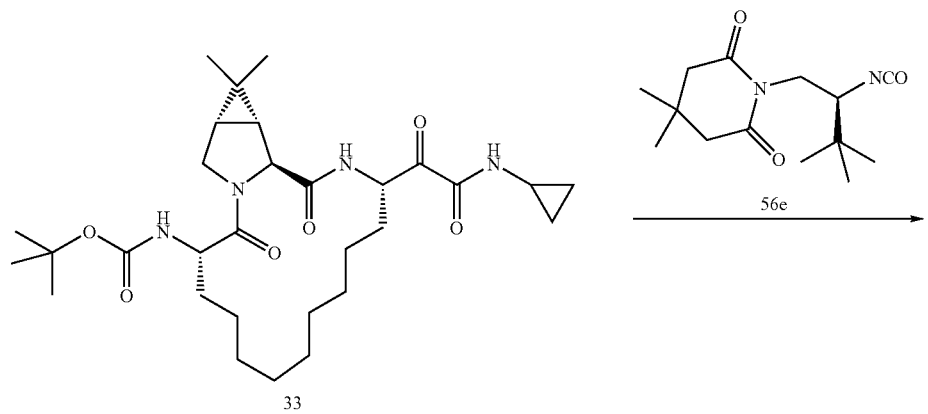

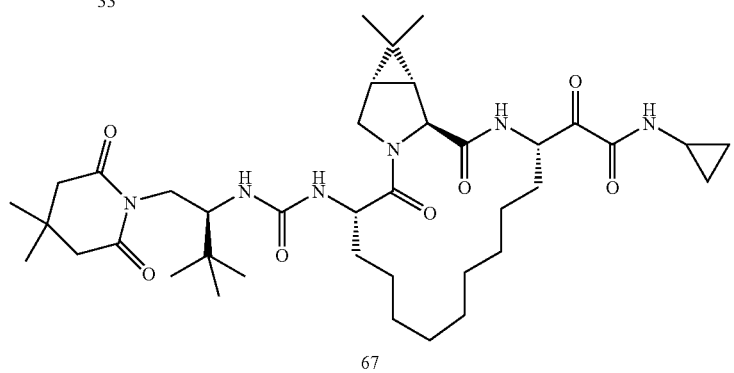

67

The N-Boc amine 33 (60 mg) was dissolved in 10 mL of 4M HCl solution in dioxanes. The resulting solution was stirred at room temperature for 30 min. All the volatiles were removed under reduced pressure and the residue was placed under high vacuum overnight. The resulting amine salt was dissolved in 5 mL of dry dichloromethane and cooled to 0° C. Then, N-methylmorpholine (2 eq, 0.03 mL, d 0.920) was added. After 10 min, a soln of the isocyanate 56e was added dropwise (1.5 eq, 0.8 mL of a 0.2M solution in toluene) and stirring was continued for 10 min. The cooling bath was removed and the mixture was stirred at room temp for 2 h. The reaction mixture was diluted with ethyl acetate (50 mL) and washed with aq 1M HCl (10 mL) and brine (10 mL). The organic layer was dried over magnesium sulfate, filtered and concentrated under reduced pressure. The residue was chromatographed on silica gel (gradient: acetone/hexanes; 2:8 to 1:1) to afford the product 67 (50 mg, 64%) as a white solid. $^1$H NMR (500 MHz, CDCl$_3$): δ 8.14 (d, 1H, J=6.9 Hz), 7.66-7.82 (br s, 1H), 6.11 (br s, 1H), 5.70 (br s, 1H), 5.32 (br s, 1H), 4.63 (br s, 1H), 4.60 (s, 1H), 4.19 (d, 1H, J=10.0 Hz), 3.96 (dd, 1H, J 5.0, 10.0 Hz), 3.91 (m, 3H), 2.91 (ddd, 1H, J=3.7, 7.8, 15.1 Hz), 2.57 (d, 2H, J=16.7 Hz), 2.50 (d, 2H, J=16.7 Hz), 1.86 (m, 3H), 1.69 (m, 1H), 1.18-1.61 (m, 16H), 1.10 (s, 6H), 1.01 (s, 3H), 0.95 (s, 9H), 0.89 (m, 2H), 0.87 (s, 3H), 0.71 (m, 2H); $^{13}$C NMR (CDCl$_3$, 125 MHz) δ 199.2, 173.5, 172.9, 171.9, 160.7, 158.0, 60.5, 56.6, 51.5, 48.5, 46.8, 39.9, 35.0, 34.2, 31.4, 29.4, 28.1, 27.8, 27.6, 27.4, 27.3, 27.0, 26.9, 26.5, 26.1, 23.4, 23.1, 19.4, 13.6, 6.8, 6.7 ppm.

Preparative Example 68

Preparation of

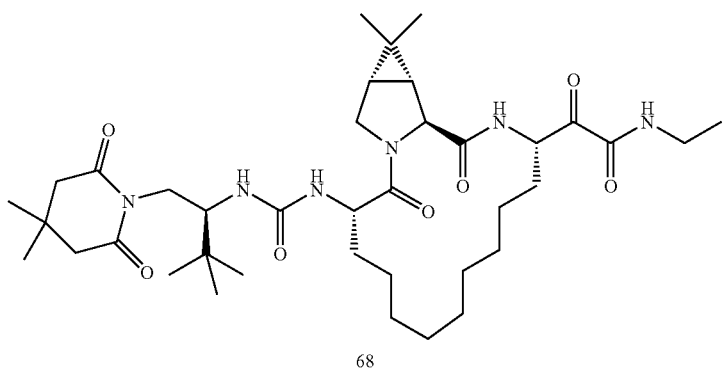

68

Step A

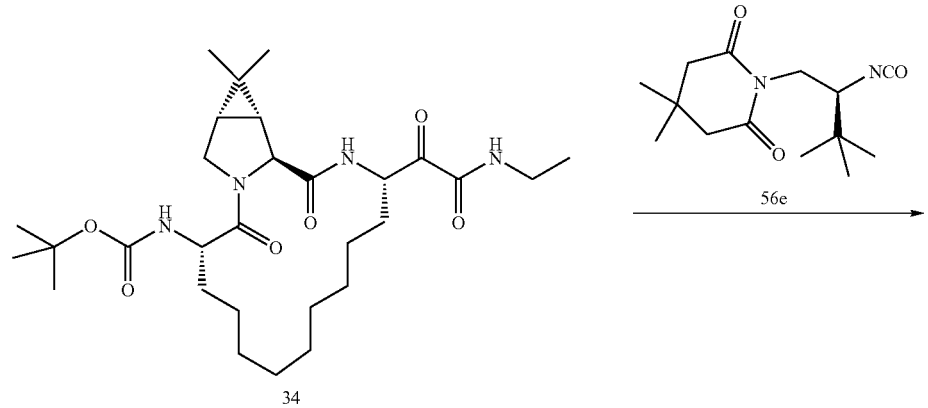

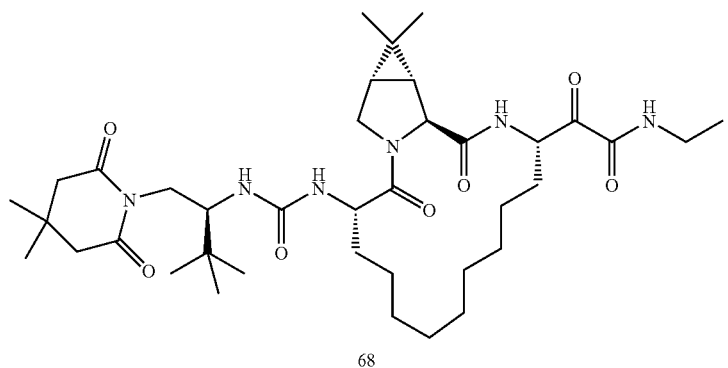

68

The N-Boc amine 34 (60 mg) was dissolved in 10 mL of 4M HCl solution in dioxanes. The resulting solution was stirred at room temperature for 30 min. All the volatiles were removed under reduced pressure and the residue was placed under high vacuum for 3 h. The resulting amine salt was dissolved in 5 mL of dry dichloromethane and cooled to 0° C. Then, N-methylmorpholine (2 eq, 0.02 mL, d 0.920) was added. After 10 min, a soln of the isocyanate 56e was added dropwise (1.4 eq, 0.6 mL of a 0.241M solution in toluene) and stirring was continued for 10 min. The cooling bath was removed and the mixture was stirred at room temp for 2 h. The reaction mixture was diluted with ethyl acetate (50 mL) and washed with aq 1M HCl (10 mL) and brine (10 mL). The organic layer was dried over magnesium sulfate, filtered and concentrated under reduced pressure. The residue was chromatographed on silica gel (gradient: acetone/hexanes; 1:9 to 45:55) to afford the product 68 (44 mg, 56%) as a white solid. $^1$H NMR (500 MHz, CDCl$_3$): δ 8.08 (br s, 1H), 7.52-7.77 (br s, 1H), 6.06 (br s, 1H), 5.70 (br s, 1H), 5.26 (br s, 1H), 4.63 (m, 2H), 4.20 (d, 1H, J=10.0 Hz), 3.97 (dd, 1H, J=5.0, 10.0 Hz), 3.92 (m, 3H), 3.43 (m, 2H), 2.57 (d, 2H, J=16.7 Hz), 2.50 (d, 2H, J=16.7 Hz), 1.90 (m, 1H), 1.74 (m, 2H), 1.27 (t, 3H, J=7.2 Hz), 1.20-1.62 (m, 17H), 1.11 (s, 6H), 1.02 (s, 3H), 0.96 (s, 9H), 0.88 (s, 3H); $^{13}$C NMR (CDCl$_3$, 125 MHz) δ 199.1, 173.5, 172.9, 171.8, 159.3, 157.9, 60.6, 56.6, 51.5, 48.5, 46.8, 40.0, 34.9, 34.8, 34.1, 32.8, 29.4, 28.1, 27.8, 27.5, 27.4, 27.3, 27.0, 26.9, 26.5, 26.0, 25.1, 23.4, 19.4, 14.8, 13.6 ppm; HRMS calcd for C$_{38}$H$_{63}$N$_6$O$_7$ [M+H]$^+$: 715.4758, found 715.4751.

Preparative Example 69

Preparation of

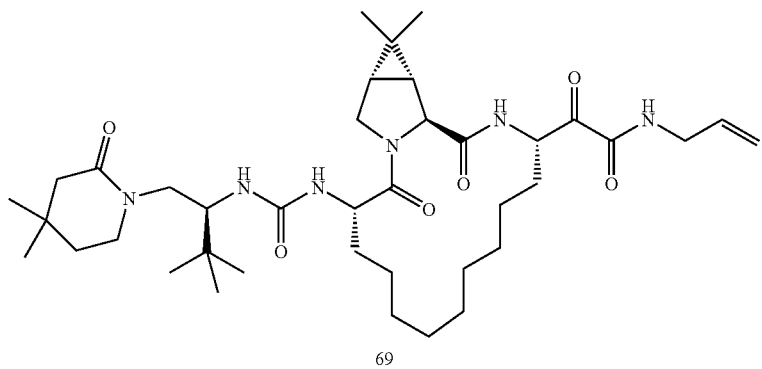

Step A

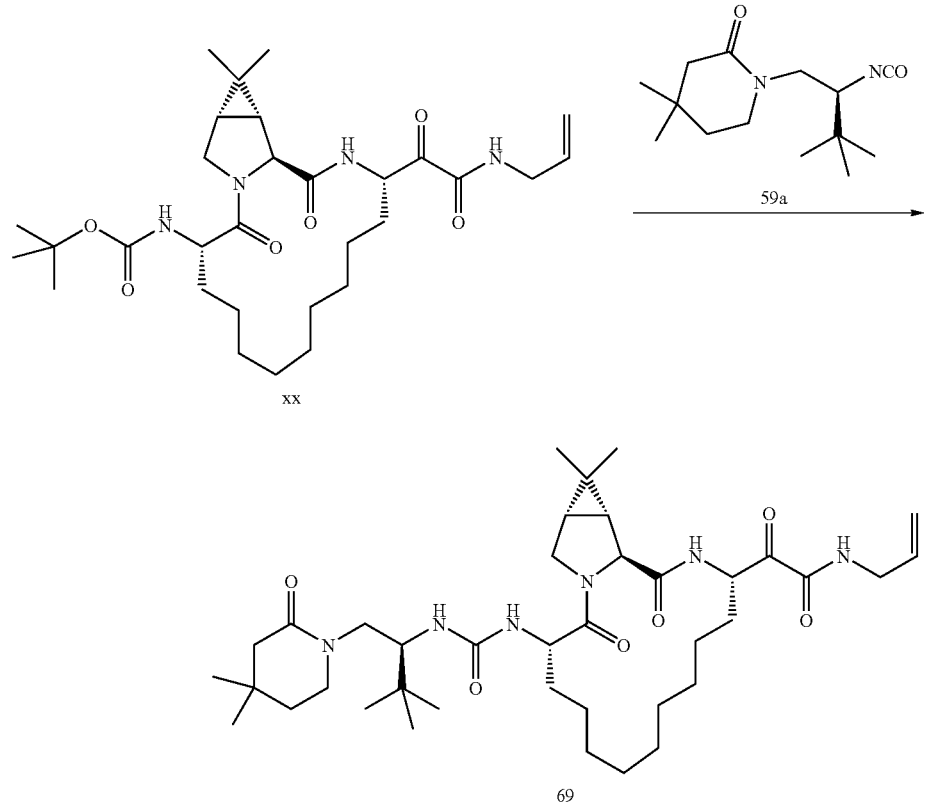

The N-Boc amine XX (93 mg) was dissolved in 10 mL of 4M HCl solution in dioxanes. The resulting solution was stirred at room temperature for 30 min. All the volatiles were removed under reduced pressure and the residue was placed under high vacuum for 3 h. The resulting amine salt was dissolved in 5 mL of dry dichloromethane and cooled to 0° C. Then, N-methylmorpholine (2 eq, 0.04 mL, d 0.920) was added. After 10 min, a soln of the isocyanate 59a in toluene was added dropwise (1.2 eq) and stirring was continued for 10 min. The cooling bath was removed and the mixture was stirred at room temp for 2 h. The reaction mixture was diluted with ethyl acetate (50 mL) and washed with aq 1M HCl (10 mL) and brine (10 mL). The organic layer was dried over magnesium sulfate, filtered and concentrated under reduced pressure. The residue was chromatographed on silica gel (gradient: acetone/hexanes; 1:9 to 45:55) to afford the product 69 (45 mg, 38%) as a white solid. $^1$H NMR (500 MHz, CDCl$_3$): δ8.26-8.67 (br s, 1H), 8.17 (br s, 1H), 6.19 (br s, 1H), 5.92 (ddt, 1H, J=5.6, 10.4, 17.3 Hz), 5.74 (dd, 1H, J=8.8, 9.1 Hz), 5.41 (br s, 1H), 5.26 (dd, 1H, J=1.2, 17.3 Hz), 5.20 (d, 1H, J=10.0 Hz), 4.67 (br s, 1H), 4.62 (s, 1H), 4.35 (dd, 1H, J=1.9, 12.9 Hz), 4.20 (d, 1H, J=9.8 Hz), 3.99 (m, 4H), 3.58 (ddd, 1H, J=5.9, 6.9, 12.6 Hz), 3.18 (ddd, 1H, J=5.9, 5.9, 11.9 Hz), 2.69 (d, 1H, J=10.7 Hz), 2.18 (d, 1H, J=17.0 Hz), 2.12 (d, 1H, J=17.0 Hz), 1.96 (m, 1H), 1.18-1.89 (m, 20H), 1.12 (m, 1H), 1.04 (s, 3H), 1.03 (s, 3H), 1.00 (s, 3H), 0.92 (s, 9H), 0.91 (s, 3H); $^{13}$C NMR (CDCl$_3$, 125 MHz) δ 199.3, 173.3, 171.8, 171.1, 159.4, 158.2, 133.7, 117.3, 60.4, 55.3, 51.5, 48.3, 46.3, 45.0, 42.3, 35.8, 34.6, 34.0, 31.2, 30.3, 28.6, 27.8, 27.7, 27.6, 27.3, 27.2, 27.0, 26.3, 25.9, 25.4, 23.2, 19.3, 13.5 ppm.

Preparative Example 70

Preparation of

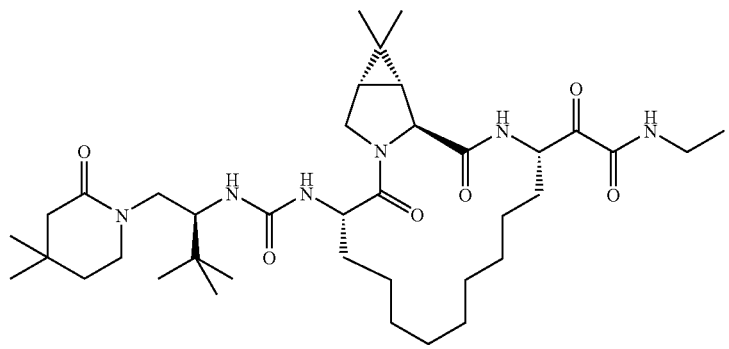

70

Step A

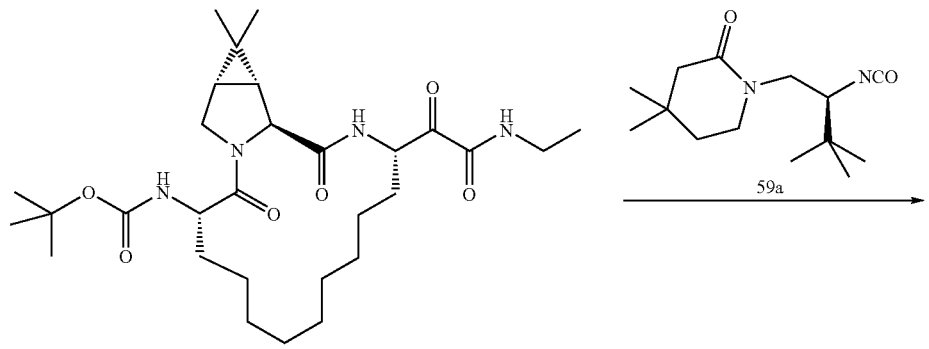

34

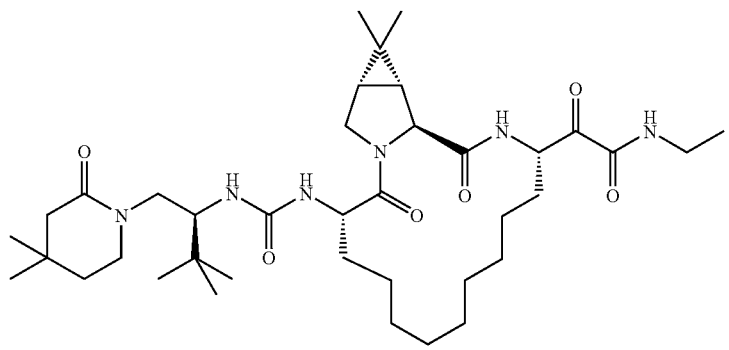

70

The N-Boc amine 34 (73 mg) was dissolved in 10 mL of 4M HCl solution in dioxanes. The resulting solution was stirred at room temperature for 30 min. All the volatiles were removed under reduced pressure and the residue was placed under high vacuum for 3 h. The resulting amine salt was dissolved in 5 mL of dry dichloromethane and cooled to 0° C. Then, N-methylmorpholine (2 eq, 0.03 mL, d 0.920) was added. After 10 min, a soln of the isocyanate 59a in toluene was added dropwise (1.2 eq) and stirring was continued for 10 min. The cooling bath was removed and the mixture was stirred at room temp for 2 h. The reaction mixture was diluted with ethyl acetate (50 mL) and washed with aqueous 1M HCl (10 mL) and brine (10 mL). The organic layer was dried over magnesium sulfate, filtered and concentrated under reduced pressure. The residue was chromatographed on silica gel (gradient: acetone/hexanes; 1:9 to 45:55) to afford the product 70 (63 mg, 69%) as a white solid. $^1$H NMR (500 MHz, CDCl$_3$): δ 8.20-8.43 (br s, 1H), 8.17 (br s, 1H), 6.20 (br s, 1H), 5.75 (dd, 1H, J=8.2, 9.4 Hz), 5.41 (br s, 1H), 4.66 (d, 1H, J=9.1 Hz), 4.63 (s, 1H), 4.36 (dd, 1H, J=12.6, 13.2 Hz), 4.18 (d, 1H, J=10.4 Hz), 3.96 (m, 2H), 3.57 (m, 1H), 3.41 (m, 2H), 3.18 (ddd, 1H, J=5.9, 11.9 Hz), 2.69 (d, 1H, J=13.2 Hz), 2.19 (d, 1H, J=17.0 Hz), 2.14 (d, 1H, 17.0 HZ), 1.76-1.99 (m, 4H), 1.25 (t, 3H, J=7.2 Hz), 1.18-1.75 (m, 17H), 1.12 (m, 1H), 1.04 (s, 3H), 1.02 (s, 3H), 1.01 (s, 3H), 0.92 (s, 9H), 0.91 (s, 3H); $^{13}$C NMR (CDCl$_3$, 125 MHz) δ 199.9, 173.3, 171.8, 171.1, 159.4, 158.2, 60.4, 55.2, 53.5, 51.5, 48.3, 46.3, 35.8, 34.8, 34.6, 31.3, 30.3, 28.7, 27.8, 27.7, 27.6, 27.3, 27.0, 26.4, 26.0, 23.2, 19.3, 14.8, 13.5 ppm; HRMS calcd for C$_{38}$H$_{65}$N$_6$O$_6$ [M+H]$^+$: 701.4966, found 701.4960.

Preparative Example 71

Preparation of

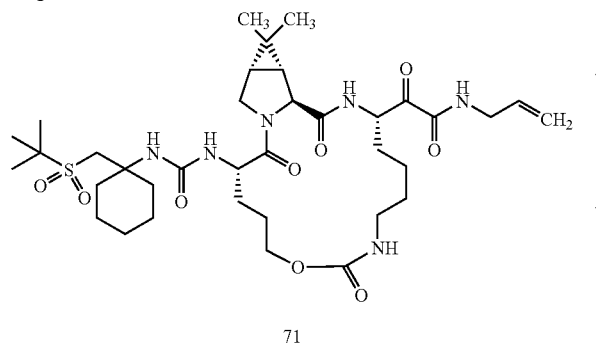

71

Step A:

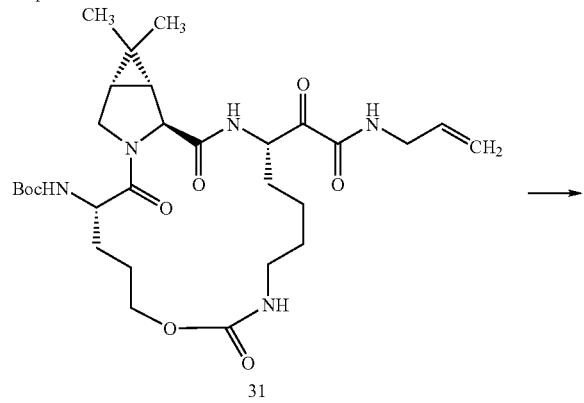

31

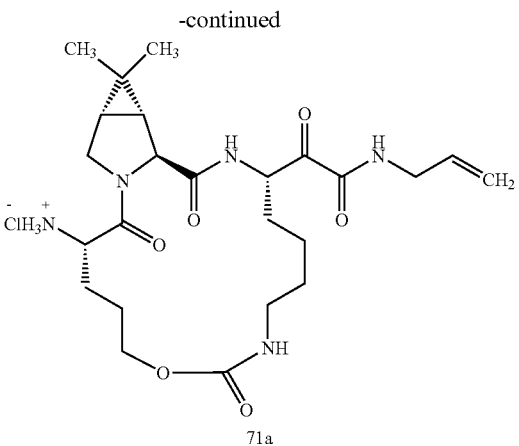

71a

A solution of 31 (100 mg, 0.169 mmol) in 4 N. HCl in dioxane (5 ml) was stirred at room temperature for 1 hour. Solvent was removed to dryness to give 71a (120 mg) which was used without further purification Step B:

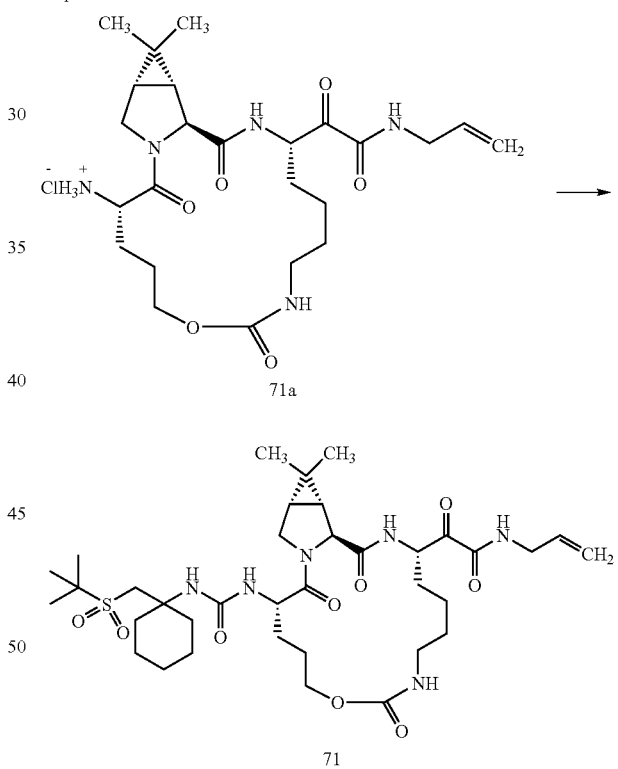

A solution of 71a (89 mg, 0.169 mmol) in CH$_2$Cl$_2$ (10 ml) was treated with isocyanate 27b (3 equiv), sat. NaHCO$_3$ (3 ml) and stirred vigorously for 2 hours. The solution was allowed to stand at 5° C. for 12 hours. The CH$_2$Cl$_2$ layer was separated, washed with water, brine and filtered through Na$_2$SO$_4$. Solvent was removed to dryness and the residue was purified on silica gel column (40% to 60% acetone/hexanes) to give 71 (73 mg). MS (ES) m/z relative intensity 773 [(M+Na)$^+$, 20]; 751 [(M+1)$^+$, 100]. Calcd. for C$_{36}$H$_{59}$N$_6$O$_9$S [M+1]$^+$: 751.4064; Found 751.4075.

Preparative Example 72

Preparation of

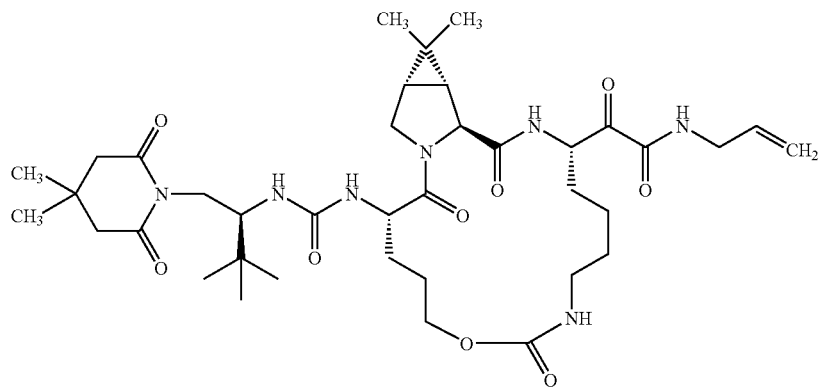

72

Step A:

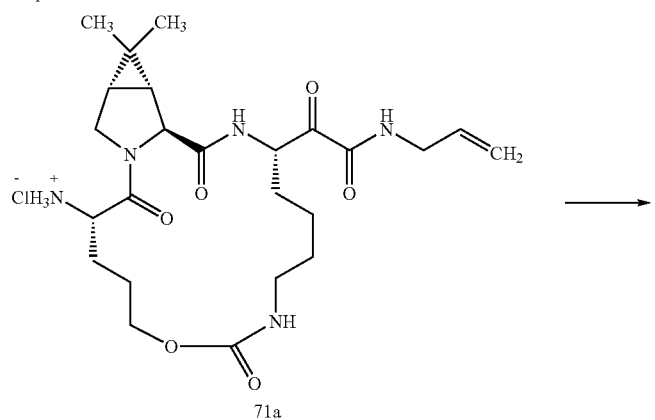

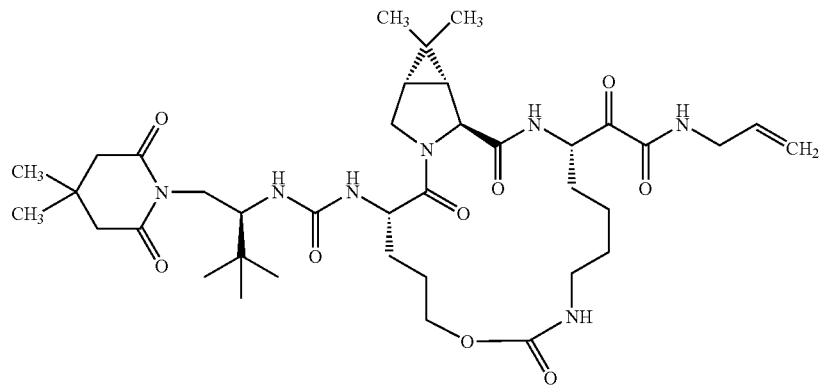

72

A solution of 71a (89 mg, 0.169 mmol) in $CH_2Cl_2$ (10 ml) was treated with isocyanate 51c (1.5 equiv), sat. $NaHCO_3$ (4 ml) and stirred vigorously for 30 minutes. The solution was allowed to stand at 5° C. for 12 hours. The $CH_2Cl_2$ layer was separated, washed with water, brine and filtered through $Na_2SO_4$. Solvent was removed to dryness and the residue was purified on silica gel column (40% to 50% acetone/hexanes) to give 72 (95 mg). MS (ES) m/z relative intensity 790 [(M+$CH_3OH$+1)$^+$, 40]; 758 [(M+1)$^+$, 100]. Calcd. for $C_{38}H_{59}N_7O_9$ [M+1]$^+$: 758.4453; Found 758.4449.

Preparative Example 73

Preparation of

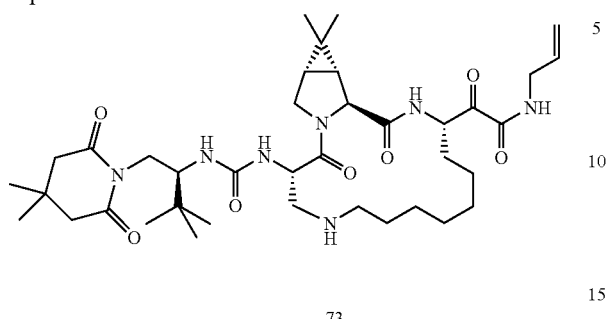

73

Step A

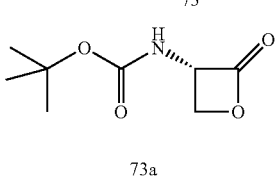

73a

The N-(tert-Butoxycarbonyl)-L-serine-beta-lactone 73a will be prepared according to the procedure described by Vederas and co-workers (Arnold, L. D.; Kalantar, T. H.; Vederas, J. C. *J. Am. Chem. Soc.* 1985, 107, 7105-7109) starting from commercially available N-Boc-L-Ser-OH.

Step B

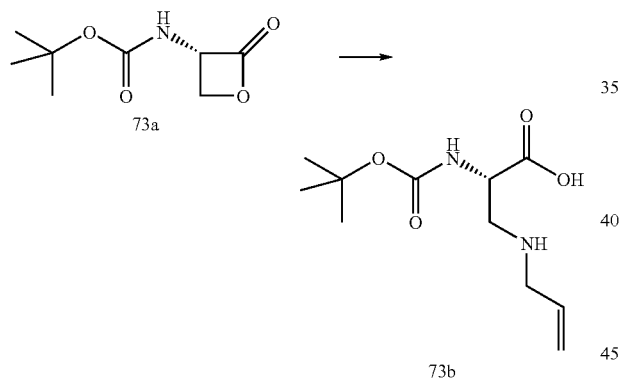

A solution of N-(tert-Butoxylcarbonyl)-L-serine-beta-lactone 73a (1 mmol) in 20 mL of dry acetonitrile will be added dropwise at ambient temperature over 1 h to a stirred solution of allylamine (25 mmol) in 30 mL dry acetonitrile. After 2 h, the solution will be concentrated under reduced pressure. The residue will be slurried with acetonitrile and the acid product 73b will be recovered by filtration.

Step C

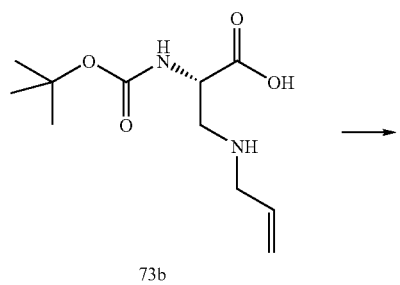

73b

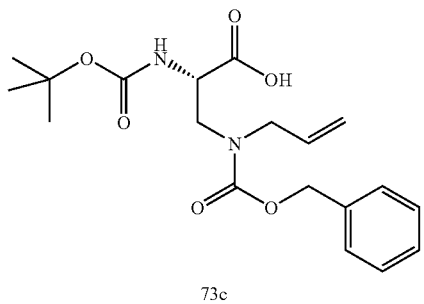

73c

A solution of acid 2 (1 mmol) in aqueous saturated sodium bicarbonate solution (4 mL) and water (1 mL) at room temperature will be treated with benzyl chloroformate (1.12 mmol) in acetone (1 mL). The reaction mixture will be stirred for 2 h. The mixture will be partitioned between ether (20 mL) and water (20 mL). The aqueous layer will be cooled in an ice-water bath, brought to pH 2 using 5% aqueous HCl and extracted with dichloromethane (3×30 mL). The combined organic layers will be dried over magnesium sulfate, filtered and concentrated to afford the acid product 73c.

Step D

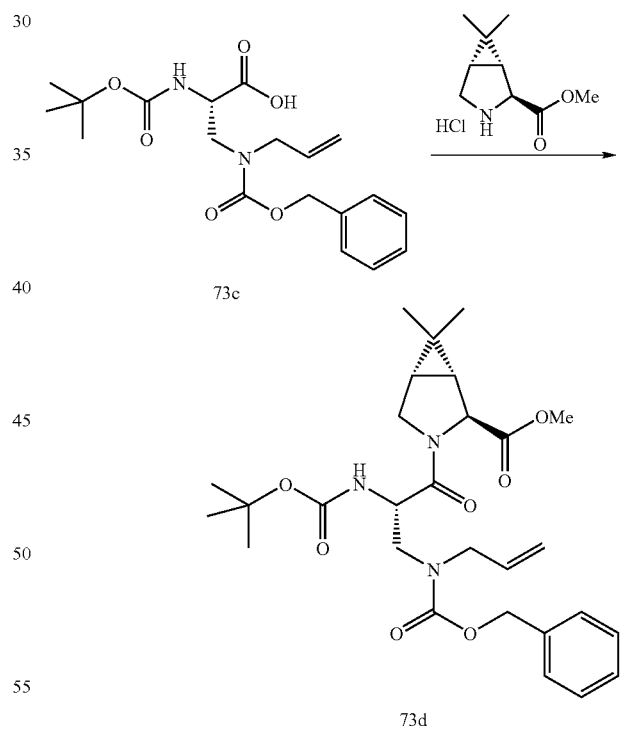

A solution of acid 73c (1 mmol) in 10 mL of dry dichloromethane and 10 mL of dry DMF will be stirred at 0° C. and treated with HATU (1.4 mmol). The amine hydrochloride (1.3 mmol) and N-methylmorpholine (4 mmol) will be successively added. The reaction mixture will be gradually warmed to room temperature and stirred overnight. All the volatiles will be removed under vacuum and the residue will be taken into 100 mL of ethyl acetate. The organic layer will be washed with water (20 mL), aqueous 1N HCl (20 mL), aqueous saturated sodium bicarbonate solution (20 mL), and brine (20 mL). The organic layer will be dried over magnesium sulfate, filtered, and concentrated under reduced pressure. The product 73d will be purified by column chromatography on silica gel.

Step E

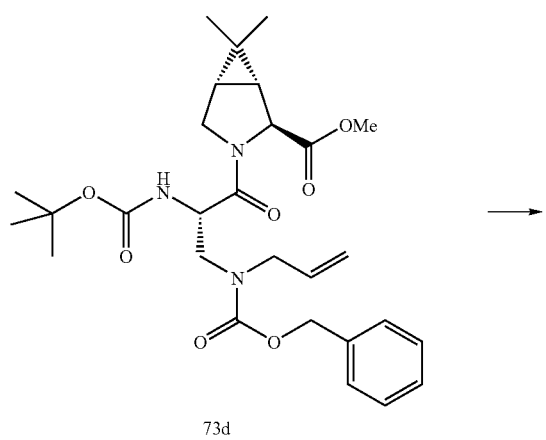

73d

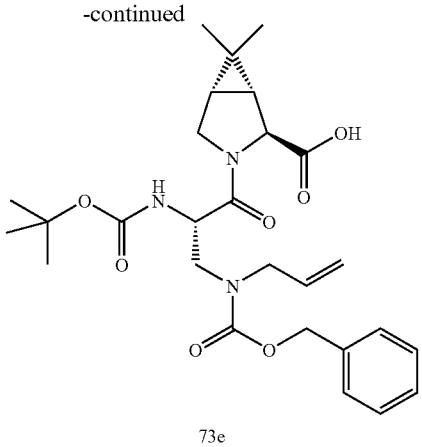

73e

A solution of methyl ester 73d (1 mmol) in 15 mL of a mixture of THF/MeOH/H$_2$O (1:1:1) will be treated with lithium hydroxide monohydrate (2.5 mmol) at 0° C. The cooling bath will be removed and the reaction mixture stirred at room temperature and monitored by TLC (acetone/hexanes; 2:8). After 1 h, 10 mL of aqueous 1N HCl will be added and all the volatiles will be removed under reduced pressure. The residue will be partitioned between 30 mL of aqueous 1N HCl and 100 mL of dichloromethane. The aqueous layer will be back extracted with dichloromethane (2×50 mL). The combined organic layers will be dried over magnesium sulfate, filtered, and concentrated under reduced pressure to give the acid product 73e.

Step F

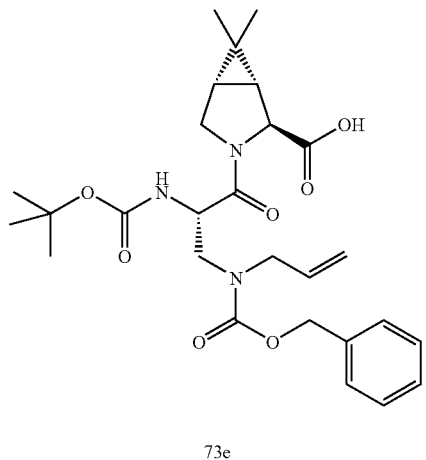

73e

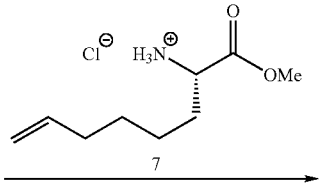

7

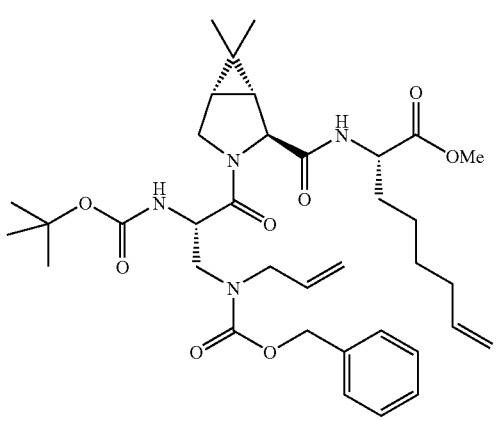

73f

A solution of acid 73e (1 mmol) in 10 mL of dry dichloromethane and 10 mL of dry DMF will be stirred at 0° C. and treated with HATU (1.4 eq, 1.15 g). The amine hydrochloride 7 (1.2 mmol) will be added in 10 mL of dichloromethane followed by N-methylmorpholine (4 mmol). The reaction mixture will be stirred overnight (temp from 0 to 25° C.). All the volatiles will be removed under vacuum and the residue will be dissolved in 100 mL of ethyl acetate. The organic layer will be washed with water (20 mL), aqueous 1N HCl (20 mL), aqueous saturated sodium bicarbonate solution (20 mL), and brine (20 mL). The organic layer will be dried over magnesium sulfate, filtered and concentrated under reduced pressure. The product 73f will be purified by column chromatography on silica gel.

Step G

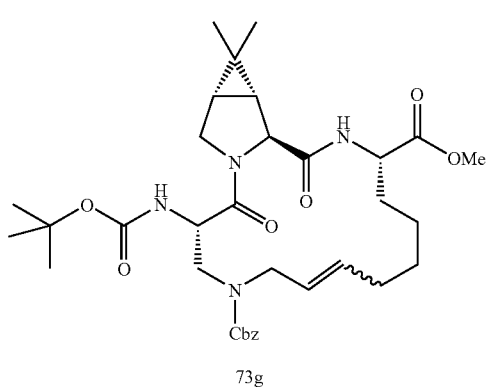

73f

Step H

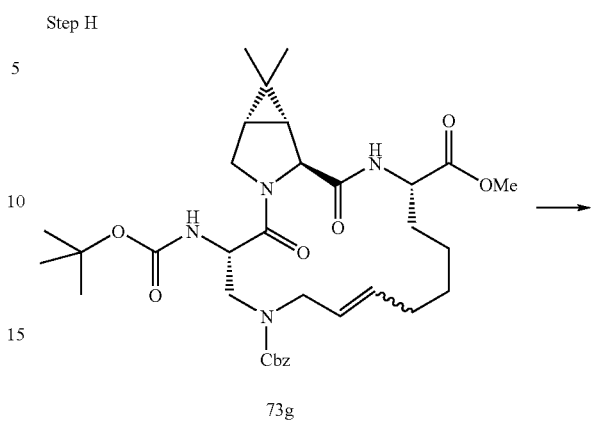

73g

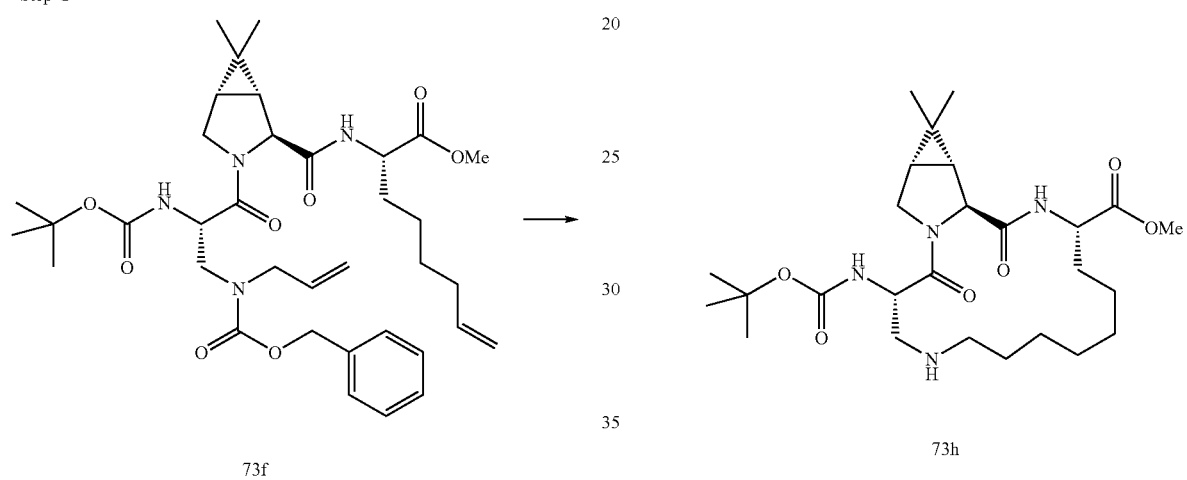

A 0.01M solution of diene 73f (1 mmol) in toluene will be degassed for 30 min (argon bubbling) and treated with Grubb's catalyst (0.2 mmol). The pink solution will be heated to 60° C. for 16 h. The solvent will be removed under reduced pressure and the residue will chromatographed on silica gel to afford the alkene product 73g as a mixture of E- and Z-isomers.

A solution of alkene 73g (1 mmol) in 20 mL of methanol will be treated with 5% palladium on carbon (0.1 mol %). The mixture will be hydrogenated at 50 psi until all the starting material is consumed. The reaction mixture will be diluted with 100 mL of dichloromethane and filtered thru a short path of celite. The filtrate will be concentrated and the product 73h will be purified by column chromatography on silica gel.

Step I

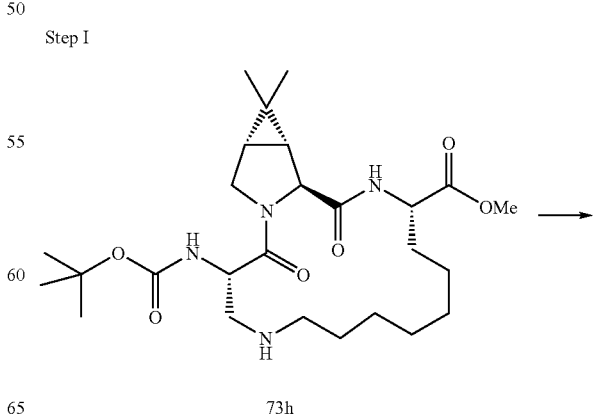

73h

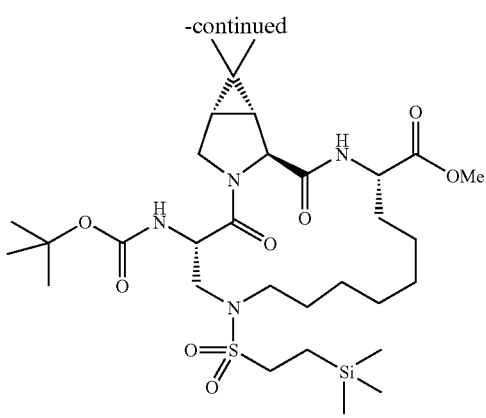

73i

A solution of macrocyclic amine 73h (1 mmol) in 10 mL of dichloromethane will be treated with potassium carbonate (2 mmol) and (trimethylsilyl)ethanesulfonyl chloride (1 mmol). The mixture is stirred for 1 day and solvent will be evaporated. The product 73i will be purified by column chromatography on silica gel.

Step J

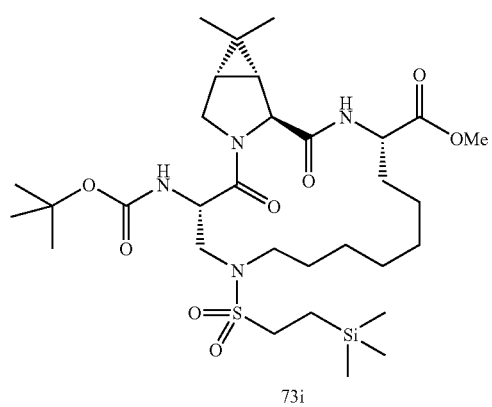

73i

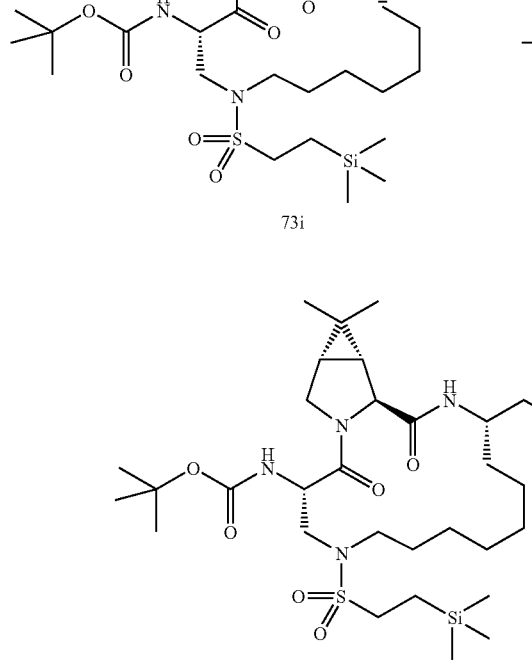

73j

A solution of methyl ester 73i (1 mmol) in 10 mL of dry THF will be treated with lithium borohydride (2.1 mmol). The reaction mixture will be stirred at room temperature. After 5 h, the excess lithium borohydride will be quenched by addition of aqueous saturated ammonium chloride solution (3 mL). The mixture will be partitioned between ethyl acetate (50 mL) and aqueous saturated sodium bicarbonate solution (30 mL). The aqueous layer will be back extracted with ethyl acetate (2×30 mL) and dichloromethane (2×30 mL). The combined organic layers will be dried over magnesium sulfate, filtered and concentrated under reduced pressure. The residue will be chromatographed on silica gel to afford the product 73j.

Step K

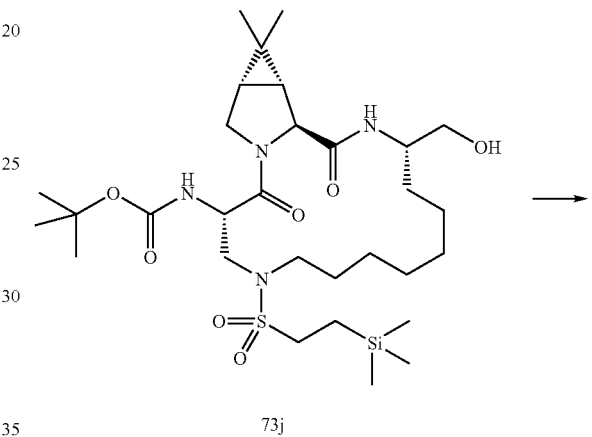

73j

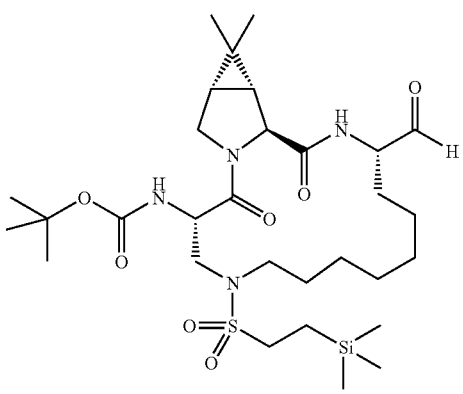

73k

A solution of alcohol 73j (1 mmol) in 20 mL of dry dichloromethane will be treated with Dess-Martin period inane (1.5 mmol). The reaction mixture will be stirred at room temperature for 45 min. The mixture will be treated with aqueous 1M sodium thiosulfate solution (10 mL) and aqueous saturated sodium bicarbonate solution (20 mL) and stirred for 15 ml. The mixture will be extracted with dichloromethane (3×40 mL). The combined organic layers will be dried over magnesium sulfate, filtered, and concentrated. The residue will be chromatographed on silica gel to afford the aldehyde product 73k.

Step L

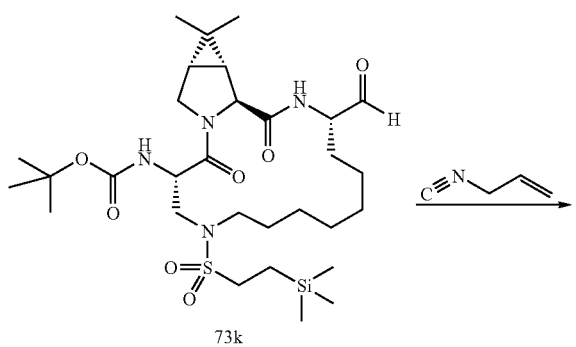

73k

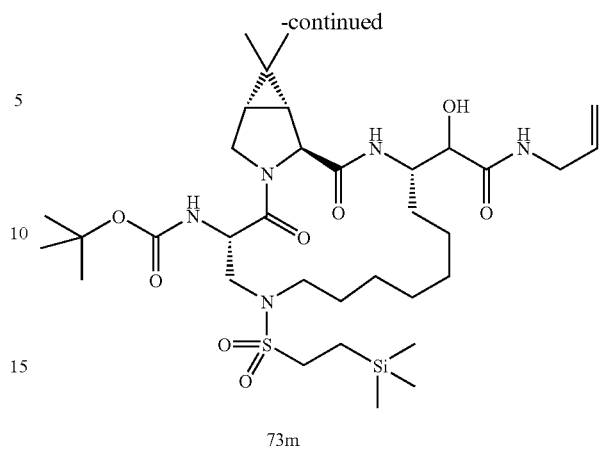

73m

The acetate 73l (1 mmol) will be dissolved in 16 mL of a 1:1 mixture of THF/water and treated with lithium hydroxide monohydrate (2.5 mmol). After 30 min the mixture will be partitioned between dichloromethane (50 mL) and aqueous saturated sodium bicarbonate solution (20 mL). The aqueous layer will be back extracted with dichloromethane (3×30 mL). The combined organic layers will be dried over magnesium sulfate, filtered, and concentrated. The hydroxyamide product 73m will be used without further purification.

Step N

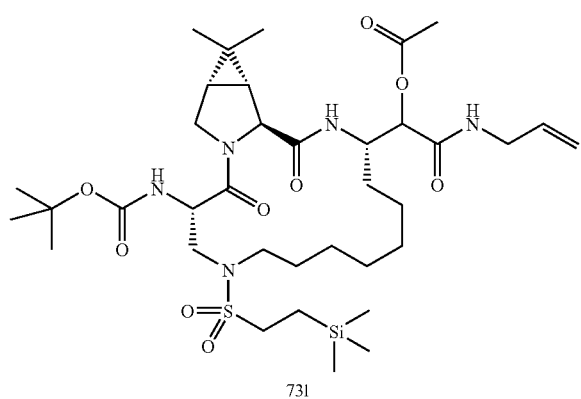

73l

A solution of aldehyde 73k (1 mmol) in 10 mL of dry dichloromethane will be treated with allylisocyanide (2 mmol) and acetic acid (2 mmol). The mixture will be stirred for about 5 h. All the volatiles will be removed under vacuum and the residue will be chromatographed on silica gel to afford the acetate product 73l.

Step M

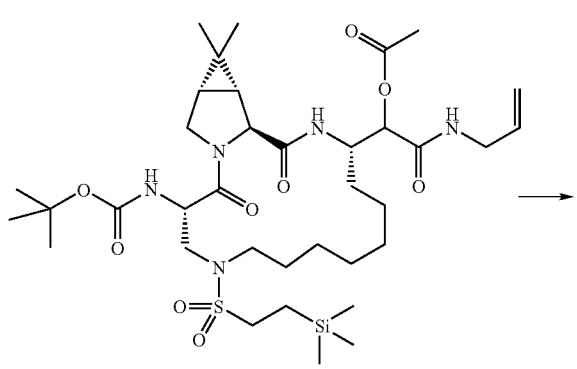

73j

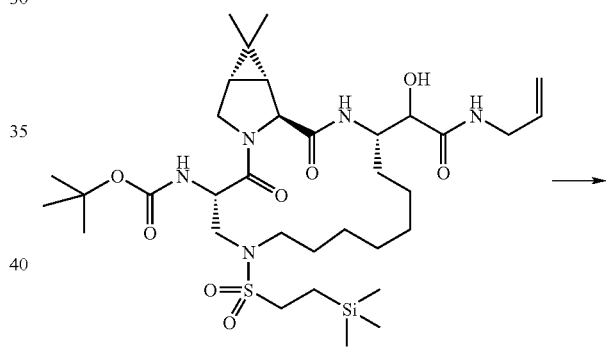

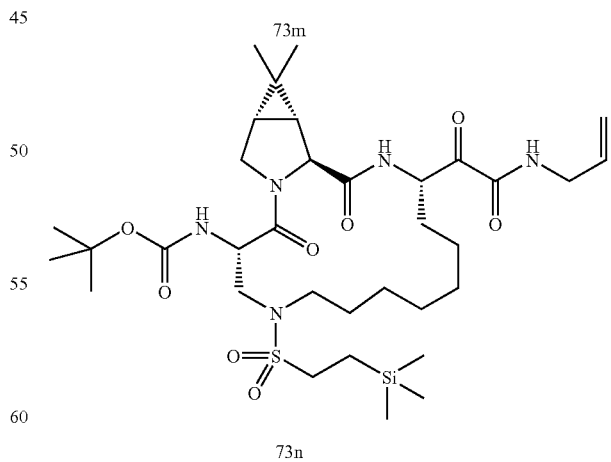

73n

A solution of hydroxyamide 73m (1 mmol) in 20 mL of dry dichloromethane will be treated with Dess-Martin periodinane (2.5 mmol). The reaction mixture will be stirred at room temperature for 30 min. The mixture will be treated with aqueous 1M sodium thiosulfate solution (20 mL) and aqueous saturated sodium bicarbonate solution (10 mL) and stirred for 15 min. The mixture will be extracted with dichloromethane (3×30 mL). The combined organic layers will be dried over magnesium sulfate, filtered, and concentrated. The ketoamide product 73n will be purified by column chromatography.

Step O

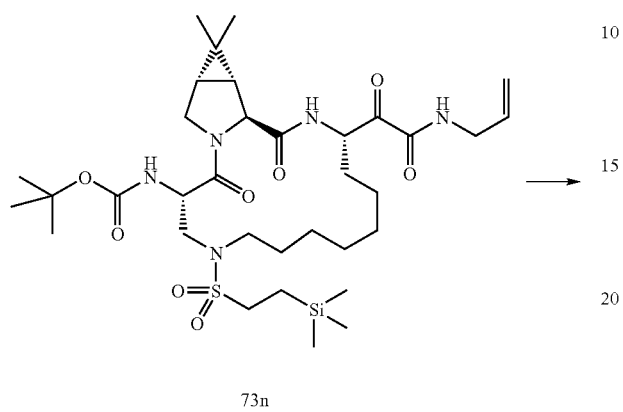

73n

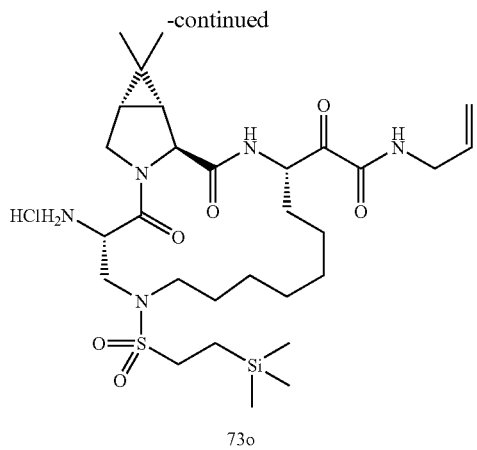

73o

The N-Boc protected amine 73n (0.1 mmol) will be dissolved in 5 mL of 4M HCl solution in dioxanes. The resulting solution will be stirred for 30 min and then evaporated under reduced pressure to give the amine hydrochloride product 73o.

Step P

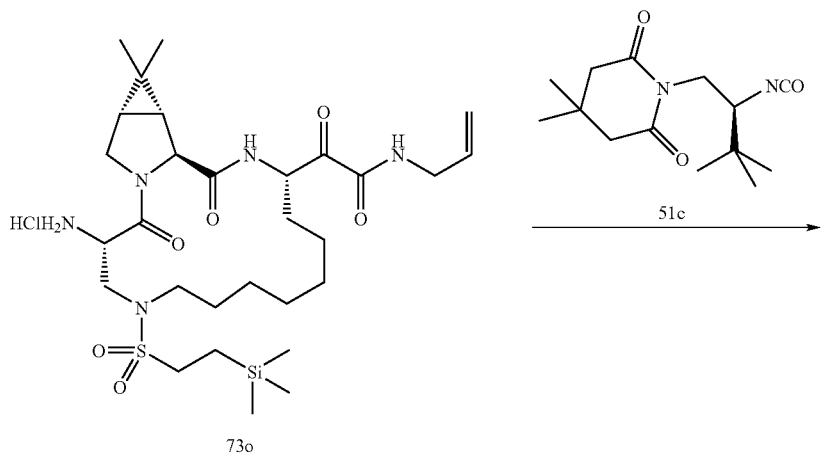

73o

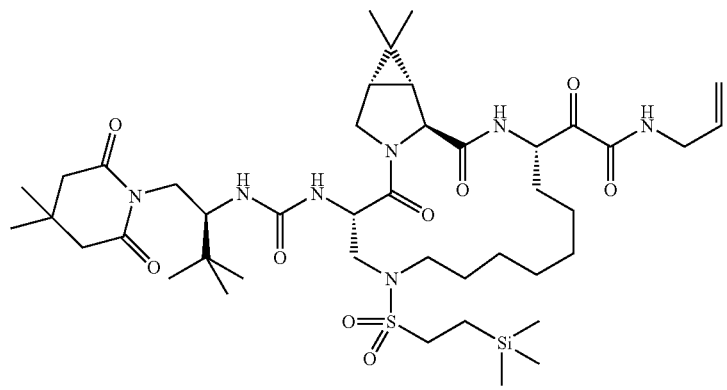

73p

The amine hydrochloride 73o (0.1 mmol) will be dissolved in 5 mL of dichloromethane and treated with 20 drops of aqueous saturated sodium bicarbonate solution followed by a solution of isocyanate 51c (0.12 mmol) in toluene. The mixture will be stirred for 5 h and then diluted with 50 mL of dichloromethane and dried over magnesium sulfate. The mixture will be filtered, and concentrated under reduced pressure. The product 73p will be purified by column chromatography on silica gel.

Step Q

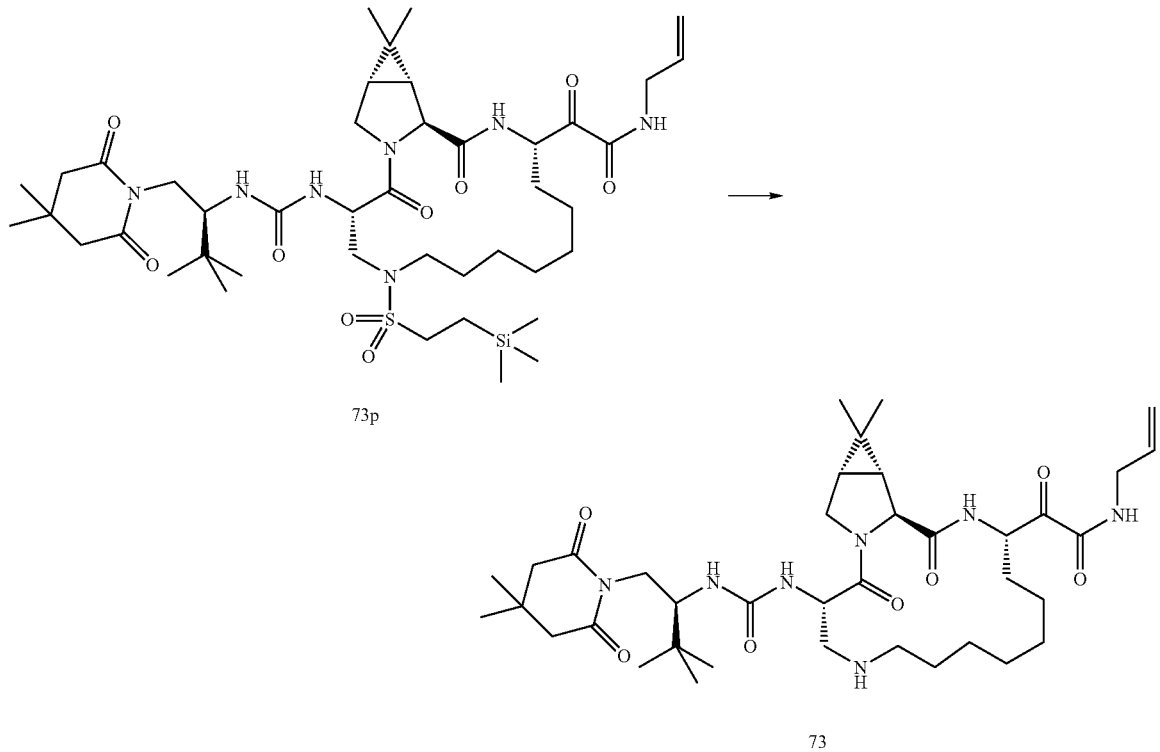

The SES-protected amine 73p (0.1 mmol) will be dissolved in 2 mL of DMF and treated with cesium fluoride (0.4 mmol). The reaction mixture will be stirred at room temperature for 4 h and poured onto water (10 mL). The mixture will be extracted with ethyl acetate (3×20 mL). The combined organic layers will be dried over magnesium sulfate, filtered and concentrated under reduced pressure. The macrocyclic amine 73 will be purified by column chromatography on silica gel.

Preparative Example 74

Preparation of

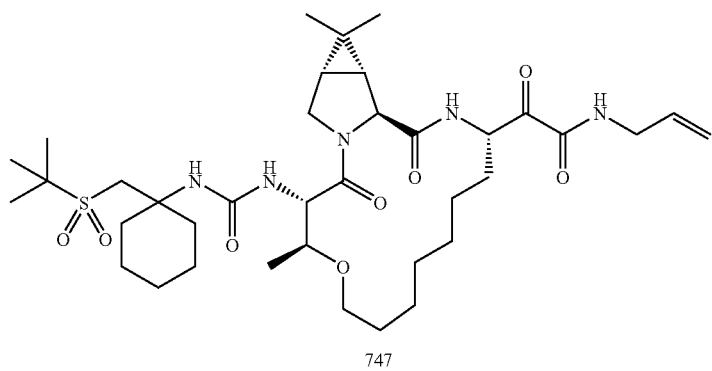

Step A

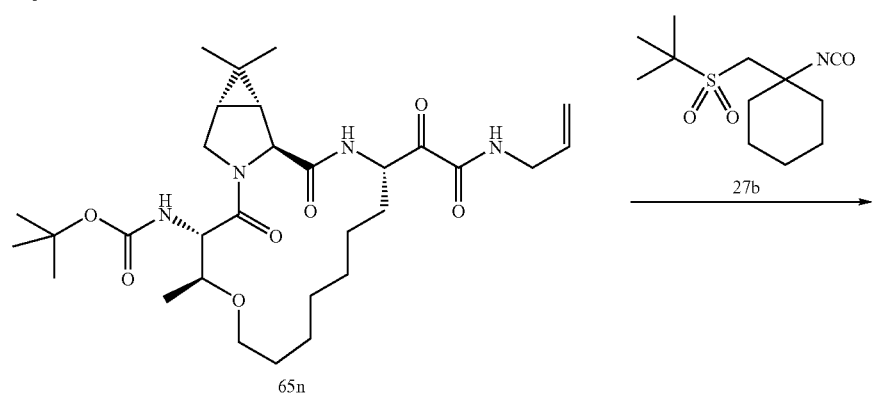

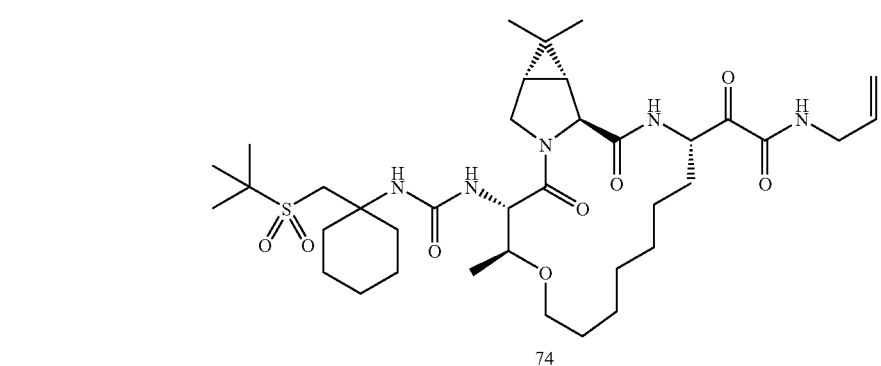

The N-Boc amine 65n (60 mg) was dissolved in 10 mL of 4M HCl solution in dioxanes. The resulting solution was stirred at room temperature for 30 min. All the volatiles were removed under reduced pressure and the residue was placed under high vacuum for 3 h. The resulting amine salt was dissolved in 5 mL of dry dichloromethane and cooled to 0° C. Then, 20 drops of aqueous saturated sodium bicarbonate solution were added followed by a soln. of the isocyanate 27b in toluene (1.2 eq, 0.6 mL of a 0.2M soln. in toluene) and stirring was continued for 10 min. The cooling bath was removed and the mixture was stirred at room temp for 2 h. The reaction mixture was diluted with dichloromethane (60 mL) and dried over magnesium sulfate, filtered and concentrated under reduced pressure. The residue was chromatographed on silica gel (gradient: acetone/hexanes; 1:9 to 1:1) to afford the product 74 (45 mg, 59%) as a white solid. $^1$H NMR (500 MHz, CDCl$_3$): δ 8.11 (br s, 1H), 7.40-7.69 (br s, 1H), 6.08-6.43 (br s, 1H), 5.91 (ddt, 1H, J=5.6, 10.4, 17.3 Hz), 5.70 (br s, 1H), 5.29 (dd, 1H, J=1.2, 17.3 Hz), 5.24 (dd, 1H, J=1.2, 10.4 Hz), 4.66 (d, 1H, J=9.4 Hz), 4.46 (br s, 1H), 4.38 (m, 1H), 4.25 (d, 1H, J=10.7 Hz), 4.06 (m, 2H), 3.98 (m, 1H), 3.71 (dq, 5.6, 11.6 Hz), 3.64 (ddd, 1H, J=5.0, 5.3, 9.7 Hz), 3.25 (m, 1H), 2.88 (d, 1H, J=13.5 Hz), 2.47 (br s, 1H), 2.19 (d, 1H, J=11.6 Hz), 1.39 (s, 9H), 1.28-1.99 (m, 22H), 1.21 (d, 3H, J=5.6 Hz), 1.13 (m, 1H), 1.04 (s, 3H), 0.91 (s, 3H); $^{13}$C NMR (CDCl$_3$, 125 MHz) δ 198.7, 173.0, 171.3, 159.4, 157.0, 133.4, 117.7, 75.2, 67.7, 61.2, 60.8, 55.6, 54.6, 48.7, 42.2, 36.3, 31.6, 28.9, 27.9, 27.8, 27.1, 26.8, 25.9, 24.8, 24.0, 23.6, 21.9, 21.5, 19.4, 15.8, 13.4 ppm; HRMS calcd for C$_{37}$H$_{62}$N$_5$O$_8$S [M+H]$^+$: 736.4319, found 736.4325.

Preparative Example 75

Preparation of

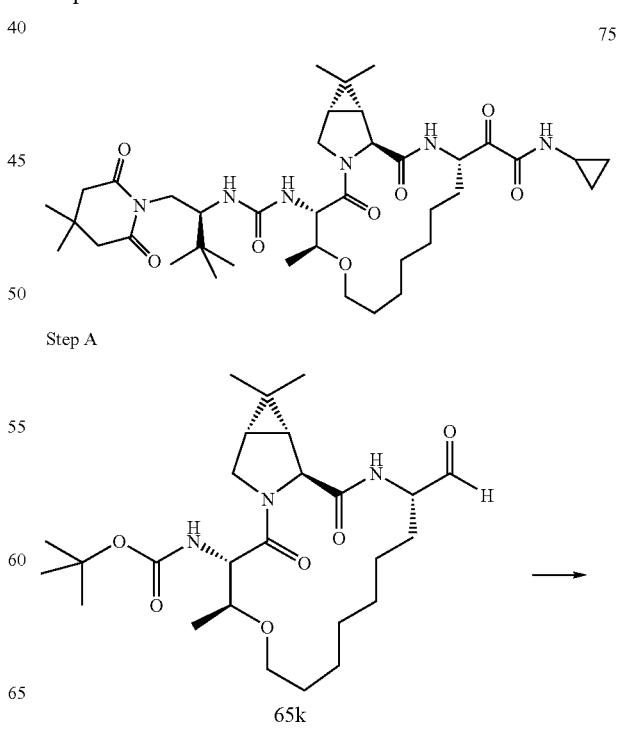

Step A

-continued

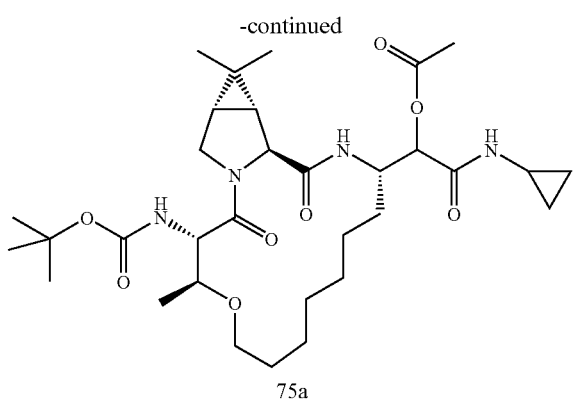
75a

A solution of aldehyde 65k (710 mg) in 30 mL of dry dichloromethane was treated with cyclopropylisocyanide (Oakwood Prod., 2.0 eq, 0.25 mL, d 0.8) and acetic acid (2 eq, 0.16 mL, d 1.049). The mixture was stirred at room temp for 5 h. All the volatiles were removed under reduced pressure and the residue was chromatographed on silica gel (gradient: acetone/hexanes; 15:85 to 55:45) to afford the product 75a (740 mg, 83%) as a white solid.

Step B

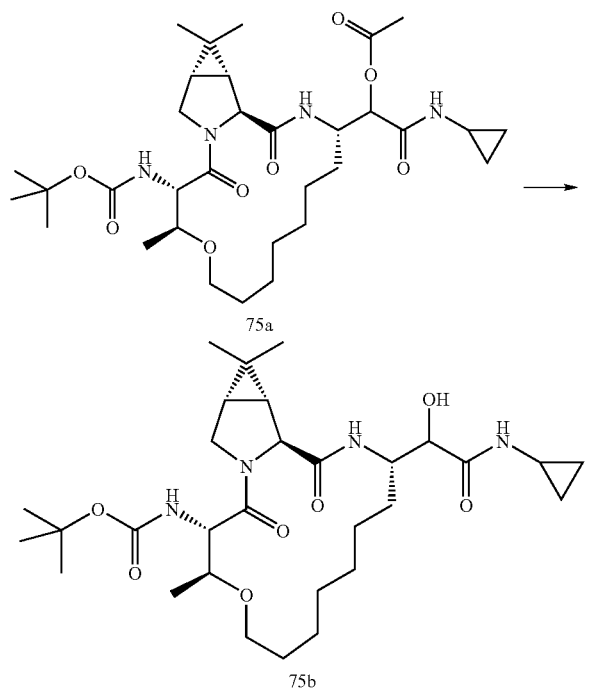
75a

75b

Step D

A solution of acetate 75a (740 mg) in 20 mL of a 2:1 mixture of THF/water was treated with lithium hydroxide monohydrate (2.5 eq, 125 mg) and stirred for approx 30 min until all the starting material had been consumed as determined by TLC analysis (ethyl acetate/hexanes; 8:2). The reaction mixture was diluted with 50 mL of aqueous saturated sodium bicarbonate solution and extracted with dichloromethane (3×80 mL). The combined organic layers were dried over magnesium sulfate, filtered and concentrated to afford the product 75b (688 mg, 98%) as a colorless semi-solid which was used without further purification.

Step C

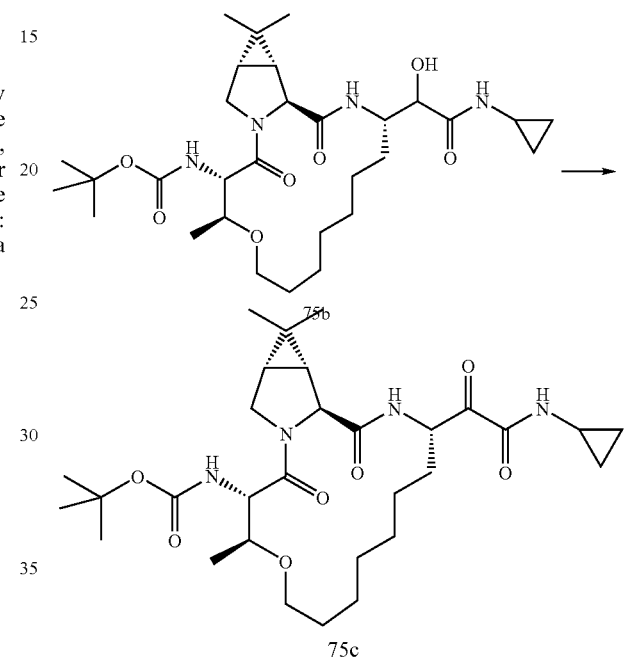
75b

75c

A solution of hydroxyamide 75b (1.192 mmol) in 25 mL of dry dichloromethane was treated with Dess-Martin periodinane (2.0 eq, 1.01 g). The reaction mixture was stirred at room temperature for 30 min. The mixture was treated with aqueous 1M sodium thiosulfate solution (30 mL) and stirred for 5 min. Aqueous saturated sodium bicarbonate solution (30 mL) was also added and stirring was continued for further 10 min. The mixture was extracted with dichloromethane (3×80 mL). The combined organic layers were dried over magnesium sulfate, filtered, and concentrated. The residue was chromatographed on silica gel (gradient: acetone/hexanes; 5:95 to 4:6) to afford the product 75c (476 mg, 69%) as white solid.

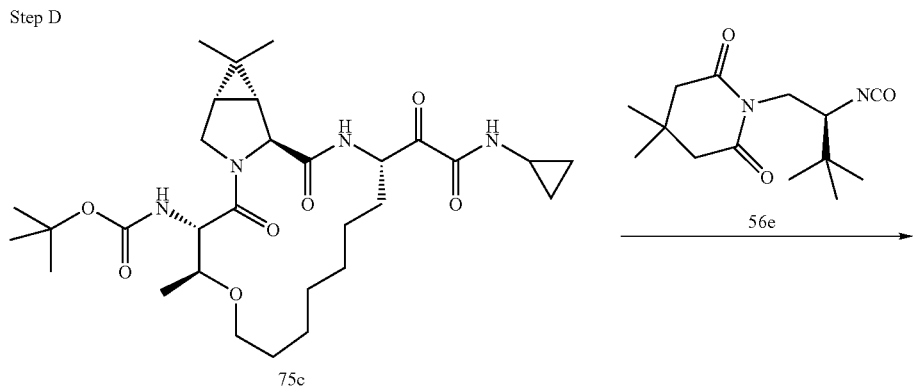
75c

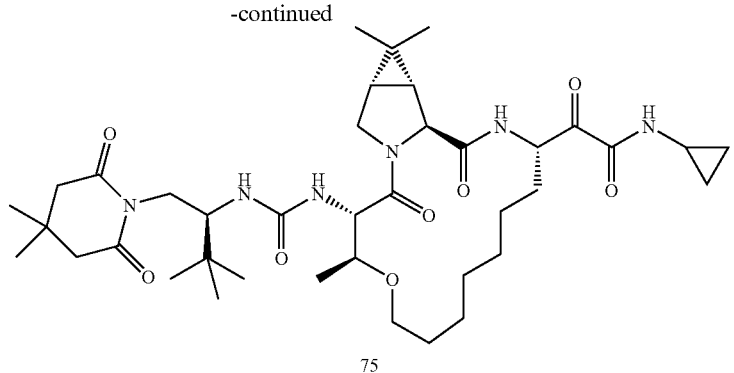

75

The N-Boc amine 75c (60 mg) was dissolved in 10 mL of 4M HCl solution in dioxanes. The resulting solution was stirred at room temperature for 30 min. All the volatiles were removed under reduced pressure and the residue was placed under high vacuum for 3 h. The resulting amine salt was dissolved in 5 mL of dry dichloromethane and cooled to 0° C. Then, 10 drops of aqueous saturated sodium bicarbonate solution were added. After 10 min, a soln of the isocyanate 56e was added dropwise (1.2 eq, 0.59 mL of a 0.216M solution in toluene) and stirring was continued for 10 min. The cooling bath was removed and the mixture was stirred at room temp for 2 h. The reaction mixture was diluted with dichloromethane (70 mL) and dried over magnesium sulfate, filtered and concentrated under reduced pressure. The residue was chromatographed on silica gel (gradient: acetone/hexanes; 1:9 to 1:1) to afford the product 75 (41 mg, 53%) as a white solid. $^1$H NMR (500 MHz, CDCl$_3$): δ 8.12 (br s, 1H), 7.40-7.70 (br s, 1H), 6.28 (br s, 1H), 5.68 (br s, 1H), 5.37 (br s, 1H), 4.62 (s, 1H), 4.49 (br s, 1H), 4.22 (d, 1H, J=10.7 Hz), 4.05 (dd, 1H, J=5.0, 10.4 Hz), 3.94 (d, 1H, J=1.6 Hz), 3.88 (dd, 1H, J=10.4, 10.7 Hz), 3.82 (q, 1H, J=11.0 Hz), 3.69 (m, 1H), 3.62 (ddd, 1H, J=5.0, 5.6, 9.4 Hz), 3.20 (m, 1H), 2.89 (ddd, 1H, J=3.4, 7.2, 14.8 Hz), 2.55 (d, 2H, J=17.0 Hz), 2.48 (d, 2H, J=17.0 Hz), 1.79-1.99 (m, 4H), 1.28-1.69 (m, 10H), 1.14 (d, 3H, J=6.0 Hz), 1.10 (s, 6H), 1.00 (s, 3H), 0.99 (s, 9H), 0.90 (m, 2H), 0.83 (s, 3H), 0.71 (m, 2H); $^{13}$C NMR (CDCl$_3$, 125 MHz) δ 198.8, 172.8, 171.5, 160.9, 157.8, 75.5, 68.1, 60.8, 57.2, 55.9, 48.7, 46.8, 35.2, 29.3, 28.6, 28.3, 27.7, 26.9, 26.8, 24.8, 24.4, 23.1, 19.3, 16.3, 13.6, 6.8 ppm; HRMS calcd for C$_{39}$H$_{63}$N$_6$O$_8$ [M+H]$^+$: 743.4707, found 743.4686.

Preparative Example 76

Preparation of

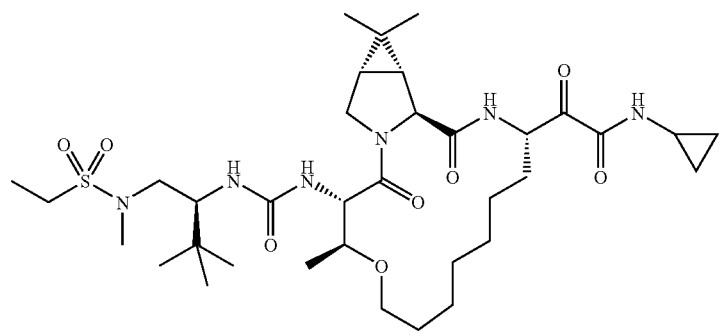

76

Step A

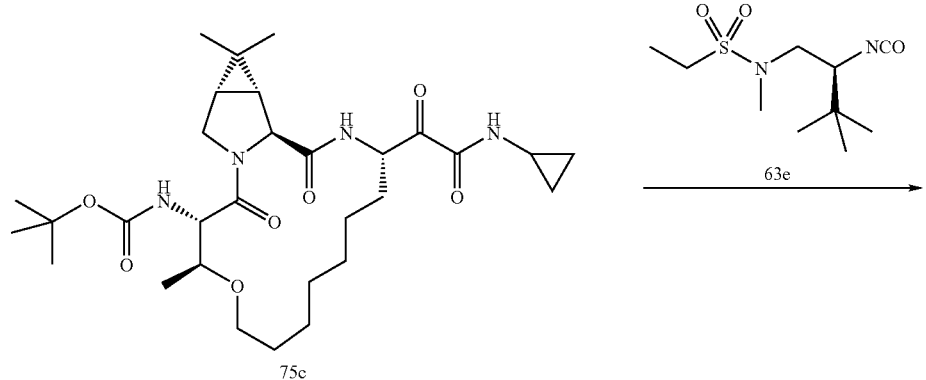

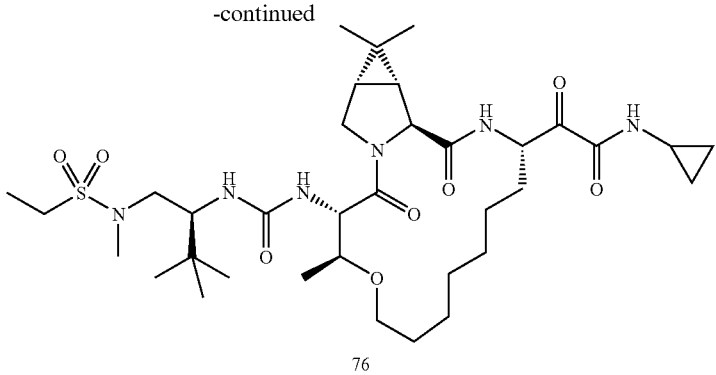

76

The N-Boc amine 75c (60 mg) was dissolved in 10 mL of 4M HCl solution in dioxanes. The resulting solution was stirred at room temperature for 30 min. All the volatiles were removed under reduced pressure and the residue was placed under high vacuum overnight. The resulting amine salt was dissolved in 5 mL of dichloromethane and cooled to 0° C. Then, 10 drops of aqueous saturated sodium bicarbonate solution were added. After 10 min a soln. of the isocyanate 63e was added dropwise (1.2 eq, 0.95 mL of a 0.131M solution in toluene) and stirring was continued for 10 min. The cooling bath was removed and the mixture was stirred at room temp for 3 h. The reaction mixture was diluted with dichloromethane (70 mL) and dried over magnesium sulfate, filtered and concentrated under reduced pressure. The residue was chromatographed on silica gel (gradient: acetone/hexanes; 2:8 to 6:4) to afford the product 76 (54 mg, 72%) as a white solid. $^1$H NMR (500 MHz, CDCl$_3$): δ 8.22 (br s, 1H), 7.58 (br s, 1H), 6.13 (br s, 1H), 5.75 (br s, 1H), 5.15 (d, 1H, J=8.5 Hz), 4.68 (br s, 1H), 4.56 (s, 1H), 4.28 (d, 1H, J=10.7 Hz), 4.06 (dd, 1H, J=4.7, 10.4 Hz), 3.99 (dd, 1H, J=9.1, 9.7 Hz), 3.60 (m, 2H), 3.47 (dd, 1H, J 12.2, 13.2 Hz), 3.19 (m, 1H), 3.07 (m, 3H), 2.94 (s, 3H), 2.87 (ddd, 1H, J=4.0, 7.8, 15.1 Hz), 1.72-1.99 (m, 4H), 1.37 (t, 3H, J=7.5 Hz), 1.27-1.68 (m, 9H), 1.21 (d, 3H, J=6.0 Hz), 1.13 (m, 1H), 1.01 (s, 3H), 0.92 (s, 9H), 0.89 (s, 3H), 0.87 (m, 2H), 0.71 (m, 2H); $^{13}$C NMR (CDCl$_3$, 125 MHz) δ 199.5, 172.8, 171.6, 160.8, 158.1, 75.8, 68.4, 60.6, 56.2, 54.4, 50.4, 48.5, 45.7, 34.7, 34.5, 32.1, 31.6, 28.6, 27.8, 27.7, 27.0, 26.9, 26.7, 24.9, 24.6, 23.0, 19.2, 16.2, 13.5, 8.5, 6.7 ppm; HRMS calcd for C$_{35}$H$_{61}$N$_6$O$_8$S [M+H]$^+$: 725.4272, found 725.4292.

Preparative Example 77

Preparation of

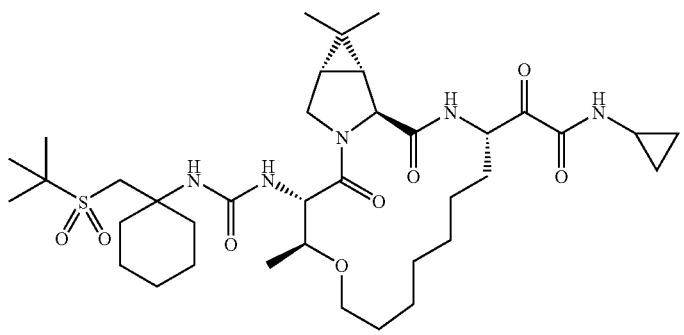

77

Step A

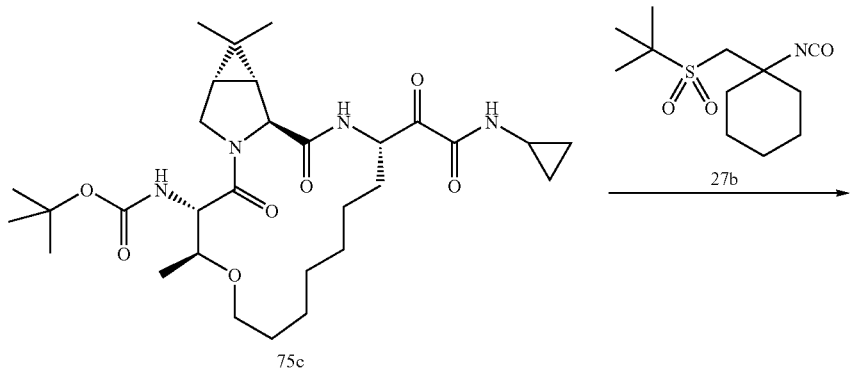

75c

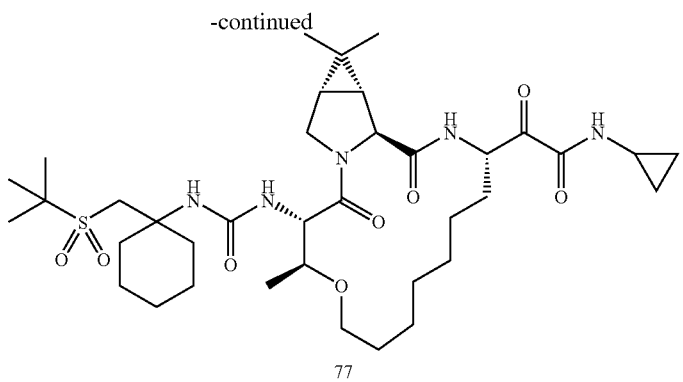

77

The N-Boc amine 75c (60 mg) was dissolved in 10 mL of 4M HCl solution in dioxanes. The resulting solution was stirred at room temperature for 30 min. All the volatiles were removed under reduced pressure and the residue was placed under high vacuum for 3 h. The resulting amine salt was dissolved in 5 mL of dry dichloromethane and cooled to 0° C. Then, 20 drops of aqueous saturated sodium bicarbonate solution were added followed by a soln of the isocyanate 27b in toluene (1.2 eq, 0.6 mL of a 0.2M soln in toluene) and stirring was continued for 10 min. The cooling bath was removed and the mixture was stirred at room temp for 2 h. The reaction mixture was diluted with dichloromethane (60 mL) and dried over magnesium sulfate, filtered and concentrated under reduced pressure. The residue was chromatographed on silica gel (gradient: acetone/hexanes; 2:8 to 6:4) to afford the product 77 (50 mg, 65%) as a white solid. $^1$H NMR (500 MHz, CDCl$_3$): δ 8.12 (br s, 1H), 7.33-7.63 (br s, 1H), 6.07-6.47 (br s, 1H), 5.67 (br s, 1H), 4.65 (d, 1H, J=9.7 Hz), 4.45 (br s, 1H), 4.37 (m, 1H), 4.24 (d, 1H, J=10.7 Hz), 4.07 (dd, 1H, J=5.0, 10.7 Hz), 3.70 (dq, 1H, 5.9, 9.7 Hz), 3.64 (ddd, 1H, J=5.0, 5.6, 9.7 Hz), 3.24 (m, 1H), 2.89 (ddd, 1H, J=3.7, 7.5, 14.5 Hz), 2.88 (m, 1H), 2.47 (br s, 1H), 2.18 (d, 1H, J=12.6 Hz), 1.74-1.97 (m, 5H), 1.39 (s, 9H), 1.27-1.73 (m, 17H), 1.20 (d, 3H, J=6.3 Hz), 1.11 (m, 1H), 1.04 (s, 3H), 0.91 (s, 3H), 0.90 (m, 2H), 0.73 (m, 2H); $^{13}$C NMR (CDCl$_3$, 125 MHz) δ 198.7, 173.0, 171.3, 161.0, 157.0, 75.2, 67.8, 61.1, 60.8, 55.5, 54.6, 50.1, 48.6, 36.3, 31.6, 28.8, 27.9, 27.0, 26.9, 25.9, 24.8, 24.0, 23.6, 23.1, 21.9, 21.5, 19.4, 15.8, 13.4, 6.9, 6.8 ppm. HRMS calcd for C$_{37}$H$_{62}$N$_5$O$_8$S [M+1]$^+$: 736.4319, found 736.4329.

Preparative Example 78

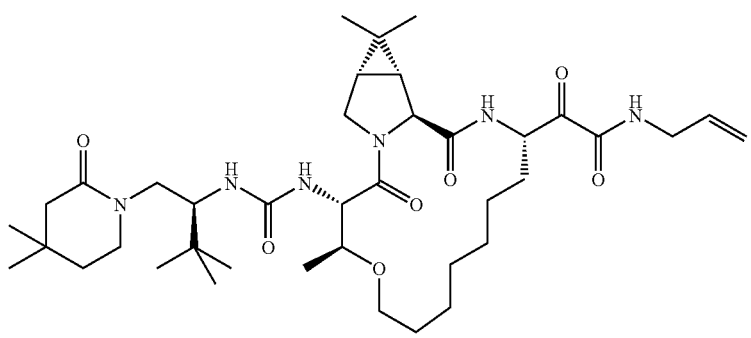

78

Step A

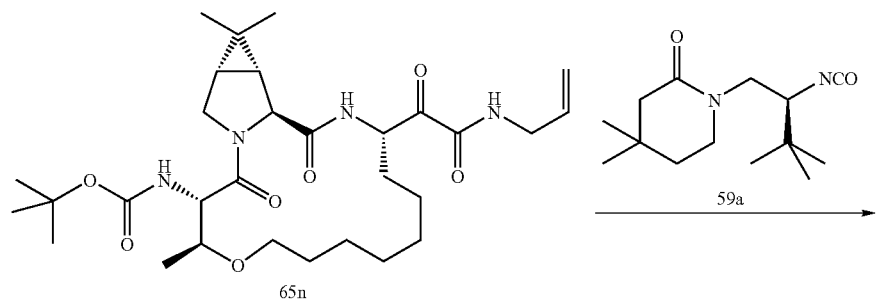

65n 59a

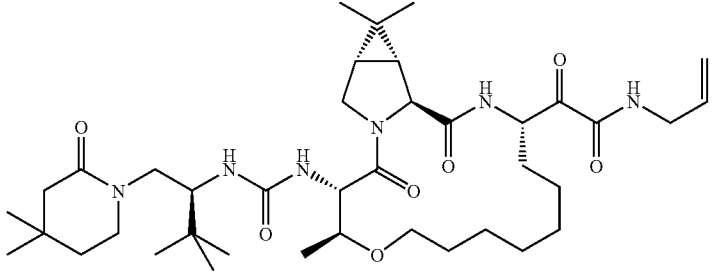

78

The N-Boc amine 65n (60 mg) was dissolved in 10 mL of 4M HCl solution in dioxanes. The resulting solution was stirred at room temperature for 30 min. All the volatiles were removed under reduced pressure and the residue was placed under high vacuum for 3 h. The resulting amine salt was dissolved in 5 mL of dry dichloromethane and cooled to 0° C. Then, 20 drops of aqueous saturated sodium bicarbonate solution were added followed by a solution of the isocyanate 59a in toluene (1.2 eq, 0.6 mL of a 0.2M soln in toluene) and stirring was continued for 10 min. The cooling bath was removed and the mixture was stirred at room temp for 3 h. The reaction mixture was diluted with dichloromethane (60 mL) and dried over magnesium sulfate, filtered and concentrated under reduced pressure. The residue was chromatographed on silica gel (gradient: acetone/(hexanes-dichloromethane; 1:1); 1:9 to 1:1) to afford the product 78 (51 mg, 67%) as a white solid. $^1$H NMR (CDCl$_3$, 500 MHz) δ 8.17 (br s, 1H), 6.42-6.79 (br s, 1H), 5.90 (ddt, 1H, J=5.6, 10.7, 17.0 Hz), 5.73 (br s, 1H), 5.57 (br s, 1H), 5.27 (d, 1H, J=17.0 Hz), 5.22 (d, 1H, J=10.0 Hz), 4.62 (dd, 1H, J=9.1, 9.7 Hz), 4.52 (br s, 1H), 4.29 (m, 2H), 3.86-4.11 (m, 4H), 3.64 (m, 3H), 3.17 (m, 2H), 2.74 (d, 1H, J=11.9 Hz), 2.24 (d, 1H, J=17.3 Hz), 2.10 (d, 1H, J=17.0 Hz), 1.95 (m, 4H), 1.24-1.68 (m, 11H), 1.16 (d, 3H, J=5.9 Hz), 1.11 (m, 1H), 1.02 (s, 3H), 1.01 (s, 6H), 0.95 (s, 9H), 0.87 (s, 3H); $^{13}$C NMR (CDCl$_3$, 125 MHz) δ 196.8, 172.9, 171.6, 170.7, 159.4, 158.2, 133.6, 117.5, 75.7, 68.2, 60.8, 56.0, 55.3, 48.5, 46.8, 46.2, 44.9, 42.3, 35.7, 34.8, 32.3, 31.6, 30.2, 28.6, 28.4, 27.8, 27.7, 27.1, 27.0, 26.8, 24.8, 24.5, 19.3, 16.5, 13.6 ppm. HRMS calcd for C$_{39}$H$_{65}$N$_6$O$_7$ [M+1]$^+$: 729.4915, found 729.4917.

Preparative Example 79

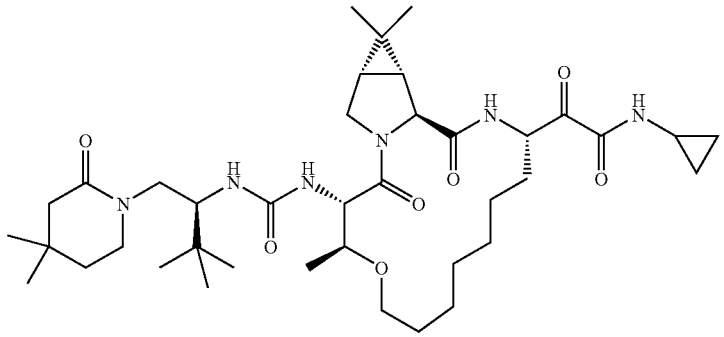

79

Step A

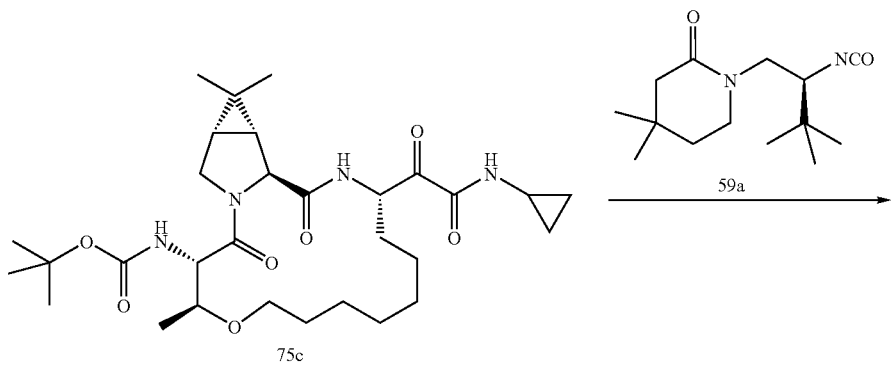

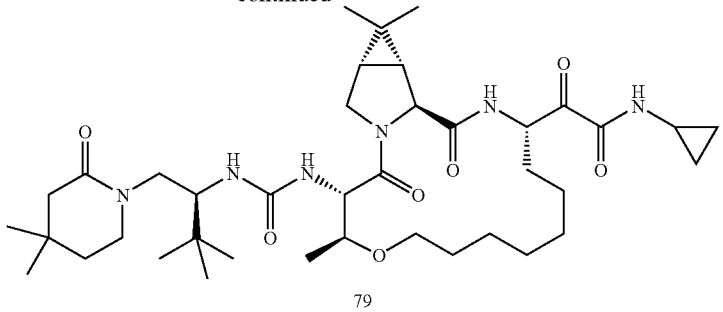

The N-Boc amine 75c (60 mg) was dissolved in 10 mL of 4M HCl solution in dioxanes. The resulting solution was stirred at room temperature for 30 min. All the volatiles were removed under reduced pressure and the residue was placed under high vacuum for 3 h. The resulting amine salt was dissolved in 5 mL of dry dichloromethane and cooled to 0° C. Then, 20 drops of aqueous saturated sodium bicarbonate solution were added followed by a solution of the isocyanate 59a in toluene (1.2 eq, 0.6 mL of a 0.2M soln in toluene) and stirring was continued for 10 min. The cooling bath was removed and the mixture was stirred at room temp for 3 h. The reaction mixture was diluted with dichloromethane (60 mL) and dried over magnesium sulfate, filtered and concentrated under reduced pressure. The residue was chromatographed on silica gel (gradient: acetone/(hexanes-dichloromethane, 1:1); 1:9 to 1:1) to afford the product 79 (36 mg, 48%) as a white solid. $^1$H NMR (CDCl$_3$, 500 MHz) δ 8.19 (br s, 1H), 6.38-6.70 (br s, 1H), 5.73 (br s, 1H), 5.55 (d, 1H, J=7.8 Hz), 4.61 (t, 1H, J=9.7 Hz), 4.51 (br s, 1H), 4.27 (m, 2H), 4.05 (dd, 1H, J=5.0, 10.4 Hz), 3.95 (dd, 1H, J=9.4, 9.7 Hz); 3.62 (m, 3H), 3.18 (m, 2H), 2.90 (ddd, 1H, J=3.7, 7.2, 14.8 Hz), 2.73 (d, 1H, J=12.6 Hz), 2.21 (d, 1H, J=17.0 Hz), 2.09 (d, 1H, J=17.3 Hz), 1.93 (br s, 4H), 1.27-1.68 (m, 11H), 1.15 (d, 3H, J=5.9 Hz), 1.11 (m, 1H), 1.02 (s, 3H), 1.00 (s, 6H), 0.94 (s, 9H), 0.87 (m, 2H), 0.86 (s, 3H), 0.73 (m, 2H); $^{13}$C NMR (CDCl$_3$, 125 MHz) δ 197.1, 172.9, 171.6, 170.6, 160.9, 158.2, 75.6, 68.3, 60.7, 56.0, 55.3, 48.5, 46.7, 46.3, 44.9, 35.7, 34.8, 32.4, 31.6, 30.2, 29.7, 28.6, 28.5, 27.8, 27.7, 27.0, 26.7, 24.8, 24.7, 23.1, 19.3, 16.5, 13.6, 6.7, 6.6 ppm. HRMS calcd for C$_{39}$H$_{65}$N$_6$O$_7$ [M+1]$^+$: 729.4915, found 729.4926.

Preparative Example 80

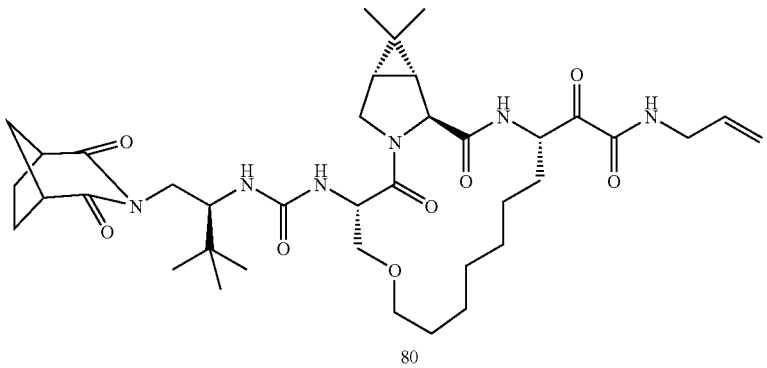

Step A

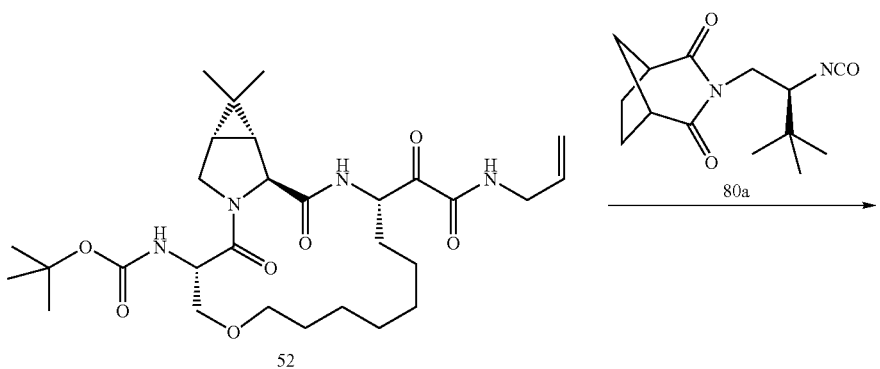

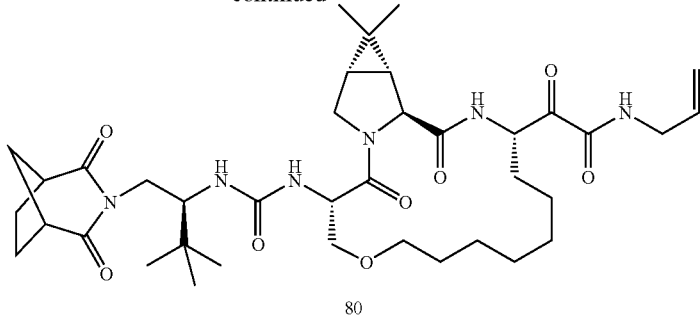

80

The N-Boc amine 52 (60 mg) was dissolved in 10 mL of 4M HCl solution in dioxanes. The resulting solution was stirred at room temperature for 30 min. All the volatiles were removed under reduced pressure and the residue was placed under high vacuum for 3 h. The resulting amine salt was dissolved in 5 mL of dry dichloromethane and cooled to 0° C. Then, 20 drops of aqueous saturated sodium bicarbonate solution were added followed by a solution of the isocyanate 80a in toluene (1.2 eq, 0.8 mL of a 0.155M soln in toluene) and stirring was continued for 10 min. The cooling bath was removed and the mixture was stirred at room temp for 3 h. The reaction mixture was diluted with dichloromethane (60 mL) and dried over magnesium sulfate, filtered and concentrated under reduced pressure. The residue was chromatographed on silica gel (gradient: acetone/hexanes; 2:8 to 6:4) to afford the product 80 (41 mg, 61%) as a white solid. $^1$H NMR (CDCl$_3$, 500 MHz) δ, 8.01 (d, 1H, J=8.2 Hz), 7.65 (br s, 1H), 6.01 (br s, 1H), 5.91 (ddt, 1H, J=5.6, 10.0, 17.0 Hz), 5.68 (dd, 1H, J=9.1, 9.4 Hz), 5.27 (dd, 1H, J=1.2, 17.0 Hz), 5.23 (dd, 1H, J=1.2, 10.0 Hz), 5.20 (m, 1H), 4.98 (br s, 1H); 4.59 (s, 1H), 4.13 (d, 1H, J=10.7 Hz), 4.01 (m, 3H), 3.89 (ddd, 1H, J=2.2, 10.4, 10.7 Hz), 3.79 (dd, 1H, J=3.4, 12.9 Hz), 3.76 (m, 1H), 3.56 (m, 2H), 3.36 (dd, 1H, J=4.1, 7.5 Hz), 3.31 (m, 1H), 3.18 (br s, 1H), 3.14 (br s, 1H), 2.22 (d, 1H, J=10.7 Hz), 2.07 (br s, 2H), 1.73-2.00 (m, 5H), 1.25-1.70 (m, 11H), 1.16 (m, 1H), 1.02 (s, 3H), 0.96 (s, 9H), 0.86 (s, 3H); $^{13}$C NMR (CDCl$_3$, 125 MHz) δ 198.8, 177.4, 172.1, 171.3, 159.3, 157.9, 133.4, 117.7, 71.4, 70.7, 60.7, 56.7, 53.4, 50.8, 48.6, 45.4, 45.2, 42.2, 39.4, 34.7, 33.1, 32.2, 31.0, 28.7, 27.7, 27.5, 27.3, 26.9, 24.3, 19.3, 13.5 ppm. HRMS calcd for C$_{38}$H$_{59}$N$_6$O$_8$ [M+1]$^+$: 727.4394, found 727.4387.

Preparative Example 81

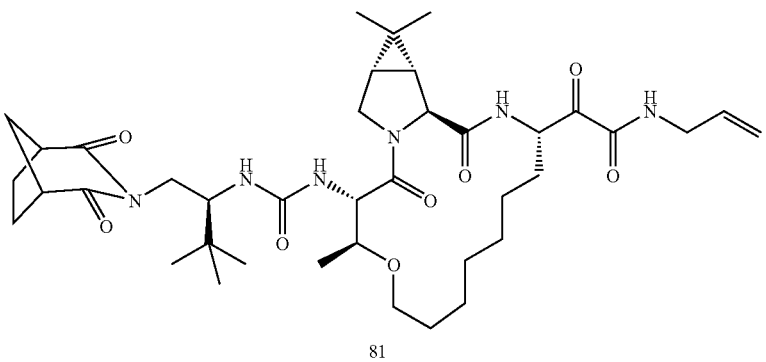

81

Step A

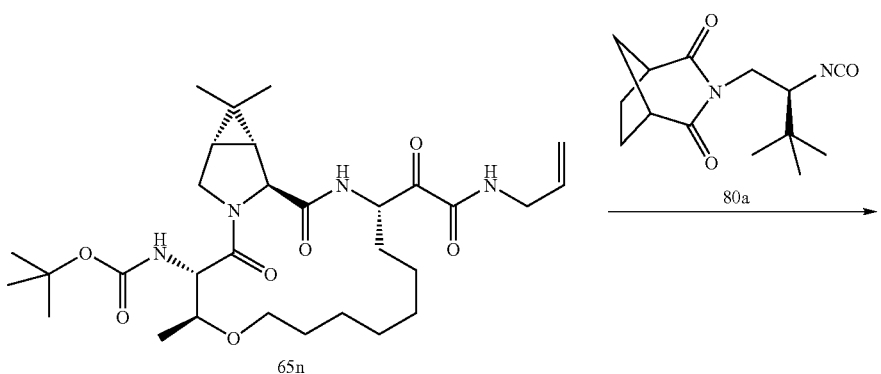

-continued

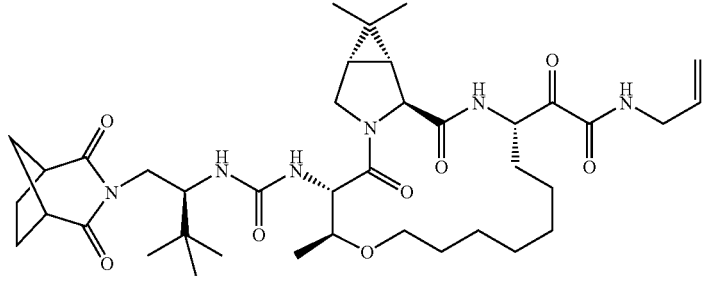

81

The N-Boc amine 65n (60 mg) was dissolved in 10 mL of 4M HCl solution in dioxanes. The resulting solution was stirred at room temperature for 30 min. All the volatiles were removed under reduced pressure and the residue was placed under high vacuum for 3 h. The resulting amine salt was dissolved in 5 mL of dry dichloromethane and cooled to 0° C. Then, 20 drops of aqueous saturated sodium bicarbonate solution were added followed by a solution of the isocyanate 80a in toluene (1.2 eq, 0.8 mL of a 0.155M soln in toluene) and stirring was continued for 10 min. The cooling bath was removed and the mixture was stirred at room temp for 3 h. The reaction mixture was diluted with dichloromethane (60 mL) and dried over magnesium sulfate, filtered and concentrated under reduced pressure. The residue was chromatographed on silica gel (gradient: acetone/hexanes; 2:8 to 6:4) to afford the product 81 (54 mg, 70%) as a white solid. $^1$H NMR (CDCl$_3$, 500 MHz) δ, 8.12 (br s, 1H), 7.39-7.79 (br s, 1H), 6.29 (br s, 1H), 5.91 (ddt, 1H, J=5.9, 10.4, 17.0 Hz), 5.71 (br s, 1H), 5.40 (br s, 1H), 5.27 (dd, 1H, J=1.2, 17.0 Hz), 5.23 (dd, 1H, J=1.2, 10.4 Hz), 4.67 (dd, 1H, J=7.8, 8.1 Hz); 4.50 (br s, 1H), 4.24 (d, 1H, J=10.7 Hz), 4.07 (dd, 1H, J=5.3, 10.4 Hz), 4.03 (m, 1H), 3.97 (ddd, 1H, J=5.6, 5.9, 15.7 Hz), 3.81 (m, 2H), 3.73 (m, 1H), 3.67 (d, 1H, J=12.2 Hz), 3.62 (m, 1H), 3.20 (s, 2H), 3.07 (s, 1H), 2.29 (d, 1H, J=11.0 Hz), 2.07 (br s, 3H), 1.93 (br s, 2H), 1.83 (br s, 3H), 1.28-1.68 (m, 10H), 1.17 (d, 3H, J=5.9 Hz), 1.11 (m, 1H), 1.01 (s, 3H), 0.99 (s, 9H), 0.83 (s, 3H); $^{13}$C NMR (CDCl$_3$, 125 MHz) δ 198.5, 177.1, 172.8, 171.5, 159.4, 158.0, 133.4, 117.7, 75.5, 68.1, 60.8, 57.4, 55.9, 48.7, 45.4, 42.3, 40.4, 34.8, 32.8, 31.7, 28.6, 27.8, 27.6, 27.4, 26.9, 26.8, 24.7, 24.4, 19.4, 16.2, 13.5 ppm. HRMS calcd for C$_{39}$H$_{61}$N$_6$O$_8$ [M+1]$^+$: 741.4551, found 741.4543.

Preparative Example 82

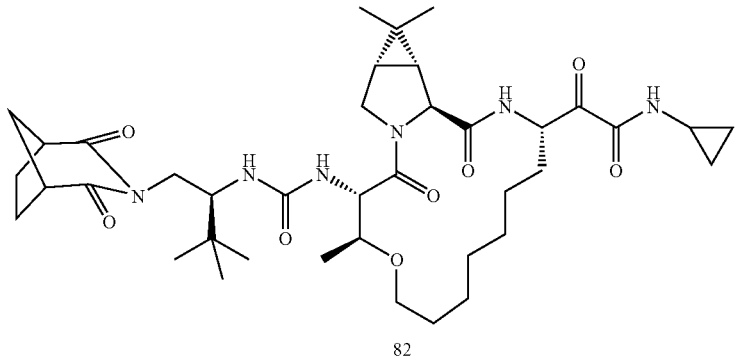

82

Step A

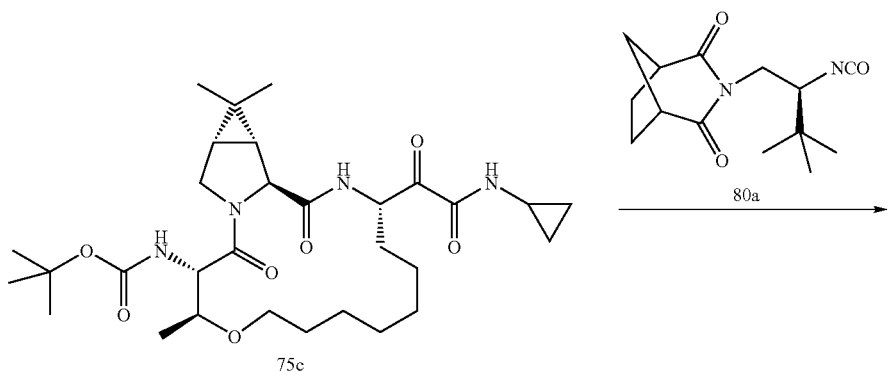

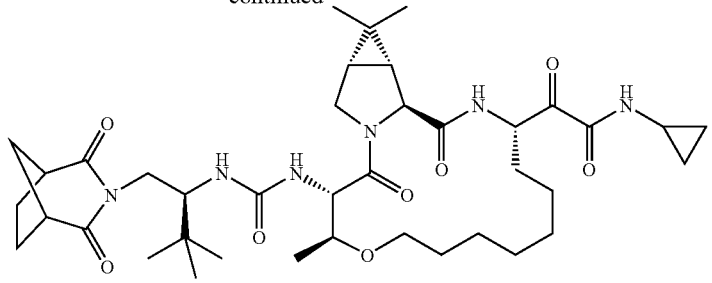

82

The N-Boc amine 75c (60 mg) was dissolved in 10 mL of 4M HCl solution in dioxanes. The resulting solution was stirred at room temperature for 30 min. All the volatiles were removed under reduced pressure and the residue was placed under high vacuum for 3 h. The resulting amine salt was dissolved in 5 mL of dry dichloromethane and cooled to 0° C. Then, 20 drops of aqueous saturated sodium bicarbonate solution were added followed by a solution of the isocyanate 80a in toluene (1.2 eq, 0.8 mL of a 0.155M soln in toluene) and stirring was continued for 10 min. The cooling bath was removed and the mixture was stirred at room temp for 3 h. The reaction mixture was diluted with dichloromethane (60 mL) and dried over magnesium sulfate, filtered and concentrated under reduced pressure. The residue was chromatographed on silica gel (gradient: acetone/hexanes; 2:8 to 6:4) to afford the product 82 (50 mg, 65%) as a white solid. $^1$H NMR (CDCl$_3$, 500 MHz) δ 8.12 (br s, 1H), 7.38-7.68 (br s, 1H), 6.28 (br s, 1H), 5.68 (br s, 1H), 5.39 (br s, 1H), 4.66 (dd, 1H, J=7.5, 7.5 Hz), 4.49 (br s, 1H), 4.23 (d, 1H, J=10.4 Hz), 4.06 (dd, 1H, J=5.0, 10.4 Hz); 3.81 (m, 2H), 3.71 (m, 1H), 3.67 (d, 1H, J=12.2 Hz), 3.61 (m, 1H), 3.19 (br s, 2H), 3.07 (s, 1H), 2.89 (ddd, 1H, J=3.7, 7.5, 14.8 Hz), 2.29 (d, 1H, J=11.0 Hz), 1.98-2.13 (m, 3H), 1.75-1.96 (m, 6H), 1.26-1.67 (m, 9H), 1.17 (d, 3H, J=5.9 Hz), 1.10 (m, 1H), 1.00 (s, 3H), 0.98 (s, 9H), 0.90 (m, 2H), 0.83 (s, 3H), 0.72 (m, 2H); $^{13}$C NMR (CDCl$_3$, 125 MHz) δ 198.9, 178.8, 172.8, 171.5, 160.9, 158.0, 75.5, 68.1, 60.8, 57.4, 55.9, 48.7, 45.4, 40.2, 34.8, 32.8, 31.7, 28.6, 27.8, 27.7, 27.4, 26.9, 26.8, 24.8, 24.4, 23.1, 19.3, 16.2, 13.5, 6.9, 6.8 ppm.

Preparative Example 83

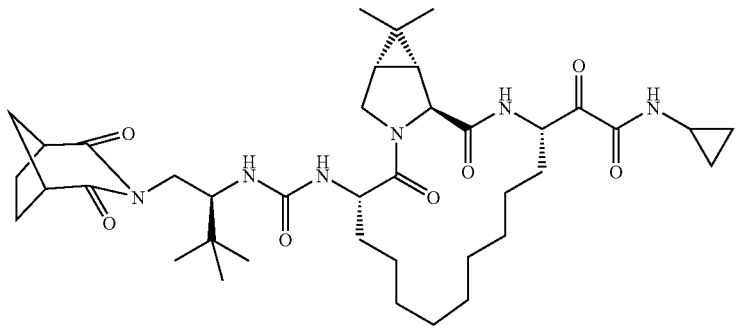

83

Step A

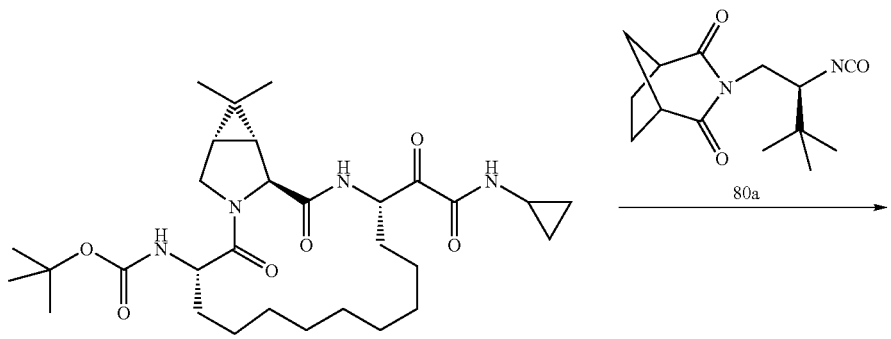

-continued

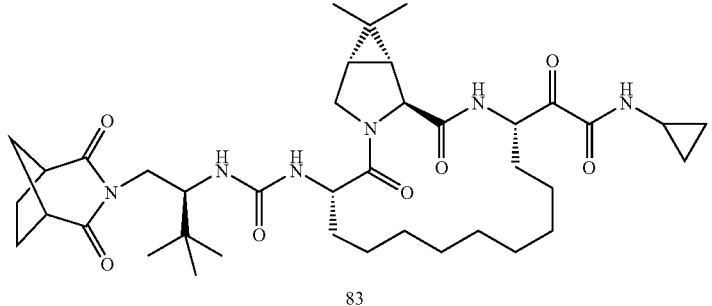

83

The N-Boc amine 33 (60 mg) was dissolved in 10 mL of 4M HCl solution in dioxanes. The resulting solution was stirred at room temperature for 30 min. All the volatiles were removed under reduced pressure and the residue was placed under high vacuum for 3 h. The resulting amine salt was dissolved in 5 mL of dry dichloromethane and cooled to 0° C. Then, 20 drops of aqueous saturated sodium bicarbonate solution were added followed by a solution of the isocyanate 80a in toluene (1.2 eq, 0.8 mL of a 0.155M soln in toluene) and stirring was continued for 10 min. The cooling bath was removed and the mixture was stirred at room temp for 3 h. The reaction mixture was diluted with dichloromethane (60 mL) and dried over magnesium sulfate, filtered and concentrated under reduced pressure. The residue was chromatographed on silica gel (gradient: acetone/hexanes; 1:9 to 1:1) to afford the product 83 (63 mg, 81%) as a white solid.

Example compounds are shown in Tables 1 and 2 below. The Ki values for the compounds are rated as follows:

"A" for Ki values less than 100 nM, "B" for Ki values greater than or equal to 100 nM but less than 1 μM and "C" for Ki values greater than or equal to 1 μM.

TABLE 1

| Example | Structure | Binding Activity |
|---|---|---|
| 1 | 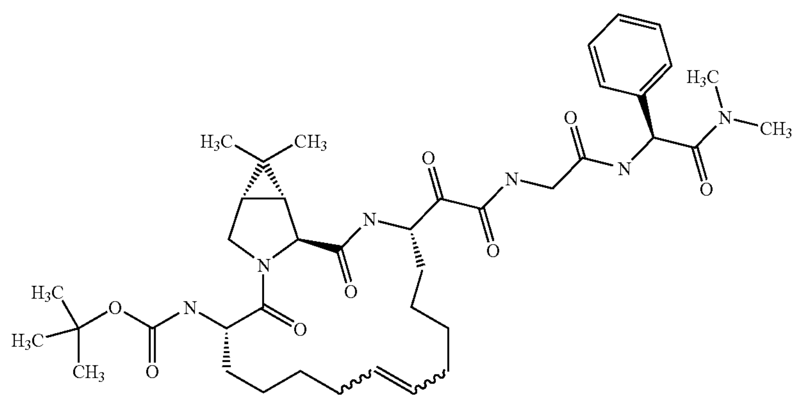 | A |
| 2 | 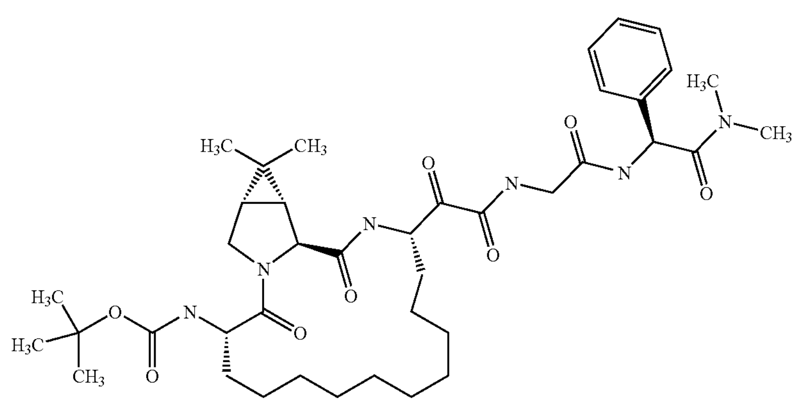 | A |

TABLE 1-continued

| Example | Structure | Binding Activity |
|---------|-----------|------------------|
| 3 | 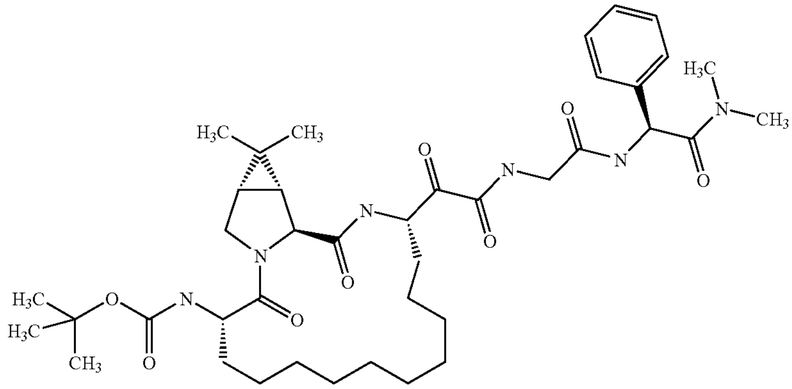 | A |
| 4 | 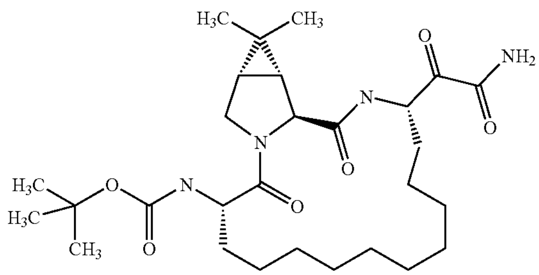 | A |
| 5 | 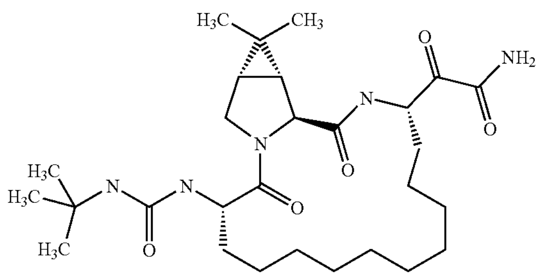 | A |
| 6 | 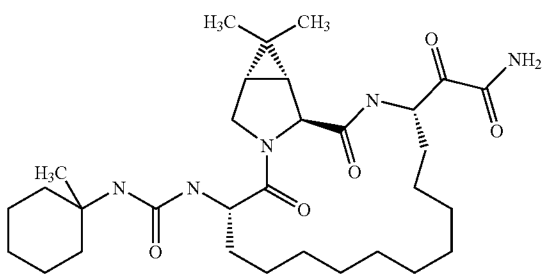 | A |
| 7 | 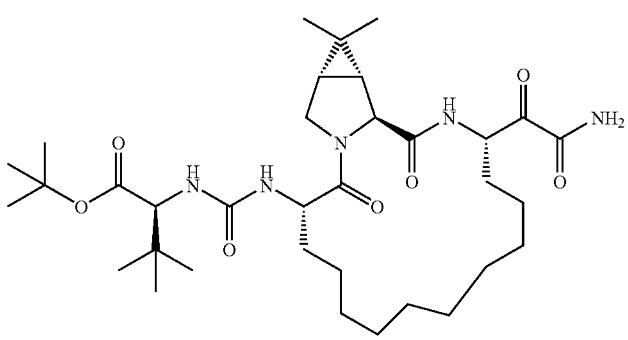 | A |

TABLE 1-continued

| Example | Structure | Binding Activity |
|---------|-----------|------------------|
| 8 | 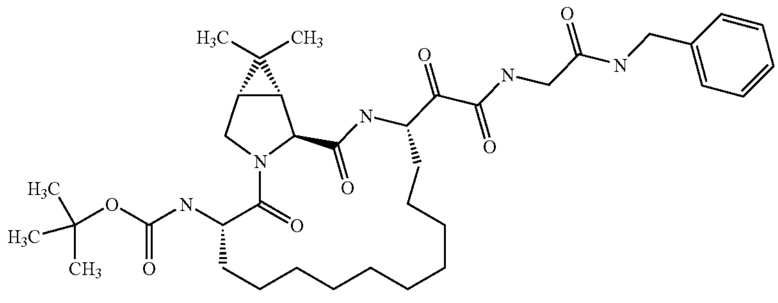 | A |
| 9 | 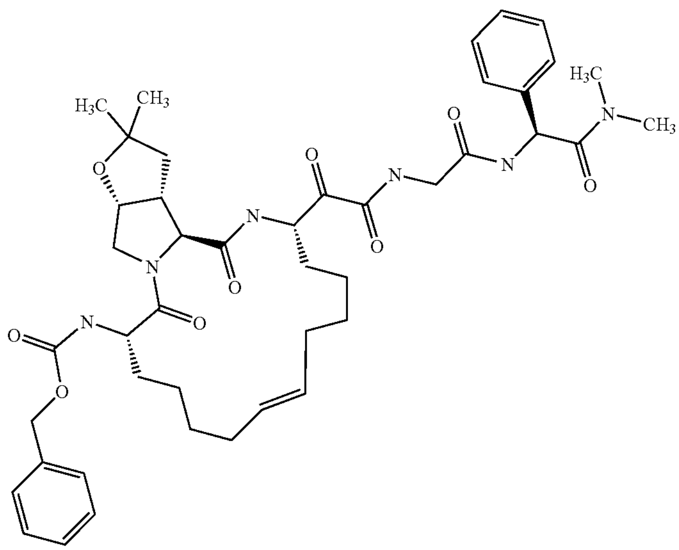 | A |
| 10 | 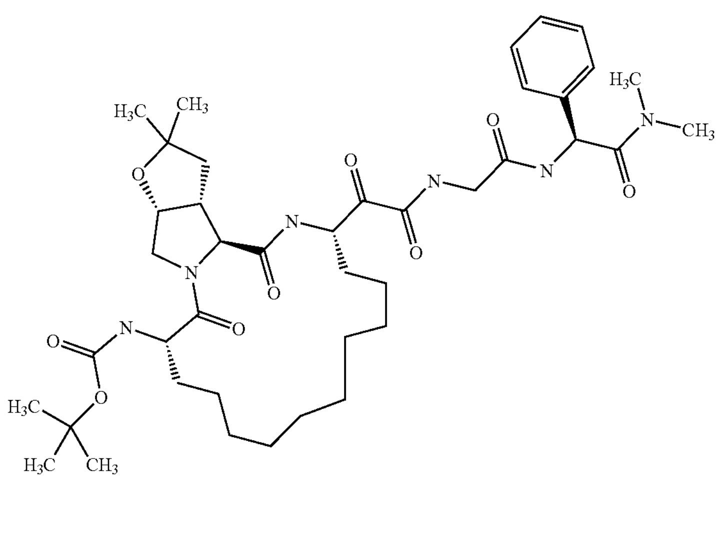 | A |

TABLE 1-continued

| Example | Structure | Binding Activity |
|---------|-----------|------------------|
| 11 | 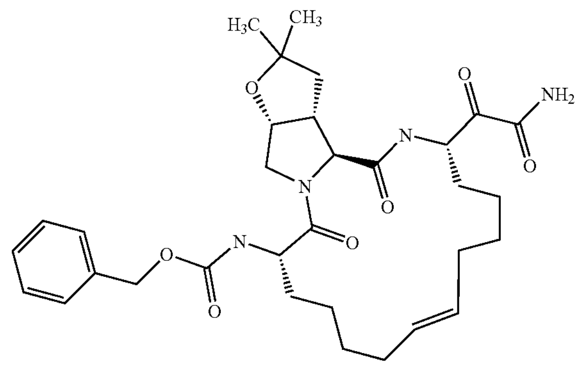 | C |
| 12 | 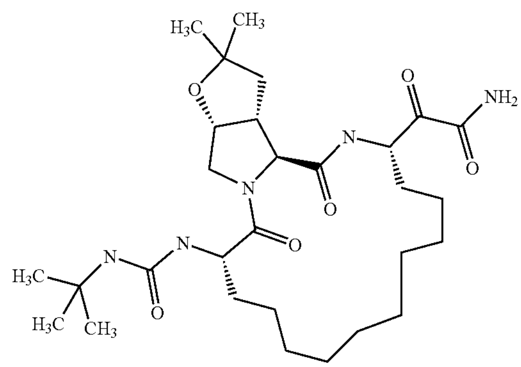 | B |
| 13 | 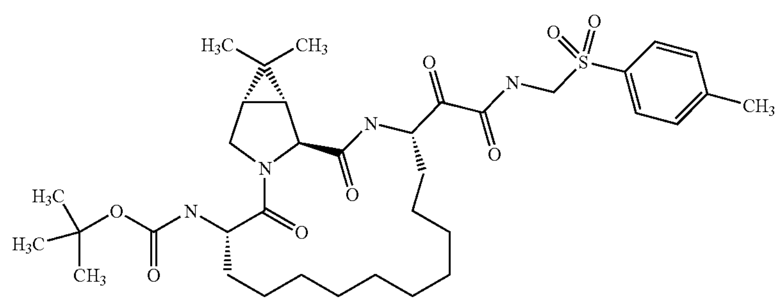 | A |
| 14 | 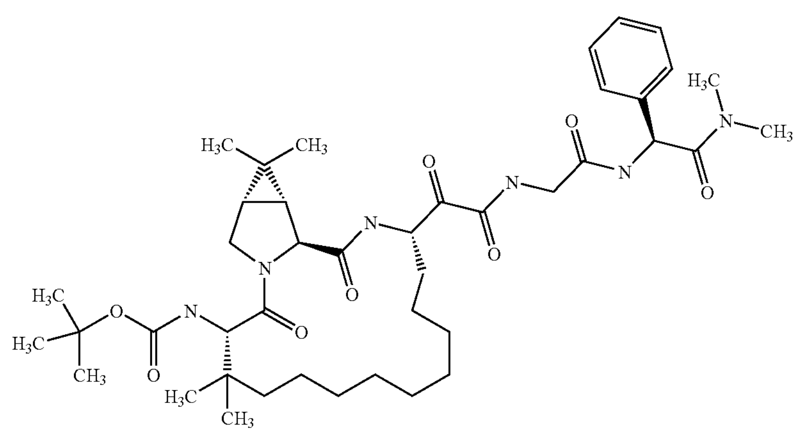 | A |

TABLE 1-continued

| Example | Structure | Binding Activity |
|---|---|---|
| 15 | 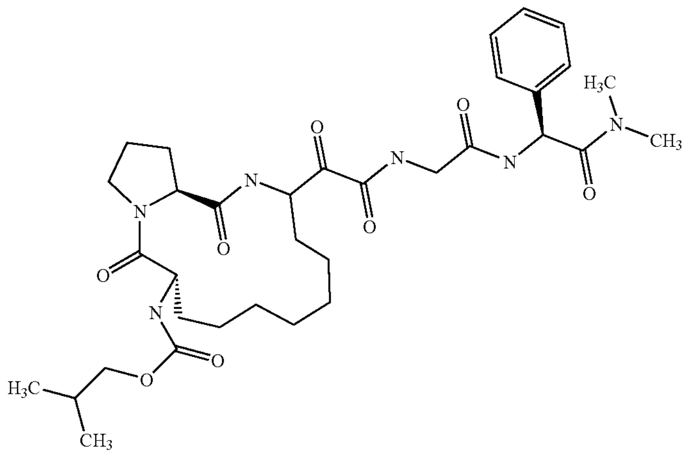 | C |
| 16 | 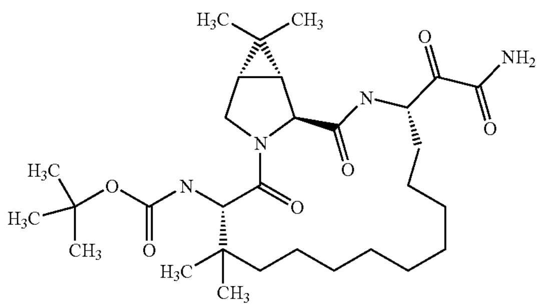 | C |
| 17 | 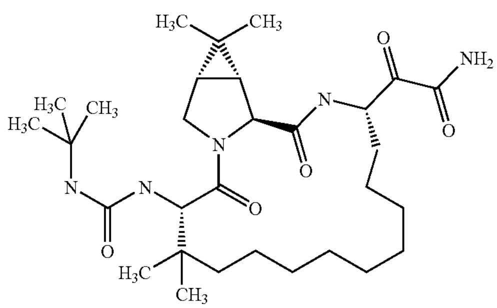 | A |
| 18 | 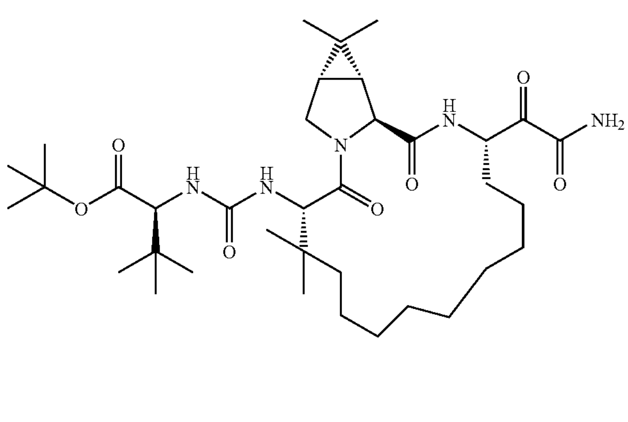 | A |

TABLE 1-continued

| Example | Structure | Binding Activity |
|---|---|---|
| 19 | 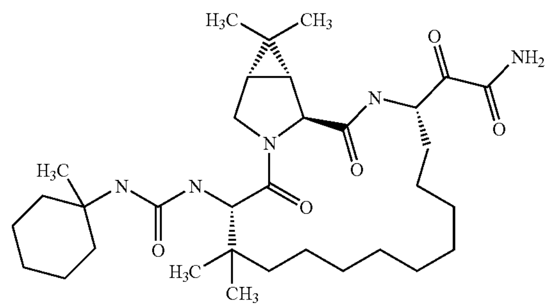 | A |
| 20 | 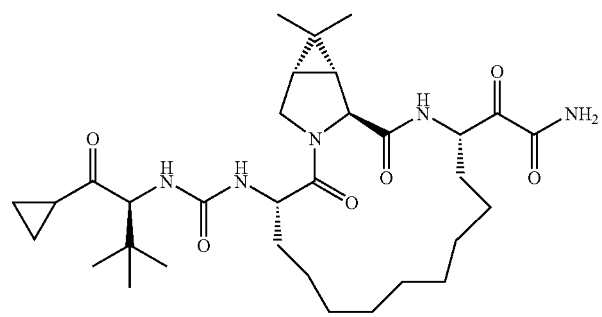 | A |
| 21 | 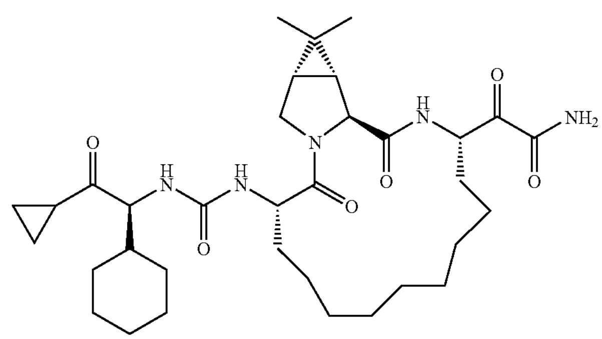 | A |
| 22 | 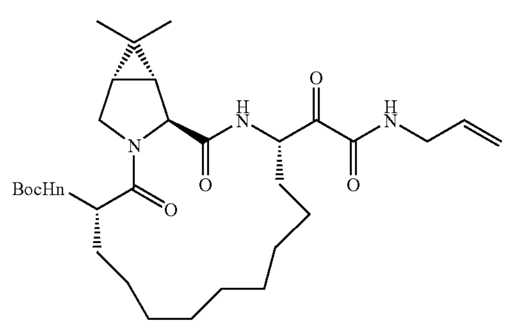 | A |

TABLE 1-continued

| Example | Structure | Binding Activity |
|---------|-----------|------------------|
| 23 | 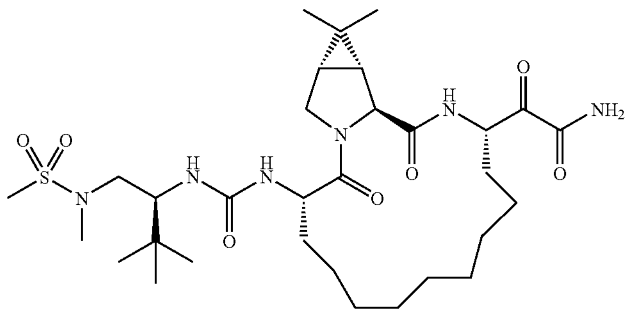 | A |
| 24 | 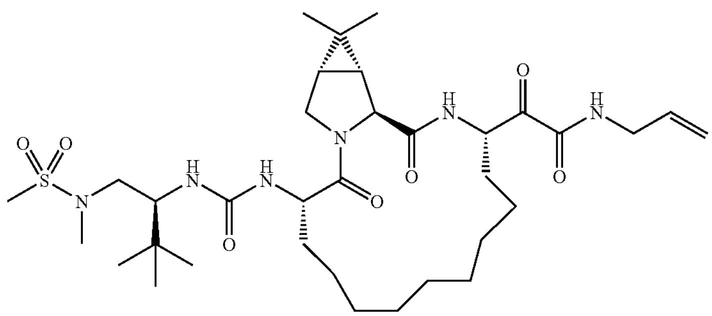 | A |
| 25 | 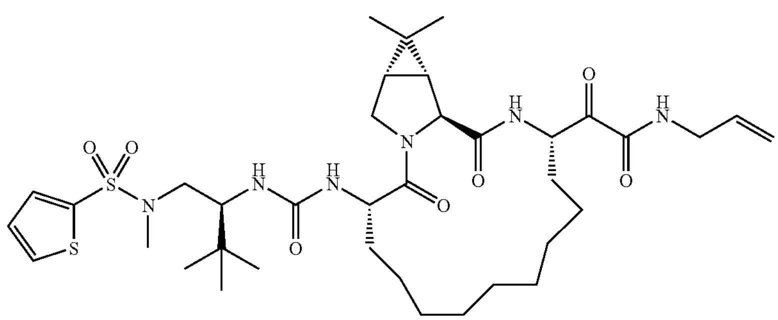 | A |
| 26 | 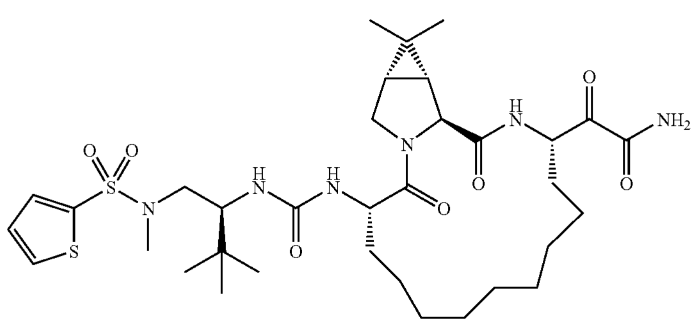 | A |
| 27 | 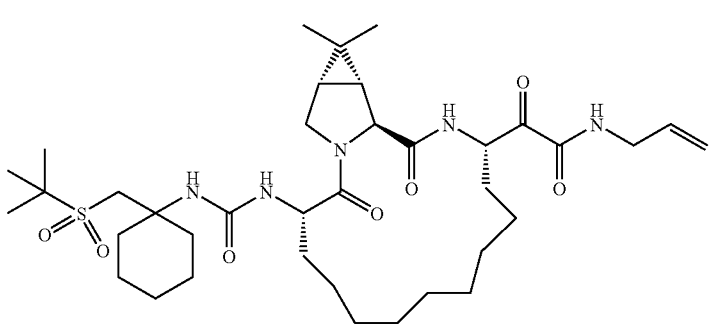 | A |

TABLE 1-continued

| Example | Structure | Binding Activity |
|---------|-----------|------------------|
| 28 | 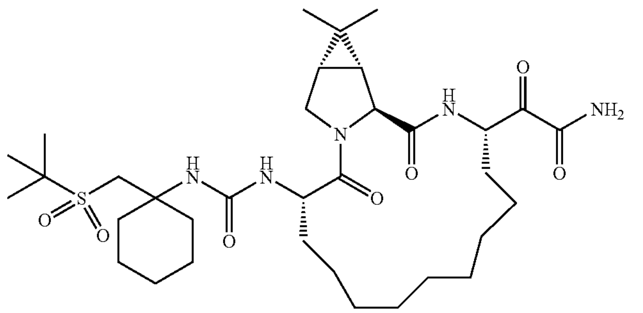 | A |
| 29 | 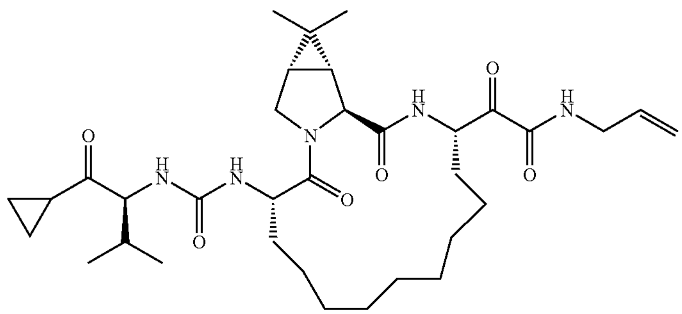 | A |
| 30 | 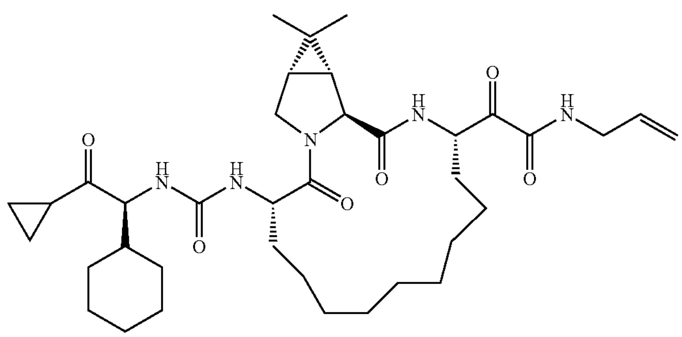 | A |

Additional representative compounds of the invention which exhibit excellent HCV protease inhibitory activity are listed below in Table 2.

TABLE 2

| Entry | Structure | Activity $K_i^*$ (nM) |
|-------|-----------|------------------------|
| 31 | 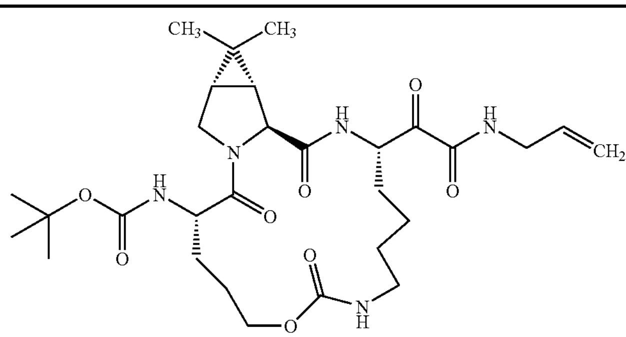 | — |

TABLE 2-continued

| Entry | Structure | Activity $K_i^*$ (nM) |
|---|---|---|
| 32 | 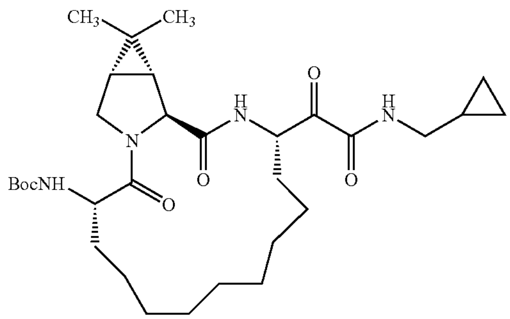 | B |
| 33 | 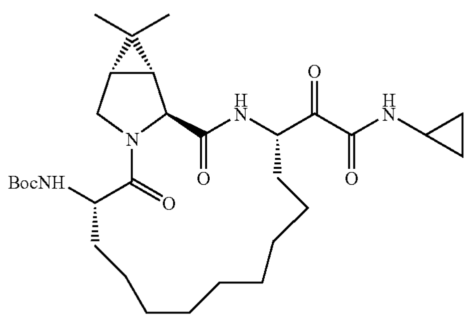 | A |
| 34 | 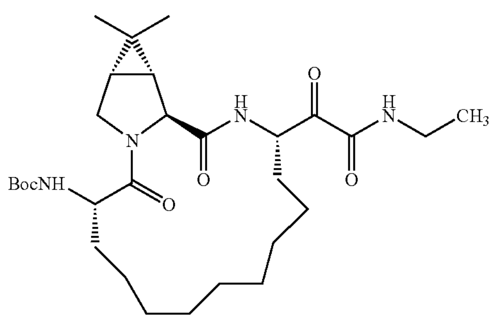 | A |
| 35 | 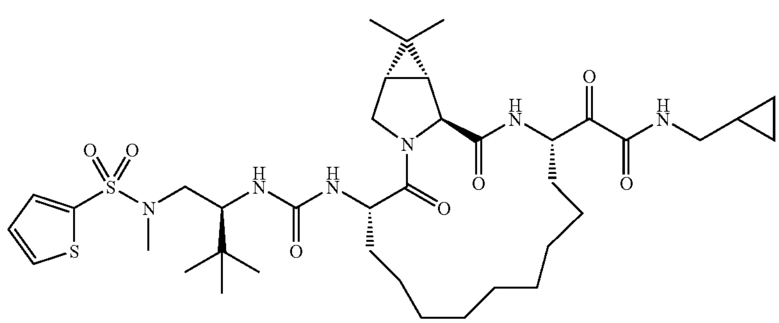 | A |

TABLE 2-continued

| Entry | Structure | Activity $K_i^*$ (nM) |
|---|---|---|
| 36 | 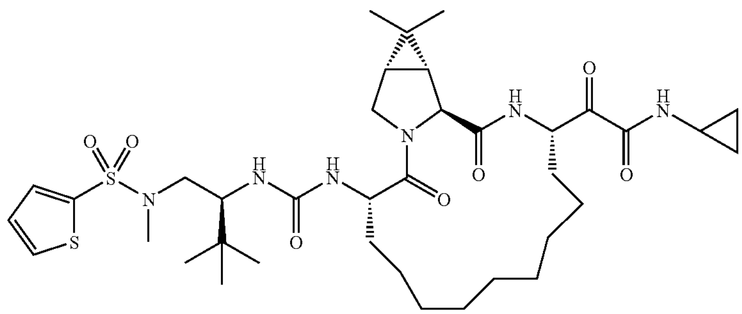 | A |
| 37 | 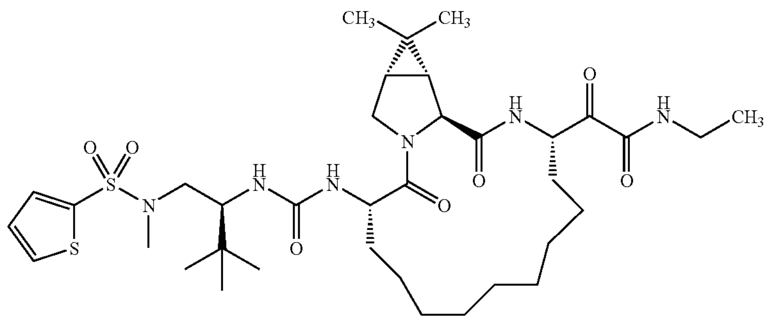 | A |
| 38 | 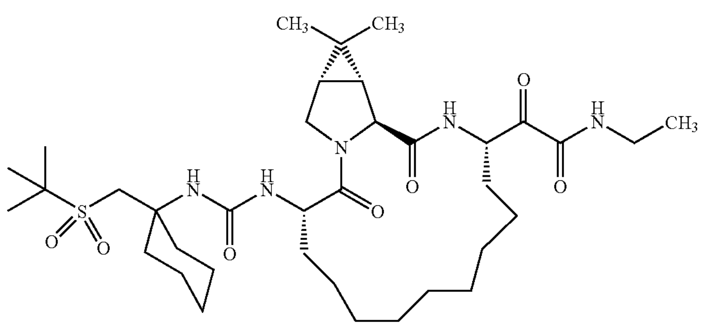 | A |
| 39 | 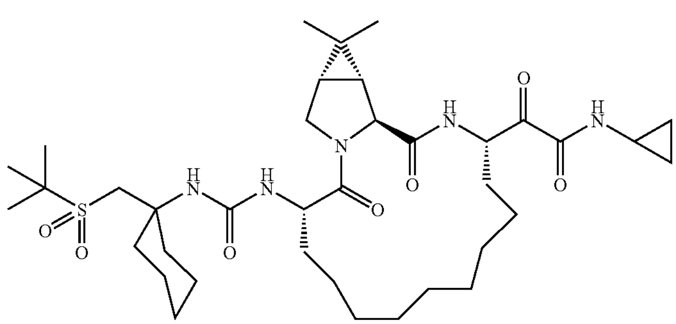 | A |

TABLE 2-continued

| Entry | Structure | Activity $K_i^*$ (nM) |
|---|---|---|
| 40 | 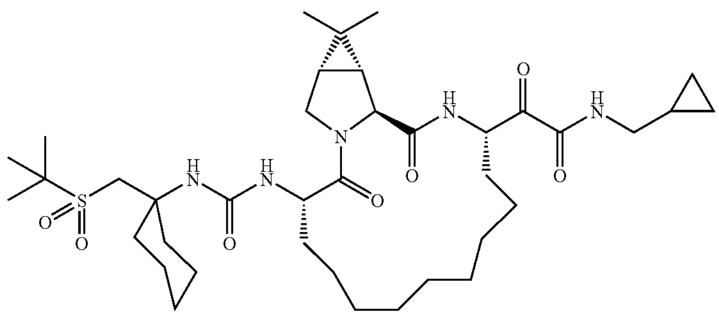 | A |
| 41 | 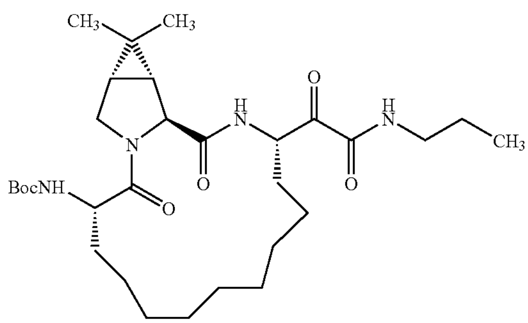 | NA |
| 42 | 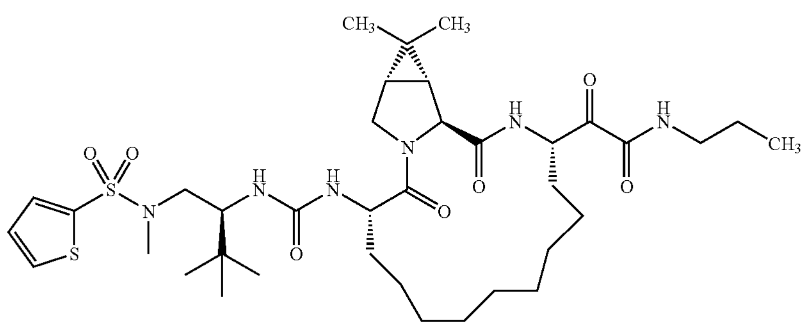 | A |
| 43 | 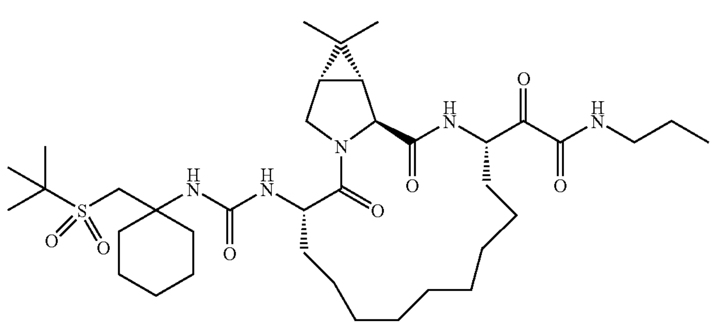 | A |

TABLE 2-continued
| Entry | Structure | Activity $K_i^*$ (nM) |
|---|---|---|
| 44 | 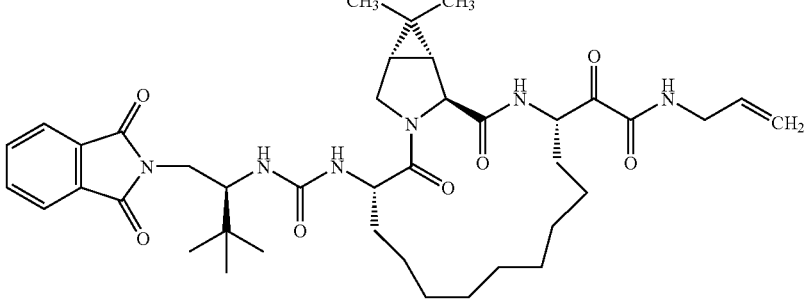 | A |
| 45 | 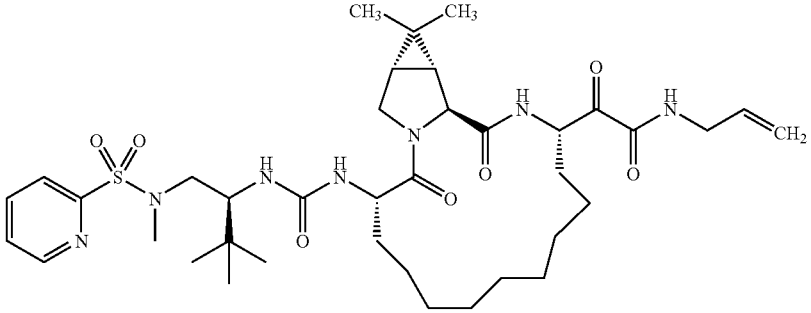 | A |
| 46 | 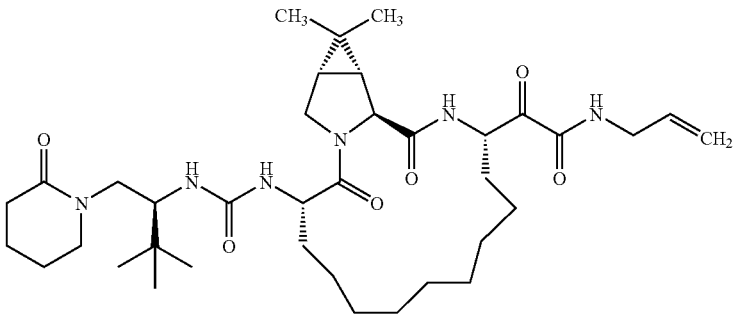 | A |
| 47 | 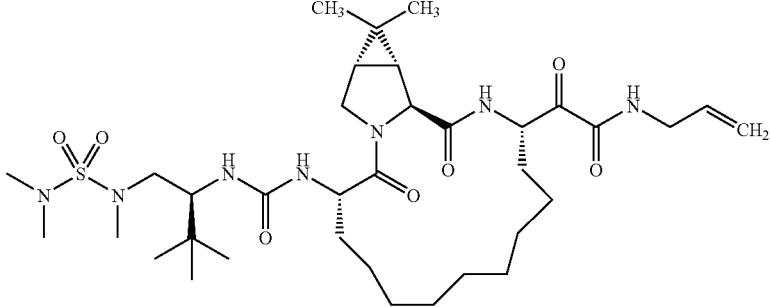 | A |

TABLE 2-continued

| Entry | Structure | Activity $K_i^*$ (nM) |
|---|---|---|
| 48 | 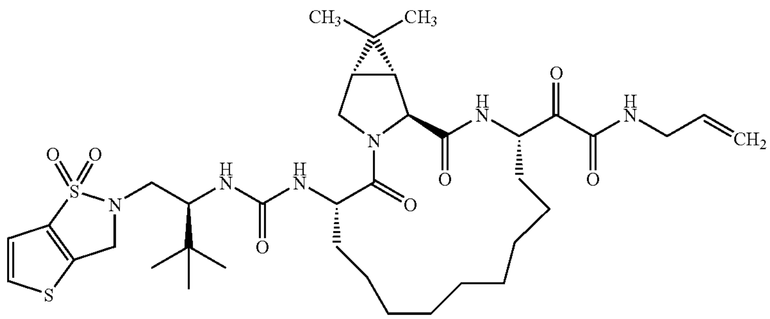 | A |
| 49 | 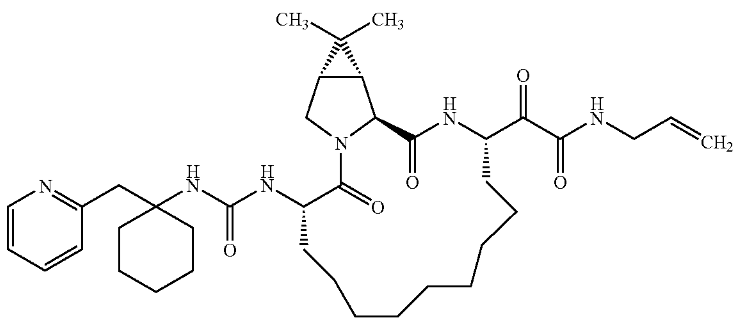 | A |
| 50 | 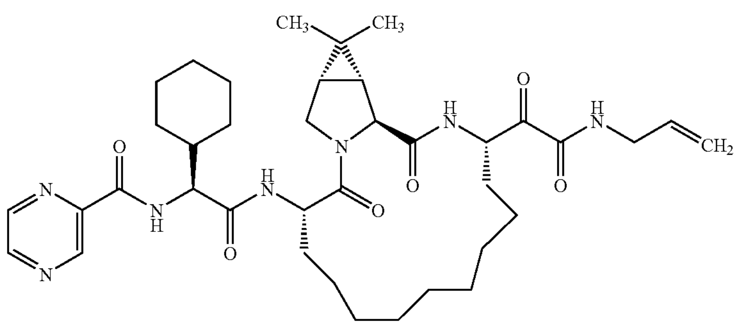 | A |
| 51 | 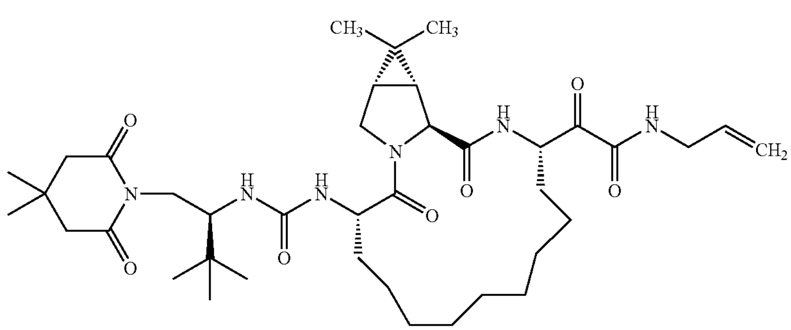 | A |

TABLE 2-continued

| Entry | Structure | Activity $K_i^*$ (nM) |
|---|---|---|
| 52 | 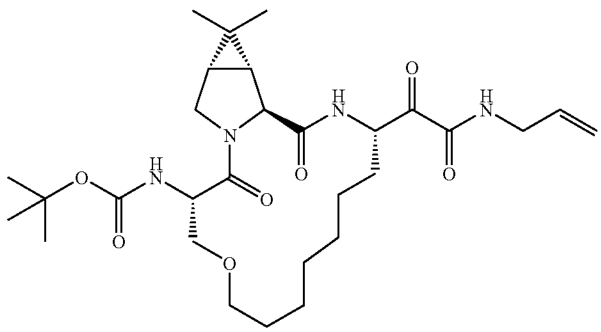 | B |
| 53 | 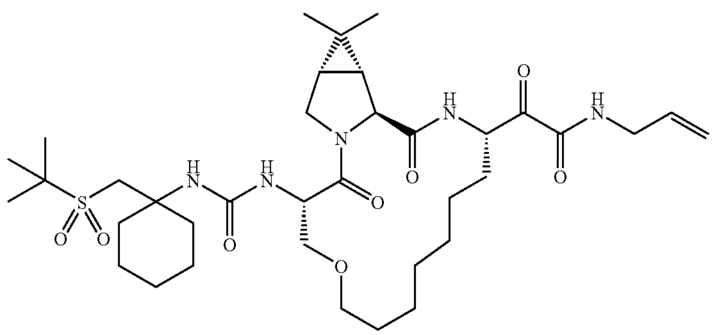 | A |
| 54 | 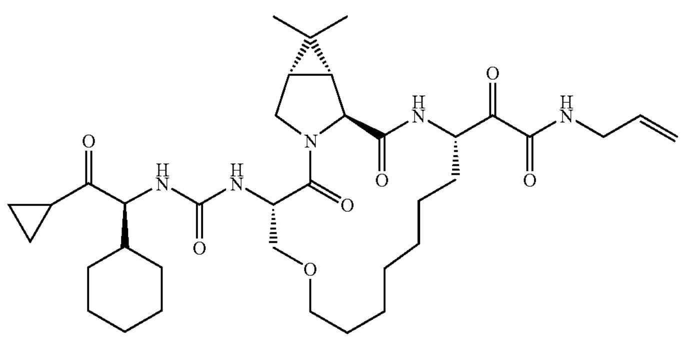 | B |
| 55 | 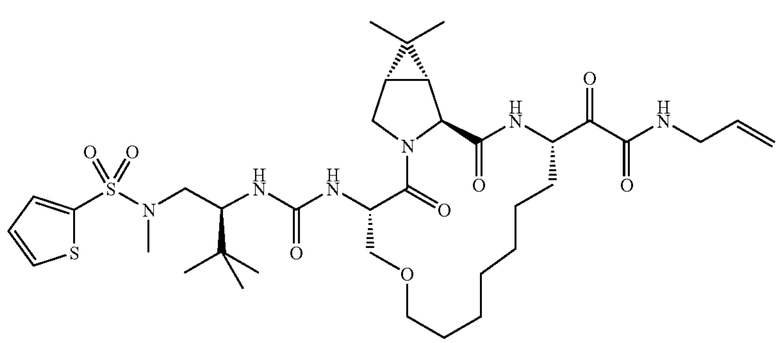 | A |

TABLE 2-continued

| Entry | Structure | Activity $K_i^*$ (nM) |
|---|---|---|
| 56 | 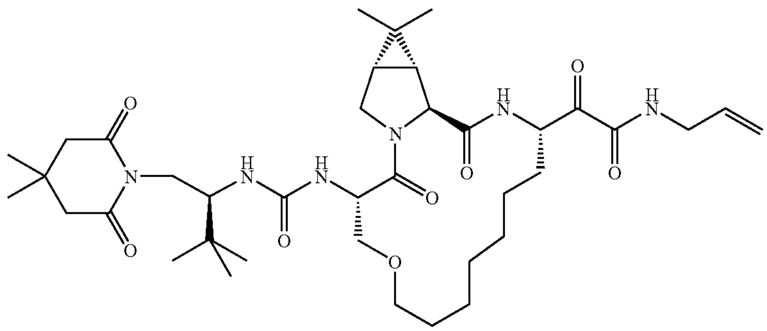 | A |
| 57 | 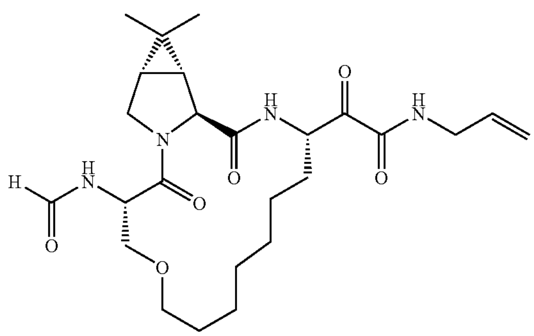 | C |
| 58 | 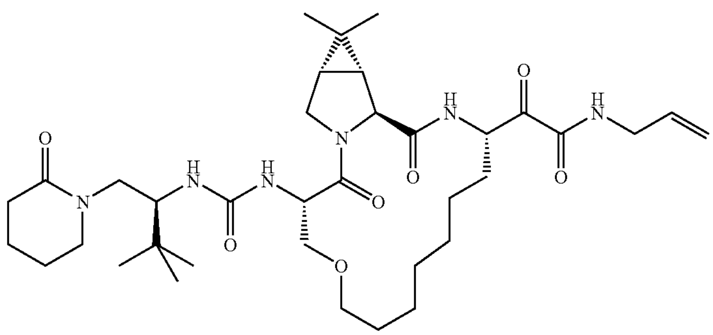 | A |
| 59 | 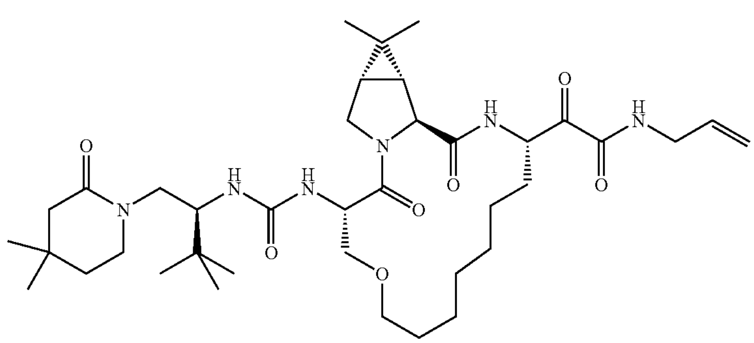 | A |

TABLE 2-continued

| Entry | Structure | Activity $K_i^*$ (nM) |
|---|---|---|
| 60 | 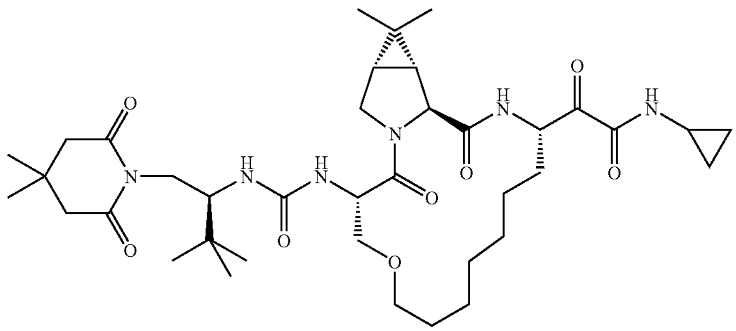 | A |
| 61 | 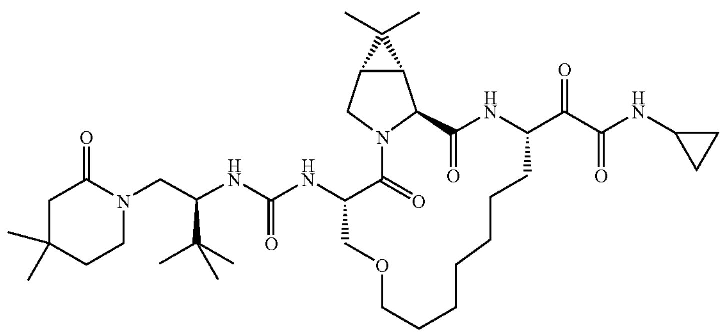 | A |
| 62 | 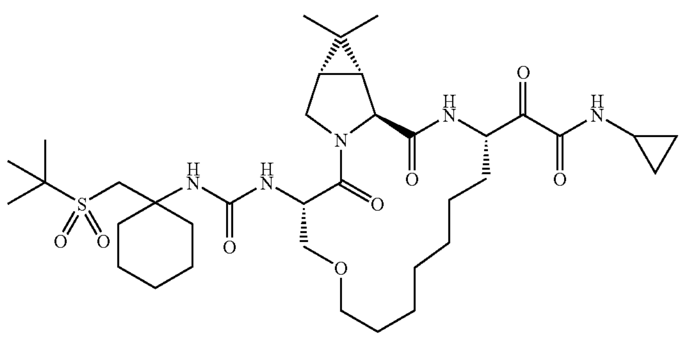 | A |
| 63 | 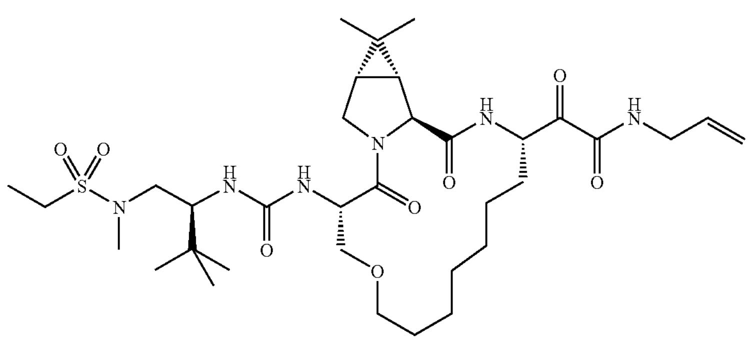 | A |

TABLE 2-continued

| Entry | Structure | Activity $K_i^*$ (nM) |
|---|---|---|
| 64 | 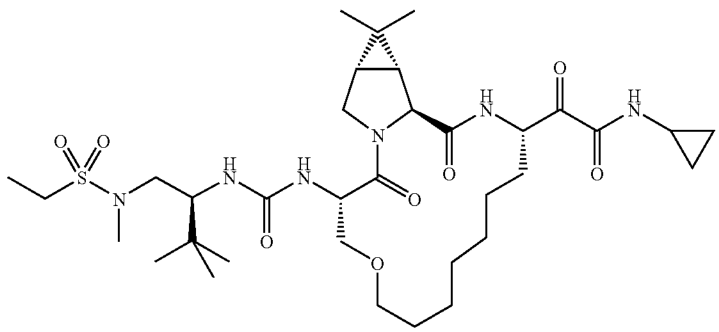 | A |
| 65 | 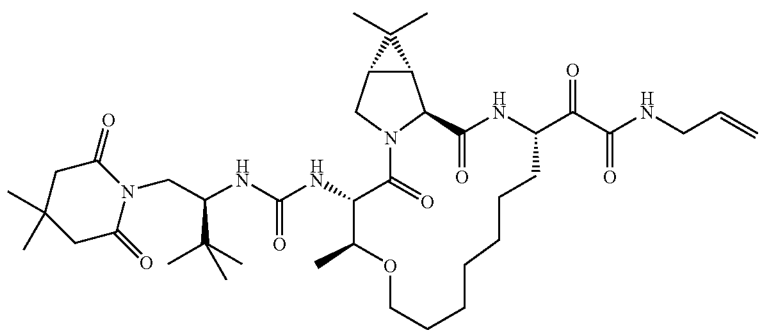 | A |
| 66 | 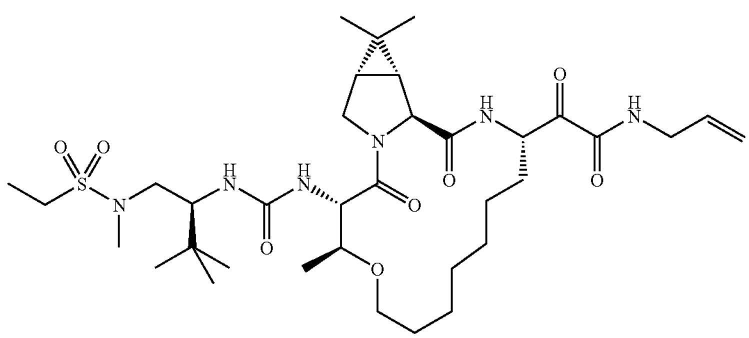 | A |
| 67 | 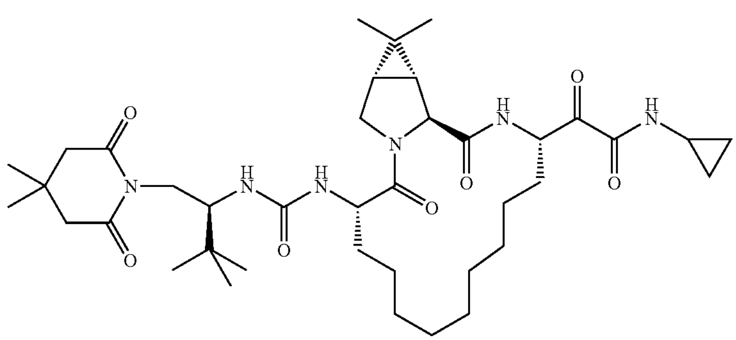 | A |

TABLE 2-continued

| Entry | Structure | Activity $K_i^*$ (nM) |
|---|---|---|
| 68 | 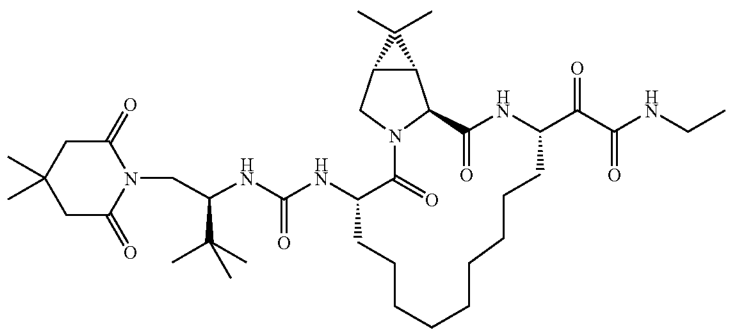 | A |
| 69 | 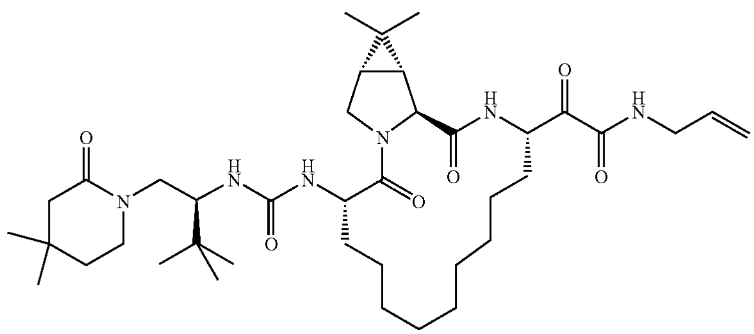 | A |
| 70 | 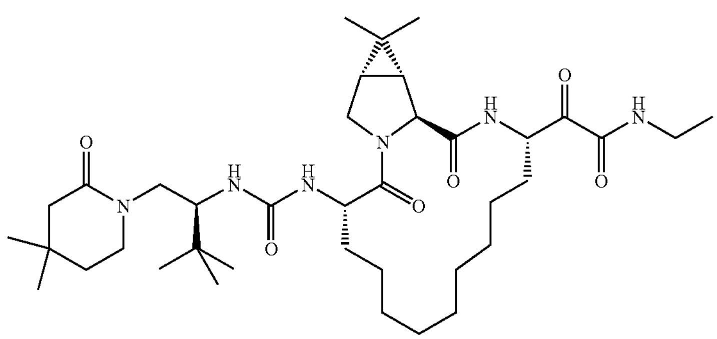 | A |
| 71 | 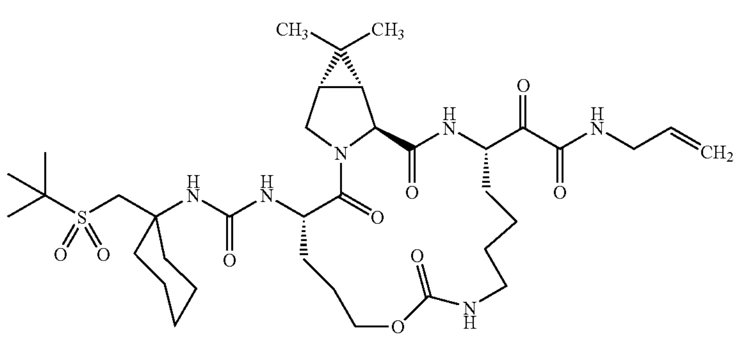 | A |

TABLE 2-continued

| Entry | Structure | Activity $K_i^*$ (nM) |
|---|---|---|
| 72 | 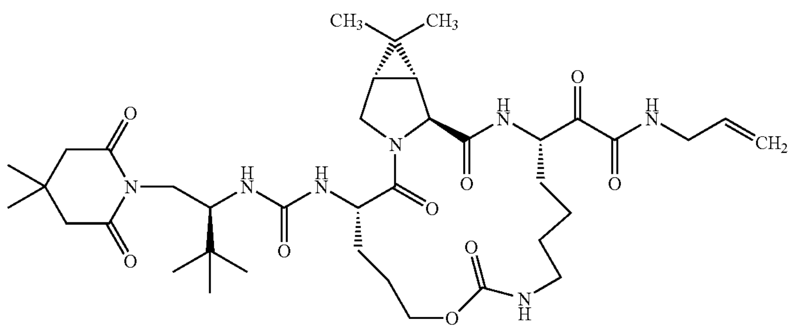 | A |
| 73 | 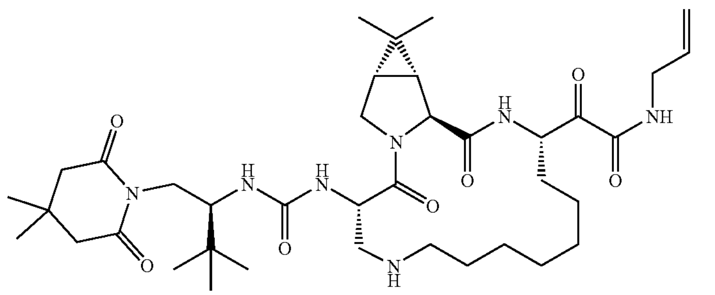 | NA |
| 74 | 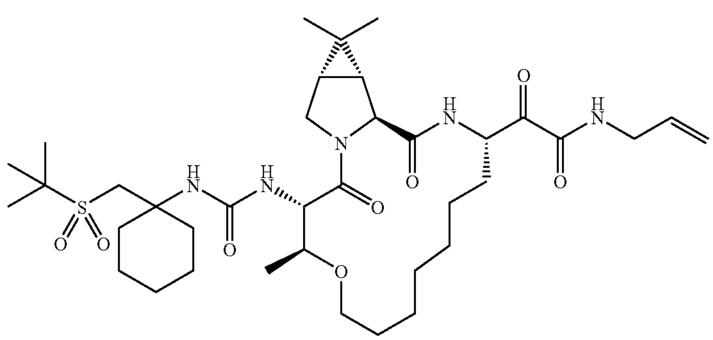 | A |
| 75 | 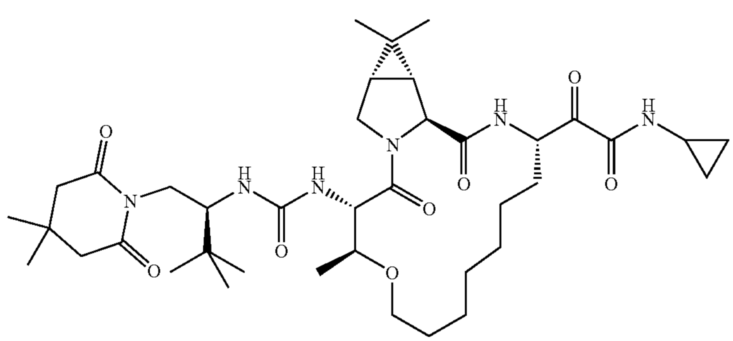 | A |

TABLE 2-continued

| Entry | Structure | Activity $K_i^*$ (nM) |
|---|---|---|
| 76 | 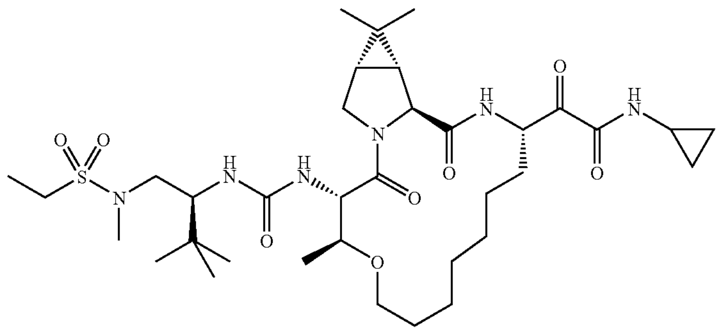 | A |
| 77 | 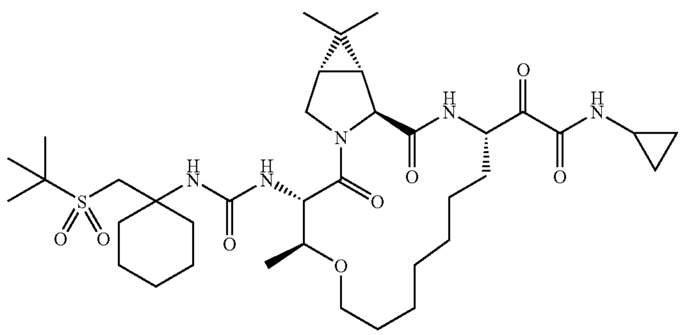 | A |

Still additional compounds are shown in Table 2A:

TABLE 2A

| Example | Structure | Binding Activity |
|---|---|---|
| 78 | 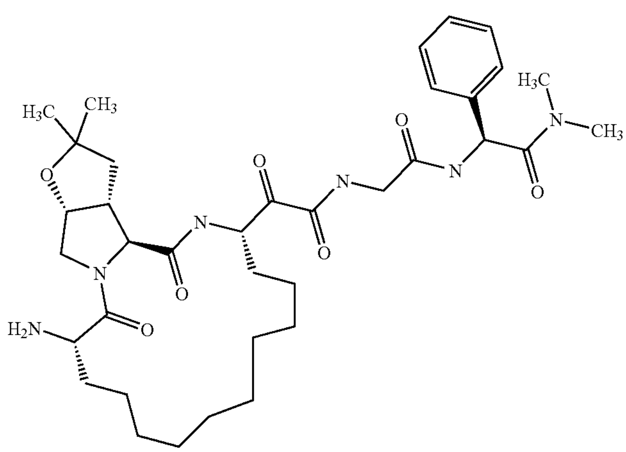 | C |

TABLE 2A-continued
| Example | Structure | Binding Activity |
|---|---|---|
| 79 | 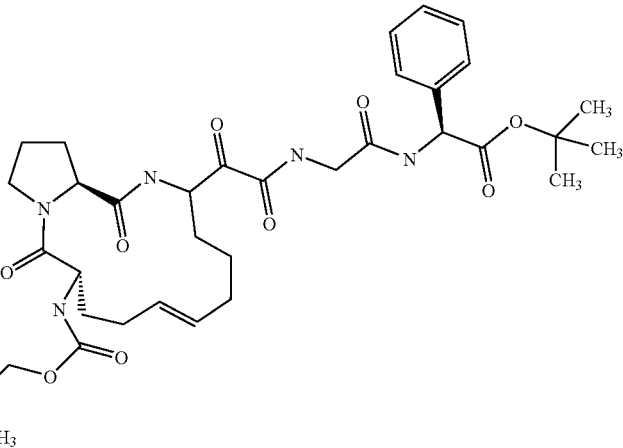 | C |
| 80 | 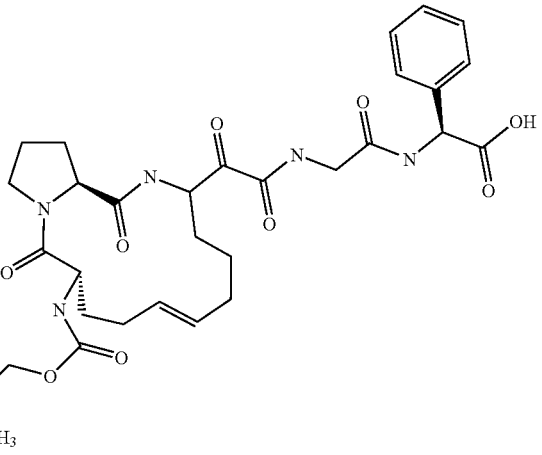 | C |
| 81 | 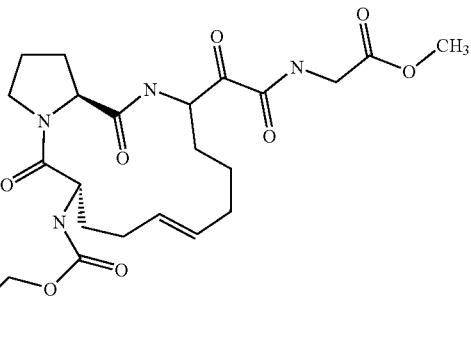 | C |

TABLE 2A-continued
| Example | Structure | Binding Activity |
|---|---|---|
| 82 | 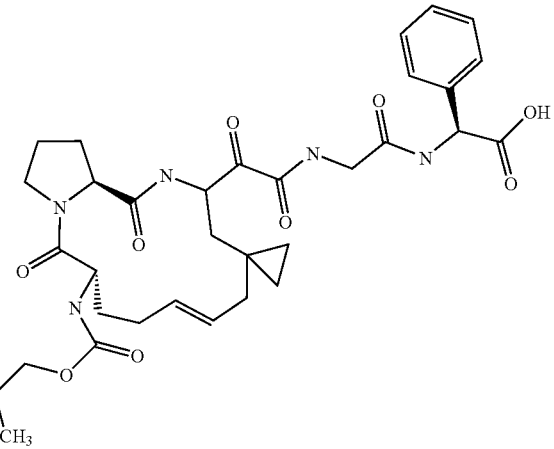 | C |
| 83 | 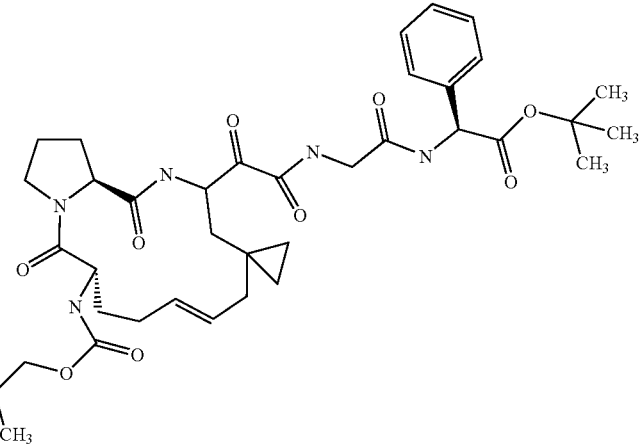 | C |
| 84 | 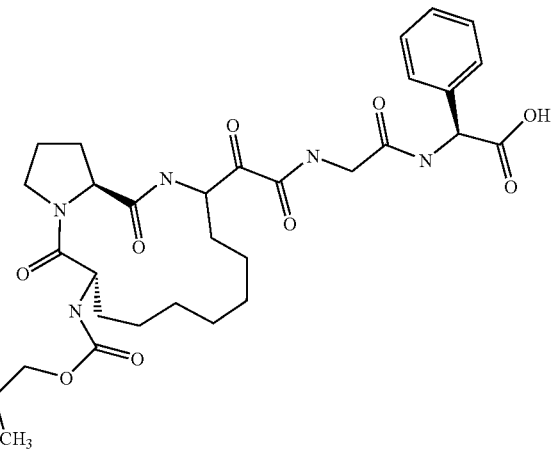 | B |

TABLE 2A-continued

| Example | Structure | Binding Activity |
|---------|-----------|------------------|
| 85 | 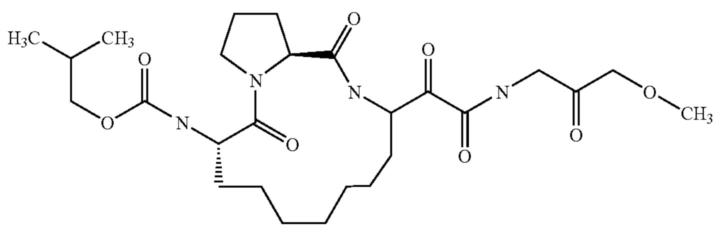 | C |
| 86 | 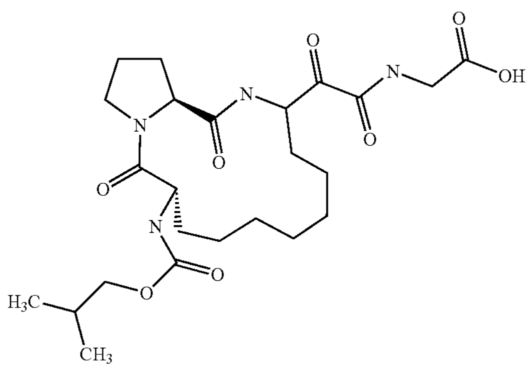 | C |
| 87 | 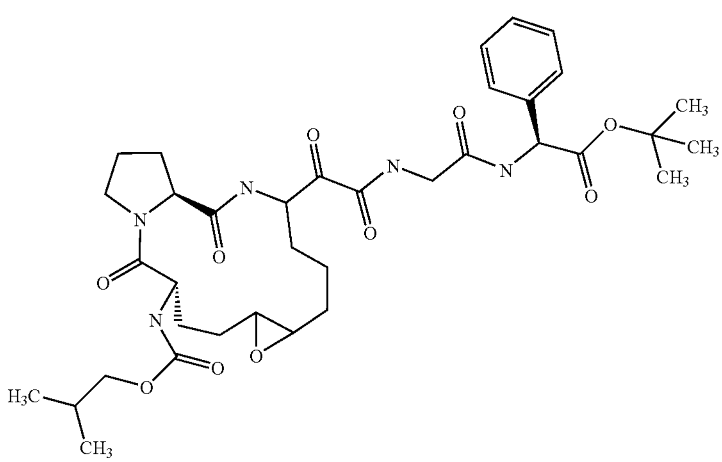 | C |
| 88 | 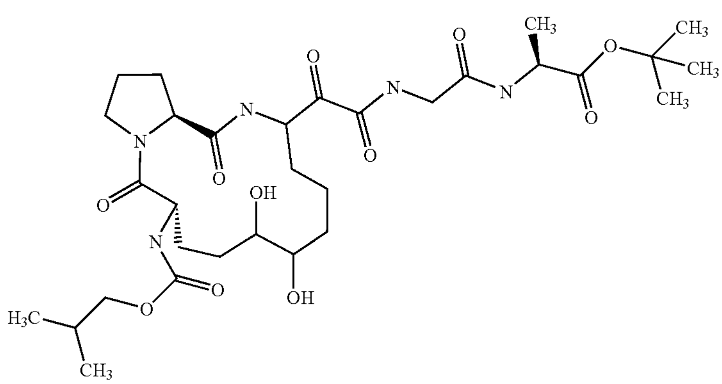 | C |

TABLE 2A-continued

| Example | Structure | Binding Activity |
|---------|-----------|------------------|
| 89 | 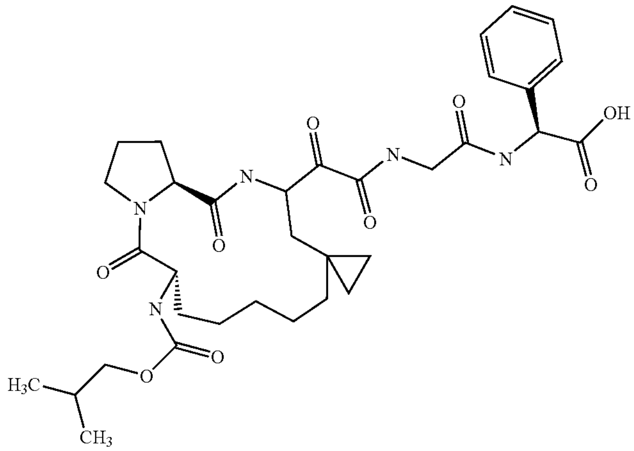 | C |
| 90 | 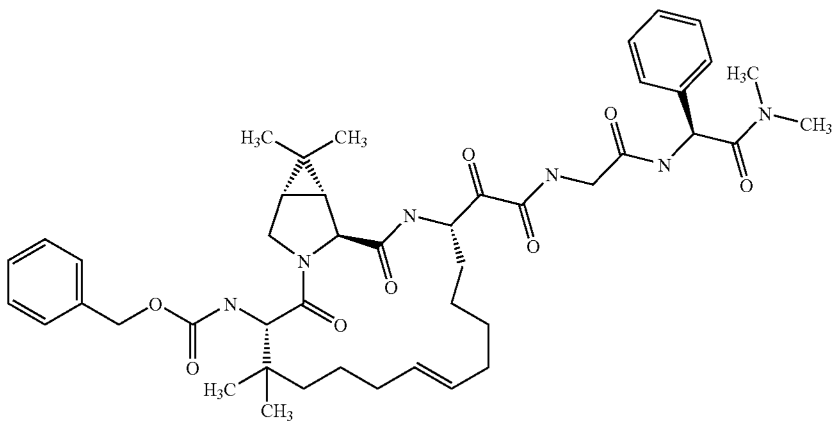 | B |

Table 3 shows the activities (Ki*) of certain representative compounds of the invention.

TABLE 3

Representative compounds with inhibitory activity

| Entry | Compound number | Structure | Activity $K_i^*$ (nM) |
|-------|-----------------|-----------|----------------------|
| 1 | 20 | 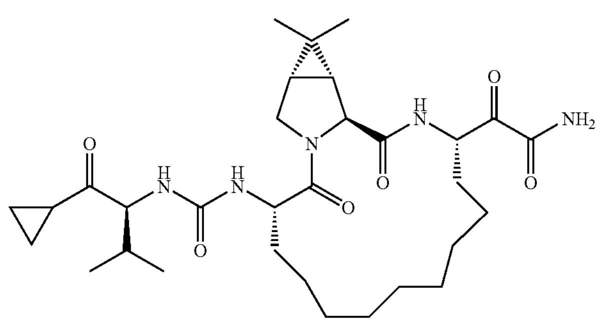 | 11 |

TABLE 3-continued

Representative compounds with inhibitory activity

| Entry | Compound number | Structure | Activity $K_i^*$ (nM) |
|---|---|---|---|
| 2 | 21 | 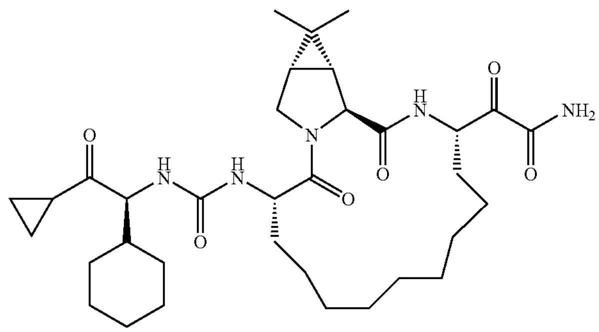 | 11 |
| 3 | 22 | 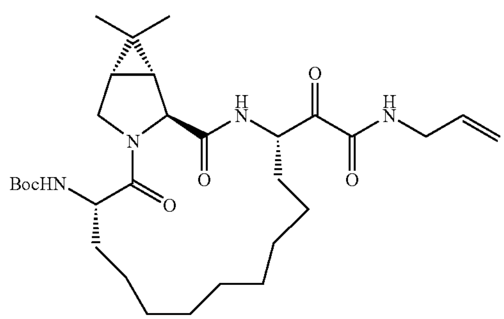 | 36 |
| 4 | 23 | 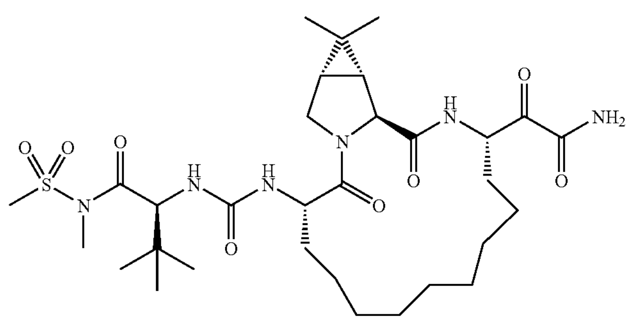 | 3 |
| 5 | 24 | 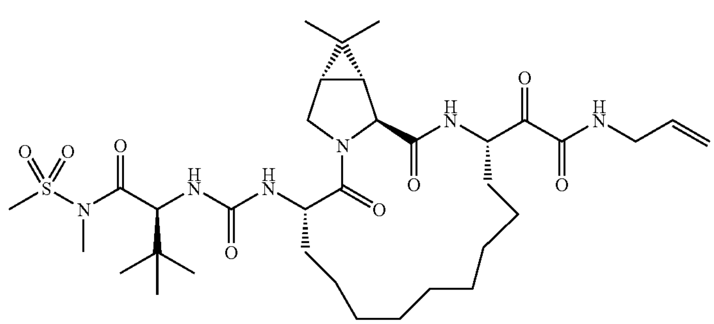 | 3 |

TABLE 3-continued

Representative compounds with inhibitory activity

| Entry | Compound number | Structure | Activity $K_i^*$ (nM) |
|---|---|---|---|
| 6 | 25 | 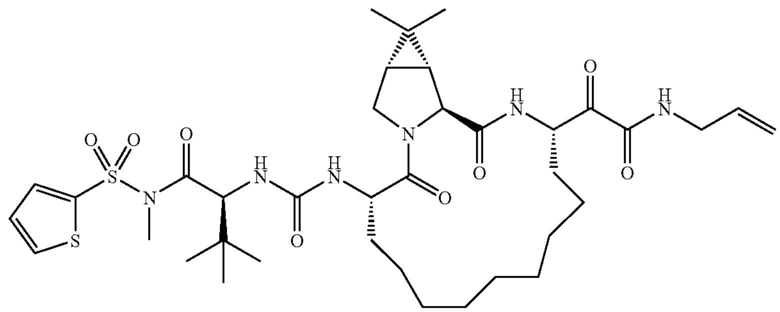 | 3 |
| 7 | 26 | 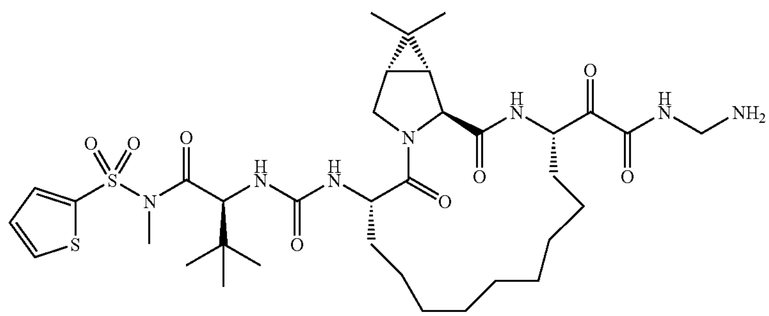 | 2 |
| 8 | 27 | 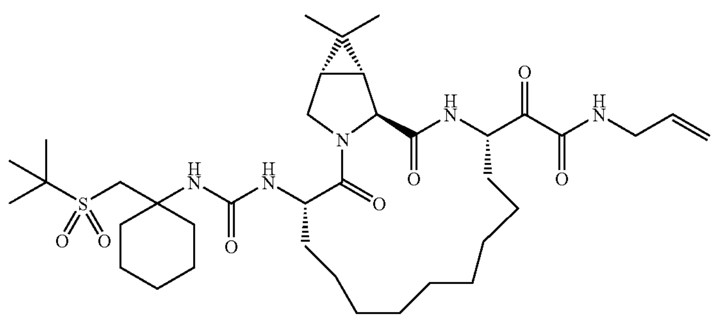 | 5 |
| 9 | 28 | 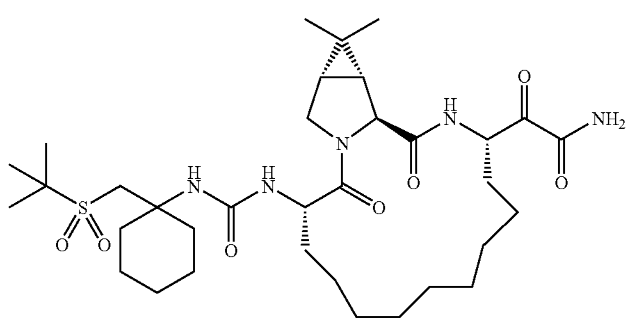 | 5 |

TABLE 3-continued
Representative compounds with inhibitory activity
| Entry | Compound number | Structure | Activity $K_i^*$ (nM) |
|---|---|---|---|
| 10 | 29 | 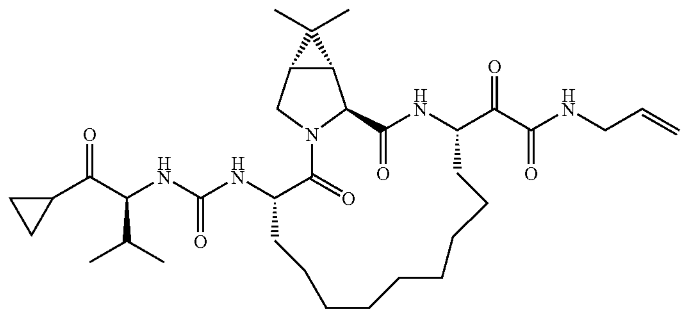 | 20 |
| 11 | 30 | 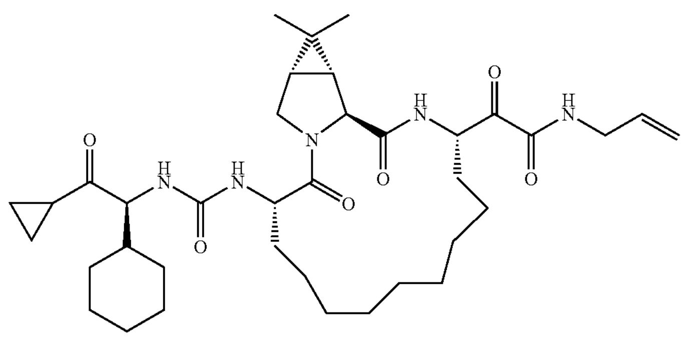 | 5 |
Following generally the procedures described above, the following compounds can also be prepared and used as HCV protease inhibitors:
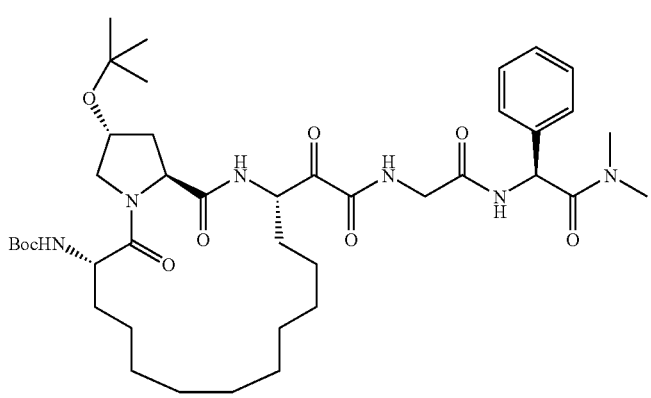

-continued
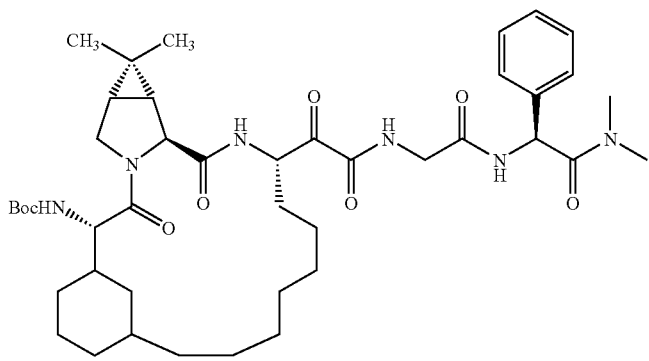
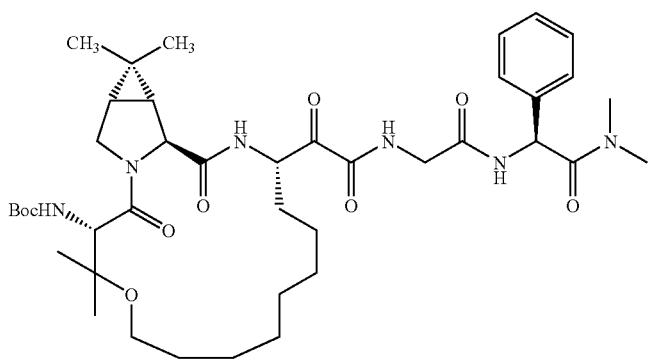
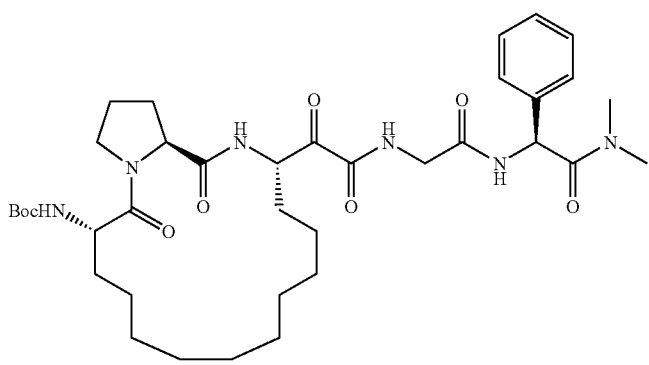
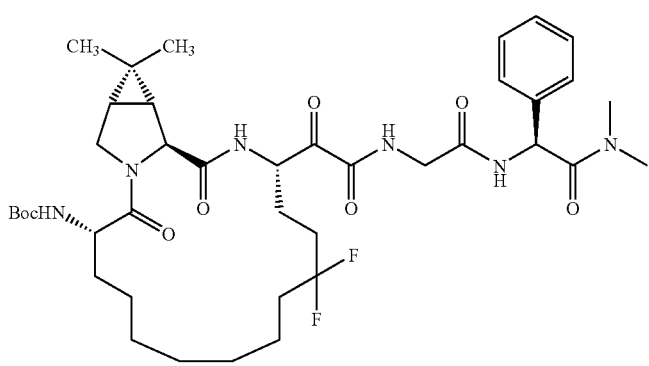

-continued
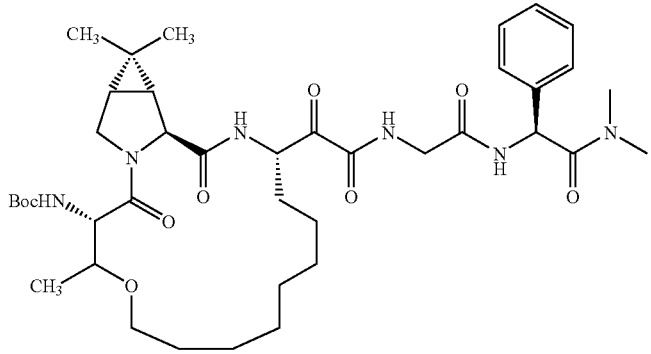
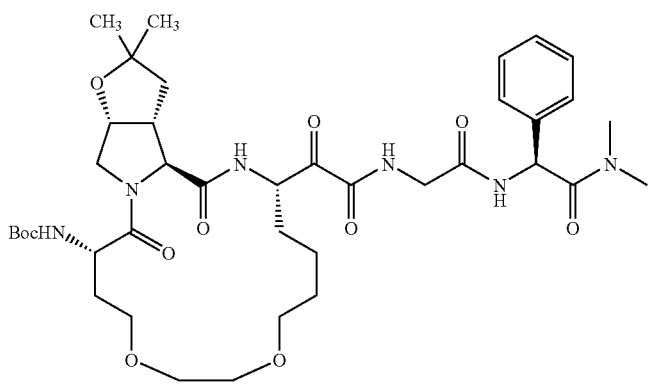
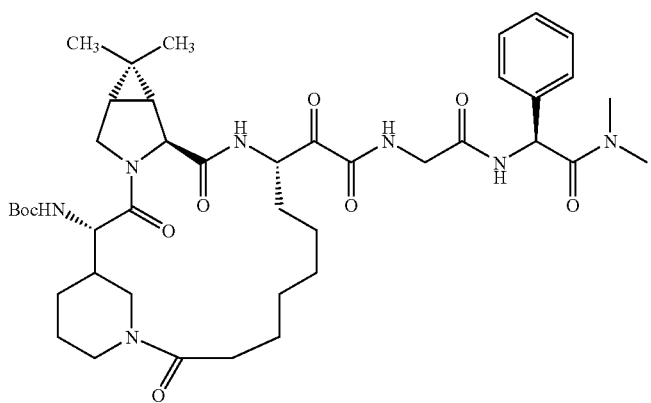
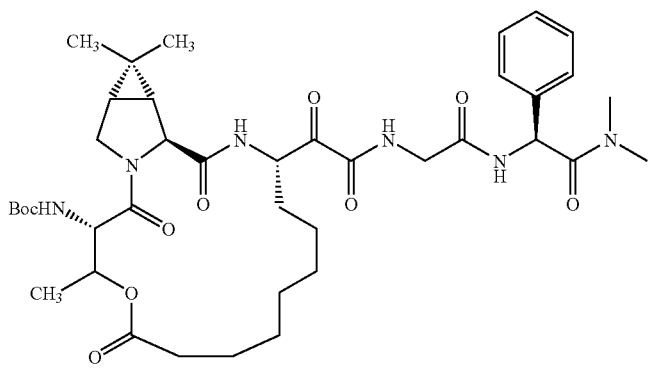

-continued
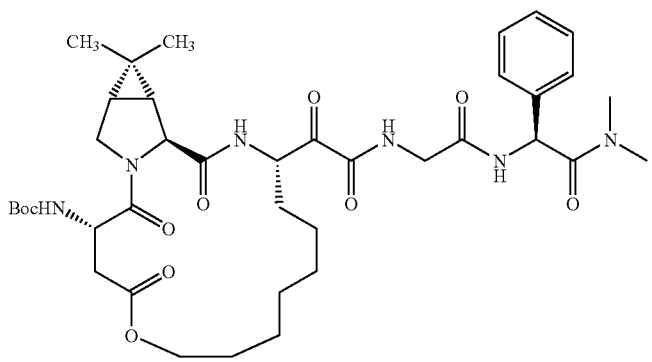
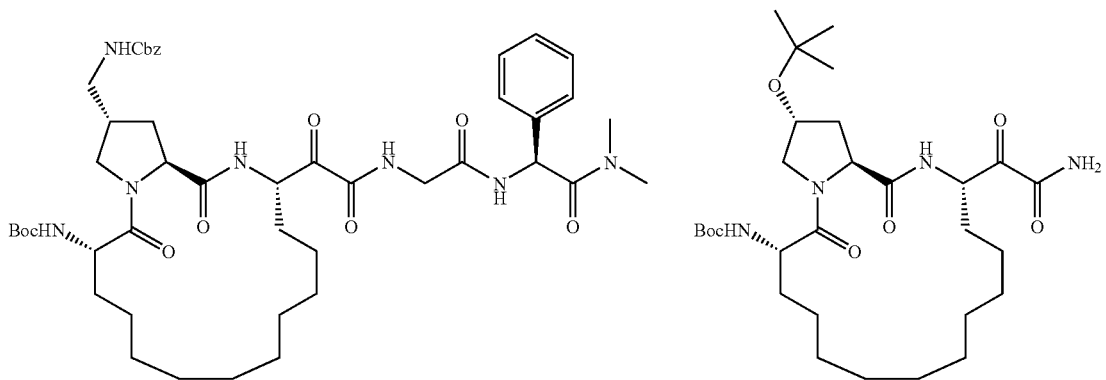
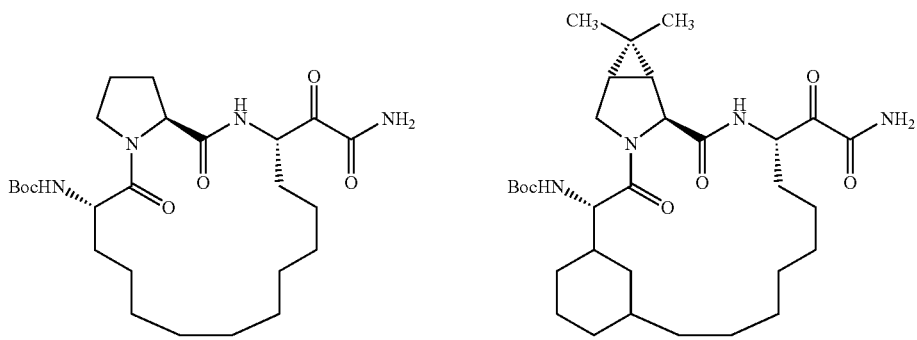
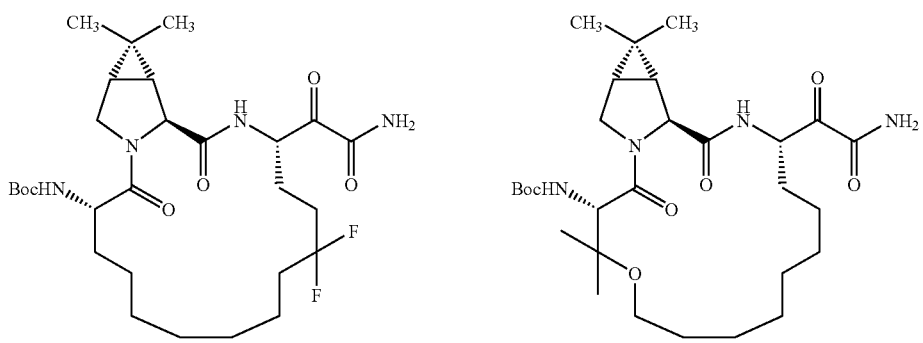

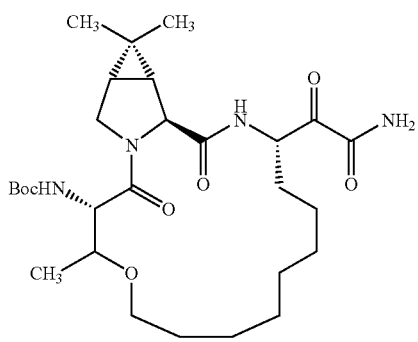
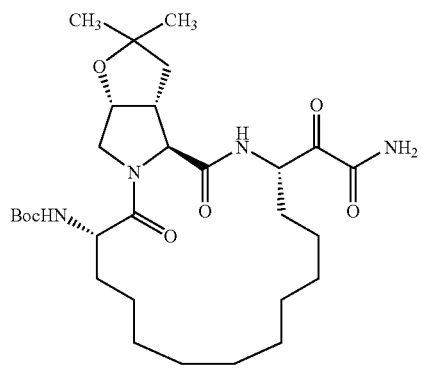
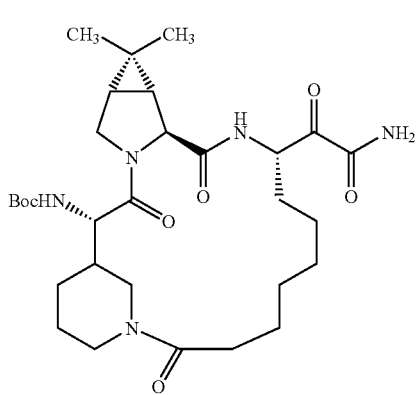
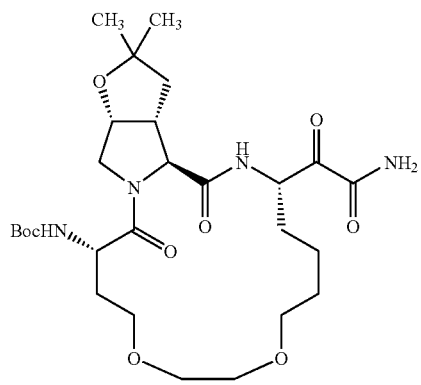
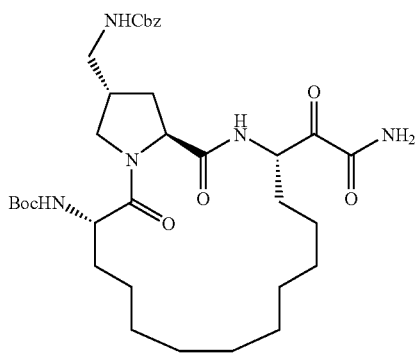
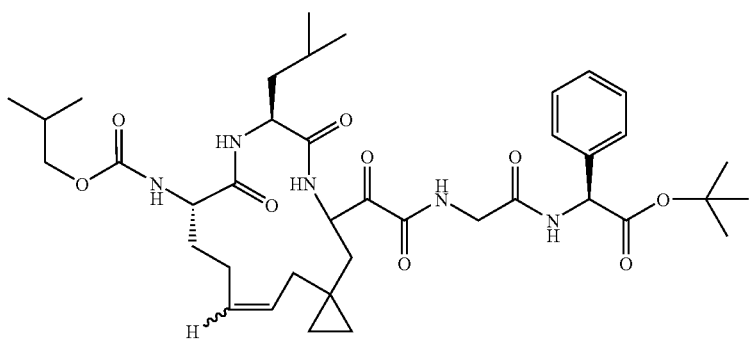

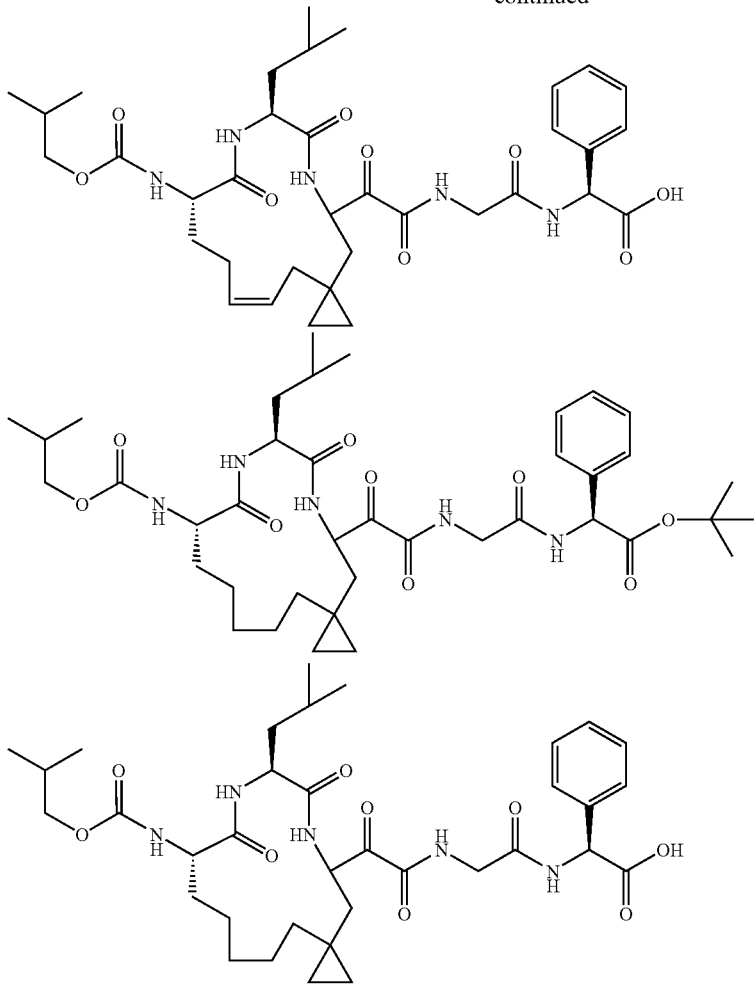

The present invention relates to novel HCV protease inhibitors. This utility is manifested in their ability to inhibit the HCV NS2/NS4a serine protease as demonstrated by the following in vitro assays.

Assay for HCV Protease Inhibitory Activity:

Spectrophotometric Assay: Spectrophotometric assays for the HCV serine protease was performed on the inventive compounds by following the procedure described by R. Zhang et al, *Analytical Biochemistry*, 270 (1999) 268-275, the disclosure of which is incorporated herein by reference. The assay based on the proteolysis of chromogenic ester substrates is suitable for the continuous monitoring of HCV NS3 protease activity. The substrates were derived from the P side of the NS5A-NS5B junction sequence (Ac-DTEDVVX (Nva), where X=A or P) whose C-terminal carboxyl groups were esterified with one of four different chromophoric alcohols (3- or 4-nitrophenol, 7-hydroxy-4-methyl-coumarin, or 4-phenylazophenol). Presented below are the synthesis, characterization and application of these novel spectrophotometric ester substrates to high throughput screening and detailed kinetic evaluation of HCV NS3 protease inhibitors.

Materials and Methods:

Materials: Chemical reagents for assay related buffers were obtained from Sigma Chemical Company (St. Louis, Mo.). Reagents for peptide synthesis were from Aldrich Chemicals, Novabiochem (San Diego, Calif.), Applied Biosystems (Foster City, Calif.) and Perseptive Biosystems (Framingham, Mass.). Peptides were synthesized manually or on an automated ABI model 431A synthesizer (from Applied Biosystems). UV/VIS Spectrometer model LAMBDA 12 was from Perkin Elmer (Norwalk, Conn.) and 96-well UV plates were obtained from Corning (Corning, N.Y.). The prewarming block was from USA Scientific (Ocala, Fla.) and the 96-well plate vortexer was from Labline Instruments (Melrose Park, Ill.). A Spectramax Plus microtiter plate reader with monochrometer was obtained from Molecular Devices (Sunnyvale, Calif.).

Enzyme Preparation: Recombinant heterodimeric HCV NS3/NS4A protease (strain 1a) was prepared by using the procedures published previously (D. L. Sali et al, *Biochemistry*, 37 (1998) 3392-3401). Protein concentrations were determined by the Biorad dye method using recombinant HCV protease standards previously quantified by amino acid analysis. Prior to assay initiation, the enzyme storage buffer (50 mM sodium phosphate pH 8.0, 300 mM NaCl, 10% glycerol, 0.05% lauryl maltoside and 10 mM DTT) was exchanged for the assay buffer (25 mM MOPS pH 6.5, 300 mM NaCl, 10% glycerol, 0.05% lauryl maltoside, 5 µM EDTA and 5 µM DTT) utilizing a Biorad Bio-Spin P-6 prepacked column.

Substrate Synthesis and Purification: The synthesis of the substrates was done as reported by R. Zhang et al, (ibid.) and was initiated by anchoring Fmoc-Nva-OH to 2-chlorotrityl chloride resin using a standard protocol (K. Barlos et al, Int. J. Pept. Protein Res., 37 (1991), 513-520). The peptides were subsequently assembled, using Fmoc chemistry, either manually or on an automatic ABI model 431 peptide synthesizer. The N-acetylated and fully protected peptide fragments were cleaved from the resin either by 10% acetic acid (HOAc) and 10% trifluoroethanol (TFE) in dichloromethane (DCM) for 30 min, or by 2% trifluoroacetic acid (TFA) in DCM for 10 min. The combined filtrate and DCM wash was evaporated azeotropically (or repeatedly extracted by aqueous $Na_2CO_3$ solution) to remove the acid used in cleavage. The DCM phase was dried over $Na_2SO_4$ and evaporated.

The ester substrates were assembled using standard acid-alcohol coupling procedures (K. Holmber et al, Acta Chem. Scand.; B33 (1979) 410-412). Peptide fragments were dissolved in anhydrous pyridine (30-60 mg/ml) to which 10 molar equivalents of chromophore and a catalytic amount (0.1 eq.) of para-toluenesulfonic acid (pTSA) were added. Dicyclohexylcarbodiimide (DCC, 3 eq.) was added to initiate the coupling reactions. Product formation was monitored by HPLC and found to be complete following 12-72 hour reaction at room temperature. Pyridine solvent was evaporated under vacuum and further removed by azeotropic evaporation with toluene. The peptide ester was deprotected with 95% TFA in DCM for two hours and extracted three times with anhydrous ethyl ether to remove excess chromophore. The deprotected substrate was purified by reversed phase HPLC on a C3 or C8 column with a 30% to 60% acetonitrile gradient (using six column volumes). The overall yield following HPLC purification was approximately 20-30%. The molecular mass was confirmed by electrospray ionization mass spectroscopy. The substrates were stored in dry powder form under desiccation.

Spectra of Substrates and Products: Spectra of substrates and the corresponding chromophore products were obtained in the pH 6.5 assay buffer. Extinction coefficients were determined at the optimal off-peak wavelength in 1-cm cuvettes (340 nm for 3-Np and HMC, 370 nm for PAP and 400 nm for 4-Np) using multiple dilutions. The optimal off-peak wavelength was defined as that wavelength yielding the maximum fractional difference in absorbance between substrate and product (product OD−substrate OD)/substrate OD).

Protease Assay: HCV protease assays were performed at 30° C. using a 200 µl reaction mix in a 96-well microtiter plate. Assay buffer conditions (25 mM MOPS pH 6.5, 300 mM NaCl, 10% glycerol, 0.05% lauryl maltoside, 5 µM EDTA and 5 µM DTT) were optimized for the NS3/NS4A heterodimer (D. L. Sali et al, ibid.)). Typically, 150 µl mixtures of buffer, substrate and inhibitor were placed in wells (final concentration of DMSO≦4% v/v) and allowed to pre-incubate at 30° C. for approximately 3 minutes. Fifty µls of prewarmed protease (12 nM, 30° C.) in assay buffer, was then used to initiate the reaction (final volume 200 µl). The plates were monitored over the length of the assay (60 minutes) for change in absorbance at the appropriate wavelength (340 nm for 3-Np and HMC, 370 nm for PAP, and 400 nm for 4-Np) using a Spectromax Plus microtiter plate reader equipped with a monochrometer (acceptable results can be obtained with plate readers that utilize cutoff filters). Proteolytic cleavage of the ester linkage between the Nva and the chromophore was monitored at the appropriate wavelength against a no enzyme blank as a control for non-enzymatic hydrolysis. The evaluation of substrate kinetic parameters was performed over a 30-fold substrate concentration range (~6-200 µM). Initial velocities were determined using linear regression and kinetic constants were obtained by fitting the data to the Michaelis-Menten equation using non-linear regression analysis (Mac Curve Fit 1.1, K. Raner). Turnover numbers ($k_{cat}$) were calculated assuming the enzyme was fully active.

Evaluation of Inhibitors and Inactivators: The inhibition constants (Ki*) for the competitive inhibitors Ac-D-(D-Gla)-L-1-(Cha)-C-OH (27), Ac-DTEDVVA(Nva)-OH and Ac-DT-EDWP(Nva)-OH were determined experimentally at fixed concentrations of enzyme and substrate by plotting $v_o/v_i$ vs. inhibitor concentration ($[I]_o$) according to the rearranged Michaelis-Menten equation for competitive inhibition kinetics: $v_o/v_i=1+[I]_o/(K_i(1+[S]_o/K_m))$, where $v_o$ is the uninhibited initial velocity, $v_i$ is the initial velocity in the presence of inhibitor at any given inhibitor concentration ($[I]_o$) and $[S]_o$ is the substrate concentration used. The resulting data were fitted using linear regression and the resulting slope, $1/(K_i(1+[S]_o/K_m))$, was used to calculate the Ki* value.

The obtained $K_i$ values for the various macrocycles of the present invention are given in Tables 1, 2 and 2A, where the compounds have been arranged in the order of ranges of Ki* values, as well as in Table 3. From these test results, it will be apparent to the skilled artisan that the compounds of the invention have excellent utility as NS3-serine protease inhibitors.

What is claimed is:

1. A compound having the general structure shown in Formula 1:

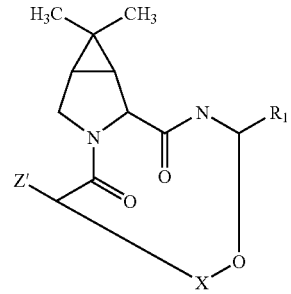

Formula 1 or pharmaceutically acceptable salts, of said compound wherein:

(1) $R^1$ is —C(O)$R^5$ or —B(OR)$_2$;

(2) $R^5$ is H, —OH, —OR$^8$, —NR$^9$R$^{10}$, —C(O)OR$^8$, —C(O)NR$^9$R$^{10}$, —CF$_3$, —C$_2$F$_5$, —C$_3$F$_7$, —CF$_2$R$^6$, —R$^6$, —C(O)R$^7$ or NR$^7$SO$_2$R$^8$;

(3) $R^7$ is H, —OH, —OR$^8$, or —CHR$^9$R$^{10}$;

(4) $R^6$, $R^8$, $R^9$ and $R^{10}$ can be the same or different, each being independently selected from the group consisting of H: alkyl, alkenyl, aryl, heteroalkyl, heteroaryl, cycloalkyl, arylalkyl, heteroarylalkyl, R$^{14}$, —CH(R$^{1'}$)CH(R$^{1'}$)C(O)OR$^{11}$, —[CH(R$^{1'}$)]$_p$C(O)OR$^{11}$, —[CH(R$^{1'}$)]$_p$C(O)NR$^{12}$R$^{13}$, —[CH(R$^{1'}$)]$_p$S(O$_2$)R$^{11}$, —[CH(R$^{1'}$)]$_p$C(O)R$^{11}$, —[CH(R$^{1'}$)]$_p$S(O$_2$)NR$^{12}$R$^{13}$, —CH(R$^{1'}$)C(O)N(H)CH(R$^{2'}$)(R'), —CH(R$^{1'}$)CH(R$^{1'}$)C(O)NR$^{12}$R$^{13}$, —CH(R$^{1'}$)CH(R$^{1'}$)S(O$_2$)R$^{11}$, —CH(R$^{1'}$)CH(R$^{1'}$)S(O$_2$)NR$^{12}$R$^{13}$, —CH(R$^{1'}$)CH(R$^{1'}$)C(O)R$^{11}$, —[CH(R$^{1'}$)]$_p$CH(OH)R$^{11}$, —CH(R$^{1'}$)C(O)N(H)CH(R$^{2'}$)C(O)OR$^{11}$, —C(O)N(H)CH(R$^{2'}$)C(O)OR$^{11}$, —C(O)N(H)CH(R$^{2'}$)C(O)R$^{11}$, —CH(R$^{1'}$)C(O)N(H)CH(R$^{2'}$)C(O)NR$^{12}$R$^{13}$, —CH(R$^{1'}$)C(O)N(H)CH(R$^{2'}$)R', —CH(R$^{1'}$)C(O)N(H)CH(R$^{2'}$)C(O)N(H)CH(R$^{3'}$)C (O)OR¹¹, —CH(R¹')C(O)N(H)CH(R²')C(O)CH(R³')NR¹²R¹³, —CH(R¹')C(O)N(H)CH(R²')C(O)N(H)CH(R³')C(O)NR¹²R¹³, —CH(R¹')C(O)N(H)CH(R²')C(O)N(H)CH(R³')C(O)N(H)CH(R⁴')C(O)OR¹¹, —CH(R¹')C(O)N(H)CH(R²')C(O)N(H)CH(R³')C(O)N(H)CH(R⁴')C(O)NR¹²R¹³, —CH(R¹')C(O)N(H)CH(R²')C(O)N(H)CH(R³')C(O)N(H)CH(R⁴')C(O)N(H)CH(R⁵')C(O)OR¹¹, and —CH(R¹')C(O)N(H)CH(R²')C(O)N(H)CH(R³')C(O)N(H)CH(R⁴')C(O)N(H)CH(R⁵')C(O)NR¹²R¹³;

wherein R¹', R²', R³', R⁴', R⁵', R¹¹, R¹² and R¹³ can be the same or different, each being independently selected from the group consisting of: H, halogen, alkyl, aryl, heteroalkyl, heteroaryl, cycloalkyl, alkoxy, aryloxy, alkenyl, alkynyl, alkyl-aryl, alkyl-heteroaryl, heterocycloalkyl, aryl-alkyl and heteroaralkyl;

or R¹² and R¹³ are linked together such that the combination is cycloalkyl, heterocycloalkyl, aryl or heteroaryl;

R¹⁴ is present or not and if present is selected from the group consisting of: H, alkyl, aryl, heteroalkyl, heteroaryl, cycloalkyl, alkyl-aryl, allyl, alkyl-heteroaryl, alkoxy, aryl-alkyl, alkenyl, alkynyl and heteroaralkyl;

(5) R and R' are present or not and if present can be the same or different, each being independently selected from the group consisting of: H, OH, $C_1$-$C_{10}$ alkyl, $C_2$-$C_{10}$ alkenyl, $C_3$-$C_8$ cycloalkyl, $C_3$-$C_8$ heterocycloalkyl, alkoxy, aryloxy, alkylthio, arylthio, alkylamino, arylamino, amino, amido, arylthioamino, arylcarbonylamino, arylaminocarboxy, alkylaminocarboxy, heteroalkyl, alkenyl, alkynyl, (aryl)alkyl, heteroarylalkyl, ester, carboxylic acid, carbamate, urea, ketone, aldehyde, cyano, nitro, halogen, (cycloalkyl)alkyl, aryl, heteroaryl, (alkyl)aryl, alkylheteroaryl, alkyl-heterocyclyl and (heterocycloalkyl)alkyl, wherein said cycloalkyl is made of three to eight carbon atoms, and zero to six oxygen, nitrogen, sulfur, or phosphorus atoms, and said alkyl is of one to six carbon atoms;

(6) Z' is represented by either (i), (ii), (iii), (iv) or (v) shown below:

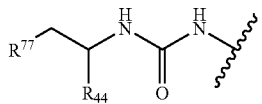

Formula A wherein:

R⁴⁴ is selected from the group consisting of:

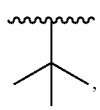 , 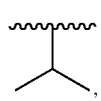 ,

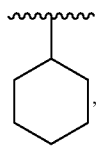 , 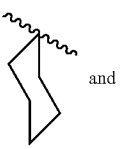 and 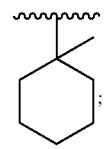 ;

and R⁷⁷ is selected from the group consisting of:

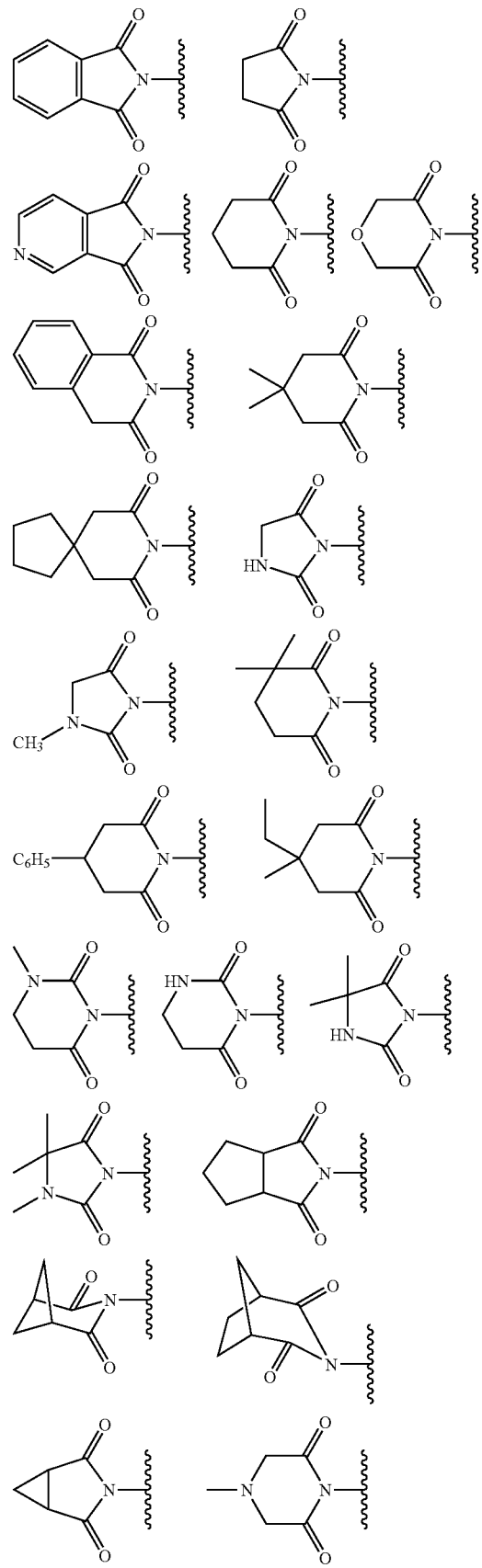

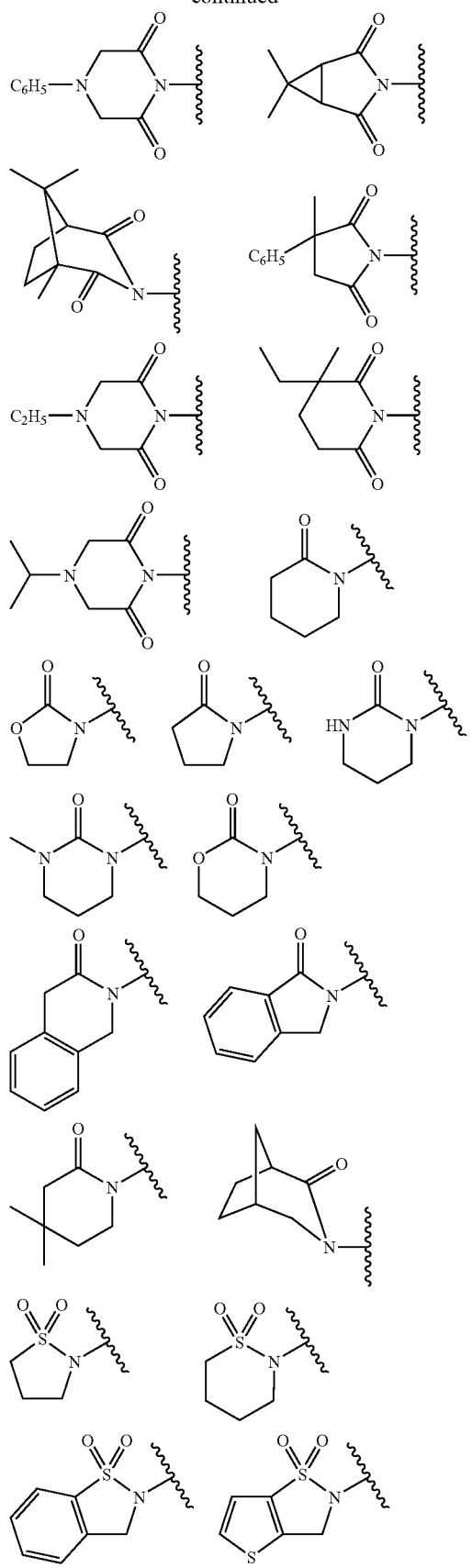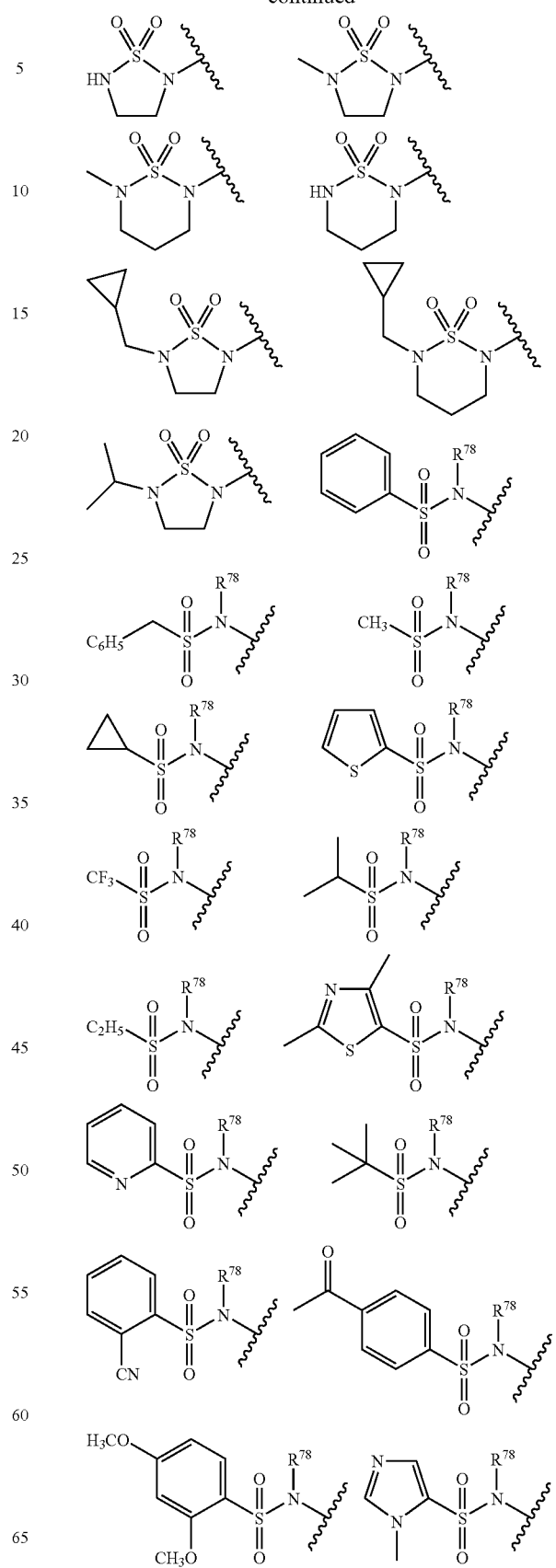

-continued
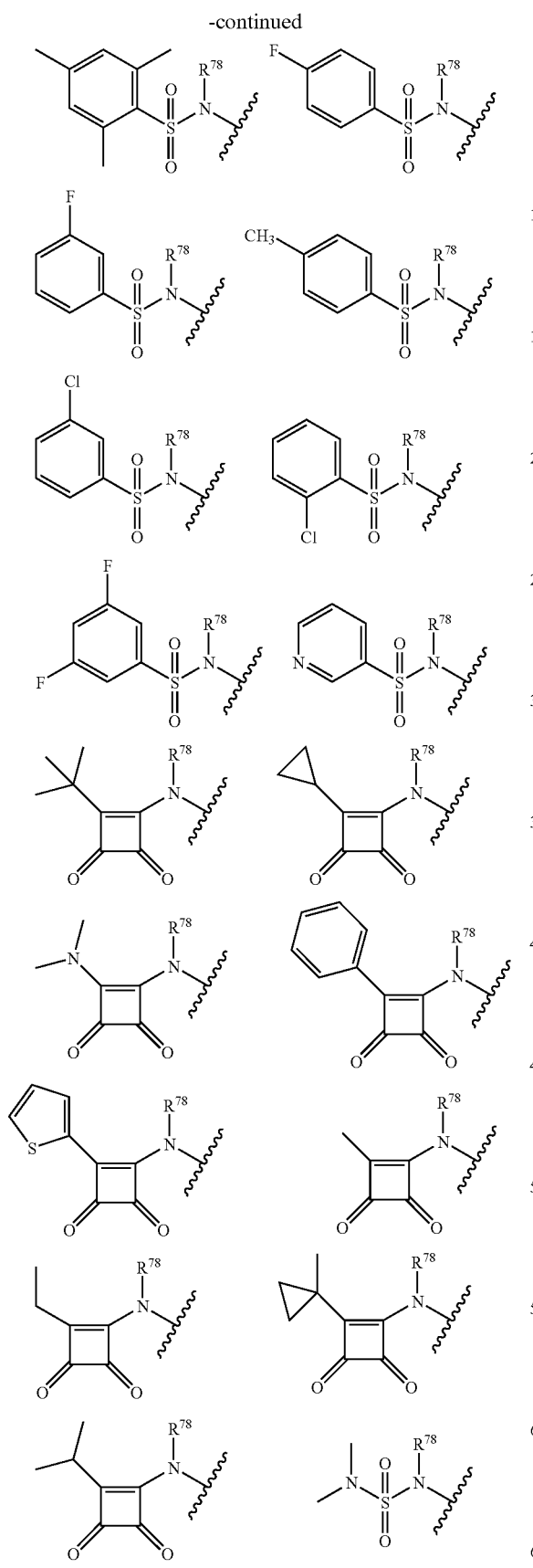
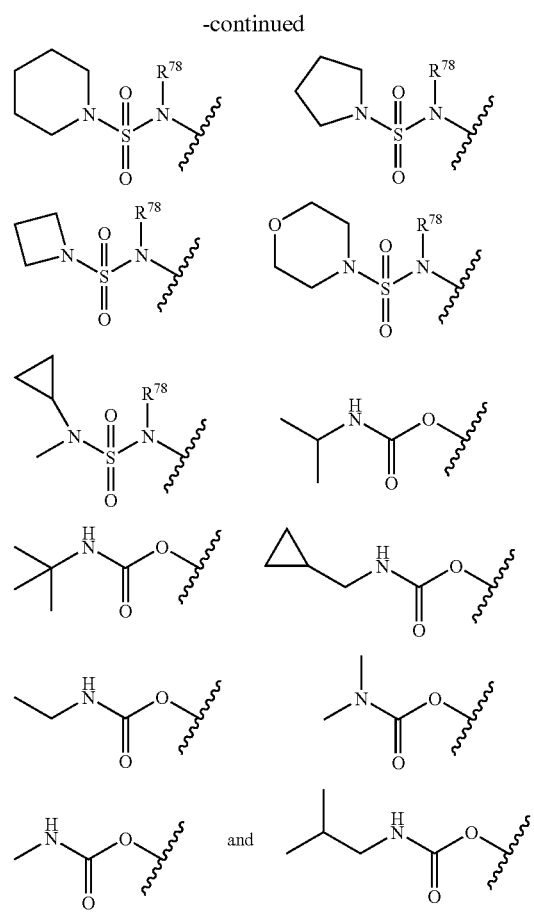
where R[78] is selected from methyl, ethyl, isopropyl, tert-butyl and phenyl;
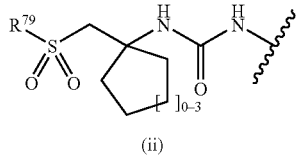
Formula B
(ii)
where R[79] is selected from the group consisting of:
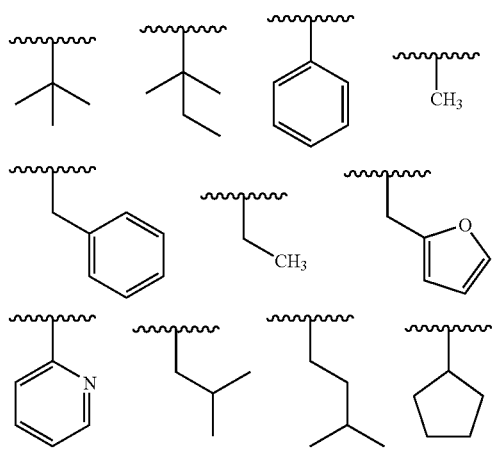

-continued
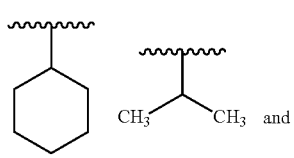 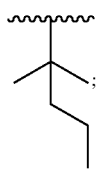
Formula C
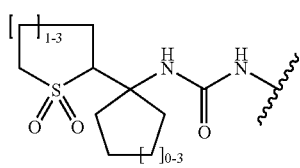
(iii)
wherein the sulfone ring is optionally substituted with alkyl and cycloalkyl;
(iv) the moiety:
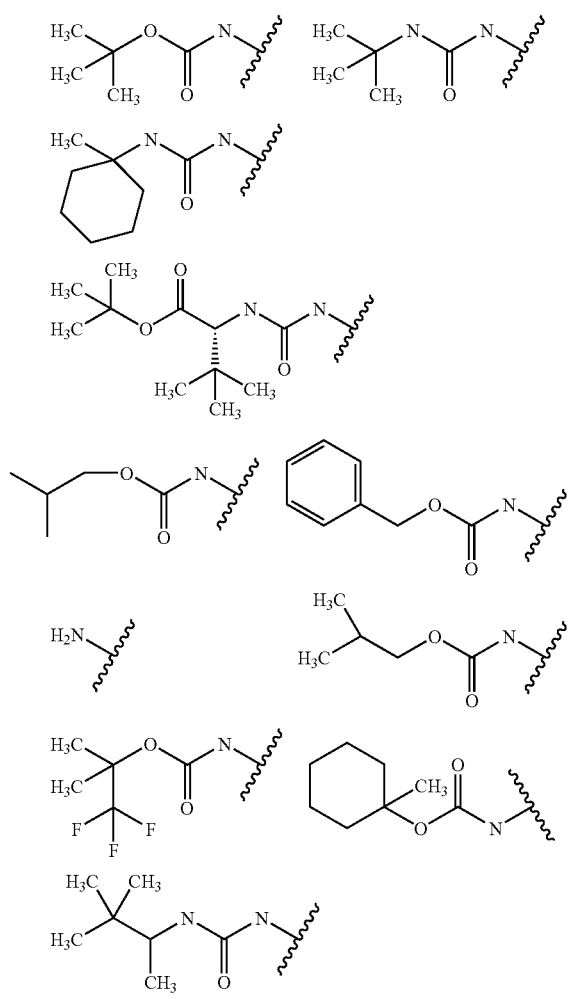
-continued
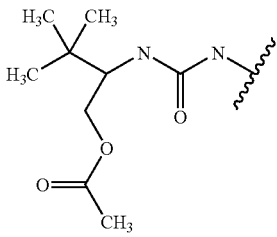
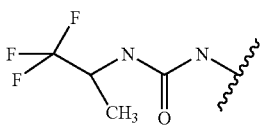 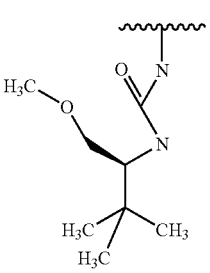
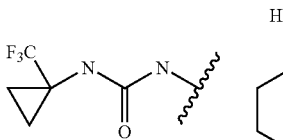 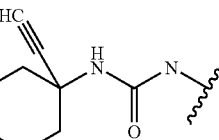
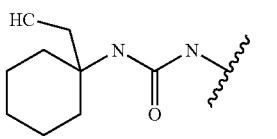
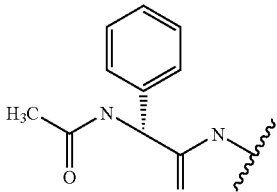
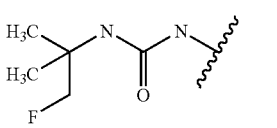
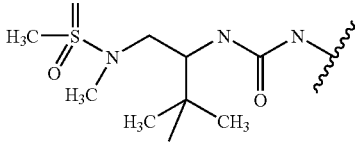
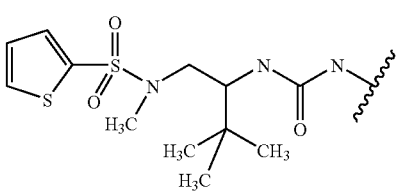
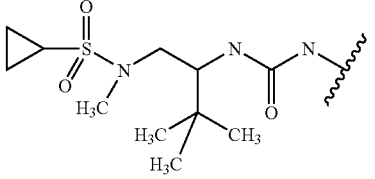

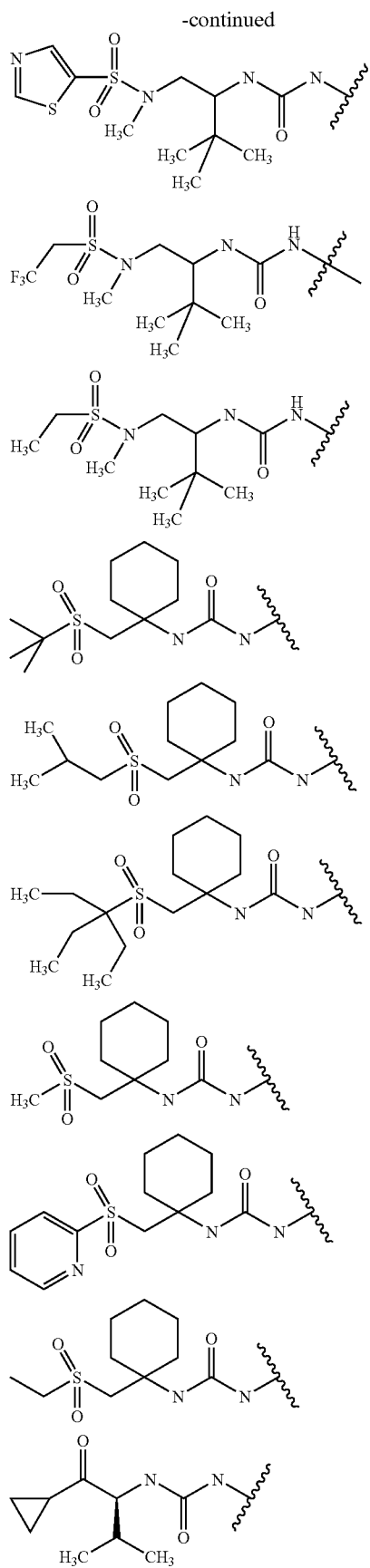
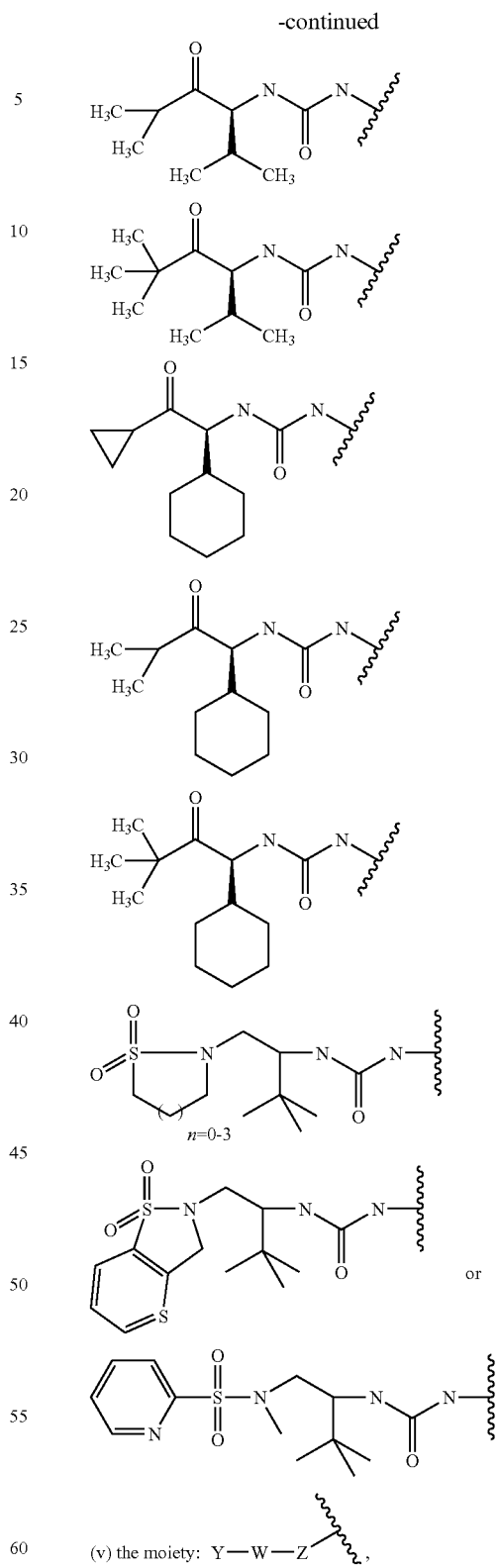
(v) the moiety: Y—W—Z⁀,
wherein W is —C(=O)— or —S(O₂)—;
Z is O or N;
and Y is selected from the group consisting of:

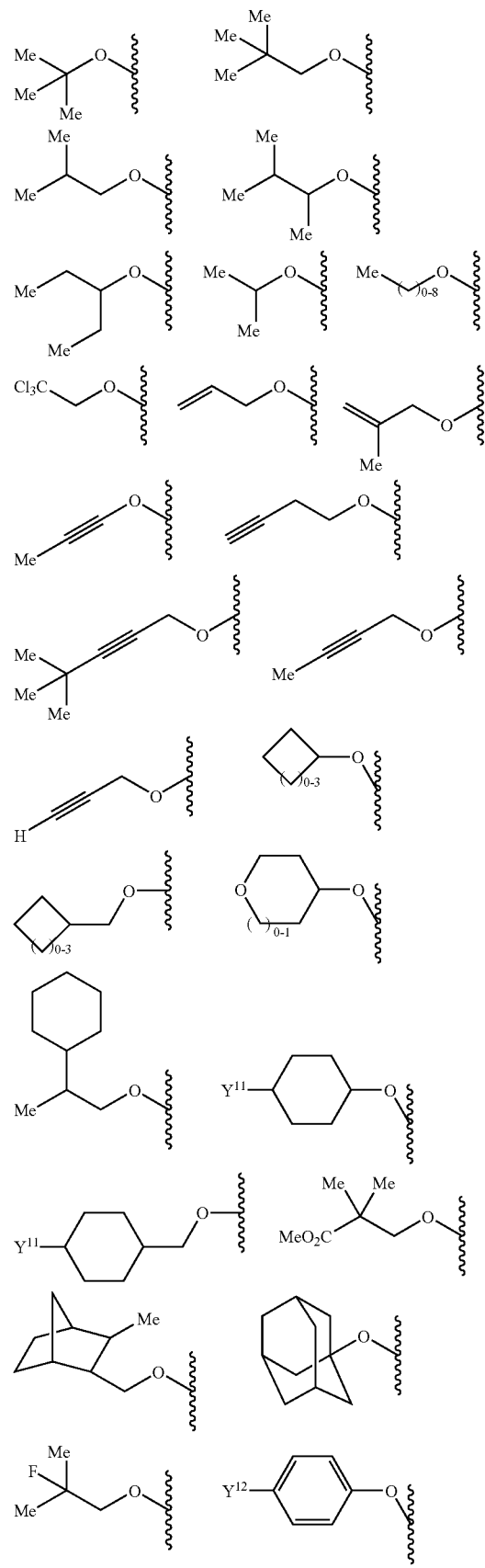
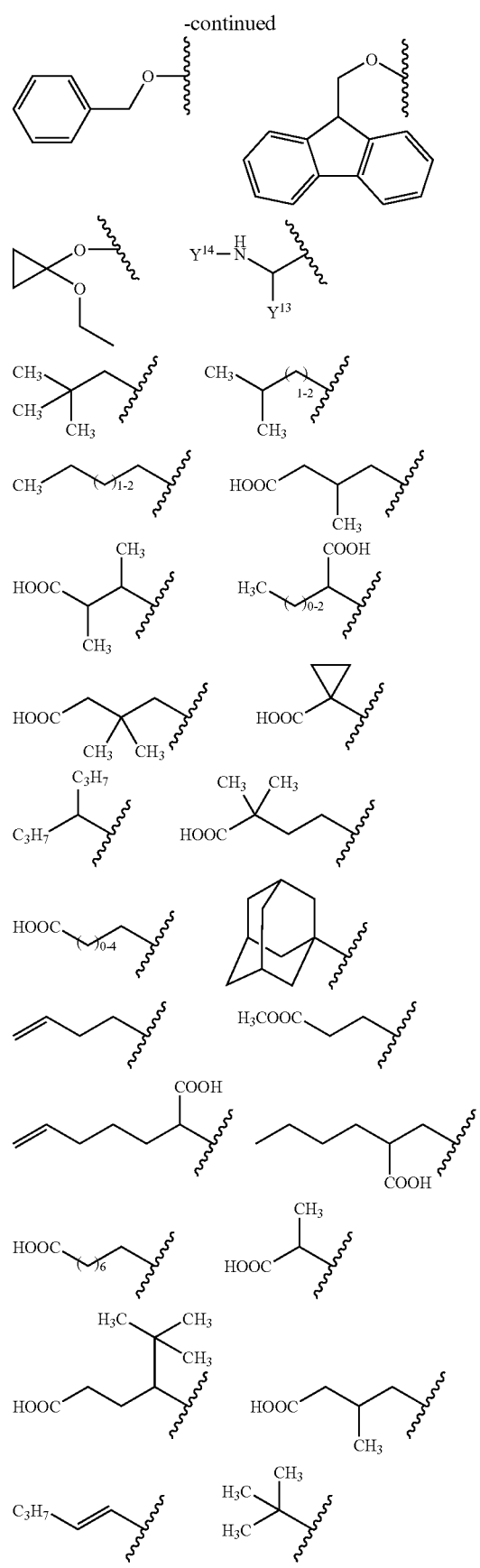
-continued

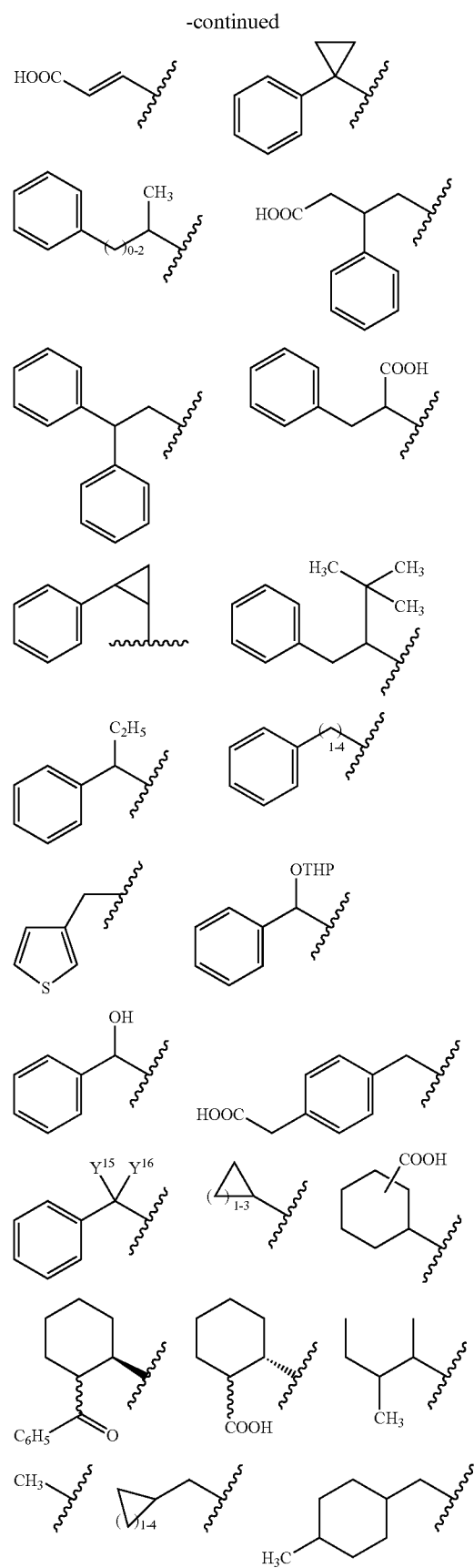
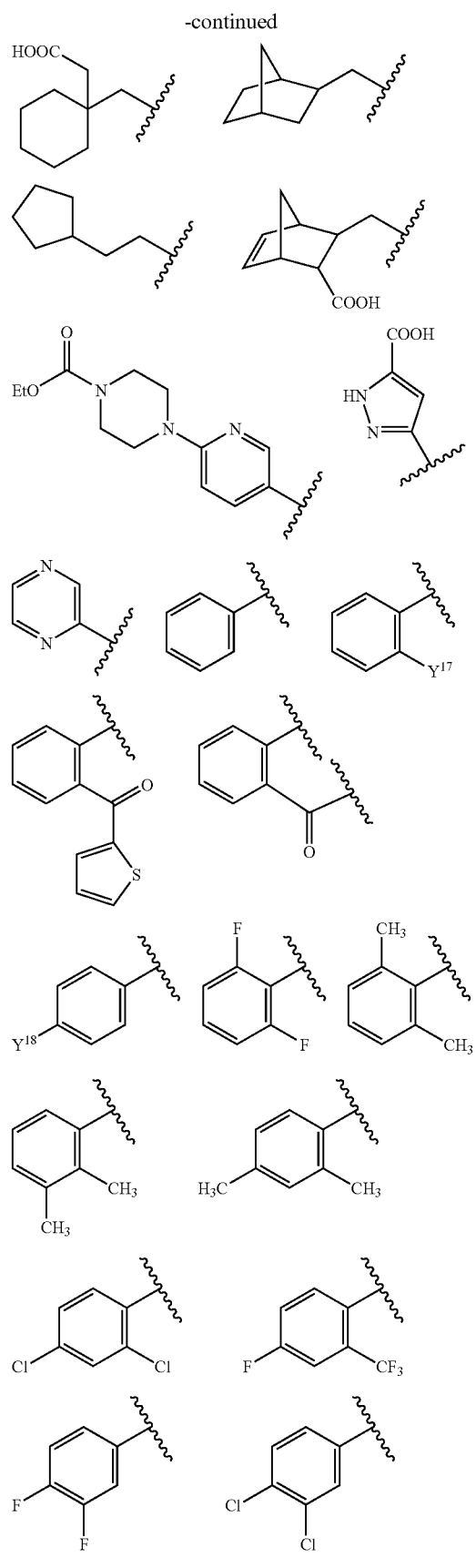

-continued
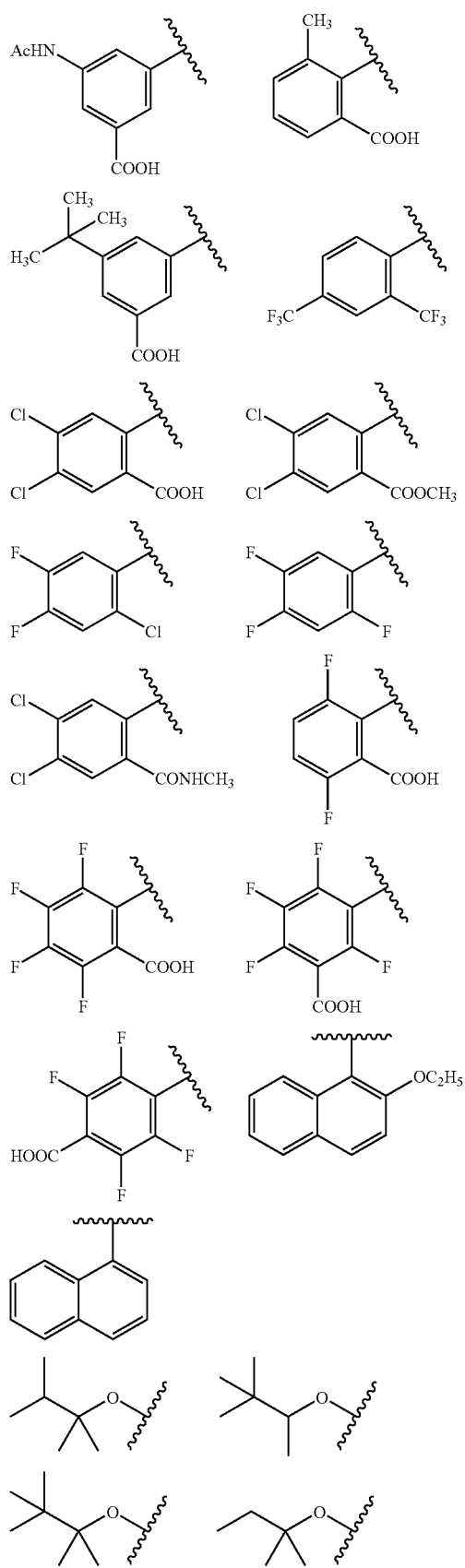
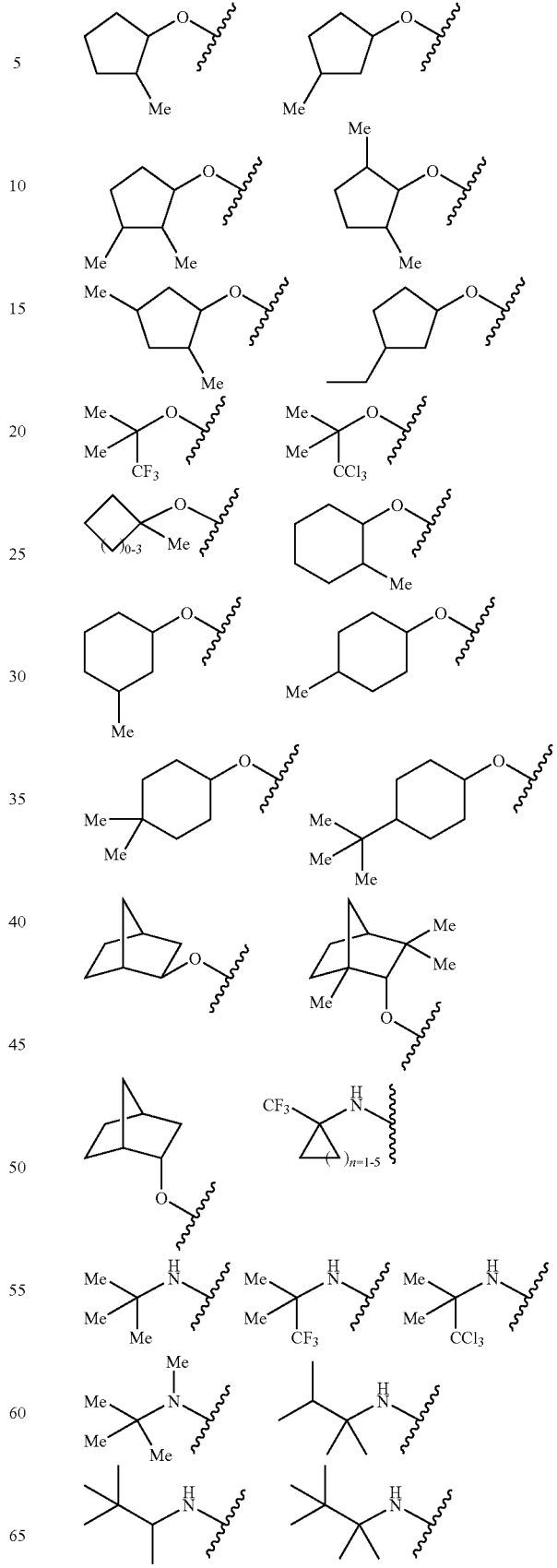

-continued

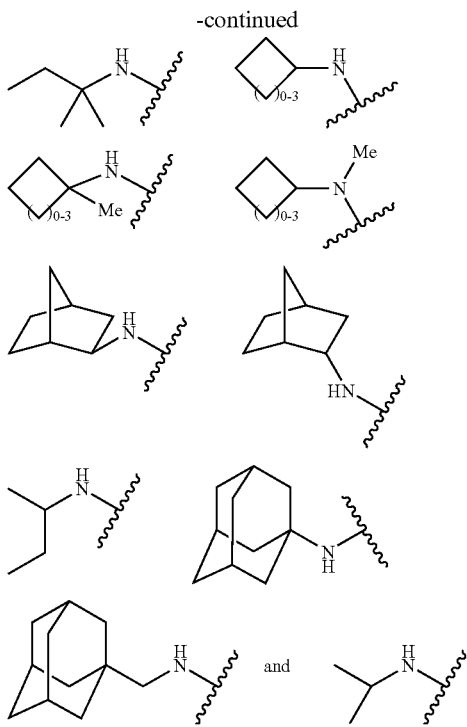

wherein:

Y[11] is selected from the group consisting of: H, —C(O)OH, —C(O)OEt, —OMe, —Ph, —OPh, —NHMe, —NHAc, —NHPh, —CH(Me)$_2$, 1-triazolyl, 1-imidazolyl and —NHCH$_2$COOH;

Y[12] is selected from the group consisting of: H, —C(O)OH, —C(O)OMe, —OMe, F, Cl and Br;

Y[13] is selected from the group consisting of the following moieties:

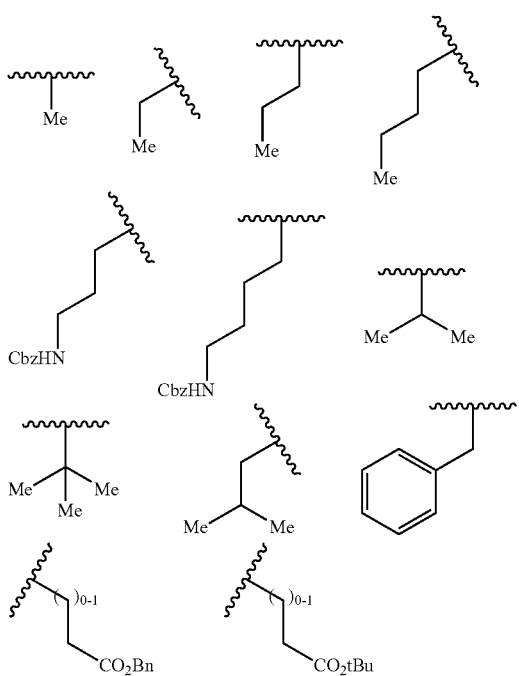

-continued

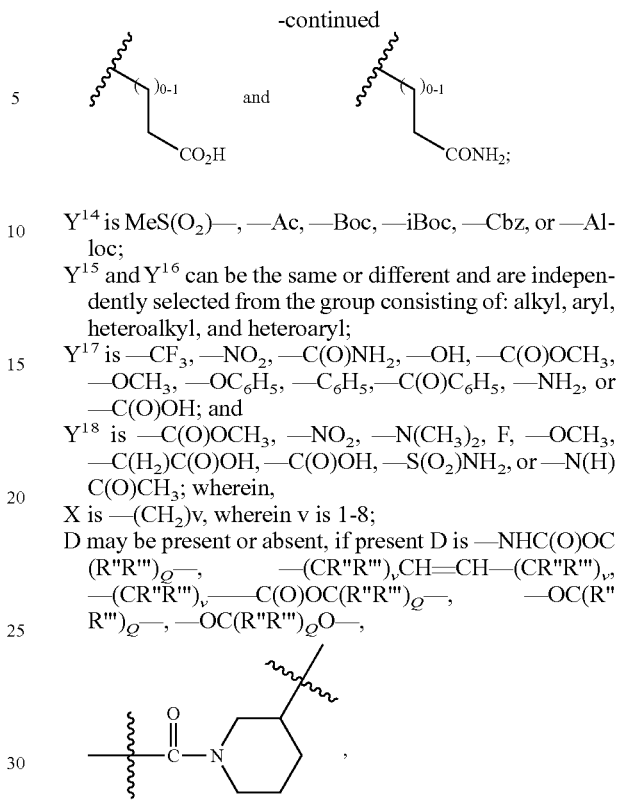

Y[14] is MeS(O$_2$)—, —Ac, —Boc, —iBoc, —Cbz, or —Alloc;

Y[15] and Y[16] can be the same or different and are independently selected from the group consisting of: alkyl, aryl, heteroalkyl, and heteroaryl;

Y[17] is —CF$_3$, —NO$_2$, —C(O)NH$_2$, —OH, —C(O)OCH$_3$, —OCH$_3$, —OC$_6$H$_5$, —C$_6$H$_5$, —C(O)C$_6$H$_5$, —NH$_2$, or —C(O)OH; and Y[18] is —C(O)OCH$_3$, —NO$_2$, —N(CH$_3$)$_2$, F, —OCH$_3$, —C(H$_2$)C(O)OH, —C(O)OH, —S(O$_2$)NH$_2$, or —N(H)C(O)CH$_3$; wherein, X is —(CH$_2$)v, wherein v is 1-8;

D may be present or absent, if present D is —NHC(O)OC(R"R''')$_Q$—, —(CR"R''')$_v$CH═CH—(CR"R''')$_v$, —(CR"R''')$_v$—C(O)OC(R"R''')$_Q$—, —OC(R"R''')$_Q$—, —OC(R"R''')$_Q$O—, —O(CO)—C(R"R''')$_Q$—, —NHC(R"R''')$_Q$—, wherein R" and R''' are independently selected from the group consisting of H, (C$_1$-C$_6$)alkyl and bond or R" and R''' together with the R" and R''' of the adjoining C form a cycloalkyl group, further wherein Q is 1-3.

2. The compound according to claim 1, wherein X is —(CH$_2$)$_v$, wherein v is 1-8.

3. The compound according to claim 1, wherein R[1] is a ketoamide, ketoaldehyde, diketone, ketoacid or ketoester.

4. The compound according to claim 3, wherein R[1] is —C(O)C(O)NR[9]R[10]; R[9] is H; and R[10] is H, —R[14], —[CH(R[1'])]$_p$C(O)OR[11], —[CH(R[1'])]$_p$C(O)NR[12]R[13], —[CH(R[1'])]$_p$S(O$_2$)R[11], —[CH(R[1'])]$_p$S(O$_2$)NR[12]R[13], —[CH(R[1'])]$_p$C(O)R[11], —CH(R[1'])C(O)N(H)CH(R[2'])C(O)OR[11], —CH(R[1'])C(O)N(H)CH(R[2'])C(O)NR[12]R[13] or —CH(R[1'])C(O)N(H)CH(R[2'])(R').

5. The compound according to claim 4, wherein:

R[10] is H, —R[14], —CH(R[1'])C(O)OR[11], —CH(R[1'])CH(R[1'])C(O)OR[11], —CH(R[1'])C(O)NR[12]R[13], —CH(R[1'])CH(R[1'])C(O)NR[12]R[13], —CH(R[1'])CH(R[1'])S(O$_2$)R[11], —CH(R[1'])CH(R[1'])S(O$_2$)NR[12]R[13], —CH(R[1'])CH(R[1'])C(O)R[11], —CH(R[1'])C(O)N(H)CH(R[2'])C(O)OR[11], —CH(R[1'])C(O)N(H)CH(R[2'])C(O)NR[12]R[13], or —CH(R[1'])C(O)N(H)CH(R[2'])(R');

R[1'] is H or alkyl; and

R[2'] is phenyl, substituted phenyl, hetero atom-substituted phenyl, cycloalkyl, heterocycloalkyl, piperidyl or pyridyl.

6. The compound according to claim 5, wherein R[1'] is H.

7. The compound according to claim 4, wherein

R[11] is H, methyl, ethyl, allyl, tert-butyl, benzyl, α-methylbenzyl, α,α-dimethylbenzyl, 1-methylcyclopropyl or 1-methylcyclopentyl;

R' is hydroxymethyl or —CH$_2$C(O)NR[12]R[13];

R² is independently selected from the group consisting of the following structures:

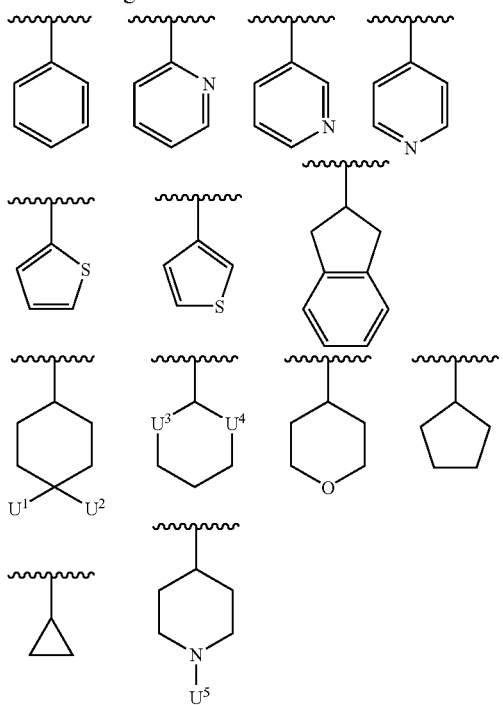

wherein U¹ and U² may be same or different and are independently selected from the group consisting of: H, F, —CH₂C(O)OH, —CH₂C(O)OMe, —CH₂C(O)NH₂, —CH₂C(O)NHMe, —CH₂C(O)NMe₂, azido, amino, hydroxyl, substituted amino and substituted hydroxyl;
U³ and U⁴ are the same or different and are independently O or S;
U⁵ is alkyl sulfonyl, aryl sulfonyl, heteroalkyl sulfonyl, heteroaryl sulfonyl, alkyl carbonyl, aryl carbonyl, heteroalkyl carbonyl, heteroaryl carbonyl, alkoxycarbonyl, aryloxycarbonyl, heteroaryloxycarbonyl, alkylaminocarbonyl, arylaminocarbonyl, or heteroarylaminocarbonyl or a combination thereof;
NR¹²R¹³ is selected from the group consisting of:

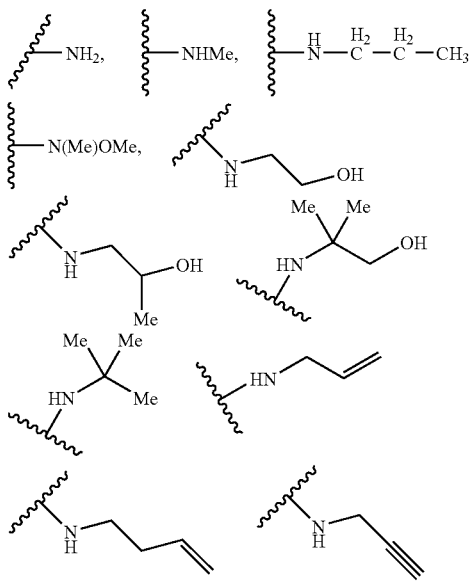

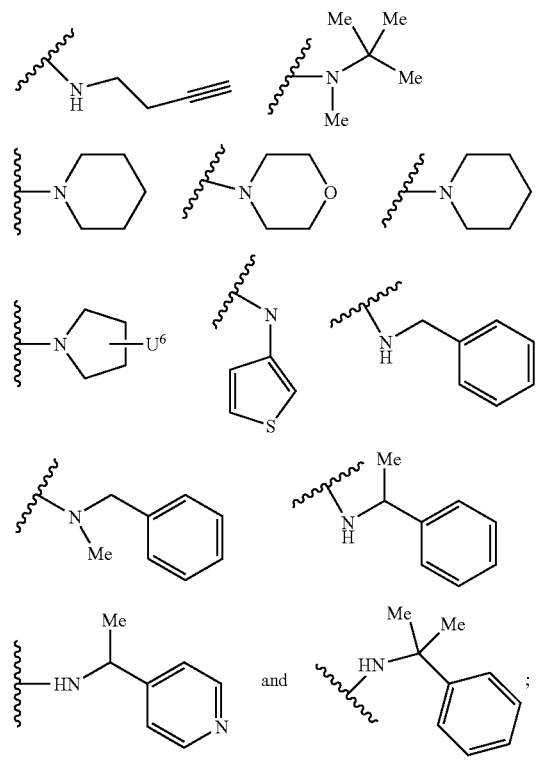

U⁶ is H, OH, or CH₂OH, and
R¹⁴ is selected from the group consisting of: H, —CH₃, Et, n-propyl, methoxy, cyclopropyl, n-butyl, 1-but-3-ynyl, benzyl, α-methylbenzyl, phenethyl, allyl, 1-but-3-enyl, —OCH₃ and cyclopropylmethyl.

8. The compound according to claim 1, wherein R¹ is selected from the following structures:

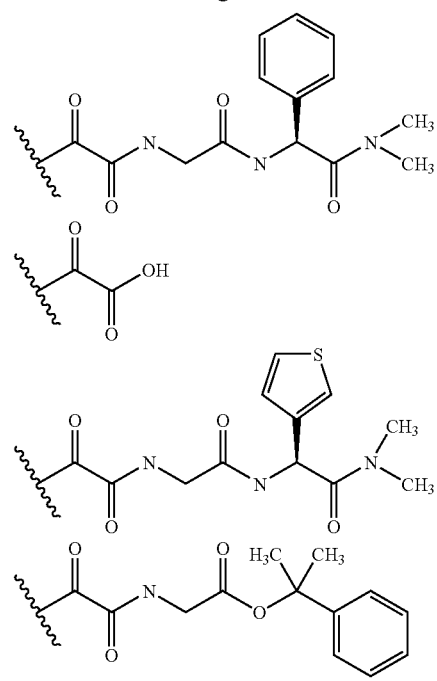

-continued

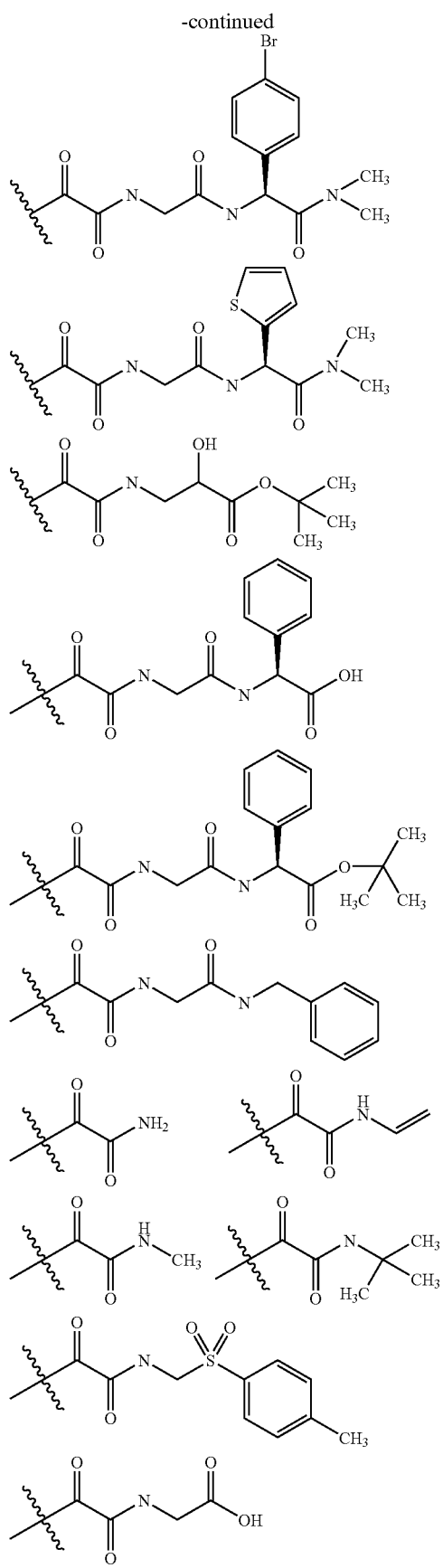

-continued

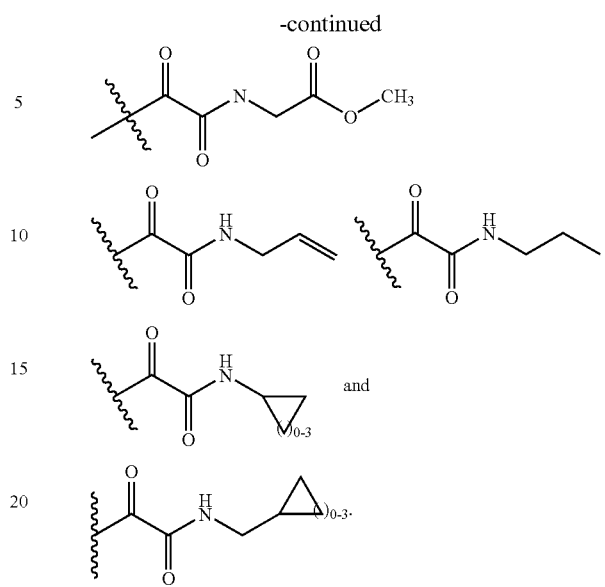

9. The compound according to claim 1, wherein D and X taken together form a divalent $C_7$-$C_{12}$ unbranched paraffinic linking chain forming a portion of a 14-19 member macrocycle.

10. The compound according to claim 9, wherein D and X taken together form a $C_8$ or $C_9$ unbranched paraffinic linking chain forming a portion of a 15 or 16 membered heterocycle.

11. The compound according to claim 1, wherein D and X taken together form a divalent $C_7$-$C_{12}$ unbranched olefinic linking chain forming a portion of a 14-19 member macrocycle having a single degree of unsaturation.

12. The compound according to claim 11, wherein D and X taken together form a $C_8$ or $C_9$ unbranched olefinic linking claim forming a portion of a 15 or 16 member heterocycle having a single degree of unsaturation.

13. The compound according to claim 1, wherein D and X taken together form a divalent $C_2$-$C_{12}$ unbranched aliphatic chain forming a portion of a 9-19 membered heterocycle.

14. The compound according to claim 1, wherein the portion represented by the part

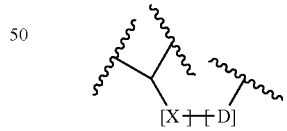

in the moiety

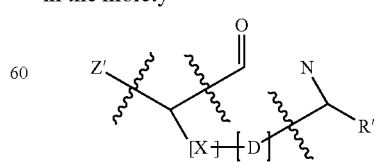

in Formula 1 is selected from the following structures:

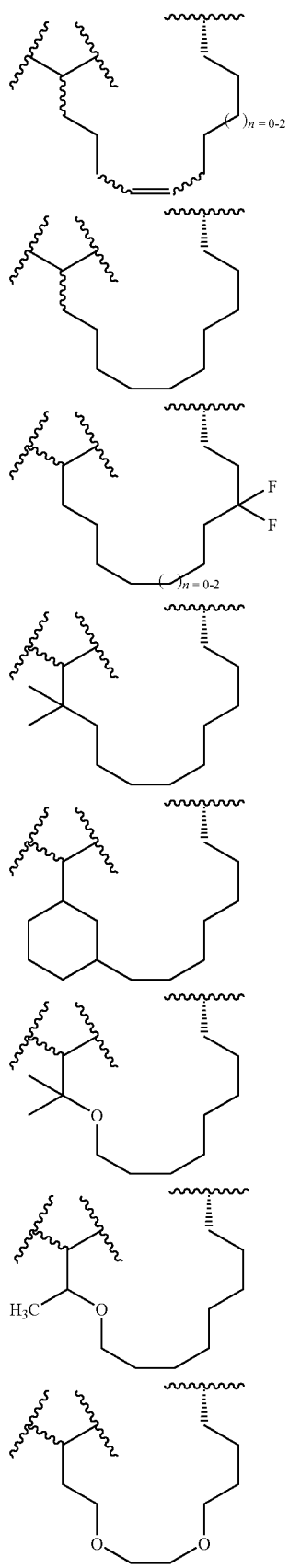
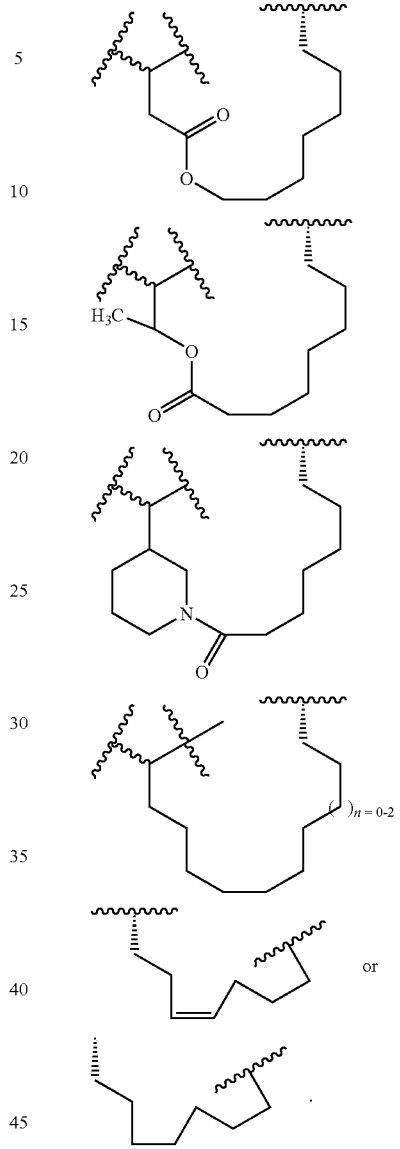
15. The compound according to claim 1, wherein Z' is selected from the group consisting of:
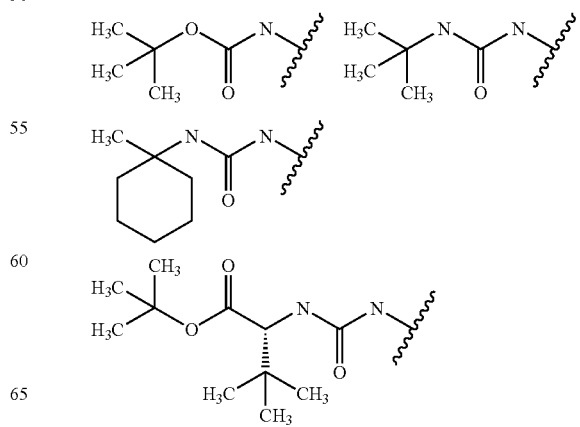

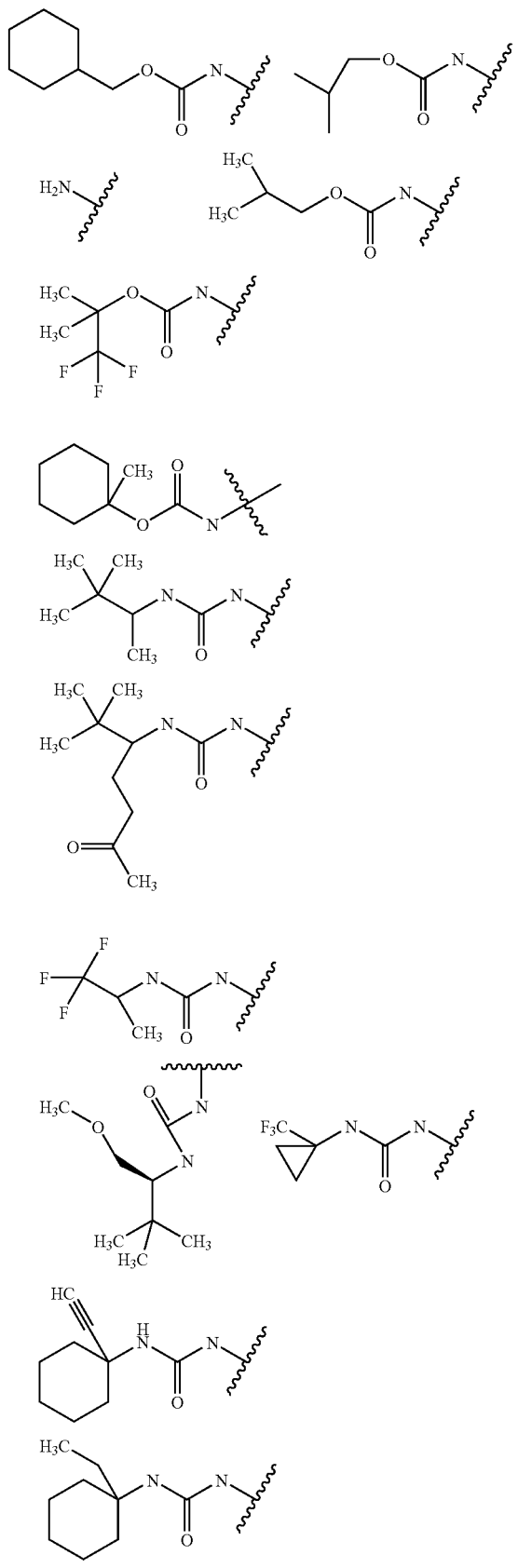
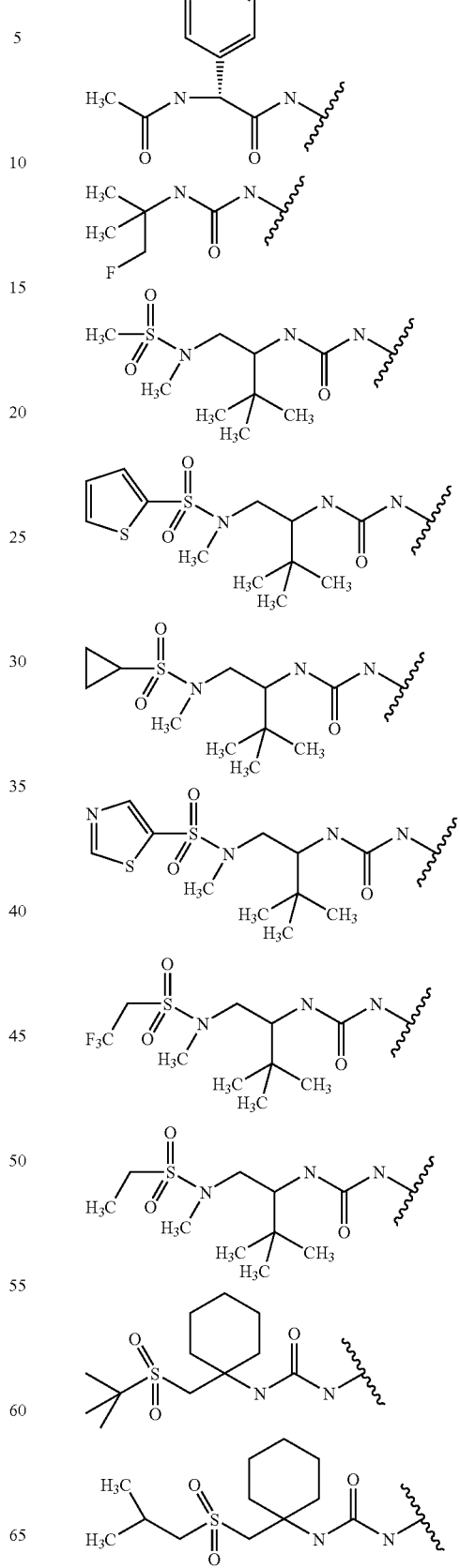

-continued
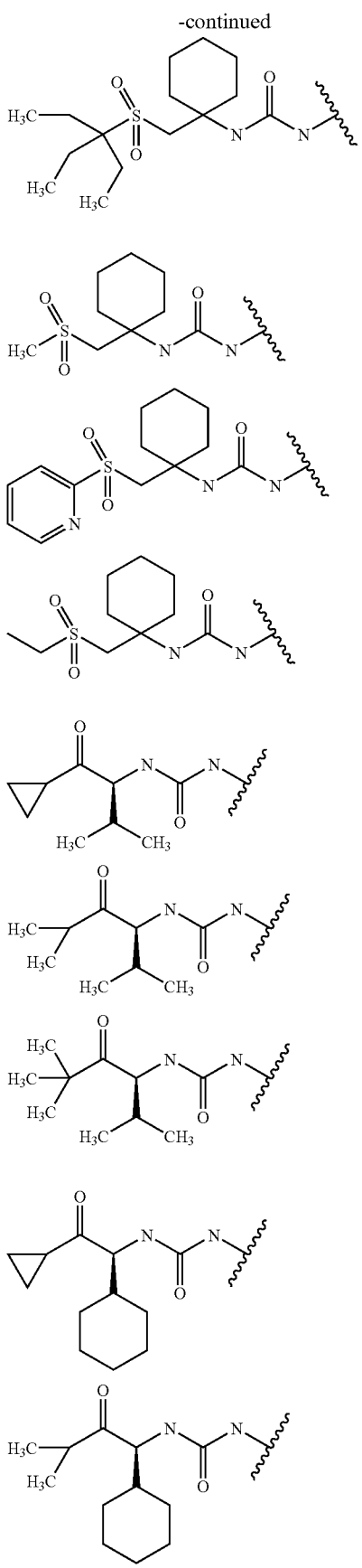
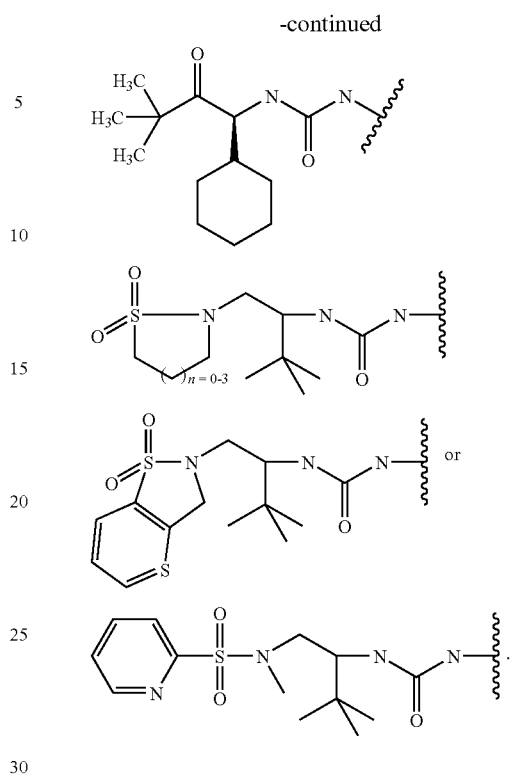
16. The compound according to claim 1, wherein W is C=O.
17. The compound according to claim 1, wherein Z is N.
18. The compound according to claim 1, wherein Y is selected from the group consisting of the following structures:
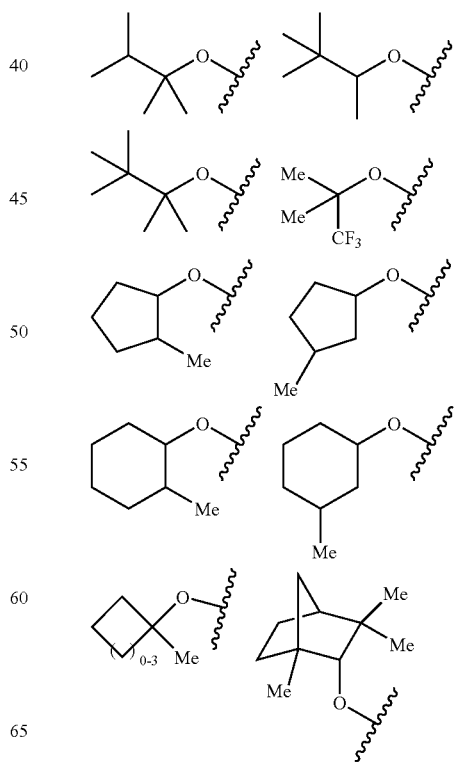

421
-continued
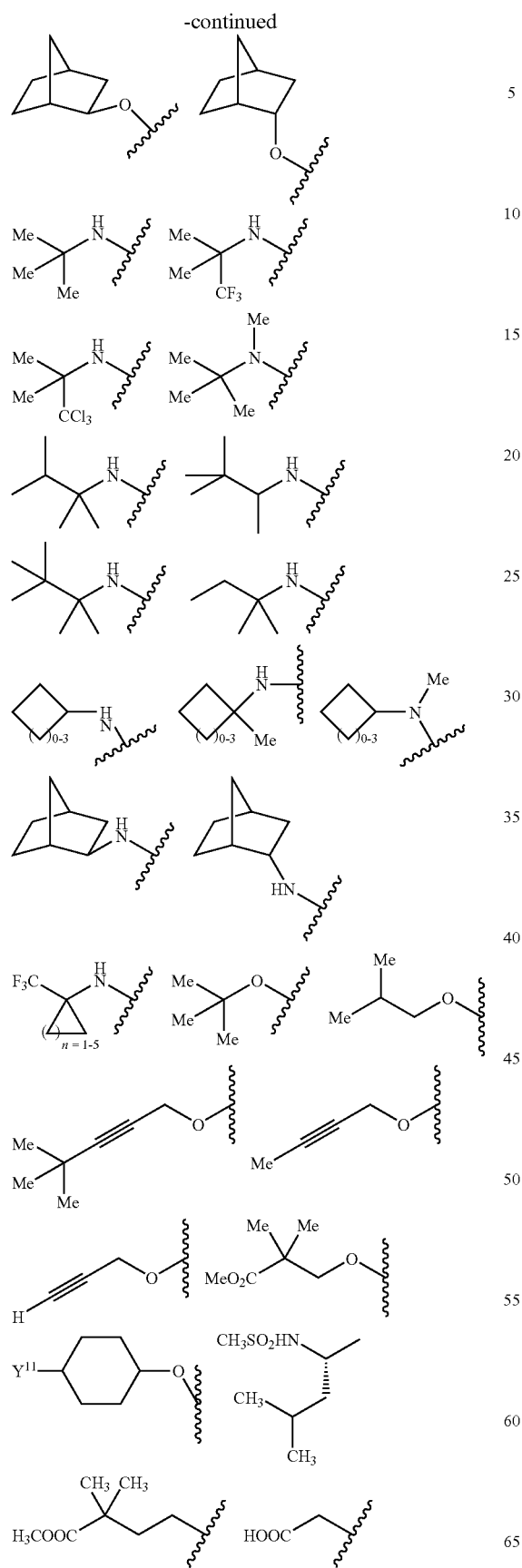
422
-continued
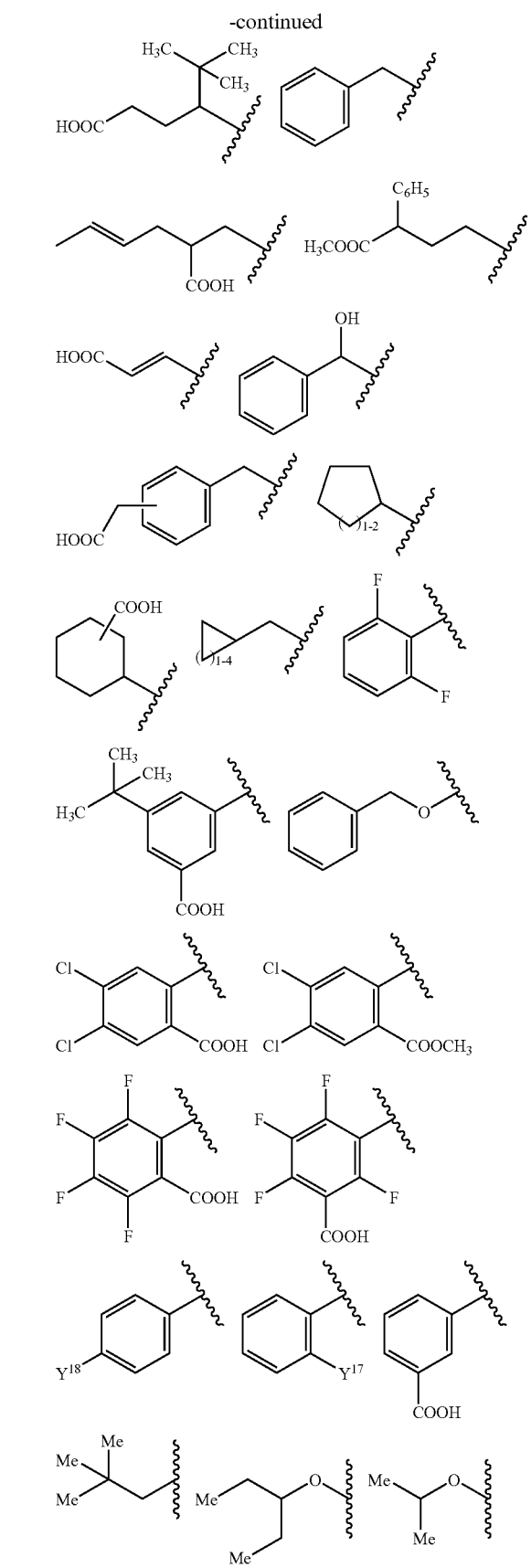

-continued
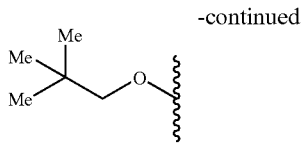
wherein $Y^{17}$ is $CF_3$, $NO_2$, $C(O)NH_2$, $OH$, $NH_2$ or $C(O)OH$; and
$Y^{18}$ is F or $C(O)OH$.
19. The compound according to claim 18, wherein Y is selected from the group consisting of the following structures:
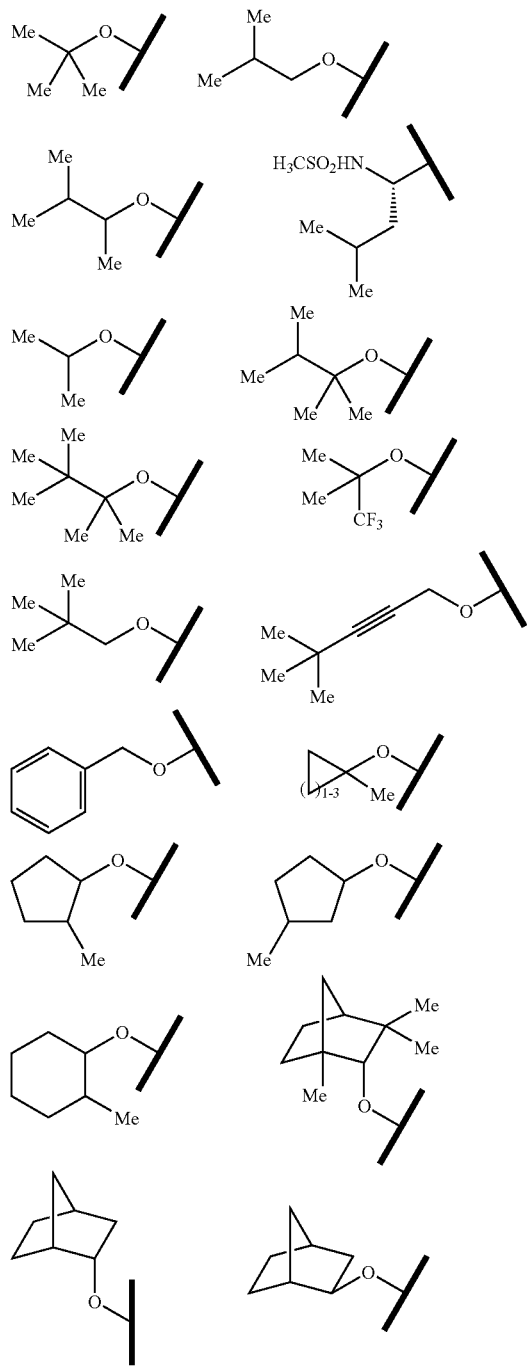
-continued
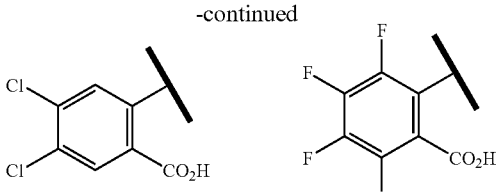
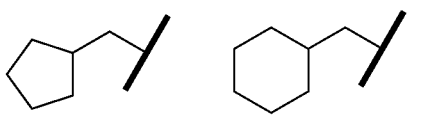
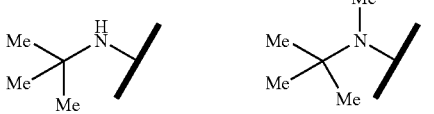
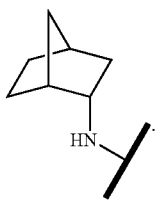
and
20. The compound according to claim 1, wherein Y is selected from the group consisting of the following structures:
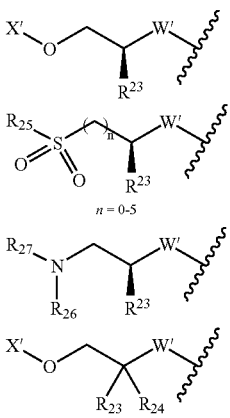

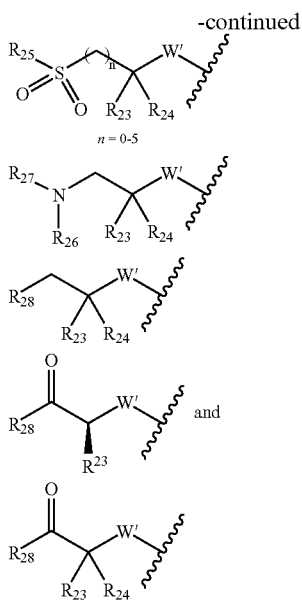

W' is N or O;

R²³ is H, alkyl, aryl, heteroaryl, cycloalkyl or heterocycloalkyl wherein each of said aryl, heteroaryl, cycloalkyl, heterocycloalkyl may be substituted with an alkyl moiety;

R²⁴ is H, alkyl, aryl, heteroaryl, cycloalkyl or heterocycloalkyl wherein each of said aryl, heteroaryl, cycloalkyl, heterocycloalkyl may be substituted with an alkyl moiety;

or R²³ and R²⁴ taken together form a cyclic ring containing a carbocycle or heterocycle;

R²⁵ is H, alkyl, heteroalkyl, aryl, heteroaryl, alkylamino, arylamino, heteroalkylamino or cycloalkyl, R²⁶ is selected from the group consisting of: H, carbamate, sulfonamides, alkylcarbonyl, alkylsulfonyl, arylsulfonyl, heteroaryl, sulfonyl, heteroalkylsulfonyl, aryloxycarbonyl, heteroalkoxycarbonyl, heteroaryloxycarbonyl, alkylaminoarbonyl, arylaminocarbonyl and urea;

R²⁷ is H, alkyl, cycloalkyl, aryl or heteroaryl;

R²⁸ is H, alkyl, heteroalkyl, aryl or heteroaryl; and

X'—O— is an ether, ester or carbamate.

21. The compound according to claim 1, selected form the group consisting of:

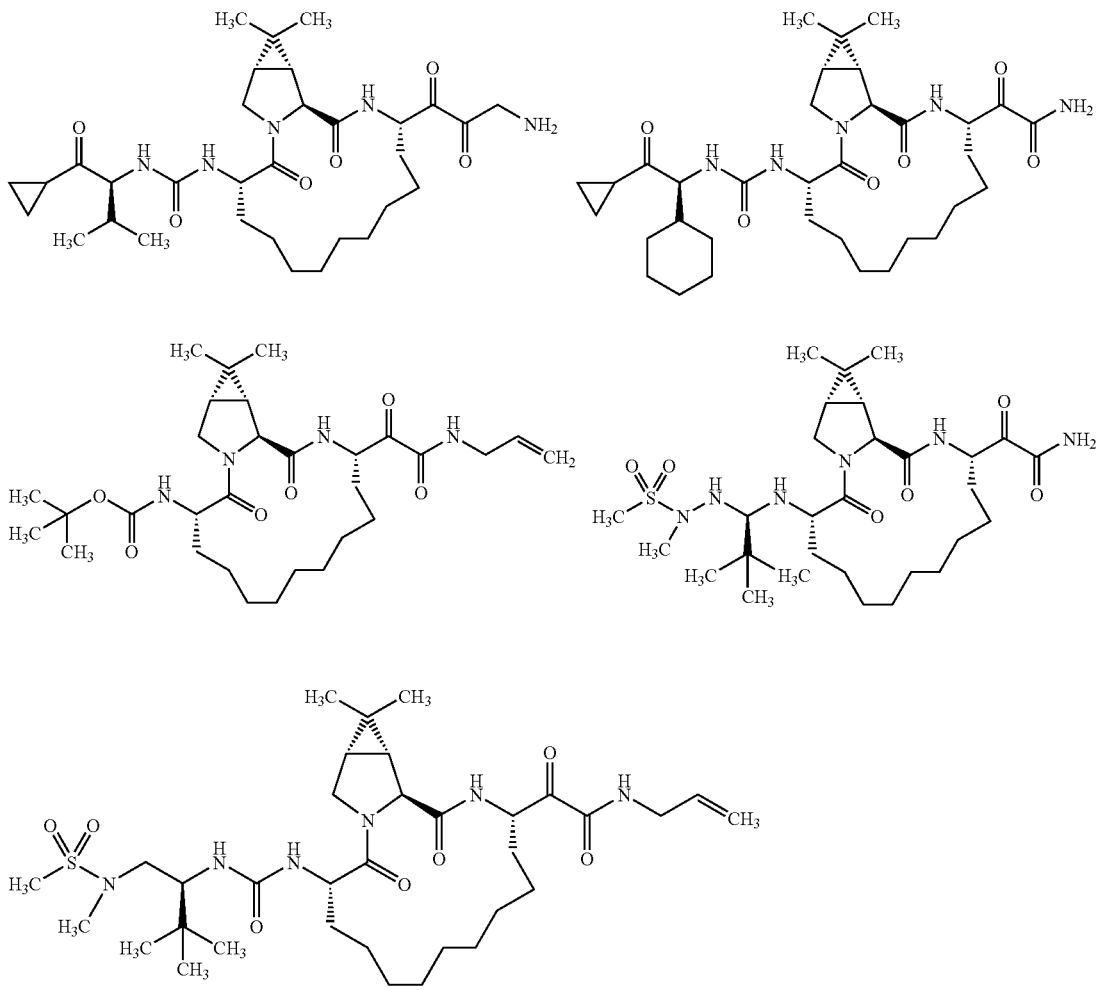

-continued
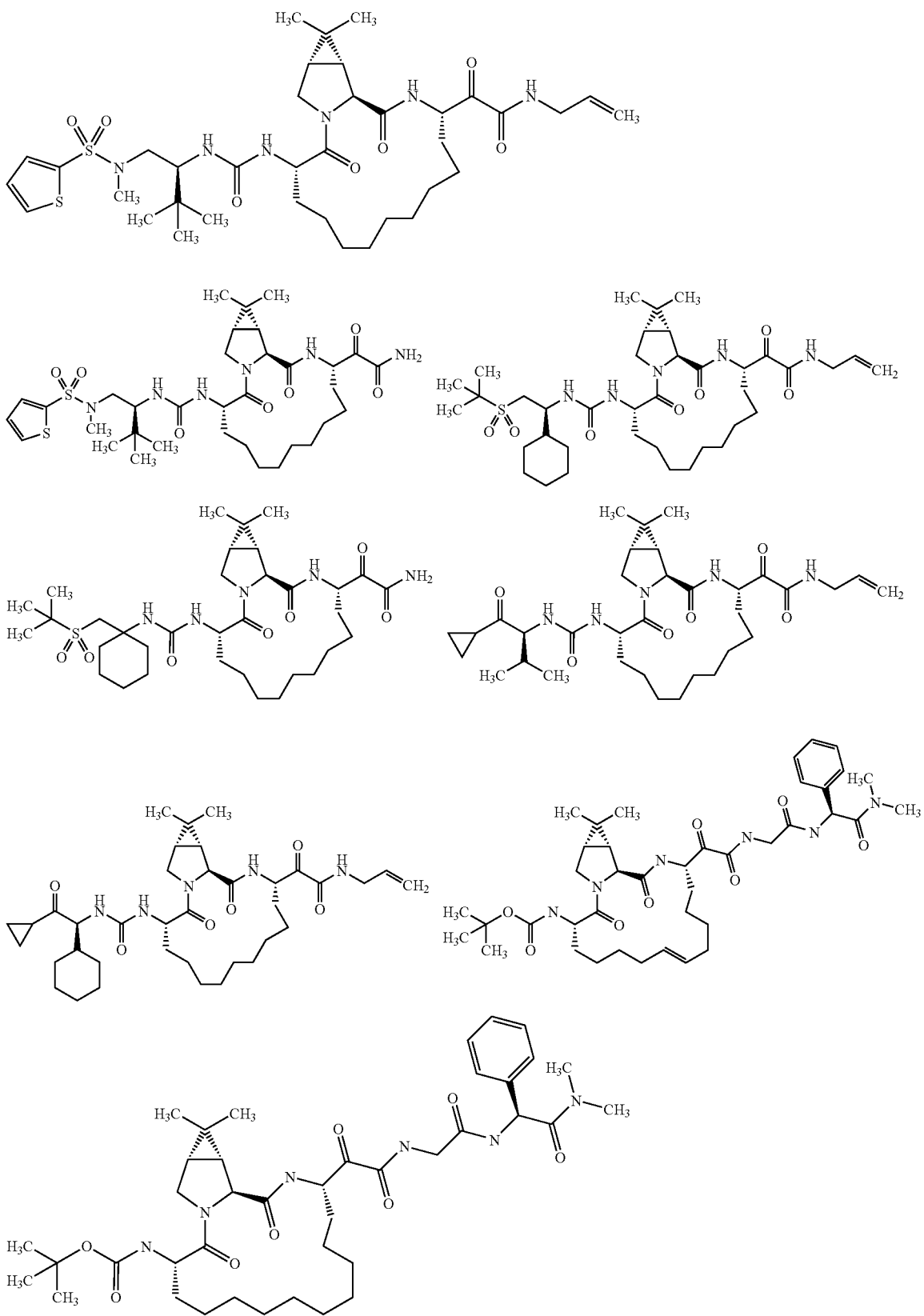

-continued
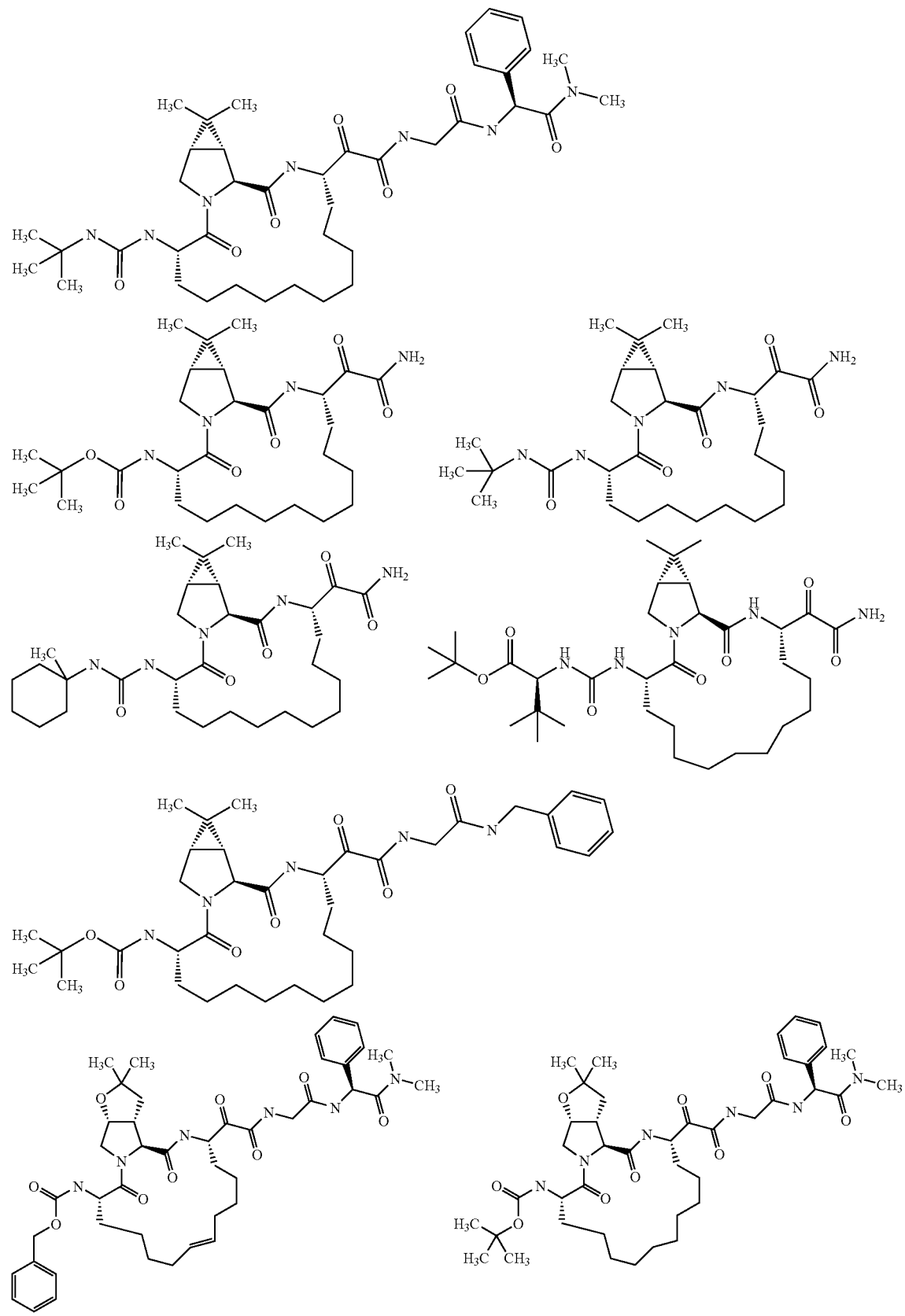

-continued
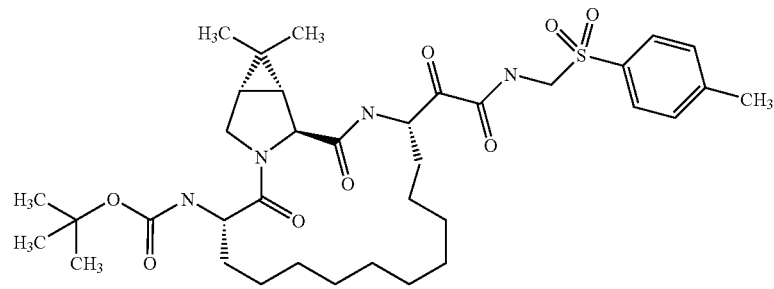
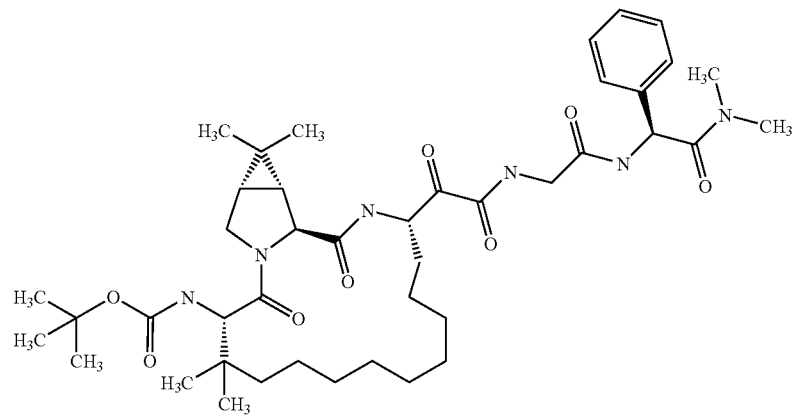
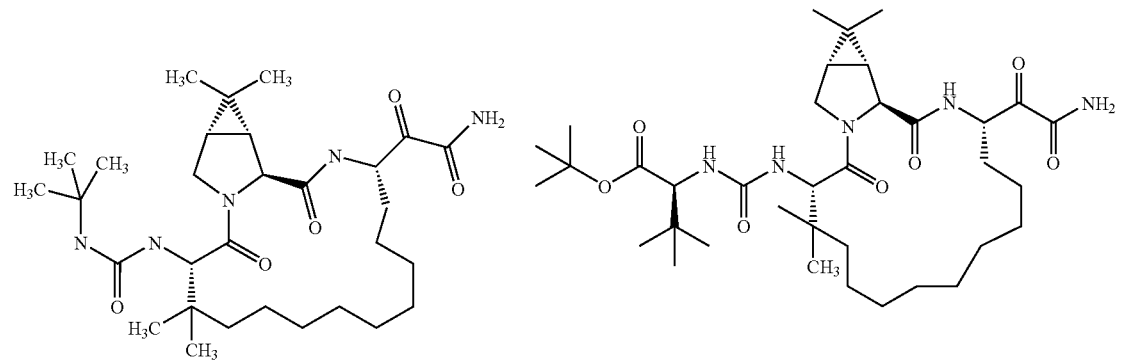
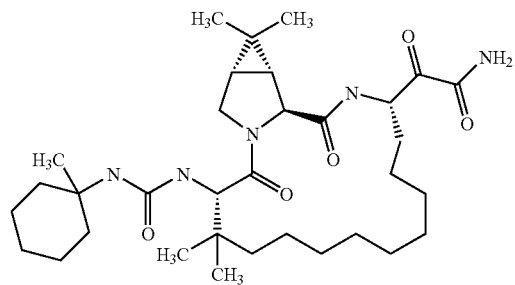
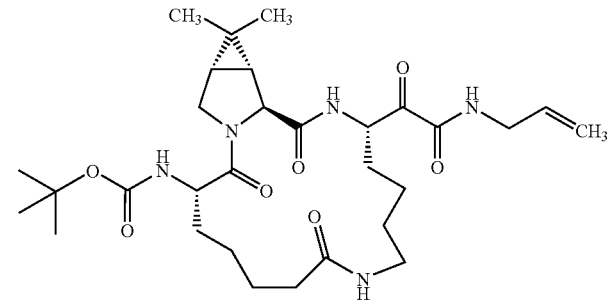
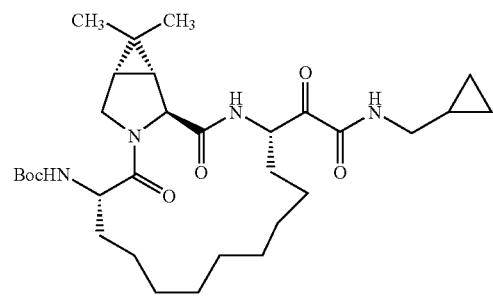
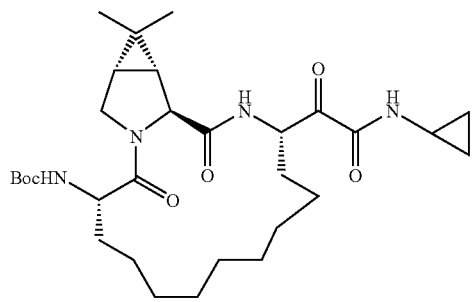

-continued
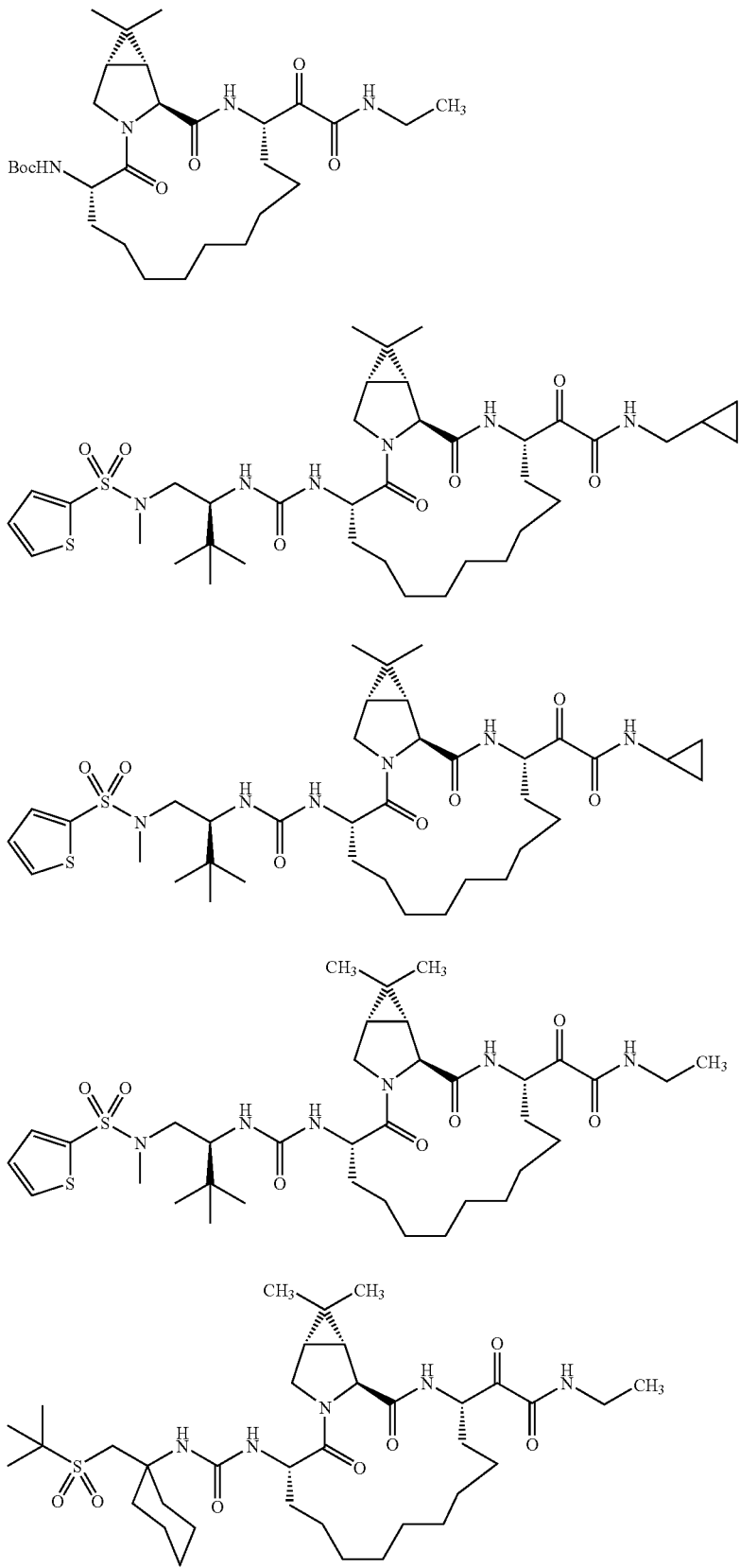

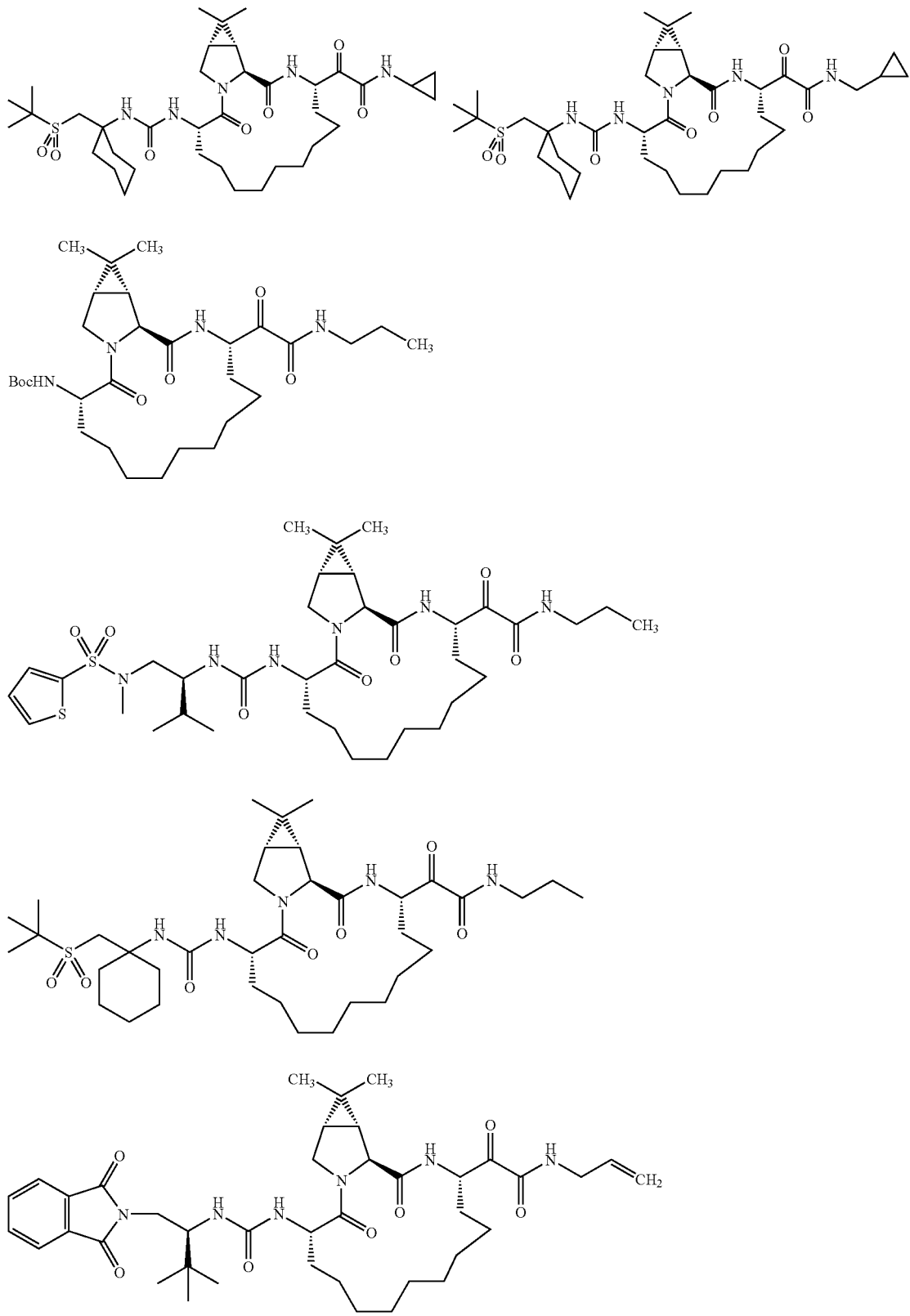

-continued
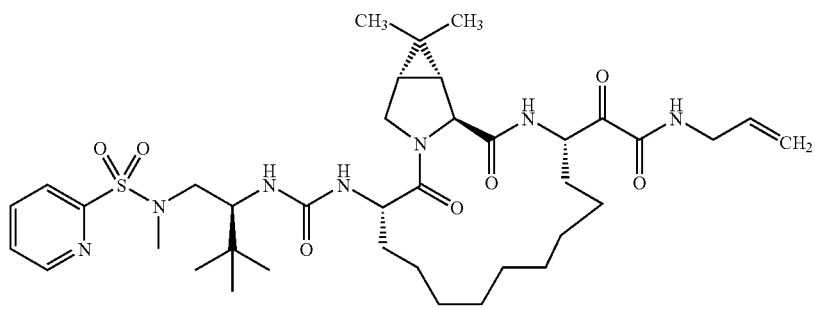
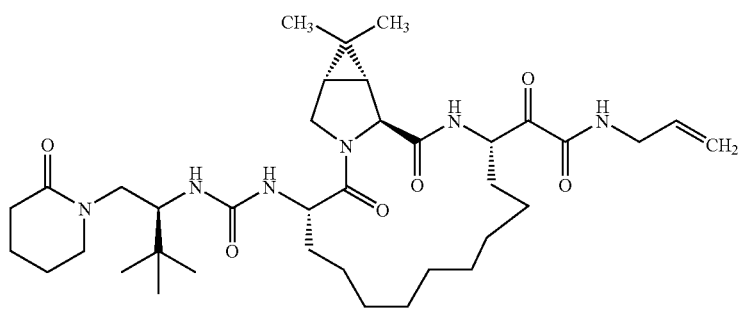
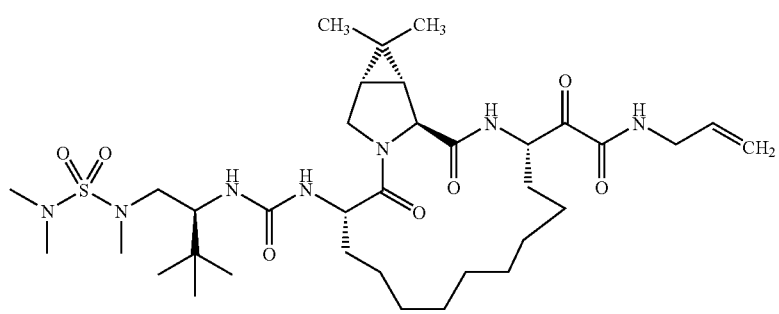
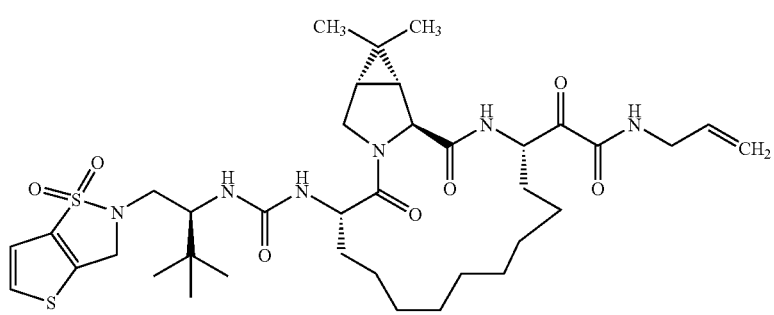
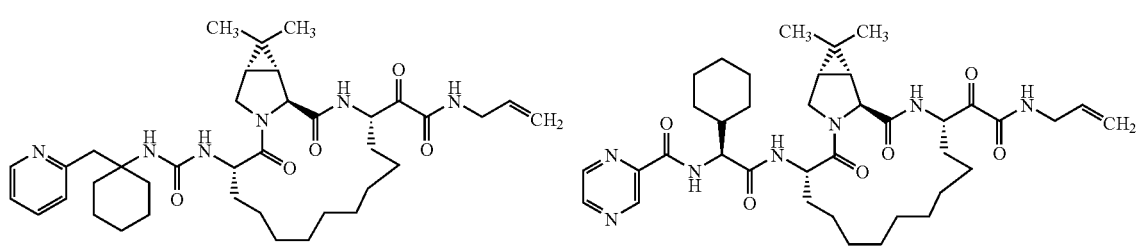

-continued
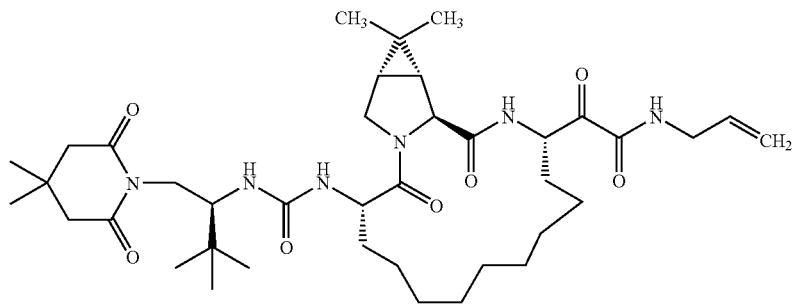
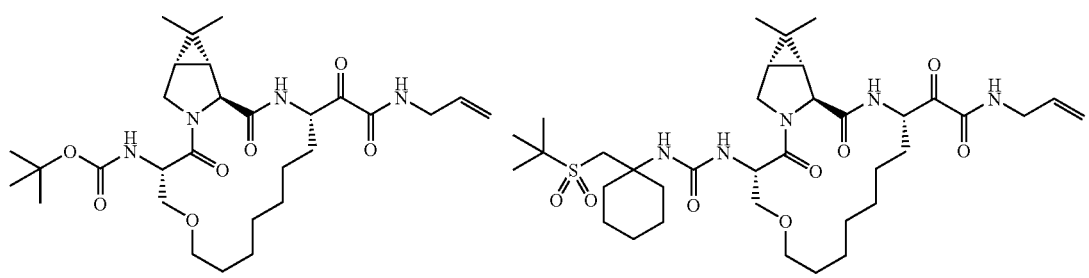
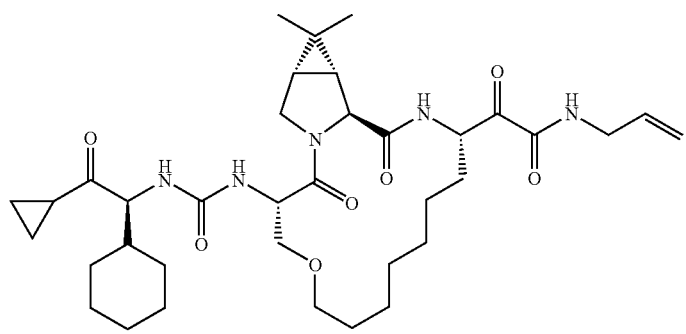
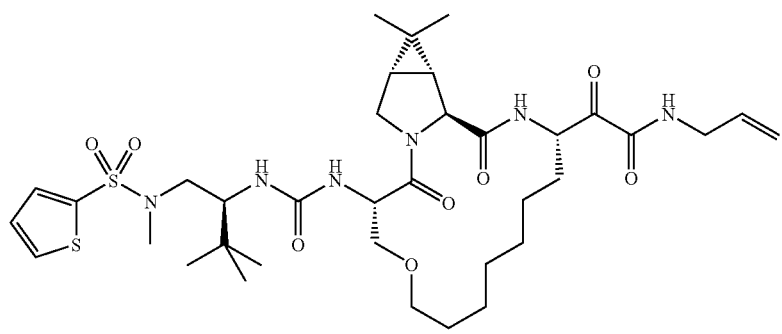
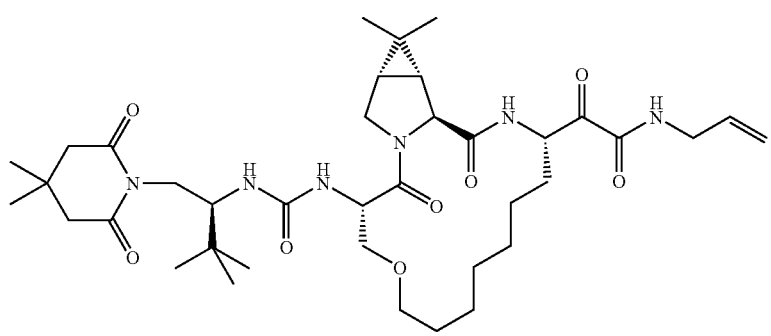

441 442
-continued
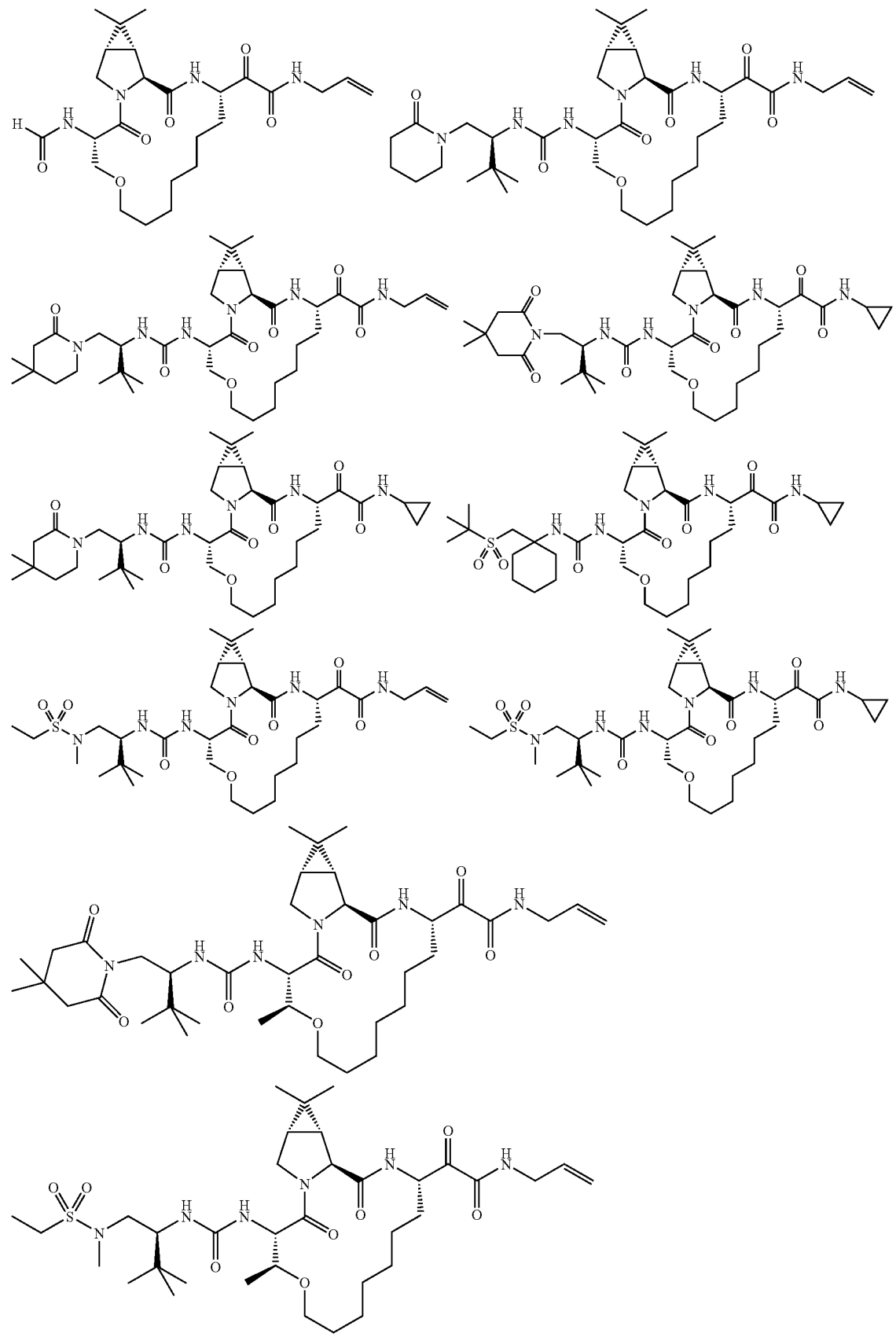

-continued
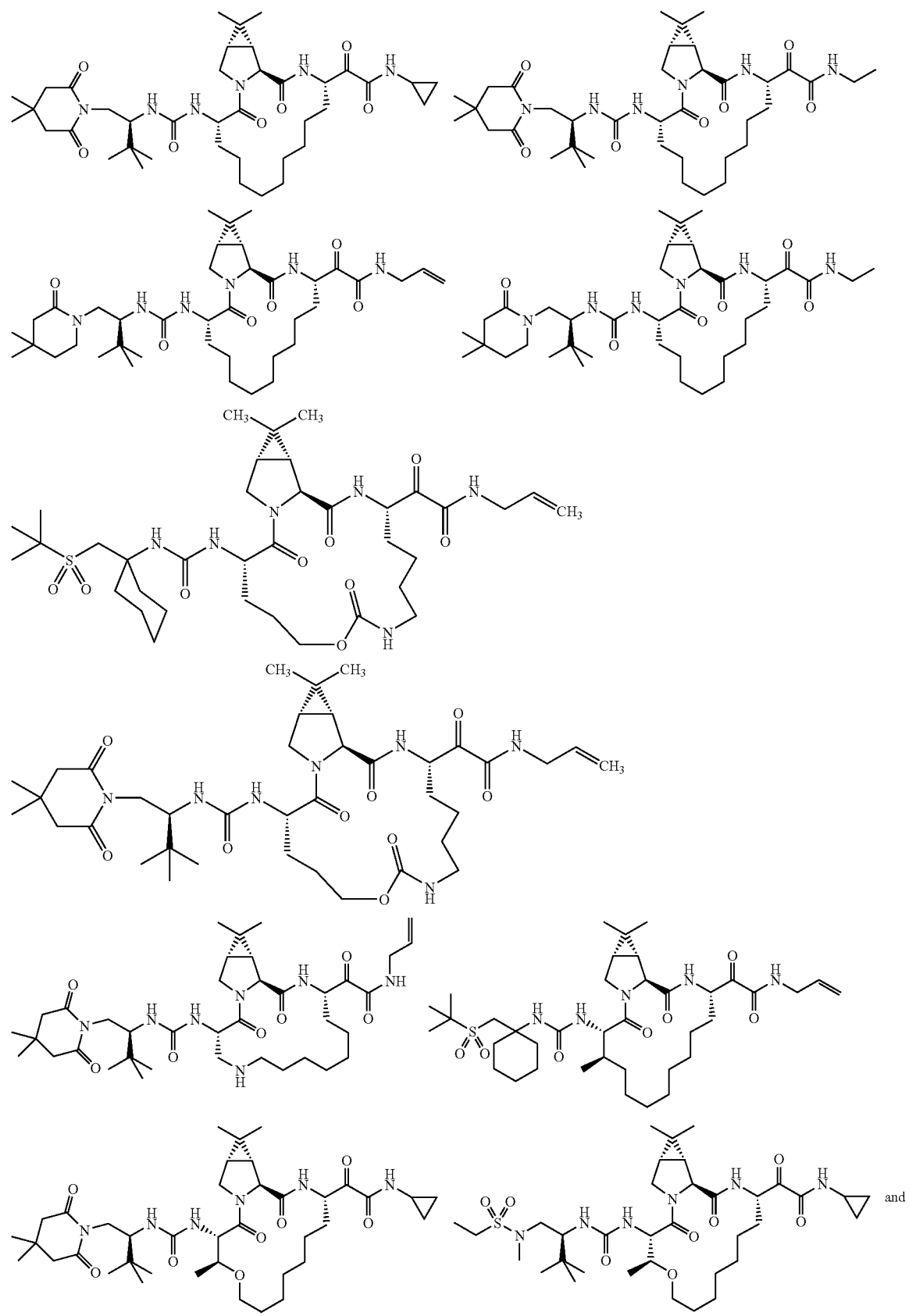
443  444
and

-continued
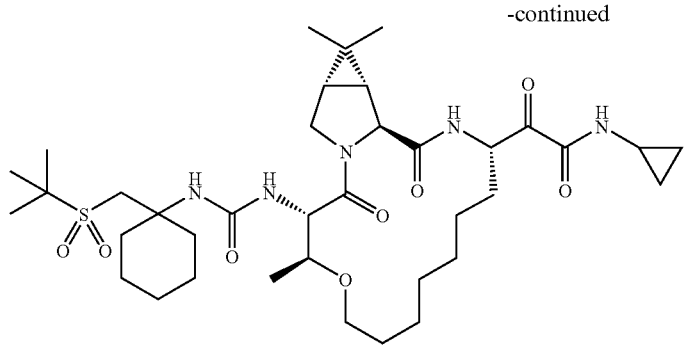
or pharmaceutically acceptable salts of said compound.
22. The compound according to claim 21, selected from the group consisting of:
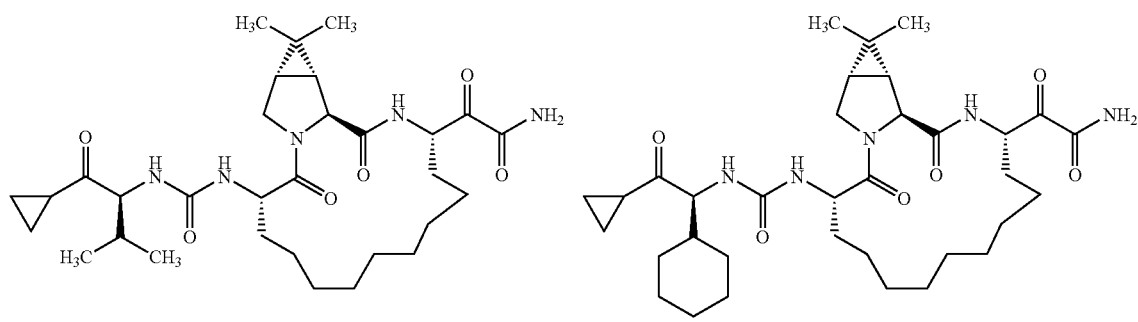
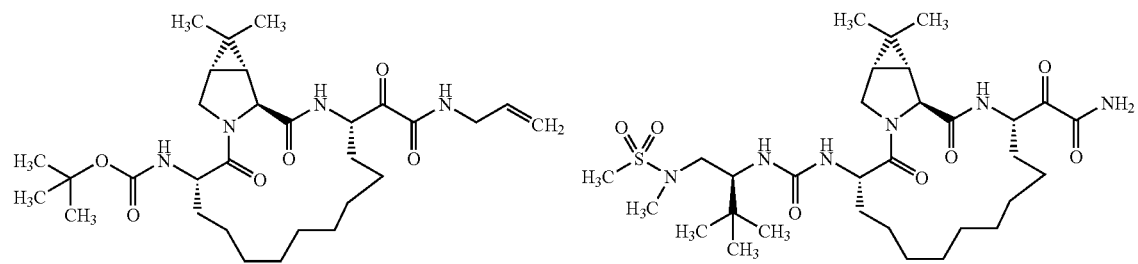
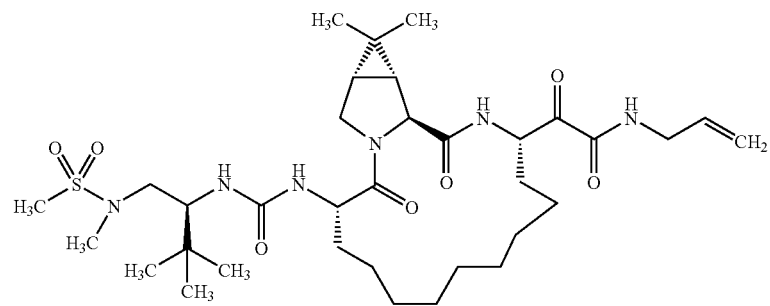

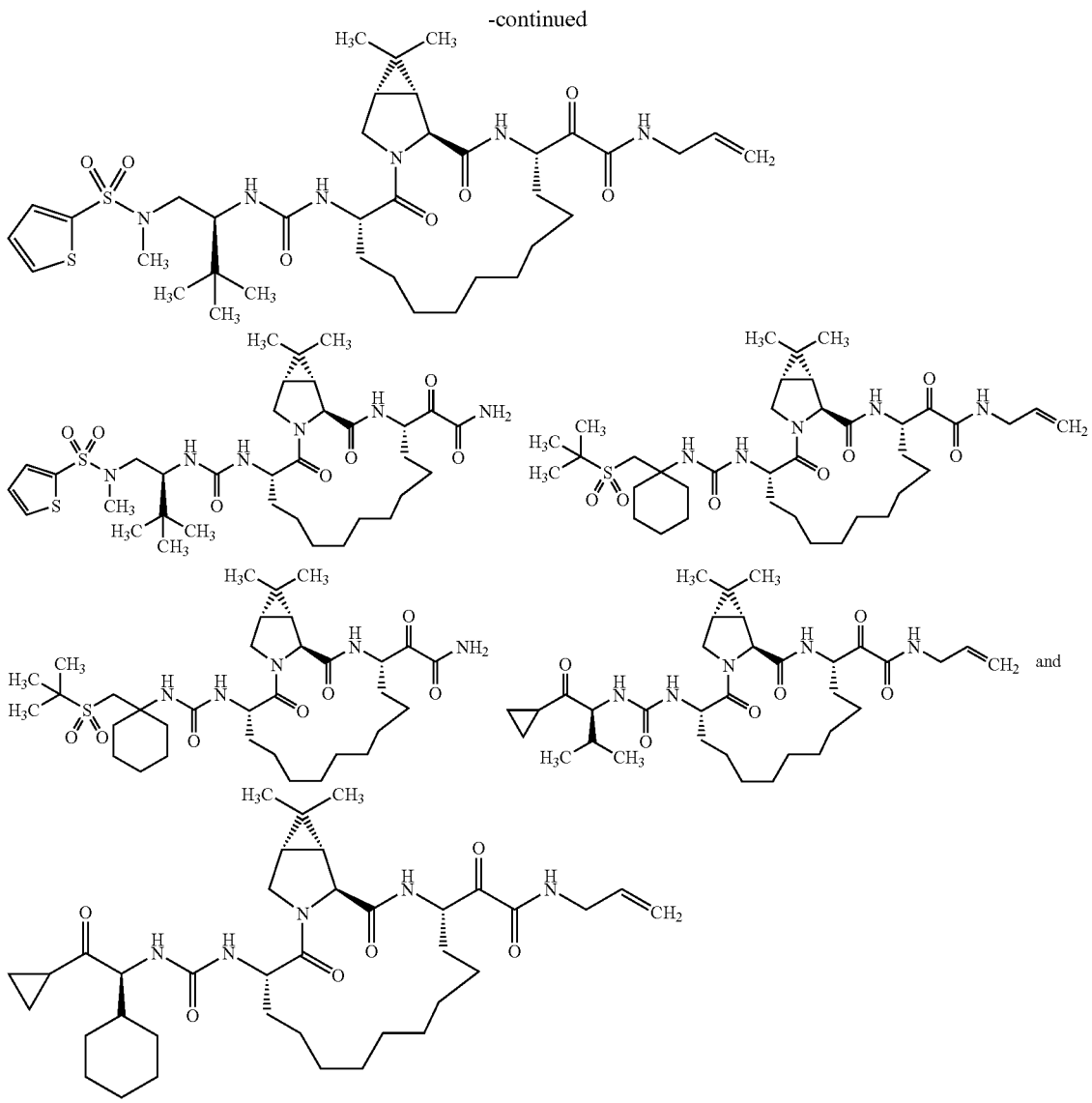

or pharmaceutically acceptable salts of said compound.

23. The compound of claim 1, wherein $R^1$ is ketoamide, acid, ketoacid, ketoester, ketoaldehyde, diketone, boronic acid or trifluoroketone.

24. A pharmaceutical composition comprising a compound according to claim 1 and a pharmaceutically acceptable carrier.

25. The pharmaceutical composition according to claim 24 suitable for treating HCV infections.

26. The pharmaceutical composition according to claim 24, additionally containing an antiviral agent.

27. The pharmaceutical composition according to claim 26, additionally containing an interferon or pegylated interfeon.

28. The pharmaceutical composition according to claim 27, wherein said antiviral agent is ribavirin and said interferon is α-interferon.

29. A method of treating the HCV infections, said method comprising administering to a patient in need of such treatment therapeutically effective amounts of a compound according to claim 1.

30. A method of treating the HCV infections, said method comprising administering to a patient in need of such treatment a pharmaceutical composition which comprises therapeutically effective amounts of a compound according to claim 1.

31. The method according to claim 30, wherein said administration is subcutaneous.

32. A pharmaceutical composition for treating HCV infections, said composition comprising therapeutically effective amount of one or more compounds in claim 22 and a pharmaceutically acceptable carrier.

33. The pharmaceutical composition according to claim 32, additionally containing an antiviral agent.

34. The pharmaceutical composition according to claim 33, still additionally containing an interferon or a pegylated interferon.

35. The pharmaceutical composition according to claim 34, wherein said antiviral agent is ribavirin and said interferon is α-interferon.
36. A compound selected from the group consisting of:
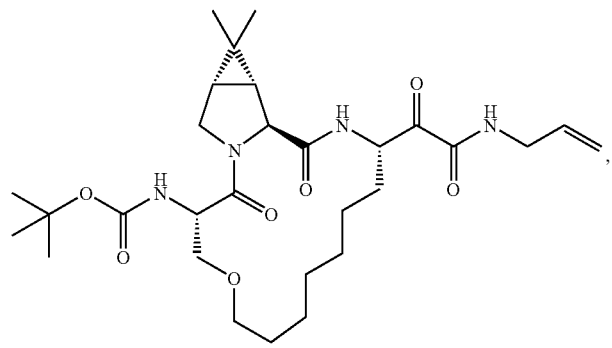
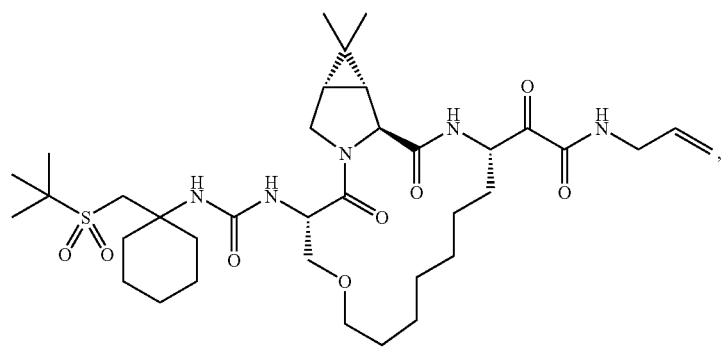
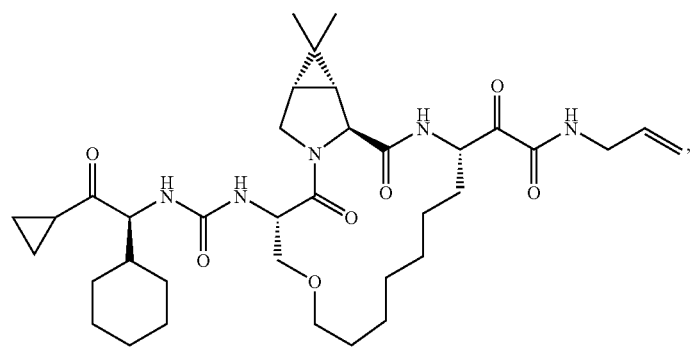
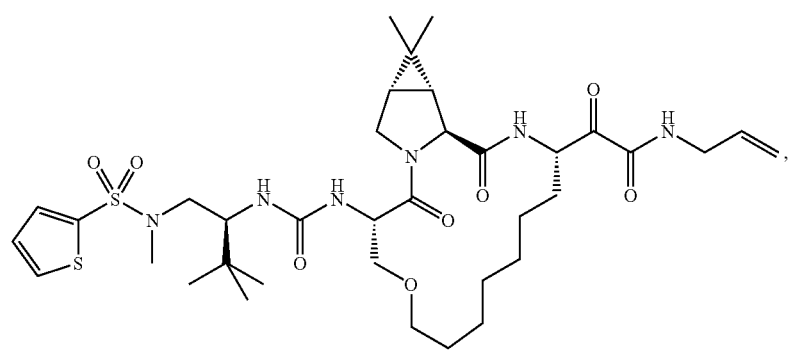

-continued
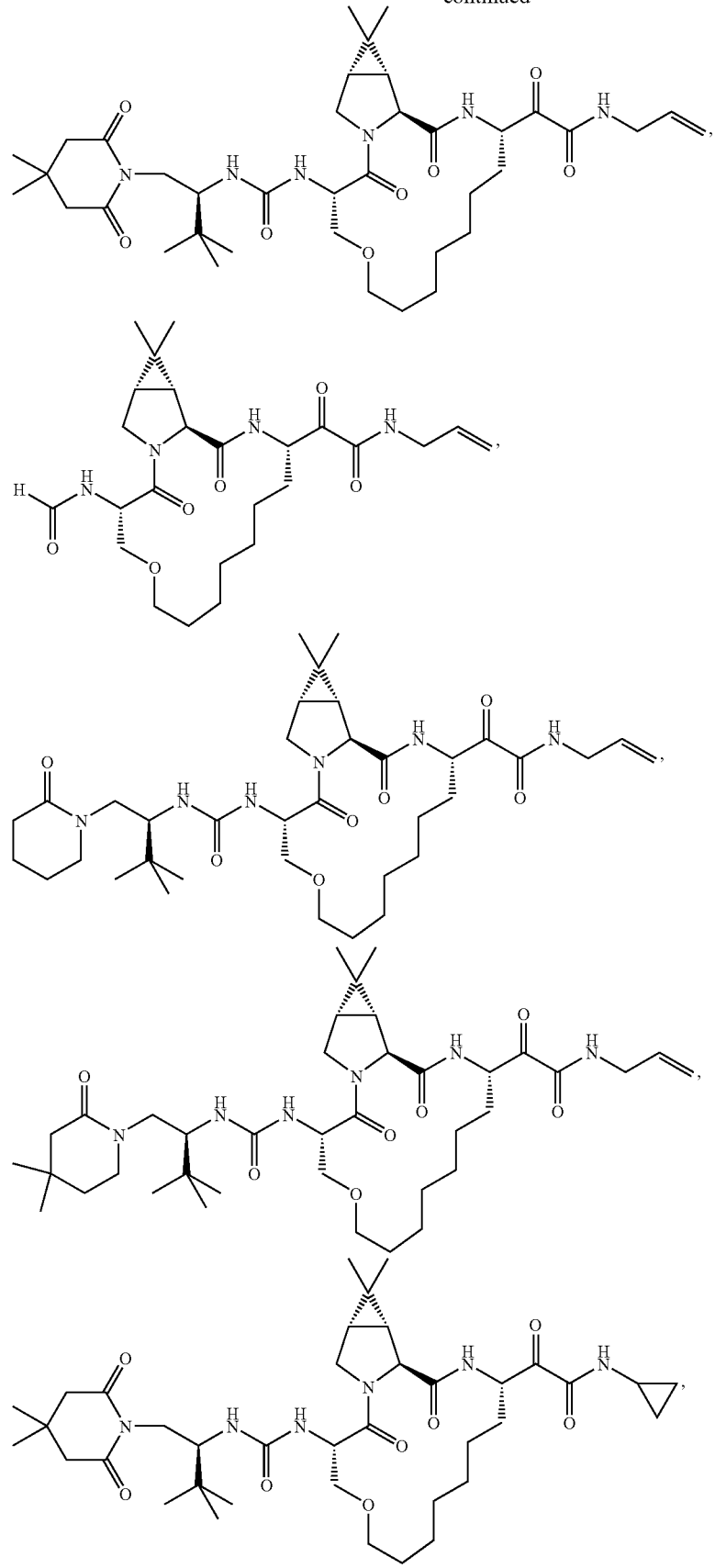

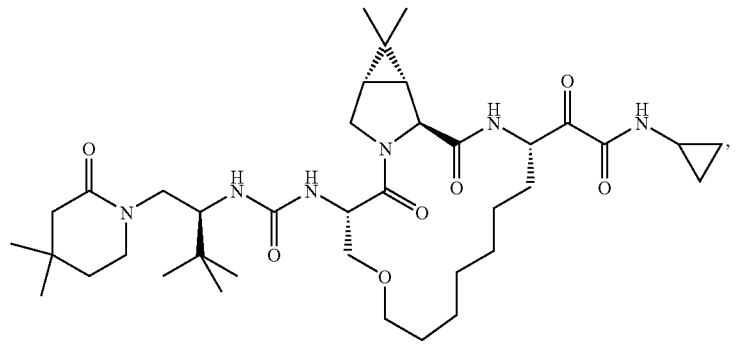
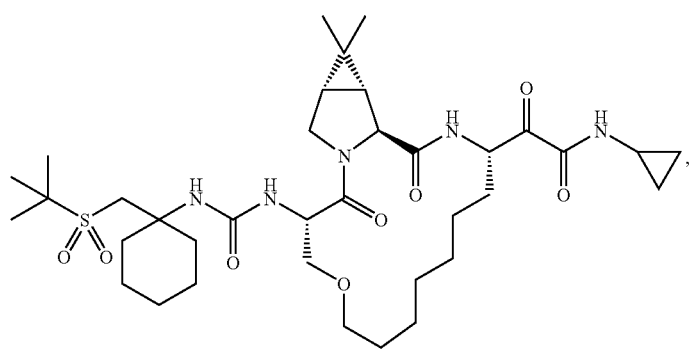
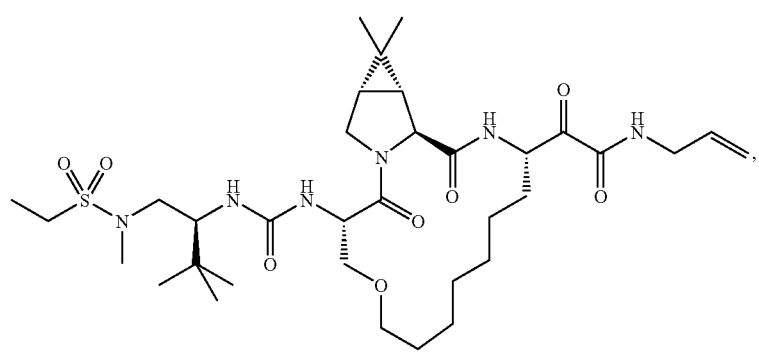
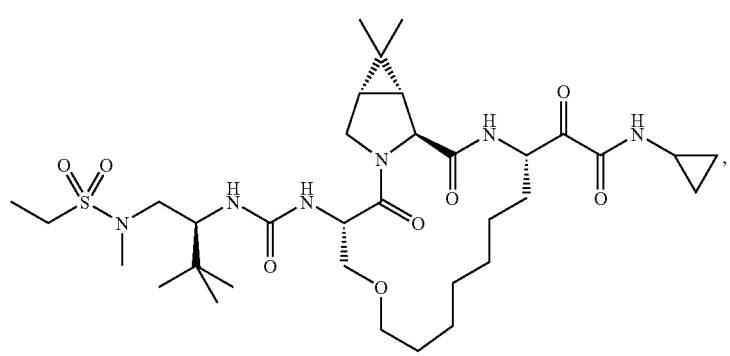

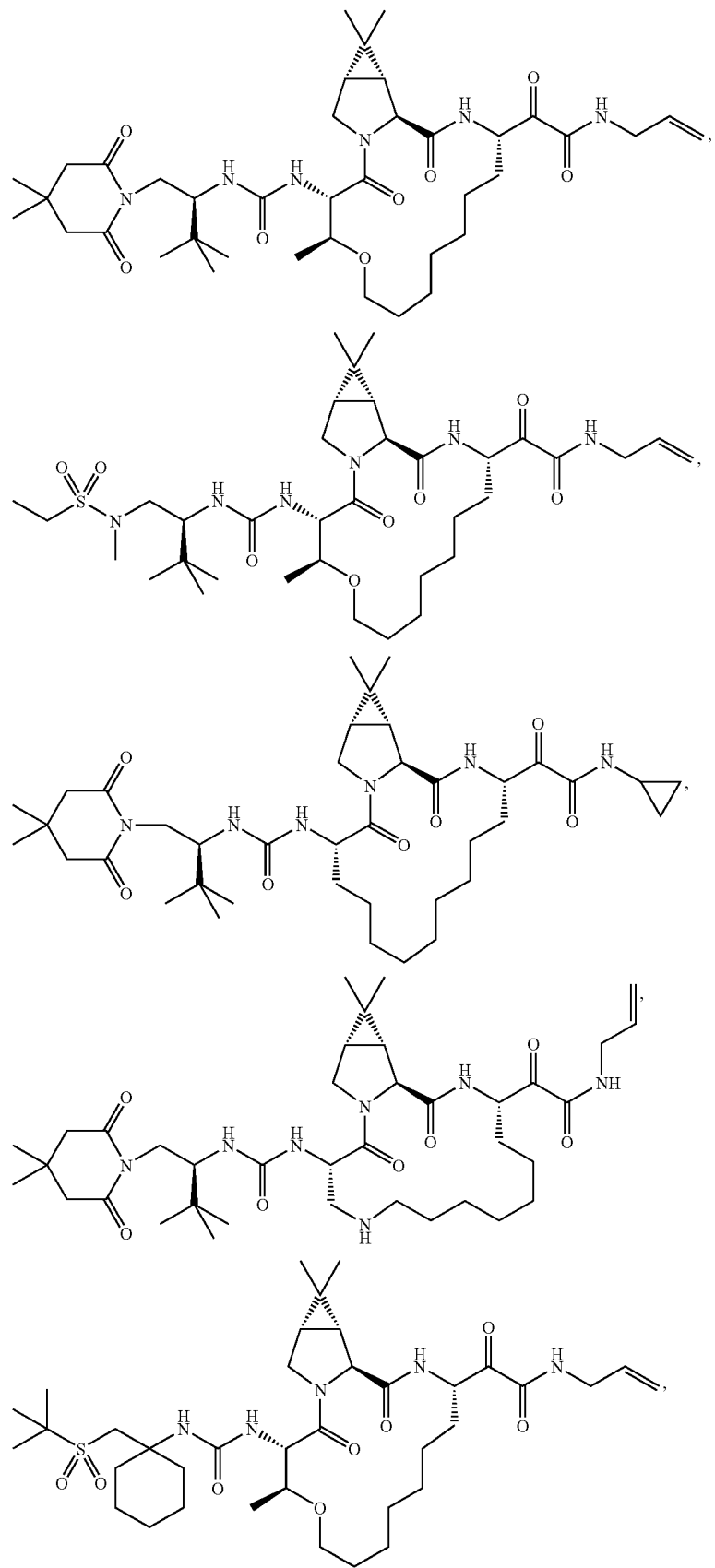

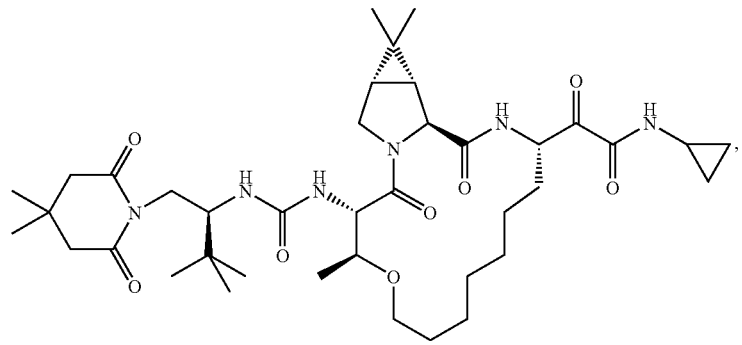
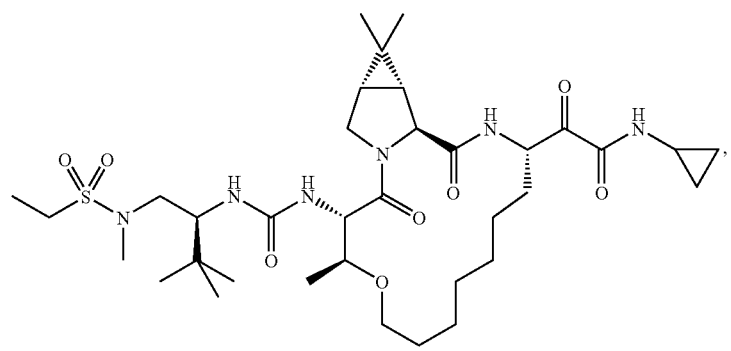
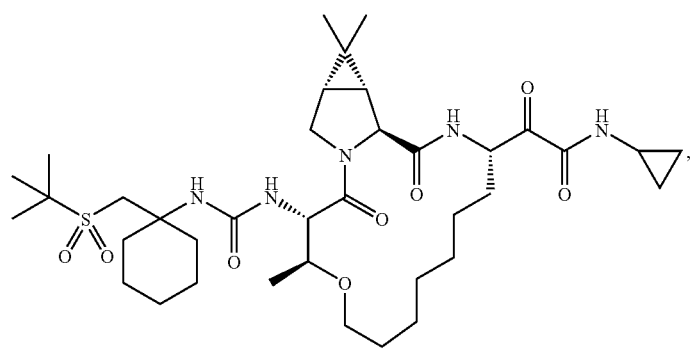
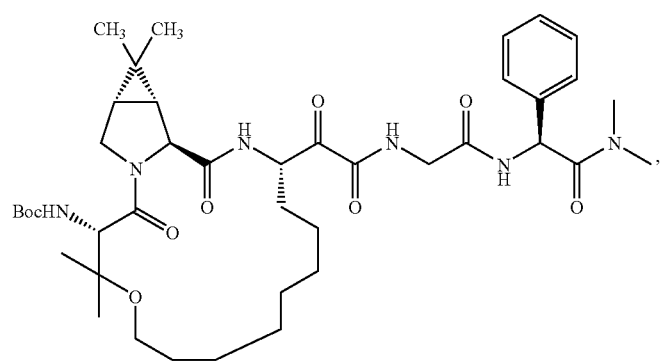

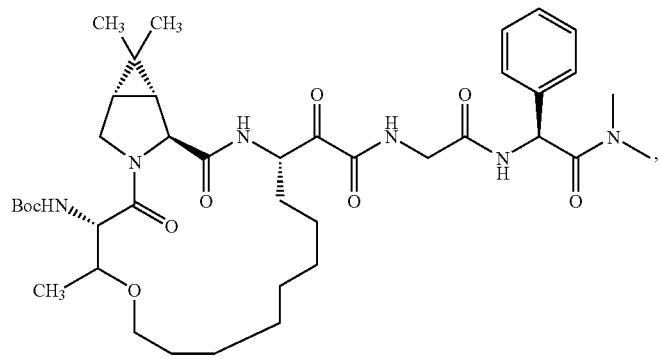
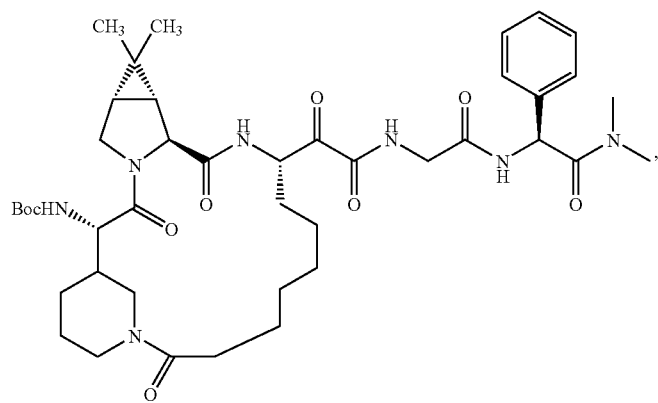
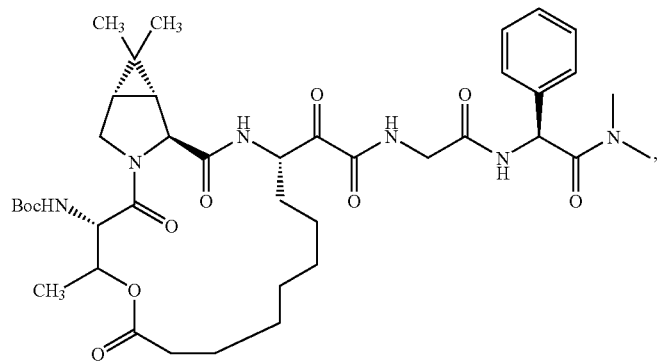
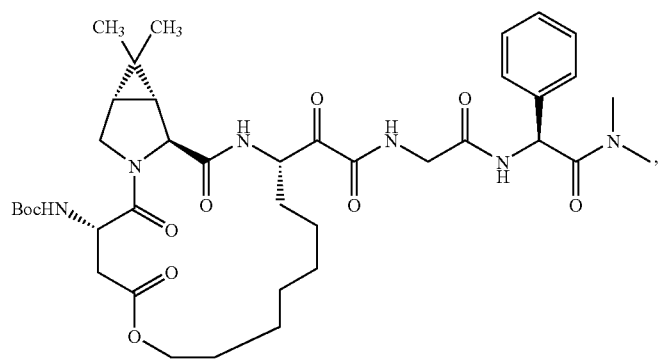

461
462
-continued
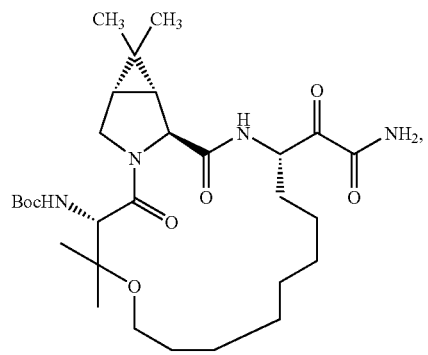 and 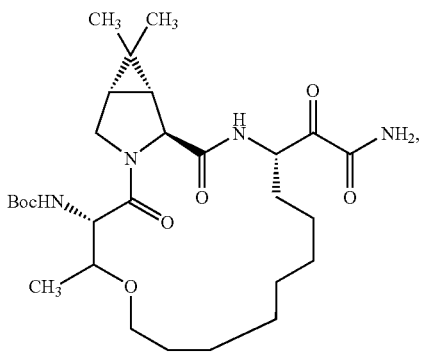
or pharmaceutically acceptable salts of said compound.
* * * * *

UNITED STATES PATENT AND TRADEMARK OFFICE
CERTIFICATE OF CORRECTION

PATENT NO. : 7,592,419 B2  
APPLICATION NO. : 10/948367  
DATED : September 22, 2009  
INVENTOR(S) : Srikanth Venkatraman et al.

It is certified that error appears in the above-identified patent and that said Letters Patent is hereby corrected as shown below:

Claim 1 at Column 392, lines 32-43 delete " 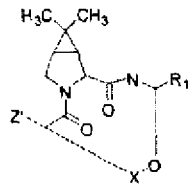 " and replace it with -- 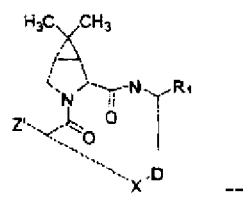 --.

Claim 15 at Column 417, lines 1-9 delete " 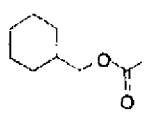 " and replace it with -- 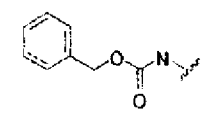 --.

Claim 21 at Column 425, lines 55-65 delete " 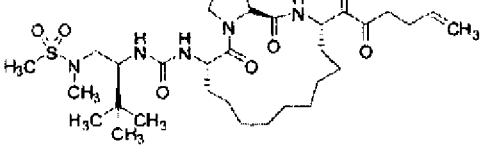 " and replace it with -- 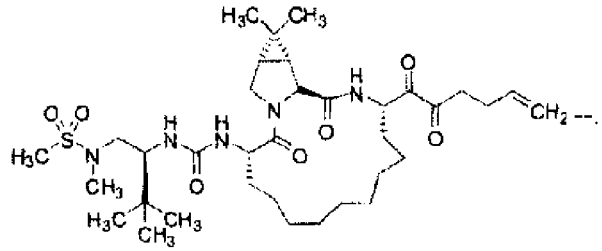 --.

Claim 21 at Column 427, lines 5-15 delete " 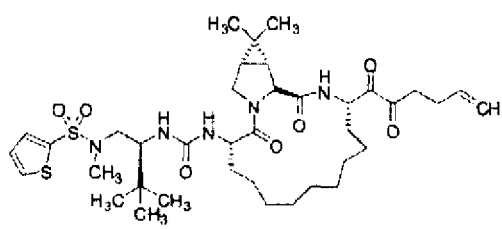 "

CERTIFICATE OF CORRECTION (continued)
U.S. Pat. No. 7,592,419 B2 and replace it with

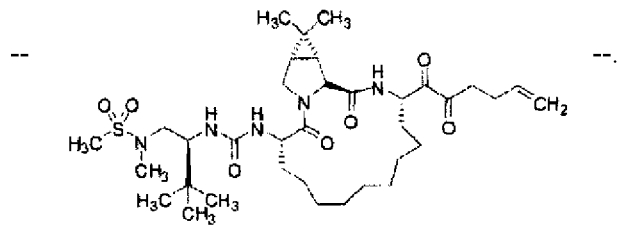

--.

Claim 21 at Column 428, lines 40-50 delete

" 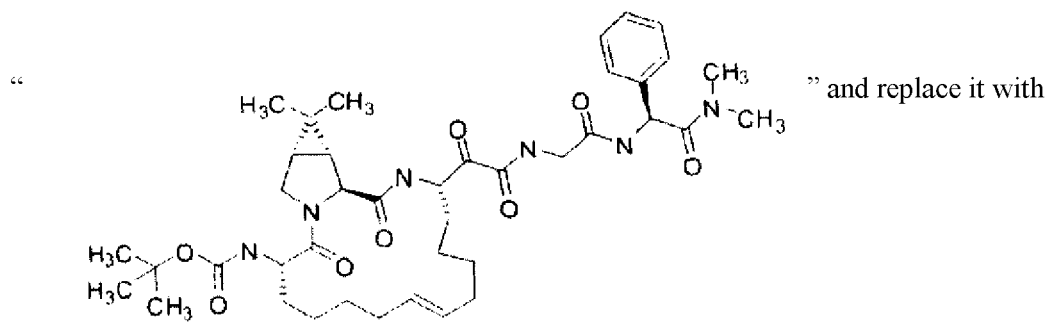 " and replace it with

-- 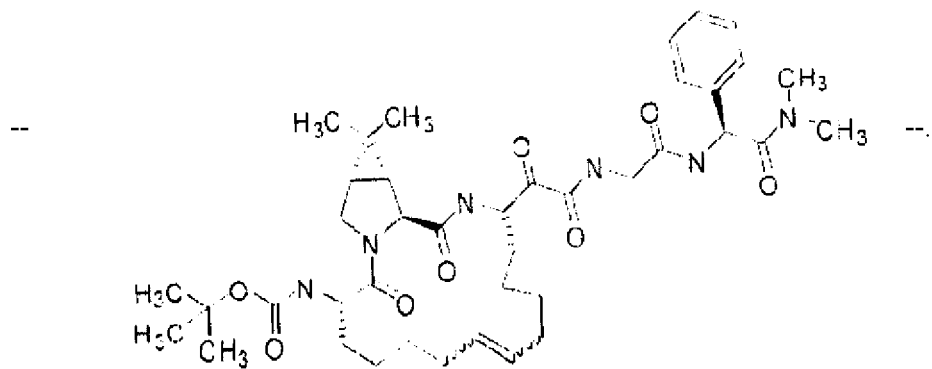 --.

Signed and Sealed this

Ninth Day of February, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,592,419 B2 | Page 1 of 1 |
| APPLICATION NO. | : 10/948367 | |
| DATED | : September 22, 2009 | |
| INVENTOR(S) | : Srikanth Venkatraman | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 514 days.

Signed and Sealed this
Eighth Day of March, 2011

David J. Kappos
*Director of the United States Patent and Trademark Office*